United States Patent
Johnson et al.

(10) Patent No.: US 10,676,460 B2
(45) Date of Patent: *Jun. 9, 2020

(54) QUINAZOLINES AS POTASSIUM ION CHANNEL INHIBITORS

(71) Applicant: BRISTOL-MYERS SQUIBB COMPANY, Princeton, NJ (US)

(72) Inventors: James A. Johnson, Pennington, NJ (US); John Lloyd, Yardley, PA (US); Heather Finlay, Skillman, NJ (US); James Neels, Holland, PA (US); Naveen Kumar Dhondi, Secunderabad (IN); Prashantha Gunaga, Karnataka (IN); Abhisek Banerjee, Howrah (IN); Ashokkumar Adisechan, Pondicherry (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/243,400

(22) Filed: Jan. 9, 2019

(65) Prior Publication Data
US 2019/0144426 A1 May 16, 2019

Related U.S. Application Data

(63) Continuation of application No. 15/724,566, filed on Oct. 4, 2017, now Pat. No. 10,214,511, which is a continuation of application No. 15/249,710, filed on Aug. 29, 2016, now Pat. No. 9,822,096, which is a continuation of application No. 14/038,814, filed on Sep. 27, 2013, now Pat. No. 9,458,114, which is a continuation of application No. 13/393,328, filed as application No. PCT/US2010/047430 on Sep. 1, 2010, now Pat. No. 8,575,184.

(Continued)

(51) Int. Cl.

| | |
|---|---|
| *C07D 401/14* | (2006.01) |
| *C07D 239/95* | (2006.01) |
| *C07D 401/12* | (2006.01) |
| *C07D 403/04* | (2006.01) |
| *C07D 403/12* | (2006.01) |
| *C07D 407/12* | (2006.01) |
| *C07D 413/14* | (2006.01) |
| *C07D 417/12* | (2006.01) |
| *C07D 417/14* | (2006.01) |
| *A61K 31/517* | (2006.01) |
| *A61K 31/5377* | (2006.01) |
| *A61K 31/549* | (2006.01) |
| *A61K 45/06* | (2006.01) |
| *C07D 239/94* | (2006.01) |
| *C07D 405/12* | (2006.01) |
| *C07D 471/04* | (2006.01) |
| *C07D 513/04* | (2006.01) |

(52) U.S. Cl.
CPC .......... *C07D 401/14* (2013.01); *A61K 31/517* (2013.01); *A61K 31/5377* (2013.01); *A61K 31/549* (2013.01); *A61K 45/06* (2013.01); *C07D 239/94* (2013.01); *C07D 239/95* (2013.01); *C07D 401/12* (2013.01); *C07D 403/04* (2013.01); *C07D 403/12* (2013.01); *C07D 405/12* (2013.01); *C07D 407/12* (2013.01); *C07D 413/14* (2013.01); *C07D 417/12* (2013.01); *C07D 417/14* (2013.01); *C07D 471/04* (2013.01); *C07D 513/04* (2013.01)

(58) Field of Classification Search
CPC .................................................... C07D 239/95
See application file for complete search history.

(56) References Cited

U.S. PATENT DOCUMENTS

| | | |
|---|---|---|
| 5,324,839 A | 6/1994 | Clemence et al. |
| 5,457,105 A | 10/1995 | Barker |

(Continued)

FOREIGN PATENT DOCUMENTS

| | | |
|---|---|---|
| CN | 101575333 | 11/2009 |
| EP | 0579496 | 1/1994 |

(Continued)

OTHER PUBLICATIONS

Patent Abstracts of Japan—JP 06263744; "Production of 2,4-Diaminoquinazolines" Pub Date: Sep. 20, 1994.

*Primary Examiner* — Paul V Ward
(74) *Attorney, Agent, or Firm* — Mary K. VanAtten

(57) ABSTRACT

A compound of formula I

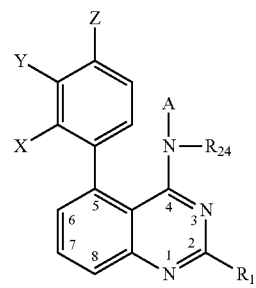

wherein A, X, Y, Z, $R_1$ and $R_{24}$ are described herein. The compounds are useful as inhibitors of potassium channel function and in the treatment and prevention of arrhythmia, $I_{Kur}$-associated disorders, and other disorders mediated by ion channel function.

15 Claims, No Drawings

Related U.S. Application Data

(60) Provisional application No. 61/239,452, filed on Sep. 3, 2009.

(56) References Cited

U.S. PATENT DOCUMENTS

| | | |
|---|---|---|
| 5,475,001 A | 12/1995 | Barker |
| 5,478,938 A | 12/1995 | Clemence et al. |
| 5,569,658 A | 10/1996 | Barker |
| 5,580,870 A | 12/1996 | Barker et al. |
| 5,616,582 A | 4/1997 | Barker |
| 5,654,307 A | 8/1997 | Bridges et al. |
| 5,679,683 A | 10/1997 | Bridges et al. |
| 5,707,989 A | 1/1998 | Himmelsbach et al. |
| 5,955,464 A | 9/1999 | Barker |
| 6,084,095 A | 7/2000 | Bridges et al. |
| 6,184,226 B1 | 2/2001 | Chakravarty et al. |
| 6,248,771 B1 | 6/2001 | Shenoy et al. |
| 6,265,410 B1 | 7/2001 | Bridges et al. |
| 6,391,874 B1 | 5/2002 | Cockerill et al. |
| 6,455,534 B2 | 9/2002 | Bridges et al. |
| 6,476,031 B1 | 11/2002 | Chakravarty et al. |
| 6,521,620 B1 | 2/2003 | Bridges et al. |
| 6,596,726 B1 | 7/2003 | Bridges et al. |
| 6,605,615 B2 | 8/2003 | Medina et al. |
| 6,713,484 B2 | 8/2004 | Bridges et al. |
| 6,828,320 B2 | 12/2004 | Cockerill et al. |
| 7,547,702 B2 | 6/2009 | Mederski et al. |
| 7,678,802 B2 | 3/2010 | Gonzalez et al. |
| 7,713,983 B2 | 5/2010 | Gonzalez et al. |
| 7,829,566 B2 | 11/2010 | Mederski et al. |
| 8,039,505 B2 | 10/2011 | Trede |
| 8,153,642 B2 | 4/2012 | Gonzalez et al. |
| 8,575,184 B2 | 11/2013 | Johnson et al. |
| 9,458,114 B2 * | 10/2016 | Johnson .............. C07D 239/95 |
| 9,603,848 B2 | 3/2017 | Servent et al. |
| 9,822,096 B2 | 11/2017 | Johnson et al. |
| 2003/0220357 A1 | 11/2003 | Bankston et al. |
| 2004/0014774 A1 | 1/2004 | Myers et al. |
| 2004/0044204 A1 | 3/2004 | Mederski et al. |
| 2004/0248890 A1 | 12/2004 | Gonzalez et al. |
| 2005/0096327 A1 | 5/2005 | Caprathe et al. |
| 2005/0220784 A1 | 10/2005 | Chakravarty et al. |
| 2006/0025406 A1 | 2/2006 | Zembower et al. |
| 2007/0049559 A1 | 3/2007 | Pfeffer et al. |
| 2007/0054894 A1 | 3/2007 | Trotter et al. |
| 2009/0306102 A1 | 12/2009 | Eriksen et al. |

FOREIGN PATENT DOCUMENTS

| | | |
|---|---|---|
| EP | 1878727 | 1/2008 |
| JP | 8-3144 A | 1/1996 |
| JP | 2009-519995 A | 5/2009 |
| WO | WO 1995/015758 | 6/1995 |
| WO | WO 1996/009294 | 3/1996 |
| WO | WO 1997/003069 | 1/1997 |
| WO | WO 1997/23462 | 7/1997 |
| WO | WO 1998/029397 | 7/1998 |
| WO | WO 2001/021596 | 3/2001 |
| WO | WO 2001/083456 | 11/2001 |
| WO | WO 2002/024667 | 3/2002 |
| WO | WO 2002/062767 | 8/2002 |
| WO | WO2002/092579 A1 | 11/2002 |
| WO | WO 2004/017950 | 3/2004 |
| WO | WO 2004/030671 | 4/2004 |
| WO | WO 2004/030672 | 4/2004 |
| WO | WO 2004/056801 | 7/2004 |
| WO | WO 2004/056812 | 7/2004 |
| WO | WO 2004/069145 | 8/2004 |
| WO | WO 2004/078733 | 9/2004 |
| WO | WO2004/087680 A1 | 10/2004 |
| WO | WO 2004/111057 | 12/2004 |
| WO | WO 2005/003100 | 1/2005 |
| WO | WO 2005/007672 | 1/2005 |
| WO | WO 2005/080377 | 9/2005 |
| WO | WO 2005/087742 | 9/2005 |
| WO | WO 2005/087749 A1 | 9/2005 |
| WO | WO 2005/121149 | 12/2005 |
| WO | WO 2006/004722 | 1/2006 |
| WO | WO 2006/061642 | 6/2006 |
| WO | WO 2006/071095 | 7/2006 |
| WO | WO 2006/089150 | 8/2006 |
| WO | WO 2006/100310 | 9/2006 |
| WO | WO2006097441 A1 | 9/2006 |
| WO | WO 2006/105063 | 10/2006 |
| WO | WO 2007/066127 | 6/2007 |
| WO | WO 2007/071055 | 6/2007 |
| WO | WO 2007/104560 | 9/2007 |
| WO | WO 2008/003702 | 1/2008 |
| WO | WO 2008/023357 | 2/2008 |
| WO | WO 2008/030120 | 3/2008 |
| WO | WO 2008/045529 | 4/2008 |
| WO | WO 2009/006141 | 1/2009 |
| WO | WO 2009/137797 | 11/2009 |
| WO | WO 2009/143246 | 11/2009 |
| WO | WO 2011/029054 | 3/2011 |
| WO | WO 2011/082337 | 7/2011 |

* cited by examiner

QUINAZOLINES AS POTASSIUM ION CHANNEL INHIBITORS

RELATED APPLICATION

This application is a continuation of U.S. application No. Ser. No. 15/724,566, filed Oct. 4, 2017 (allowed), which is a continuation of U.S. application Ser. No. 15/249,710, filed Aug. 29, 2016, U.S. Pat. No. 9,822,096, which is a continuation of U.S. application Ser. No. 14/038,814, filed Sep. 27, 2013, U.S. Pat. No. 9,458,114, which is a continuation of U.S. application Ser. No. 13/393,328 filed Feb. 29, 2012, which was the National Stage of International Application No. PCT/US2010/047430, filed on Sep. 1, 2010, which claims the benefit of U.S. Provisional Application No. 61/239,452, filed on Sep. 3, 2009, each incorporated herein by reference in its entirety.

FIELD OF THE INVENTION

The present invention provides for quinazolines useful as inhibitors of potassium channel function (especially inhibitors of the $K_v1$ subfamily of voltage gated $K^+$ channels, more especially inhibitors of $K_v1.5$ (which have been linked to the ultra-rapidly activating delayed rectifier $K^+$ current $I_{Kur}$), and/or $K_v1.3$ channels, and/or $K_v1.1$ channels) and to pharmaceutical compositions containing such compounds. The present invention further provides for methods of using such compounds in the treatment and prevention of arrhythmia, $I_{Kur}$-associated disorders, and other disorders mediated by ion channel function.

BACKGROUND OF THE INVENTION

The ultra-rapidly activating delayed rectifier $K^+$ current ($I_{Kur}$) is believed to represent the native counterpart to a cloned potassium channel designated $K_v1.5$ and, while present in human atrium, it appears to be absent in human ventricle. Furthermore, because of its rapidity of activation and limited slow inactivation, $I_{Kur}$ is believed to contribute significantly to repolarization in human atrium. Consequently, a specific blocker of $I_{Kur}$, that is a compound which blocks $K_v1.5$, would overcome the short coming of other compounds by prolonging refractoriness by retarding repolarization in the human atrium without causing the delays in ventricular repolarization that underlie arrhythmogenic after depolarizations and acquired long QT syndrome observed during treatment with current Class III antiarrhythmic agents. (Antiarrhythmic agents of Class III are drugs that cause a selective prolongation of the duration of the action potential without significant cardiac depression.)

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma. Although the underlying pathogenesis of each of these conditions may vary, they have in common the appearance of a variety of auto-antibodies and self-reactive lymphocytes. Such self-reactivity may be due, in part, to a loss of the homeostatic controls under which the normal immune system operates. Similarly, following a bone-marrow or an organ transplantation, lymphocytes recognize the foreign tissue antigens and begin to produce immune mediators which lead to graft rejection or graft-vs-host rejection.

One end result of an autoimmune or a rejection process is tissue destruction caused by inflammatory cells and the mediators they release. Anti-inflammatory agents such as NSAIDs act principally by blocking the effect or secretion of these mediators but do nothing to modify the immunologic basis of the disease. On the other hand, cytotoxic agents, such as cyclophosphamide, act in such a nonspecific fashion in which both the normal and autoimmune responses are shut off. Indeed, patients treated with such nonspecific immunosuppressive agents are as likely to succumb to infection as they are to their autoimmune disease.

Cyclosporin A, which was approved by the US FDA in 1983 is currently the leading drug used to prevent rejection of transplanted organs. In 1993, FK-506 (PROGRAF®) was approved by the US FDA for the prevention of rejection in liver transplantation. Cyclosporin A and FK-506 act by inhibiting the body's immune system from mobilizing its vast arsenal of natural protecting agents to reject the transplant's foreign protein. In 1994, Cyclosporin A was approved by the US FDA for the treatment of severe psoriasis and has been approved by European regulatory agencies for the treatment of atopic dermatitis. Though these agents are effective in fighting transplant rejection, Cyclosporin A and FK-506 are known to cause several undesirable side effects including nephrotoxicity, neurotoxicity, and gastrointestinal discomfort. Therefore, a selective immunosuppressant without these side effects still remains to be developed. Potassium channel inhibitors as described here promise to be the solution to this problem, since inhibitors of $K_v1.3$, for example, are immunosuppressive. See Wulff et al., "Potassium channels as therapeutic targets for autoimmune disorders," *Curr. Opin. Drug Discov. Devel.*, 6(5):640-647 (September 2003); Shah et al., "Immunosuppressive effects of a $K_v1.3$ inhibitor," *Cell Immunol.*, 221(2):100-106 (February 2003); Hanson et al., "UK-78, 282, a novel piperidine compound that potently blocks the $K_v1.3$ voltage-gated potassium channel and inhibits human T cell activation," *Br. J. Pharmacol.*, 126(8): 1707-1716 (April 1999).

Inhibitors of $K_v1.5$ and other $K_v1.x$ channels stimulate gastrointestinal motility. Thus, the compounds of the invention are believed to be useful in treating motility disorders such as reflux esophagitis. See Frey et al., "Blocking of cloned and native delayed rectifier K channels from visceral smooth muscles by phencyclidine," *Neurogastroenterol. Motil.*, 12(6):509-516 (December 2000); Hatton et al., "Functional and molecular expression of a voltage-dependent K(+) channel ($K_v1.1$) in interstitial cells of Cajal," *J. Physiol.*, 533(Pt 2):315-327 (Jun. 1, 2001); Vianna-Jorge et al., "Shaker-type $K_v1$ channel blockers increase the peristaltic activity of guinea-pig ileum by stimulating acetylcholine and tachykinins release by the enteric nervous system," *Br. J. Pharmacol.*, 138(1):57-62 (January 2003); Koh et al., "Contribution of delayed rectifier potassium currents to the electrical activity of murine colonic smooth muscle," *J. Physiol.*, 515(Pt. 2):475-487 (Mar. 1, 1999).

Inhibitors of $K_v1.5$ relax pulmonary artery smooth muscle. Thus, the compounds of the invention are believed to be useful in treating hypertension and otherwise improving vascular health. See Davies et al., "$K_v$ channel subunit expression in rat pulmonary arteries," *Lung*, 179(3):147-161 (2001), Epub. Feb. 4, 2002; Pozeg et al., "In vivo gene transfer of the O2-sensitive potassium channel $K_v1.5$ reduces pulmonary hypertension and restores hypoxic pulmonary vasoconstriction in chronically hypoxic rats," *Circulation*, 107(15):2037-2044 (Apr. 22, 2003), Epub. Apr. 14, 2003.

Inhibitors of $K_v1.3$ increase insulin sensitivity. Hence, the compounds of the invention are believed to be useful in treating diabetes. See Xu et al., "The voltage-gated potassium channel $K_v1.3$ regulates peripheral insulin sensitivity," *Proc. Natl. Acad. Sci. U.S.A.*, 101(9):3112-3117 (Mar. 2, 2004), Epub. Feb. 23, 2004; MacDonald et al., "Members of the $K_v1$ and $K_v2$ voltage-dependent K(+) channel families regulate insulin secretion," *Mol. Endocrinol.*, 15(8):1423-1435 (August 2001); MacDonald et al., "Voltage-dependent K(+) channels in pancreatic beta cells: role, regulation and potential as therapeutic targets," *Diabetologia*, 46(8): 1046-1062 (August 2003), Epub. Jun. 27, 2003.

Stimulation of $K_v1.1$ is believed to reduce seizure activity by hyperpolarizing neurons. Thus, the compounds of the invention are believed to be useful in treating seizures, including seizures associated with epilepsy and other neurological diseases. See Rho et al., "Developmental seizure susceptibility of kv1.1 potassium channel knockout mice," *Dev. Neurosci.*, 21(3-5):320-327 (November 1999); Coleman et al., "Subunit composition of $K_v1$ channels in human CNS," *J Neurochem.*, 73(2):849-858 (August 1999); Lopantsev et al., "Hyperexcitability of CA3 pyramidal cells in mice lacking the potassium channel subunit $K_v1.1$," *Epilepsia*, 44(12):1506-1512 (December 2003); Wickenden, "Potassium channels as anti-epileptic drug targets," *Neuropharmacology*, 43(7): 1055-1060 (December 2002).

Inhibition of $K_v1.x$ channels improves cognition in animal models. Thus, the compounds of the invention are believed to be useful in improving cognition and/or treating cognitive disorders. See Cochran et al., "Regionally selective alterations in local cerebral glucose utilization evoked by charybdotoxin, a blocker of central voltage-activated K+-channels," *Eur. J. Neurosci.*, 14(9): 1455-1463 (November 2001); Kourrich et al., "Kaliotoxin, a $K_v1.1$ and $K_v1.3$ channel blocker, improves associative learning in rats," *Behav. Brain Res.*, 120(1):35-46 (Apr. 8, 2001).

SUMMARY OF THE INVENTION

In accordance with the present invention, acyclic compounds and related compounds are provided that have the general structure of formula I:

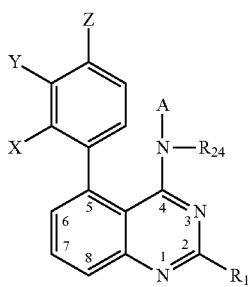

wherein A, X, Y, Z, $R_1$ and $R_{24}$ are defined below.

By use of a respective effective amount of at least one compound described herein, provided are methods of treating (including ameliorating) or preventing arrhythmias, atrial fibrillation, atrial flutter, supraventricular arrhythmias, gastrointestinal disorders (such as reflux esauphagitis or a motility disorder), inflammatory or immunological disease (such as chronic obstructive pulmonary disease), diabetes, cognitive disorders, migraine, epilepsy, hypertension, or treating $I_{Kur}$-associated conditions, or controlling heart rate.

Also provided are pharmaceutical compositions comprising a therapeutically effective amount of at least one compound described herein and a pharmaceutically acceptable vehicle or carrier thereof. Such compositions can further comprise one or more other agent(s). For example, at least one other anti-arrhythmic agent (such as sotalol, dofetilide, diltiazem or Verapamil), or at least one calcium channel blocker, or at least one anti-platelet agent (such as clopidogrel, cangrelor, ticlopidine, CS-747, ifetroban and aspirin), or at least one anti-hypertensive agent (such as a beta adrenergic blocker, ACE inhibitor (e.g., captopril, zofenopril, fosinopril, enalapril, ceranopril, cilazopril, delapril, pentopril, quinapril, ramipril, or lisinopril), A II antagonist, ET antagonist, Dual ET/A II antagonist, or vasopepsidase inhibitor (e.g., omapatrilat or gemopatrilat)), or at least one anti thrombotic/anti thrombolytic agent (such as tPA, recombinant tPA, TNK, nPA, factor VIIa inhibitors, factor Xa inhibitors (such as razaxaban), factor XIa inhibitors or thrombin inhibitors), or at least one anti coagulant (such as warfarin or a heparin), or at least one HMG-CoA reductase inhibitor (pravastatin, lovastatin, atorvastatin, simvastatin, NK-104 or ZD-4522), or at least one anti diabetic agent (such as a biguanide or a biguanide/glyburide combination), or at least one thyroid mimetic, or at least one mineralocorticoid receptor antagonist (such as spironolactone or eplerinone), or at least one cardiac glycoside (such as *digitalis* or ouabain).

Definitions

The terms "alk" or "alkyl" refer to straight or branched chain hydrocarbon groups having 1 to 12 carbon atoms, or 1 to 8 carbon atoms, such as methyl, ethyl, n-propyl, i-propyl, n-butyl, i-butyl, t-butyl, pentyl, hexyl, heptyl, octyl, or any subset of the foregoing. The term "substituted alkyl" refers to alkyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkenyl" refers to straight or branched chain hydrocarbon groups having 2 to 12 carbon atoms, or 2 to 4 carbon atoms, and at least one double carbon to carbon bond (either cis or trans), such as ethenyl. The term "substituted alkenyl" refers to alkenyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkynyl" refers to straight or branched chain hydrocarbon groups having 2 to 12 carbon atoms, or 2 to 4 carbon atoms, and at least one triple carbon to carbon bond, such as ethynyl. The term "substituted alkynyl" refers to alkynyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "aryl" refers to aromatic homocyclic (i.e., hydrocarbon) mono-, bi- or tricyclic ring-containing groups such as having 6 to 12 members such as phenyl, naphthyl and biphenyl. Phenyl is an example of an aryl group. The term "substituted aryl" refers to aryl groups substituted with one or more groups (such as by groups described above in the definition of $R^{10}$), such as selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane and sulfonyl, or any subset of the foregoing, where optionally one or more pair of substituents together with the atoms to which they are bonded form a 3 to 7 member ring.

The term "cycloalkyl" refers to mono-, bi- or tri homocyclic ring groups of 3 to 15 carbon atoms which are, respectively, fully saturated and partially unsaturated. The rings of multi-ring cycloalkyl groups may be fused, bridged and/or joined through one or more spiro unions. The term "substituted cycloalkyl" refers to a cycloalkyl group substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The terms "halogen" and "halo" refer to fluorine, chlorine, bromine and iodine.

The terms "heterocycle", "heterocyclic", "heterocyclic group" or "heterocyclo" refer to fully saturated or partially or completely unsaturated, including aromatic ("heteroaryl") or nonaromatic cyclic groups (for example, 3 to 13 ring member monocyclic, 7 to 17 ring member bicyclic, or 10 to 20 ring member tricyclic ring systems, such as, in certain embodiments, a monocyclic or bicyclic ring containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl,

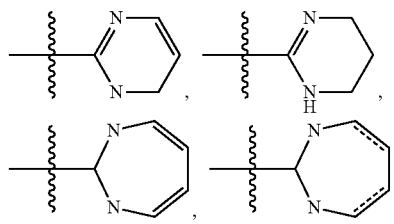

and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranyl, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl),

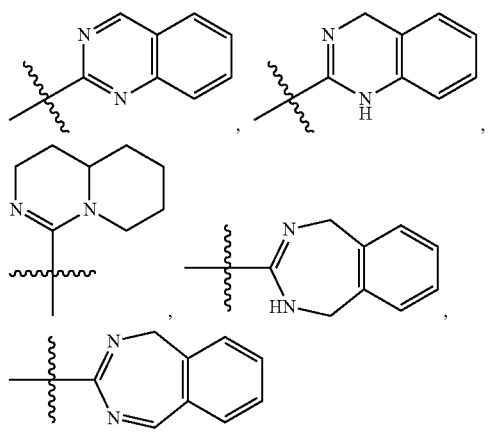

and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclo" refer to heterocycle, heterocyclic and heterocyclo groups substituted with one or more groups (such as by groups described above in the definition of $R^{10}$), such as selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, or any subset of the foregoing, where optionally one or more pair of substituents together with the atoms to which they are bonded form a 3 to 7 member ring.

The term "alkanoyl" refers to alkyl group (which may be optionally substituted as described above) linked to a carbonyl group (i.e., —C(O)-alkyl). Similarly, the term "aroyl" refers to an aryl group (which may be optionally substituted as described above) linked to a carbonyl group (i.e., —C(O)-aryl).

Throughout the specification, groups and substituents thereof may be chosen to provide stable moieties and compounds.

The compounds described herein form salts or solvates which are also within the scope of this invention. Reference to a compound described herein is understood to include reference to salts thereof, unless otherwise indicated. The term "salt(s)", as employed herein, denotes acidic and/or basic salts formed with inorganic and/or organic acids and bases. In addition, when a compound described herein contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds described herein may be formed, for example, by reacting a compound with an amount of acid or base, such as an equivalent amount, in a medium such as one in which the salt precipitates or in an aqueous medium followed by lyophilization.

The compounds described herein which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds described herein which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g, benzyl and phenethyl bromides), and others.

Any compound that can be converted in vivo to provide the bioactive agent (i.e., the compound of formula I) is a prodrug within the scope and spirit of the invention.

The term "prodrugs" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Chapter 31, Academic Press (1996);

b) *Design of Prodrugs*, H. Bundgaard, ed., Elsevier (1985);

c) Bundgaard, H., Chapter 5, "Design and Application of Prodrugs," *A Textbook of Drug Design and Development*, pp. 113-191, P. Krosgaard-Larsen et al., eds., Harwood Academic Publishers (1991); and d) Testa, B. et al., *Hydrolysis in Drug and Prodrug Metabolism*, Wiley-VCH (2003).

In addition, compounds described herein are, subsequent to their preparation, preferably isolated and purified to obtain a composition containing an amount by weight equal to or greater than 99% of the compound described herein ("substantially pure" compound), which is then used or formulated as described herein. Such "substantially pure" compounds described herein are also contemplated herein as part of the present invention.

To the extent that compounds described herein, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms are contemplated within the scope of this invention. Individual stereoisomers of the compounds of the invention may, for example, be substantially free of other isomers, or may be admixed, for example, as racemates or with all other, or other selected, stereoisomers.

The terms "including", "such as", "for example" and the like are intended to refer to exemplary embodiments and not to limit the scope of the present invention.

DETAILED DESCRIPTION OF THE INVENTION

In accordance with the present invention, compounds of formula I are provided

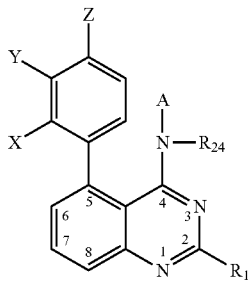

I or enantiomers, diastereomers, tautomers, prodrugs or salts thereof wherein:

X is H, —OH, F, Cl, Br, I, $C_{1-10}$ alkyl, $C_{1-10}$ alkoxy, halo$C_{1-10}$ alkyl, $C_{2-12}$ alkenyl, $C_{2-12}$ alkynyl, $C_{3-10}$ cycloalkyl, a 4- to 12-membered heteroaryl, 4- to 12-membered heterocyclyl, —CN, —NO$_2$, —NR$_{11}$SO$_2$R$_{12}$, —SO$_2$NR$_{11}$R$_{12}$, —CONR$_{11}$R$_{12}$, —NR$_{11}$CONR$_{11}$R$_{12}$, —NCOR$_{11}$, —NR$_{11}$SO$_2$NR$_{11}$R$_{12}$, —OCONR$_{11}$R$_{12}$, —CO$_2$R$_{11}$ or —NR$_{11}$R$_{12}$;

Y is H, —OH, F, Cl, Br, I, $C_{1-10}$ alkyl, $C_{1-10}$ alkoxy, halo$C_{1-10}$ alkyl, $C_{2-12}$ alkenyl, $C_{2-12}$ alkynyl, $C_{3-10}$ cycloalkyl, a 4- to 12-membered heteroaryl, 4- to 12-membered heterocyclyl, —CN, —NO$_2$, —NR$_{11}$SO$_2$R$_{12}$, —SO$_2$NR$_{11}$R$_{12}$, —CONR$_{11}$R$_{12}$, —NR$_{11}$CONR$_{11}$R$_{12}$, —NCOR$_{11}$, —NR$_{11}$SO$_2$NR$_{11}$R$_{12}$, —OCONR$_{11}$R$_{12}$, —CO$_2$R$_{11}$ or —NR$_{11}$R$_{12}$;

Z is H, —OH, F, Cl, Br, I, $C_{1-10}$ alkyl, $C_{1-10}$ alkoxy, halo$C_{1-10}$ alkyl, $C_{2-12}$ alkenyl, $C_{2-12}$ alkynyl, $C_{3-10}$ cycloalkyl, a 4- to 12-membered heteroaryl, 4- to 12-membered heterocyclyl, —CN, —NO$_2$, —NR$_{11}$SO$_2$R$_{12}$, —SO$_2$NR$_{11}$R$_{12}$, —CONR$_{11}$R$_{12}$, —NR$_{11}$CONR$_{11}$R$_{12}$, —NCOR$_{11}$, —NR$_{11}$SO$_2$NR$_{11}$R$_{12}$, —OCONR$_{11}$R$_{12}$, —CO$_2$R$_{11}$ or —NR$_{11}$R$_{12}$;

A is —(CH$_2$)$_m$—R$_2$, —CH(R$_{25}$)(R$_{26}$), —(CH$_2$)$_m$—C(O)—R$_{2a}$, —CH(R$_{26}$)—CO$_2$—R$_{2a}$ or —(CH$_2$)$_{n-1}$—NR$_{25}$—CO$_2$—R$_{24}$;

m is 0 to 4;
n is 1 to 4;
n−1 is 2 to 4;

R$_1$ is —OH, F, Cl, Br, I, $C_{1-10}$ alkyl, halo$C_{1-10}$ alkyl, $C_{2-12}$ alkenyl, $C_{3-10}$ cycloalkyl, —CN, —(CH$_2$)$_m$—SO$_2$R$_{11}$, —(CH$_2$)$_n$—SO$_2$NR$_{11}$R$_{12}$, —(CH$_2$)$_n$—CO$_2$R$_{11}$ or —(CH$_2$)$_n$—NR$_{11}$SO$_2$R$_{12}$, wherein the alkenyl and cycloalkyl may be optionally substituted with one or more R$_{13}$'s; or R$_1$ is a 4- to 12-membered heteroaryl or 4- to 12-membered heterocyclyl, wherein: (i) the heteroaryl and heterocyclyl may be optionally substituted with one or more R$_{13a}$, R$_{13b}$, R$_{13c}$, R$_{13d}$, R$_{13e}$, R$_{13f}$, R$_{13g}$, R$_{13h}$, R$_{13hh}$, R$_{13j}$, R$_{13m}$, R$_{13m-1}$, R$_{13n-1}$, R$_{13p}$, R$_{13p-1}$, R$_{13q}$ and R$_{13q-1}$; (ii) the heteroaryl and heterocyclyl consist of carbon atoms and 1, 2, 3, or 4 heteroatoms independently selected from the group consisting of N, S, or O; and (iii) the heteroaryl and heterocyclyl are connected to the quinazolinyl ring via a carbon atom; or R$_1$ is phenyl, which may be optionally substituted with one or more R$_{13aa}$, R$_{13bb}$, R$_{13cc}$, R$_{13dd}$, and R$_{13ee}$;

R$_2$ is $C_{1-10}$ alkyl, $C_{3-10}$ cycloalkyl, $C_{3-10}$ cycloalkenyl or —NR$_{14}$R$_{14}$, wherein the cycloalkyl may be optionally substituted with one or more R$_{13}$'s or R$_{13bb}$'s and the cycloalkenyl may be optionally substituted with one or more R$_{13b}$'s; provided that R$_2$ is not —NR$_{14}$R$_{14}$ when m is 0, 1 or 3; or R$_2$ is $C_{6-10}$ aryl, which is optionally substituted with one or more R$_{13a-1}$, R$_{13b-1}$, R$_{13c-1}$, R$_{13d-1}$ and R$_{13e-1}$; or R$_2$ is a 4- to 12-membered heteroaryl or 4- to 12-membered heterocyclyl, both of which are optionally substituted with one or more R$_{13a-2}$, R$_{13b-2}$, R$_{13c-2}$, R$_{13d-2}$, R$_{13e-2}$, R$_{13g-2}$, R$_{13a-4}$, R$_{13b-4}$, R$_{13c-4}$, R$_{13d-4}$, R$_{13b-5}$, R$_{13c-5}$, R$_{13h-1}$, R$_{13hh-1}$, R$_{13hh-2}$, R$_{13m-1}$, R$_{13n-1}$, R$_{13n-2}$, R$_{13p-1}$, R$_{13p-2}$, R$_{13q-1}$, and R$_{13q-2S}$; and the heteroaryl and heterocyclyl consist of carbon atoms and 1, 2, 3, or 4 heteroatoms independently selected from the group consisting of N, S, or O;

R$_{2a}$ is $C_{1-10}$ alkyl, $C_{3-10}$ cycloalkyl, $C_{6-10}$ aryl, —NR$_{14}$R$_{14}$, a 4- to 12-membered heteroaryl or 4- to 12-membered heterocyclyl, any of which is optionally substituted with one or more R$_{13}$'s and the heteroaryl and heterocyclyl consist of carbon atoms and 1, 2, 3, or 4 heteroatoms independently selected from the group consisting of N, S, or O;

R$_{11}$ and R$_{12}$, at each occurrence, are independently selected from H, $C_{1-10}$ alkyl, halo$C_{1-10}$ alkyl, $C_{3-10}$ cycloalkyl, $C_{6-10}$aryl, a 4- to 12-membered heteroaryl and a 4- to 12-membered heterocyclyl, wherein the alkyl, cycloalkyl, aryl, heteroaryl and heterocyclyl may be optionally substituted with one or more R$_{13}$'s and the heteroaryl and heterocyclyl consist of carbon atoms and 1, 2, 3, or 4 heteroatoms independently selected from the group consisting of N, S, or O; or R$_{11}$ and R$_{12}$ are taken together with the nitrogen to which they are attached to form a 4- to 12-membered heterocyclyl, wherein the heterocyclyl may be optionally substituted with one or more R$_{13}$'s and the heterocyclyl consists of carbon atoms and 1, 2, 3, or 4 heteroatoms independently selected from the group consisting of N, S, or O;

R$_{13}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O; provided that when R$_{13}$ is alkyl substituted with one R$_{14a}$, R$_{14a}$ is not —OH;

R$_{13a}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13aa}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a-2}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a-4}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13bb}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b-2}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b-4}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b-5}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_n$—$OCONR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{26}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13cc}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$, or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c-2}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c-4}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c\text{-}5}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13dd}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d\text{-}1}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d\text{-}2}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d\text{-}4}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13ee}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13e-1}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13e-2}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13f}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13g}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13g-2}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13h}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13h-1}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13hh}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13hh-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13hh-2}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13j}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13m}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13m-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13n-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13p}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —C(=$NOR_{14}$)$NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13p-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —C(=$NOR_{14}$)$NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13p-2}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —C(=$NOR_{14}$)$NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13q}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —C(=$NOR_{14}$)$NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13q-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —C(=$NOR_{14}$)$NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13q-2}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —C(=$NOR_{14}$)$NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be optionally substituted with be optionally substituted with 0-3 $R_{14a}$ and the heteroaryl and heterocyclyl consist of carbon atoms and 1, 2, 3, or 4 heteroatoms independently selected from the group consisting of N, S, or O; or two $R_{14}$'s are taken together with the atoms to which they are attached to form a cyclic ring, wherein the cyclic ring may be optionally substituted with one or more $R_{24a}$'s and optionally contain 1, 2, 3, or 4 heteroatoms independently selected from the group consisting of N, S, or O;

$R_{14a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —$NO_2$, —$CO_2H$, —$CO_2R_{26}$, —$OCONR_{24}R_{24}$, —$CO_2NR_{24}R_{24}$, —$OCF_3$, —$OR_{25}$, =O, —$CONR_{24}R_{24}$, —$COR_{24}$, —$SO_2R_{24}$, —$NR_{24}R_{24}$, —$NR_{24}CO_2R_{24}$, —$SO_2NR_{24}R_{24}$, or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{24}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the alkyl, aryl, heteroaryl and heterocyclyl may be optionally substituted with one or more $R_{24a}$'s and the heteroaryl and heterocyclyl consist of carbon atoms and 1, 2, 3, or 4 heteroatoms independently selected from the group consisting of N, S, or O; or two $R_{24}$'s are taken together with the atoms to which they are attached to form a cyclic ring, wherein the cyclic ring may be optionally substituted with one or more $R_{24a}$'s and optionally contain 1, 2, 3, or 4 heteroatoms independently selected from the group consisting of N, S, or O;

$R_{24a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, —CN, —NO$_2$, —CO$_2R_{25}$, —OCF$_3$, —OR$_{25}$, =O, —CONR$_{25}R_{25}$, —COR$_{25}$, —NR$_{25}R_{25}$, —NR$_{25}$CO$_2R_{25}$, or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{25}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O; and $R_{26}$, at each occurrence, is independently selected from $C_{1-10}$alkyl, halo$C_{1-10}$alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O.

In one embodiment, compounds, enantiomers, diastereomers, tautomers, prodrugs or salts thereof, of formula I, are provided wherein $R_1$ is a 4- to 12-membered heteroaryl or 4- to 12-membered heterocyclyl, wherein: (i) the heteroaryl and heterocyclyl may be optionally substituted with one or more $R_{13a}$, $R_{13b}$, $R_{13c}$, $R_{13d}$, $R_{13e}$, $R_{13f}$, $R_{13g}$, $R_{13h}$, $R_{13hh}$, $R_{13j}$, $R_{13m}$, $R_{13m-1}$, $R_{13n-1}$, $R_{13p}$, $R_{13p-1}$, $R_{13q}$ and $R_{13q-1}$; (ii) the heteroaryl and heterocyclyl consist of carbon atoms and 1, 2, 3, or 4 heteroatoms independently selected from the group consisting of N, S, or O; and (iii) the heteroaryl and heterocyclyl are connected to the quinazolinyl ring via a carbon atom.

In another embodiments of the invention, compounds, enantiomers, diastereomers, tautomers, prodrugs or salts thereof, of formula I, are provided wherein $R_1$ is —OH, F, Cl, Br, I, $C_{1-10}$ alkyl, halo$C_{1-10}$ alkyl, $C_{2-12}$ alkenyl, $C_{3-10}$ cycloalkyl, —CN, —(CH$_2$)$_m$—SO$_2R_{11}$, —(CH$_2$)$_n$—SO$_2$NR$_{11}R_{12}$, —(CH$_2$)$_n$—CO$_2R_{11}$ or —(CH$_2$)$_n$—NR$_{11}$SO$_2R_{12}$, wherein the alkenyl and cycloalkyl may be optionally substituted with one or more $R_{13}$'s.

In yet another embodiment, compounds, enantiomers, diastereomers, tautomers, prodrugs or salts thereof, of formula I, are provided wherein $R_2$ is $C_{6-10}$ aryl, which is optionally substituted with one or more $R_{13a-1}$, $R_{13b-1}$, $R_{13c-1}$, $R_{13d-1}$ and $R_{13e-1}$.

In still yet another embodiment, compounds, enantiomers, diastereomers, tautomers, prodrugs or salts thereof, of formula I, are provided wherein $R_2$ is a 4- to 12-membered heteroaryl or 4- to 12-membered heterocyclyl, both of which are optionally substituted with one or more $R_{13a-2}$, $R_{13b-2}$, $R_{13c-2}$, $R_{13d-2}$, $R_{13e-2}$, $R_{13g-2}$, $R_{13a-4}$, $R_{13b-4}$, $R_{13c-4}$, $R_{13d-4}$, $R_{13b-5}$, $R_{13c-5}$, $R_{13h-1}$, $R_{13hh-1}$, $R_{13hh-2}$, $R_{13m-1}$, $R_{13n-1}$, $R_{13n-2}$, $R_{13p-1}$, $R_{13p-2}$, $R_{13q-1}$, and $R_{13q-2S}$; and the heteroaryl and heterocyclyl consist of carbon atoms and 1, 2, 3, or 4 heteroatoms independently selected from the group consisting of N, S, or O.

In one embodiment, compounds, enantiomers, diastereomers, tautomers, prodrugs or salts thereof, of formula I, are provided wherein $R_2$ is a 4- to 12-membered heteroaryl or 4- to 12-membered heterocyclyl, both of which are optionally substituted with one or more $R_{13a-2}$, $R_{13b-2}$, $R_{13c-2}$, $R_{13d-2}$, $R_{13e-2}$, $R_{13g-2}$, $R_{13a-4}$, $R_{13b-4}$, $R_{13c-4}$, $R_{13d-4}$, $R_{13b-5}$, $R_{13c-5}$, $R_{13h-1}$, $R_{13hh-1}$, $R_{13hh-2}$, $R_{13m-1}$, $R_{13n-1}$, $R_{13n-2}$, $R_{13p-1}$, $R_{13p-2}$, $R_{13q-1}$, and $R_{13q-2S}$; and the heteroaryl and heterocyclyl consist of carbon atoms and at least one N heteroatom.

In yet another embodiment, compounds, enantiomers, diastereomers, tautomers, prodrugs or salts thereof, of formula I, are provided wherein:

X is H, —OH, F, Cl, Br, I, $C_{1-10}$ alkyl, $C_{1-10}$ alkoxy, halo$C_{1-10}$ alkyl, $C_{2-12}$ alkenyl, $C_{2-12}$ alkynyl, $C_{3-10}$ cycloalkyl, a 4- to 12-membered heteroaryl, 4- to 12-membered heterocyclyl, —CN, —NO$_2$, —NR$_{11}$SO$_2R_{12}$, —SO$_2$NR$_{11}R_{12}$, —CONR$_{11}R_{12}$, —NR$_{11}$CONR$_{11}R_{12}$, —NCOR$_{11}$, —NR$_{11}$SO$_2$NR$_{11}R_{12}$, —OCONR$_{11}R_{12}$, —CO$_2R_{11}$ or —NR$_{11}R_{12}$;

Y is H, —OH, F, Cl, Br, I, $C_{1-10}$ alkyl, $C_{1-10}$ alkoxy, halo$C_{1-10}$ alkyl, $C_{2-12}$ alkenyl, $C_{2-12}$ alkynyl, $C_{3-10}$ cycloalkyl, a 4- to 12-membered heteroaryl, 4- to 12-membered heterocyclyl, —CN, —NO$_2$, —NR$_{11}$SO$_2R_{12}$, —SO$_2$NR$_{11}R_{12}$, —CONR$_{11}R_{12}$, —NR$_{11}$CONR$_{11}R_{12}$, —NCOR$_{11}$, —NR$_{11}$SO$_2$NR$_{11}R_{12}$, —OCONR$_{11}R_{12}$, —CO$_2R_{11}$ or —NR$_{11}R_{12}$;

Z is H, —OH, F, Cl, Br, I, $C_{1-10}$ alkyl, $C_{1-10}$ alkoxy, halo$C_{1-10}$ alkyl, $C_{2-12}$ alkenyl, $C_{2-12}$ alkynyl, $C_{3-10}$ cycloalkyl, a 6- to 12-membered heteroaryl, 4- to 12-membered heterocyclyl, —CN, —NO$_2$, —NR$_{11}$SO$_2R_{12}$, —SO$_2$NR$_{11}R_{12}$, —CONR$_{11}R_{12}$, —NR$_{11}$CONR$_{11}R_{12}$, —NCOR$_{11}$, —NR$_{11}$SO$_2$NR$_{11}R_{12}$, —OCONR$_{11}R_{12}$, —CO$_2R_{11}$ or —NR$_{11}R_{12}$;

A is —(CH$_2$)$_m$—R$_2$, —CH(R$_{25}$)(R$_{26}$), —(CH$_2$)$_m$—C(O)—R$_{2a}$, —CH(R$_{26}$)—CO$_2$—R$_{2a}$ or —(CH$_2$)$_{n-1}$—NR$_{25}$—CO$_2$—R$_{24}$;

m is 0 to 4;

n is 1 to 4;

n-1 is 2 to 4;

$R_1$ is —OH, F, Cl, Br, I, $C_{1-10}$ alkyl, halo$C_{1-10}$ alkyl, $C_{2-12}$ alkenyl, $C_{3-10}$ cycloalkyl, —CN, —(CH$_2$)$_m$—SO$_2R_{11}$, —(CH$_2$)$_n$—SO$_2$NR$_{11}R_{12}$, —(CH$_2$)$_n$—CO$_2R_{11}$ or —(CH$_2$)$_n$—NR$_{11}$SO$_2R_{12}$, wherein the alkenyl and cycloalkyl may be optionally substituted with one or more $R_{13}$'s; or $R_1$ is selected from the group consisting of:

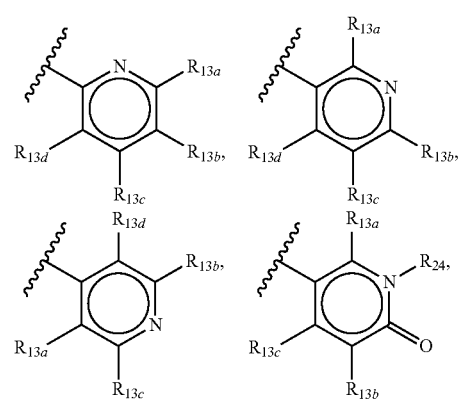

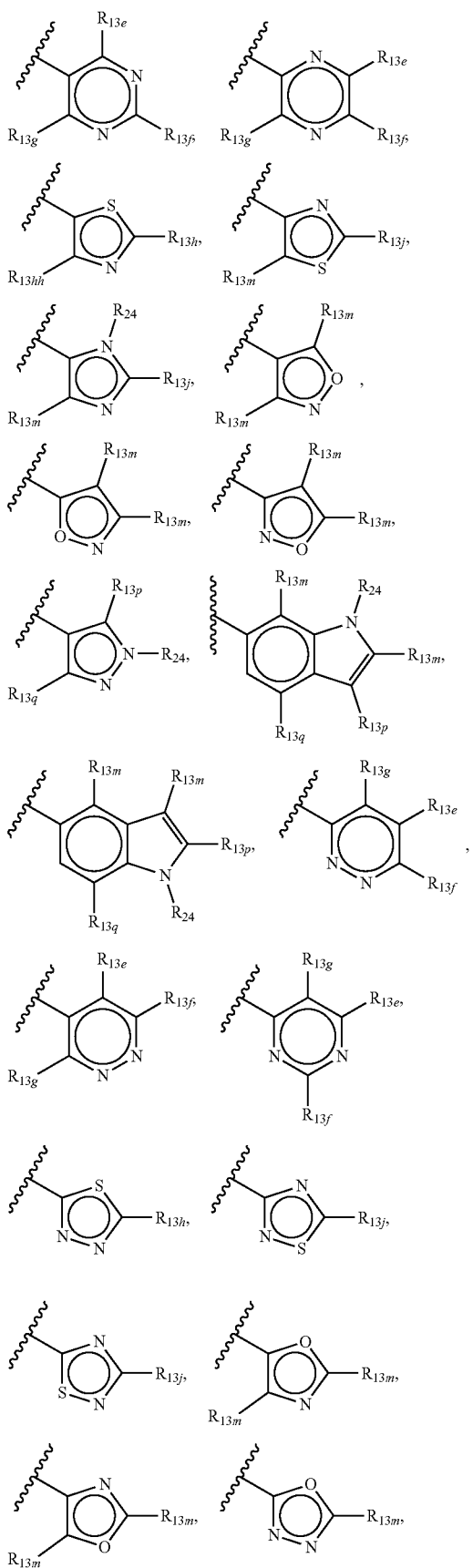
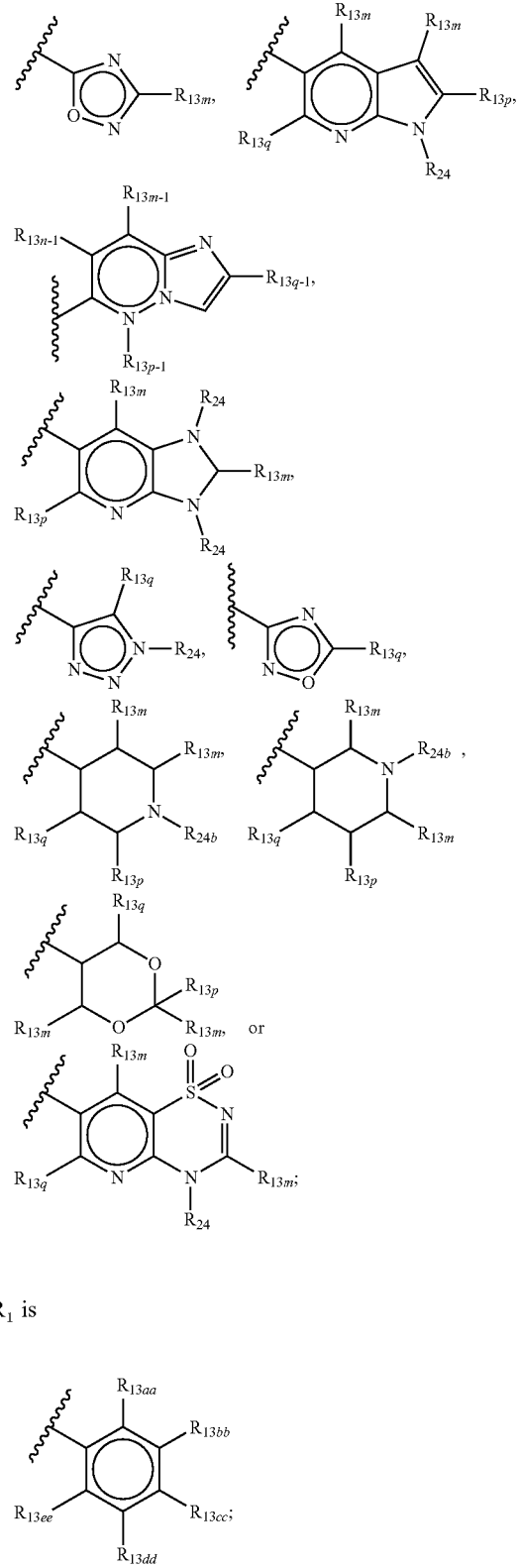
or
R₁ is
R₂ is C$_{1-10}$ alkyl, cyclopropyl optionally substituted with one or more R$_{13}$'s; C$_{4-10}$ cycloalkyl optionally substituted with one or more R$_{13bb}$'s; C$_{3-10}$ cycloalkenyl optionally substituted with one or more R$_{13}$b'S; or —NR$_{14}$R$_{14}$; provided that R$_2$ is not —NR$_{14}$R$_{14}$ when m is 0, 1 or 3; or $R_2$ is
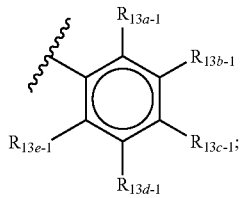
or
$R_2$ is selected from the group consisting of:
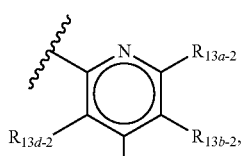 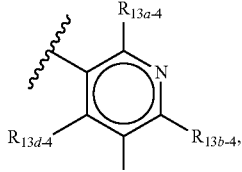
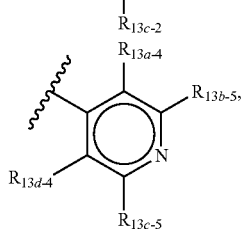 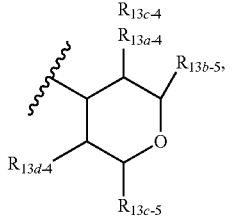
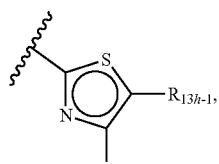
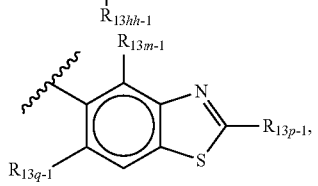
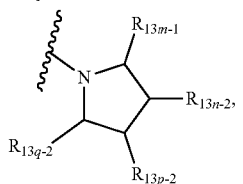 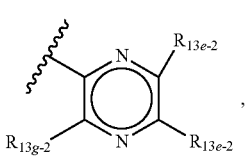
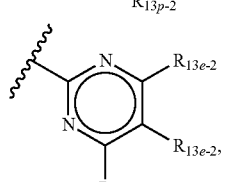
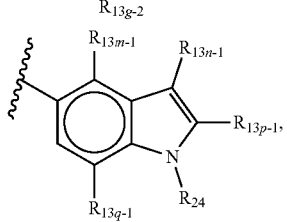
-continued
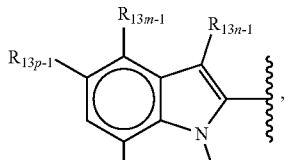
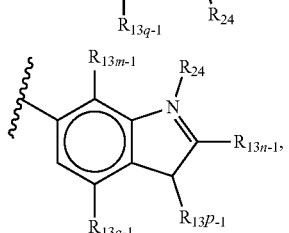
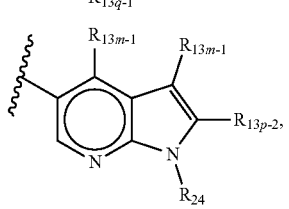
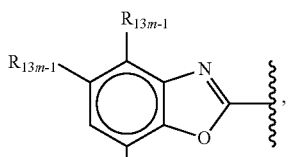
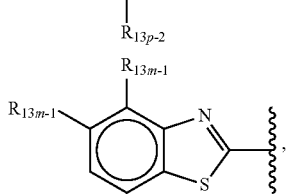
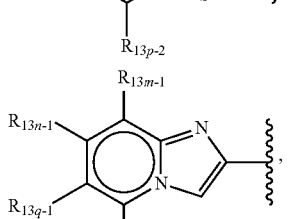
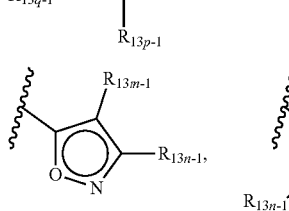
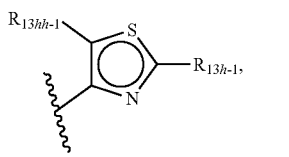
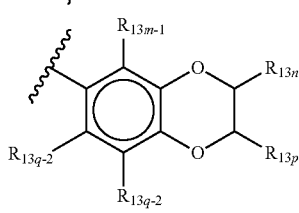

-continued

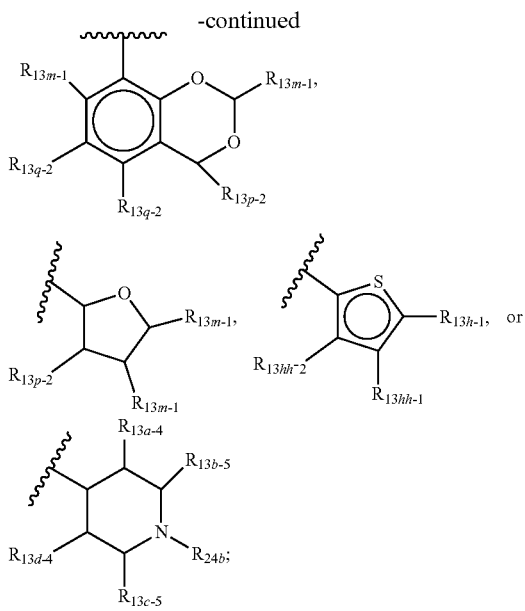

R$_{2a}$ is C$_{1-10}$ alkyl, C$_{3-10}$ cycloalkyl, C$_{6-10}$ aryl, —NR$_{14}$R$_{14}$, a 4- to 12-membered heteroaryl or 4- to 12-membered heterocyclyl, any of which is optionally substituted with one or more R$_{13}$'s and the heteroaryl and heterocyclyl consist of carbon atoms and 1, 2, 3, or 4 heteroatoms independently selected from the group consisting of N, S, or O;

R$_{11}$ and R$_{12}$, at each occurrence, are independently selected from H, C$_{1-10}$ alkyl, haloC$_{1-10}$ alkyl, C$_{3-10}$ cycloalkyl, C$_{6-10}$aryl, a 4- to 12-membered heteroaryl and a 4- to 12-membered heterocyclyl, wherein the alkyl, cycloalkyl, aryl, heteroaryl and heterocyclyl may be optionally substituted with one or more R$_{13}$'s and the heteroaryl and heterocyclyl consist of carbon atoms and 1, 2, 3, or 4 heteroatoms independently selected from the group consisting of N, S, or O; or R$_{11}$ and R$_{12}$ are taken together with the nitrogen to which they are attached to form a 4- to 12-membered heterocyclyl, wherein the heterocyclyl may be optionally substituted with one or more R$_{13}$'s and the heterocyclyl consists of carbon atoms and 1, 2, 3, or 4 heteroatoms independently selected from the group consisting of N, S, or O;

R$_{13}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O; provided that when R$_{13}$ is alkyl substituted with one R$_{14a}$, R$_{14a}$ is not —OH;

R$_{13a}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13aa}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13a-1}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13a-2}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a\text{-}4}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13bb}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b\text{-}1}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b\text{-}2}$, at each occurrence, is independently H, —OH, F, Cl, Br, I, $C_{1\text{-}10}$ alkyl, $C_{1\text{-}10}$ alkoxy, halo$C_{2\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b\text{-}4}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b\text{-}5}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$(CH_2)_n$—$OCONR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{26}$, —$NR_{14}R_{14}$, —$NR_{14}CONR_{14}R_{14}$, —C(=$NOR_{14}$)$NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13cc}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —C(=$NOR_{14}$)$NR_{14}R_{14}$, —$CONR_{14}OR_{14}$, or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c-1}$, at each occurrence, is independently H, —OH, F, Cl, Br, I, $C_{1-10}$ alkyl, $C_{1-10}$ alkoxy, halo$C_{2-10}$ alkyl, $C_{3-10}$ cycloalkyl, $C_{2-12}$ alkenyl, $C_{2-12}$ alkynyl, $C_{6-10}$aryl, a 6- to 12-membered heteroaryl, a 6- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —C(=$NOR_{14}$)$NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c-2}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —C(=$NOR_{14}$)$NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c-4}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —C(=$NOR_{14}$)$NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c-5}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —C(=$NOR_{14}$)$NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d}$, at each occurrence, is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —C(=$NOR_{14}$)$NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13dd}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13d-1}$, at each occurrence, is independently H, —OH, F, Cl, Br, I, C$_{1-10}$ alkyl, C$_{1-10}$ alkoxy, haloC$_{2-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13d-2}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13d-4}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13e}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13ee}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13e-1}$, at each occurrence, is independently H, —OH, F, Cl, Br, I, C$_{1-10}$ alkyl, C$_{1-10}$ alkoxy, haloC$_{2-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13e-2}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13f}$, at each occurrence, is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13g}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13g-2}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13h}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13h-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{7-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13hh}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13hh-1}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13hh-2}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13j}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13m}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13m-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13n-1}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13p}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13p}$-1, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13p}$-2, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13q}$, at each occurrence, is independently H, —OH, F, Cl, Br, I, $C_{2-10}$ alkyl, $C_{1-10}$ alkoxy, halo$C_{2-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13q-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13q-2}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be optionally substituted with be optionally substituted with 0-3 $R_{14a}$ and the heteroaryl and heterocyclyl consist of carbon atoms and 1, 2, 3, or 4 heteroatoms independently selected from the group consisting of N, S, or O; or two $R_{14}$'s are taken together with the atoms to which they are attached to form a cyclic ring, wherein the cyclic ring may be optionally substituted with one or more $R_{24a}$'s and optionally contain 1, 2, 3, or 4 heteroatoms independently selected from the group consisting of N, S, or O;

$R_{14a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —NO$_2$, —CO$_2$H, —CO$_2$R$_{26}$, —OCONR$_{24}$R$_{24}$, —CO$_2$NR$_{24}$R$_{24}$, —OCF$_3$, —OR$_{25}$, =O, —CONR$_{24}$R$_{24}$, —COR$_{24}$, —SO$_2$R$_{24}$, —NR$_{24}$R$_{24}$, —NR$_{24}$CO$_2$R$_{24}$, —SO$_2$NR$_{24}$R$_{24}$, or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{24}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the alkyl, aryl, heteroaryl and heterocyclyl may be optionally substituted with one or more $R_{24}$a'S and the heteroaryl and heterocyclyl consist of carbon atoms and 1, 2, 3, or 4 heteroatoms independently selected from the group consisting of N, S, or O; or two $R_{24}$'s are taken together with the atoms to which they are attached to form a cyclic ring, wherein the cyclic ring may be optionally substituted with one or more $R_{24a}$'s and optionally contain 1, 2, 3, or 4 heteroatoms independently selected from the group consisting of N, S, or O;

$R_{24a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, —CN, —NO$_2$, —CO$_2$R$_{25}$, —OCF$_3$, —OR$_{25}$, =O, —CONR$_{25}$R$_{25}$, —COR$_{25}$, —NR$_{25}$R$_{25}$, —NR$_{25}$CO$_2$R$_{25}$, or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{24b}$, at each occurrence, is independently selected from $C_{1-10}$ alkyl, $C_{6-10}$aryl, $C_{3-10}$cycloalkyl, a 4- to 12-membered heteroaryl, a 4- to 12-membered heterocyclyl, —CO$_2$R$_{25}$, —SO$_2$NR$_{25}$R$_{25}$, —COR$_{25}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{25}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O; and $R_{26}$, at each occurrence, is independently selected from $C_{1-10}$alkyl, halo$C_{1-10}$ alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O;

provide that:

(i) $R_1$ is not $C_1$ when m is 0, 1 or 2; $R_{13a-1}$ is H, —CF$_3$, or methoxy; $R_{13c-1}$ is H, OH, methoxy or dimethylamino; X, Y, Z, $R_{13b-1}$, $R_{13d-1}$, $R_{13a-2}$, $R_{13b-2}$, $R_{13c-2}$, $R_{13d-2}$, $R_{13e-2}$, $R_{13g-2}$, $R_{13a-4}$, $R_{13b-4}$, $R_{13c-4}$, $R_{13d-4}$, $R_{13b-5}$, $R_{13c-5}$, $R_{13m-1}$, $R_{13n-1}$, $R_{13p-1}$, and $R_{13q-1}$ are H; and (ii) m is not 0 or 1 when X, Y, $R_{13a}$, $R_{13d}$, $R_{13e}$, $R_{13g}$, $R_{13a-2}$, $R_{13b-2}$, $R_{13c-2}$, $R_{13d-2}$, $R_{13a-4}$, $R_{13b-4}$, $R_{13c-4}$, $R_{13d-4}$ $R_{13b-5}$, $R_{13c-5}$, $R_{13h-1}$ and $R_{13hh-1}$ are H; $R_{13b}$ is H or —SO$_2$NH$_2$; $R_{13}$c is H, —CONH$_2$, —SO$_2$N(C$_2$H$_4$OH)$_2$, —SO₂NHCOCH₃, —SO₂NH₂, -tetrazolyl or (4-aminopiperidinyl)sulfonyl; R₁₃f is H or —NHC₂H₄OCH₃; and Z is H, —CO₂H, or —CO₂CH₃.

In still yet another embodiment, compounds, enantiomers, diastereomers, tautomers, prodrugs or salts thereof, of formula I, are provided wherein:

X is H, —OH, F, Cl, Br, I, $C_{1-10}$ alkyl, $C_{1-10}$ alkoxy, halo$C_{1-10}$ alkyl, $C_{2-12}$ alkenyl, $C_{2-12}$ alkynyl, $C_{3-10}$ cycloalkyl, a 4- to 12-membered heteroaryl, 4- to 12-membered heterocyclyl, —CN, —NO₂, —NR₁₁SO₂R₁₂, —SO₂NR₁₁R₁₂, —CONR₁₁R₁₂, —NR₁₁CONR₁₁R₁₂, —NCOR₁₁, —NR₁₁SO₂NR₁₁R₁₂, —OCONR₁₁R₁₂, —CO₂R₁₁ or —NR₁₁R₁₂;

Y is H, F, Cl, Br, I, $C_{1-10}$ alkyl, $C_{1-10}$ alkoxy, halo$C_{1-10}$ alkyl, $C_{2-12}$ alkenyl, $C_2$-12 alkynyl, $C_{3-10}$ cycloalkyl, a 4- to 12-membered heteroaryl, 4- to 12-membered heterocyclyl, —CN, —NO₂, —SO₂NR₁₁R₁₂, —CONR₁₁R₁₂, —NR₁₁CONR₁₁R₁₂, —NCOR₁₁, —NR₁₁SO₂NR₁₁R₁₂, —OCONR₁₁R₁₂, —CO₂R₁₁ or —NR₁₁R₁₂;

Z is H, Cl, Br, I, $C_{1-10}$ alkyl, $C_{1-10}$ alkoxy, halo$C_{1-10}$ alkyl, $C_{2-12}$ alkenyl, $C_{2-12}$ alkynyl, $C_{3-10}$ cycloalkyl, a 6- to 12-membered heteroaryl, 4- to 12-membered heterocyclyl, —NO₂, —NR₁₁SO₂R₁₂, —SO₂NR₁₁R₁₂, —NR₁₁CONR₁₁R₁₂, —NCOR₁₁, —NR₁₁SO₂NR₁₁R₁₂, —OCONR₁₁R₁₂, —CO₂R₁₁ or —NR₁₁R₁₂;

A is —(CH₂)ₘ—R₂, —CH(R₂₅)(R₂₆), —CH(R₂₆)—CO₂—R₂ₐ or —(CH₂)ₙ₋₁—NR₂₅—CO₂—R₂₄;

m is 0 to 4;

n is 1 to 4;

n–1 is 2 to 4;

R₁ is —OH, F, Cl, Br, I, $C_{1-10}$ alkyl, halo$C_{1-10}$ alkyl, $C_{2-12}$ alkenyl, $C_{3-10}$ cycloalkyl, —CN, —(CH₂)ₙ—SO₂NR₁₁R₁₂, —(CH₂)ₙ—CO₂R₁₁ or —(CH₂)ₙ—NR₁₁SO₂R₁₂, wherein the alkenyl and cycloalkyl may be optionally substituted with one or more R₁₃'s; or R₁ is selected from the group consisting of:

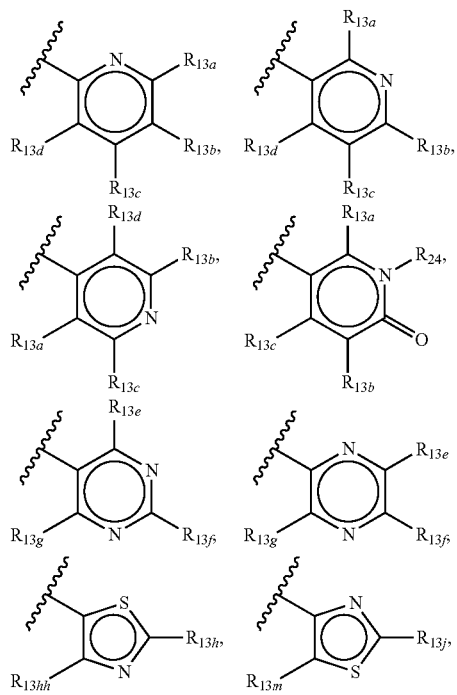

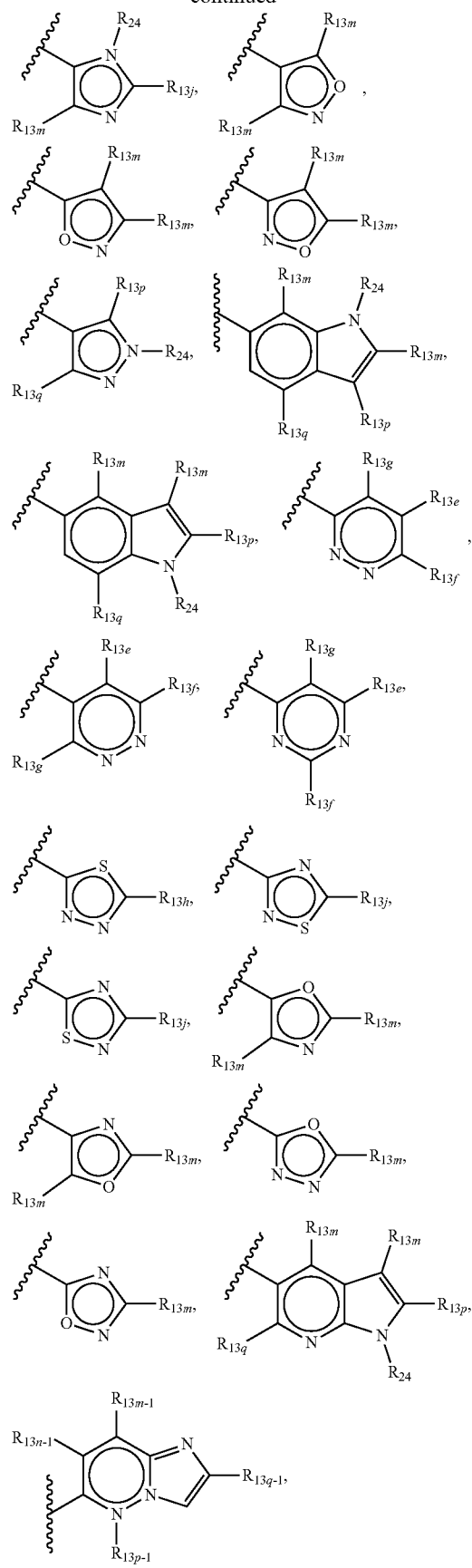

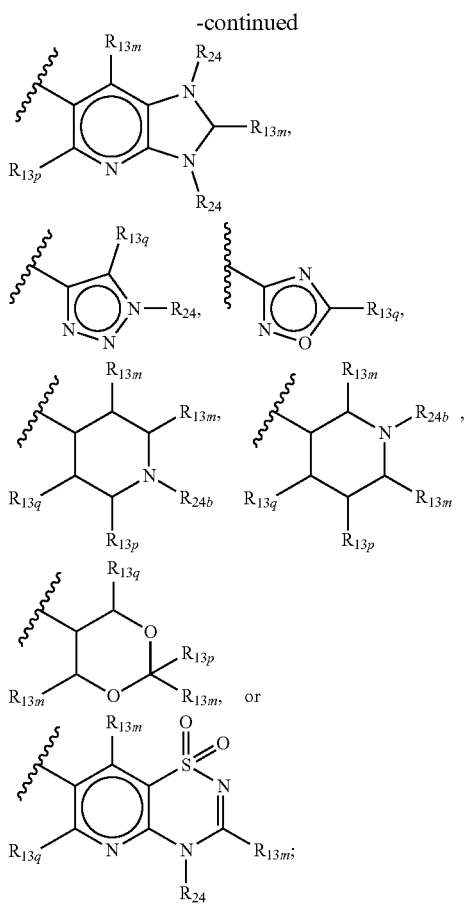
or
R₁ is
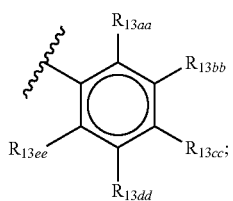
R₂ is C₁₋₁₀ alkyl, cyclopropyl optionally substituted with one or more $R_{13}$'s; C₄₋₁₀ cycloalkyl optionally substituted with one or more $R_{13bb}$'s; C₃₋₁₀ cycloalkenyl optionally substituted with one or more $R_{13b}$'s; or —NR₁₄R₁₄; provided that R₂ is not —NR₁₄R₁₄ when m is 0, 1 or 3; or
R₂ is
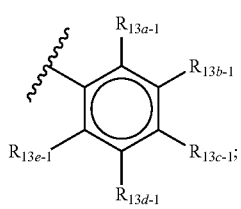
or
R₂ is selected from the consisting of:
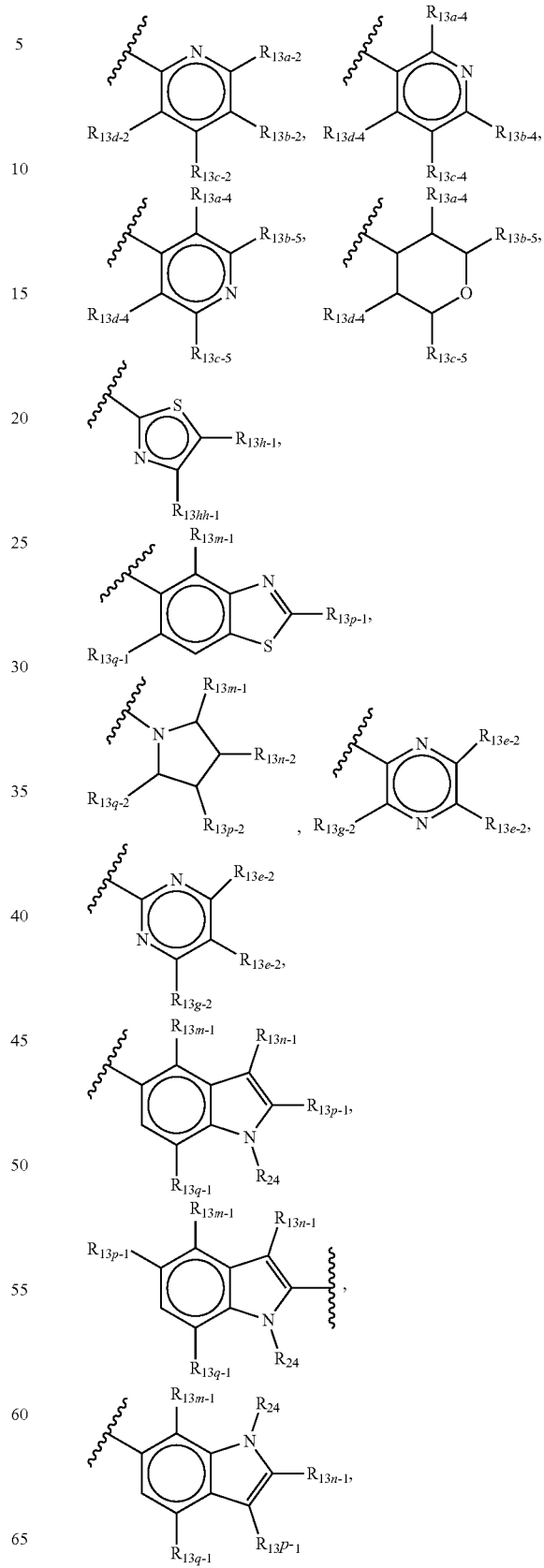

-continued

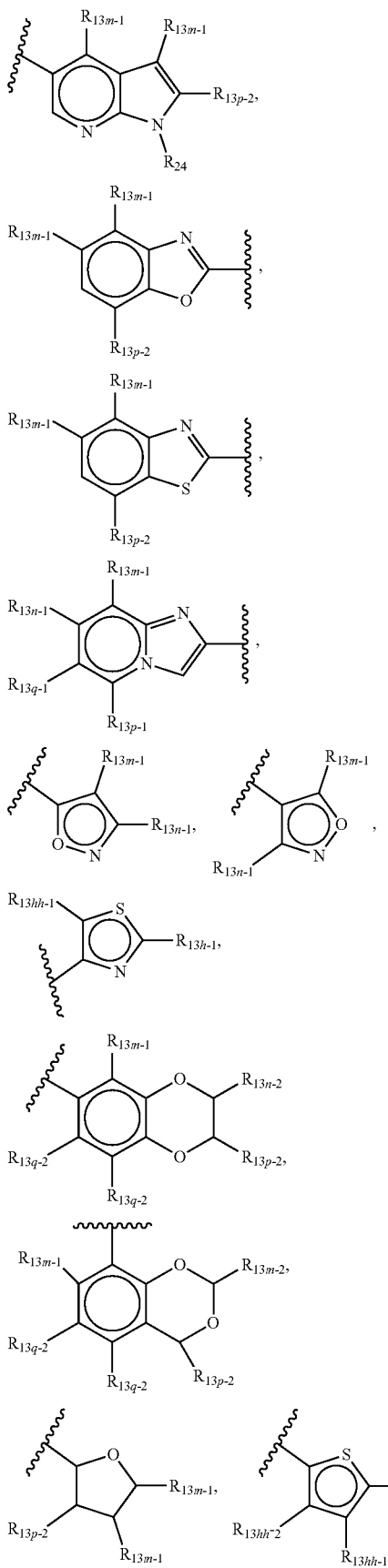

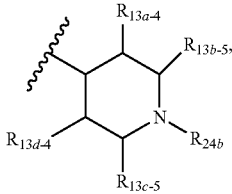

$R_{2a}$ is $C_{1-10}$ alkyl, $C_{3-10}$ cycloalkyl, $C_{6-10}$ aryl, —$NR_{14}R_{14}$, a 4- to 12-membered heteroaryl or 4- to 12-membered heterocyclyl, any of which is optionally substituted with one or more $R_{13}$'s and the heteroaryl and heterocyclyl consist of carbon atoms and 1, 2, 3, or 4 heteroatoms independently selected from the group consisting of N, S, or O;

$R_{11}$ and $R_{12}$, at each occurrence, are independently selected from H, $C_{1-10}$ alkyl, halo$C_{1-10}$ alkyl, $C_{3-10}$ cycloalkyl, $C_{6-10}$aryl, a 4- to 12-membered heteroaryl and a 4- to 12-membered heterocyclyl, wherein the alkyl, cycloalkyl, aryl, heteroaryl and heterocyclyl may be optionally substituted with one or more $R_{13}$'s and the heteroaryl and heterocyclyl consist of carbon atoms and 1, 2, 3, or 4 heteroatoms independently selected from the group consisting of N, S, or O; or $R_{11}$ and $R_{12}$ are taken together with the nitrogen to which they are attached to form a 4- to 12-membered heterocyclyl, wherein the heterocyclyl may be optionally substituted with one or more $R_{13}$'s and the heterocyclyl consists of carbon atoms and 1, 2, 3, or 4 heteroatoms independently selected from the group consisting of N, S, or O;

$R_{13}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O; provided that when $R_{13}$ is alkyl substituted with one $R_{14a}$, $R_{14a}$ is not —OH;

$R_{13a}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13aa}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13a-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13a-2}$, at each occurrence, is independently H, —OH, F, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13a-4}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13b}$, at each occurrence, is independently H, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13bb}$, at each occurrence, is independently H, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13b-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13b-2}$, at each occurrence, is independently H, —OH, Cl, Br, I, $C_{1-10}$ alkyl, $C_{1-10}$ alkoxy, halo$C_{2-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13b-4}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13b-5}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13c}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —(CH$_2$)$_n$—OCONR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —NR$_{14}$CO$_2$R$_{14}$, —CO$_2$R$_{26}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13cc}$, at each occurrence, is independently H, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$, or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13c-1}$, at each occurrence, is independently H, —OH, F, Cl, Br, I, C$_{1-10}$ alkyl, C$_{1-10}$ alkoxy, haloC$_{2-10}$ alkyl, C$_{3-10}$ cycloalkyl, C$_{2-12}$ alkenyl, C$_{2-12}$ alkynyl, C$_{6-10}$aryl, a 6- to 12-membered heteroaryl, a 6- to 12-membered heterocyclyl, a 4- to 12-membered heteroaryl-C$_{1-10}$ alkyl, —NO$_2$, —NR$_{14}$SO$_2$R$_{14}$, =O, —(CH$_2$)$_m$—NR$_{14}$SO$_2$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —NR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13c-2}$, at each occurrence, is independently H, —OH, F, Cl, Br, I, C$_{2-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13c-4}$, at each occurrence, is independently H, —OH, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13c-5}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d}$, at each occurrence, is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13dd}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d\text{-}1}$, at each occurrence, is independently H, —OH, F, Cl, Br, I, $C_{1-10}$ alkyl, $C_{1-10}$ alkoxy, halo$C_{2-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d\text{-}2}$, at each occurrence, is independently H, —OH, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d\text{-}4}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13ee}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, —$C(=NOR_{14})NR_{14}R_{14}$, —$CONR_{14}OR_{14}$ or —$NCOR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e\text{-}1}$, at each occurrence, is independently H, —OH, Cl, Br, I, $C_{1\text{-}10}$ alkyl, $C_{1\text{-}10}$ alkoxy, halo$C_{2\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e\text{-}2}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13f}$, at each occurrence, is independently H, —OH, F, Cl, Br, I, $C_{1\text{-}10}$ alkyl, $C_{2\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13g}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13g\text{-}2}$, at each occurrence, is independently H, —OH, F, Cl, Br, I, $C_{2\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13h}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13h\text{-}1}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{7\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13hh}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13hh\text{-}1}$, at each occurrence, is independently H, —OH, F, Cl, Br, I, C$_{2\text{-}10}$ alkyl, C$_{1\text{-}10}$ alkoxy, haloC$_{1\text{-}10}$ alkyl, C$_{3\text{-}10}$ cycloalkyl, C$_{2\text{-}12}$ alkenyl, C$_{2\text{-}12}$ alkynyl, C$_{6\text{-}10}$aryl, a 4- to 12-membered heteroaryl, a 4- to 12-membered heterocyclyl, a 4- to 12-membered heteroaryl-C$_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13hh\text{-}2}$, at each occurrence, is independently H, —OH, F, Cl, Br, I, C$_{1\text{-}10}$ alkyl, C$_{1\text{-}10}$ alkoxy, haloC$_{1\text{-}10}$ alkyl, C$_{3\text{-}10}$ cycloalkyl, C$_{2\text{-}12}$ alkenyl, C$_{2\text{-}12}$ alkynyl, C$_{6\text{-}10}$aryl, a 4- to 12-membered heteroaryl, a 4- to 12-membered heterocyclyl, a 4- to 12-membered heteroaryl-C$_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13j}$, at each occurrence, is independently H, —OH, F, Cl, Br, I, C$_{1\text{-}10}$ alkyl, C$_{1\text{-}10}$ alkoxy, haloC$_{1\text{-}10}$ alkyl, C$_{3\text{-}10}$ cycloalkyl, C$_{2\text{-}12}$ alkenyl, C$_{2\text{-}12}$ alkynyl, C$_{6\text{-}10}$aryl, a 4- to 12-membered heteroaryl, a 4- to 12-membered heterocyclyl, a 4- to 12-membered heteroaryl-C$_{1\text{-}10}$ alkyl, —CN, —NO$_2$, —(CH$_2$)$_m$—SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13m}$, at each occurrence, is independently H, —OH, F, Cl, Br, I, C$_{1\text{-}10}$ alkyl, C$_{1\text{-}10}$ alkoxy, haloC$_{1\text{-}10}$ alkyl, C$_{3\text{-}10}$ cycloalkyl, C$_{2\text{-}12}$ alkenyl, C$_{2\text{-}12}$ alkynyl, C$_{6\text{-}10}$aryl, a 4- to 12-membered heteroaryl, a 4- to 12-membered heterocyclyl, a 4- to 12-membered heteroaryl-C$_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13m\text{-}1}$, at each occurrence, is independently H, —OH, F, Cl, Br, I, C$_{1\text{-}10}$ alkyl, C$_{1\text{-}10}$ alkoxy, haloC$_{1\text{-}10}$ alkyl, C$_{3\text{-}10}$ cycloalkyl, C$_{2\text{-}12}$ alkenyl, C$_{2\text{-}12}$ alkynyl, C$_{6\text{-}10}$aryl, a 4- to 12-membered heteroaryl, a 4- to 12-membered heterocyclyl, a 4- to 12-membered heteroaryl-C$_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13n\text{-}1}$, at each occurrence, is independently H, —OH, F, Cl, Br, I, C$_{2\text{-}10}$ alkyl, C$_{1\text{-}10}$ alkoxy, haloC$_{1\text{-}10}$ alkyl, C$_{3\text{-}10}$ cycloalkyl, C$_{2\text{-}12}$ alkenyl, C$_{2\text{-}12}$ alkynyl, C$_{6\text{-}10}$aryl, a 4- to 12-membered heteroaryl, a 4- to 12-membered heterocyclyl, a 4- to 12-membered heteroaryl-C$_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13p}$, at each occurrence, is independently H, —OH, F, Cl, Br, I, C$_{1\text{-}10}$ alkyl, C$_{1\text{-}10}$ alkoxy, haloC$_{1\text{-}10}$ alkyl, C$_{3\text{-}10}$ cycloalkyl, C$_{2\text{-}12}$ alkenyl, C$_{2\text{-}12}$ alkynyl, C$_{6\text{-}10}$aryl, a 4- to 12-membered heteroaryl, a 4- to 12-membered heterocyclyl, a 4- to 12-membered heteroaryl-C$_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13p\text{-}1}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13p\text{-}2}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13q}$, at each occurrence, is independently H, —OH, F, Cl, Br, I, $C_{2\text{-}10}$ alkyl, $C_{1\text{-}10}$ alkoxy, halo$C_{2\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13q\text{-}1}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13q\text{-}2}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, —C(=NOR$_{14}$)NR$_{14}$R$_{14}$, —CONR$_{14}$OR$_{14}$ or —NCOR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{14}$, at each occurrence, is independently selected from hydrogen, $C_{1\text{-}10}$ alkyl, $C_{3\text{-}10}$ cycloalkyl, $C_{6\text{-}10}$ aryl, a 4- to 12-membered heteroaryl or a 4- to 12-membered heterocyclyl, wherein the alkyl, cycloalkyl, aryl, heteroaryl and heterocyclyl may be optionally substituted with be optionally substituted with 0-3 $R_{14a}$ and the heteroaryl and heterocyclyl consist of carbon atoms and 1, 2, 3, or 4 heteroatoms independently selected from the group consisting of N, S, or O; or two $R_{14}$'s are taken together with the atoms to which they are attached to form a cyclic ring, wherein the cyclic ring may be optionally substituted with one or more $R_{24a}$'s and optionally contain 1, 2, 3, or 4 heteroatoms independently selected from the group consisting of N, S, or O;

$R_{14a}$, at each occurrence, is independently selected from F, Cl, Br, I, $C_{1\text{-}10}$ alkyl, halo$C_{1\text{-}10}$alkyl, $C_{6\text{-}10}$aryl, $C_{3\text{-}10}$cycloalkyl, a 4- to 12-membered heteroaryl, a 4- to 12-membered heterocyclyl, F, Cl, Br, I, —CN, —NO$_2$, —CO$_2$R$_{26}$, —CO$_2$NR$_{24}$R$_{24}$, —OCF$_3$, —OR$_{25}$, =O, —CONR$_{24}$R$_{24}$, —COR$_{24}$, —SO$_2$R$_{24}$, —NR$_{24}$R$_{24}$, —NR$_{24}$CO$_2$R$_{24}$, —SO$_2$NR$_{24}$R$_{24}$, or $C_{6\text{-}10}$aryl$C_{1\text{-}10}$alkyl, wherein the heteroaryl and heterocyclyl consist of carbon atoms and 1, 2, 3, or 4 heteroatoms independently selected from the group consisting of N, S, or O;

$R_{24}$, at each occurrence, is independently selected from hydrogen, $C_{1\text{-}10}$alkyl, $C_{3\text{-}10}$cycloalkyl, $C_{6\text{-}10}$aryl, a 4- to 12-membered heteroaryl or 4- to 12-membered heterocyclyl, wherein the alkyl, aryl, heteroaryl and heterocyclyl may be optionally substituted with one or more $R_{24}$a'S and the heteroaryl and heterocyclyl consist of carbon atoms and 1, 2, 3, or 4 heteroatoms independently selected from the group consisting of N, S, or O; or two $R_{24}$'s are taken together with the atoms to which they are attached to form a cyclic ring, wherein the cyclic ring may be optionally substituted with one or more $R_{24a}$'s and optionally contain 1, 2, 3, or 4 heteroatoms independently selected from the group consisting of N, S, or O;

$R_{24a}$, at each occurrence, is independently selected from F, Cl, Br, I, $C_{1\text{-}10}$ alkyl, halo$C_{1\text{-}10}$alkyl, $C_{6\text{-}10}$aryl, $C_{3\text{-}10}$cycloalkyl, a 4- to 12-membered heteroaryl, a 4- to 12-membered heterocyclyl, —CN, —NO$_2$, —CO$_2$R$_{25}$, —OCF$_3$, —OR$_{25}$, =O, —CONR$_{25}$R$_{25}$, —COR$_{25}$, —NR$_{25}$R$_{25}$, —NR$_{25}$CO$_2$R$_{25}$, or C$_{6-10}$arylC$_{1-10}$alkyl, wherein the heteroaryl and heterocyclyl consist of carbon atoms and 1, 2, 3, or 4 heteroatoms independently selected from the group consisting of N, S, or O;

R$_{24b}$, at each occurrence, is independently selected from C$_{1-10}$ alkyl, C$_{6-10}$aryl, C$_{3-10}$cycloalkyl, a 4- to 12-membered heteroaryl, a 4- to 12-membered heterocyclyl, —CO$_2$R$_{25}$, —SO$_2$NR$_{25}$R$_{25}$, —COR$_{25}$ or C$_{6-10}$arylC$_{1-10}$alkyl, wherein the heteroaryl and heterocyclyl consist of carbon atoms and 1, 2, 3, or 4 heteroatoms independently selected from the group consisting of N, S, or O;

R$_{25}$, at each occurrence, is independently selected from hydrogen, C$_{1-10}$alkyl, C$_{3-10}$cycloalkyl, C$_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O; and R$_{26}$, at each occurrence, is independently selected from C$_{1-10}$alkyl, haloC$_{1-10}$ alkyl, C$_{3-10}$cycloalkyl, C$_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O;

provide that:

(i) R$_1$ is not C$_1$ when m is 0, 1 or 2; R$_{13a-1}$ is H, —CF$_3$, or methoxy; R$_{13c-1}$ is H, OH, methoxy or dimethylamino; X, Y, Z, R$_{13b-1}$, R$_{13d-1}$, R$_{13a-2}$, R$_{13b-2}$, R$_{13c-2}$, R$_{13d-2}$, R$_{13e-2}$, R$_{13g-2}$, R$_{13a-4}$, R$_{13b-4}$, R$_{13c-4}$, R$_{13d-4}$, R$_{13b-5}$, R$_{13c-5}$, R$_{13m-1}$, R$_{13n-1}$, R$_{13p-1}$, and R$_{13q-1}$ are H; and (ii) m is not 0 or 1 when X, Y, R$_{13a}$, R$_{13d}$, R$_{13e}$, R$_{13g}$, R$_{13a-2}$, R$_{13b-2}$, R$_{13c-2}$, R$_{13d-2}$, R$_{13a-4}$, R$_{13b-4}$, R$_{13c-4}$, R$_{13d-4}$ R$_{13b-5}$, R$_{13c-5}$, R$_{13h-1}$ and R$_{13hh-1}$ are H; R$_{13b}$ is H or —SO$_2$NH$_2$;

R$_{13c}$ is H, —CONH$_2$, —SO$_2$N(C$_2$H$_4$OH)$_2$, —SO$_2$NHCOCH$_3$, —SO$_2$NH$_2$, -tetrazolyl or (4-aminopiperidinyl)sulfonyl; R$_{13}$f is H or —NHC$_2$H$_4$OCH$_3$; and Z is H, —CO$_2$H, or —CO$_2$CH$_3$.

In one embodiment, compounds, enantiomers, diastereomers, tautomers, prodrugs or salts thereof, of formula I, are provided wherein X is H.

In another embodiment, compounds, enantiomers, diastereomers, tautomers, prodrugs or salts thereof, of formula I, are provided wherein X and Y are H.

In yet another embodiment, compounds, enantiomers, diastereomers, tautomers, prodrugs or salts thereof, of formula I, are provided wherein X, Y and Z are H.

In one embodiment, compounds, enantiomers, diastereomers, tautomers, prodrugs or salts thereof, of formula I, are provided wherein R$_1$ is F, Cl, Br or I.

In one embodiment, compounds, enantiomers, diastereomers, tautomers, prodrugs or salts thereof, of formula I, are provided wherein R$_1$ is C$_1$.

In one embodiment, compounds, enantiomers, diastereomers, tautomers, prodrugs or salts thereof, of formula I, are provided wherein R$_1$ is selected from the group consisting of

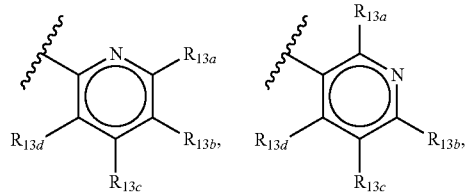

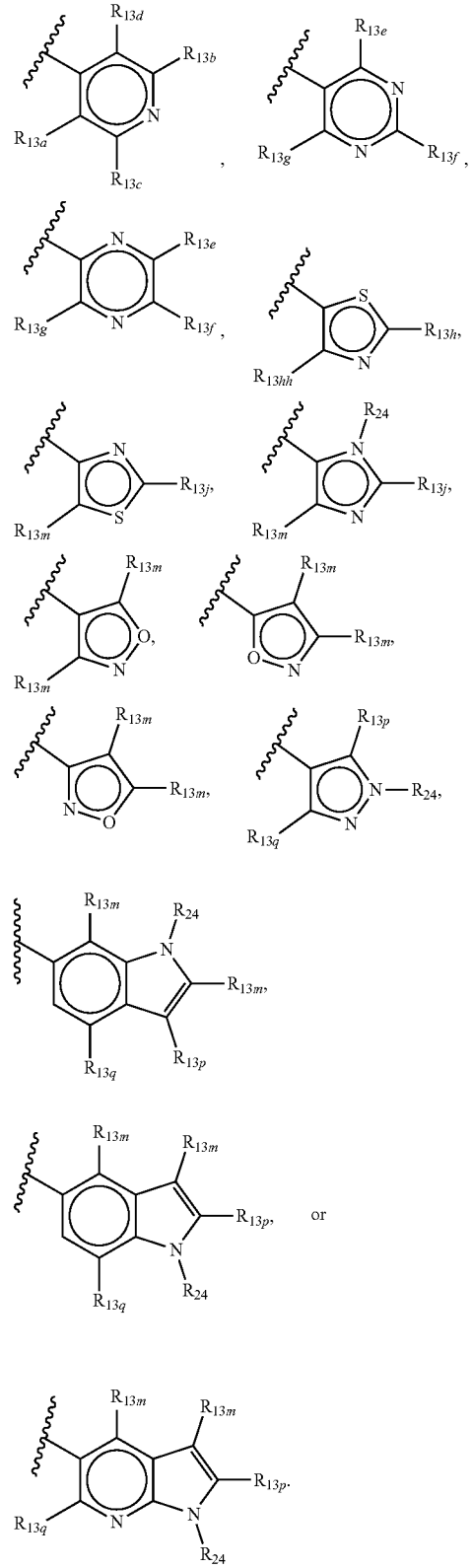

In another embodiment, compounds, enantiomers, diastereomers, tautomers, prodrugs or salts thereof, of formula I, are provided wherein R$_1$ is selected from the group consisting of:

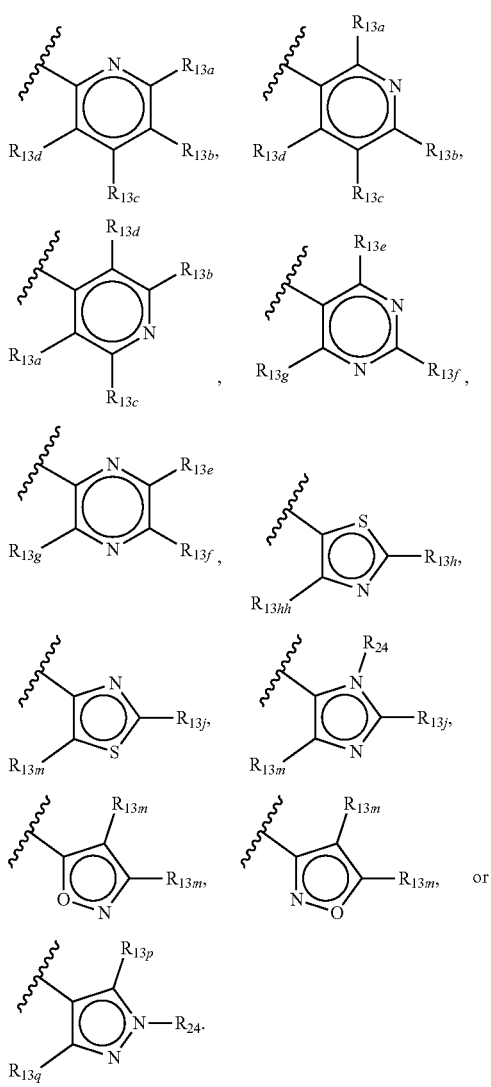

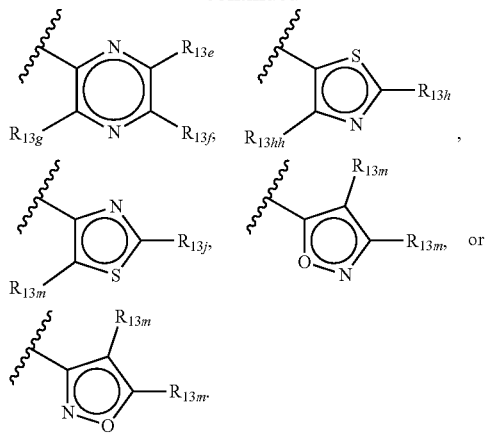

In one embodiment, compounds, enantiomers, diastereomers, tautomers, prodrugs or salts thereof, of formula I, are provided wherein $R_1$ is selected from the group consisting of:

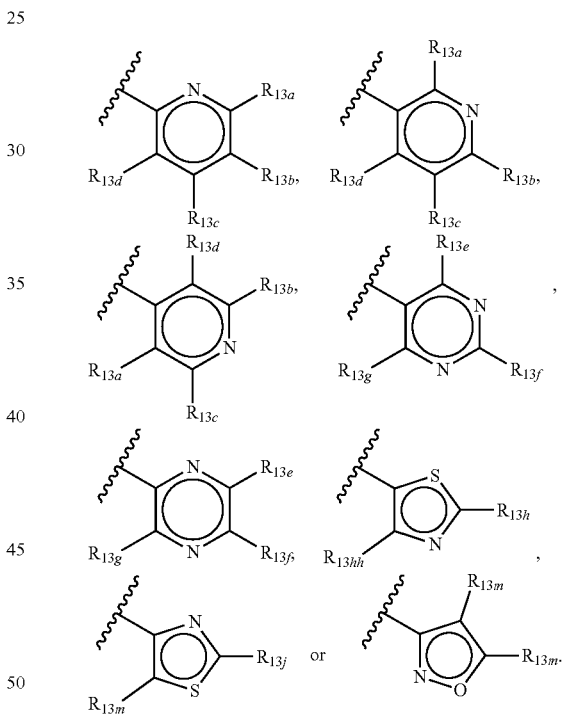

In yet another embodiment, compounds, enantiomers, diastereomers, tautomers, prodrugs or salts thereof, of formula I, are provided wherein $R_1$ is selected from the group consisting of:

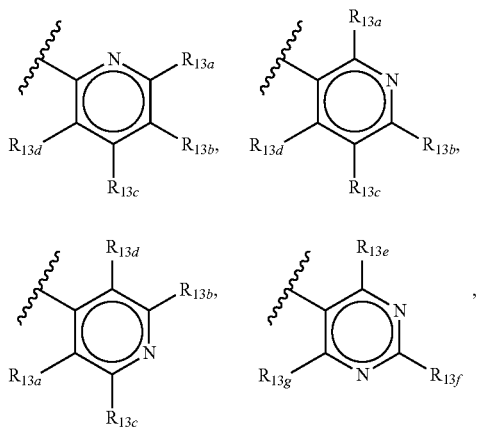

In one embodiment, compounds, enantiomers, diastereomers, tautomers, prodrugs or salts thereof, of formula I, are provided wherein $R_1$ is

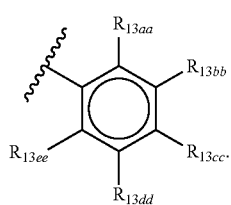

In one embodiment, compounds, enantiomers, diastereomers, tautomers, prodrugs or salts thereof, of formula I, are provided wherein $R_1$ is

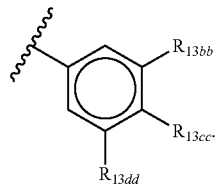

In one embodiment, compounds, enantiomers, diastereomers, tautomers, prodrugs or salts thereof, of formula I, are provided wherein:

X is H, —OH, F, Cl, Br, I, $C_{1-10}$ alkyl, $C_{1-10}$ alkoxy, halo$C_{1-10}$ alkyl, $C_{2-12}$ alkenyl, $C_{2-12}$ alkynyl, $C_{3-10}$ cycloalkyl, a 4- to 12-membered heteroaryl, 4- to 12-membered heterocyclyl, —CN, —NO$_2$, —SO$_2$NR$_{11}$R$_{12}$, —CONR$_{11}$R$_{12}$, —NR$_{11}$CONR$_{11}$R$_{12}$, —NCOR$_{11}$, —CO$_2$R$_{11}$ or —NR$_{11}$R$_{12}$;

Y is H, F, Cl, Br, I, $C_{1-10}$ alkyl, $C_{1-10}$ alkoxy, halo$C_{1-10}$ alkyl, $C_{2-12}$ alkenyl, $C_2$-12 alkynyl, $C_{3-10}$ cycloalkyl, a 4- to 12-membered heteroaryl, 4- to 12-membered heterocyclyl, —CN, —NO$_2$, —SO$_2$NR$_{11}$R$_{12}$, —CONR$_{11}$R$_{12}$, —NR$_{11}$CONR$_{11}$R$_{12}$, —NCOR$_{11}$, —CO$_2$R$_{11}$ or —NR$_{11}$R$_{12}$;

Z is H, Cl, Br, I, $C_{1-10}$ alkyl, $C_{1-10}$ alkoxy, halo$C_{1-10}$ alkyl, $C_{2-12}$ alkenyl, $C_{2-12}$ alkynyl, $C_{3-10}$ cycloalkyl, a 6- to 12-membered heteroaryl, 4- to 12-membered heterocyclyl, —NO$_2$, —SO$_2$NR$_{11}$R$_{12}$, —NCOR$_{11}$, —NR$_{11}$SO$_2$NR$_{11}$R$_{12}$, —OCONR$_{11}$R$_{12}$ or —NR$_{11}$R$_{12}$;

A is —(CH$_2$)$_m$—R$_2$, —CH(R$_{25}$)(R$_{26}$) or —CH(R$_{26}$)—CO$_2$—R$_2$a;

m is 0 to 4;

n is 1 to 4;

$R_1$ is —OH, F, Cl, Br, I, $C_{1-10}$ alkyl, halo$C_{1-10}$ alkyl, $C_{2-12}$ alkenyl, $C_{3-10}$ cycloalkyl, —CN, —(CH$_2$)$_n$—SO$_2$NR$_{11}$R$_{12}$ or —(CH$_2$)$_n$—NR$_{11}$SO$_2$R$_{12}$, wherein the alkenyl and cycloalkyl may be optionally substituted with one or more $R_{13}$'s; or $R_1$ is selected from the group consisting of:

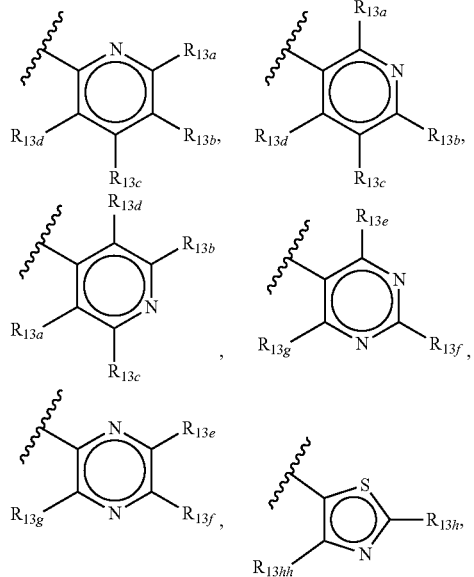

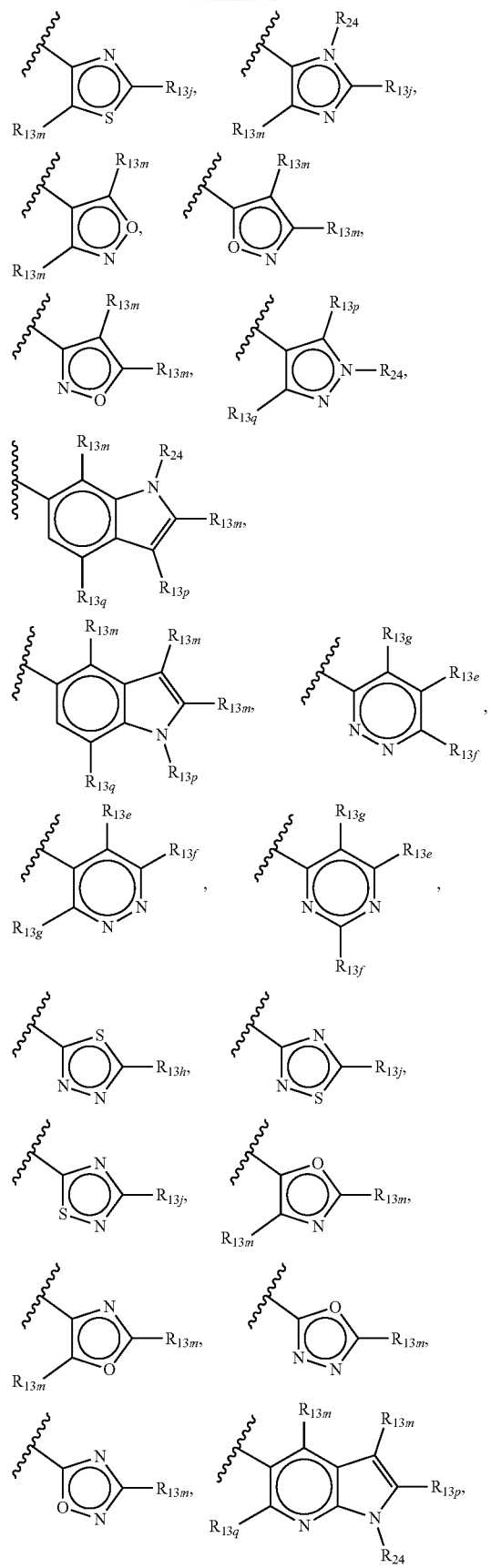

-continued
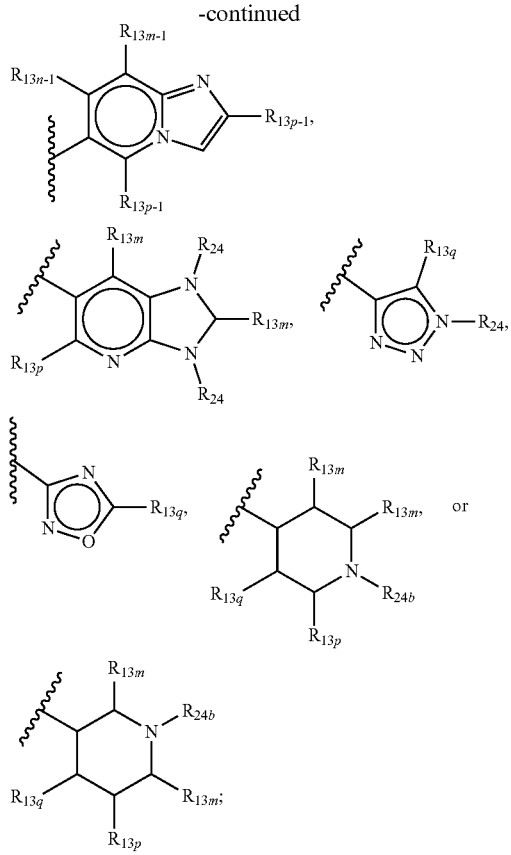
or
R<sub>1</sub> is
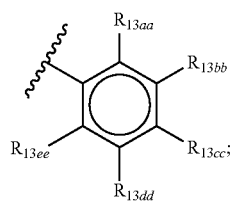
R<sub>2</sub> is C$_{1-10}$ alkyl, cyclopropyl optionally substituted with one or more R$_{13}$'s; C$_{4-10}$ cycloalkyl optionally substituted with one or more R$_{13bb}$ S; or —NR$_{14}$R$_{14}$; provided that R$_2$ is not —NR$_{14}$R$_{14}$ when m is 0, 1 or 3; or
R<sub>2</sub> is
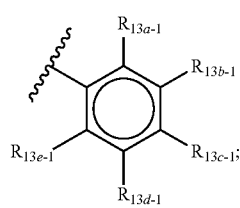
or
R<sub>2</sub> is selected from the group consisting of:
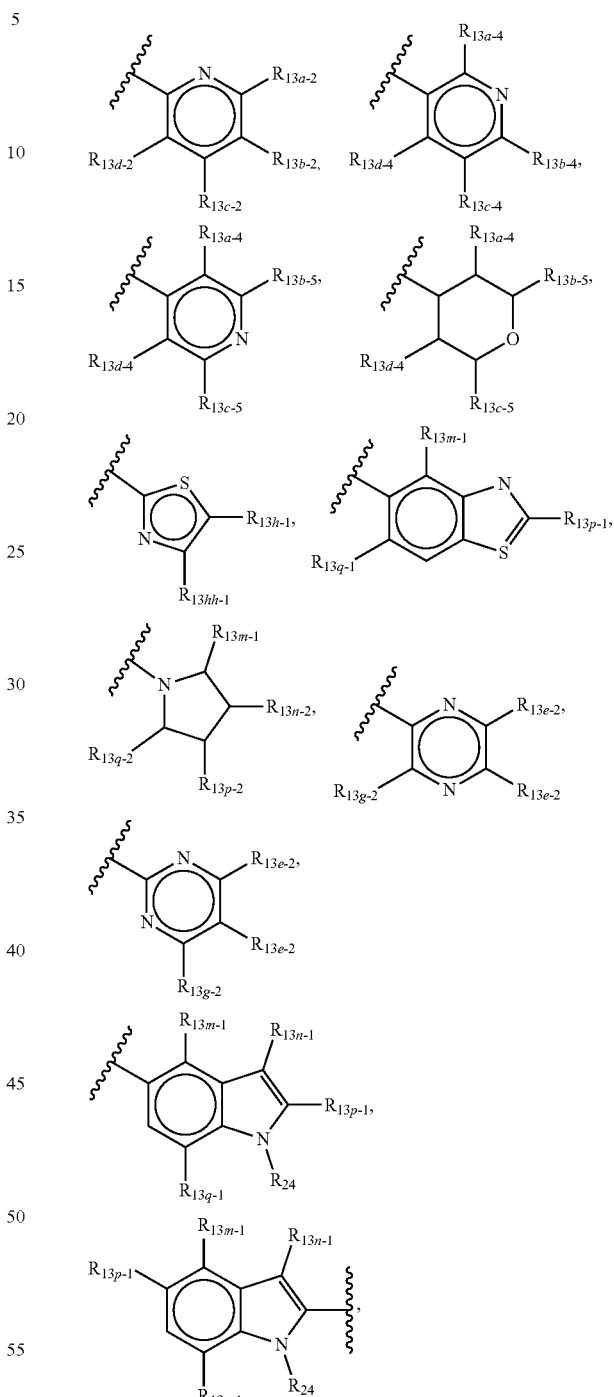
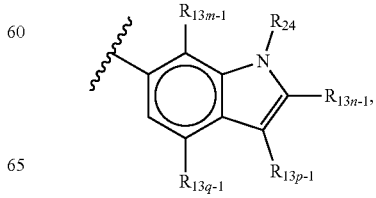

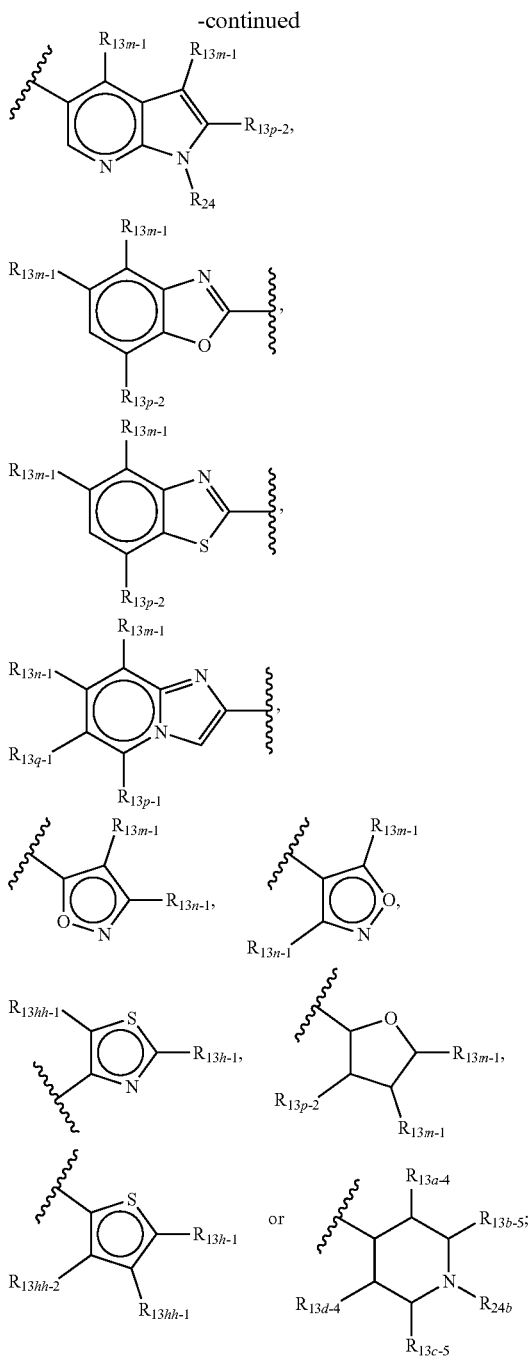

$R_{2a}$ is $C_{1-10}$ alkyl, $C_{3-10}$ cycloalkyl, $C_{6-10}$ aryl, —$NR_{14}R_{14}$, a 4- to 12-membered heteroaryl or 4- to 12-membered heterocyclyl, any of which is optionally substituted with one or more $R_{13}$'s and the heteroaryl and heterocyclyl consist of carbon atoms and 1, 2, 3, or 4 heteroatoms independently selected from the group consisting of N, S, or O;

$R_{11}$ and $R_{12}$, at each occurrence, are independently selected from H, $C_{1-10}$ alkyl, halo$C_{1-10}$ alkyl, $C_{3-10}$ cycloalkyl, $C_{6-10}$aryl, a 4- to 12-membered heteroaryl and a 4- to 12-membered heterocyclyl, wherein the alkyl, cycloalkyl, aryl, heteroaryl and heterocyclyl may be optionally substituted with one or more $R_{13}$'s and the heteroaryl and heterocyclyl consist of carbon atoms and 1, 2, 3, or 4 heteroatoms independently selected from the group consisting of N, S, or O; or $R_{11}$ and $R_{12}$ are taken together with the nitrogen to which they are attached to form a 4- to 12-membered heterocyclyl, wherein the heterocyclyl may be optionally substituted with one or more $R_{13}$'s and the heterocyclyl consists of carbon atoms and 1, 2, 3, or 4 heteroatoms independently selected from the group consisting of N, S, or O;

$R_{13}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O; provided that when $R_{13}$ is alkyl substituted with one $R_{14a}$, $R_{14a}$ is not —OH;

$R_{13a}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, —$CONR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13aa}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, —$CONR_{14}R_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13a-2}$, at each occurrence, is independently H, —OH, F, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13a-4}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13b}$, at each occurrence, is independently H, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13bb}$, at each occurrence, is independently H, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13b-1}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or -CONR$_{14}$OR$_{14}$, wherein the alkyl, cycloalkyl, alkenyl, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13b-2}$, at each occurrence, is independently H, —OH, Cl, Br, I, C$_{1-10}$ alkyl, C$_{1-10}$ alkoxy, haloC$_{2-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13b-4}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13b-5}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$NR_{14}CO_2R_{14}$, —$CO_2R_{26}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13cc}$, at each occurrence, is independently H, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c-1}$, at each occurrence, is independently H, —OH, F, Cl, Br, I, $C_{1-10}$ alkyl, $C_{1-10}$ alkoxy, halo$C_{2-10}$ alkyl, $C_{3-10}$ cycloalkyl, $C_{2-12}$ alkenyl, $C_{2-12}$ alkynyl, $C_{6-10}$aryl, a 6- to 12-membered heteroaryl, a 6- to 12-membered heterocyclyl, a 4- to 12-membered heteroaryl-$C_{1-10}$ alkyl, —$NO_2$, —$NR_{14}SO_2R_{14}$, =O, —$(CH_2)_m$—$NR_{14}SO_2R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$NR_{14}R_{14}$, —$NR_{14}CONR_{14}R_{14}$ or —$CONR_{14}OR_{14}$, wherein the alkyl, cycloalkyl, alkenyl, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c-2}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c-4}$, at each occurrence, is independently H, —OH, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c-5}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d}$, at each occurrence, is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13dd}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d\text{-}1}$, at each occurrence, is independently H, —OH, F, Cl, Br, I, $C_{1-10}$ alkyl, $C_{1-10}$ alkoxy, halo$C_{2-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}CONR_{14}R_{14}$ or —$CONR_{14}OR_{14}$, wherein the alkyl, cycloalkyl, alkenyl, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d\text{-}2}$, at each occurrence, is independently H, —OH, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d\text{-}4}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13ee}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e\text{-}1}$, at each occurrence, is independently H, —OH, Cl, Br, I, $C_{1-10}$ alkyl, $C_{1-10}$ alkoxy, halo$C_{2-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e\text{-}2}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, =O, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13f}$, at each occurrence, is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heteroaryl- $C_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13g}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13g\text{-}2}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13h}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13h\text{-}1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{7-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13hh}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13hh\text{-}1}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13hh\text{-}2}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13j}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13m}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13m-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13n-1}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13p}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13p}$-1, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or -CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13p-2}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13q}$, at each occurrence, is independently H, —OH, F, Cl, Br, I, $C_{2-10}$ alkyl, $C_{1-10}$ alkoxy, halo$C_{2-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13q}$-1, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13q}$-2, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be optionally substituted with be optionally substituted with 0-3 $R_{14a}$ and the heteroaryl and heterocyclyl consist of carbon atoms and 1, 2, 3, or 4 heteroatoms independently selected from the group consisting of N, S, or O; or two $R_{14}$'s are taken together with the atoms to which they are attached to form a cyclic ring, wherein the cyclic ring may be optionally substituted with one or more $R_{24a}$'s and optionally contain 1, 2, 3, or 4 heteroatoms independently selected from the group consisting of N, S, or O;

$R_{14a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —NO$_2$, —CO$_2$R$_{26}$, —OCONR$_{24}$R$_{24}$, —CO$_2$NR$_{24}$R$_{24}$, —OCF$_3$, —OR$_{25}$, —CONR$_{24}$R$_{24}$, —COR$_{24}$, —SO$_2$R$_{24}$, —NR$_{24}$R$_{24}$, —NR$_{24}$CO$_2$R$_{24}$, —SO$_2$NR$_{24}$R$_{24}$, or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{24}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the alkyl, aryl, heteroaryl and heterocyclyl may be optionally substituted with one or more $R_{24a}$'s and the heteroaryl and heterocyclyl consist of carbon atoms and 1, 2, 3, or 4 heteroatoms independently selected from the group consisting of N, S, or O; or two $R_{24}$'s are taken together with the atoms to which they are attached to form a cyclic ring, wherein the cyclic ring may be optionally substituted with one or more $R_{24a}$'s and optionally contain 1, 2, 3, or 4 heteroatoms independently selected from the group consisting of N, S, or O;

$R_{24a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, —CN, —NO$_2$, —CO$_2$R$_{25}$, —OCF$_3$, —OR$_{25}$, —CONR$_{25}$R$_{25}$, —COR$_{25}$, —NR$_{25}$R$_{25}$, —NR$_{25}$CO$_2$R$_{25}$, or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{24b}$, at each occurrence, is independently selected from $C_{1-10}$ alkyl, $C_{6-10}$aryl, $C_{3-10}$cycloalkyl, a 4- to 12-membered heteroaryl, a 4- to 12-membered heterocyclyl, —CO$_2$R$_{25}$, —SO$_2$NR$_{25}$R$_{25}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{25}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O; and $R_{26}$, at each occurrence, is independently selected from $C_{1-10}$alkyl, halo$C_{1-10}$ alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O.

In one embodiment, compounds, enantiomers, diastereomers, tautomers, prodrugs or salts thereof, of formula I, are provided wherein:

X is H, —OH, F, Cl, Br, I, $C_{1-10}$ alkyl, $C_{1-10}$ alkoxy, halo$C_{1-10}$ alkyl, $C_{2-12}$ alkenyl, $C_{2-12}$ alkynyl, $C_{3-10}$ cycloalkyl, a 4- to 12-membered heteroaryl, 4- to 12-membered heterocyclyl, —CN, —NO$_2$, —CO$_2$R$_{11}$ or —NR$_{11}$R$_{12}$;

Y is H, F, Cl, Br, I, $C_{1-10}$ alkyl, $C_{1-10}$ alkoxy, halo$C_{1-10}$ alkyl, $C_{2-12}$ alkenyl, $C_2$-12 alkynyl, $C_{3-10}$ cycloalkyl, a 4- to 12-membered heteroaryl, 4- to 12-membered heterocyclyl, —CN, —NO$_2$, —CO$_2$R$_{11}$ or —NR$_{11}$R$_{12}$;

Z is H, Cl, Br, I, $C_{1-10}$ alkyl, $C_{1-10}$ alkoxy, halo$C_{1-10}$ alkyl, $C_{2-12}$ alkenyl, $C_{2-12}$ alkynyl, $C_{3-10}$ cycloalkyl, a 6- to 12-membered heteroaryl, 4- to 12-membered heterocyclyl, —NO$_2$ or —NR$_{11}$R$_{12}$;

A is —(CH$_2$)$_m$—R$_2$ or —CH(R$_{25}$)(R$_{26}$);

m is 0 to 4;

n is 1 to 4;

$R_1$ is F, Cl, Br, I, $C_{1-10}$ alkyl, halo$C_{1-10}$ alkyl, $C_{2-12}$ alkenyl, $C_{3-10}$ cycloalkyl, —(CH$_2$)$_n$—SO$_2$NR$_{11}$R$_{12}$ or —(CH$_2$)$_n$—NR$_{11}$SO$_2$R$_{12}$, wherein the alkenyl and cycloalkyl may be optionally substituted with one or more $R_{13}$'s; or $R_1$ is selected from the group consisting of:
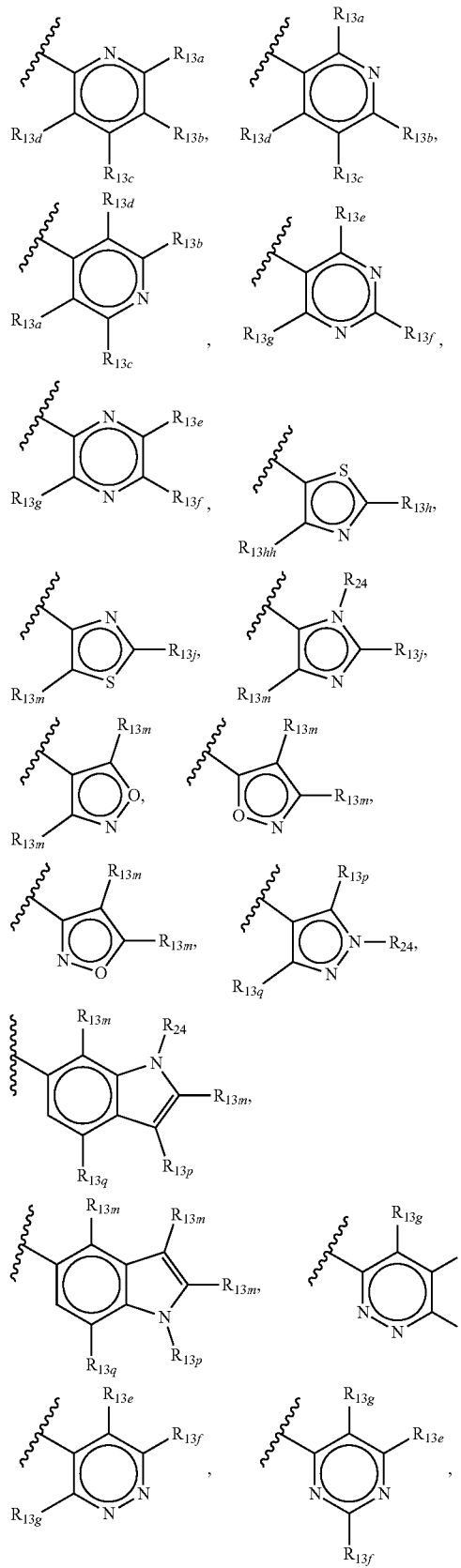
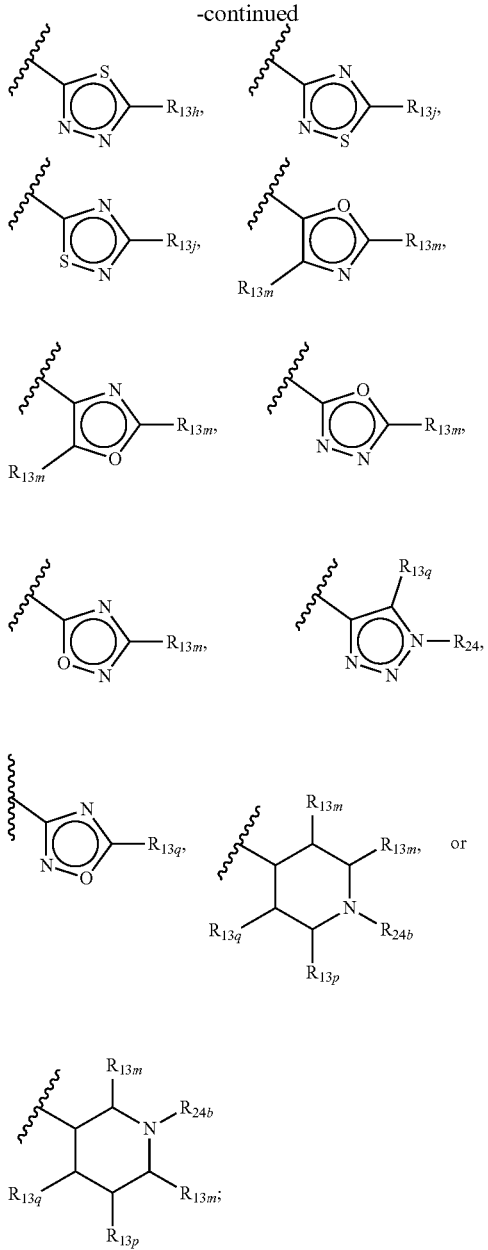
or $R_1$ is
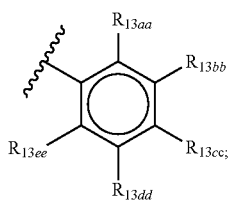
$R_2$ is $C_{1-10}$ alkyl, cyclopropyl optionally substituted with one or more $R_{13}$ s; or $C_{4-10}$ cycloalkyl optionally substituted with one or more $R_{13bb}$'S; or R$_2$ is

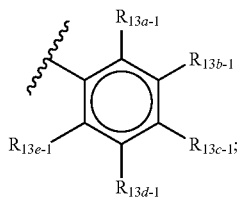

or

R$_2$ is selected from the group consisting of:

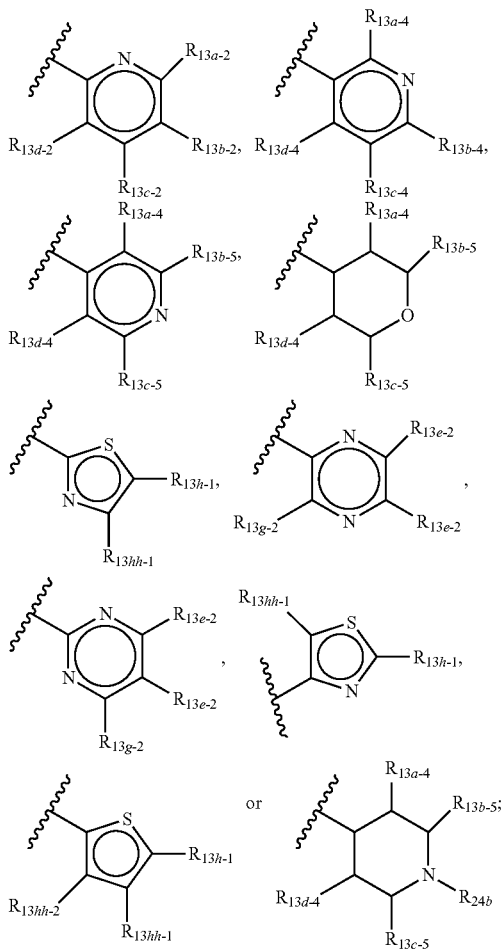

R$_{11}$ and R$_{12}$, at each occurrence, are independently selected from H, C$_{1-10}$ alkyl, haloC$_{1-10}$ alkyl, C$_{3-10}$ cycloalkyl, C$_{6-10}$aryl, a 4- to 12-membered heteroaryl and a 4- to 12-membered heterocyclyl, wherein the alkyl, cycloalkyl, aryl, heteroaryl and heterocyclyl may be optionally substituted with one or more R$_{13}$'s and the heteroaryl and heterocyclyl consist of carbon atoms and 1, 2, 3, or 4 heteroatoms independently selected from the group consisting of N, S, or O; or R$_{11}$ and R$_{12}$ are taken together with the nitrogen to which they are attached to form a 4- to 12-membered heterocyclyl, wherein the heterocyclyl may be optionally substituted with one or more R$_{13}$'s and the heterocyclyl consists of carbon atoms and 1, 2, 3, or 4 heteroatoms independently selected from the group consisting of N, S, or O;

R$_{13}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O; provided that when R$_{13}$ is alkyl substituted with one R$_{14a}$, R$_{14a}$ is not —OH;

R$_{13a}$, at each occurrence, is independently H, —OH, F, Cl, Br, I, C$_{2-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13aa}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13a-1}$, at each occurrence, is independently —OH, F, Cl, Br, I, C$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a\text{-}2}$, at each occurrence, is independently H, —OH, F, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a\text{-}4}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b}$, at each occurrence, is independently H, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —CO$_2$NR$_{14}$R$_{14}$, —NR$_{14}$SO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13bb}$, at each occurrence, is independently H, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b\text{-}1}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b\text{-}2}$, at each occurrence, is independently H, —OH, Cl, Br, I, $C_{1\text{-}10}$ alkyl, $C_{1\text{-}10}$ alkoxy, halo$C_{2\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b\text{-}4}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b\text{-}5}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13c}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —NR$_{14}$CO$_2$R$_{14}$, —CO$_2$R$_{26}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13cc}$, at each occurrence, is independently H, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13c-1}$, at each occurrence, is independently H, —OH, F, Cl, Br, I, C$_{1-10}$ alkyl, C$_{1-10}$ alkoxy, haloC$_{2-10}$ alkyl, C$_{3-10}$ cycloalkyl, C$_{2-12}$ alkenyl, C$_{2-12}$ alkynyl, C$_{6-10}$aryl, a 6- to 12-membered heteroaryl, a 6- to 12-membered heterocyclyl, a 4- to 12-membered heteroaryl-C$_{1-10}$ alkyl, —NO$_2$, —NR$_{14}$SO$_2$R$_{14}$, =O, —(CH$_2$)$_m$—NR$_{14}$SO$_2$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13c-2}$, at each occurrence, is independently H, —OH, F, Cl, Br, I, C$_{2-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13c-4}$, at each occurrence, is independently H, —OH, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13c-5}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13d}$, at each occurrence, is independently H, —OH, F, Cl, Br, I, C$_{1-10}$ alkyl, C$_{2-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13dd}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d\text{-}1}$, at each occurrence, is independently H, —OH, F, Cl, Br, I, $C_{1\text{-}10}$ alkyl, $C_{1\text{-}10}$ alkoxy, halo$C_{2\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$CONR$_{14}$R$_{14}$ or —CONR$_{14}$OR$_{14}$, wherein the alkyl, cycloalkyl, alkenyl, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d\text{-}2}$, at each occurrence, is independently H, —OH, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d\text{-}4}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13ee}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e\text{-}1}$, at each occurrence, is independently H, —OH, Cl, Br, I, $C_{1\text{-}10}$ alkyl, $C_{1\text{-}10}$ alkoxy, halo$C_{2\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e\text{-}2}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13f}$, at each occurrence, is independently —OH, F, Cl, Br, I, $C_{1\text{-}10}$ alkyl, $C_{2\text{-}10}$ alkoxy, halo$C_{1\text{-}10}$ alkyl, $C_{3\text{-}10}$ cycloalkyl, $C_{2\text{-}12}$ alkenyl, $C_{2\text{-}12}$ alkynyl, $C_{6\text{-}10}$aryl, a 4- to 12-membered heteroaryl, a 4- to 12-membered heteroaryl-$C_{1\text{-}10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13g}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13g\text{-}2}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13h}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13h\text{-}1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{7-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$;

—NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13hh}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13hh\text{-}1}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13hh\text{-}2}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13j}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or -CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13m}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13p}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13q}$, at each occurrence, is independently H, —OH, F, Cl, Br, I, C$_{2-10}$ alkyl, C$_{1-10}$ alkoxy, haloC$_{2-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$_{14}$, —NR$_{14}$SO$_2$R$_{14}$, =O, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$ or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{14}$, at each occurrence, is independently selected from hydrogen, C$_{1-10}$ alkyl, C$_{3-10}$ cycloalkyl, C$_{6-10}$ aryl, a 4- to 12-membered heteroaryl or a 4- to 12-membered heterocyclyl, wherein the alkyl, cycloalkyl, aryl, heteroaryl and heterocyclyl may be optionally substituted with be optionally substituted with 0-3 R$_{14a}$ and the heteroaryl and heterocyclyl consist of carbon atoms and 1, 2, 3, or 4 heteroatoms independently selected from the group consisting of N, S, or O; or two R$_{14}$'s are taken together with the atoms to which they are attached to form a cyclic ring, wherein the cyclic ring may be optionally substituted with one or more R$_{24a}$'s and optionally contain 1, 2, 3, or 4 heteroatoms independently selected from the group consisting of N, S, or O;

R$_{14a}$, at each occurrence, is independently selected from F, Cl, Br, I, C$_{1-10}$ alkyl, haloC$_{1-10}$alkyl, C$_{6-10}$aryl, C$_{3-10}$cycloalkyl, a 4- to 12-membered heteroaryl, a 4- to 12-membered heterocyclyl, F, Cl, Br, I, —CN, —NO$_2$, —CO$_2$R$_{26}$, —CO$_2$NR$_{24}$R$_{24}$, —OCF$_3$, —OR$_{25}$, —CONR$_{24}$R$_{24}$, —COR$_{24}$, —SO$_2$R$_{24}$, —NR$_{24}$R$_{24}$, —NR$_{24}$CO$_2$R$_{24}$, —SO$_2$NR$_{24}$R$_{24}$, or C$_{6-10}$arylC$_{1-10}$alkyl, wherein the heteroaryl and heterocyclyl consist of carbon atoms and 1, 2, 3, or 4 heteroatoms independently selected from the group consisting of N, S, or O;

R$_{24}$, at each occurrence, is independently selected from hydrogen, C$_{1-10}$alkyl, C$_{3-10}$cycloalkyl, C$_{6-10}$aryl, a 4- to 12-membered heteroaryl or 4- to 12-membered heterocyclyl, wherein the alkyl, aryl, heteroaryl and heterocyclyl may be optionally substituted with one or more R$_{24}$a'S and the heteroaryl and heterocyclyl consist of carbon atoms and 1, 2, 3, or 4 heteroatoms independently selected from the group consisting of N, S, or O; or two R$_{24}$'s are taken together with the atoms to which they are attached to form a cyclic ring, wherein the cyclic ring may be optionally substituted with one or more R$_{24}$a'S and optionally contain 1, 2, 3, or 4 heteroatoms independently selected from the group consisting of N, S, or O;

R$_{24a}$, at each occurrence, is independently selected from F, Cl, Br, I, C$_{1-10}$ alkyl, haloC$_{1-10}$alkyl, C$_{6-10}$aryl, C$_{3-10}$cycloalkyl, a 4- to 12-membered heteroaryl, a 4- to 12-membered heterocyclyl, —CN, —NO$_2$, —CO$_2$R$_{25}$, —OCF$_3$, —OR$_{25}$, —CONR$_{25}$R$_{25}$, —COR$_{25}$, —NR$_{25}$CO$_2$R$_{25}$, or C$_{6-10}$arylC$_{1-10}$alkyl, wherein the heteroaryl and heterocyclyl consist of carbon atoms and 1, 2, 3, or 4 heteroatoms independently selected from the group consisting of N, S, or O;

R$_{24b}$, at each occurrence, is independently selected from C$_{1-10}$ alkyl, C$_{6-10}$aryl, C$_{3-10}$cycloalkyl, a 4- to 12-membered heteroaryl, a 4- to 12-membered heterocyclyl, —CO$_2$R$_{25}$, —SO$_2$NR$_{25}$R$_{25}$ or C$_{6-10}$arylC$_{1-10}$alkyl, wherein the heteroaryl and heterocyclyl consist of carbon atoms and 1, 2, 3, or 4 heteroatoms independently selected from the group consisting of N, S, or O;

R$_{25}$, at each occurrence, is independently selected from hydrogen, C$_{1-10}$alkyl, C$_{3-10}$cycloalkyl, C$_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O; and R$_{26}$, at each occurrence, is independently selected from C$_{1-10}$alkyl, haloC$_{1-10}$ alkyl, C$_{3-10}$cycloalkyl, C$_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O.

In one embodiment, compounds, enantiomers, diastereomers, tautomers, prodrugs or salts thereof, of formula I, are provided wherein:

X is H, —OH, F, Cl, Br, I, C$_{1-10}$ alkyl, C$_{1-10}$ alkoxy, haloC$_{1-10}$ alkyl, C$_{3-10}$ cycloalkyl, a 4- to 12-membered heteroaryl, 4- to 12-membered heterocyclyl, —CO$_2$R$_{11}$ or —NR$_{11}$R$_{12}$;

Y is H, F, Cl, Br, I, C$_{1-10}$ alkyl, C$_{1-10}$ alkoxy, haloC$_{1-10}$ alkyl, C$_{3-10}$ cycloalkyl, a 4- to 12-membered heteroaryl, 4- to 12-membered heterocyclyl, —CO$_2$R$_{11}$ or —NR$_{11}$R$_{12}$;

Z is H, Cl, Br, I, $C_{1-10}$ alkyl, $C_{1-10}$ alkoxy, halo$C_{1-10}$ alkyl, $C_{3-10}$ cycloalkyl, a 6- to 12-membered heteroaryl, 4- to 12-membered heterocyclyl or —$NR_{11}R_{12}$;

A is —$(CH_2)_m$—$R_2$ or —$CH(R_{25})(R_{26})$;

m is 0 to 3;

n is 1 to 3;

$R_1$ is F, Cl, Br, I, $C_{1-10}$ alkyl, $C_{2-12}$ alkenyl, $C_{3-10}$ cycloalkyl, —$(CH_2)_n$—$SO_2NR_{11}R_{12}$ or —$(CH_2)_n$—$NR_{11}SO_2R_{12}$, wherein the alkenyl and cycloalkyl may be optionally substituted with one or more $R_{13}$'s; or $R_1$ is selected from the group consisting of:

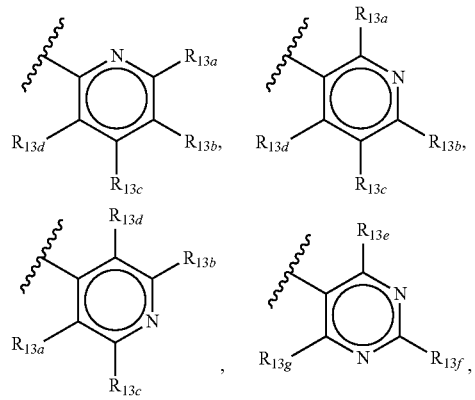

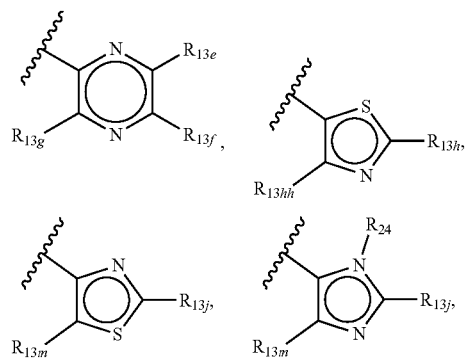

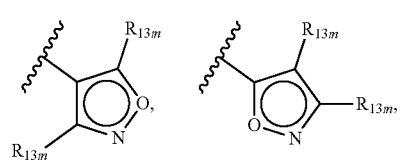

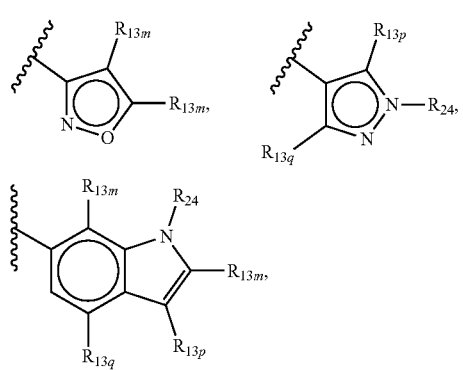

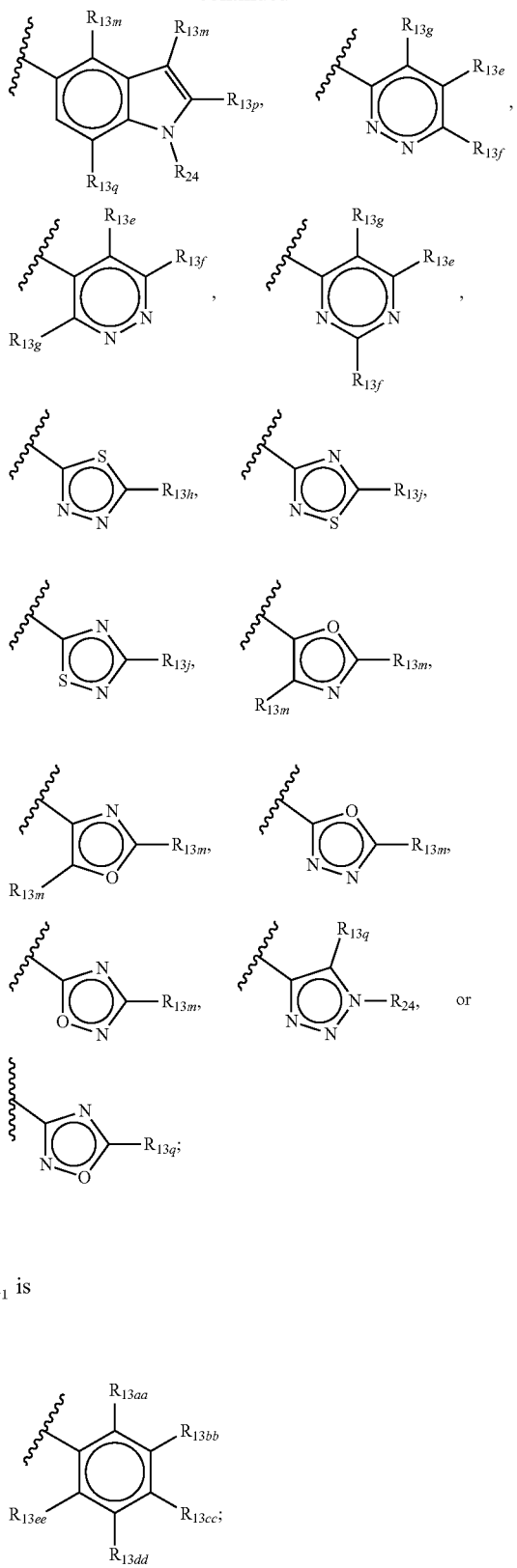

or $R_1$ is $R_2$ is $C_{1-10}$ alkyl, cyclopropyl optionally substituted with one or more $R_{13}$'s; or $C_{4-10}$ cycloalkyl optionally substituted with one or more $R_{13bb}$'s; or R₂ is

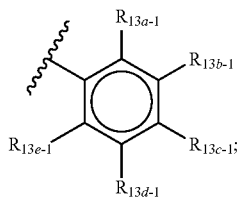

or

R₂ is selected from the group consisting of:

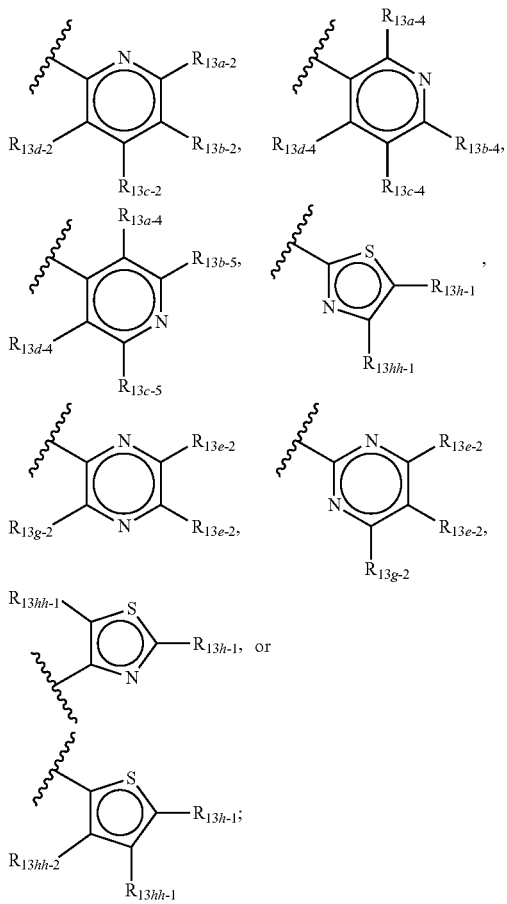

R₁₁ and R₁₂, at each occurrence, are independently selected from H, $C_{1-10}$ alkyl, halo$C_{1-10}$ alkyl, $C_{3-10}$ cycloalkyl, $C_{6-10}$aryl, a 4- to 12-membered heteroaryl and a 4- to 12-membered heterocyclyl, wherein the alkyl, cycloalkyl, aryl, heteroaryl and heterocyclyl may be optionally substituted with one or more $R_{13}$'s and the heteroaryl and heterocyclyl consist of carbon atoms and 1, 2, 3, or 4 heteroatoms independently selected from the group consisting of N, S, or O; or R₁₁ and R₁₂ are taken together with the nitrogen to which they are attached to form a 4- to 12-membered heterocyclyl, wherein the heterocyclyl may be optionally substituted with one or more $R_{13}$'s and the heterocyclyl consists of carbon atoms and 1, 2, 3, or 4 heteroatoms independently selected from the group consisting of N, S, or O;

$R_{13}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO₂, —(CH₂)$_m$—SO₂R₁₄, —CONR₁₄R₁₄, —(CH₂)$_m$—SO₂NR₁₄R₁₄, —(CH₂)$_m$—NR₁₄SO₂R₁₄, —(CH₂)$_n$—NR₁₄SO₂NR₁₄R₁₄, —NR₁₄SO₂NR₁₄R₁₄, —CO₂NR₁₄R₁₄, —NR₁₄CO₂NR₁₄R₁₄, —NR₁₄COR₁₄, —SO₂NR₁₄COR₁₄, —SO₂NR₁₄CONR₁₄R₁₄, —NR₁₄CO₂R₁₄, —CO₂R₁₄ or —NR₁₄R₁₄, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O; provided that when $R_{13}$ is alkyl substituted with one $R_{14a}$, $R_{14a}$ is not —OH;

$R_{13a}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO₂, —(CH₂)$_m$—SO₂R₁₄, —NR₁₄SO₂R₁₄, —CONR₁₄R₁₄, —(CH₂)$_m$—NR₁₄SO₂R₁₄, —(CH₂)$_n$—NR₁₄SO₂NR₁₄R₁₄, —NR₁₄SO₂NR₁₄R₁₄, —CO₂NR₁₄R₁₄, —NR₁₄CO₂NR₁₄R₁₄, —NR₁₄COR₁₄, —SO₂NR₁₄COR₁₄, —SO₂NR₁₄CONR₁₄R₁₄, —NR₁₄CO₂R₁₄, —CO₂R₁₄ or —NR₁₄R₁₄, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13aa}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO₂, —(CH₂)$_m$—SO₂R₁₄, —NR₁₄SO₂R₁₄, —CONR₁₄R₁₄, —(CH₂)$_m$—SO₂NR₁₄R₁₄, —(CH₂)$_m$—NR₁₄SO₂R₁₄, —(CH₂)$_n$—NR₁₄SO₂NR₁₄R₁₄, —NR₁₄SO₂NR₁₄R₁₄, —CO₂NR₁₄R₁₄, —NR₁₄CO₂NR₁₄R₁₄, —NR₁₄COR₁₄, —SO₂NR₁₄COR₁₄, —SO₂NR₁₄CONR₁₄R₁₄, —NR₁₄CO₂R₁₄, —CO₂R₁₄ or —NR₁₄R₁₄, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO₂, —(CH₂)$_m$—SO₂R₁₄, —NR₁₄SO₂R₁₄, —CONR₁₄R₁₄, —(CH₂)$_m$—SO₂NR₁₄R₁₄, —(CH₂)$_m$—NR₁₄SO₂R₁₄, —(CH₂)$_n$—NR₁₄SO₂NR₁₄R₁₄, —NR₁₄SO₂NR₁₄R₁₄, —CO₂NR₁₄R₁₄, —NR₁₄CO₂NR₁₄R₁₄, —NR₁₄COR₁₄, —SO₂NR₁₄COR₁₄, —SO₂NR₁₄CONR₁₄R₁₄, —NR₁₄CO₂R₁₄, —CO₂R₁₄, —NR₁₄R₁₄, —NR₁₄CONR₁₄R₁₄, or —CONR₁₄OR₁₄, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a-2}$, at each occurrence, is independently H, —OH, F, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13a-4}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13b}$, at each occurrence, is independently H, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13bb}$, at each occurrence, is independently H, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13b-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13b-2}$, at each occurrence, is independently H, —OH, Cl, Br, I, $C_{1-10}$ alkyl, $C_{1-10}$ alkoxy, halo$C_{2-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13b-4}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13b-5}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

$R_{13c}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—

$NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-NR_{14}CO_2R_{14}$, $-CO_2R_{26}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13cc}$, at each occurrence, is independently H, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, $-CN$, $-NO_2$, $-(CH_2)_m-SO_2R_{14}$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-SO_2NR_{14}CONR_{14}R_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c-1}$, at each occurrence, is independently H, $-OH$, F, Cl, Br, I, $C_{1-10}$ alkyl, $C_{1-10}$ alkoxy, halo$C_{2-10}$ alkyl, $C_{3-10}$ cycloalkyl, $C_{2-12}$ alkenyl, $C_{2-12}$ alkynyl, $C_{6-10}$aryl, a 6- to 12-membered heteroaryl, a 6- to 12-membered heterocyclyl, a 4- to 12-membered heteroaryl-$C_{1-10}$ alkyl, $-NO_2$, $-NR_{14}SO_2R_{14}$, $-(CH_2)_m-NR_{14}SO_2R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-SO_2NR_{14}CONR_{14}R_{14}$, $-NR_{14}CO_2R_{14}$ or $-NR_{14}R_{14}$, wherein the alkyl, cycloalkyl, alkenyl, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c-2}$, at each occurrence, is independently H, $-OH$, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, $-CN$, $-NO_2$, $-(CH_2)_m-SO_2R_{14}$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-SO_2NR_{14}CONR_{14}R_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c-4}$, at each occurrence, is independently H, $-OH$, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, $-CN$, $-NO_2$, $-(CH_2)_m-SO_2R_{14}$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-SO_2NR_{14}CONR_{14}R_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c-5}$, at each occurrence, is independently H, $-OH$, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, $-CN$, $-NO_2$, $-(CH_2)_m-SO_2R_{14}$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-SO_2NR_{14}CONR_{14}R_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d}$, at each occurrence, is independently H, $-OH$, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, $-CN$, $-NO_2$, $-(CH_2)_m-SO_2R_{14}$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-SO_2NR_{14}CONR_{14}R_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13dd}$, at each occurrence, is independently H, $-OH$, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, $-CN$, $-NO_2$, $-(CH_2)_m-SO_2R_{14}$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-SO_2NR_{14}CONR_{14}R_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d-1}$, at each occurrence, is independently H, $-OH$, F, Cl, Br, I, $C_{1-10}$ alkyl, $C_{1-10}$ alkoxy, halo$C_{2-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, $-CN$, $-NO_2$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-SO_2NR_{14}CONR_{14}R_{14}$, $-NR_{14}CO_2R_{14}$ or $-CO_2R_{14}$, wherein the alkyl, cycloalkyl, alkenyl, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d-2}$, at each occurrence, is independently H, —OH, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d-4}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13ee}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e-1}$, at each occurrence, is independently H, —OH, Cl, Br, I, $C_{1-10}$ alkyl, $C_{1-10}$ alkoxy, halo$C_{2-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e-2}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13f}$, at each occurrence, is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13g}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13g-2}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$_{14}$, —NR$_{14}$SO$_2$R$_{14}$, —CONR$_{14}$R$_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13h}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13h-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{7-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, —$NR_{14}CONR_{14}R_{14}$ or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13hh}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13hh-1}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13hh-2}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13m}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13p}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13q}$, at each occurrence, is independently H, —OH, F, Cl, Br, I, $C_{2-10}$ alkyl, $C_{1-10}$ alkoxy, halo$C_{2-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NO_2$, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be optionally substituted with be optionally substituted with 0-3 $R_{14a}$ and the heteroaryl and heterocyclyl consist of carbon atoms and 1, 2, 3, or 4 heteroatoms independently selected from the group consisting of N, S, or O; or two $R_{14}$'s are taken together with the atoms to which they are attached to form a cyclic ring, wherein the cyclic ring may be optionally substituted with one or more $R_{24a}$'s and optionally contain 1, 2, 3, or 4 heteroatoms independently selected from the group consisting of N, S, or O;

$R_{14a}$, at each occurrence, is independently selected from F, Cl, Br, I, $C_{1-10}$ alkyl, haloC$_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —NO$_2$, —CO$_2$R$_{26}$, —CO$_2$NR$_{24}$R$_{24}$, —OCF$_3$, —OR$_{25}$, —CONR$_{24}$R$_{24}$, —COR$_{24}$, —SO$_2$R$_{24}$, —NR$_{24}$R$_{24}$ or $C_{6-10}$arylC$_{1-10}$alkyl, wherein the heteroaryl and heterocyclyl consist of carbon atoms and 1, 2, 3, or 4 heteroatoms independently selected from the group consisting of N, S, or O;

$R_{24}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the alkyl, aryl, heteroaryl and heterocyclyl may be optionally substituted with one or more $R_{24}$a'S and the heteroaryl and heterocyclyl consist of carbon atoms and 1, 2, 3, or 4 heteroatoms independently selected from the group consisting of N, S, or O; or two $R_{24}$'s are taken together with the atoms to which they are attached to form a cyclic ring, wherein the cyclic ring may be optionally substituted with one or more $R_{24a}$'s and optionally contain 1, 2, 3, or 4 heteroatoms independently selected from the group consisting of N, S, or O;

$R_{24a}$, at each occurrence, is independently selected from F, Cl, Br, I, $C_{1-10}$ alkyl, haloC$_{1-10}$alkyl, $C_{6-10}$aryl, $C_{3-10}$cycloalkyl, a 4- to 12-membered heteroaryl, a 4- to 12-membered heterocyclyl, —CN, —NO$_2$, —CO$_2$R$_{25}$, —OCF$_3$, —OR$_{25}$, —CONR$_{25}$R$_{25}$, —COR$_{25}$, —NR$_{25}$R$_{25}$ or $C_{6-10}$arylC$_{1-10}$alkyl, wherein the heteroaryl and heterocyclyl consist of carbon atoms and 1, 2, 3, or 4 heteroatoms independently selected from the group consisting of N, S, or O;

$R_{25}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O; and $R_{26}$, at each occurrence, is independently selected from $C_{1-10}$alkyl, haloC$_{1-10}$ alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O.

In one embodiment, compounds, enantiomers, diastereomers, tautomers, prodrugs or salts thereof, of formula I, are provided wherein:

X is H, F, Cl, Br, I, $C_{1-10}$ alkyl, $C_{1-10}$ alkoxy, haloC$_{1-10}$ alkyl, 4- to 12-membered heterocyclyl, —CO$_2$R$_{11}$ or —NR$_{11}$R$_{12}$;

Y is H, F, Cl, Br, I, $C_{1-10}$ alkyl, $C_{1-10}$ alkoxy, haloC$_{1-10}$ alkyl, 4- to 12-membered heterocyclyl, —CO$_2$R$_{11}$ or —NR$_{11}$R$_{12}$;

Z is H, Cl, Br, I, $C_{1-10}$ alkyl, $C_{1-10}$ alkoxy, haloC$_{1-10}$ alkyl, 4- to 12-membered heterocyclyl or —NR$_{11}$R$_{12}$;

A is —(CH$_2$)$_m$—R$_2$;

m is 0 to 3;

n is 1 to 3;

$R_1$ is F, Cl, Br, I, $C_{1-10}$ alkyl, $C_{2-12}$ alkenyl, $C_{3-10}$ cycloalkyl, wherein the alkenyl and cycloalkyl may be optionally substituted with one or more $R_{13}$'s; or $R_1$ is selected from the group consisting of:

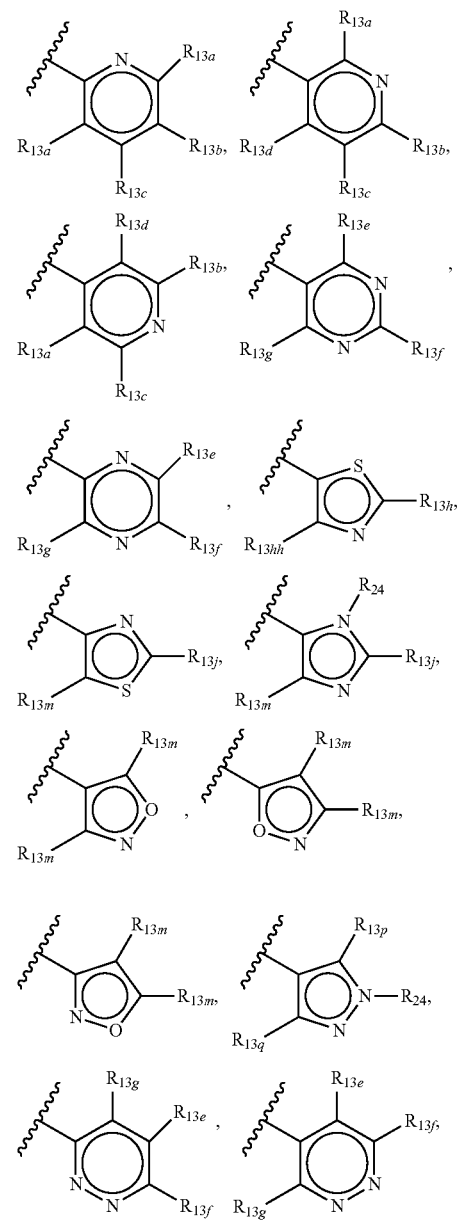

-continued

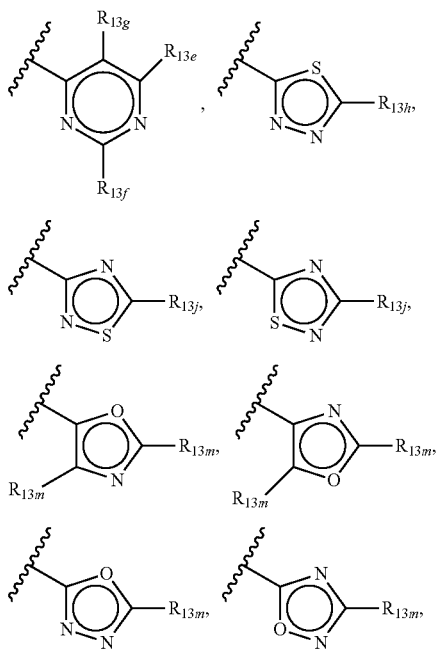

or
R₁ is

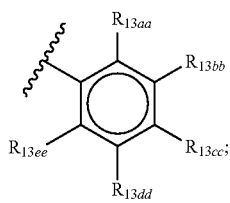

R₂ is cyclopropyl optionally substituted with one or more R₁₃'S; or C₄₋₁₀ cycloalkyl optionally substituted with one or more R₁₃ᵦᵦ's; or R₂ is

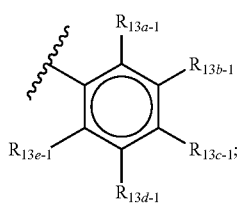

or
R₂ is selected from the group consisting of:

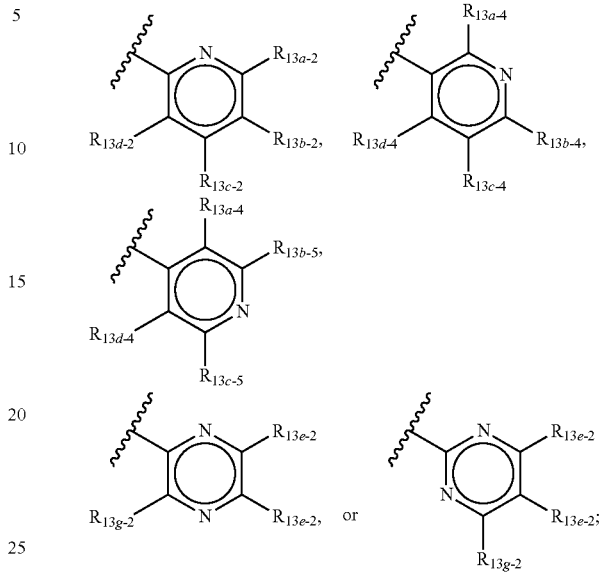

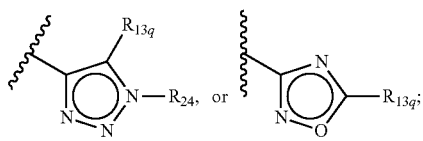

$R_{11}$ and $R_{12}$, at each occurrence, are independently selected from H, $C_{1-10}$ alkyl, halo$C_{1-10}$ alkyl, $C_{3-10}$ cycloalkyl, $C_{6-10}$aryl, a 4- to 12-membered heteroaryl and a 4- to 12-membered heterocyclyl, wherein the alkyl, cycloalkyl, aryl, heteroaryl and heterocyclyl may be optionally substituted with one or more $R_{13}$'s and the heteroaryl and heterocyclyl consist of carbon atoms and 1, 2, 3, or 4 heteroatoms independently selected from the group consisting of N, S, or O; or $R_{11}$ and $R_{12}$ are taken together with the nitrogen to which they are attached to form a 4- to 12-membered heterocyclyl, wherein the heterocyclyl may be optionally substituted with one or more $R_{13}$'s and the heterocyclyl consists of carbon atoms and 1, 2, 3, or 4 heteroatoms independently selected from the group consisting of N, S, or O;

$R_{13}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —(CH$_2$)$_m$—SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O; provided that when $R_{13}$ is alkyl substituted with one $R_{14a}$, $R_{14a}$ is not —OH;

$R_{13a}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13aa}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{6-10}$aryl, a 4- to 12-membered heteroaryl, a 4- to 12-membered heterocyclyl, a 4- to 12-membered heteroaryl-C$_{1-10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13a\text{-}1}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{6-10}$aryl, a 4- to 12-membered heteroaryl, a 4- to 12-membered heterocyclyl, a 4- to 12-membered heteroaryl-C$_{1-10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$, —NR$_{14}$R$_{14}$, —NR$_{14}$CONR$_{14}$R$_{14}$, or —CONR$_{14}$OR$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13a\text{-}2}$, at each occurrence, is independently H, —OH, F, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{6-10}$aryl, a 4- to 12-membered heteroaryl, a 4- to 12-membered heterocyclyl, a 4- to 12-membered heteroaryl-C$_{1-10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13a\text{-}4}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{6-10}$aryl, a 4- to 12-membered heteroaryl, a 4- to 12-membered heterocyclyl, a 4- to 12-membered heteroaryl-C$_{1-10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13b}$, at each occurrence, is independently H, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{6-10}$aryl, a 4- to 12-membered heteroaryl, a 4- to 12-membered heterocyclyl, a 4- to 12-membered heteroaryl-C$_{1-10}$ alkyl, —CN, —(CH$_2$)$_m$—SO$_2$R$_{14}$, —NR$_{14}$SO$_2$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13bb}$, at each occurrence, is independently H, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{6-10}$aryl, a 4- to 12-membered heteroaryl, a 4- to 12-membered heterocyclyl, a 4- to 12-membered heteroaryl-C$_{1-10}$ alkyl, —CN, —(CH$_2$)$_m$—SO$_2$R$_{14}$, —NR$_{14}$SO$_2$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13b\text{-}1}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{6-10}$aryl, a 4- to 12-membered heteroaryl, a 4- to 12-membered heterocyclyl, a 4- to 12-membered heteroaryl-C$_{1-10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, aryl, heteroaryl and heterocyclyl may be optionally substituted with one or more R$_{14a}$'s and the heteroaryl and heterocyclyl consist of carbon atoms and 1, 2, 3, or 4 heteroatoms independently selected from the group consisting of N, S, or O;

R$_{13b\text{-}2}$, at each occurrence, is independently H, —OH, Cl, Br, I, C$_{1-10}$ alkyl, C$_{1-10}$ alkoxy, haloC$_{2-10}$ alkyl, C$_{3-10}$ cycloalkyl, C$_{2-12}$ alkenyl, C$_{6-10}$aryl, a 4- to 12-membered heteroaryl, a 4- to 12-membered heterocyclyl, a 4- to 12-membered heteroaryl-C$_{1-10}$ alkyl, —CN, —(CH$_2$)$_m$—SO$_2$R$_{14}$, —NR$_{14}$SO$_2$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b\text{-}4}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b\text{-}5}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{6\text{-}10}$aryl, a 4- to 12-membered heteroaryl, a 4- to 12-membered heterocyclyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —NR$_{14}$CO$_2$R$_{14}$, —CO$_2$R$_{26}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13cc}$, at each occurrence, is independently H, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c\text{-}1}$, at each occurrence, is independently H, —OH, F, Cl, Br, I, $C_{1\text{-}10}$ alkyl, $C_{1\text{-}10}$ alkoxy, halo$C_{2\text{-}10}$ alkyl, $C_{3\text{-}10}$ cycloalkyl, $C_{2\text{-}12}$ alkenyl, $C_{6\text{-}10}$aryl, a 6- to 12-membered heteroaryl, a 6- to 12-membered heterocyclyl, a 4- to 12-membered heteroaryl-$C_{1\text{-}10}$ alkyl, —NR$_{14}$SO$_2$R$_{14}$, —(CH$_2$)$_m$—NR$_{14}$SO$_2$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$ or —NR$_{14}$R$_{14}$, wherein the alkyl, cycloalkyl, alkenyl, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c\text{-}2}$, at each occurrence, is independently H, —OH, F, Cl, Br, I, $C_{2\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c\text{-}4}$, at each occurrence, is independently H, —OH, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c\text{-}5}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d}$, at each occurrence, is independently H, —OH, F, Cl, Br, I, $C_{1\text{-}10}$ alkyl, $C_{2\text{-}10}$ alkoxy, halo$C_{1\text{-}10}$ alkyl, $C_{3\text{-}10}$ cycloalkyl, $C_{2\text{-}12}$ alkenyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —(CH$_2$)$_m$—

$SO_2R_{14}$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-SO_2NR_{14}CONR_{14}R_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13dd}$, at each occurrence, is independently H, $-OH$, F, Cl, Br, I, $C_{1-10}$ alkyl, $C_{1-10}$ alkoxy, haloC$_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-C$_{1-10}$ alkyl, $-CN$, $-(CH_2)_m-SO_2R_{14}$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-SO_2NR_{14}CONR_{14}R_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d-1}$, at each occurrence, is independently H, $-OH$, F, Cl, Br, I, $C_{1-10}$ alkyl, $C_{1-10}$ alkoxy, haloC$_2$-10 alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-C$_{1-10}$ alkyl, $-CN$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-SO_2NR_{14}CONR_{14}R_{14}$, $-NR_{14}CO_2R_{14}$ or $-CO_2R_{14}$, wherein the alkyl, cycloalkyl, alkenyl, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d-2}$, at each occurrence, is independently H, $-OH$, Cl, Br, I, $C_{1-10}$ alkyl, $C_{1-10}$ alkoxy, haloC$_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-C$_{1-10}$ alkyl, $-CN$, $-(CH_2)_m-SO_2R_{14}$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-SO_2NR_{14}CONR_{14}R_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d-4}$, at each occurrence, is independently H, $-OH$, F, Cl, Br, I, $C_{1-10}$ alkyl, $C_{1-10}$ alkoxy, haloC$_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-C$_{1-10}$ alkyl, $-CN$, $-(CH_2)_m-SO_2R_{14}$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-SO_2NR_{14}CONR_{14}R_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e}$, at each occurrence, is independently H, $-OH$, F, Cl, Br, I, $C_{1-10}$ alkyl, $C_{1-10}$ alkoxy, haloC$_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-C$_{1-10}$ alkyl, $-CN$, $-(CH_2)_m-SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-SO_2NR_{14}CONR_{14}R_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13ee}$, at each occurrence, is independently H, $-OH$, F, Cl, Br, I, $C_{1-10}$ alkyl, $C_{1-10}$ alkoxy, haloC$_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-C$_{1-10}$ alkyl, $-CN$, $-(CH_2)_m-SO_2R_{14}$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-SO_2NR_{14}CONR_{14}R_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e-1}$, at each occurrence, is independently H, $-OH$, Cl, Br, I, $C_{1-10}$ alkyl, $C_{1-10}$ alkoxy, haloC$_{2-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-C$_{1-10}$ alkyl, $-CN$, $-(CH_2)_m-SO_2R_{14}$, $-NR_{14}SO_2R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-SO_2NR_{14}COR_{14}$, $-SO_2NR_{14}CONR_{14}R_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e-2}$, at each occurrence, is independently H, $-OH$, F, Cl, Br, I, $C_{1-10}$ alkyl, $C_{1-10}$ alkoxy, haloC$_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-C$_{1-10}$ alkyl, $-CN$, $-(CH_2)_m-SO_2R_{14}$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-SO_2NR_{14}COR_{14}$, $-SO_2NR_{14}CONR_{14}R_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13f}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13g}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13g-2}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13h}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13hh}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13m}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$NR$_{14}$R$_{14}$, —NR$_{14}$CO$_2$NR$_{14}$R$_{14}$, —NR$_{14}$COR$_{14}$, —SO$_2$NR$_{14}$COR$_{14}$, —SO$_2$NR$_{14}$CONR$_{14}$R$_{14}$, —NR$_{14}$CO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be optionally substituted with be optionally substituted with 0-3 $R_{14a}$ and the heteroaryl and heterocyclyl consist of carbon atoms and 1, 2, 3, or 4 heteroatoms independently selected from the group consisting of N, S, or O;

$R_{14a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —CO$_2$R$_{26}$, —CO$_2$NR$_{24}$R$_{24}$, —OCF$_3$, —OR$_{25}$, —CONR$_{24}$R$_{24}$, —SO$_2$R$_{24}$, —NR$_{24}$R$_{24}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{24}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the alkyl, aryl, heteroaryl and heterocyclyl may be optionally substituted with one or more $R_{24a}$'s and the heteroaryl and heterocyclyl consist of carbon atoms and 1, 2, 3, or 4 heteroatoms independently selected from the group consisting of N, S, or O;

$R_{24a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, —CN, —CO$_2$R$_{25}$, —OCF$_3$, —OR$_{25}$, —CONR$_{25}$R$_{25}$, —NR$_{25}$R$_{25}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{25}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O; and $R_{26}$, at each occurrence, is independently selected from $C_{1-10}$alkyl, halo$C_{1-10}$ alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O.

In yet another embodiment, compounds, enantiomers, diastereomers, tautomers, prodrugs or salts thereof, of formula I, are provided wherein:

X is H, F, Cl, Br, I, $C_{1-10}$ alkoxy, halo$C_{1-10}$ alkyl, 4- to 12-membered heterocyclyl, —$CO_2R_{11}$ or —$NR_{11}R_{12}$;

Y is H, F, Cl, Br, I, $C_{1-10}$ alkoxy, halo$C_{1-10}$ alkyl, 4- to 12-membered heterocyclyl, —$CO_2R_{11}$ or —$NR_{11}R_{12}$;

Z is H, Cl, Br, I, $C_{1-10}$ alkoxy, halo$C_{1-10}$ alkyl, 4- to 12-membered heterocyclyl or —$NR_{11}R_{12}$;

A is —$(CH_2)_m$—$R_2$;

m is 0 to 3;

n is 1 to 3;

$R_1$ is $C_1$, $C_{2-12}$ alkenyl, $C_{3-10}$ cycloalkyl, wherein the alkenyl and cycloalkyl may be optionally substituted with one or more $R_{13}$'s; or $R_1$ is selected from the group consisting of:

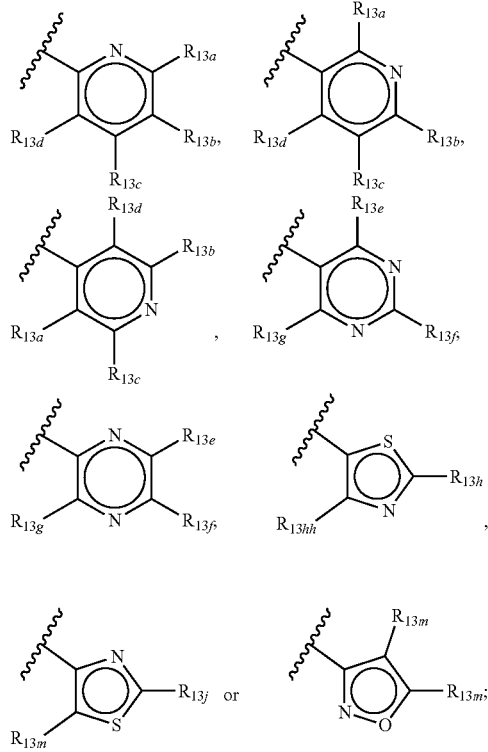

$R_1$ is

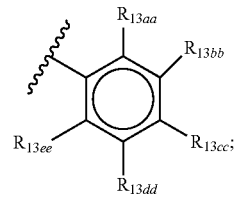

$R_2$ is cyclopropyl optionally substituted with one or more $R_{13}$'s; or $R_2$ is

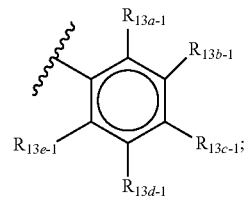

or $R_2$ is selected from the group consisting of:

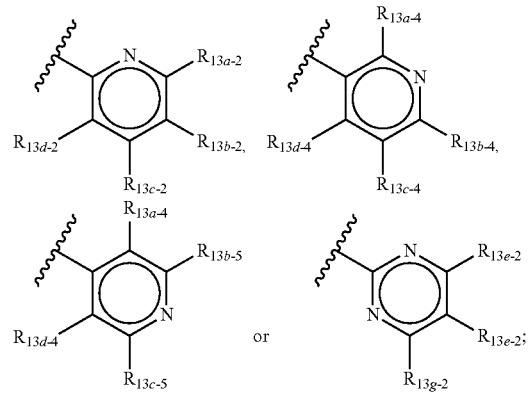

$R_{11}$ and $R_{12}$, at each occurrence, are independently selected from H, $C_{1-10}$ alkyl, halo$C_{1-10}$ alkyl, $C_{3-10}$ cycloalkyl, $C_{6-10}$aryl, a 4- to 12-membered heteroaryl and a 4- to 12-membered heterocyclyl, wherein the alkyl, cycloalkyl, aryl, heteroaryl and heterocyclyl may be optionally substituted with one or more $R_{13}$'s and the heteroaryl and heterocyclyl consist of carbon atoms and 1, 2, 3, or 4 heteroatoms independently selected from the group consisting of N, S, or O;

$R_{13}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O; provided that when $R_{13}$ is alkyl substituted with one $R_{14a}$, $R_{14a}$ is not —OH;

$R_{13a}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13aa}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$, —$NR_{14}CONR_{14}R_{14}$, or —$CONR_{14}OR_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a-2}$, at each occurrence, is independently H, —OH, F, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a-4}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b}$, at each occurrence, is independently H, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13bb}$, at each occurrence, is independently H, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b-1}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b\text{-}2}$, at each occurrence, is independently H, —OH, Cl, Br, I, $C_{1\text{-}10}$ alkyl, $C_{1\text{-}10}$ alkoxy, halo$C_{2\text{-}10}$ alkyl, $C_{3\text{-}10}$ cycloalkyl, $C_{2\text{-}12}$ alkenyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —$(CH_2)_m$—$SO_2R_{14}$, —$NR_{14}SO_2R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b\text{-}4}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$NR_{14}SO_2NR_{14}R_{14}$, —$CO_2NR_{14}R_{14}$, —$NR_{14}CO_2NR_{14}R_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b\text{-}5}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$NR_{14}CO_2R_{14}$, —$CO_2R_{26}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13cc}$, at each occurrence, is independently H, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c\text{-}1}$, at each occurrence, is independently H, —OH, F, Cl, Br, I, $C_{1\text{-}10}$ alkyl, $C_{1\text{-}10}$ alkoxy, halo$C_{2\text{-}10}$ alkyl, $C_{3\text{-}10}$ cycloalkyl, $C_{2\text{-}12}$ alkenyl, $C_{6\text{-}10}$aryl, a 6- to 12-membered heteroaryl, a 6- to 12-membered heterocyclyl, a 4- to 12-membered heteroaryl-$C_{1\text{-}10}$ alkyl, —$NR_{14}SO_2R_{14}$, —$(CH_2)_m$—$NR_{14}SO_2R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$ or —$NR_{14}R_{14}$, wherein the alkyl, cycloalkyl, alkenyl, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c\text{-}2}$, at each occurrence, is independently H, —OH, F, Cl, Br, I, $C_{2\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c\text{-}4}$, at each occurrence, is independently H, —OH, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c\text{-}5}$, at each occurrence, is independently H, —OH, F, Cl, Br, I, $C_{1\text{-}10}$ alkyl, $C_{1\text{-}10}$ alkoxy, halo$C_{1\text{-}10}$ alkyl, $C_{3\text{-}10}$ cycloalkyl, $C_{2\text{-}12}$ alkenyl, $C_{6\text{-}10}$aryl, a 4- to 12-membered heteroaryl, a 4- to 12-membered heterocyclyl, a 4- to 12-membered heteroaryl-$C_{1\text{-}10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d}$, at each occurrence, is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13dd}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d-1}$, at each occurrence, is independently H, —OH, F, Cl, Br, I, $C_{1-10}$ alkyl, $C_{1-10}$ alkoxy, halo$C_{2-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$ or —$CO_2R_{14}$, wherein the alkyl, cycloalkyl, alkenyl, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d-2}$, at each occurrence, is independently H, —OH, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d-4}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13ee}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e-1}$, at each occurrence, is independently H, —OH, Cl, Br, I, $C_{1-10}$ alkyl, $C_{1-10}$ alkoxy, halo$C_{2-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13e-2}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13f}$, at each occurrence, is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13g}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13g-2}$, at each occurrence, is independently H, —OH, F, Cl, Br, I, $C_{2-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be optionally substituted with be optionally substituted with 0-3 $R_{14a}$ and the heteroaryl and heterocyclyl consist of carbon atoms and 1, 2, 3, or 4 heteroatoms independently selected from the group consisting of N, S, or O;

$R_{14a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —$CO_2R_{26}$, —$CO_2NR_{24}R_{24}$, —$OCF_3$, —$OR_{25}$, —$CONR_{24}R_{24}$, —$SO_2R_{24}$, —$NR_{24}R_{24}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{24}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the alkyl, aryl, heteroaryl and heterocyclyl may be optionally substituted with one or more $R_{24}$a'S and the heteroaryl and heterocyclyl consist of carbon atoms and 1, 2, 3, or 4 heteroatoms independently selected from the group consisting of N, S, or O;

$R_{24a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, —CN, —$CO_2R_{25}$, —$OCF_3$, —$OR_{25}$, —$CONR_{25}R_{25}$, —$NR_{25}R_{25}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{25}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O; and $R_{26}$, at each occurrence, is independently selected from $C_{1-10}$alkyl, halo$C_{1-10}$ alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O.

In yet another embodiment, compounds, enantiomers, diastereomers, tautomers, prodrugs or salts thereof, of formula I, are provided wherein the compounds are compounds of formula Ia:

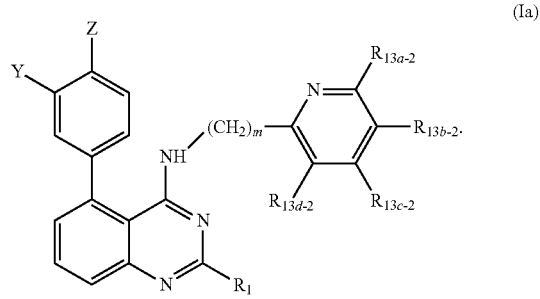

(Ia)

In yet another embodiment, compounds, enantiomers, diastereomers, tautomers, prodrugs or salts thereof, of formula I, are provided wherein the compounds are compounds of formula Ib or Ic:

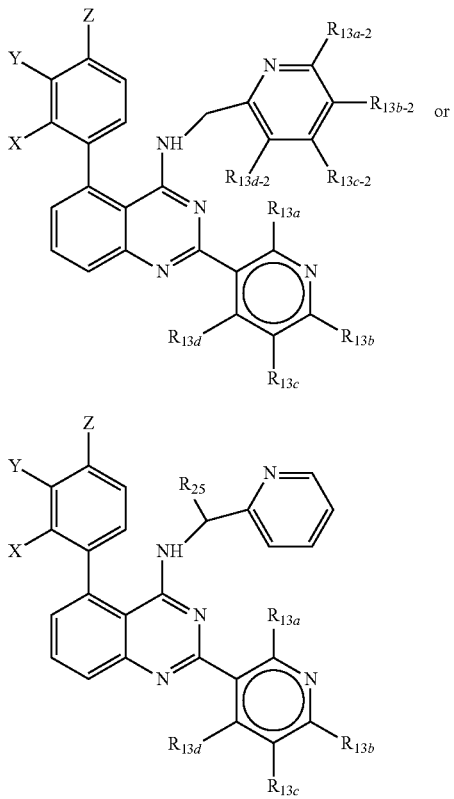

wherein:

X is H, F, Cl, Br, I, $C_{1-10}$ alkoxy, halo$C_{1-10}$ alkyl, 4- to 12-membered heterocyclyl, —$CO_2R_{11}$ or —$NR_{11}R_{12}$;

Y is H, F, Cl, Br, I, $C_{1-10}$ alkoxy, halo$C_{1-10}$ alkyl, 4- to 12-membered heterocyclyl, —$CO_2R_{11}$ or —$NR_{11}R_{12}$;

Z is H, Cl, Br, I, $C_{1-10}$ alkoxy, halo$C_{1-10}$ alkyl, 4- to 12-membered heterocyclyl or —$NR_{11}R_{12}$;

$R_{11}$ and $R_{12}$, at each occurrence, are independently selected from H, $C_{1-10}$ alkyl, halo$C_{1-10}$ alkyl, $C_{3-10}$ cycloalkyl, $C_{6-10}$aryl, a 4- to 12-membered heteroaryl and a 4- to 12-membered heterocyclyl, wherein the alkyl, cycloalkyl, aryl, heteroaryl and heterocyclyl may be optionally substituted with one or more $R_{13}$'s and the heteroaryl and heterocyclyl consist of carbon atoms and 1, 2, 3, or 4 heteroatoms independently selected from the group consisting of N, S, or O;

$R_{13}a$ is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a-2}$ is independently H, —OH, F, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b}$ is independently H, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$CONR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$, —$NR_{14}R_{14}$ or —$NR_{14}CONR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b-2}$ is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13}c$ is independently H, —OH, Cl, Br, I, $C_{1-10}$ alkyl, hydroxy$C_{1-10}$ alkyl, cyano$C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, —CN, —$(CH_2)_m$—$SO_2R_{14}$, —$(CH_2)_n$—$OCONR_{14}R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$NR_{14}CO_2R_{14}$, —$CO_2R_{26}$, —$NR_{14}R_{14}$, —C(=$NOR_{14}$)$NR_{14}R_{14}$ or —$NR_{14}CONR_{14}R_{14}$, wherein the cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, or 3 heteroatoms independently selected from the group consisting of N, S, or O;

$R_{13c-2}$ is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d}$ is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$(CH_2)_m$—$SO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d-2}$ is independently H, —OH, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$SO_2NR_{14}COR_{14}$, —$SO_2NR_{14}CONR_{14}R_{14}$, —$NR_{14}CO_2R_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be optionally substituted with be optionally substituted with 0-3 $R_{14a}$ and the heteroaryl and heterocyclyl consist of carbon atoms and 1, 2, 3, or 4 heteroatoms independently selected from the group consisting of N, S, or O;

$R_{14a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —$CO_2H$, —$CO_2R_{26}$, —$OCONR_{24}R_{24}$, —$CO_2NR_{24}R_{24}$, —$OCF_3$, —$OR_{25}$, —$CONR_{24}R_{24}$, —$SO_2R_{24}$, —$NR_{24}R_{24}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{24}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the alkyl, aryl, heteroaryl and heterocyclyl may be optionally substituted with one or more $R_{24}a$'S and the heteroaryl and heterocyclyl consist of carbon atoms and 1, 2, 3, or 4 heteroatoms independently selected from the group consisting of N, S, or O; or two $R_{24}$'s are taken together with the atoms to which they are attached to form a cyclic ring, wherein the cyclic ring may be optionally substituted with one or more $R_{24a}$'s and optionally contain 1, 2, 3, or 4 heteroatoms independently selected from the group consisting of N, S, or O;

$R_{24a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, —CN, —$CO_2R_{25}$, —$OCF_3$, —$OR_{25}$, —$CONR_{25}R_{25}$, —$NR_{25}R_{25}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{25}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O; and $R_{26}$, at each occurrence, is independently selected from $C_{1-10}$alkyl, halo$C_{1-10}$ alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O;

provided that X, Y, Z, $R_{13a}$, $R_{13b}$, $R_{13d}$, $R_{13a-2}$, $R_{13b-2}$, $R_{13c-2}$ and $R_{13d-2}$ is not all H when $R_{13}c$ is —C(=O)N$(C_2H_4OCH_3)_2$, —$SO_2N(C_2H_4OH)_2$.

In yet another embodiment, compounds, enantiomers, diastereomers, tautomers, prodrugs or salts thereof, of formula Ib are provided.

In still yet another embodiment, compounds, enantiomers, diastereomers, tautomers, prodrugs or salts thereof, of formula Ib or Ic, are provided wherein:

X is H, F, Cl, Br, I, $C_{1-10}$ alkoxy, halo$C_{1-10}$ alkyl, —$CO_2R_{11}$ or —$NR_{11}R_{12}$;

Y is H, F, Cl, Br, I, $C_{1-10}$ alkoxy, halo$C_{1-10}$ alkyl, —$CO_2R_{11}$ or —$NR_{11}R_{12}$;

Z is H, Cl, Br, I, $C_{1-10}$ alkoxy, halo$C_{1-10}$ alkyl or —$NR_{11}R_{12}$;

$R_{11}$ and $R_{12}$, at each occurrence, are independently selected from H, $C_{1-10}$ alkyl, halo$C_{1-10}$ alkyl, $C_{3-10}$ cycloalkyl, $C_{6-10}$aryl, a 4- to 12-membered heteroaryl and a 4- to 12-membered heterocyclyl, wherein the alkyl, cycloalkyl, aryl, heteroaryl and heterocyclyl may be optionally substituted with one or more $R_{13}$'s and the heteroaryl and heterocyclyl consist of carbon atoms and 1, 2, 3, or 4 heteroatoms independently selected from the group consisting of N, S, or O;

$R_{13}$a is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$(CH_2)_m$—$SO_2R_{14}$, —$NR_{14}SO_2R_{14}$, —$CONR_{14}R_{14}$, —$(CH_2)_m$—$NR_{14}SO_2R_{14}$, —$(CH_2)_n$—$NR_{14}SO_2NR_{14}R_{14}$, —$NR_{14}SO_2NR_{14}R_{14}$, —$CO_2NR_{14}R_{14}$, —$NR_{14}CO_2NR_{14}R_{14}$, —$NR_{14}COR_{14}$, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a-2}$ is independently H, —OH, F, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl- $C_{1-10}$ alkyl, $-(CH_2)_m-SO_2R_{14}$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b}$ is independently H, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, $-CN$, $-(CH_2)_m-SO_2R_{14}$, $-NR_{14}SO_2R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-NR_{14}CO_2R_{14}$, $-CO_2R_{14}$, $-NR_{14}R_{14}$, or $-NR_{14}CONR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b-2}$ is independently H, $-OH$, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, $-CN$, $-(CH_2)_m-SO_2R_{14}$, $-NR_{14}SO_2R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-NR_{14}CO_2NR_{14}R_{14}$, $-NR_{14}COR_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c}$ is independently H, $-OH$, Cl, Br, I, $C_{1-10}$ alkyl, hydroxy$C_{1-10}$ alkyl, cyano$C_{1-10}$ alkyl, $C_{1-10}$ alkoxy, halo $C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, $-CN$, $-(CH_2)_m-SO_2R_{14}$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-NR_{14}SO_2NR_{14}R_{14}$, $-CO_2NR_{14}R_{14}$, $-NR_{14}COR_{14}$, $-SO_2NR_{14}COR_{14}$, $-NR_{14}CO_2R_{14}$, $-CO_2R_{26}$, $-NR_{14}R_{14}$, $-C(=NOR_{14})NR_{14}R_{14}$ or $-NR_{14}CONR_{14}R_{14}$, wherein the cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2 or 3 heteroatoms independently selected from the group consisting of N, S, or O;

$R_{13c-2}$ is independently H, $-OH$, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, $-CN$, $-(CH_2)_m-SO_2R_{14}$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d}$ is independently H, $-OH$, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, $-CN$, $-(CH_2)_m-SO_2R_{14}$, $-NR_{14}SO_2R_{14}$, $-CONR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d-2}$ is independently H, $-OH$, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, $-CN$, $-(CH_2)_m-SO_2R_{14}$, $-NR_{14}SO_2R_{14}$, $-CONR_{14}R_{14}$, $-(CH_2)_m-SO_2NR_{14}R_{14}$, $-(CH_2)_m-NR_{14}SO_2R_{14}$, $-(CH_2)_n-NR_{14}SO_2NR_{14}R_{14}$, $-NR_{14}SO_2NR_{14}R_{14}$, $-CO_2NR_{14}R_{14}$, $-NR_{14}CO_2NR_{14}R_{14}$, $-NR_{14}COR_{14}$, $-NR_{14}CO_2R_{14}$, $-CO_2R_{14}$ or $-NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be optionally substituted with be optionally substituted with 0-3 $R_{14a}$ and the heteroaryl and heterocyclyl consist of carbon atoms and 1, 2, 3, or 4 heteroatoms independently selected from the group consisting of N, S, or O;

$R_{14a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, $-CN$, $-CO_2R_{26}$, $-CO_2NR_{24}R_{24}$, $-OCF_3$, $-OR_{25}$, $-CONR_{24}R_{24}$, $-SO_2R_{24}$, $-NR_{24}R_{24}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{24}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the alkyl, aryl, heteroaryl and heterocyclyl may be optionally substituted with one or more $R_{24}$a'S and the heteroaryl and heterocyclyl consist of carbon atoms and 1, 2, 3, or 4 heteroatoms independently selected from the group consisting of N, S, or O;

$R_{24a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, $-CN$, $-CO_2R_{25}$, $-OCF_3$, $-OR_{25}$, $-CONR_{25}R_{25}$, $-NR_{25}R_{25}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{25}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O; and $R_{26}$, at each occurrence, is independently selected from $C_{1-10}$alkyl, halo$C_{1-10}$ alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O.

In one embodiment, compounds, enantiomers, diastereomers, tautomers, prodrugs or salts thereof, of formula Ib or Ic, are provided wherein:

X is H, F, Cl, Br, I, $C_{1-10}$ alkoxy or halo$C_{1-10}$ alkyl;

Y is H, F, Cl, Br, I, $C_{1-10}$ alkoxy or halo$C_{1-10}$ alkyl;

Z is H, Cl, Br, I, $C_{1-10}$ alkoxy or halo$C_{1-10}$ alkyl;

$R_{13}a$ is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a-2}$ is independently H, —OH, F, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b}$ is independently H, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —(CH$_2$)$_m$—SO$_2$R$_{14}$, —NR$_{14}$SO$_2$R$_{14}$, —CO$_2$NR$_{14}$R$_{14}$, —NR$_{14}$CO$_2$NR$_{14}$R$_{14}$, —NR$_{14}$COR$_{14}$, —NR$_{14}$CO$_2$R$_{14}$, —CO$_2$R$_{14}$, —NR$_{14}$R$_{14}$, or —NR$_{14}$CONR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b-2}$ is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —(CH$_2$)$_m$—SO$_2$R$_{14}$, —NR$_{14}$SO$_2$R$_{14}$, —(CH$_2$)$_m$—SO$_2$NR$_{14}$R$_{14}$, —(CH$_2$)$_m$—NR$_{14}$SO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13}c$ is independently H, —OH, Cl, Br, I, $C_{1-10}$ alkyl, hydroxy$C_{1-10}$ alkyl, cyano$C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —NR$_{14}$SO$_2$NR$_{14}$R$_{14}$, —NR$_{14}$COR$_{14}$, —NR$_{14}$CO$_2$R$_{14}$, —NR$_{14}$R$_{14}$, —C(=NOR$_{14}$)NR$_{14}$R$_{14}$ or —NR$_{14}$CONR$_{14}$R$_{14}$, wherein the cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2 or 3 heteroatoms independently selected from the group consisting of N, S, or O;

$R_{13c-2}$ is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d}$ is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—NR$_{14}$SO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d-2}$ is independently H, —OH, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{14}$ is independently selected from hydrogen, $C_{1-10}$ alkyl, $C_{3-10}$ cycloalkyl, $C_6$-10 aryl, a 4- to 12-membered heteroaryl or a 4- to 12-membered heterocyclyl, wherein the alkyl, cycloalkyl, aryl, heteroaryl and heterocyclyl may be optionally substituted with be optionally substituted with 0-3 $R_{14a}$ and the heteroaryl and heterocyclyl consist of carbon atoms and 1, 2, 3, or 4 heteroatoms independently selected from the group consisting of N, S, or O;

$R_{14a}$ is independently selected from F, Cl, Br, I, $C_{1-10}$ alkyl, halo$C_{1-10}$alkyl, $C_6$-10aryl, $C_{3-10}$cycloalkyl, a 4- to 12-membered heteroaryl, a 4- to 12-membered heterocyclyl, F, Cl, Br, I, —CN, —CO$_2$R$_{26}$, —CO$_2$NR$_{24}$R$_{24}$, —OCF$_3$, —OR$_{25}$, —SO$_2$R$_{24}$, —NR$_{24}$R$_{24}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{24}$ is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the alkyl, aryl, heteroaryl and heterocyclyl may be optionally substituted with one or more $R_{24a}$'s and the heteroaryl and heterocyclyl consist of carbon atoms and 1, 2, 3, or 4 heteroatoms independently selected from the group consisting of N, S, or O;

$R_{24}a$ is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, —CN, —CO$_2$R$_{25}$, —OCF$_3$, —OR$_{25}$, —CONR$_{25}$R$_{25}$, —NR$_{25}$R$_{25}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{25}$ is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O; and $R_{26}$ is independently selected from $C_{1-10}$alkyl, halo$C_{1-10}$alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O.

In another embodiment, compounds, enantiomers, diastereomers, tautomers, prodrugs or salts thereof, of formula Ib or Ic, are provided wherein:

X is H, F, Cl, Br, I, or $C_{1-10}$ alkoxy;

Y is H, F, Cl, Br, I, or $C_{1-10}$ alkoxy;

Z is H, Cl, Br, I, $C_{1-10}$ alkoxy or halo$C_{1-10}$ alkyl;

$R_{13}a$ is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —CONR$_{14}$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a-2}$ is independently H, —OH, F, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CONR$_{14}$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b}$ is independently H, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —CO$_2$NR$_{14}$R$_{14}$, —NR$_{14}$COR$_{14}$, —CO$_2$R$_{14}$, —NR$_{14}$R$_{14}$, or —NR$_{14}$CONR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b-2}$ is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c}$ is independently H, Cl, Br, I, $C_{1-10}$ alkyl, hydroxy$C_{1-10}$ alkyl, cyano$C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, —CN, —(CH$_2$)$_m$—SO$_2$R$_{14}$, —NR$_{14}$SO$_2$R$_{14}$, —CONR$_{14}$R$_{14}$, —(CH$_2$)$_m$—SO$_2$NR$_{14}$R$_{14}$, —(CH$_2$)$_m$—NR$_{14}$SO$_2$R$_{14}$, —NR$_{14}$SO$_2$NR$_{14}$R$_{14}$, —NR$_{14}$COR$_{14}$, —NR$_{14}$CO$_2$R$_{14}$, —NR$_{14}$R$_{14}$, —C(=NOR$_{14}$)NR$_{14}$R$_{14}$ or —NR$_{14}$CONR$_{14}$R$_{14}$, wherein the cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, or 3 heteroatoms independently selected from the group consisting of N, S, or O;

$R_{13c-2}$ is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —(CH$_2$)$_m$—SO$_2$NR$_{14}$R$_{14}$, —(CH$_2$)$_m$—NR$_{14}$SO$_2$R$_{14}$, —(CH$_2$)$_n$—NR$_{14}$SO$_2$NR$_{14}$R$_{14}$, —NR$_{14}$SO$_2$NR$_{14}$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d}$ is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —CONR$_{14}$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d-2}$ is independently H, —OH, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —CONR$_{14}$R$_{14}$, —CO$_2$R$_{14}$ or —NR$_{14}$R$_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{14}$ is independently selected from hydrogen, $C_{1-10}$ alkyl, $C_{3-10}$ cycloalkyl, $C_6$-10 aryl, a 4- to 12-membered heteroaryl or a 4- to 12-membered heterocyclyl, wherein the alkyl, cycloalkyl, aryl, heteroaryl and heterocyclyl may be optionally substituted with be optionally substituted with 0-3 $R_{14a}$ and the heteroaryl and heterocyclyl consist of carbon atoms and 1, 2, 3, or 4 heteroatoms independently selected from the group consisting of N, S, or O;

$R_{14a}$ is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —$CO_2R_{26}$, —$CO_2NR_{24}R_{24}$, —$OCF_3$, —$OR_{25}$, —$SO_2R_{24}$, —$NR_{24}R_{24}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{24}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the alkyl, aryl, heteroaryl and heterocyclyl may be optionally substituted with one or more $R_{24a}$'S and the heteroaryl and heterocyclyl consist of carbon atoms and 1, 2, 3, or 4 heteroatoms independently selected from the group consisting of N, S, or O;

$R_{24a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, —CN, —$CO_2R_{25}$, —$OCF_3$, —$OR_{25}$, —$CONR_{25}R_{25}$, —$NR_{25}R_{25}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{25}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O; and $R_{26}$, at each occurrence, is independently selected from $C_{1-10}$alkyl, halo$C_{1-10}$ alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O.

In still yet another embodiment, compounds, enantiomers, diastereomers, tautomers, prodrugs or salts thereof, of formula Ib or Ic, are provided wherein:

X is H, F, Cl, Br, I or $C_{1-10}$ alkoxy;

Y is H, F, Cl, Br, I or $C_{1-10}$ alkoxy;

Z is H, Cl, Br, I or $C_{1-10}$ alkoxy;

$R_{13}a$ is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl or —CN, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13a-2}$ is independently H, —OH, F, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl or a 4- to 12-membered heteroaryl-$C_{1-10}$ alkyl, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b}$ is independently H, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$CO_2NR_{14}R_{14}$, —$NR_{14}COR_{14}$, —$NR_{14}R_{14}$, or —$NR_{14}CONR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13b-2}$ is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl or a 4- to 12-membered heteroaryl-$C_{1-10}$ alkyl, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13c}$ is independently H, Cl, Br, I, $C_{1-10}$ alkyl, hydroxy$C_{1-10}$ alkyl, cyano$C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$NR_{14}SO_2NR_{14}R_{14}$, —$NR_{14}COR_{14}$, —$NR_{14}CO_2R_{14}$, —$NR_{14}R_{14}$, —C(=$NOR_{14}$)$NR_{14}R_{14}$ or —$NR_{14}CONR_{14}R_{14}$, wherein the cycloalkyl, alkenyl, alkoxy, aryl and heteroaryl may be optionally substituted with one or more $R_{14a}$'s and the heteroaryl consists of carbon atoms and 1, 2 or 3 heteroatoms independently selected from the group consisting of N, S, or O;

$R_{13c-2}$ is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN, —$CO_2R_{14}$ or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d}$ is independently H, —OH, F, Cl, Br, I, $C_{1-10}$ alkyl, $C_{2-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl, —CN or —$NR_{14}R_{14}$, wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{13d-2}$ is independently H, —OH, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{6-10}$aryl, a 4- to 12-membered heteroaryl, a 4- to 12-membered heterocyclyl, a 4- to 12-membered heteroaryl-$C_{1-10}$ alkyl or —CN wherein the alkyl, cycloalkyl, alkenyl, alkoxy, aryl, heteroaryl and heterocyclyl may be optionally substituted with one or more $R_{14a}$'s and the heteroaryl and heterocyclyl consist of carbon atoms and 1, 2, 3, or 4 heteroatoms independently selected from the group consisting of N, S, or O;

$R_{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be optionally substituted with be optionally substituted with 0-3 $R_{14a}$ and the heteroaryl and heterocyclyl consist of carbon atoms and 1, 2, 3, or 4 heteroatoms independently selected from the group consisting of N, S, or O;

$R_{14a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —$CO_2R_{26}$, —$CO_2NR_{24}R_{24}$, —$OCF_3$, —$OR_{25}$, —$SO_2R_{24}$, —$NR_{24}R_{24}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{24}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the alkyl, aryl, heteroaryl and heterocyclyl may be optionally substituted with one or more $R_{24}a$'S and the heteroaryl and heterocyclyl consist of carbon atoms and 1, 2, 3, or 4 heteroatoms independently selected from the group consisting of N, S, or O;

$R_{24a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, —CN, —$CO_2R_{25}$, —$OCF_3$, —$OR_{25}$, —$CONR_{25}R_{25}$, —$NR_{25}R_{25}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{25}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O; and $R_{26}$, at each occurrence, is independently selected from $C_{1-10}$alkyl, halo$C_{1-10}$ alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O.

In one embodiment, compounds, enantiomers, diastereomers, tautomers, prodrugs or salts thereof, of formula Ib or Ic, are provided wherein:

X is H or $C_{1-10}$ alkoxy;
Y is H or $C_{1-10}$ alkoxy;
Z is H or $C_{1-10}$ alkoxy;
$R_{13a}$, at each occurrence, is independently H or —CN;
$R_{13a-2}$, at each occurrence, is independently H, F, $C_{1-10}$ alkyl, $C_{1-10}$ alkoxy, halo$C_{1-10}$ alkyl or $C_{3-10}$ cycloalkyl, wherein the alkyl, cycloalkyl and alkoxy may be optionally substituted with one or more $R_{14a}$'s;
$R_{13b}$, at each occurrence, is independently H, $C_{1-10}$ alkoxy, —CN, —$CO_2NR_{14}R_{14}$, —$NR_{14}COR_{14}$, —$NR_{14}R_{14}$, or —$NR_{14}CONR_{14}R_{14}$;
$R_{13b-2}$, at each occurrence, is independently H or F;
$R_{13c}$, at each occurrence, is independently H, $C_{1-10}$ alkyl, $C_{1-10}$ alkoxy, $C_{3-10}$ cycloalkyl, $C_{2-12}$ alkenyl, a 4- to 12-membered heteroaryl, —CN, —$(CH_2)_m$—$SO_2R_{14}$, —$NR_{14}SO_2R_{14}$, —$CONR_{14}R_{14}$, —$(CH_2)_m$—$SO_2NR_{14}R_{14}$, —$(CH_2)_m$—$NR_{14}SO_2R_{14}$, —$NR_{14}SO_2NR_{14}R_{14}$, —$NR_{14}COR_{14}$, —$NR_{14}CO_2R_{14}$, —$NR_{14}R_{14}$, —C(=$NOR_{14}$)$NR_{14}R_{14}$ or —$NR_{14}CONR_{14}R_{14}$, wherein the cycloalkyl, alkenyl, alkoxy and heteroaryl may be optionally substituted with one or more $R_{14a}$'s and the heteroaryl consists of carbon atoms and 1, 2 or 3 heteroatoms independently selected from the group consisting of N, S, or O;

$R_{13c-2}$, $R_{13d}$, and $R_{13d-2}$ are H;

$R_{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be optionally substituted with be optionally substituted with 0-3 $R_{14a}$ and the heteroaryl and heterocyclyl consist of carbon atoms and 1, 2, 3, or 4 heteroatoms independently selected from the group consisting of N, S, or O;

$R_{14a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —$CO_2R_{26}$, —$CO_2NR_{24}R_{24}$, —$OCF_3$, —$OR_{25}$, —$SO_2R_{24}$, —$NR_{24}R_{24}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{24}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the alkyl, aryl, heteroaryl and heterocyclyl may be optionally substituted with one or more $R_{24}a$'S and the heteroaryl and heterocyclyl consist of carbon atoms and 1, 2, 3, or 4 heteroatoms independently selected from the group consisting of N, S, or O;

$R_{24a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, —CN, —$CO_2R_{25}$, —$OCF_3$, —$OR_{25}$, —$CONR_{25}R_{25}$, —$NR_{25}R_{25}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{25}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O; and $R_{26}$, at each occurrence, is independently selected from $C_{1-10}$alkyl, halo$C_{1-10}$ alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O.

In another embodiment, compounds, enantiomers, diastereomers, tautomers, prodrugs or salts thereof, of formula Ib or Ic, are provided wherein:

X, Y, Z, $R_{13a}$, $R_{13a-2}$, $R_{13b-2}$, $R_{13c-2}$, $R_{13d}$ and $R_{13d-2}$ are H;

$R_{13b}$, at each occurrence, is independently H, $C_{1-10}$ alkoxy, or —$NR_{14}R_{14}$;

$R_{13c}$, at each occurrence, is independently H, $C_{1-10}$ alkyl, $C_{3-10}$ cycloalkyl, a 4- to 12-membered heteroaryl, —$(CH_2)_m$—$SO_2NR_{14}R_{14}$, —$CONR_{14}R_{14}$ or —$NR_{14}R_{14}$, wherein the cycloalkyl, and heteroaryl may be optionally substituted with one or more $R_{14a}$'s and the heteroaryl consists of carbon atoms and 1, 2 or 3 heteroatoms independently selected from the group consisting of N, S, or O;

$R_{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be optionally substituted with be optionally substituted with 0-3 $R_{14a}$ and the heteroaryl and heterocyclyl consist of carbon atoms and 1, 2, 3, or 4 heteroatoms independently selected from the group consisting of N, S, or O;

$R_{14a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —$CO_2R_{26}$, —$CO_2NR_{24}R_{24}$, —$OCF_3$, —$OR_{25}$, —$SO_2R_{24}$, —$NR_{24}R_{24}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{24}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the alkyl, aryl, heteroaryl and heterocyclyl may be optionally substituted with one or more $R_{24a}$'s and the heteroaryl and heterocyclyl consist of carbon atoms and 1, 2, 3, or 4 heteroatoms independently selected from the group consisting of N, S, or O;

$R_{24a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, —CN, —$CO_2R_{25}$, —$OCF_3$, —$OR_{25}$, —$CONR_{25}R_{25}$, —$NR_{25}R_{25}$ or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R_{25}$, at each occurrence, is independently selected from hydrogen, $C_{1-10}$alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O; and $R_{26}$, at each occurrence, is independently selected from $C_{1-10}$alkyl, halo$C_{1-10}$ alkyl, $C_{3-10}$cycloalkyl, $C_{6-10}$aryl, a 4- to 12-membered heteroaryl or 4- to 12-membered heterocyclyl, wherein the heteroaryl and heterocyclyl consist of carbon atoms and 1, 2, 3, or 4 heteroatoms independently selected from the group consisting of N, S, or O.

In another embodiment, compounds, enantiomers, diastereomers, tautomers, or salt thereof, of the present invention are selected from the compounds exemplified in the examples, preferably, Examples 7, 22, 29, 31, 32, 38, 40, 42, 46, 50, 97, 105, 107, 108, 110, 111, 130, 134 and 137 more preferably, Examples 7, 32, and 101, even more preferably, Examples 7 and 101.

In one embodiment, pharmaceutical compositions comprising a therapeutically effective amount of at least one compound of formula I, Ia, Ib, and/or Ic, preferably compounds exemplified in the examples, more preferably, Examples 7, 22, 29, 31, 32, 38, 40, 42, 46, 50, 97, 105, 107, 108, 110, 111, 130, 134 and 137, even more preferably, Examples 7, 32, and 101, still even more preferably, Examples 7 and 101, are provided.

In another embodiment, pharmaceutical compositions comprising a therapeutically effective amount of at least one compound of formula I, Ia, Ib, and/or Ic, preferably compounds exemplified in the examples, more preferably, Examples 7, 22, 29, 31, 32, 38, 40, 42, 46, 50, 97, 105, 107, 108, 110, 111, 130, 134 and 137, even more preferably, Examples 7, 32, and 101, still even more preferably, Examples 7 and 101, and at least one other therapeutic agent, for example, anti-arrhythmic agents, calcium channel blockers, anti-platelet agents, anti-hypertensive agents, anti thrombotic/anti thrombolytic agents, anti coagulants, HMG-CoA reductase inhibitors, anti diabetic agents, thyroid mimetics, mineralocorticoid receptor antagonists, and cardiac glycosides, are provided.

In yet another embodiment, pharmaceutical compositions comprising a therapeutically effective amount of at least one compound of formula I, Ia, Ib, and/or Ic, preferably compounds exemplified in the examples, more preferably, Examples 7, 22, 29, 31, 32, 38, 40, 42, 46, 50, 97, 105, 107, 108, 110, 111, 130, 134 and 137, even more preferably, Examples 7, 32, and 101, still even more preferably, Examples 7 and 101, and at least one other therapeutic agent, for example, sotalol, dofetilide, diltiazem, verapamil, clopidogrel, cangrelor, ticlopidine, CS-747, ifetroban, aspirin, a beta adrenergic blocker, an ACE inhibitor, an A II antagonist, an ET antagonist, a dual ET/A II antagonist, a vasopepsidase inhibitor, tPA, recombinant tPA, TNK, nPA, a factor VIIa inhibitor, a factor Xa inhibitor, a factor XIa inhibitor, a thrombin inhibitor, warfarin, a heparin, pravastatin, lovastatin, atorvastatin, simvastatin, NK-104, ZD-4522, a biguanide, a biguanide/glyburide combination, spironolactone, eplerinone, *digitalis* and ouabain, are provided.

In still yet another embodiment, pharmaceutical compositions comprising a therapeutically effective amount of at least one compound of formula I, Ia, Ib, and/or Ic, preferably compounds exemplified in the examples, more preferably, Examples 7, 22, 29, 31, 32, 38, 40, 42, 46, 50, 97, 105, 107, 108, 110, 111, 130, 134 and 137, even more preferably, Examples 7, 32, and 101, still even more preferably, Examples 7 and 101, and at least one other therapeutic agent, for example, captopril, zofenopril, fosinopril, enalapril, ceranopril, cilazopril, delapril, pentopril, quinapril, ramipril, lisinopril, omapatrilat, gemopatrilat, and razaxaban, are provided.

In one embodiment, methods of treating or preventing arrhythmia comprising administering to a patient in need thereof an effective amount of at least one compound of formula I, Ia, Ib, and/or Ic, preferably compounds exemplified in the examples, more preferably, Examples 7, 22, 29, 31, 32, 38, 40, 42, 46, 50, 97, 105, 107, 108, 110, 111, 130, 134 and 137, even more preferably, Examples 7, 32, and 101, still even more preferably, Examples 7 and 101, are provided.

In another embodiment, methods of treating or preventing supraventricular arrhythmia, for example, atrial fibrillation and atrial flutter, comprising administering to a patient in need thereof an effective amount of at least one compound of formula I, Ia, Ib, and/or Ic, preferably compounds exemplified in the examples, more preferably, Examples 7, 22, 29, 31, 32, 38, 40, 42, 46, 50, 97, 105, 107, 108, 110, 111, 130, 134 and 137, even more preferably, Examples 7, 32, and 101, still even more preferably, Examples 7 and 101, are provided.

In one embodiment, a method of controlling heart rate comprising administering to a patient in need thereof an effective amount of at least one compound of formula I, Ia, Ib, and/or Ic, preferably compounds exemplified in the examples, more preferably, Examples 7, 22, 29, 31, 32, 38, 40, 42, 46, 50, 97, 105, 107, 108, 110, 111, 130, 134 and 137, even more preferably, Examples 7, 32, and 101, still even more preferably, Examples 7 and 101, is provided.

In another embodiment, methods of treating an $I_{Kur}$-associated conditions, for example, gastrointestinal disorders, such as reflux esauphagitis and a motility disorder; inflammatory and/or immunological diseases, such as chronic obstructive pulmonary disease; diabetes; cognitive disorders; migraines; epilepsy; and hypertension, comprising administering to a patient in need thereof an effective amount of at least one compound of formula I, Ia, Ib, and/or Ic, preferably compounds exemplified in the examples, more preferably, Examples 7, 22, 29, 31, 32, 38, 40, 42, 46, 50, 97, 105, 107, 108, 110, 111, 130, 134 and 137, even more preferably, Examples 7, 32, and 101, still even more preferably, Examples 7 and 101, are provided.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

The compounds of the present invention may be prepared by the exemplary processes described in the following schemes and working examples, as well as relevant published literature procedures that are used by one skilled in the art. Exemplary reagents and procedures for these reactions appear hereinafter and in the working examples. Protection and de-protection of functional groups in the processes below may be carried out by procedures generally known in the art (see, for example, Greene, T. W. et al., *Protecting Groups in Organic Synthesis*, 3$^{rd}$ Ed., Wiley (1999). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); March, J., *Advanced Organic Chemistry: Reactions, Mechanisms, and Structure*, 4$^{th}$ Ed., Wiley & Sons, New York, N.Y. (1992); Katritzky, A. R. et al., eds., *Comprehensive Organic Functional Groups Transformations*, 1$^{st}$ Ed., Elsevier Science Inc., Tarrytown, N.Y. (1995); Larock, R. C., *Comprehensive Organic Transformations*, VCH Publishers, Inc., New York, N.Y. (1989); and references therein.

Solvents, temperatures, pressures, and other reaction conditions may readily be selected by one of ordinary skill in the art. Starting materials are commercially available or can be readily prepared by one of ordinary skill in the art using known methods. For all of the schemes and compounds described below Y, Z, A, $R_1$ and $R_{24}$ are as described for a compound of Formula (I).

The following are the definitions of symbols used throughout Schemes 1 to 3 and the examples:

Me=Methyl
Et=Ethyl
Pr=Propyl
i-Pr=Isopropyl
Bu=Butyl
i-Bu=Isobutyl
t-Bu=tert-butyl
Ph=Phenyl
Bn=Benzyl
Boc=tert-butyloxycarbonyl
AcOH or HOAc=acetic acid
$AlCl_3$=aluminum chloride
$CH_2Cl_2$=Dichloromethane
$CH_3CN$ or CAN=Acetonitrile
$CDCl_3$=deutero-chloroform
$CHCl_3$=Chloroform
mCPBA or m-CPBA=meta-chloroperbenzoic acid
$Cs_2CO_3$=cesium carbonate
DCM=Dichloromethane
DEA=Diethylamine
DIC=Diisopropylcarbodiimide
dil=dilute
DIPEA or Hunig's base=Diisopropylethylamine
DME=1,2-dimethyoxyethane
DMF=Dimethylformamide
DMSO=dimethyl sulfoxide
cDNA=complimentary DNA
EDC=N-(3-dimethylaminopropyl)-N'-ethylcarbodiimide
EDTA=ethylenediaminetetraacetic acid
$Et_3N$ or TEA=Triethylamine
EtOAc=ethyl acetate
$Et_2O$=diethyl ether
EtOH=Ethanol
eq=equivalents
HCl=hydrochloric acid
HOBt=1-hydroxybenzotriazole
HAUT=(2-(7-Aza-1H-benzotriazole-1-yl)-1,1,3,3-tetramethyluronium hexafluorophosphate)
$H_2SO_4$=sulfuric acid
$K_2CO_3$=potassium carbonate
KOAc=potassium acetate
$K_3PO_4$=potassium phosphate LG=leaving group
LiOH=lithium hydroxide
MeOH=Methanol
min=minute or minutes
$MgSO_4$=magnesium sulfate
MsOH or MSA=methylsulfonic acid
NaCl=sodium chloride
NaH=sodium hydride
$NaHCO_3$=sodium bicarbonate
$Na_2CO_3$=sodium carbonate
NaOH=sodium hydroxide
$Na_2SO_3$=sodium sulfite
$Na_2SO_4$=sodium sulfate
$NH_3$=Ammonia
$NH_4C_1$=ammonium chloride
$NH_4OH$=ammonium hydroxide
$Pd(OAc)_2$=palladium(II) acetate
Pd/C=palladium on carbon
$Pd(dppf)Cl_2$=[1,1'-bis(diphenylphosphino)-ferrocene]dichloropalladium(II)
$Ph_3PCl_2$=triphenylphosphine dichloride
$Pd(TRIPHENYLPHOSPHINE)_2C_{12}$=Bis(triphenylphosphine)palladium(II)chloride
PG=protecting group
$POCl_3$=phosphorus oxychloride
i-PrOH or IPA=Isopropanol
PS=Polystyrene
PyBOP=(benzotriazol-1-yloxy)tripyrrolidinophosphonium hexafluorophosphate
PyBrop=Bromo-tris-pyrrolidino phosphoniumhexafluorophosphate
$SiO_2$=silica oxide
$SnCl_2$=tin(II) chloride
TFA=trifluoroacetic acid
THF=Tetrahydrofuran
TOSMIC=Toluenesulfonylmethyl isocyanide Scheme 1

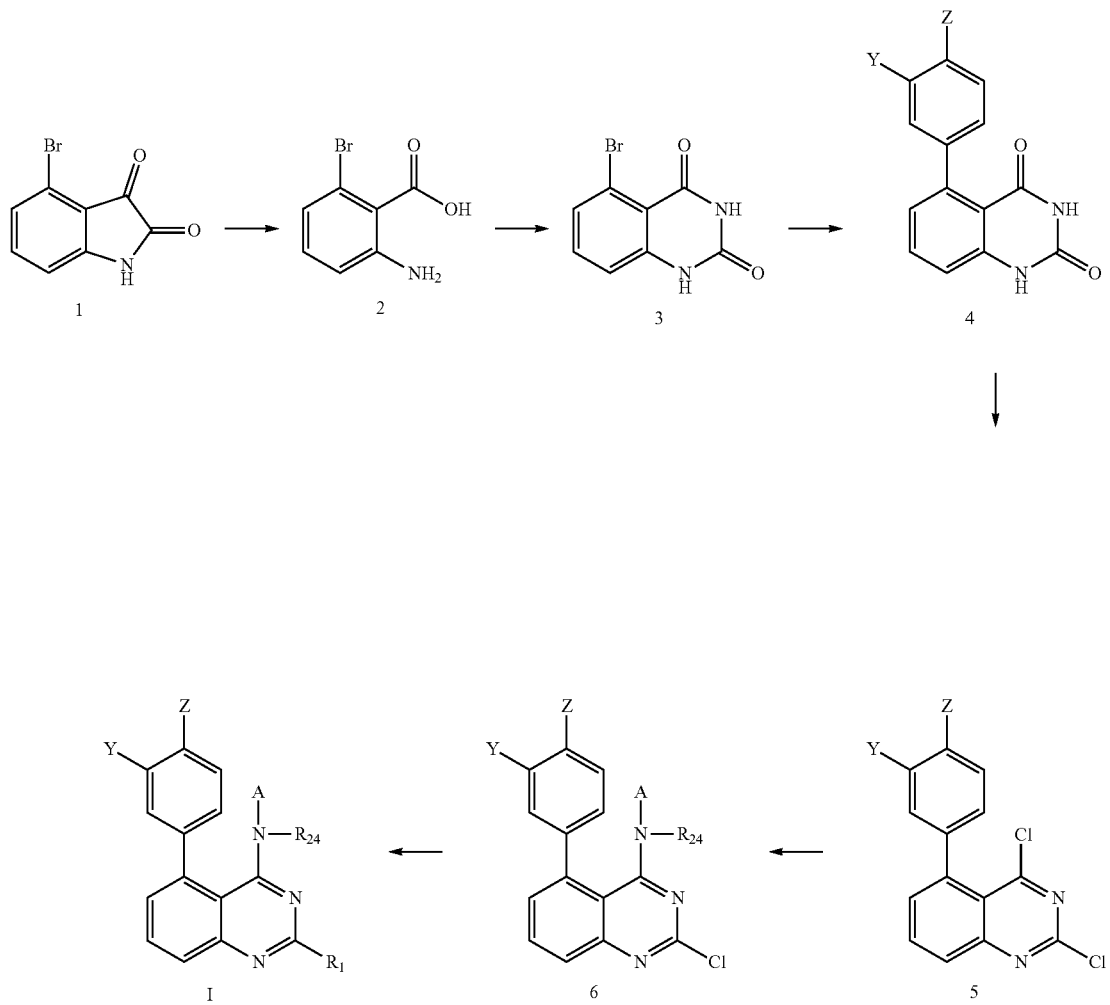

Compounds of formula I may be synthesized according to Scheme 1. Commercially available 4-bromoindoline-2,3-dione may be hydrolyzed to 2-amino-6-bromobenzamide followed by condensation with sodium isocyanate to form 5-bromoquinazoline-2,4(1H,3H)-dione. The protocols include, but are not limited to, palladium mediated cross coupling between 5-bromoquinazoline-2,4(1H,3H)-dione and the aryl boronic acid or ester to form the intermediate 5-substituted quinazoline-2,4(1H, 3H)-dione. Conversion to the corresponding dichloro quinazoline and sequential displacement at the 4-position followed by transition metal mediated cross coupling or displacement of the $C_2$ chloride forms compounds I as described.

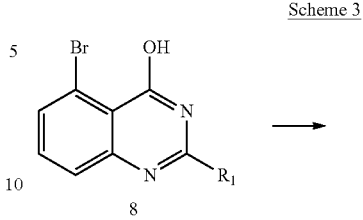

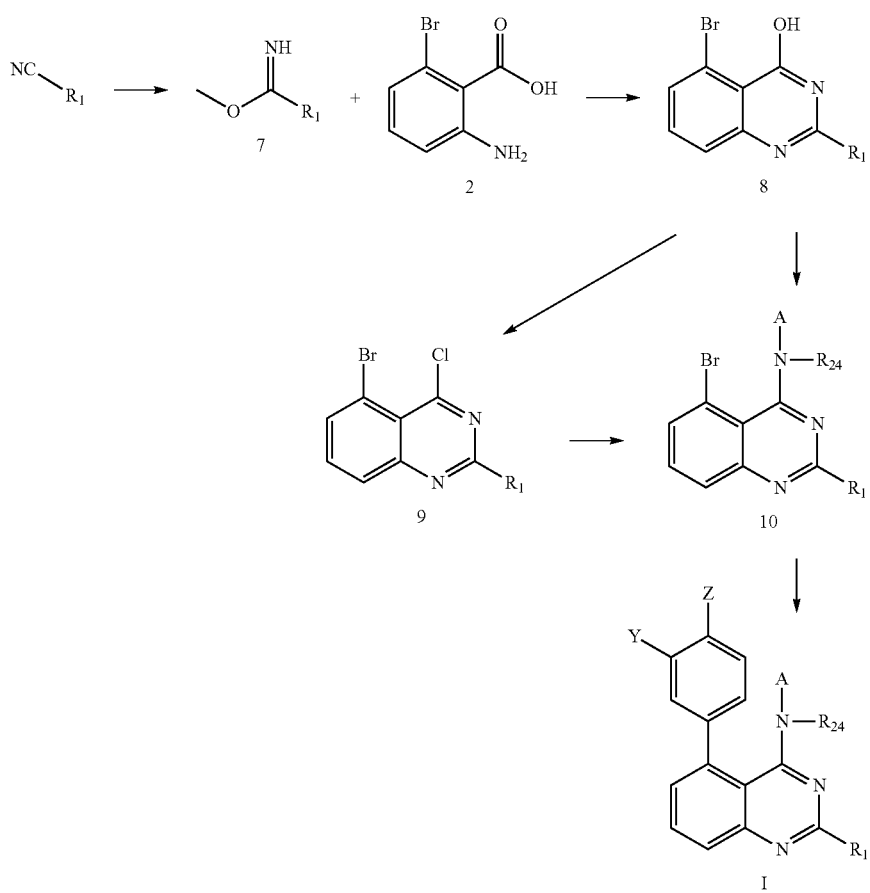

Alternatively, compounds of formula I may also be synthesized according to Scheme 2. Formation of the methylcarbimidate from the corresponding nitrile and subsequent condensation with 2-amino-6-bromobenzamide provides compounds of formula 8. Subsequent conversion of 8 to 4-chloroquinazoline intermediate 9 and displacement of the chloride provides 5-bromoquinazoline 10. Compounds of formula 10 may be obtained directly from 8 utilizing coupling reagents, for example but not limited to, PyBOP in suitable solvents. The protocols include but are not limited to palladium mediated cross coupling between quinazoline 10 and a suitable aryl boronic acid or ester to obtain compounds of formula I.

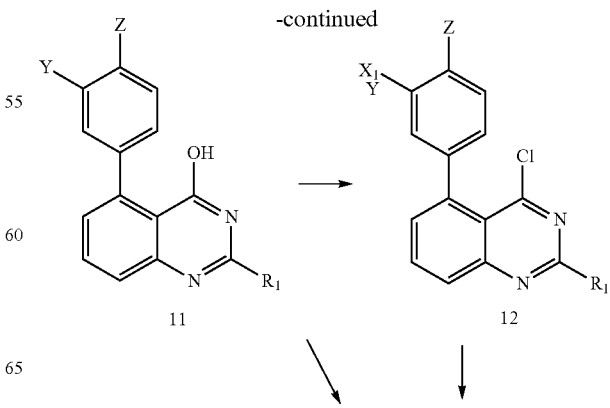

-continued

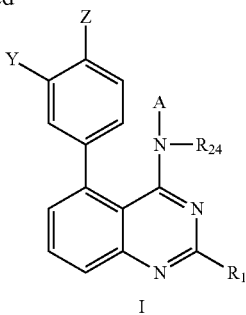

I

Alternatively, compounds of formula I may also be synthesized according to Scheme 3. Compounds of formula 8 may be subjected to cross coupling conditions, for example, but not limited to palladium mediated cross coupling of aryl boronic acids or esters, followed by subsequent conversion to the quinazoline intermediate 12 and displacement of the $C_4$ chloro group to obtain compounds of Formula I.

It should be recognized that the above schemes are only illustrations of some general synthetic routes to prepare compounds of the present invention. The experimental details for the synthesis of various specific examples of the present invention will be further described in the examples set forth below. Additional functional group manipulations of compounds obtained in the above schemes using methods known in the art should provide additional compounds of this invention.

EXAMPLES

The following examples are offered to illustrate, but not limit, some of the preferred embodiments of the present invention and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

General Methods

The following methods were used in the working Examples, except where noted otherwise.
Analytical HPLC and HPLC/MS Methods Employed in Characterization of the examples are as follows:
Reverse phase analytical HPLC/MS was performed on Shimadzu LC10AS systems coupled with Waters ZMD Mass Spectrometers (methods A-C, E and F) or Waters AQUITY® system coupled with a Waters MICROMASS® ZQ Mass Spectrometer (method D). Chiral analytical LC was performed on a Berger Analytical SFC instrument (method G).
Method A:
Linear gradient of 0 to 100% B over 2 min, with 3 min hold at 100% B;
UV visualization at 220 nm;
Column: PHENOMENEX® Luna C18 4.6×30 mm;
Flow rate: 5 ml/min;
Solvent A: 0.1% trifluoroacetic acid, 90% water, 10% acetonitrile;
Solvent B: 0.1% trifluoroacetic acid, 90% acetonitrile, 10% water.

Method B:
Linear gradient of 0 to 100% B over 10 min, with 5 min hold at 100% B;
UV visualization at 220 nm;
Column: Xbridge phenyl 4.6×150 mm;
Flow rate: 1 ml/min;
Solvent A: 0.1% trifluoroacetic acid, 90% water, 10% acetonitrile;
Solvent B: 0.1% trifluoroacetic acid, 90% acetonitrile, 10% water.
Method C:
Linear gradient of 0 to 100% B over 4 min, with 1 min hold at 100% B;
UV visualization at 220 nm;
Column: PHENOMENEX® Luna C18 4.6×50 mm;
Flow rate: 4 ml/min;
Solvent A: 10 mM ammonium acetate, 90% water, 10% methanol;
Solvent B: 10 mM ammonium acetate, 90% methanol, 10% water.
Method D:
Linear gradient of 2 to 98% B over 1 min, with 0.5 min hold time at 98% B;
UV visualization at 220 nm;
Column: Waters BEH C18 2.1×50 mm;
Flow rate: 0.8 ml/min;
Solvent A: 0.05% TFA, 100% water;
Solvent B: 0.05% TFA, 100% ACN.
Method E:
Linear gradient of 0 to 100% B over 4 min, with 1 min hold time at 100% B;
UV visualization at 220 nm;
Column: Ascentis Express 4.6×50 C18 at 45° C.;
Flow rate: 4 ml/min;
Solvent A: 10 mM ammonium acetate, 5% ACN, 95% water;
Solvent B: 10 mM ammonium acetate, 95% ACN, 5% water.
Method F:
Linear gradient of 0 to 100% B over 8 min, with 1 min hold at 100% B;
UV visualization at 220 nm;
Column: PHENOMENEX® Luna C18 4.6×75 mm;
Flow rate: 2.5 ml/min;
Solvent A: 10 mM ammonium acetate, 90% water, 10% methanol;
Solvent B: 10 mM ammonium acetate, 90% methanol, 10% water.
Method G:
Isocratic 80/20 $CO_2$/MeOH containing 0.1% DEA;
UV visualization at 220 nm;
Column: CHIRALPAK® AC, 250×4.6 mm, 10 uM;
Flow rate: 3.0 ml/min.
Preparative HPLC methods employed in the purification of the examples are as follows:
Method H:
Linear gradient of 0 to 100% B over 10 min, with 5 min hold time at 100% B;
Shimadzu LC-8A binary pumps;
Waters ZQ mass spectrometer using Waters Masslynx 4.0 SP4 MS software;
UV visualization at 220 nm;
Column: Waters SunFire 19×100 mm 5 um C18;
Flow rate: 20 ml/min;
Peak collection triggered by mass spectrometry;
Solvent A: 0.1% TFA, 10% ACN, 90% water;
Solvent B: 0.1% TFA, 90% ACN, 10% water.

Method I:
Linear gradient of 20 to 100% B over 10 min, with 5 min hold time at 100% B;
Shimadzu LC-8A binary pumps;
Shimadzu SPD-20A UV detector;
UV visualization at 220 nm;
Column: PHENOMENEX® Luna AXIA 21.1×100 mm 5 um C18;
Flow rate: 20 ml/min;
Peak collection triggered by UV absorbance;
Solvent A: 0.1% TFA, 10% MeOH, 90% water;
Solvent B: 0.1% TFA, 90% MeOH, 10% water.
Method J:
Linear gradient of 20 to 100% B over 10 min, with 2 min hold time at 100% B;
Shimadzu LC-8A binary pumps;
Shimadzu SPD-10A UV detector;
UV visualization at 220 nm;
Column: PHENOMENEX® Luna AXIA 21.1×100 mm 5 um C18;
Flow rate: 20 ml/min;
Peak collection triggered by UV absorbance;
Solvent A: 0.1% TFA, 10% ACN, 90% water;
Solvent B: 0.1% TFA, 90% ACN, 10% water.
Method K:
Isocratic 80/20 $CO_2$/$CH_3OH$ containing 0.1% DEA;
Berger Multigram II SFC instrument;
UV visualization at 220 nm;
Column: CHIRALPAK® AD-H 250×21 cm ID, 5 uM;
Flow rate: 65 ml/min;
Peak collection triggered by UV absorbance.
Additional Analytical HPLC and HPLC/MS Methods Employed in Characterization of Examples are as follows:
Method L:
Solvent A-5% ACN, 95% water, 10 mM $NH_4OAc$;
Solvent B-95% ACN, 5% Water, 10 mM $NH_4OAc$;
Flow rate: 4.0 ml/min;
Column: Ascentis Express C18 (4.6×50 cm) mm, 2.7 um;
Time (min): 0-4.0 gradient % B: 0-100.
Method M:
Linear gradient of 0 to 100% B over 2 min;
UV visualization at 220 nm;
Column: PHENOMENEX® Luna C18 4.6×30 mm;
Flow rate: 5 mL/min;
Solvent A: 0.1% trifluoroacetic acid, 90% water, 10% methanol;
Solvent B: 0.1% trifluoroacetic acid, 90% methanol, 10% water.
Method N:
Linear gradient of 0 to 5% B over 0.25 min then 5 to 100% B up to 2 min with 0.5 min hold at 100% B;
UV visualization at 220 nm;
Column: BEH C18 50×2.1 mm–1.7 μm;
Flow rate: 0.6 mL/min;
Solvent A: 0.1% formic acid, 95% water, 5% acetonitrile;
Solvent B: 0.1% formic acid, 95% acetonitrile, 5% water.
Method O:
Linear gradient of 0 to 100% B over 2 min;
UV visualization at 220 nm;
Column: CHROMOLITH® SpeedROD C18 4.6×30 mm
Flow rate: 5 mL/min;
Solvent A: 0.1% trifluoroacetic acid, 90% water, 10% methanol;
Solvent B: 0.1% trifluoroacetic acid, 90% methanol, 10% water.
Method P:
Linear gradient of 40 to 95% B over 3 min with 3 min hold at 95% B;
UV visualization at 220 nm;
Column: Atlantis dC18 C18 50×4.6 mm–5 μm;
Flow rate: 1.5 mL/min;
Solvent A: 0.1% formic acid in water;
Solvent B: acetonitrile.
Method Q:
Linear gradient of 0 to 100% B over 2 min;
UV visualization at 220 nm;
Column: PHENOMENEX® Luna C18 4.6×30 mm;
Flow rate: 5 mL/min;
Solvent A: 10 mM ammonium acetate, 90% water, 10% methanol;
Solvent B: 10 mM ammonium acetate, 90% methanol, 10% water.
Method R:
Linear gradient of 30 to 95% B over 3 min with 1 min hold at 95% B;
UV visualization at 220 nm;
Column: Atlantis dC18 C18 50×4.6 mm–5 μm;
Flow rate: 1 mL/min;
Solvent A: 10 mM ammonium acetate in water;
Solvent B: acetonitrile.
Method S:
Linear gradient of 40 to 95% B over 3 min with 1 min hold at 95% B;
UV visualization at 220 nm;
Column: Atlantis dC18 C18 50×4.6 mm–5 μm;
Flow rate: 1.5 mL/min;
Solvent A: 10 mM ammonium acetate in water;
Solvent B: acetonitrile.
Method T:
Linear gradient of 0 to 100% B over 2 min
Agilent 1200 series systems coupled with DADetector using Agilent chemstation & using Chemstation B.04.01 (482) software, with ESI ionization source in Positive mode only.
UV visualization at 220 nm;
Column: Agilent Zorbax SB C18 4.6×50 mm 5 um
Gradient Programme: Time (min)/% B: 0/0,2/100,3/0.
Flow rate: 5.0 ml/min;
Buffer: 0.1% Trifluoroacetic acid in water.
Mobile Phase A: Buffer: Methanol:90:10
Mobile Phase B: Buffer: Methanol:10:90
Method U:
Linear gradient of 0 to 100% B over 2 min;
UV visualization at 220 nm;
Column: Chromolith SpeedROD C18 4.6×30 mm;
Flow rate: 5 mL/min;
Solvent A: 0.1% trifluoroacetic acid, 90% water, 10% methanol;
Solvent B: 0.1% trifluoroacetic acid, 90% methanol, 10% water.
Method V:
Linear gradient of 0 to 100% B over 1.5 min, with 1.7 min hold at 100% B;
Agilent 1200 series systems coupled with DADetector using Agilent chemstation & using Chemstation B.04.01 (482) software; with ESI ionization source in both Positive & Negative mode.
UV visualization at 220 nm;
Column: Waters Xbridge Phenyl 4.6×30 mm 3.5 um
Gradient Programme: Time (min)/% B: 0/0,1.5/100,3.2/100, 3.6/0,4.0/0
Flow rate: 1.8 ml/min;
Buffer: 10 mM Ammonium Formate in water.
Mobile Phase A: Buffer: Acetonitrile: 98:02
Mobile Phase B: Buffer: Acetonitrile: 02:98

Method W:
Linear gradient of 0 to 100% B over 2.50 min, with 0.5 min hold at 100% B;
Agilent 1200 series systems coupled with DADetector using Agilent chemstation &
Chemstation B.04.01 (482) software with Multi mode ionization source in both
Positive & Negative mode.
UV visualization at 220 nm;
Column: Merck Puroshpere @ Star RP-18 4×5 mm, 3u
Gradient Programme: Time (min)/% B: 0/0,2.0/100,2.5/100, 3.0/0,3.5/0
Flow rate: 2.5 ml/min;
Buffer: 20 mM Ammonium Acetate in water.
Mobile Phase A: Buffer: Acetonitrile: 90:10
Mobile Phase B: Buffer: Acetonitrile: 10:90
Method X:
Linear gradient of 0 to 100% B over 2 min;
UV visualization at 220 nm;
Column: Phenomenex Luna C18 4.6×30 mm;
Flow rate: 5 mL/min;
Solvent A: 10 mM ammonium acetate, 90% water, 10% methanol;
Solvent B: 10 mM ammonium acetate, 90% methanol, 10% water.
Method Y:
Reverse phase analytical HPLC/MS was performed on Agilent 1200 series systems coupled with DADetector, Ion-Trap 6330 Mass Spectrometer, 1200 ELSD (Agilent) using Agilent chemstation & Brooker 4.0 Build 234 software in both Positive & Negative mode.
Linear gradient of 0 to 100% B over 1.2 min, with 1.8 min hold at 100% B;
Agilent 1200 series systems coupled with DADetector
UV visualization at 220 nm;
Column: Ascentis Express C18 2.1×50 mm, 2.7u
Gradient Programme: Time (min)/% B: 0/0,1.2/100,3.0/100, 3.4/0,4.0/0
Flow rate: 1.0 ml/min;
Buffer: 10 mM Ammonium Formate in water.
Mobile Phase A: Buffer: Acetonitrile: 98:02
Mobile Phase B: Buffer: Acetonitrile: 02:98
Method Z:
Reverse phase analytical HPLC/MS was performed on Agilent 1200 series systems coupled with DADetector, Ion-Trap 6330 Mass Spectrometer, 1200 ELSD (Agilent) using Agilent chemstation & Brooker 4.0 Build 234 software in both Positive & Negative mode.
Linear gradient of 0 to 100% B over 1.2 min, with 1.8 min hold at 100% B;
Agilent 1200 series systems coupled with DADetector
UV visualization at 220 nm;
Column: Zorbax AQ C18 4.6×50 mm, 3.5u
Gradient Programme: Time (min)/% B: 0/2,1.5/20,4.0/95, 4.5/2,6/2
Flow rate: 1.0 ml/min;
Buffer: 0.1% Formic Acid in water.
Mobile Phase A: 0.1% Formic Acid in water.
Mobile Phase B: Acetonitrile.
Method Z1:
Method info:
A: Water:ACN (95:5); 10 mM ammonium acetate
B: Water:ACN (5:95); 10 mM ammonium acetate
Flow: 4 ml/min
Temp: 45° C.
Column: Ascentis Express C18 (50×4.6), 2.7 μm
Time (min): 0-4

Method A1:
Linear gradient of 10 to 100% B over 12 min, with 3 min hold at 100% B;
Gradient Programme: T/% B: 0/10, 12/100, 15/100, 18/10, 23/10
UV visualization at 220 & 254 nm;
Waters Sunfire C18 (4.6×150 mm, 3.5u)
Flow rate: 1 ml/min
Buffer: 0.05% Trifluoroacetic acid in water pH adjusted to 2.5 with dil Ammonia
Mobile Phase A: Buffer: Acetonitrile: 95:05
Mobile Phase B: Buffer: Acetonitrile: 05:95
Method A2:
Linear gradient of 10 to 100% B over 12 min, with 3 min hold at 100% B;
Gradient Programme: T/% B: 0/10, 12/100, 15/100, 18/10, 23/10
UV visualization at 220 & 254 nm;
Waters Xbridge Phenyl (4.6×150 mm, 3.5u)
Flow rate: 1 ml/min
Buffer: 0.05% Trifluoroacetic acid in water pH adjusted to 2.5 with dil Ammonia
Mobile Phase A: Buffer: Acetonitrile: 95:05
Mobile Phase B: Buffer: Acetonitrile: 05:95
Method A3:
Linear gradient of 10 to 100% B over 12 min, with 8 min hold at 100% B;
Gradient Programme: Time (min)/% B: 0/10, 12/100, 20/100, 23/10, 26/10
UV visualization at 220 & 254 nm;
Waters Xbridge Phenyl (4.6×150 mm, 3.5u)
Flow rate: 1.0 ml/min;
Mobile Phase A: 10 mM Ammonium Bicarbonate in water pH adjusted to 9.5 with dil Ammonia
Mobile Phase B: Methanol
Method A4:
Linear gradient of 0 to 100% B over 10 min, with 5 min hold at 100% B;
UV visualization at 220 nm;
Column: X-bridge phenyl 4.6×150 mm;
Flow rate: 1 ml/min;
Solvent A: 0.1% trifluoroacetic acid, 90% water, 10% acetonitrile;
Solvent B: 0.1% trifluoroacetic acid, 90% acetonitrile, 10% water.

$^1$H NMR spectra were obtained with Bruker or JEOL FOURIER® transform spectrometers operating at frequencies as follows: $^1$H NMR: 400 MHz (Bruker or JEOL) or 500 MHz (JEOL). $^{13}$C NMR: 100 MHz (Bruker or JEOL). Spectra data are reported in the format: chemical shift (multiplicity, coupling constants, and number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

Example 1

5-Phenyl-N-(pyridin-2-ylmethyl)-2-(pyrimidin-5-yl)quinazolin-4-amine

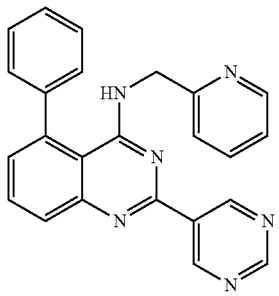

Step 1. Preparation of 2-amino-6-bromobenzoic acid

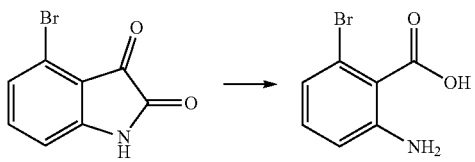 [SMILES: O=C1Nc2cccc(Br)c2C1=O ; Nc1cccc(Br)c1C(=O)O]

To 4-bromoindoline-2,3-dione (8.94 g, 39.6 mmol) was added 1.0 M sodium hydroxide (40 mL, 120 mmol) to give a dark brown mixture. The mixture was heated to 80° C. then 20% hydrogen peroxide (9 mL, 88 mmol) was added slowly over 15 min (caution: a strong exotherm was observed upon reagent addition). The mixture was then stirred at 80° C. for 1 h. After this time, the mixture was cooled in an ice bath to −10° C. and then concentrated to a residue. HCl was added cautiously to the residue until the pH of the mixture was 4-5. Once at the prescribed pH, the mixture was then concentrated to dryness and MeOH (150 ml) was added. The resulting suspension stirred for 15 min and then filtered. The filtrate was concentrated to dryness and dried under vacuum for 14 h to yield 2-amino-6-bromobenzoic acid (9.18 g) as a brown solid. $^1$H NMR (400 MHz, DMSO-d$_6$) δ ppm 6.72 (1H, t, J=7.91 Hz), 6.60 (1H, dd, J=7.78, 1.00 Hz), 6.52 (1H, dd, J=7.91, 1.13 Hz). LCMS Method D: retention time 0.68 min, [M+1] 200.0.

Step 2. Preparation of 5-bromoquinazoline-2,4(1H,3H)-dione

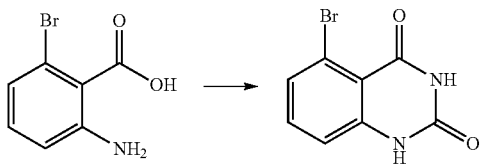 [SMILES: Nc1cccc(Br)c1C(=O)O ; O=c1[nH]c(=O)c2c(Br)cccc2[nH]1]

2-Amino-6-bromobenzoic acid (2.97 g, 13.7 mmol) was suspended in a mixture of water (100 mL) and acetic acid (1.5 mL) at 35° C. then a suspension of sodium cyanate (2.23 g, 34.4 mmol) in 10 mL of water was added slowly to the mixture. Upon completion of addition, the resulting mixture was stirred at 35° C. for 30 minutes and then sodium hydroxide (24.7 g, 619 mmol) pellets were slowly added to the mixture to yield a thick precipitate. The mixture was cooled to 5° C. in an ice bath and the pH of the suspension was adjusted to 4 using concentrated HCl. Once at the prescribed pH, the suspension was filtered and the solid was washed with water and dried under vacuum while heating at 100° C. to give 5-bromo-1H-quinazoline-2,4-dione (1.91 g) as a brown solid. $^1$H NMR (400 MHz, DMSO-d$_6$) δ ppm 11.30 (1H, br. s.), 11.26 (1H, br. s.), 7.43-7.48 (1H, m), 7.40 (1H, dd, J=7.78, 1.25 Hz), 7.16 (1H, dd, J=7.91, 1.13 Hz).

Step 3. Preparation of 2,4-dichloro-5-phenylquinazoline

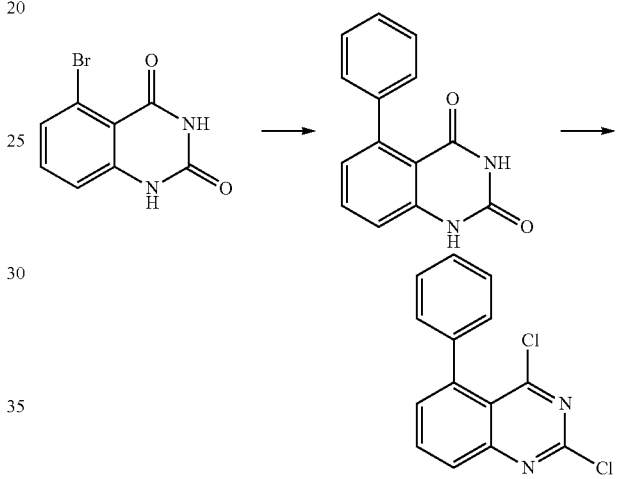

See *J. Med. Chem.*, 50(7):1675 (2007), 76759-011. To a mixture of 5-bromoquinazoline-2,4(1H,3H)-dione (900 mg, 3.73 mmol) and Pd(Ph$_3$P)$_4$ (216 mg, 0.187 mmol) in DME (90 mL) was added phenylboronic acid (683 mg, 5.60 mmol) followed by a solution of sodium bicarbonate (941 mg, 11.2 mmol) in water (30 mL) and the reaction heated at reflux for 40 h. At the conclusion of this period, the organic solvent was removed under reduced pressure. The resulting mixture was filtered and the solid washed with water. The solid was concentrated under reduced pressure from MeOH/DCM to remove the water to yield 5-phenylquinazoline-2,4(1H,3H)-dione as an off-white solid. The 5-phenylquinazoline-2,4(1H,3H)-dione (9.64 g, 40.4 mmol) was added to POCl$_3$ (75 mL, 810 mmol) followed by PhN(CH$_3$)$_2$ (10.3 mL, 81.0 mmol). Upon completion of addition, the reaction mixture was heated to reflux (105° C.) where it was stirred for 2 hours. After this time, the reaction mixture was allowed to cool to ambient temperature. Once at the prescribed temperature, the reaction mixture was concentrated under reduced pressure, diluted with DCM and then quenched by the addition of cold 1M K$_3$PO$_4$ solution. The organic layer was separated and the aqueous layer was extracted twice with DCM. The combined organic layers were dried over MgSO$_4$, filtered and concentrated under reduced pressure to yield a residue. The residue was purified by ISCO chromatography (330 g column) using hexanes/EtOAc (0-25% over 20 min, flow rate 100 mL/min) to give 2,4-dichloro-5-phenylquinazoline (7.11 g, 63.9% yield) as a yellow solid.

¹H NMR (400 MHz, chloroform-d) ppm 8.04 (1H, m) 7.96 (1H, m) 7.59 (1H, dd, J=7.28, 1.25 Hz) 7.45 (3H, dd, J=5.02, 1.76 Hz) 7.32 (2H, m).

Step 4. Preparation of 2-chloro-5-phenyl-N-(pyridin-2-ylmethyl)quinazolin-4-amine

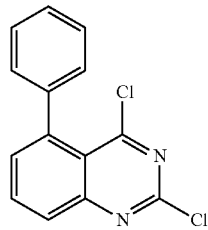 

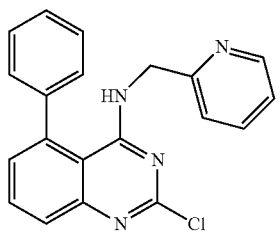

2,4-Dichloro-5-phenylquinazoline (1.38 g, 5.03 mmol) was dissolved in THF (80 mL) and triethylamine (1.33 mL, 9.56 mmol) was added dropwise. The mixture was stirred for 5 min at room temperature and then pyridin-2-ylmethanamine (0.57 mL, 5.53 mmol) was added dropwise. The resulting mixture was stirred at ambient temperature for 14 hours. After this time, the mixture was filtered through a medium porosity glass frit, concentrated to dryness under reduced pressure and then purified by ISCO flash column chromatography (80 g silica gel column) eluting with 0-100% ethyl acetate/hexanes over 30 min to provide 2-chloro-5-phenyl-N-(pyridin-2-ylmethyl)quinazolin-4-amine (1.32 g, 75%). LCMS Method A [M+1] observed 347.1. HPLC Method B: Purity 99.1% retention time 6.66 min. ¹H NMR (400 MHz, chloroform-d) δ ppm 8.16 (1H, d, J=4.77 Hz), 7.79 (1H, d, J=7.28 Hz), 7.70 (1H, t, J=7.78 Hz), 7.59 (1H, dt, J=7.53, 1.51 Hz), 7.40-7.55 (5H, m), 7.08-7.25 (4H, m), 4.66 (2H, d, J=4.02 Hz).

Step 5. Example 1

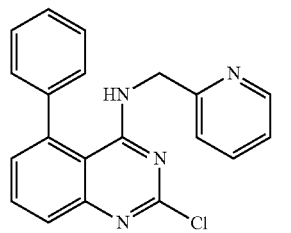 

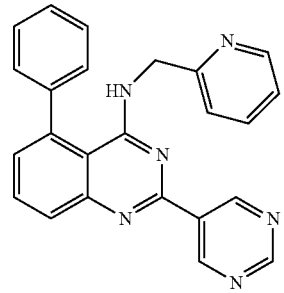

2-Chloro-5-phenyl-N-(pyridin-2-ylmethyl)quinazolin-4-amine (225 mg, 0.649 mmol), pyrimidin-5-ylboronic acid (121 mg, 0.973 mmol), and bis (triphenylphosphine)palladium (II) chloride (23 mg, 0.032 mmol) were combined in a microwave tube which was sealed, evacuated and then backfilled with argon. Under argon, previously degassed dioxane (1 mL) and a sodium carbonate (0.33 mL, 0.330 mmol) in water (0.33 mL) solution were added to the reaction mixture. The resulting mixture was heated under microwave irradiation to 100° C. where it was maintained for 60 min. After this time, additional pyrimidin-5-ylboronic acid (91 mg, 0.7773 mmol) and bis (triphenylphosphine) palladium (II) chloride (17 mg, 0.024 mmol) were added. Upon completion of addition, the resulting mixture was heated under microwave irradiation at 100° C. for 40 min and then allowed to cool to room temperature where it stirred for 14 h. At the conclusion of this period, the reaction mixture was diluted with 50 mL each of water and ethyl acetate. The organic layer was separated and the aqueous portion was extracted with ethyl acetate. The combined organic portions were washed with 50 mL of brine, dried over Na₂SO₄, decanted and concentrated under reduced pressure to yield a crude residue. The crude residue was purified by ISCO (40 g silica gel column) eluting with 0-5% MeOH over 15 min and then 5% MeOH for 10 min to yield Example 1 (212 mg, 84%). ¹H NMR (400 MHz, CDCl₃) ppm 4.74 (d, J=4.27 Hz, 2H) 6.73-6.81 (m, 1H) 7.09-7.16 (m, 2H) 7.25-7.29 (m, 1H) 7.44-7.52 (m, 5H) 7.58 (dt, J=7.72, 1.88 Hz, 1H) 7.73 (dd, J=8.28, 7.28 Hz, 1H) 7.93 (dd, J=8.28, 1.25 Hz, 1H) 8.23-8.26 (m, 1H) 9.29 (s, 1H) 9.78 (s, 2H). LCMS Method D: retention time 0.76 min, [M+1]=391; HPLC Method B: purity 99%, retention time 5.6 min.

Alternatively, Example 1 can be synthesized as follows:

Step 1. Preparation of methyl pyrimidine-5-carbimidate

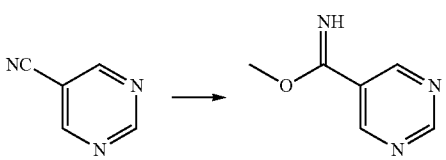

To a stirred suspension of 5-cyanopyrimidine (5.0 g, 47 mmol) in methanol (50 mL) was added 25% by weight sodium methoxide in methanol (1.2 g, 23 mmol). The mixture was stirred at room temperature for 17 h under nitrogen atmosphere and then acetic acid (2.72 ml, 47 mmol) was added dropwise. The resulting mixture was stirred for 4 h and then evaporated under reduced pressure to remove methanol and yield a residue. The residue was dissolved in ether (150 mL) and the solids were removed by filtration. The filtrate was concentrated under reduced pressure to yield methyl pyrimidine-5-carbimidate (4.9 g, 75% yield). The crude product was used without further purification. ¹H NMR (400 MHz, DMSO-d₆, δ): 3.83 (s, 3H); 9.18 (s, 2H); 9.30 (s, 1H); 9.54 (s, 1H). ES-MS: [M⁺+1]=138.

Step 2. Preparation of 5-bromo-2-(pyrimidin-5-yl)quinazolin-4-ol

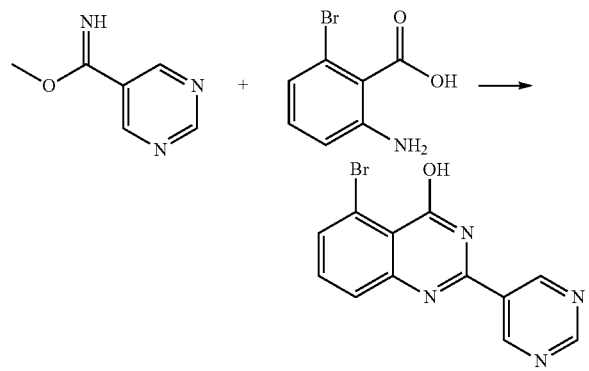

To a stirred suspension of methyl pyrimidine-5-carbimidate (2.00 g, 14.5 mmol) in methanol (20 mL) was added 2-amino-6-bromobenzoic acid (3.1 g, 14.5 mmol). The mixture was heated to reflux where it stirred for 16 h under the nitrogen atmosphere. At the conclusion of this period, acetic acid (2.72 ml, 47 mmol) was added drop wise. Upon completion of addition, methanol was evaporated under reduced pressure to yield a residue. The residue was triturated with ether (100 mL), ethyl acetate (50 mL) and the resulting solid was dried to yield 5-bromo-2-(pyrimidin-5-yl)quinazolin-4-ol (1.2 g, 27%) as an off-white solid. The crude product was used without further purification. ¹H NMR (400 MHz, DMSO-d₆, δ): 7.64 (dd, J=7.2 Hz, 8.4 Hz, 1H); 7.73-7.75 (m, 2H); 9.35 (s, 1H); 9.46 (s, 2H); 12.9 (br s, 1H). ES-MS: [M⁺+1]=303 and [M⁺+3]=305.

Step 3. Preparation of 5-bromo-N-(pyridin-2-ylmethyl)-2-(pyrimidin-5-yl)quinazolin-4-amine

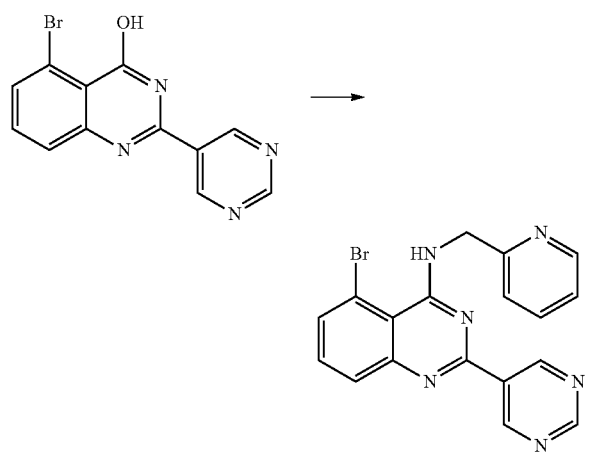

To a stirred suspension of 5-bromo-2-(pyrimidin-5-yl)quinazolin-4-ol (2.0 g, 6.5 mmol) in DMF (20 mL) was added diisopropylethyl amine (3.4 ml, 19 mmol) followed by PyBroP (3.7 g, 7.9 mmol). After 5 min stirring at room temperature, 2-aminomethylpyridine (1.0 mL, 9.8 mmol) was added to the reaction. Upon completion of addition, the reaction mixture was warmed to 80° C. where it stirred for 2 h (during which time reaction became a clear solution). At the conclusion of this period, the reaction mixture was quenched by the addition of cold water and then extracted into 50% ethyl acetate and hexane mixture (200 mL). The organic extracts were dried, concentrated, purified by column chromatography using ethyl acetate and hexanes as eluent to yield the crude produce. The crude product was further purified by trituration with ethyl acetate and hexane to yield 5-bromo-N-(pyridin-2-ylmethyl)-2-(pyrimidin-5-yl)quinazolin-4-amine (0.5 g, 20% yield). ¹H NMR (400 MHz, CDCl₃, δ): 5.07 (d, J=4.4 Hz, 2H); 7.26 (m, 1H); 7.41 (d, J=7.6 Hz, 1H); 7.53 (t, J=8 Hz, 1H); 7.71-7.73 (m, 2H); 7.86 (dd, J=0.8 Hz, 8.4 Hz, 1H); 8.65 (d, J=4 Hz, 1H); 9.30 (s, 1H); 9.38 (br s, 1H); 9.75 (s, 2H). ES-MS: [M⁺+1]=393 and [M⁺+3]=395.

Step 4. Example 1

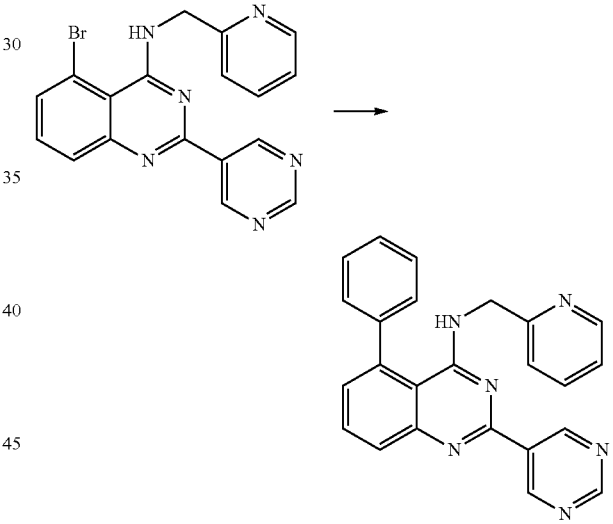

A stirred suspension of 5-bromo-N-(pyridin-2-ylmethyl)-2-(pyrimidin-5-yl)quinazolin-4-amine (1.0 g, 2.5 mmol), phenylboronic acid (0.46 g, 3.8 mmol) and potassium carbonate (1.0 g, 7.6 mmol) in dimethoxyethane-water (3-1, 10 mL) was degassed and charged with tetrakistriphenylphosphene palladium (0.14 g, 0.12 mmol). The reaction mixture was then heated to 90° C. where it stirred for 16 h under a nitrogen atmosphere. After this time, the reaction mixture was quenched with water (5 mL) and then extracted with ethyl acetate (3×25 mL). The combined organic extracts were dried and then concentrated to yield the crude product. The crude product was purified by preparative TLC using chloroform and methanol (95:5) as the solvent system to yield Example 1 (40 mg, 4% yield). ¹H NMR (400 MHz, DMSO-d₆, δ): 5.01 (d, J=5.6 Hz, 2H); 7.27 (t, J=4.0 Hz, 1H); 7.41-7.56 (m, 5H); 7.66-7.79 (m, 4H); 7.91 (d, J=6.8 Hz, 1H); 8.42 (d, J=8 Hz, 1H); 8.55 (d, J=4.8 Hz, 1H); 9.23 (s, 1H); 9.32 (t, J=6 Hz, 1H); 9.40 (s, 2H). LCMS Method O: retention time 1.67 min, [M+1]=391. HPLC Method B: purity 99%, retention time 8.5 min.

Example 1 can also be synthesized as follows:

Step 1. Preparation of 5-phenyl-2-(pyrimidin-5-yl)quinazolin-4-ol

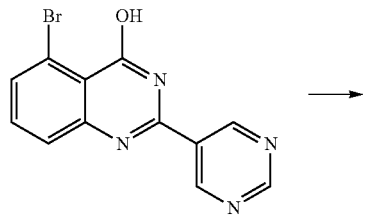

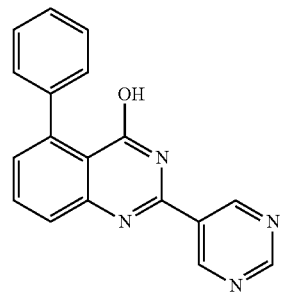

A stirred suspension of 5-bromo-2-(pyrimidin-5-yl)quinazolin-4-ol (2.0 g, 6.6 mmol), phenylboronic acid (1.2 g, 9.9 mmol) and a solution of potassium carbonate (2.6 g, 19.8 mmol) in dimethoxyethane and water (3:1, 15 mL) was degassed and charged with 1,1'-bis(diphenylphosphino)ferrocene palladium dichloride (0.24 g, 0.33 mmol). The reaction mixture was heated to 90° C. where it stirred for 24 h under nitrogen atmosphere. At the conclusion of this period, the reaction mixture was concentrated to yield the crude product. The crude product was purified by flash column chromatography on silica gel using 2% methanol in dichloromethane as eluent to yield 5-phenyl-2-(pyrimidin-5-yl)quinazolin-4-ol (800 mg, 27% yield). $^1$H NMR (400 MHz, DMSO-$d_6$, δ): 7.29-7.40 (m, 6H); 7.79-7.87 (m, 4H); 9.37 (s, 1H); 9.45 (s, 2H); 12.59 (br s, 1H). LCMS Method O: retention time 1.68 min, [M+1]=301.

Step 2: Example 1

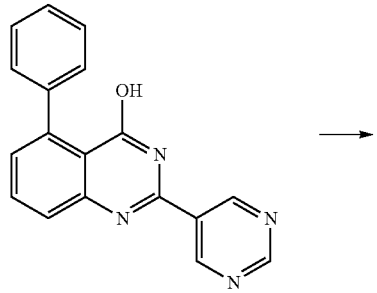

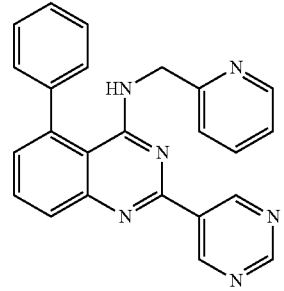

5-Phenyl-2-(pyrimidin-5-yl)quinazolin-4-ol was subsequently converted to Example 1 utilizing the reagents and conditions described for the preparation of 5-bromo-N-(pyridin-2-ylmethyl)-2-(pyrimidin-5-yl)quinazolin-4-amine in step 3 above.

Example 2

5-Phenyl-N-(pyridin-2-ylmethyl)-2-(trifluoromethyl)quinazolin-4-amine

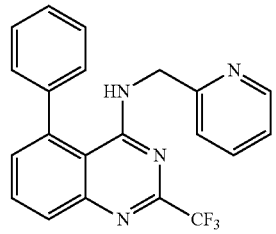 [SMILES: FC(F)(F)c1nc(NCc2ccccn2)c2c(-c3ccccc3)cccc2n1]

Step 1. Preparation of 5-chloro-2-(trifluoromethyl)quinazolin-4(3H)-one

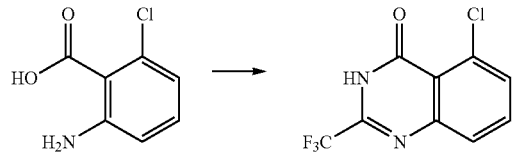 [SMILES: Nc1cccc(Cl)c1C(=O)O ; O=c1[nH]c(C(F)(F)F)nc2cccc(Cl)c12]

See U.S. Pat. No. 3,843,791. To a solution of 2-amino-6-chlorobenzoic acid (1.91 g, 11.13 mmol) in a mixture of chloroform (22 mL) and dry pyridine (1.5 mL) at 0° C. was added trifluoroacetic anhydride (3.52 mL, 24.94 mmol). Upon completion of addition, the reaction mixture was heated to reflux where it stirred for 2 h. After this time, the reaction mixture was cooled to room temperature and concentrated to yield a crude material. The crude material was dissolved in chloroform (22 mL), saturated with ammonia gas and then stirred for 30 min at room temperature. After this time, the mixture was concentrated and the resulting solid was washed with 1N HCl (2×20 mL) and diluted with ethyl acetate (100 mL) and water (100 mL). The organic layer was separated and the aqueous layer was extracted with ethyl acetate (100 mL). The organic layer was dried over MgSO$_4$, filtered and concentrated to yield the crude product. The crude product was purified by flash chromatography on silica gel eluting with 2-15% ethyl acetate/hexanes to afford 5-chloro-2-(trifluoromethyl)quinazolin-4(3H)-one (1.3 g, 46%) as a white solid. $^1$H NMR (400 MHz, chloroform-d) ppm 10.23 (1H, br. s.), 7.71-7.82 (2H, m), 7.64 (1H, d, J=7.15 Hz). LCMS Method A: retention time 0.65 min [M+1]=250.

Step 2. Preparation of 5-phenyl-2-(trifluoromethyl)quinazolin-4(3H)-one

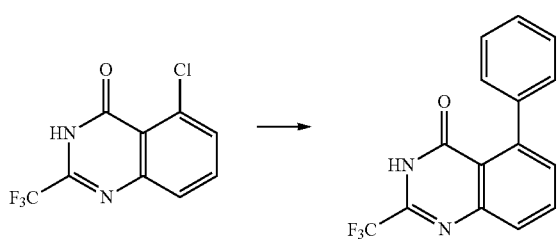 [SMILES: O=c1[nH]c(C(F)(F)F)nc2cccc(Cl)c12 ; O=c1[nH]c(C(F)(F)F)nc2cccc(-c3ccccc3)c12]

Palladium (II) acetate (19 mg, 0.085 mmol), potassium fluoride (498 mg, 8.57 mmol), 2-(di-tert-butylphosphino) biphenyl (51.1 mg, 0.171 mmol), and phenylboronic acid (522 mg, 4.27 mmol) were combined in a microwave vial under an argon atmosphere. A solution of 5-chloro-2-(trifluoromethyl)quinazolin-4(3H)-one (710 mg, 2.86 mmol) in dry THF (9 mL) was added and the mixture was heated in the microwave at 100° C. for 30 min. After this time, the reaction mixture was diluted with ethyl acetate (50 mL) and washed with 1N NaOH (25 mL) and saturated NaCl (25 mL). The organic layer was separated, dried over sodium sulfate and then concentrated under reduced pressure to give the crude product (968 mg), which was used in the next step without further purification.

Step 3. Preparation of 4-chloro-5-phenyl-2-(trifluoromethyl)quinazoline

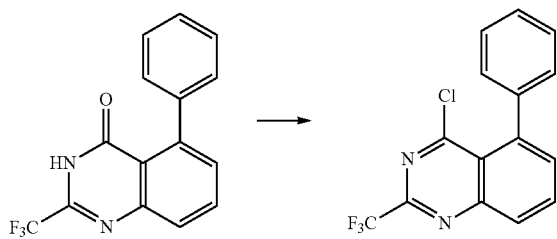 [SMILES: O=c1[nH]c(C(F)(F)F)nc2cccc(-c3ccccc3)c12 ; FC(F)(F)c1nc(Cl)c2c(-c3ccccc3)cccc2n1]

To the crude material from Step 2, Example 3, was added phosphorous oxychloride (2.86 mL, 307 mmol) and N,N-dimethylaniline (425 µL, 3.34 mmol). The reaction mixture was heated to 100° C. where it stirred for 10 min. After this time, the reaction mixture was cooled to room temperature. Once at the prescribed temperature, the solvents were removed under reduced pressure to yield a residue, which was then dissolved in dichloromethane (20 mL). The dichloromethane solution was added to 50 mL of a 1.5 M KH$_2$PO$_4$ solution. Upon completion of addition, the dichloromethane was removed under reduced pressure and the aqueous layer was extracted with DCM (3×50 mL). The combined organic portions were dried over sodium sulfate and concentrated under reduced pressure to yield a second residue. The second residue was purified by flash chromatography on silica gel eluting with 100% DCM to yield 4-chloro-5-phenyl-2-(trifluoromethyl)quinazoline (612 mg, 59% yield) as a white solid. $^1$H NMR (400 MHz, chloroform-d) ppm 8.27 (1H, d, J=8.53 Hz), 8.07 (1H, t, J=7.78 Hz), 7.75 (1H, d, J=7.03 Hz), 7.42-7.54 (3H, m), 7.29-7.38 (2H, m). LCMS Method D: retention time 1.07 min [M+1]=309.

Step 4. Example 2

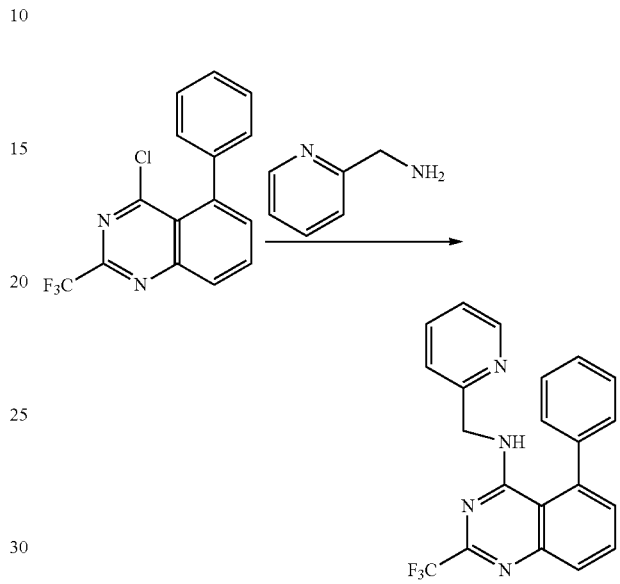

To a solution of 4-chloro-5-phenyl-2-(trifluoromethyl)quinazoline (200 mg, 0.648 mmol) in THF (15 mL) was added triethylamine (0.172 mL, 1.231 mmol). Upon completion of addition, the reaction mixture was stirred and pyridin-2-ylmethanamine was added (0.080 mL, 0.777 mmol). The resulting reaction mixture was stirred at room temperature for 1 h and then filtered. The filtrate was concentrated under reduced pressure to yield a residue. The residue was purified by flash chromatography on silica gel eluting with 0-75% ethyl acetate/hexanes to yield Example 2 (217 mg, 88% yield) as a white solid. $^1$H NMR (400 MHz, chloroform-d) ppm 8.20 (1H, d, J=4.55 Hz), 7.99 (1H, d, J=8.34 Hz), 7.78 (1H, t, J=7.71 Hz), 7.59 (1H, t, J=7.58 Hz), 7.42-7.54 (5H, m), 7.35 (1H, d, J=7.33 Hz), 7.03-7.22 (3H, m), 4.69 (2H, d, J=4.04 Hz). LCMS Method D: retention time 0.90 min [M+1]=381.

Example 3

2-Cyclopropyl-5-phenyl-N-(pyridin-2-ylmethyl)quinazolin-4-amine

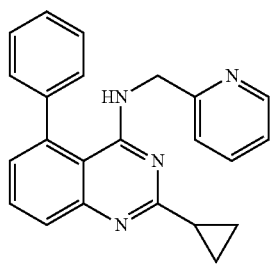 [SMILES: c1ccc(-c2cccc3nc(C4CC4)nc(NCc4ccccn4)c23)cc1]

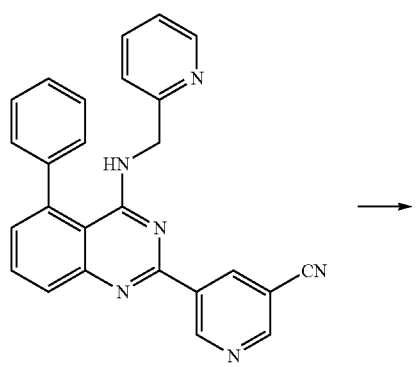

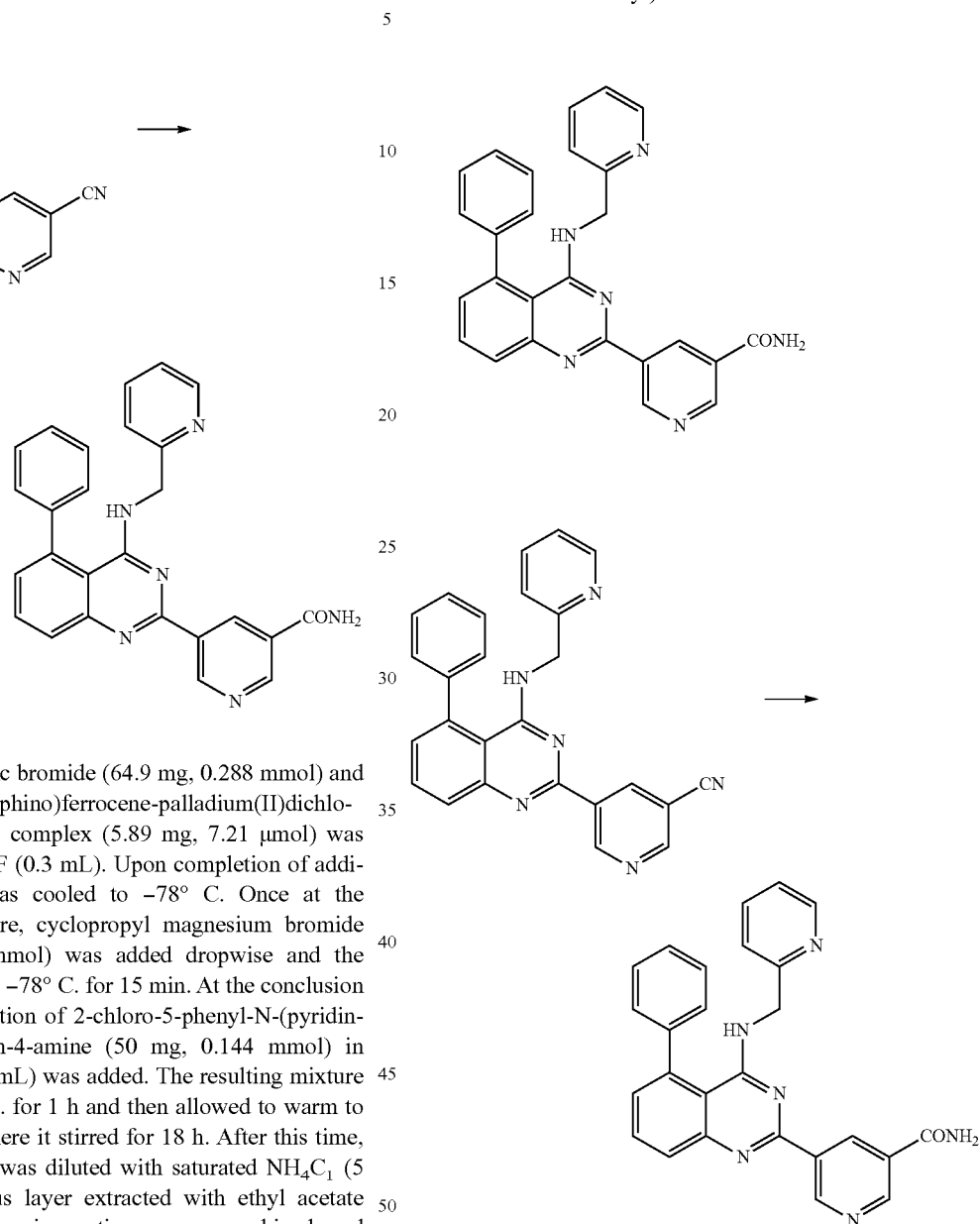

Example 6

5-(5-Phenyl-4-(pyridin-2-ylmethylamino)quinazolin-2-yl)nicotinamide

To a mixture of zinc bromide (64.9 mg, 0.288 mmol) and 1,1'-bis(diphenylphosphino)ferrocene-palladium(II)dichloride dichloromethane complex (5.89 mg, 7.21 μmol) was added anhydrous THF (0.3 mL). Upon completion of addition, the mixture was cooled to −78° C. Once at the prescribed temperature, cyclopropyl magnesium bromide (0.288 mL, 0.144 mmol) was added dropwise and the mixture was stirred at −78° C. for 15 min. At the conclusion of this period, a solution of 2-chloro-5-phenyl-N-(pyridin-2-ylmethyl)quinazolin-4-amine (50 mg, 0.144 mmol) in anhydrous THF (1.5 mL) was added. The resulting mixture was stirred at −78° C. for 1 h and then allowed to warm to room temperature where it stirred for 18 h. After this time, the reaction mixture was diluted with saturated $NH_4C_1$ (5 mL) and the aqueous layer extracted with ethyl acetate (3×20 mL). The organic portions were combined and washed with saturated NaCl, dried over sodium sulfate and concentrated under reduced pressure to yield the crude product. The crude product was purified by preparative HPLC (YMC Sunfire 5u C18 30×100 mm, Mobile Phase A: 10% MeOH-90% $H_2O$-0.1% TFA, Mobile Phase B: 90% MeOH-10% $H_2O$-0.1% TFA, 20-100% B over 10 min, 100% B for 2 min) to yield Example 3 (3.73 mg, 7% yield) as a pale yellow solid. $^1$H NMR (400 MHz, chloroform-d) ppm 8.27-8.30 (1H, m), 7.77 (1H, dd, J=8.46, 0.88 Hz), 7.63 (1H, dd, J=8.34, 7.07 Hz), 7.56 (1H, td, J=7.71, 1.77 Hz), 7.41-7.48 (5H, m), 7.04-7.15 (3H, m), 6.30 (1H, br. s.), 4.57 (2H, d, J=4.55 Hz), 2.11-2.20 (1H, m), 1.10-1.16 (2H, m), 0.92-0.98 (2H, m). LCMS Method D: retention time 0.76 min [M+1]=353.

To a solution of 5-(5-phenyl-4-(pyridin-2-ylmethylamino)quinazolin-2-yl)nicotinonitrile (prepared in a similar manner to the procedures described in Example 1, 200 mg, 0.48 mmol) in THF (5 mL) was slowly added a solution of sodium hydroxide (77 mg, 1.92 mmol) in $H_2O$ (2 mL). The resulting mixture was cooled to 0° C. and 30% $H_2O_2$ (0.2 mL, 1.92 mmol) was added. Upon completion of addition, the reaction mixture was allowed to warm to room temperature where it stirred for 16 h. At the conclusion of this period, the reaction mixture was filtered and purified by preparative TLC using 5% chloroform in methanol to afford Example 6 (50 mg) as brown solid. $^1$H NMR (400 MHz, DMSO-$d_6$) δ (ppm): 9.74 (d, J=1.8 Hz, 1H), 9.18-9.15 (dd, J=11.2, 1.6 Hz, 2H), 8.34 (s, 1H), 8.24 (d, J=4.4 Hz, 1H), 7.95-7.93 (dd, J=8.4, 1.2 Hz, 1H), 7.88-7.84 (dt, J=7.2, 1.6 Hz, 1H), 7.76-7.71 (dt, J=8.0, 1.6 Hz, 2H), 7.59-7.52 (m, 5H), 7.37-7.31 (dd, J=13.6, 8.0 Hz, 2H), 7.24 (t, J=6.0 Hz, 1H), 6.94 (t, J=4.0 Hz, 1H), 4.78 (d, J=4.0 Hz, 2H). LCMS Method O: retention time 1.39 min; [M+1]=433.0. HPLC Method B: purity 97.9%, retention time 8.06 min.

Example 7

5-(5-Phenyl-4-(pyridin-2-ylmethylamino)quinazolin-2-yl)pyridine-3-sulfonamide

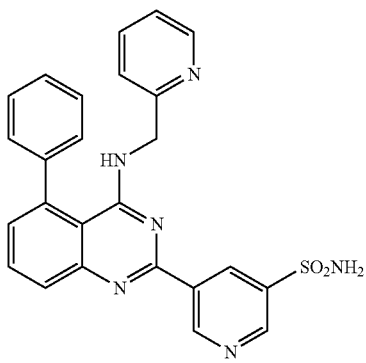 [SMILES: NS(=O)(=O)c1cncc(-c2nc(NCc3ccccn3)c3c(-c4ccccc4)cccc3n2)c1]

Step 1. Preparation of 5-Bromopyridine-3-sulfonamide

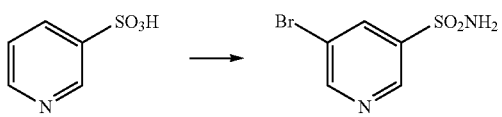 [SMILES: O=S(=O)(O)c1cccnc1 ; NS(=O)(=O)c1cncc(Br)c1]

See also U.S. Publication Nos. 2006/217387 and 2006/375834, and *J. Org. Chem.*, 54:389 (1989). A mixture of pyridine-3-sulfonic acid (10.3 g, 64.8 mmol), phosphorous pentachloride (20.82 g, 100 mmol) and phosphorous oxychloride (10 mL, 109 mmol) was heated to reflux where it stirred for 4 h. At the conclusion of this period, the reaction mixture was allowed to cool to room temperature. Once at the prescribed temperature, the reaction mixture was evaporated to dryness under reduced pressure to yield a residue. The residue was treated with bromine (6.00 mL, 116 mmol) and then heated to reflux where it stirred for 14 h. After this time, the reaction mixture was cooled to 0° C. and then a saturated solution of NH$_4$OH in H$_2$O (40 mL) was slowly added. The resulting mixture was allowed to warm to room temperature where it stirred for 30 min. The reaction mixture was then filtered and the filter cake was washed with hexane to afford 5-bromopyridine-3-sulfonamide (6.0 g) as an off-white solid. The product was used without further purification. LCMS Method Q: retention time 0.75 min; [M+1]=237.0.

Step 2. Preparation of pyridine-3-sulfonamide-5-ylboronic acid pinacol ester

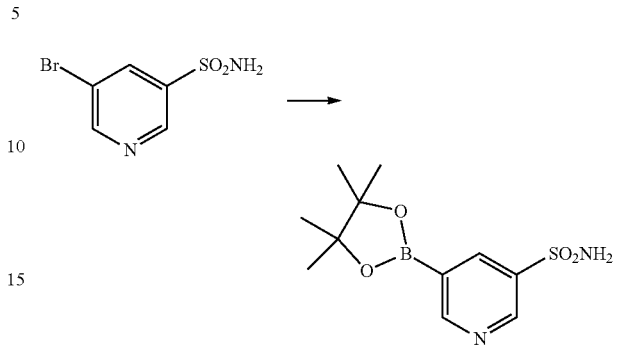

See also WO2008/150827 A1 and WO2008/144463. A mixture of 5-bromopyridine-3-sulfonamide (1.5 g, 6.33 mmol), bis(pinacolato)diboron (2.41 g, 9.5 mmol) and potassium acetate (1.86 g, 19.0 mmol) in 1,4-dioxane (15 mL) was degassed with nitrogen for 15 min then (1,1'-bis(diphenylphosphino)-ferrocene)palladium (II) chloride dichloromethane complex (232 mg, 0.317 mmol) was added and the resulting mixture was degassed again with nitrogen for 10 min. At the conclusion of this period, the reaction mixture was heated in a microwave at 120° C. for 45 min. After this time, the reaction mixture was filtered through CELITE® and the filtrate was concentrated under reduced pressure to provide pyridine-3-sulfonamide-5-ylboronic acid pinacol ester (740 mg) as a brown solid. The product was used without further purification. $^1$H NMR (400 MHz, DMSO-d$_6$) δ (ppm): 8.83 (s, 1H), 8.80 (s, 1H), 8.26 (s, 1H), 7.56-7.74 (bs, 2H), 1.17 (s, 12H).

Step 3. Example 7

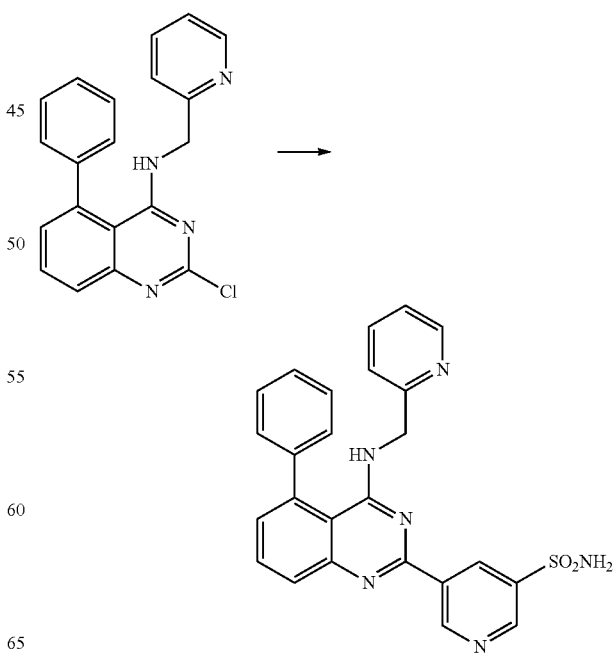

To a solution of 2-chloro-5-phenyl-N-(pyridin-2-ylmethyl)quinazolin-4-amine (150 mg, 0.43 mmol) in 1,4-dioxane (6 mL) and H$_2$O (1 mL) under nitrogen was added pyridine-3-sulfonamide-5-ylboronic acid pinacol ester (185 mg, 0.65 mmol), and potassium carbonate (119 mg, 0.86 mmol). Upon completion of addition, the mixture was degassed with nitrogen for 15 minutes and then (1,1'-bis(diphenylphosphino)ferrocene)palladium (II) chloride dichloromethane complex (31 mg, 0.043 mmol) was added. The resulting mixture was again degassed with nitrogen for 10 min. After this time, the mixture was heated to 90° C. where it stirred for 16 h. At the conclusion of this period, the reaction mixture was allowed to cool to room temperature. Once at the prescribed temperature, the reaction mixture was quenched by the addition of water and then transferred to a separation funnel. The aqueous layer was extracted with ethyl acetate. The combined organic portions were washed with water and saturated NaCl, dried over Na$_2$SO$_4$, filtered and concentrated under reduced pressure. The resulting concentrate was purified by preparative TLC using 5% methanol in dichloromethane to afford Example 7 (50 mg) as a brown solid. $^1$H NMR (400 MHz, DMSO-d$_6$) δ (ppm): 9.81 (s, 1H), 9.17 (s, 1H), 9.09 (s, 1H), 8.24 (d, J=4.4 Hz, 1H), 7.94 (d, J=7.2 Hz, 1H), 7.86 (t, J=7.6 Hz, 1H), 7.75-7.72 (t, J=7.6 Hz, 3H), 7.59-7.51 (m, 5H), 7.34 (d, J=7.2 Hz, 2H), 7.24 (t, J=6.4 Hz, 1H), 6.98 (t, J=3.2 Hz, 1H), 4.77 (d, J=4.0 Hz, 2H). LCMS Method Q: retention time 1.39 min; [M+1]=469.0. HPLC Method B: purity 98.1%, retention time=8.74 min.

Alternatively, Example 7 can be synthesized as follows:

Step 1. Preparation of 5-Bromo-pyridine-3-sulfonyl chloride

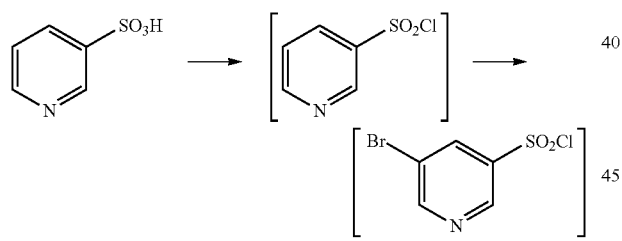

PCl$_5$ (2.95 Kg, 14.16 moles) and POCl$_3$ (2.45 Kg, 15.98 moles) were added into pyridine-3-sulfonic acid (1.5 Kg, 9.42 mol) in 10 L RB flask equipped with mechanical stirrer under inert atmosphere. The reaction mass was heated to 120-125° C. where it stirred for 18 h. After this time, the reaction progress was monitored by HPLC, which indicated the reaction was complete. Excess POCl$_3$ was removed under vacuum to give a residue. The residue was cooled to ambient temperature and bromine (1.2 Kg, 7.5 moles) was added. Upon completion of addition, the resulting mixture was heated to 120-125° C. where it stirred for 5 h. At the conclusion of this period, the reaction progress was monitored by HPLC, which indicated the reaction was complete. The reaction mixture was cooled to ambient temperature and then poured into ice-water (10 L), and the resulting mixture was extracted with DCM (10.5 L×2). The DCM extracts were combined and the solvent was removed under vacuum to yield crude product (1.8 Kg, 74.4% yield).

Step 2. Preparation of 5-bromo-N-tert-butylpyridine-3-sulfonamide

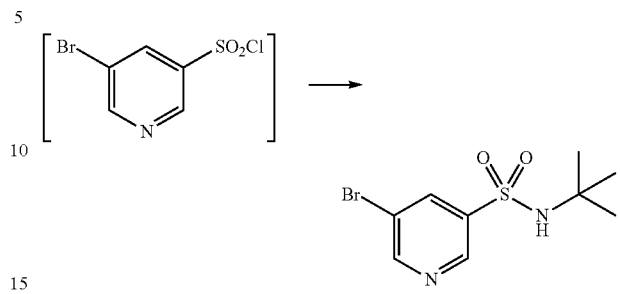

Crude 5-bromopyridine-3-sulfonyl chloride from step 1 above was dissolved in THF (14 L, 8 vol) and then transferred to a 20 L RB flask equipped with mechanical stirrer under inert atmosphere. The solution was cooled to 0-5° C. and tert-butyl amine (1.95 Kg, 26.66 moles) was added at 0-5° C. Upon completion of addition, the reaction mixture was warmed to ambient temperature where it stirred for 2 h. At the conclusion of this period, the reaction progress was monitored by HPLC, which indicated that the reaction was complete. The solvent was evaporated under vacuum to give a thick residue. The residue was dissolved in ethyl acetate (18 L, 12 vol). The organic layer was separated, washed with water (9 L, 5 vol) and then concentrated under vacuum to yield a residue. Hexanes (9 L, 5 vol) were added to the residue and the product precipitated out and was collected by filtration to yield a free flowing yellow solid (1.5 Kg, 54.28% overall yield). $^1$H NMR (DMSO-D6, 400 MHz, δ ppm); 8.99 (d, J=2 Hz, 1H), 8.81 (d, J=2 Hz, 1H), 8.29 (t, J=2 Hz, 1H). [M$^+$+1]=293.

Step 3. Preparation of 5-bromo-N-tert-butylpyridine-3-sulfonamide

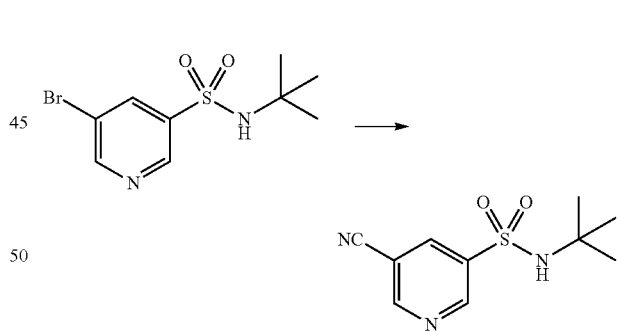

5-Bromo-N-tert-butylpyridine-3-sulfonamide (1.5 Kg, 5.11 moles) was dissolved in dimethylformamide (7.5 L, 5 vol) and the solution was added to a 20 L glass-lined reactor equipped with mechanical stirrer. The solution was degassed with nitrogen for 30 min. After this time, potassium ferrocyanide trihydrate (867 g, 2.05 moles), sodium carbonate (1.08 Kg, 10.189 moles), copper (I) iodide (73.2 g, 0.374 moles) and dichloro-bis (triphenylphosphine) palladium (II) (71.6 g, 0.102 moles) were added. Upon completion of addition, the reaction mixture was heated to 120-125° C. where it stirred for 4 h. At the conclusion of this period, the reaction progress was monitored by HPLC, which indicated the reaction was complete. The reaction mixture was cooled to ambient temperature and then filtered through a celite bed. Water (18 L, 12 vol) was added into the filtrate and the resulting mixture was extracted with ethyl acetate (7.5 L×2). The organic layers were combined, washed with water and then concentrated to yield a thick residue. Hexanes (7.5 L, 5 vol) were added to the residue. The product precipitated out and was collected by filtration to yield a free flowing yellow solid (1.0 Kg, 82.8% yield, 89% purity by HPLC). ¹H NMR (DMSO-D6, 400 MHz, δ ppm); 9.21-9.24 (d, d J=7.2 Hz, 3.2 Hz, 2H), 8.70-8.71 (m, 1H), 7.98 (s, 1H). [M⁺+1]=239.2.

Step 4. Preparation of 3-aminobiphenyl-2-carbonitrile

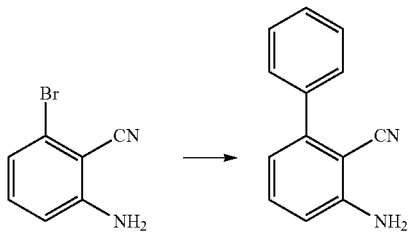 [SMILES: N#Cc1c(N)cccc1Br ; N#Cc1c(N)cccc1-c1ccccc1]

2-Amino-6-bromo-benzonitrile (1.0 Kg, 5.07 moles) and toluene (10 L, 10 vol) were added to a 20 L glass-lined reactor equipped with mechanical stirrer under inert atmosphere. Potassium acetate (996 g, 10.16 moles) and phenylboronic acid (866, 7.10 moles) were added into the solution and the solution was degassed with nitrogen for 30 min. After this time, dichloro-bis (triphenylphosphine) palladium (II) (17.8 g, 0.025 moles) was added to the reaction mixture at ambient temperature. The mixture was heated to 110° C., where it stirred for 17 h. At the conclusion of this period, the reaction progress was monitored by HPLC, which indicated the reaction was completed. The reaction mixture was filtered through a celite bed. The filtrate was transferred back to the reactor and concentrated hydrochloric acid (~35%, 2 L, 2 vol) was charged to the reactor at ambient temperature. The HCl salt of the title compound precipitated out from the reaction and was collected by filtration. The HCl salt was transferred into the 20 L reactor and then made basic with 10% NaOH solution (pH 8-9). The resulting product was extracted with ethyl acetate (10 L, 10 vol). The ethyl acetate layer was washed with water (5 L, 5 vol) and then the solvent was evaporated under vacuum to give a residue. Hexanes (5 L, 5 vol) were added to the residue at 35-40° C., and the resulting slurry was cooled to ambient temperature. Once at the prescribed temperature, the product was collected by filtration to provide a pale yellow solid (802 g, 81.4%, 99% by HPLC). ¹H NMR (DMSO-D6, 400 MHz, δ ppm); 7.43-7.52 (m, 5H), 7.33-7.37 (m, 1H), 6.83 (d, J=8 Hz, 1H), 6.62 (d, J=8 Hz, 1H), 6.1 (s, 2H). ES-MS: [M⁺+1]=194.23.

Step 5. Preparation of 5-(4-amino-5-phenylquinazolin-2-yl)-N-tert-butylpyridine-3-sulfonamide

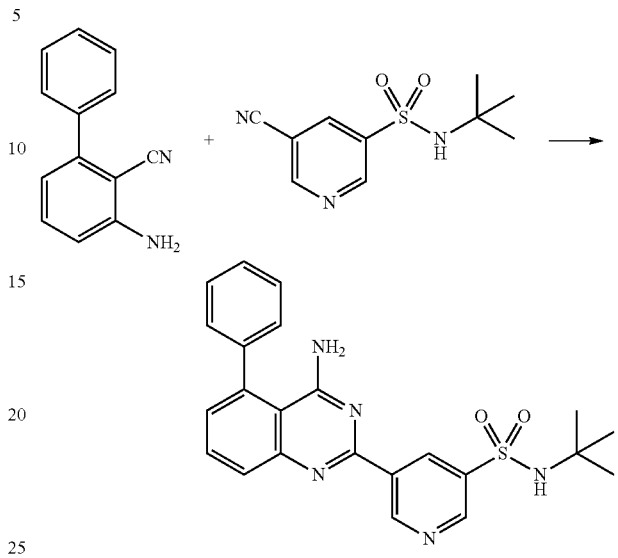

3-Aminobiphenyl-2-carbonitrile (1028 g, 5.30 moles), 5-bromo-N-tert-butylpyridine-3-sulfonamide (1440 g, 5.55 moles) and 1,4-dioxane (10 L, 10 vol) were added to a 20 L glass-lined reactor equipped with mechanical stirrer. Sodium tert-butoxide (1.275 Kg 12.870 moles) was added to the solution portion-wise at 20-30° C. Upon completion of addition, the reaction mixture was heated to reflux where it stirred for 2 h. At the conclusion of this period, the reaction progress was monitored by HPLC, which indicated the reaction was complete. The reaction mixture was cooled to 30-35° C. and then poured into water (40 L, 40 vol). The resulting mixture was extracted with DCM (20 L×2). The DCM layers were combined, washed with water (10 L, 10 vol) and then dried over sodium sulfate. The solvent was evaporated under vacuum to give a residue. Isopropyl alcohol (1.2 L, 1.2 vol) was added to the residue at 40° C. The resulting precipitate slurry was cooled to 10-15° C. and then stirred for 2 h. After this time, the precipitate was collected by filtration and dried at 50° C. for 16 h to yield the product (1.9 Kg, 82.9% yield, 99% purity by HPLC). ¹H NMR (DMSO-D6, 400 MHz, b ppm); 9.72 (s, 1H), 9.11 (s, 2H), 7.83-7.94 (m, 4H), 7.49-7.60 (m, 5H), 7.31 (d, d J=6.8 Hz, 1.2 Hz, 1H). ES-MS: [M⁺+1]=433.53.

Step 6. Preparation of N-tert-butyl-5-(5-phenyl-4-(pyridin-2-ylmethylamino) quinazolin-2-yl) pyridine-3-sulfonamide

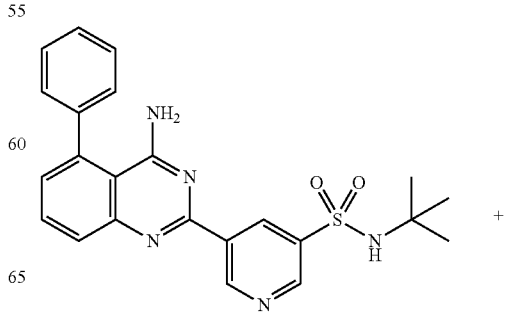

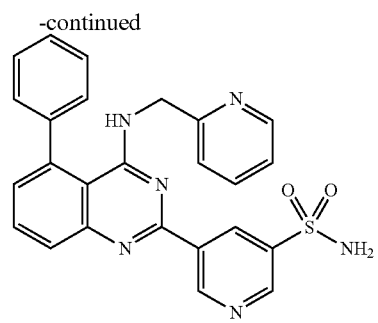

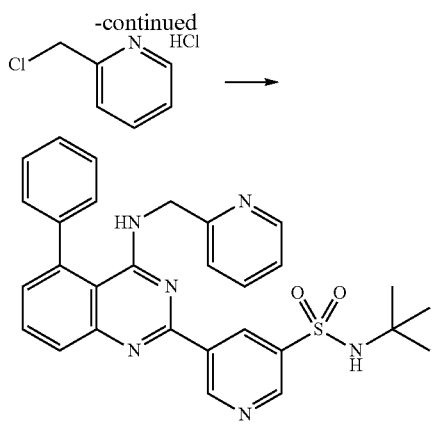

2-(Chloromethyl) pyridine hydrochloride (564 g, 3.44 moles) and dimethyl acetamide (7 L, 7 vol) were added to a 20 L RB flask-1 equipped with mechanical stirrer under inert atmosphere. The resulting solution was cooled to 0-5° C. and triethylamine (346.3, 3.44 moles) was added at 0-5° C. 5-(4-Amino-5-phenylquinazolin-2-yl)-N-tert-butlpyridine-3-sulfonamide (1.0 Kg. 2.306 moles) and dimethylacetamide (4 L, 4 vol) were added to a separate 20 L RB flask-2 equipped with mechanical stirrer under inert atmosphere. This solution was cooled to 0-5° C. and sodium tert-butoxide (884 g, 9.24 moles) was added at 0-5° C. The resulting solution was stirred to affect dissolution and then transferred to the RB flask-1 at 0-5° C. Upon completion of addition, the reaction mixture was stirred at 0-5° C. for 2 h. At the conclusion of this period, the reaction progress was monitored by HPLC, which indicated that the reaction was complete. The reaction mass was poured into water (60 L, 60 vol) with stirring. The crude product was collected by filtration and dried at 60° C. for 12 h. After this time, the dried material was dissolved in THF (20 L, 20 vol). Upon dissolution, 6M HCl in isopropyl alcohol (1 L, 1 vol) was added at 20-25° C. The crude HCL salt of the product was obtained a pale-yellow free flow solid (920 g, 71% yield, 93% purity by HPLC). The crude HCl salt (1.345 Kg, 2.56 moles), methanol (6.7 L, 5 vol) and dichloromethane (13.5 L, 10 vol) were added to a 20 L glass-lined reactor equipped with mechanical stirrer. The slurry was stirred for 20-30 min at 30° C. After this time, the solvent was distilled to 4 vol with respect to input under vacuum. The resulting slurry was cooled to 20-25° C., where stirred for 2 h. At the conclusion of this period, the slurry was filtered and dried at 50° C. for 6 h to yield the product (1.1 Kg, 82% yield, 98% purity by HPLC). ¹H NMR (DMSO-D6, 400 MHz, δ ppm); 9.72 (s, 1H), 9.10-9.14 (m, 2H), 8.39 (s, 1H), 7.92-8.03 (m, 4H), 7.56-7.58 (m, 5H), 7.43-7.49 (m, 3H), 7.1 (bs, 1H), 4.88 (s, 2H), 1.17 (2, 9H).

Step 7. Example 7

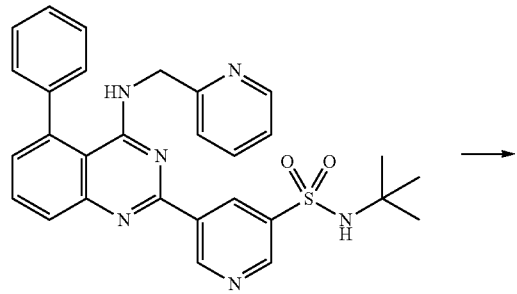

N-tert-butyl-5-(5-phenyl-4-(pyridin-2-ylmethylamino) quinazolin-2-yl) pyridine-3-sulfonamide (1.0 Kg, 1.9 moles) and concentrated hydrochloric acid (7 L, 7 vol) were added to a 20 L glass-lined reactor equipped with mechanical stirrer. The reaction mixture was heated to 90-100° C. where it stirred for 1 h. At the conclusion of this period, the reaction progress was monitored by HPLC, which indicated the reaction was complete. The reaction mixture was cooled to 5-10° C. and the pH was adjusted to 1.7 to 2.0 using 12% aqueous sodium hydroxide solution. Once at the prescribed pH, the crude HCl salt of the product was collected by filtration. The HCl salt filter cake and ethanol (5 L, 5 vol) were added to 10 L glass-lined reactor equipped with a mechanical stirrer. The resulting mixture was made basic to pH 7-8 at 20-25° C. using triethyl amine (2.25 Kg, 22.23 moles). Once at the prescribed pH, the basic mixture was stirred for 2 h. After this time, the free base of product was filtered and washed with water (10 L, 10 vol) followed by ethanol (2 L, 2 vol). The resulting product was dried at 50-55° C. for 8 h to yield Example 7 (644 g, 72% yield, 99.9% purity by HPLC). ¹H NMR (DMSO-D6, 400 MHz, δ ppm); 9.81 (d, J=2.0 Hz, 1H), 9.18 (t, J=2 Hz, 1H), 9.11 (d, J=2 Hz, 1H), 8.23 (d, J=4.4 Hz, 1H), 7.92-7.94 (m, 1H), 7.83-7.87 (m, 1H), 7.78 (s, 2H), 7.70-7.72 (m, 1H), 7.50-7.59 (m, 5H), 7.31-7.34 (m, 2H), 7.22-7.25 (m, 1H), 6.95 (t, J=4 Hz, 1H), 4.76 (d, J=4 Hz, 2H). ES-MS: [M⁺+1]=469.

Example 8

5-Phenyl-N-(pyridin-2-ylmethyl)-2-(2H-1,2,3-triazol-4-yl)quinazolin-4-amine

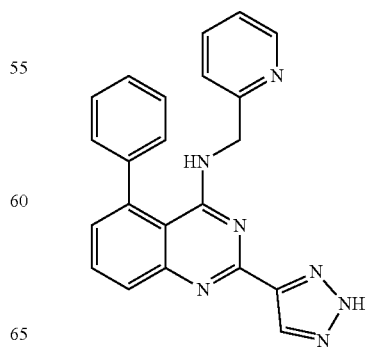

Step 1. Preparation of 2-ethynyl-5-phenyl-N-(pyridin-2-ylmethyl)quinazolin-4-amine

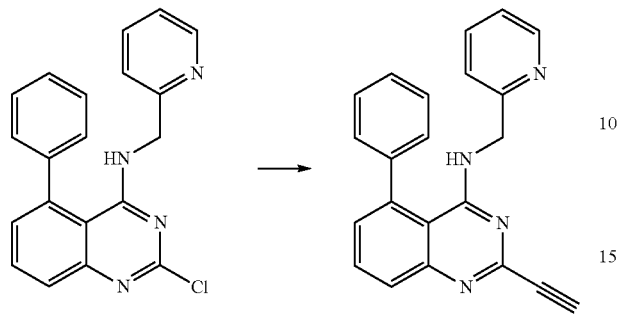

To a solution of 2-chloro-5-phenyl-N-(pyridin-2-ylmethyl)quinazolin-4-amine (1.0 g, 2.8 mmol) in DMF (10 mL) under nitrogen was added trimethylsilylacetylene (2.0 mL, 14 mmol), cupric iodide (0.11 g, 0.58 mmol) and Et$_3$N (1.2 mL, 8.4 mmol). Upon completion of addition, the mixture was degassed with nitrogen for 15 min. Tetrakis(triphenylphosphine)palladium (0.20 g, 0.28 mmol) was then added and the resulting mixture was again degassed with nitrogen for 10 min. After this time, the reaction mixture was heated in a sealed tube to 120° C. where it stirred for 16 h. At the conclusion of this period, the reaction mixture was allowed to cool to room temperature. Once at the prescribed temperature, the reaction mixture was quenched by the addition of water. The resulting reaction mixture was extracted with ethyl acetate and the organic layer was washed successively with water and brine. The combined organic layers were dried over Na$_2$SO$_4$, filtered and concentrated under reduced pressure. The resulting concentrate was dissolved in methanol and saturated with ammonia gas. The saturated solution was stirred for 2 h at 0° C. and then concentrated under reduced pressure to yield a residue. The residue was purified by flash column chromatography using ethyl acetate and petroleum ether to afford 2-ethynyl-5-phenyl-N-(pyridin-2-ylmethyl)quinazolin-4-amine (650 mg). $^1$H NMR (400 MHz, CDCl$_3$) δ (ppm): 8.15 (d, J=4.0 Hz, 1H), 7.86 (dd, J=8.4, 1.2 Hz, 1H), 7.69 (t, J=8.4 Hz, 1H), 7.56 (dt, J=3.6, 1.6 Hz, 1H), 7.49-7.42 (m, 5H), 7.26-7.23 (m, 1H), 7.13-7.08 (m, 2H), 6.94 (bs, 1H), 4.67 (d, J=10.0 Hz, 2H), 3.02 (s, 1H). LCMS Method O: retention time 1.35 min, [M+1]=337.0.

Step 2. Example 8

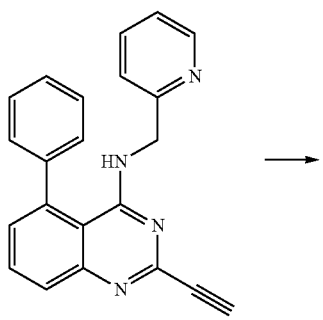

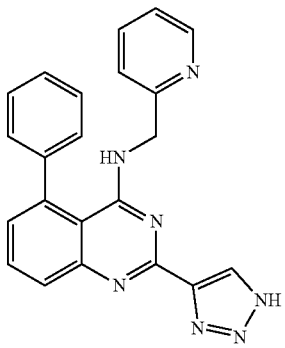 [SMILES: c1ccc(-c2cccc3nc(-c4cn[nH]n4)nc(NCc4ccccn4)c23)cc1]

To a suspension of 2-ethynyl-5-phenyl-N-(pyridin-2-ylmethyl)quinazolin-4-amine (0.17 g, 0.50 mmol) in toluene (3 mL) was added trimethylsilylazide (0.20 ml, 1.5 mmol). Upon completion of addition, the reaction mixture was heated in sealed tube to 120° C. where it was maintained for 2 days. At the conclusion of this period, the toluene was removed under reduced pressure to yield a residue. The residue was washed with water and then extracted with dichloromethane. The organic extracts were dried over Na$_2$SO$_4$, filtered and then concentrated. The resulting concentrate was purified by flash column chromatography on silica gel eluting with chloroform and methanol (ratio 95:5) to afford Example 8 (90 mg) as a yellow solid. $^1$H NMR (400 MHz, CD$_3$OD) δ (ppm): 8.42 (bs, 1H), 8.33 (d, J=10.0 Hz, 1H), 7.92 (d, J=10.0 Hz, 1H), 7.83 (t, J=11.2 Hz, 1H), 7.76-7.72 (m, 2H), 7.49 (m, 5H), 7.31 (d, J=10.8 Hz, 1H), 7.30-7.25 (m, 2H), 4.78 (s, 2H). LCMS Method O: retention time 1.36 min, [M+1]=380.2. HPLC Method B: purity 98.5%, retention time 10.03 min.

Example 10

5-(5-Phenyl-4-(pyridin-2-ylmethylamino)quinazolin-2-yl)pyridin-2(1H)-one

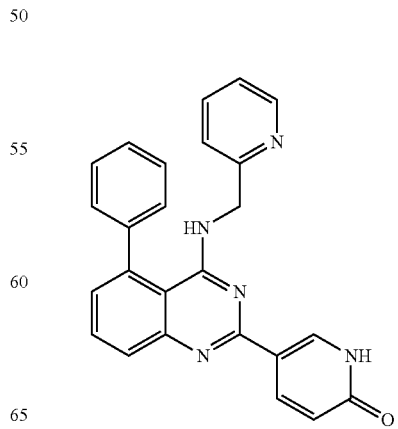

Step 1. Preparation of 2-(6-methoxypyridin-3-yl)-5-phenyl-N-(pyridin-2-ylmethyl)quinazolin-4-amine Step 2. Example 10

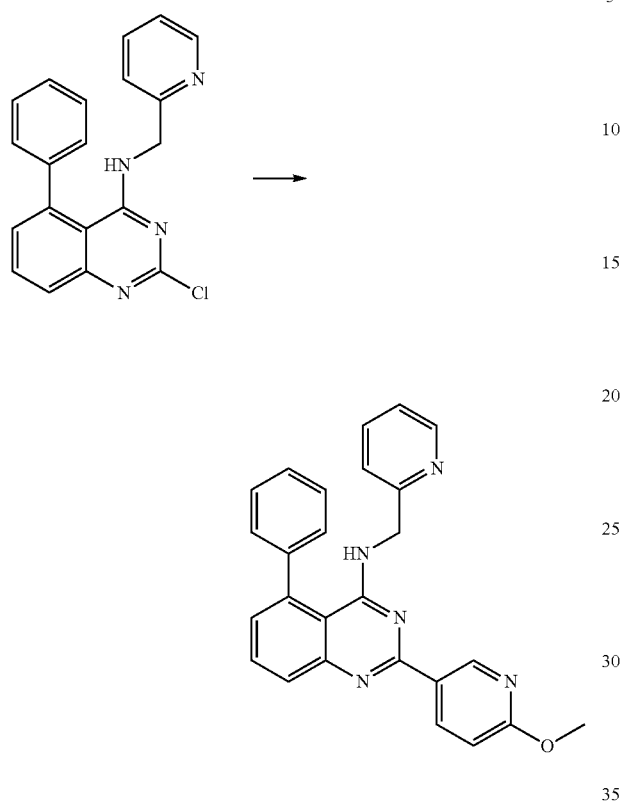

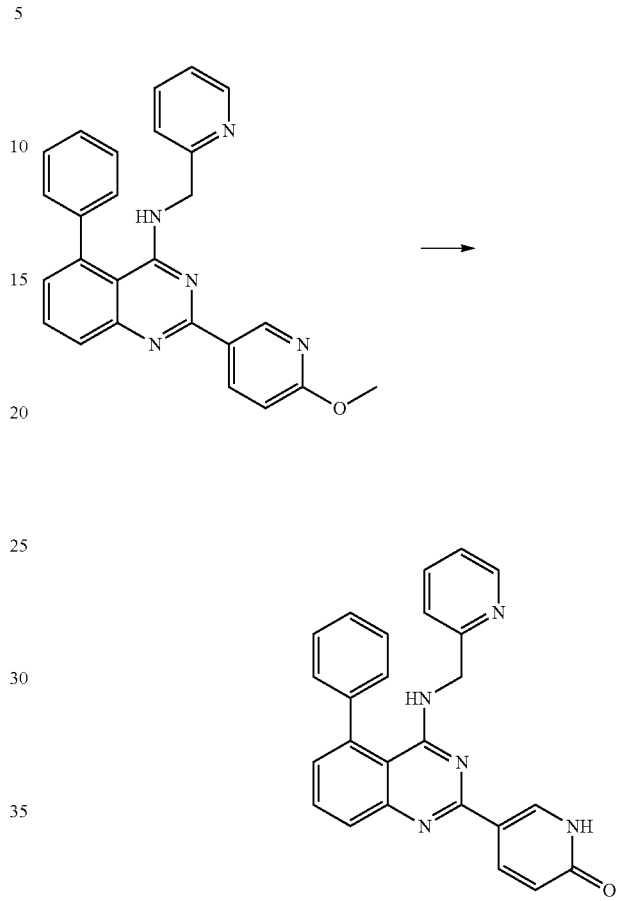

To a solution of 2-chloro-5-phenyl-N-(pyridin-2-ylmethyl)quinazolin-4-amine (200 mg, 0.58 mmol) in DMF (10 mL) and H$_2$O (2 mL) under nitrogen was added 6-methoxypyridin-3-ylboronic acid pinacol ester (202 mg, 0.86 mmol) and potassium carbonate (160 mg, 1.16 mmol). Upon completion of addition, the mixture was degassed with nitrogen for 15 min and then tetrakis(triphenylphosphine)palladium (66 mg, 0.0050 mmol) was added. The mixture was again degassed with nitrogen for 10 min. After this time, the reaction mixture was heated to 90° C. where it stirred for 12 h. The reaction mixture was then allowed to cool to room temperature and then quenched by the addition of water. The reaction mixture was extracted with ethyl acetate and the organic layer was washed successively with water and brine. The combined organic layers were dried over Na$_2$SO$_4$, filtered and concentrated under reduced pressure. The resulting concentrate was purified by flash column chromatography using 16% ethyl acetate in petroleum ether to afford 2-(6-methoxypyridin-3-yl)-5-phenyl-N-(pyridin-2-ylmethyl)quinazolin-4-amine (140 mg) as a brown solid. $^1$H NMR (400 MHz, DMSO-d$_6$) δ (ppm): 9.26 (d, J=2.4 Hz, 1H), 8.70-8.67 (dd, J=8.8, 2.4 Hz, 1H), 8.23-8.22 (d, J=5.2 Hz, 1H), 7.84-7.76 (m, 2H), 7.73-7.69 (dt, J=8.0, 2.0 Hz, 1H), 7.58-7.48 (m, 5H), 7.32-7.30 (d, J=7.6 Hz, 1H), 7.25-7.23 (m, 2H), 6.95-6.93 (d, J=8.8 Hz, 1H), 6.81-6.79 (t, J=4.0 Hz, 1H), 4.72-4.71 (d, J=4.0 Hz, 2H), 3.94 (s, 3H). LCMS Method S: retention time 3.96 min, [M+1]=420.2. HPLC Method B: purity 98.9%, retention time 8.93 min.

To a solution of 2-(6-methoxypyridin-3-yl)-5-phenyl-N-(pyridin-2-ylmethyl)quinazolin-4-amine (140 mg, 0.33 mmol) in CH$_2$Cl$_2$ (2 mL) was slowly added BBr$_3$ (416 mg, 1.66 mmol) at 0° C. The reaction mixture was stirred at room temperature for 72 h before it was quenched by the addition of aqueous solution of ammonium hydroxide. The reaction mixture was then extracted with CH$_2$Cl$_2$. The organic layer was washed successively with water and brine. The combined organic layers were dried over Na$_2$SO$_4$, filtered and concentrated under reduced pressure. The resulting concentrate was purified by preparative HPLC to afford Example 10 (75 mg) as an off-white solid. Preparative HPLC Conditions: Column: Sunfire C18 (250×19 mm), Mobile Phase A: 0.1% TFA in H$_2$O, Mobile Phase B: CH$_3$CN, Gradient: 0 to 40% B over 25 min, 100% B for 10 min., Flow Rate: 14 mL/min., Retention time: 20.5 min. $^1$H NMR (400 MHz, DMSO-d$_6$) δ (ppm): 8.68 (s, 1H), 8.41-8.38 (dd, J=9.6, 2.8 Hz, 1H), 8.23 (d, J=4.4 Hz, 1H), 8.09-7.94 (m, 3H), 7.84-7.79 (dt, J=7.6, 1.6 Hz, 1H), 7.65-7.54 (m, 5H), 7.50-7.48 (d, J=7.2 Hz, 1H), 7.40-7.38 (d, J=8.0 HZ, 1H), 7.33-7.30 (t, J=6.8 Hz, 1H), 6.62-6.60 (d, J=9.6 Hz, 1H), 4.88 (d, J=4.0 Hz, 2H). LCMS Method O: retention time 1.35 min, [M+1]=406.2. HPLC Method B: purity 99.2%, retention time 10.26 min.

Example 11

5-Phenyl-N-(pyridin-2-ylmethyl)-2-(5-(trifluoromethyl)-1,2,4-oxadiazol-3-yl)quinazolin-4-amine

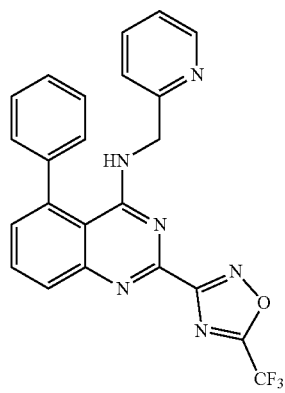 [SMILES: FC(F)(F)c1nc(-c2nc(NCc3ccccn3)c3c(-c4ccccc4)cccc3n2)no1]

Step 1. Preparation of 5-Phenyl-4-(pyridin-2-ylmethylamino)quinazoline-2-carbonitrile

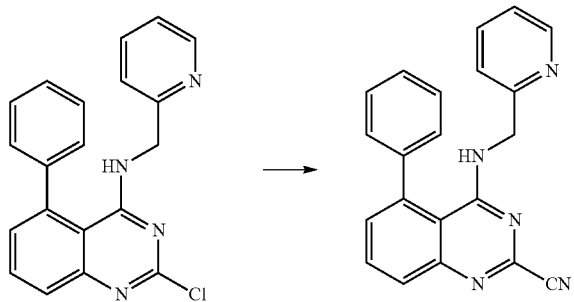 [SMILES: Clc1nc(NCc2ccccn2)c2c(-c3ccccc3)cccc2n1 ; N#Cc1nc(NCc2ccccn2)c2c(-c3ccccc3)cccc2n1]

To a solution of 2-chloro-5-phenyl-N-(pyridin-2-ylmethyl)quinazolin-4-amine (5.0 g, 14 mmol) in CH$_3$CN (50 mL) was added tetramethylammonium cyanide (4.5 g, 29 mmol) followed by DBU (4.39 g, 28.88 mmol). Upon completion of addition, the reaction mixture was heated to 80° C. where it stirred for 12 h. After this time, the reaction mixture was quenched with water and then extracted with ethyl acetate. The organic layer was washed successively with water and brine, and the combined organic layers were dried over Na$_2$SO$_4$, filtered and concentrated under reduced pressure. The resulting concentrate was purified by flash column chromatography using 28% ethyl acetate in petroleum ether to yield 5-phenyl-4-(pyridin-2-ylmethylamino) quinazoline-2-carbonitrile (2.1 g) as a brown solid. $^1$H NMR (400 MHz, DMSO-d$_6$) δ (ppm): 8.15-8.14 (d, J=4.0 Hz, 1H), 7.96-7.87 (m, 2H), 7.75-7.70 (dt, J=7.6, 2.0 Hz, 1H), 7.62-7.45 (m, 6H), 7.34-7.29 (m, 2H), 7.25-7.22 (m, 1H), 4.60 (d, J=3.6 Hz, 2H). LCMS Method O: retention time 1.52 min, [M+1]=338.2.

Step 2. Example 11

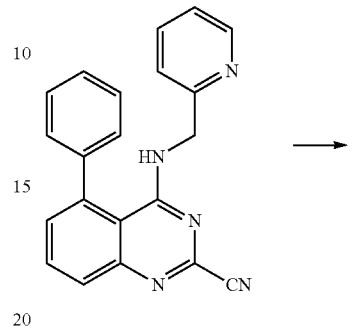

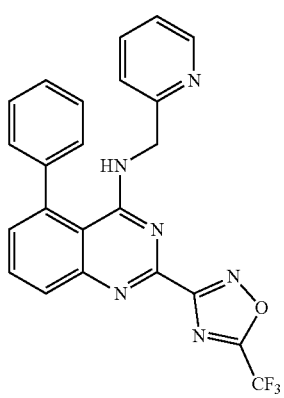

To a solution of 5-phenyl-4-(pyridin-2-ylmethylamino) quinazoline-2-carbonitrile (150 mg, 0.45 mmol) in EtOH (5 mL) was added NH$_2$O H—HCl (62 mg, 0.90 mmol) followed by Et$_3$N (125 µL, 0.90 mmol). The reaction mixture was heated to reflux where it stirred for 4 h. After this time, the reaction mixture was concentrated under reduced pressure to yield a residue. The residue was dissolved in THF (5 mL). The resulting solution was cooled to 0° C. and pyridine (145 µL, 1.80 mmol) followed by trifluoroacetic anhydride (125 µL, 0.90 mmol) were added. Upon completion of addition, the reaction mixture was warmed to room temperature where it stirred for 16 h. At the conclusion of this period, the reaction mixture was concentrated under reduced pressure to yield a residue. The residue was purified by flash column chromatography using 36% ethyl acetate in petroleum ether to afford Example 11 (65 mg) as an off-white solid. $^1$H NMR (400 MHz, DMSO-d$_6$) δ (ppm): 8.19 (d, J=4.0 Hz, 1H), 7.99-7.91 (m, 2H), 7.75-7.71 (t, J=7.2 Hz, 1H), 7.60-7.54 (m, 5H), 7.44 (d, J=6.4 Hz, 1H), 7.36 (d, J=7.6 Hz, 1H), 7.26-7.23 (m, 1H), 7.19 (m, 1H), 4.68-4.67 (d, J=3.6 Hz, 1H). LCMS Method O: retention time 1.71 min, [M+1]=449.0. HPLC Method B: purity 99.5%, retention time 9.66 min.

Example 12

4-((5-Phenyl-2-(pyrimidin-5-yl)quinazolin-4-ylamino)methyl)benzamide

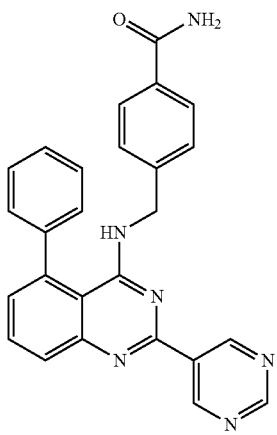 [SMILES: NC(=O)c1ccc(CNc2nc(-c3cncnc3)nc3cccc(-c4ccccc4)c23)cc1]

Step 1. Preparation of methyl 4-(aminomethyl)benzoate

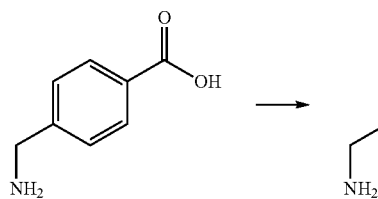

To a solution of 4-(aminomethyl)benzoic acid (1 g, 7 mmol) in MeOH (10 mL) was added dropwise concentrated $H_2SO_4$ (1 mL). Upon completion of addition, the reaction mixture was heated to 60° C. where it stirred for 12 h. After this time, the reaction mixture was concentrated under reduced pressure to yield a residue. The residue was dissolved in ethyl acetate and then carefully neutralized with a 10% NaOH solution. The organic layer was separated and washed successively with water and brine. The combined organic layers were dried over $Na_2SO_4$, filtered and concentrated under reduced pressure to afford methyl 4-(aminomethyl)benzoate (2.5 g) as a white solid. LCMS Method O: retention time 0.49 min, [M+1]=166.2.

Step 2. Preparation of methyl 4-((2-chloro-5-phenylquinazolin-4-ylamino)-methyl)benzoate

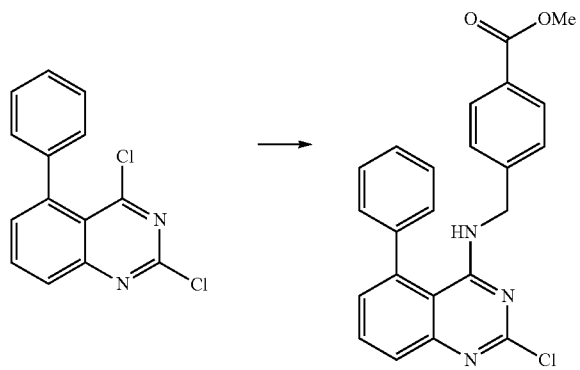 [SMILES: Clc1nc(Cl)c2c(-c3ccccc3)cccc2n1 ; COC(=O)c1ccc(CNc2nc(Cl)nc3cccc(-c4ccccc4)c23)cc1]

To a solution of 2,4-dichloro-5-phenylquinazoline (1 g, 4 mmol) in THF (15 mL) was added diisopropylethyl amine (1.86 mL, 10.9 mmol) followed by methyl 4-(aminomethyl)benzoate (1.19 g, 7.21 mmol). Upon completion of addition, the reaction mixture was stirred for 12 h. At the conclusion of this period, the reaction mixture was diluted with ethyl acetate and then washed successively with water and brine. The combined organic layers were dried over $Na_2SO_4$, filtered and concentrated to yield a residue. The residue was purified by flash column chromatography using 6% ethyl acetate in petroleum ether to afford methyl 4-((2-chloro-5-phenylquinazolin-4-ylamino)methyl)benzoate (600 mg) as a white solid. $^1$H NMR (400 MHz, CDCl$_3$) δ (ppm): 7.92 (d, J=8.0 Hz, 2H), 7.80 (d, J=8.4 Hz, 1H), 7.70 (t, J=8.0 Hz, 1H), 7.38-7.33 (m, 5H), 7.22 (d, J=7.2 Hz, 1H), 7.02 (d, J=8.0 Hz, 2H), 5.56 (bs, 1H), 4.53 (d, J=4.8 Hz, 2H), 3.39 (s, 3H). LCMS Method O: retention time 2.12 min, [M+1]=404.0. HPLC Method B: purity 97.8%, retention time 18.17 min.

Step 3. Preparation of methyl 4-((5-phenyl-2-(pyrimidin-5-yl)quinazolin-4-ylamino)methyl)benzoate

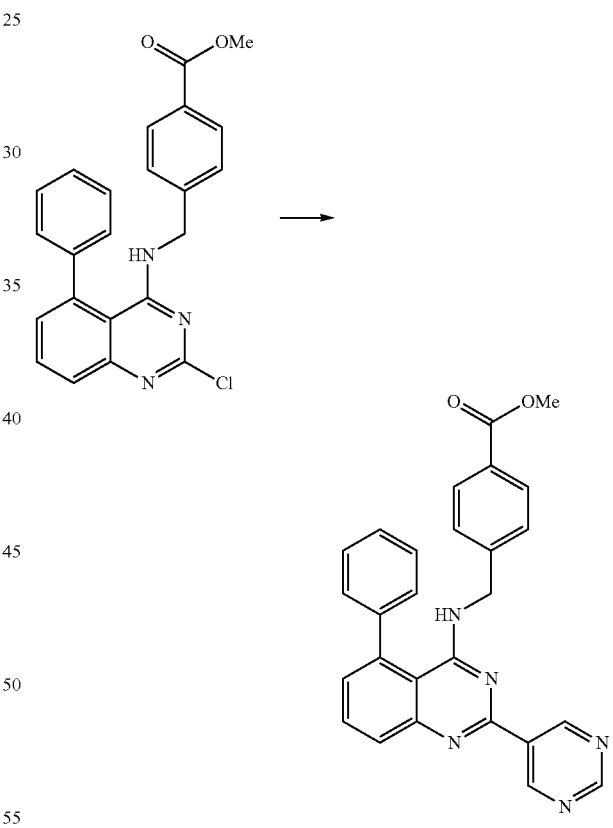

To a solution of methyl 4-((2-chloro-5-phenylquinazolin-4-ylamino)methyl)benzoate (550 mg, 1.36 mmol) in DMF (16 mL) and $H_2O$ (0.5 mL) under nitrogen were added pyrimidine-5-ylboronic acid pinacol ester (422 mg, 2.04 mmol) and potassium carbonate (377 mg, 2.72 mmol). The resulting mixture was degassed with nitrogen for 15 min and then (1,1'-bis(diphenylphosphino)ferrocene)-palladium (II) chloride dichloromethane complex (50 mg, 0.068 mmol) was added. Upon completion of addition, the reaction mixture was again degassed for 10 min. with nitrogen. The reaction mixture was then heated to 110° C. where it stirred for 12 h. After this time, the reaction mixture was allowed to cool to room temperature. Once at the prescribed temperature, the reaction mixture was quenched by the addition of water and then extracted with ethyl acetate. The organic layer was washed successively with water and brine. The combined organic layers were dried over $Na_2SO_4$, filtered and concentrated under reduced pressure. The resulting concentrate was purified by flash column chromatography using 0.5% MeOH in $CH_2Cl_2$ to afford methyl 4-((5-phenyl-2-(pyrimidin-5-yl)quinazolin-4-ylamino)methyl)benzoate (400 mg) as an off-white solid. $^1$H NMR (400 MHz, DMSO-$d_6$) δ (ppm): 9.62 (s, 2H), 9.31 (s, 1H), 7.93-7.86 (m, 4H), 7.54-7.49 (m, 5H), 7.37 (d, J=6.8 Hz, 1H), 7.28 (d, J=8.0 Hz, 2H), 5.94 (t, J=4.8 Hz, 1H), 4.71 (d, J=5.2 Hz, 1H), 3.85 (s, 3H). LCMS Method C: retention time 2.15 min, [M+1]=448.2. HPLC Method B: purity 98.5%, retention time 9.81 min.

Step 4. Preparation of 4-((5-phenyl-2-(pyrimidin-5-yl)quinazolin-4-ylamino)methyl)benzoic acid (250 mg) as a white solid. $^1$H NMR (400 MHz, DMSO-$d_6$) δ (ppm): 12.87 (bs, 1H), 9.68 (s, 2H), 9.39 (s, 1H), 8.09 (m, 1H), 7.98 (t, J=8.0 Hz, 1H), 7.86 (d, J=8.0 Hz, 2H), 7.53-7.48 (m, 6H), 7.26 (d, J=8.0 Hz, 2H), 6.65 (bs, 1H), 4.78 (d, J=5.2 Hz, 2H). LCMS Method O: retention time 1.73 min, [M+1]=434.2. HPLC Method B: purity 98.1%, retention time 8.24 min.

Step 5. Example 12

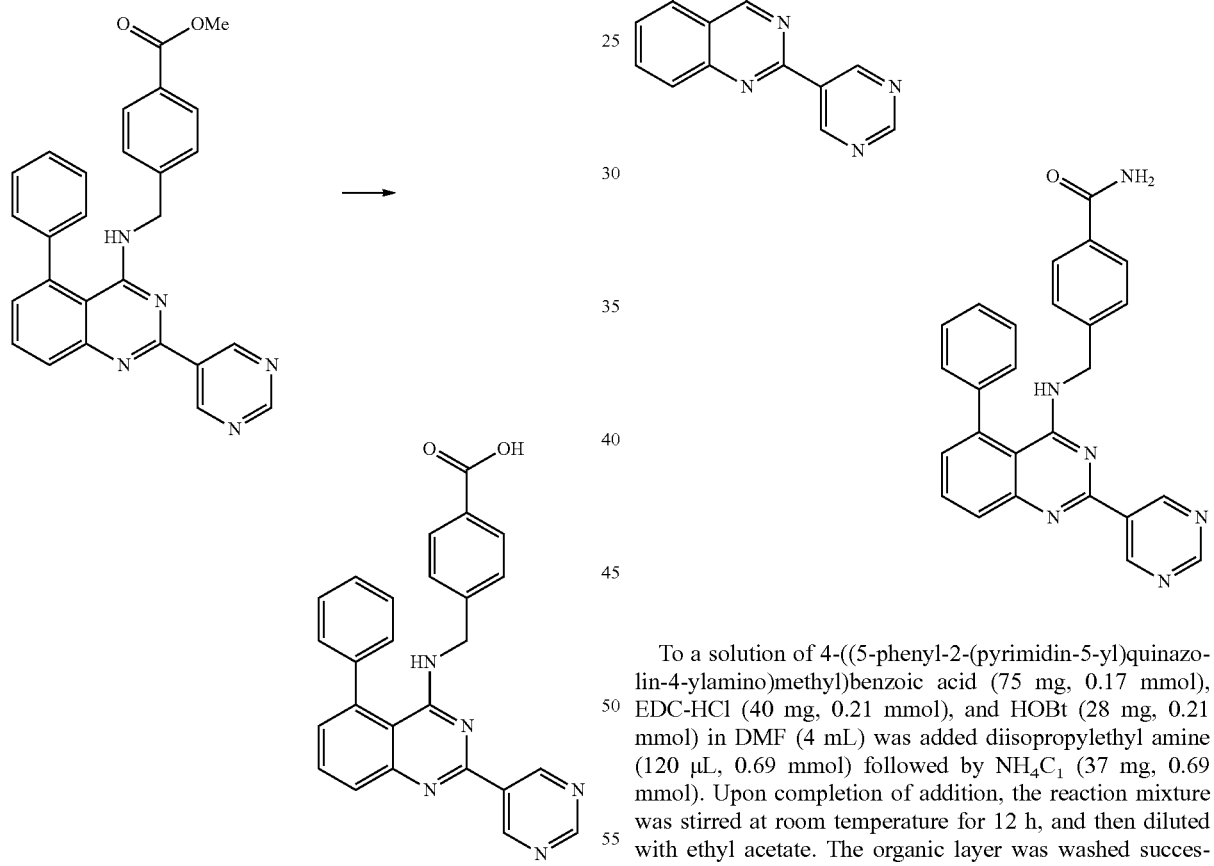

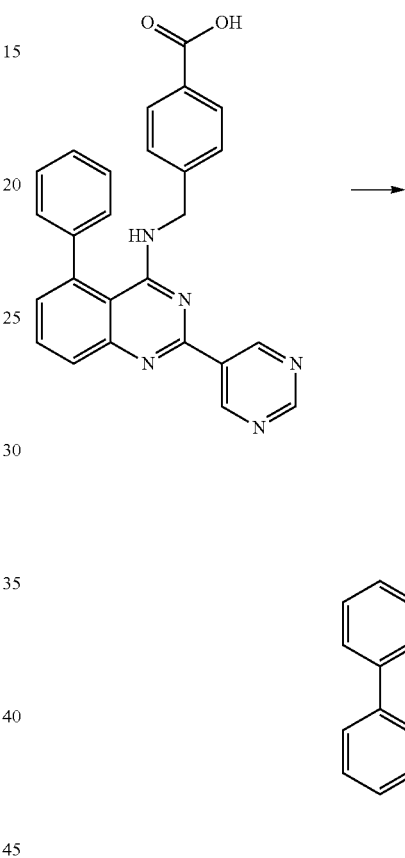

To a solution of methyl 4-((5-phenyl-2-(pyrimidin-5-yl)quinazolin-4-ylamino)methyl)benzoate (400 mg, 0.89 mmol) in MeOH-THF-$H_2O$ (6 mL-6 mL-0.5 mL) was added LiOH (112 mg, 2.67 mmol). Upon completion of addition, the reaction mixture was heated to 45° C. where it stirred for 12 h. After this time, the reaction mixture was concentrated under reduced pressure to remove the MeOH and THF and then carefully acidified with 1.5N HCl. The resulting precipitate was collected by filtration to afford 4-((5-phenyl-2-(pyrimidin-5-yl)quinazolin-4-ylamino)methyl)benzoic acid To a solution of 4-((5-phenyl-2-(pyrimidin-5-yl)quinazolin-4-ylamino)methyl)benzoic acid (75 mg, 0.17 mmol), EDC-HCl (40 mg, 0.21 mmol), and HOBt (28 mg, 0.21 mmol) in DMF (4 mL) was added diisopropylethyl amine (120 μL, 0.69 mmol) followed by $NH_4C_1$ (37 mg, 0.69 mmol). Upon completion of addition, the reaction mixture was stirred at room temperature for 12 h, and then diluted with ethyl acetate. The organic layer was washed successively with water and brine. The organic portion was separated, dried over $Na_2SO_4$, filtered and then concentrated under reduced pressure. The resulting concentrate was purified by flash column chromatography using 3% MeOH in $CH_2Cl_2$ to afford Example 12 (25 mg) as an off-white solid. $^1$H NMR (400 MHz, DMSO-$d_6$) δ (ppm): 9.65 (s, 2H), 9.31 (s, 1H), 7.94-7.85 (m, 3H), 7.79 (d, J=8.0 Hz, 2H), 7.52-7.49 (m, 5H), 7.36 (m, 2H), 7.17 (d, J=8.0 Hz, 2H), 5.89 (t, J=4.8 Hz, 1H), 4.66 (d, J=4.8 Hz, 2H). LCMS Method O: retention time 1.49 min, [M+1]=433.2. HPLC Method B: purity 98.4%, retention time 7.52 min.

Example 16

2-Chloro-5-phenyl-N-(pyridin-2-yl)quinazolin-4-amine

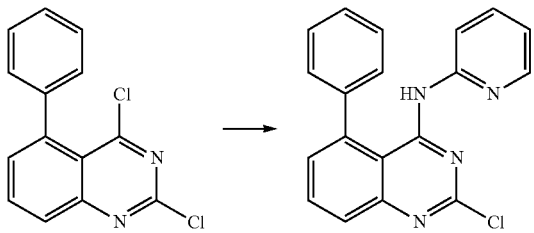 [SMILES: Clc1nc(Cl)c2c(-c3ccccc3)cccc2n1 ; Clc1nc(Nc2ccccn2)c2c(-c3ccccc3)cccc2n1]

To a suspension of NaH (13 mg, 0.547 mmol) in THF (2 mL) at 0° C. was added a solution of 3-aminopyridine (26 mg, 0.273 mmol) in THF (2 mL). Upon completion of addition, the reaction mixture was stirred at 0° C. for 30 min. At the conclusion of this period, a solution of 2,4-dichloro-5-phenylquinazoline (75 mg, 0.273 mmol) in THF (2 mL) was added. The reaction mixture was allowed to warm to room temperature where it stirred for 16 h. After this time, the reaction mixture was quenched with a saturated aqueous solution of $NH_4C_1$, and the resulting solution was extracted with ethyl acetate. The organic layer was washed successively with water and brine, dried over $Na_2SO_4$, filtered and concentrated under reduced pressure. The resulting concentrate was purified by flash column chromatography using 30% ethyl acetate in petroleum ether to afford Example 16 (15 mg) as a white solid. $^1H$ NMR (400 MHz, $CDCl_3$) δ (ppm): 8.53-8.51 (d, J=8.4 Hz, 1H), 8.11-8.09 (dd, J=4.0, 1.2 Hz, 1H), 7.92-7.88 (m, 2H), 7.82-7.78 (t, J=7.6 Hz, 1H), 7.73-7.69 (dt, J=8.0, 1.6 Hz, 1H), 7.62-7.60 (m, 3H), 7.52-7.50 (m, 2H), 7.39-7.37 (d, J=7.2 Hz, 1H), 6.97-6.94 (dd, J=7.2, 4.8 Hz, 1H). LCMS Method M: retention time 1.73 min, [M+1]=333.2. HPLC Method B: purity 99.7%, retention time 17.30 min.

Examples 19 Through 58

Examples 19 through 58 were synthesized via similar procedures described above. HPLC/MS data for each compound was collected using method E, and the molecular mass determined by MS (ES) by the formula m/z. Both the retention time and MS data for the examples are listed in Table 1a, wherein MW=molecular weight.

TABLE 1a

| Example | Structure | MW | LCMS Data | LCMS Method |
|---|---|---|---|---|
| 19 | 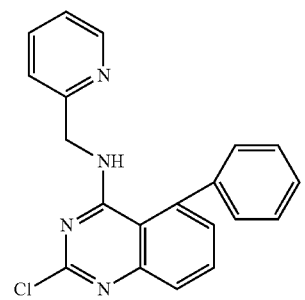 [SMILES: Clc1nc(NCc2ccccn2)c2c(-c3ccccc3)cccc2n1] | 346.813 | [M + 1] 347.0 Rt: 0.95 min | A |
| 20 | 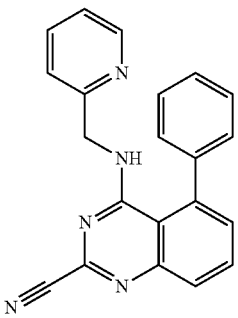 [SMILES: N#Cc1nc(NCc2ccccn2)c2c(-c3ccccc3)cccc2n1] | 337.377 | [M + 1] 338.3 Rt: 0.88 min | D |

TABLE 1a-continued

| Example | Structure | MW | LCMS Data | LCMS Method |
|---|---|---|---|---|
| 21 | 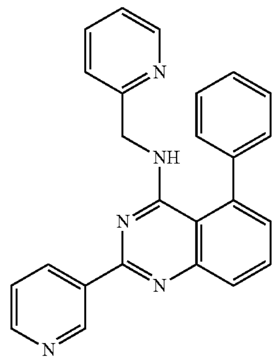 [SMILES: c1ccc(-c2cccc3nc(-c4cccnc4)nc(NCc4ccccn4)c23)cc1] | 389.452 | [M + 1] 390.3 Rt: 0.73 min | D |
| 22 | 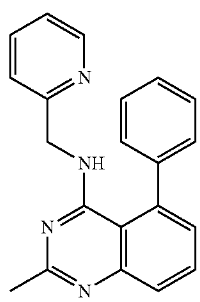 [SMILES: Cc1nc(NCc2ccccn2)c2c(-c3ccccc3)cccc2n1] | 326.394 | [M + 1] 327.1 Rt: 0.65 min | A |
| 23 | 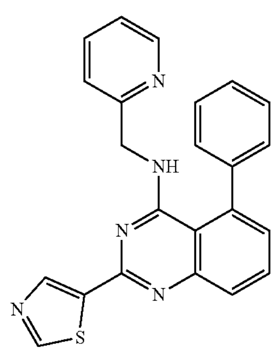 [SMILES: c1ccc(-c2cccc3nc(-c4cncs4)nc(NCc4ccccn4)c23)cc1] | 395.48 | [M + 1] 396.3 Rt: 0.86 min | D |
| 24 | 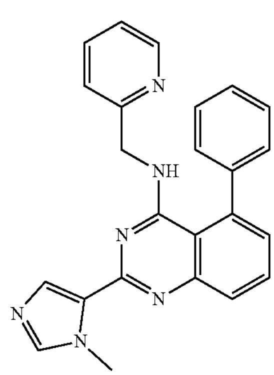 [SMILES: Cn1cncc1-c1nc(NCc2ccccn2)c2c(-c3ccccc3)cccc2n1] | 392.456 | [M + 1] 393.2 Rt: 0.72 min | A |

TABLE 1a-continued

| Example | Structure | MW | LCMS Data | LCMS Method |
|---|---|---|---|---|
| 25 | 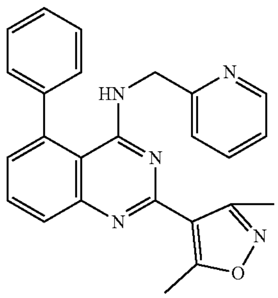 [SMILES: Cc1noc(C)c1-c1nc(NCc2ccccn2)c2c(-c3ccccc3)cccc2n1] | 407.467 | [M + 1] 408.2 Rt: 1.525 min | M |
| 26 | 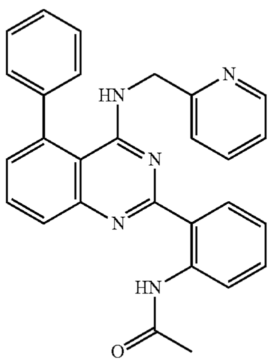 [SMILES: CC(=O)Nc1ccccc1-c1nc(NCc2ccccn2)c2c(-c3ccccc3)cccc2n1] | 445.515 | [M + 1] 446.2 Rt: 1.477 min | M |
| 27 | 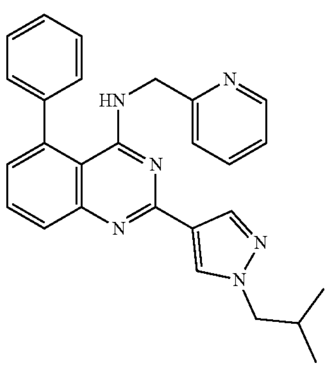 [SMILES: CC(C)Cn1cc(-c2nc(NCc3ccccn3)c3c(-c4ccccc4)cccc3n2)cn1] | 434.536 | [M + 1] 435.2 Rt: 1.667 min | M |
| 29 | 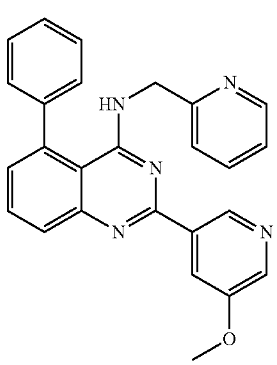 [SMILES: COc1cncc(-c2nc(NCc3ccccn3)c3c(-c4ccccc4)cccc3n2)c1] | 419.478 | [M + 1] 420.2 Rt: 1.631 min | N |

TABLE 1a-continued

| Example | Structure | MW | LCMS Data | LCMS Method |
|---------|-----------|-----|-----------|-------------|
| 30 | 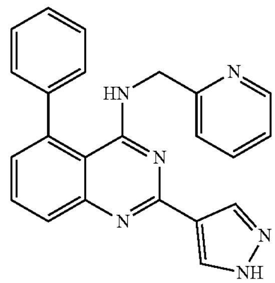 [SMILES: c1ccc(-c2cccc3nc(-c4cn[nH]c4)nc(NCc4ccccn4)c23)cc1] | 378.429 | [M + 1] 379.2 Rt: 1.359 min | M |
| 31 | 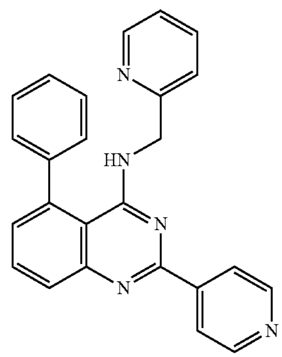 [SMILES: c1ccc(-c2cccc3nc(-c4ccncc4)nc(NCc4ccccn4)c23)cc1] | 389.452 | [M + 1] 390.2 Rt: 1.370 min | M |
| 32 | 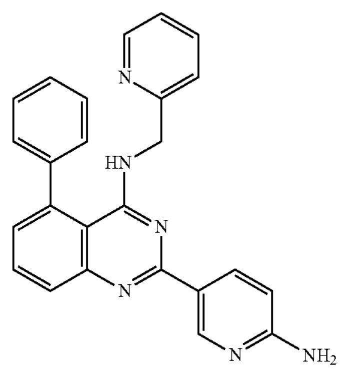 [SMILES: Nc1ccc(-c2nc(NCc3ccccn3)c3c(-c4ccccc4)cccc3n2)cn1] | 404.467 | [M + 1] 405.2 Rt: 1.298 min | M |
| 34 | 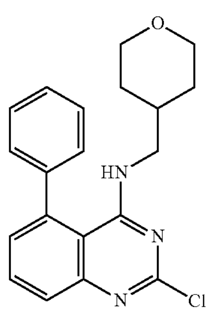 [SMILES: Clc1nc(NCC2CCOCC2)c2c(-c3ccccc3)cccc2n1] | 353.845 | [M + 1] 354.2 Rt: 1.675 min | O |
| 35 | 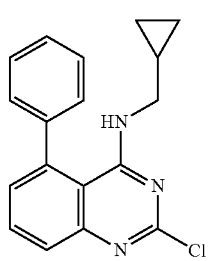 [SMILES: Clc1nc(NCC2CC2)c2c(-c3ccccc3)cccc2n1] | 309.793 | [M + 1] 310.2 Rt: 1.893 min | O |

TABLE 1a-continued

| Example | Structure | MW | LCMS Data | LCMS Method |
|---------|-----------|-----|-----------|-------------|
| 36 | 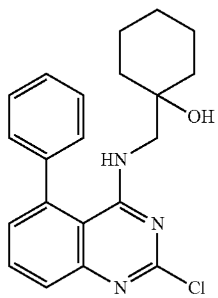 [SMILES: OC1(CNc2nc(Cl)nc3cccc(-c4ccccc4)c23)CCCCC1] | 367.872 | [M + 1] 368.2 Rt: 1.857 min | O |
| 37 | 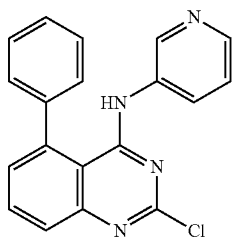 [SMILES: Clc1nc(Nc2cccnc2)c2c(-c3ccccc3)cccc2n1] | 332.786 | [M + 1] 333.2 Rt: 1.888 min | N |
| 38 | 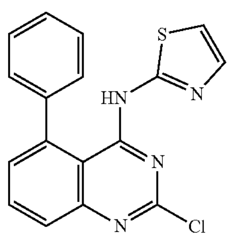 [SMILES: Clc1nc(Nc2nccs2)c2c(-c3ccccc3)cccc2n1] | 338.814 | [M + 1] 339.0 Rt: 1.907 min | O |
| 39 | 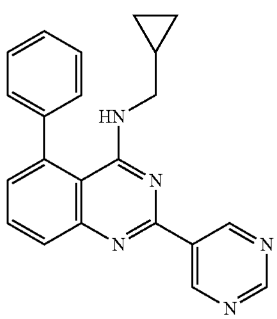 [SMILES: c1ccc(-c2cccc3nc(-c4cncnc4)nc(NCC4CC4)c23)cc1] | 353.42 | [M + 1] 354.2 Rt: 1.626 min | O |
| 40 | 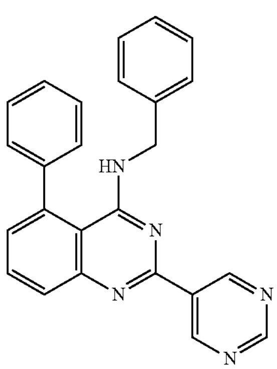 [SMILES: c1ccc(CNc2nc(-c3cncnc3)nc3cccc(-c4ccccc4)c23)cc1] | 389.452 | [M + 1] 390.2 Rt: 1.810 min | O |

TABLE 1a-continued

| Example | Structure | MW | LCMS Data | LCMS Method |
|---------|-----------|-----|-----------|-------------|
| 41 | 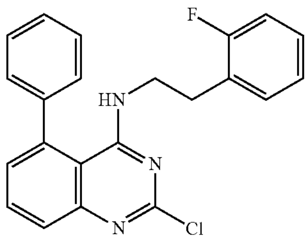 [SMILES: Fc1ccccc1CCNc1nc(Cl)nc2cccc(-c3ccccc3)c12] | 377.842 | [M + 1] 378.2 Rt: 2.042 min | O |
| 42 | 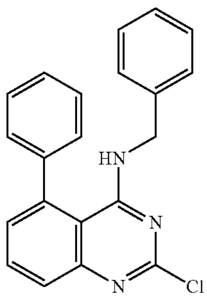 [SMILES: Clc1nc(NCc2ccccc2)c2c(-c3ccccc3)cccc2n1] | 345.825 | [M + 1] 346.2 Rt: 2.000 min | O |
| 43 | 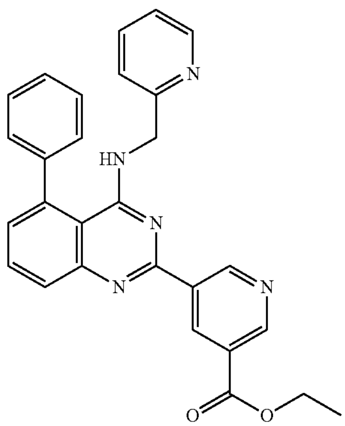 [SMILES: CCOC(=O)c1cncc(-c2nc(NCc3ccccn3)c3c(-c4ccccc4)cccc3n2)c1] | 461.515 | [M + 1] 462.2 Rt: 2.138 min | Q |
| 45 | 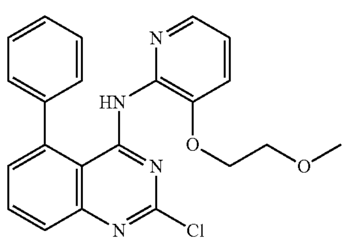 [SMILES: COCCOc1cccnc1Nc1nc(Cl)nc2cccc(-c3ccccc3)c12] | 406.865 | [M + 1] 407.2 Rt: 1.656 min | Q |
| 46 | 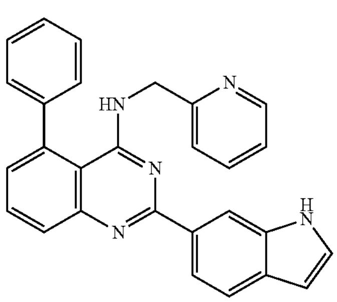 [SMILES: c1ccc(-c2cccc3nc(-c4ccc5cc[nH]c5c4)nc(NCc4ccccn4)c23)cc1] | 427.5 | [M + 1] 428.2 Rt: 1.622 min | O |

TABLE 1a-continued

| Example | Structure | MW | LCMS Data | LCMS Method |
|---------|-----------|-----|-----------|-------------|
| 47 | 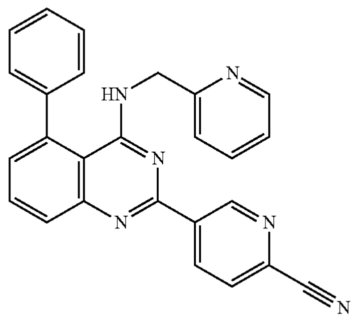 [SMILES: N#Cc1ccc(-c2nc(NCc3ccccn3)c3c(-c4ccccc4)cccc3n2)cn1] | 414.461 | [M + 1] 415.2 Rt: 2.036 min | M |
| 48 | 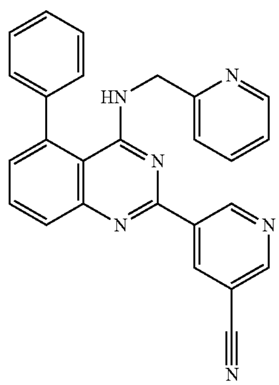 [SMILES: N#Cc1cncc(-c2nc(NCc3ccccn3)c3c(-c4ccccc4)cccc3n2)c1] | 414.461 | [M + 1] 415.2 Rt: 1.653 min | O |
| 50 | 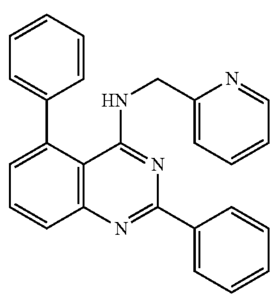 [SMILES: c1ccc(-c2nc(NCc3ccccn3)c3c(-c4ccccc4)cccc3n2)cc1] | 388.464 | [M + 1] 389.2 Rt: 1.605 min | O |
| 51 | 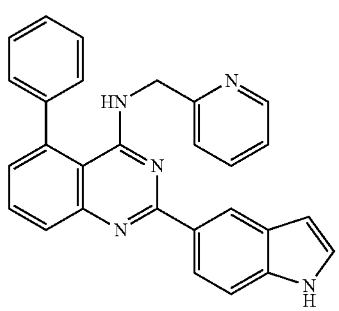 [SMILES: c1ccc(-c2cccc3nc(-c4ccc5[nH]ccc5c4)nc(NCc4ccccn4)c23)cc1] | 427.5 | [M + 1] 428.2 Rt: 1.663 min | O |
| 54 | 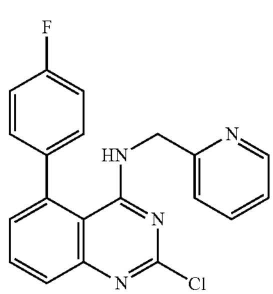 [SMILES: Fc1ccc(-c2cccc3nc(Cl)nc(NCc4ccccn4)c23)cc1] | 364.803 | [M + 1] 365.2 Rt: 1.517 min | O |

TABLE 1a-continued

| Example | Structure | MW | LCMS Data | LCMS Method |
|---|---|---|---|---|
| 55 | 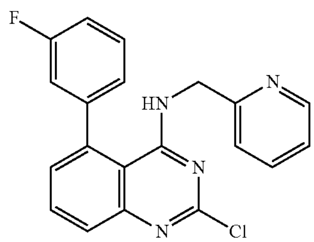 [SMILES: Fc1cccc(-c2cccc3nc(Cl)nc(NCc4ccccn4)c23)c1] | 364.803 | [M + 1] 365.2 Rt: 1.530 min | O |
| 58 | 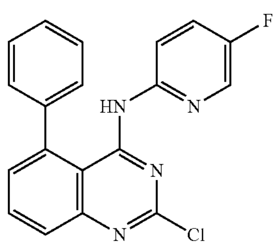 [SMILES: Fc1ccc(Nc2nc(Cl)nc3cccc(-c4ccccc4)c23)nc1] | 350.777 | [M − 1] 349.0 Rt: 3.084 min | P |

Example 62

2-(2-methoxypyrimidin-5-yl)-5-phenyl-N-(pyridin-2-ylmethyl)quinazolin-4-amine

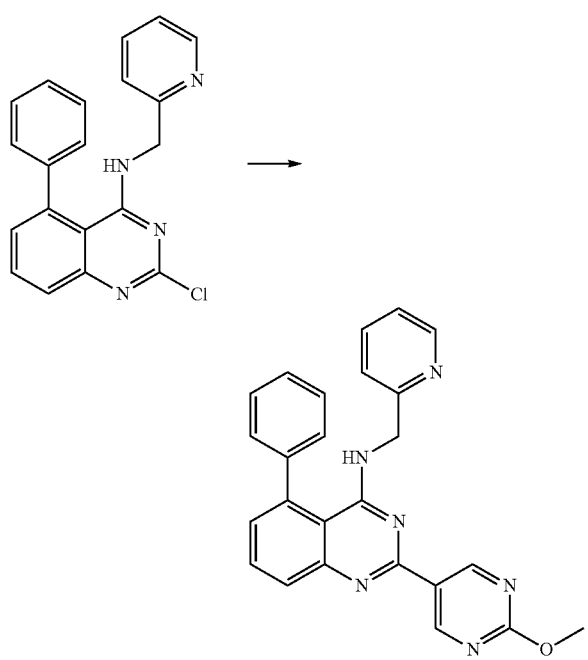

To a solution of 2-chloro-5-phenyl-N-(pyridin-2-ylmethyl)quinazolin-4-amine (300 mg, 0.87 mmol) in DMF (20 mL) and H$_2$O (2 mL) under nitrogen was added 2-methoxypyrimidin-5-ylboronic acid (199 mg, 1.30 mmol) and potassium carbonate (239 mg, 1.73 mmol). The resulting mixture was degassed with nitrogen for 15 min and then tetrakis(triphenylphosphine)palladium (100 mg, 0.086 mmol) was added. Upon completion of addition, the reaction mixture was again degassed with nitrogen for 10 min. After this time, the reaction mixture was heated to 90° C. where it stirred for 12 h. After this time, the reaction mixture was allowed to cool to room temperature and then quenched by the addition of water. The reaction mixture was extracted with ethyl acetate and the organic layer was washed successively with water and brine. The combined organic layers were dried over Na$_2$SO$_4$, filtered and concentrated under reduced pressure. The resulting concentrate was purified by preparative HPLC to afford 2-(2-methoxypyrimidin-5-yl)-5-phenyl-N-(pyridin-2-ylmethyl)quinazolin-4-amine (205 mg) as an off-white solid. Preparative HPLC Conditions: Column: Sunfire C18 (250×19 mm), Mobile Phase A: 0.1% TFA in H$_2$O, Mobile Phase B: CH$_3$CN, Gradient: 0 to 40% B over 35 min, 100% B for 10 min., Flow Rate: 14 mL/min., Retention time: 28 min. $^1$H NMR (400 MHz, DMSO-d$_6$) δ (ppm): 9.50 (s, 2H), 8.27 (d, J=4.7 Hz, 1H), 7.92 (d, J=3.6 Hz, 2H), 7.85-7.81 (t, J=8.0 Hz, 1H), 7.60-7.52 (m, 5H), 7.42-7.38 (m, 2H), 7.34-7.31 (m, 1H), 4.83 (d, J=4.2 Hz, 2H), 4.04 (s, 3H). LCMS Method O: retention time 1.45 min, [M+1]=421.2. HPLC Method B: purity 98.7%, retention time 5.53 min.

Examples 66 Through 158

Examples 66 through 158 were synthesized via similar procedures described above. HPLC/MS data for each compound was collected using method E, and the molecular mass determined by MS (ES) by the formula m/z. Both the retention time and MS data for the examples are listed in Table 1b, wherein MW=molecular weight.

TABLE 1b

| Example | Structure | MW | LCMS Data | LCMS Method |
|---|---|---|---|---|
| 66 | 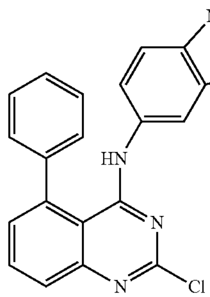 | 388.873 | [M − 1] 386.8 Rt: 5.82 min | L |
| 67 | 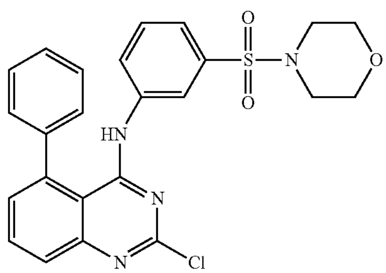 [SMILES: O=S(=O)(c1cccc(Nc2nc(Cl)nc3cccc(-c4ccccc4)c23)c1)N1CCOCC1] | 480.967 | [M] 478.7 Rt: 5.75 min | L |
| 68 | 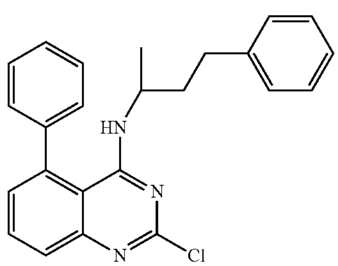 [SMILES: CC(CCc1ccccc1)Nc1nc(Cl)nc2cccc(-c3ccccc3)c12] | 387.905 | [M] 385.9 Rt: 7.09 min | L |
| 69 | 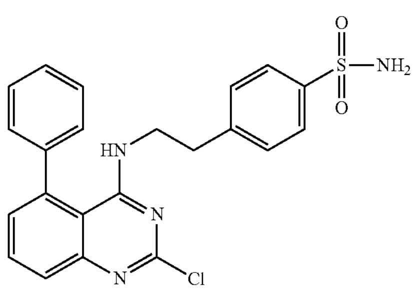 [SMILES: NS(=O)(=O)c1ccc(CCNc2nc(Cl)nc3cccc(-c4ccccc4)c23)cc1] | 438.93 | [M − 1] 436.9 Rt: 4.67 min | L |
| 70 | 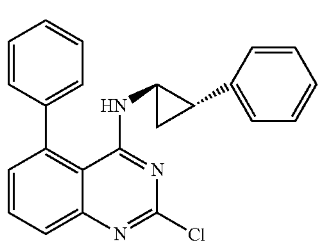 [SMILES: Clc1nc(N[C@@H]2C[C@H]2c2ccccc2)c2c(-c3ccccc3)cccc2n1] | 371.862 | [M − 1] 369.9 Rt: 6.68 min | L |

TABLE 1b-continued

| Example | Structure | MW | LCMS Data | LCMS Method |
|---------|-----------|-----|-----------|-------------|
| 72 | 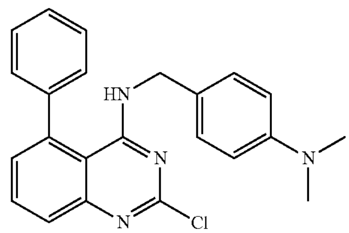 [SMILES: CN(C)c1ccc(CNc2nc(Cl)nc3cccc(-c4ccccc4)c23)cc1] | 388.893 | [M] 386.9 Rt: 6.47 min | L |
| 74 | 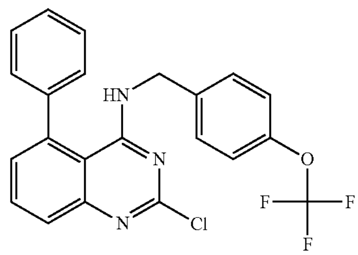 [SMILES: FC(F)(F)Oc1ccc(CNc2nc(Cl)nc3cccc(-c4ccccc4)c23)cc1] | 429.822 | [M − 1] 427.8 Rt: 6.83 min | L |
| 76 | 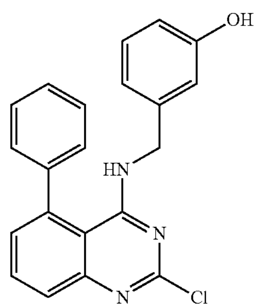 [SMILES: Oc1cccc(CNc2nc(Cl)nc3cccc(-c4ccccc4)c23)c1] | 361.824 | [M − 1] 359.9 Rt: 5.06 min | L |
| 77 | 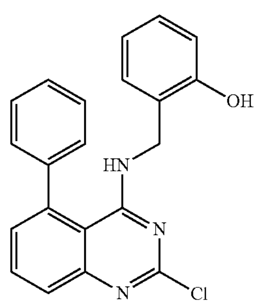 [SMILES: Oc1ccccc1CNc1nc(Cl)nc2cccc(-c3ccccc3)c12] | 361.824 | [M − 1] 359.8 Rt: 5.40 min | L |
| 84 | 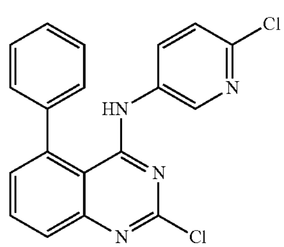 [SMILES: Clc1ccc(Nc2nc(Cl)nc3cccc(-c4ccccc4)c23)cn1] | 367.231 | [M − 1] 364.9 Rt: 6.09 min | L |
| 85 | 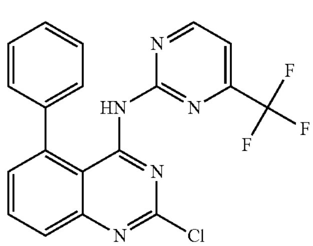 [SMILES: FC(F)(F)c1ccnc(Nc2nc(Cl)nc3cccc(-c4ccccc4)c23)n1] | 401.772 | [M − 1] 399.8 Rt: 5.42 min | L |

TABLE 1b-continued

| Example | Structure | MW | LCMS Data | LCMS Method |
|---|---|---|---|---|
| 87 | 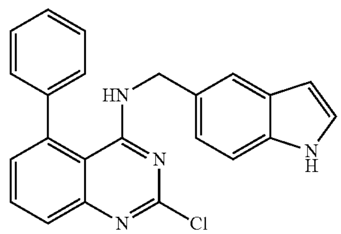 [SMILES: Clc1nc(NCc2ccc3[nH]ccc3c2)c2c(-c3ccccc3)cccc2n1] | 384.861 | [M − 1] 382.9 Rt: 5.72 min | L |
| 88 | 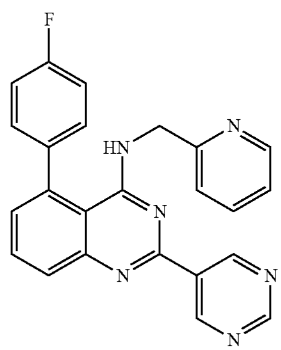 [SMILES: Fc1ccc(-c2cccc3nc(-c4cncnc4)nc(NCc4ccccn4)c23)cc1] | 408.43 | [M + 1] 409.2 Rt: 2.031 min | Q |
| 89 | 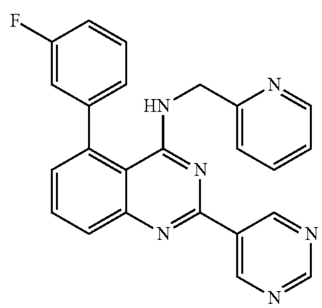 [SMILES: Fc1cccc(-c2cccc3nc(-c4cncnc4)nc(NCc4ccccn4)c23)c1] | 408.43 | [M + 1] 409.2 Rt: 2.035 min | Q |
| 92 | 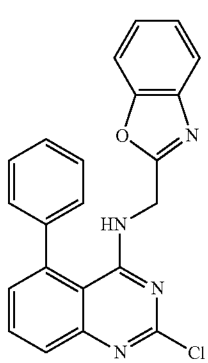 [SMILES: Clc1nc(NCc2nc3ccccc3o2)c2c(-c3ccccc3)cccc2n1] | 386.834 | [M + 1] 387.0 Rt: 2.102 min | O |

TABLE 1b-continued

| Example | Structure | MW | LCMS Data | LCMS Method |
|---|---|---|---|---|
| 93 | 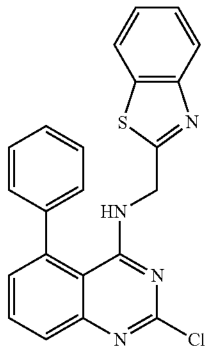 [SMILES: Clc1nc(NCc2nc3ccccc3s2)c2c(-c3ccccc3)cccc2n1] | 402.899 | [M + 1] 403.0 Rt: 2.159 min | O |
| 95 | 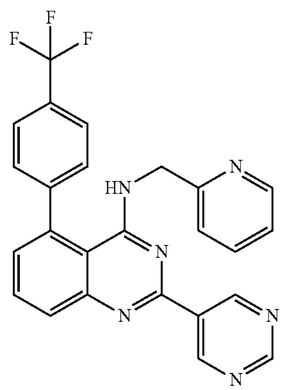 [SMILES: FC(F)(F)c1ccc(-c2cccc3nc(-c4cncnc4)nc(NCc4ccccn4)c23)cc1] | 458.438 | [M + 1] 459.2 Rt: 3.225 min | S |
| 96 | 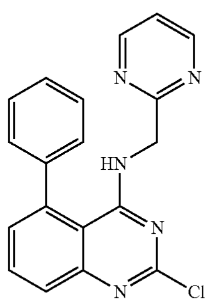 [SMILES: Clc1nc(NCc2ncccn2)c2c(-c3ccccc3)cccc2n1] | 347.801 | [M + 1] 348.2 Rt: 1.706 min | O |
| 97 | 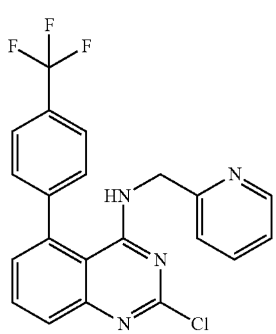 [SMILES: FC(F)(F)c1ccc(-c2cccc3nc(Cl)nc(NCc4ccccn4)c23)cc1] | 414.811 | [M + 1] 415.2 Rt: 2.016 min | Q |

TABLE 1b-continued
| Example | Structure | MW | LCMS Data | LCMS Method |
|---|---|---|---|---|
| 99 | 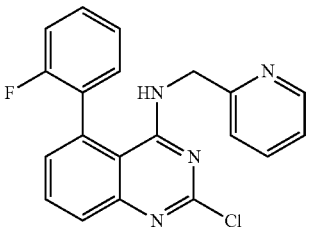 [SMILES: Fc1ccccc1-c1cccc2nc(Cl)nc(NCc3ccccn3)c12] | 364.803 | [M + 1] 365.2 Rt: 2.010 min | Q |
| 102 | 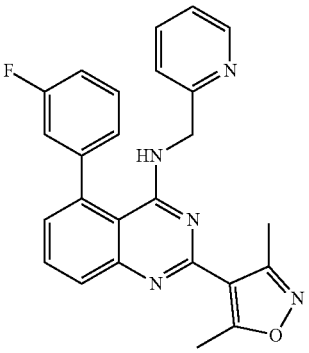 [SMILES: Cc1noc(C)c1-c1nc(NCc2ccccn2)c2c(-c3cccc(F)c3)cccc2n1] | 425.458 | [M + 1] 426.2 Rt: 3.298 min | S |
| 103 | 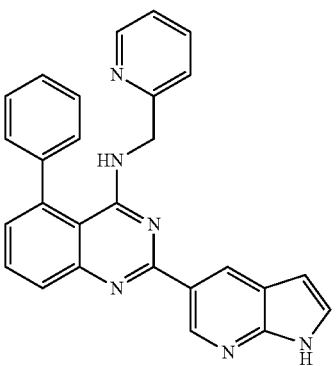 [SMILES: c1ccc(-c2cccc3nc(-c4cnc5[nH]ccc5c4)nc(NCc4ccccn4)c23)cc1] | 428.488 | [M + 1] 429.2 Rt: 2.030 min | Q |
| 104 | 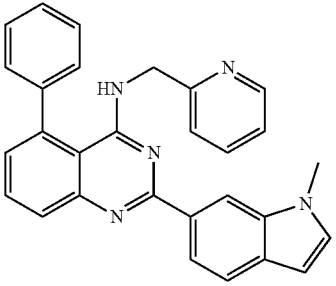 [SMILES: Cn1ccc2ccc(-c3nc(NCc4ccccn4)c4c(-c5ccccc5)cccc4n3)cc21] | 441.526 | [M + 1] 442.2 Rt: 1.755 min | O |
| 105 | 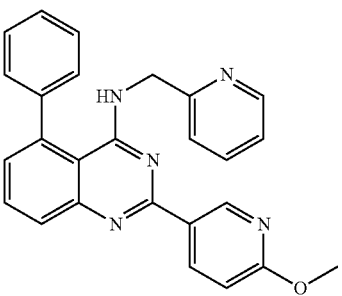 [SMILES: COc1ccc(-c2nc(NCc3ccccn3)c3c(-c4ccccc4)cccc3n2)cn1] | 419.478 | [M + 1] 420.2 Rt: 3.957 min | R |

TABLE 1b-continued
| Example | Structure | MW | LCMS Data | LCMS Method |
|---|---|---|---|---|
| 106 | 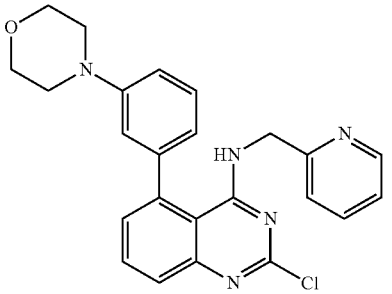 [SMILES: Clc1nc(NCc2ccccn2)c2c(-c3cccc(N4CCOCC4)c3)cccc2n1] | 431.917 | [M + 1] 432.2 Rt: 1.902 min | Q |
| 107 | 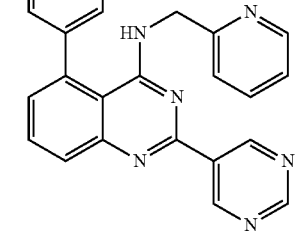 | 475.544 | [M + 1] 476.2 Rt: 1.971 min | Q |
| 108 | 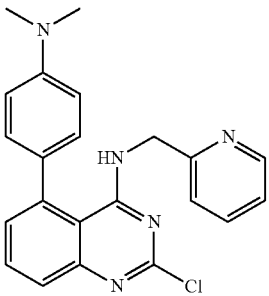 [SMILES: CN(C)c1ccc(-c2cccc3nc(Cl)nc(NCc4ccccn4)c23)cc1] | 389.881 | [M + 1] 390.2 Rt: 2.006 min | Q |
| 109 | 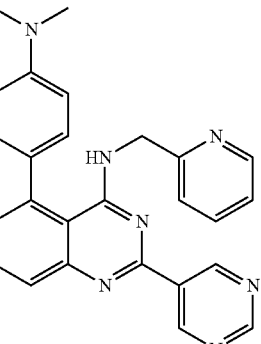 | 433.508 | [M + 1] 434.2 Rt: 2.084 min | Q |
| 110 | 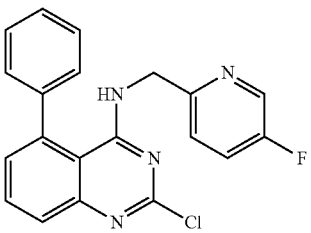 | 364.803 | [M + 1] 365.0 Rt: 1.866 min | O |

TABLE 1b-continued

| Example | Structure | MW | LCMS Data | LCMS Method |
|---|---|---|---|---|
| 111 | 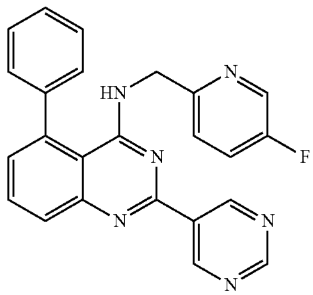 [SMILES: Fc1ccc(CNc2nc(-c3cncnc3)nc3cccc(-c4ccccc4)c23)nc1] | 408.43 | [M + 1] 409.2 Rt: 2.099 min | Q |
| 113 | 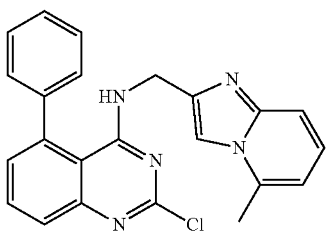 [SMILES: Cc1cccc2nc(CNc3nc(Cl)nc4cccc(-c5ccccc5)c34)cn12] | 399.876 | [M] 400.0 Rt: 3.09 min | L |
| 114 | 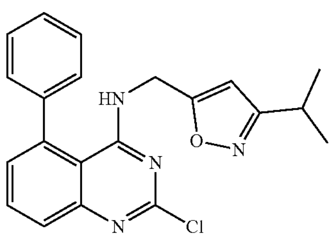 [SMILES: CC(C)c1cc(CNc2nc(Cl)nc3cccc(-c4ccccc4)c23)on1] | 378.855 | [M] 379.0 Rt: 3.68 min | L |
| 117 | 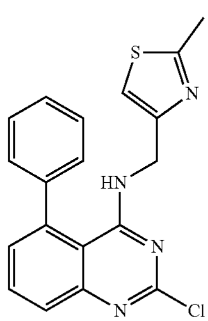 [SMILES: Cc1nc(CNc2nc(Cl)nc3cccc(-c4ccccc4)c23)cs1] | 366.867 | [M] 366.9 Rt: 3.32 min | L |
| 118 | 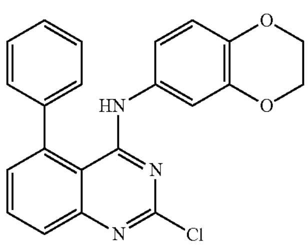 [SMILES: Clc1nc(Nc2ccc3c(c2)OCCO3)c2c(-c3ccccc3)cccc2n1] | 389.834 | [M] 388.2 Rt: 6.00 min | L |

TABLE 1b-continued

| Example | Structure | MW | LCMS Data | LCMS Method |
|---|---|---|---|---|
| 119 | 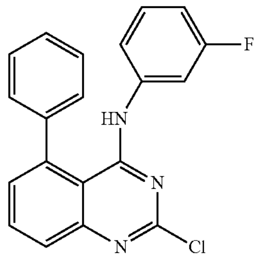 [SMILES: Fc1cccc(Nc2nc(Cl)nc3cccc(-c4ccccc4)c23)c1] | 349.789 | [M] 348.1 Rt: 6.48 min | L |
| 122 | 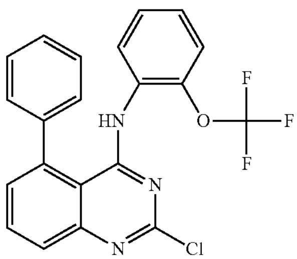 [SMILES: FC(F)(F)Oc1ccccc1Nc1nc(Cl)nc2cccc(-c3ccccc3)c12] | 415.796 | [M − 1] 414.1 Rt: 6.69 min | L |
| 126 | 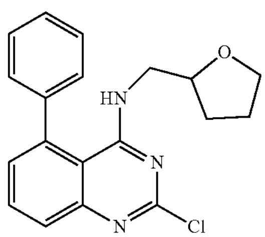 [SMILES: Clc1nc(NCC2CCCO2)c2c(-c3ccccc3)cccc2n1] | 339.819 | [M − 1] 338.2 Rt: 5.28 min | L |
| 127 | 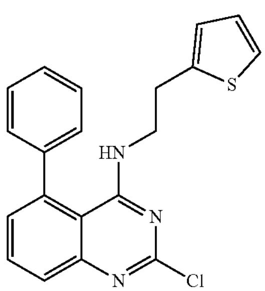 [SMILES: Clc1nc(NCCc2cccs2)c2c(-c3ccccc3)cccc2n1] | 365.879 | [M − 1] 364.2 Rt: 6.30 min | L |
| 128 | 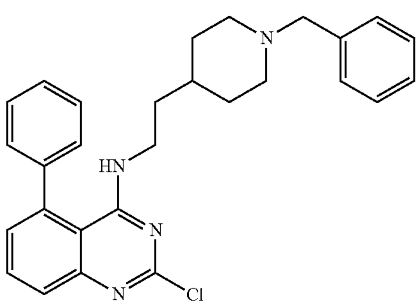 [SMILES: Clc1nc(NCCC2CCN(Cc3ccccc3)CC2)c2c(-c3ccccc3)cccc2n1] | 457.01 | [M − 1] 455.2 Rt: 5.07 min | L |
| 129 | 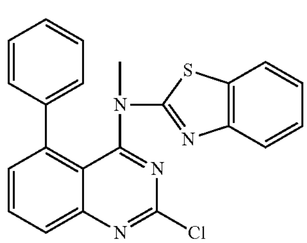 [SMILES: CN(c1nc2ccccc2s1)c1nc(Cl)nc2cccc(-c3ccccc3)c12] | 402.899 | [M − 1] 401.1 Rt: 6.17 min | L |

TABLE 1b-continued

| Example | Structure | MW | LCMS Data | LCMS Method |
|---|---|---|---|---|
| 130 | 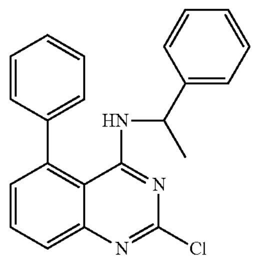 [SMILES: CC(Nc1nc(Cl)nc2cccc(-c3ccccc3)c12)c1ccccc1] | 359.851 | [M − 1] 358.2 Rt: 6.46 min | L |
| 131 | 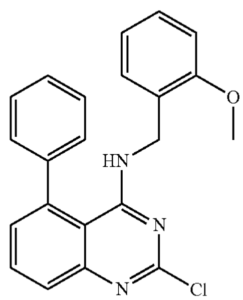 [SMILES: COc1ccccc1CNc1nc(Cl)nc2cccc(-c3ccccc3)c12] | 375.851 | [M − 1] 374.2 Rt: 6.31 min | L |
| 132 | 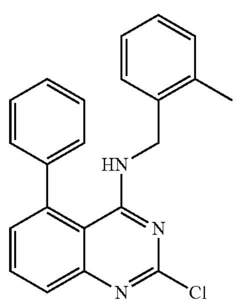 [SMILES: Cc1ccccc1CNc1nc(Cl)nc2cccc(-c3ccccc3)c12] | 359.851 | [M − 1] 358.1 Rt: 6.50 min | L |
| 133 | 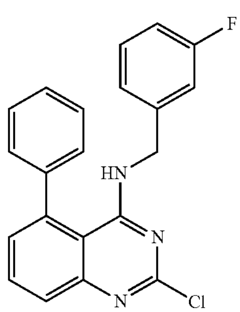 [SMILES: Fc1cccc(CNc2nc(Cl)nc3cccc(-c4ccccc4)c23)c1] | 363.815 | [M] 362.1 Rt: 6.16 min | L |
| 134 | 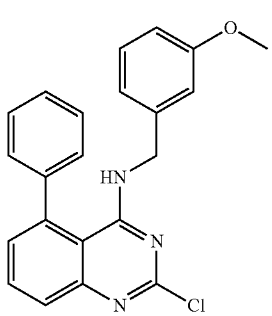 [SMILES: COc1cccc(CNc2nc(Cl)nc3cccc(-c4ccccc4)c23)c1] | 375.851 | [M − 1] 374.2 Rt: 6.06 min | L |

TABLE 1b-continued

| Example | Structure | MW | LCMS Data | LCMS Method |
|---|---|---|---|---|
| 135 | 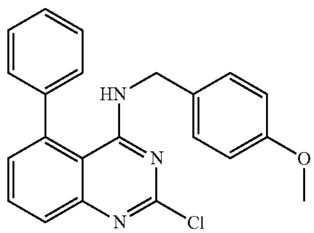 [SMILES: COc1ccc(CNc2nc(Cl)nc3cccc(-c4ccccc4)c23)cc1] | 375.851 | [M − 1] 374.3 Rt: 6.06 min | L |
| 136 | 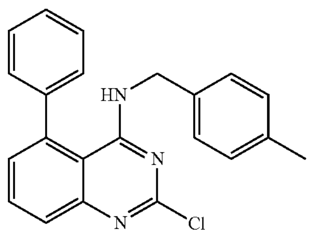 [SMILES: Cc1ccc(CNc2nc(Cl)nc3cccc(-c4ccccc4)c23)cc1] | 359.851 | [M − 1] 358.2 Rt: 6.57 min | L |
| 137 | 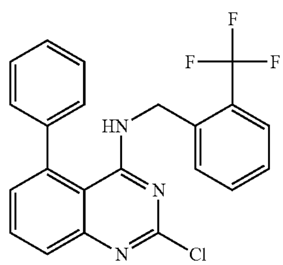 [SMILES: FC(F)(F)c1ccccc1CNc1nc(Cl)nc2cccc(-c3ccccc3)c12] | 413.823 | [M − 1] 412.1 Rt: 6.59 min | L |
| 138 | 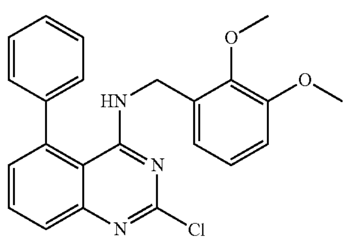 [SMILES: COc1cccc(CNc2nc(Cl)nc3cccc(-c4ccccc4)c23)c1OC] | 405.877 | [M + 1] 406.1 Rt: 6.03 min | L |
| 139 | 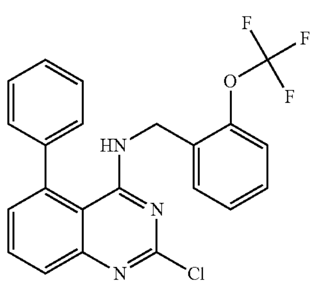 [SMILES: FC(F)(F)Oc1ccccc1CNc1nc(Cl)nc2cccc(-c3ccccc3)c12] | 429.822 | [M − 1] 428.1 Rt: 6.76 min | L |
| 143 | 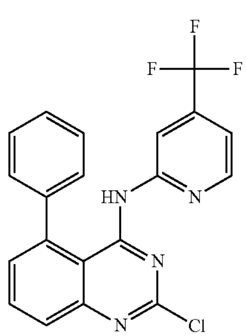 [SMILES: FC(F)(F)c1ccnc(Nc2nc(Cl)nc3cccc(-c4ccccc4)c23)c1] | 400.784 | [M − 1] 399.1 Rt: 6.92 min | L |

TABLE 1b-continued

| Example | Structure | MW | LCMS Data | LCMS Method |
|---|---|---|---|---|
| 148 | 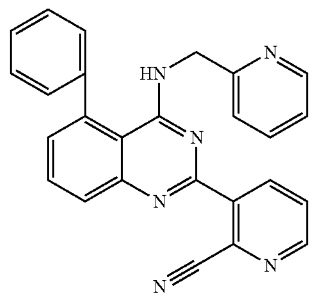 [SMILES: N#Cc1ncccc1-c1nc(NCc2ccccn2)c2c(-c3ccccc3)cccc2n1] | 414.461 | [M + 1] 415.2<br>Rt: 1.685 min | O |
| 149 | 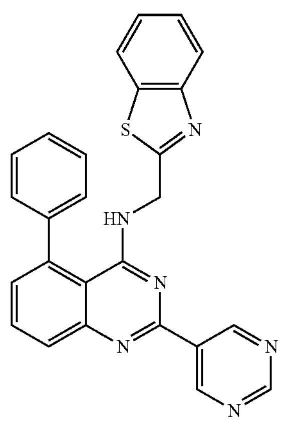 [SMILES: c1ccc(-c2cccc3nc(-c4cncnc4)nc(NCc4nc5ccccc5s4)c23)cc1] | 446.526 | [M + 1] 447.0<br>Rt: 3.991 min | S |
| 150 | 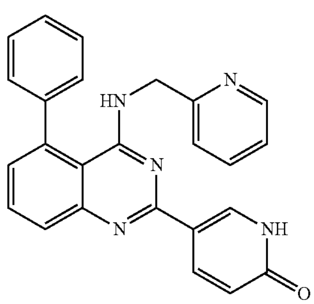 [SMILES: O=c1ccc(-c2nc(NCc3ccccn3)c3c(-c4ccccc4)cccc3n2)c[nH]1] | 405.451 | [M + 1] 406.2<br>Rt: 1.347 min | O |
| 152 | 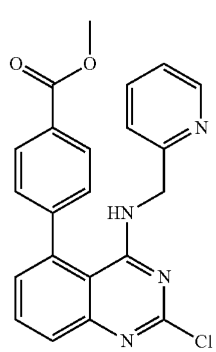 [SMILES: COC(=O)c1ccc(-c2cccc3nc(Cl)nc(NCc4ccccn4)c23)cc1] | 404.849 | [M + 1] 405.2<br>Rt: 1.909 min | Q |

TABLE 1b-continued

| Example | Structure | MW | LCMS Data | LCMS Method |
|---|---|---|---|---|
| 154 | 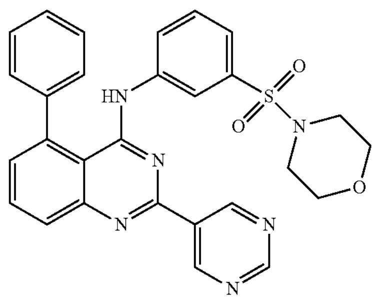 [SMILES: O=S(=O)(c1cccc(Nc2nc(-c3cncnc3)nc3cccc(-c4ccccc4)c23)c1)N1CCOCC1] | 524.594 | [M + 1] 525.2 Rt: 2.041 min | Q |
| 158 | 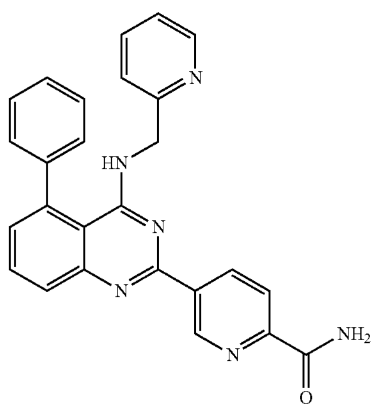 | 432.477 | [M + 1] 433.0 Rt: 1.455 min | O |

Example 159

Tert-butyl 5-(5-phenyl-4-(pyridin-2-ylmethylamino)quinazolin-2-yl)pyridin-3-ylcarbamate

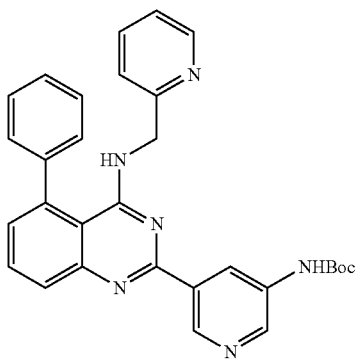 [SMILES: CC(C)(C)OC(=O)Nc1cncc(-c2nc(NCc3ccccn3)c3c(-c4ccccc4)cccc3n2)c1]

Step 1: Preparation of tert-butyl 5-bromopyridin-3-ylcarbamate

To 5-bromopyridin-3-amine (2.00 g, 11.5 mmol) in THF (25 mL) was added sodium hexamethyldisilazide (25.4 mL, 25.4 mmol, 1 M in THF) and the reaction mixture was stirred at room temperature for 20 min. Boc-anhydride (2.52 mL, 15.6 mmol) in THF (10 mL) was added slowly and the reaction mixture was stirred for an additional 24 h at room temperature. 0.1 M HCl (30 mL) was added and the reaction mixture was extracted with ethyl acetate. The combined organic extracts were washed successively with water and brine. The organic layer was dried, filtered and concentrated under reduced pressure to afford tert-butyl 5-bromopyridin-3-ylcarbamate (2.5 g, 81%), which was used without further purification. LCMS Method 0018: retention time 1.84 min, [M+1]=275.0 $^1$H NMR (400 MHz, DMSO-$d_6$) δ (ppm): 9.82 (s, 1H), 8.57 (d, 1H, J=2.4 Hz), 8.30 (d, 1H, J=2 Hz), 8.18 (s, 1H), 1.49 (s, 9H).

Step 2: Preparation of tert-butyl 5-(4,4,5,5-tetramethyl-1,3,2-dioxaborolan-2-yl)pyridin-3-ylcarbamate

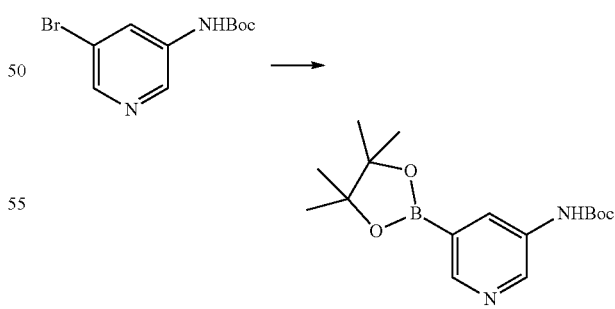

A mixture of tert-butyl 5-bromopyridin-3-ylcarbamate (0.8 g, 2.9 mmol), bis(pinacolato)diboron (0.82 g, 3.2 mmol) and potassium acetate (0.86 g, 8.7 mmol) in 1,4-dioxane (15 mL) was degassed with nitrogen for 15 min. After this time, (1,1'-Bis(diphenylphosphino)ferrocene)palladium (II) chloride dichloromethane complex (0.12 g, 0.1 mmol) was added and the mixture was again degassed for 10 min. with

229 nitrogen. Upon completion of this period, the reaction mixture was heated in the microwave at 120° C. for 45 min. After this time, the reaction mixture was filtered through celite and the filtrate was concentrated under reduced pressure to provide crude of tert-butyl 5-(4,4,5,5-tetramethyl-1,3,2-dioxaborolan-2-yl)pyridin-3-ylcarbamate (1.7 g), which was used without further purification.

Step 3. Example 159

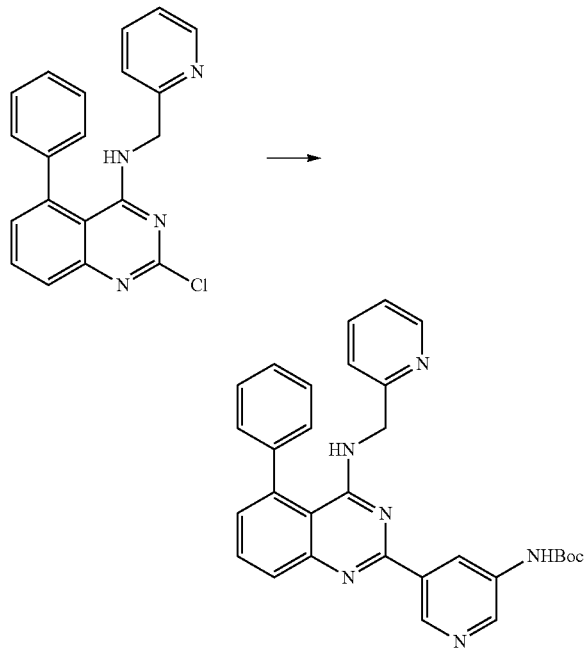

To a solution of 2-chloro-5-phenyl-N-(pyridin-2-ylmethyl)quinazolin-4-amine (1.2 g, 3.4 mmol) in 1,4-dioxane (10 mL) and H$_2$O (2.5 mL) under nitrogen was added tert-butyl 5-(4,4,5,5-tetramethyl-1,3,2-dioxaborolan-2-yl)pyridin-3-ylcarbamate (1.7 g, 5.3 mmol), and potassium carbonate (1.4 g, 10 mmol). The mixture was degassed with nitrogen for 15 min. and then (1,1'-bis(diphenylphosphino)ferrocene)palladium (II) chloride dichloromethane complex (0.25 mg, 0.3 mmol) was added. Upon completion of addition, the reaction mixture was again degassed for 10 min with nitrogen. After this time, the reaction mixture was stirred at 90° C. for 16 h, and then allowed to cool to room temperature. Once at the prescribed temperature, the reaction mixture was quenched by the addition of water and then transferred to a separation funnel. The aqueous layer was extracted with ethyl acetate. The combined organic portions were washed with water and saturated NaCl, dried over Na$_2$SO$_4$, filtered and concentrated under reduced pressure to yield a residue. The residue was purified by silica gel column chromatography using a dichloromethane/methanol mixture to afford Example 159 (0.9 g, 52% yield) as a brown solid. $^1$H NMR (400 MHz, DMSO-d$_6$) δ (ppm): 9.73 (br s, 1H); 9.25 (d, 1H, J=2 Hz); 8.95 (s, 1H); 8.76 (s, 1H); 8.25 (d, 1H, J=4 HZ); 7.91-7.80 (m, 2H); 7.73 (t, 1H, J=8 Hz); 7.60-7.50 (m, 5H); 7.39-7.29 (m, 2H); 7.25 (t, 1H, J=10 Hz); 6.83 (br s, 1H); 4.74 (d, 2H, J=3.6 Hz); 1.54 (s, 9H). LCMS Method W: retention time 2.21 min; [M+1]=505.2; HPLC Method K: purity 97.7%, retention time=15.80 min.

230

Example 160

2-(5-Aminopyridin-3-yl)-5-phenyl-N-(pyridin-2-ylmethyl)quinazolin-4-amine

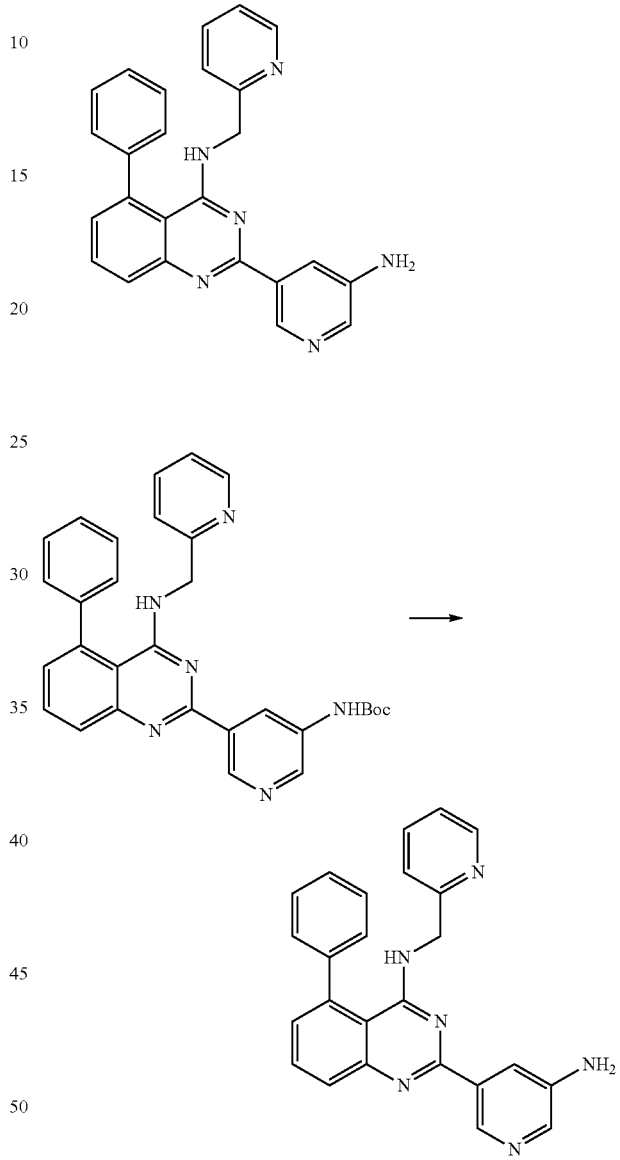

To a solution of Example 159 (750 mg, 1.48 mmol) in DCM (5 mL) at 0° C. was added 1.5 M HCl in dioxane (1.5 M). Upon completion of addition, the reaction mixture was stirred for 1 h and then concentrated to yield a residue. The residue was purified by combiflash using 3% methanol in DCM to give Example 160 (560 mg, 93% yield) as an off white solid. $^1$H NMR (400 MHz, DMSO-d$_6$, δ): 8.84 (s, 1H); 8.24 (d, 1H, J=3.6 Hz): 8.04 (s, 1H); 8.00 (s, 1H); 7.89-7.79 (m, 2H); 7.72 (t, 1H, J=7.2 Hz); 7.62-7.48 (m, 5H); 7.35-7.22 (m, 3H); 6.78 (s, 1H); 5.47 (s, 2H); 4.73 (d, 12H, J=3.6 Hz); LCMS Method X: retention time 1.91 min, [M+1]=405.2 HPLC Method A1: purity 99.3%, retention time=6.84 min.

Example 161

N-(5-(5-phenyl-4-(pyridin-2-ylmethylamino)quinazolin-2-yl)pyridin-3-yl)acetamide

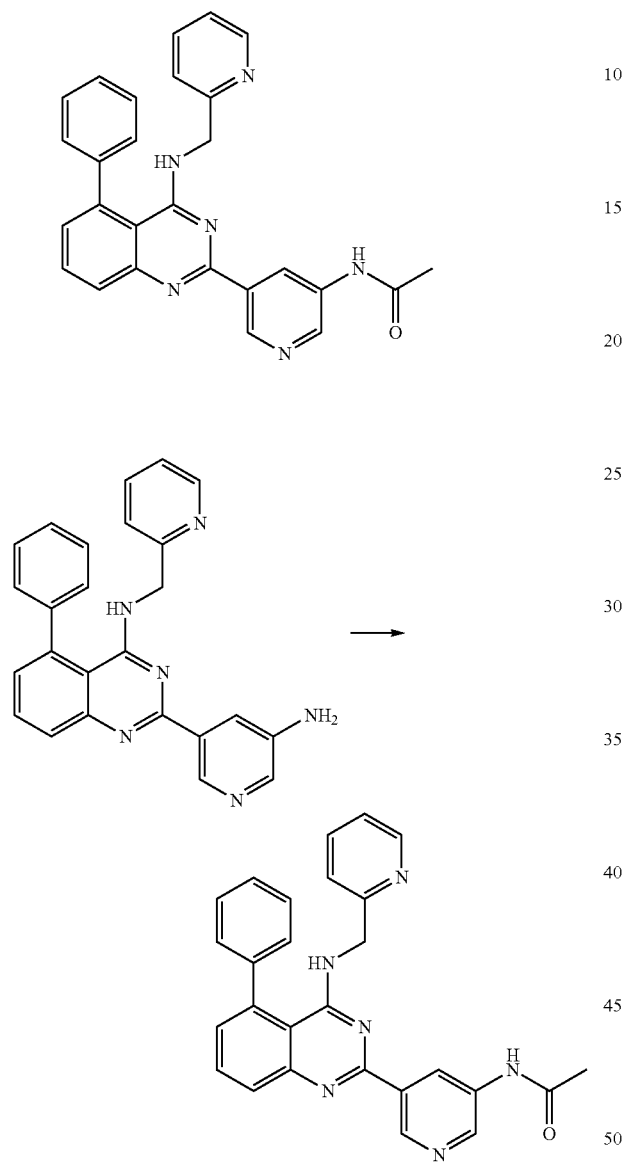

To a solution of Example 160 (0.2 g, 0.5 mmol) in acetone (20 mL) was added acetyl chloride (0.2 mL, 0.55 mmol) and potassium carbonate (0.2 g, 1.5 mmol). Upon completion of addition, the reaction mixture was stirred at room temperature for 4 h. After this time, the reaction mixture was filtered through celite, and the filtrate was concentrated to yield a residue. The residue was diluted with EtOAc and the organic portion was washed with saturated sodium bicarbonate (10 mL). The organic layer was dried, and then purified by silica gel column chromatography using dichloromethane/Methanol as the solvent to obtain Example 161 (180 mg, 82%) as a white solid. $^1$H NMR (400 MHz, DMSO-d$_6$, δ): 10.34 (s, 1H); 9.31 (d, 1H, J=2.4 Hz); 8.96 (d, 2H, J=5.2 Hz), 8.24 (d, 1H, J=4.8 Hz), 7.93-7.80 (m, 2H), 7.73 (dt, 1H, J=2.4 Hz, 7.6 Hz), 7.60-7.47 (m, 5H), 7.38-7.28 (m, 2H), 7.24 (t, 1H, J=9.2 Hz), 6.85 (br s, 1H), 4.74 (d, 2H, J=4 Hz), 2.13 (s, 3H). LCMS Method W: retention time 1.85 min, [M+1]=447.2. HPLC Method A1: purity 98.5%, retention time=7.20 min.

Example 162

N-(5-(5-phenyl-4-(pyridin-2-ylmethylamino)quinazolin-2-yl)pyridin-3-yl) sulfamide

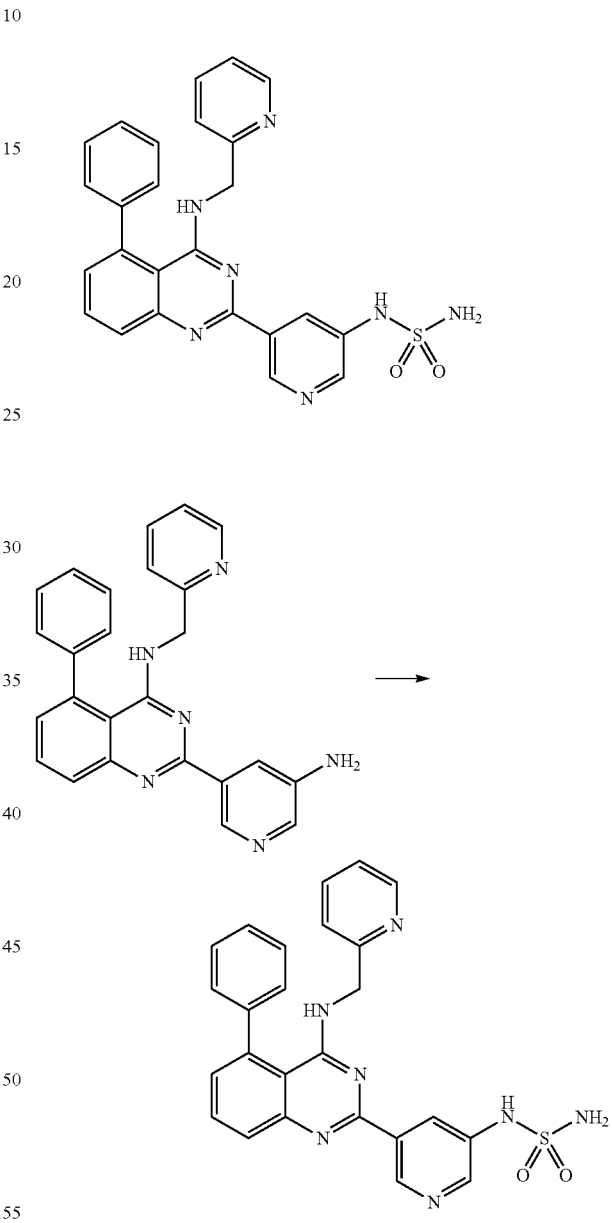

To a solution of chlorosulfonylisocyanate (0.021 mL, 0.24 mmol) in DCM (4 mL) was added t-BuOH (0.023 mL, 0.24 mmol) at RT. Upon completion of addition, the reaction mixture was stirred for 10 min. After this time, TEA was added (0.05 ml, 0.3 mmol), followed by a solution of Example 160 (0.1 g, 0.24 mmol) in DCM. The reaction mixture was stirred for an additional 3 h and then washed with a Na$_2$CO$_3$ solution. The aqueous layer was extracted with ethyl acetate. The combined organic extracts were dried, concentrated under reduced pressure and purified by silica gel column chromatography using dichloromethane/ methanol mixture to yield Example 162 (0.040 g, 34% yield). ¹H NMR (400 MHz, DMSO-d₆, δ): 9.88 (s, 1H); 9.30 (s, 1H); 8.61 (br s, 1H); 8.56 (d, 1H, J=2.4 Hz); 8.24 (d, 1H, J=4.4 Hz); 7.91-7.80 (m, 2H); 7.73 (dt, 1H, J=7.6 Hz); 7.61-7.49 (m, 5H); 7.38-7.29 (m, 4H); 7.24 (t, 1H, J=5.6 Hz); 6.86 (br t, 1H, J=3.6 Hz); 4.74 (d, 2H, J=4 Hz). LCMS Method X: retention time 1.81 min, [M+1]=484.2. HPLC Method A1: purity 97.1%, retention time=7.83 min.

Example 163

1-(5-(5-Phenyl-4-(pyridin-2-ylmethylamino)quinazolin-2-yl)pyridin-3-yl)urea

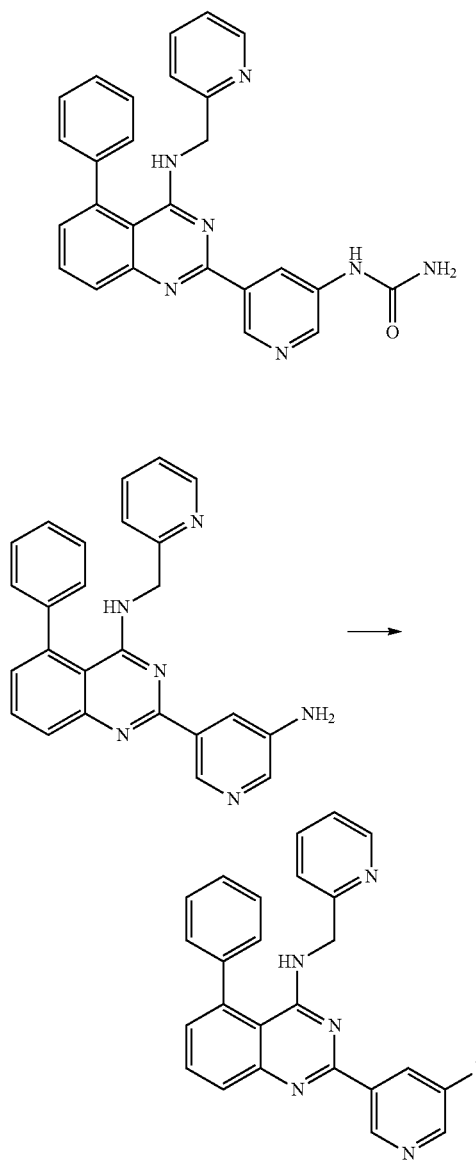

To a solution of Example 160 (0.2 g, 0.5 mmol) in DCM at 0° C. was added chlorosulfonylisocyanate (0.081 mL, 0.90 mmol). The resulting slurry was stirred at RT for 4 h and then 2 mL of 1.5 N HCl was added. Upon completion of addition, the reaction mixture was heated to 40° C. where it stirred for an additional 2 h. The resulting solution was neutralized with a sat. Na₂CO₃ solution and the aqueous portion was extracted with DCM. The combined organic extracts were dried, concentrated and purified by preparative HPLC 5% methanol in dichloromethane to yield Example 163 (0.040 g, 18% yield). ¹H NMR (400 MHz, DMSO-d₆, δ): 9.19 (s, 1H); 8.94 (s, 1H); 8.83 (s, 1H); 8.76 (d, 1H, J=2.4 Hz); 8.24 (d, 1H, J=4.8 Hz); 7.90-7.80 (m, 2H); 7.73 (t, 1H, J=8.4 Hz); 7.60-7.50 (m, 5H); 7.38-7.29 (m, 2H); 7.24 (t, 1H, J=5.2 Hz); 6.83 (br t, 1H, J=4 Hz); 6.07 (br s, 2H); 4.74 (d, 2H, J=4 Hz). LCMS Method T: retention time 1.43 min, [M+1]=448.0. HPLC Method A1: purity 98.8%, retention time=6.95 min.

Example 164

2-(2-Aminopyrimidin-5-yl)-5-phenyl-N-(pyridin-2-ylmethyl)quinazolin-4-amine

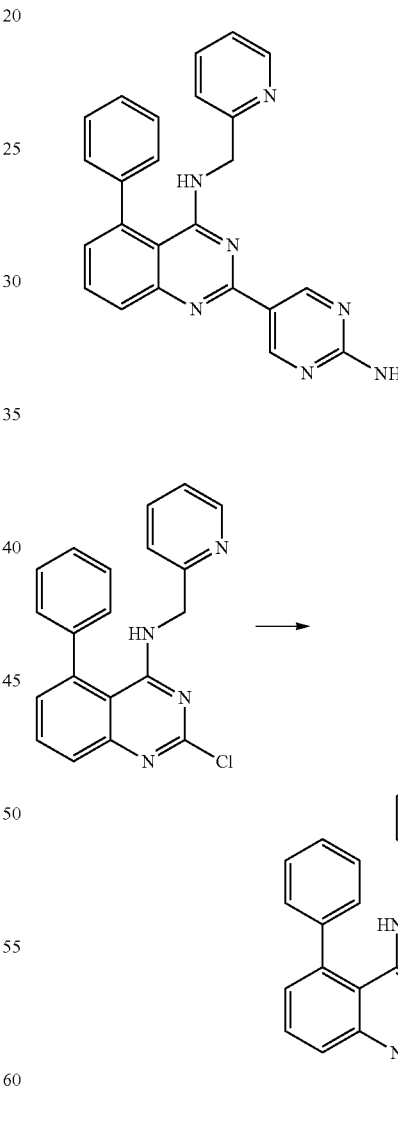

To a solution of 2-chloro-5-phenyl-N-(pyridin-2-ylmethyl)quinazolin-4-amine (0.7 g, 2.02 mmol) in 1,4-dioxane (30 mL) and H₂O (5 mL) under nitrogen was added 2-aminopyrimidin-5-ylboronic ester (670 g, 3.03 mmol), and potassium carbonate (0.55 g, 4.04 mmol). Upon completion of addition, the mixture was degassed with nitrogen for 15 min and then (1,1'-bis(diphenylphosphino)ferrocene)palladium (II) chloride dichloromethane complex (0.147 mg, 0.20 mmol) was added. The reaction mixture was again degassed for 10 min with nitrogen. After this time, the reaction mixture was heated to 90° C. where it stirred for 16 h. Aft the conclusion of this period, the reaction mixture was allowed to cool to room temperature and then quenched by the addition of water. The reaction mixture was transferred to a separation funnel and the aqueous layer was extracted with ethyl acetate. The combined organic portions were washed with water and saturated NaCl, dried over Na$_2$SO$_4$, filtered and concentrated under reduced pressure. The resulting concentrate was purified by silica gel column chromatography using dichloromethane/methanol mixture as the eluent to afford Example 164 (0.42 g, 52% yield) as a brown solid. $^1$H NMR (400 MHz, DMSO-d$_6$) δ (ppm): 9.20 (s, 2H), 8.23 (d, 1H, J=4.8 Hz), 7.78 (d, 2H, J=2.4 Hz), 7.77-7.70 (m, 1H), 7.60-7.57 (m, 5H), 7.34-7.30 (m, 1H), 7.26-7.20 (m, 2H), 7.18-7.13 (br s, 2H), 6.76 (br s, 1H), 4.67 (d, 2H, J=4.0 Hz); LCMS Method U: retention time 1.38 min; [M+1]=406; HPLC Method A1: purity 99.5%, retention time=6.74 min.

Example 165

5-(5-Phenyl-4-(pyridin-2-ylmethylamino)quinazolin-2-yl)pyrimidine-2-carbonitrile

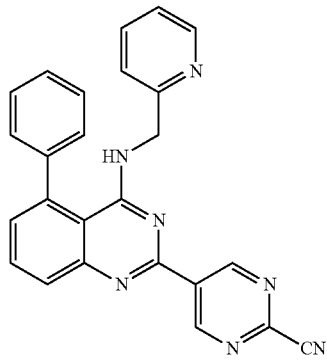

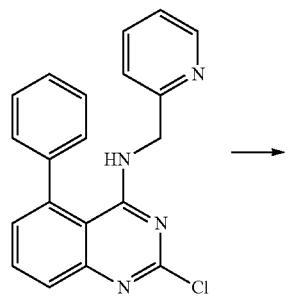

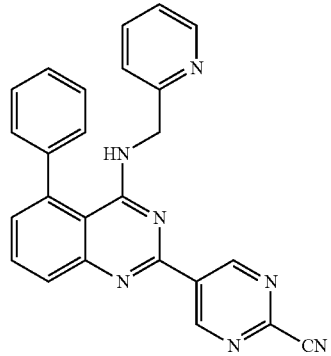 [SMILES: N#Cc1ncc(-c2nc(NCc3ccccn3)c3c(-c4ccccc4)cccc3n2)cn1]

To a solution of 2-chloro-5-phenyl-N-(pyridin-2-ylmethyl)quinazolin-4-amine (0.22 g, 0.65 mmol) in 1,4-dioxane (10 mL) and H$_2$O (2 mL) under nitrogen was added 2-cyanopyrimidin-5-ylboronic ester (0.22 g, 0.97 mmol), and potassium carbonate (0.18 g, 1.30 mmol). Upon completion of addition, the mixture was degassed with nitrogen for 15 min. After this time, (1,1'-bis(diphenylphosphino)-ferrocene)palladium (II) chloride dichloromethane complex (0.048 mg, 0.06 mmol) was added and the reaction mixture was again degassed with nitrogen for 10 min. After this time, the reaction mixture was stirred heated to 90° C. where it stirred for 16 h. At the conclusion of this period, the reaction mixture was allowed to cool to room temperature and then quenched by the addition of water. The reaction mixture was transferred to a separation funnel and the aqueous layer was extracted with ethyl acetate. The combined organic portions were washed with water and saturated NaCl, dried over Na$_2$SO$_4$, filtered and concentrated under reduced pressure. The resulting concentrate was purified by silica gel column chromatography using a dichloromethane/methanol mixture as the eluent to afford Example 165 (0.13 g, 49% yield) as a brown solid. $^1$H NMR (400 MHz, DMSO-d$_6$) δ (ppm): 9.86 (s, 2H), 8.22 (d, 1H, J=6.4 Hz), 7.94 (dd, 1H, J=1.6 Hz J=8.4 Hz), 7.89 (dd, 1H, J=3.2 Hz, J=11.2 Hz), 7.74 (dt, 1H, J=1.6 Hz, 8 Hz,), 7.63-7.50 (m, 5H), 7.40-7.32 (m, 2H), 7.25 (dd, 1H, J=5.2 Hz, 6.8 Hz), 7.08 (br t, 1H, J=4 Hz), 4.76 (d, 2H, J=4.4 Hz). LCMS Method U: retention time 1.85 min; [M+1]=416.0; HPLC Method A4: purity 97.6%, retention time=23.30 min.

Example 166

5-(5-Phenyl-4-(pyridin-2-ylmethylamino)quinazolin-2-yl)pyrimidine-2-carboxamide

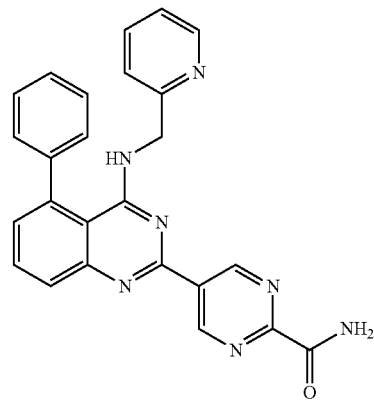 [SMILES: NC(=O)c1ncc(-c2nc(NCc3ccccn3)c3c(-c4ccccc4)cccc3n2)cn1]

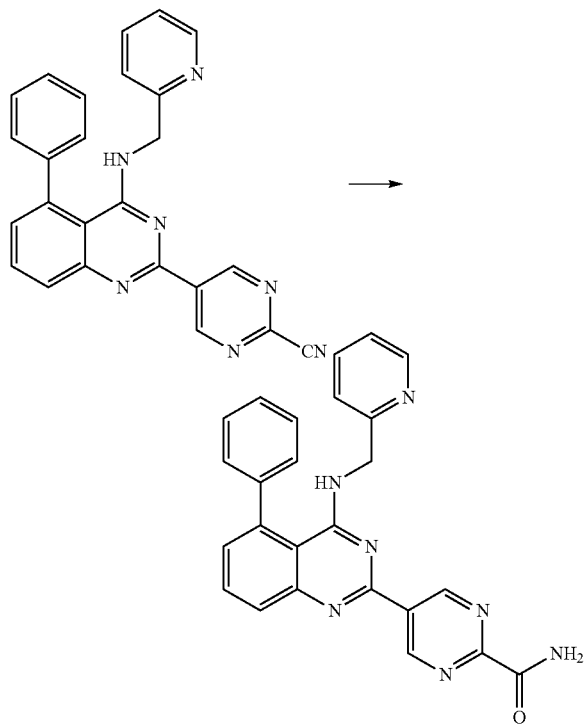

To a solution of Example 165 (0.115 g, 0.270 mmol) in THF was added NaOH (0.044 g, 1.1 mmol) and water. Upon completion of addition, the reaction mixture was cooled to 0° C. and hydrogen peroxide (0.037 g, 1.1 mmol) was added dropwise. The reaction mixture was stirred at RT for 2 h and then concentrated to yield a residue. The residue was diluted with water and the aqueous phase extracted with ethyl acetate. The combined organic extracts were dried and concentrated. The resulting residue was purified by Prep TLC using dichloromethane/methanol mixture as the eluent to yield Example 166 (0.075 g, 63% yield). $^1$H NMR (400 MHz, DMSO-d6, δ): 9.82 9s, 2H); 8.35 (d, 1H, J=4 Hz); 3.28 (s, 1H); 7.96 (dd, 1H, J=0.8, 8.4 Hz); 7.85 (t, 1H, J=7.2 Hz); 7.74 (dt, 1H, J=1.4, 7.6 Hz); 7.56-7.48 (m, 5H); 7.38 (dd, 1H, J=0.8, 7.8 Hz); 7.31-7.22 (m, 2H); 4.75 (d, 2H, J=4 Hz). LCMS Method Y: retention time 1.81 min, [M+1]=434.2. HPLC Method A1: purity 96.1%, retention time=9.30 min.

Example 167

1-Methyl-2-oxo-5-(5-phenyl-4-(pyridin-2-ylmethyl-amino)quinazolin-2-yl)-1,2-dihydropyridine-3-sulfonamide

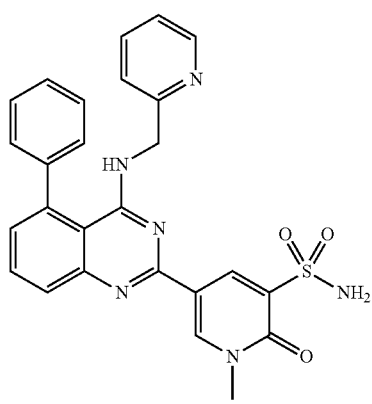 [SMILES: Cn1cc(-c2nc(NCc3ccccn3)c3c(-c4ccccc4)cccc3n2)cc(S(N)(=O)=O)c1=O]

Step 1. Preparation of 5-bromo-2-hydroxypyridine-3-sulfonamide

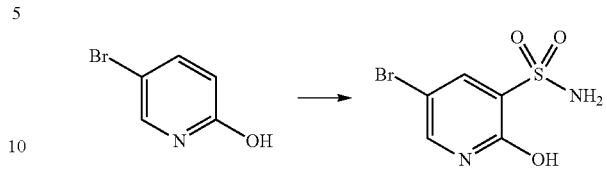

A solution of 5-bromopyridin-2-ol (0.5 g, 2.8 mmol) in chlorosulfonic acid (10 mL) was heated to 150° C. for 16 h. After this time, the reaction mixture was added dropwise to a pre-cooled aqueous ammonia solution (100 mL) at 0° C. The resulting mixture was stirred for 1 h. The aqueous layer was then extracted with ethyl acetate (150 mL), dried and concentrated to yield a residue. The residue was purified by ISCO chromatography using 3% methanol in DCM to yield 5-bromo-2-hydroxypyridine-3-sulfonamide (210 mg). $^1$H NMR (400 MHz, DMSO-d$_6$) δ (ppm): 12.67 (br s, 1H); 8.03 (d, 1H, J=2.8 Hz); 7.98 (d, 1H, J=2.8 Hz); 7.11 (s, 1H). LCMS Method U: retention time 1.85 min; [M+1]=253.0.

Step 2. Preparation of 5-bromo-2-methoxypyridine-3-sulfonamide

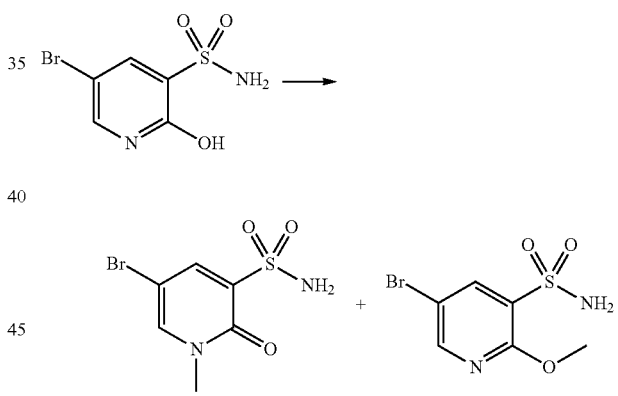

To a solution of 5-bromo-2-hydroxypyridine-3-sulfonamide (0.5 g, 1.9 mmol) in MeOH/DCM (15 mL, 1:1) at −10° C. was added trimethylsilyldiazomethane solution (2 M, 1.97 mL, 3.9 mmol). Upon completion of addition, the reaction mixture was concentrated and the resulting residue was purified by column chromatography using methanol and CHCl$_3$ to 5-bromo-1-methyl-2-oxo-1,2-dihydropyridine-3-sulfonamide yield 5-bromo-1-methyl-2-oxo-1,2-dihydropyridine-3-sulfonamide (280 mg, 53% yield) and 5-bromo-2-methoxypyridine-3-sulfonamide (180 mg, 34% yield). Data for 5-bromo-1-methyl-2-oxo-1,2-dihydropyridine-3-sulfonamide: $^1$H NMR (400 MHz, DMSO-d$_6$, δ): 8.42 (d, 1H, J=2.8 Hz); 7.99 (d, 1H, J=2.8 Hz); 7.14 (s, 1H); 3.52 (s, 3H). Data for 5-bromo-2-methoxypyridine-3-sulfonamide: $^1$H NMR (400 MHz, DMSO-d$_6$, δ): 8.54 (d, 1H, J=2.4 Hz); 8.17 (d, 1H, J=2.4 Hz); 7.51 (s, 1H); 4.00 (s, 3H).

Step 3: Example 167

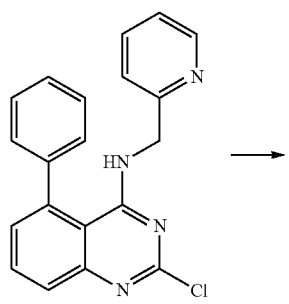

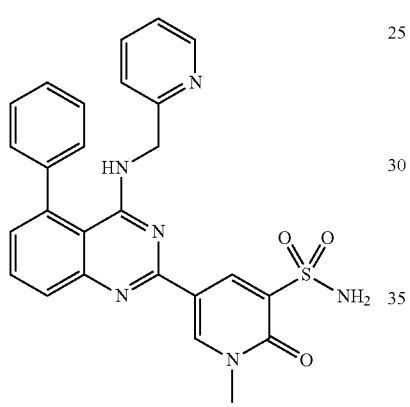

A stirred solution of 5-bromo-1-methyl-2-oxo-1,2-dihydropyridine-3-sulfonamide (0.08 g, 0.3 mmol) in dioxane: DMF (6 mL: 1 mL) was degassed for 10 min with argon. At the conclusion of this period, Pd(triphenylphosphine)$_4$ (34 mg, 0.03 mmol) and hexamethylditin (0.17 g, 0.53 mmol) were added. The reaction mixture was stirred at room temperature for 16 h. and then 2-chloro-5-phenyl-N-(pyridin-2-ylmethyl)quinazolin-4-amine (0.1 g, 0.3 mmol) was added. Upon completion of addition, the reaction mixture was heated to 100° C. where it stirred for an additional 16 h. A precipitate was formed and the resulting slurry was filtered. The filtrate was concentrated and purified by silica gel column chromatography using dichloromethane/methanol mixture as the eluent to obtain Example 167 (15 mg, 13% yield). $^1$H NMR (400 MHz, DMSO-d$_6$) δ (ppm): 9.06 (s, 1H); 9.02 (s, 1H); 8.25 (d, 1H, J=4 Hz); 7.86-7.78 (m, 2H); 7.73 (dt, 1H, J=1.6, 7.6 Hz); 7.60-7.48 (m, 5H); 7.31-7.22 (m, 3H); 7.09 (br s, 2H); 6.79 (t, 1H, J=4 Hz); 4.72 (d, 2H, J=4 Hz); 3.72 (s, 3H). LCMS Method U: retention time 1.35 min; [M+1]=499.2; HPLC Method A1: purity 96.2%, retention time=6.10 min.

Example 168

2-Amino-5-(5-phenyl-4-(pyridin-2-ylmethylamino)quinazolin-2-yl)pyridine-3-sulfonamide

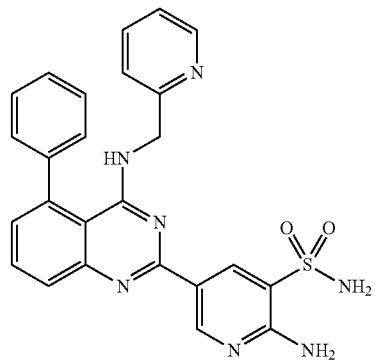 [SMILES: Nc1ncc(-c2nc(NCc3ccccn3)c3c(-c4ccccc4)cccc3n2)cc1S(N)(=O)=O]

Step 1. Preparation of 2-amino-5-bromopyridine-3-sulfonamide

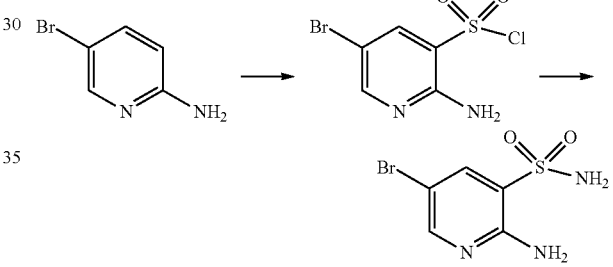

To a solution of chlorosulfonic acid (20 mL) at 0° C. was added 2-amino-5-bromopyridine (5.0 g, 0.029 mmol) portionwise. Upon completion of addition, the reaction mixture was heated to reflux where it stirred for 16 h. After this time, the reaction mixture was allowed to cool to RT. Once at the prescribed temperature, the reaction mixture was poured drop wise in to an aqueous ammonium hydroxide solution. The resulting mixture was extracted with ethyl acetate. The combined organic portions were washed with a brine solution, dried over Na$_2$SO$_4$ and concentrated under reduced pressure to yield 2-amino-5-bromopyridine-3-sulfonamide (4.7 g, 65%), which was used without further purification. LCMS Method Y: retention time 0.5 min, [M−1]=250.8.

Step 2. Preparation of 2-amino-5-(4,4,5,5-tetramethyl-1,3,2-dioxaborolan-2-yl)pyridine-3-sulfonamide which was used without further purification

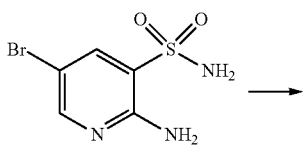

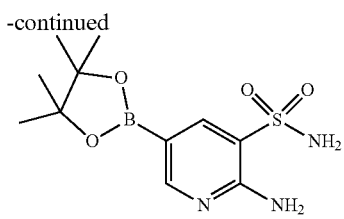

A mixture of 5-bromo-2-aminopyridine-3-sulfonamide (2.0 g, 7.9 mmol), bis(pinacolato)diboron (3.0 g, 12 mmol) and potassium acetate (2.3 g, 23 mmol) in 1,4-dioxane (20 mL) was degassed with nitrogen for 15 min. After this time, (1,1'-bis(diphenylphosphino)ferrocene)palladium (II) chloride dichloromethane complex (0.29 g, 0.36 mmol) was added and the reaction mixture was again degassed for 10 min with nitrogen. The reaction mixture was heated to 100° C. where it stirred for 12 h. At the conclusion of this period, the reaction mixture was filtered through celite and the filtrate was concentrated under reduced pressure to provide 2-amino-5-(4,4,5,5-tetramethyl-1,3,2-dioxaborolan-2-yl) pyridine-3-sulfonamide (1 g), which was used without further purification. LCMS Method X: retention time 1.29 min; [M+1]=300.

Step 3. Example 168

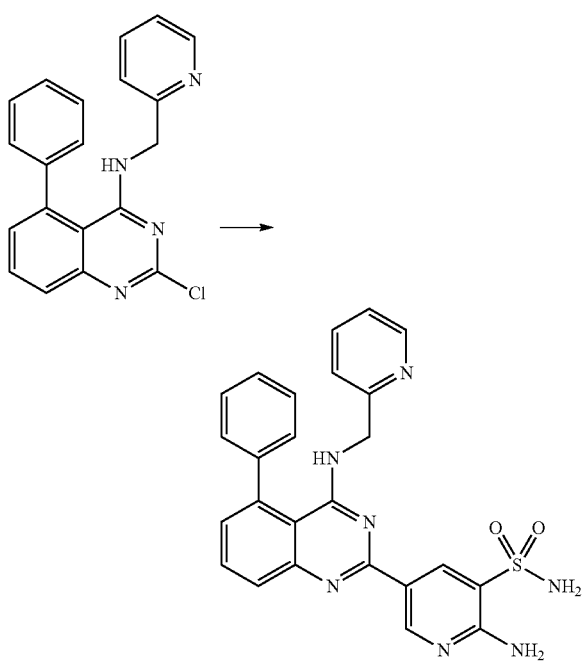

To a solution of 2-chloro-5-phenyl-N-(pyridin-2-ylmethyl)quinazolin-4-amine (0.20 g, 0.57 mmol) in 1,4-dioxane (5 mL) and H$_2$O (0.55 mL) under nitrogen was added 2-amino-5-(4,4,5,5-tetramethyl-1,3,2-dioxaborolan-2-yl) pyridine-3-sulfonamide (0.259, 0.800 mmol), and potassium carbonate (0.239 g, 1.70 mmol). Upon completion of addition, the reaction mixture was degassed with nitrogen for 15 min. After this time, (1,1'-bis(diphenylphosphino)ferrocene) palladium (II) chloride dichloromethane complex (0.023 mg, 0.020 mmol) was added and the resulting mixture was again degassed for 10 min with nitrogen. The reaction mixture was heated to 90° C. where it stirred for 16 h. At the conclusion of this period, the reaction mixture was allowed to cool to room temperature. Once at the prescribed temperature, the reaction mixture was quenched by the addition of water. The reaction mixture was transferred to a separation funnel and the aqueous layer was extracted with ethyl acetate. The combined organic portions were washed with water and saturated NaCl, dried over Na$_2$SO$_4$, filtered and concentrated under reduced pressure. The resulting concentrate was purified by silica gel column chromatography using dichloromethane/methanol mixture as the eluent and further purified by preparative HPLC using 7% methanol in dichloromethane as the eluent to afford Example 168 (0.060 g, 22% yield) as an off-white solid. $^1$H NMR (400 MHz, DMSO-d$_6$) δ (ppm): 9.14 (d, 1H, J=2.4 Hz); 9.02 (d, 1H, J=2.4 Hz); 8.37 (d, 1H, J=3.6 Hz); 7.87 (dd, 1H, J=1.2, 8.4 Hz): 7.82-7.72 (m, 2H); 7.58-7.47 (br s, 5H), 7.35-7.23 (m, 3H); 4.71 (s, 2H). LCMS Method Y: retention time 1.87 min; [M+1]=484.2; HPLC Method A2: purity 98.1%, retention time=12.93 min. Preparative HPLC Method-I.

Example 169

N-(5-(5-phenyl-4-(pyridin-2-ylmethylamino)quinazolin-2-yl)pyridin-3-yl)methane sulfonamide

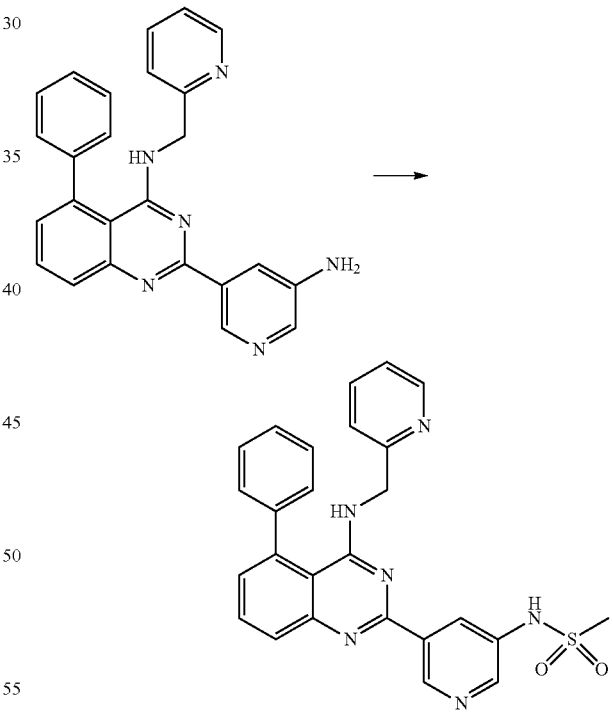

To a stirred solution of 2-(5-aminopyridin-3-yl)-5-phenyl-N-(pyridin-2-ylmethyl)quinazolin-4-amine (Example 161: 0.12 g, 0.3 mmol) and TEA (0.080 mL, 0.45 mmol) in DCM (10 mL) at RT was added methanesulfonyl chloride (0.30 mL, 0.44 mmol) dropwise at 0° C. and the reaction mixture was stirred at RT for 2 h. The reaction mixture was diluted with water and the resulting solution extracted with DCM. The combined organic extracts were washed successively with water and brine dried, filtered and the filtrate concentrated. The residue was purified by silica gel column chromatography using dichloromethane/methanol mixture (98/2) as the eluent to provide Example 169 (65 mg, 45% yield) as an off white solid. $^1$H NMR (400 MHz, DMSO-$d_6$, δ): 10.35 (br s, 1H); 9.40 (s, 1H); 8.68 (s, 1H), 8.58 (s, 1H), 7.24 (d, 1H, J=3.2 Hz), 7.90-7.82 (m, 2H), 7.73 (dd, 1H, J=1.2 Hz, 7.2 Hz), 7.62-7.50 (m, 5H), 7.34-7.30 (m, 2H), 7.23 (t, 1H, J=5.2 Hz), 6.85 (t, 1H, J=4 Hz), 4.73 (d, 2H, J=4 Hz), 3.11 (s, 3H). LCMS Method Y: retention time 1.89 min, [M+1]=483.2 HPLC Method A1: purity 97.8%, retention time=6.61 min.

Example 170

N-(2-methoxyethyl)-5-(5-phenyl-4-(pyridin-2-ylmethylamino)quinazolin-2-yl)pyridine-3-sulfonamide

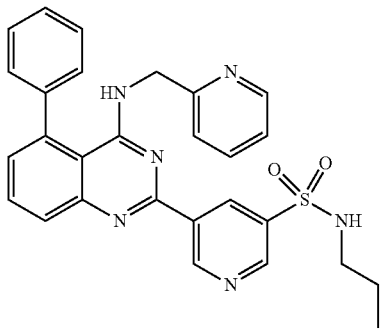 [SMILES: CCCNS(=O)(=O)c1cncc(-c2nc(NCc3ccccn3)c3c(-c4ccccc4)cccc3n2)c1]

Step 1. Preparation of 5-bromopyridine-3-sulfonyl chloride

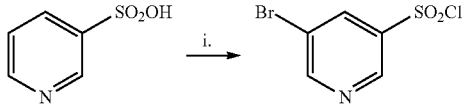

A mixture of pyridine-3-sulfonic acid (10.3 g, 64.8 mmol), phosphorous pentachloride (20.8 g, 100 mmol) and phosphorous oxychloride (10 mL, 100 mmol) was heated at reflux for 4 h. The reaction mixture was allowed to cool to room temperature and evaporated to dryness under reduced pressure. The residue was treated with bromine (6.00 mL, 116 mmol) and heated at reflux for 14 h. The reaction mixture was cooled to 0° C. then slowly quenched by the addition of ice water. The resulting mixture was diluted with ethyl acetate, the organic layer separated and the aqueous layer extracted further with ethyl acetate. The combined organic layers were dried over Na$_2$SO$_4$ then concentrated to afford 5-bromopyridine-3-sulfonyl chloride (5.0 g) as a semi solid, which was used without further purification.

Step 2. Preparation of 5-bromo-N-(2-methoxyethyl)pyridine-3-sulfonamide

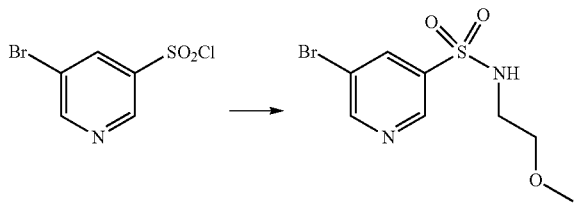

A solution of 5-bromopyridine-3-sulfonyl chloride (1.5 g, 5.8 mmol)) and 2-methoxyethanamine (1.3 g, 18 mmol) in THF (40 mL) was stirred at room temperature for 16 h. After this time, the resulting reaction mixture was partitioned between saturated aqueous sodium chloride and ethyl acetate. The organic solution was dried and evaporated. The resulting residue was purified by flash column chromatography using ethyl acetate/hexanes to yield 5-bromo-N-(2-methoxyethyl)pyridine-3-sulfonamide (460 mg, 27%). LCMS Method T: Retention time 1.13 min; [M+1]=295, 297.

Step 3. Example 170

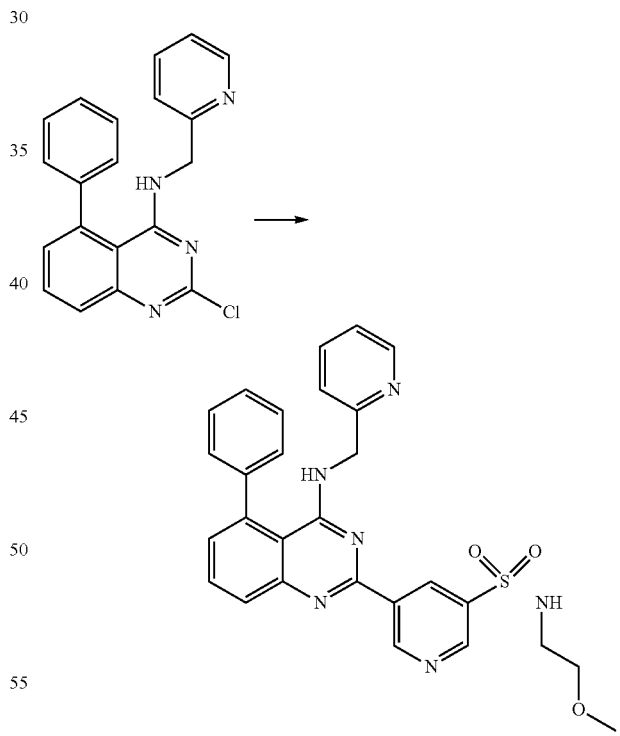

A stirred solution of 2-chloro-5-phenyl-N-(pyridin-2-ylmethyl)quinazolin-4-amine (0.15 g, 0.43 mmol) in dioxane (10 mL) was degassed for 10 min with argon and Pd(TRIPHENYLPHOSPHINE)$_4$ (0.05 g, 0.043 mmol) and hexamethylditin (0.25 g, 0.77 mmol) were added and the reaction mixture stirred at room temperature for 16 h. 5-bromo-N-(2-methoxyethyl)pyridine-3-sulfonamide (0.19 g, 0.65 mmol) was added to the reaction mixture and the resulting solution heated at 100° C. for an additional 16 h. A precipitate formed and the solids were filtered from the reaction mixture and filtrate concentrated and purified by silica gel column chromatography using dichloromethane/methanol mixture as the eluent to yield Example 170 (0.065 g, 27%) as an off white solid. $^1$H NMR (400 MHz, DMSO-d$_6$) δ (ppm): 9.83 (s, 1H), 9.11 (s. 1H), 9.06 (s, 1H), 8.24 (br s. 1H), 8.19 (t, 1H, J=5.6), 7.97-7.92 (m, 1H), 7.88 (t, 1H, J=4), 7.73 (t, 1H, J=8), 7.63-7.50 (m, 5H), 7.38-7.30 (m, 2H), 7.25 (t, 1H), 6.96 (br s, 1H), 4.76 (d, 2H, J=4.4), 3.34-3.30 (m, 2H), 3.11 (s, 3H), 3.05 (t, 2H, J=5.6). LCMS Method T: retention time 1.61 min; [M+1]=527. HPLC Method A1: purity 99.4%, retention time=8.17 min.

Example 171

Ethyl 2-(5-(5-phenyl-4-(pyridin-2-ylmethylamino)quinazolin-2-yl)pyridine-3-sulfonamido)acetate

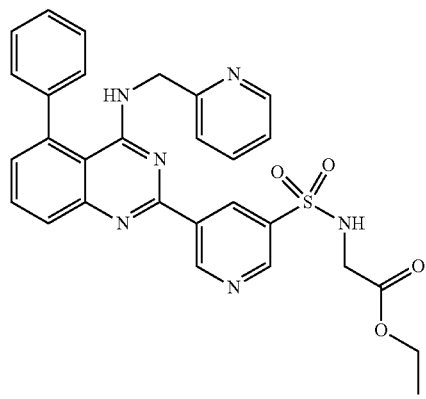 [SMILES: CCOC(=O)CNS(=O)(=O)c1cncc(-c2nc(NCc3ccccn3)c3c(-c4ccccc4)cccc3n2)c1]

Step 1. Preparation of ethyl 2-(5-bromopyridine-3-sulfonamido)acetate

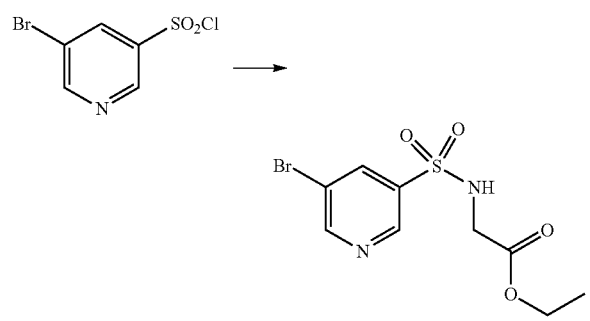

A solution of 5-bromopyridine-3-sulfonyl chloride (3.5 g, 14 mmol) (described in the synthesis of Example 170) and glycine ethylester (2.1 g, 20 mmol), diisopropyl ethyl amine (2.6 g, 20 mmol) in THF (70 mL) was stirred at room temperature for 16 h. The reaction mixture was partitioned between saturated aqueous sodium chloride and ethyl acetate. The organic solution was separated, dried and evaporated under reduced pressure. The residue was purified using flash column chromatography using ethyl acetate/hexanes as eluent to obtain ethyl 2-(5-bromopyridine-3-sulfonamido)acetate (600 mg, 14%). LCMS Method I: retention time 1.31 min; [M+1]=323,325.

Step 2. Example 171

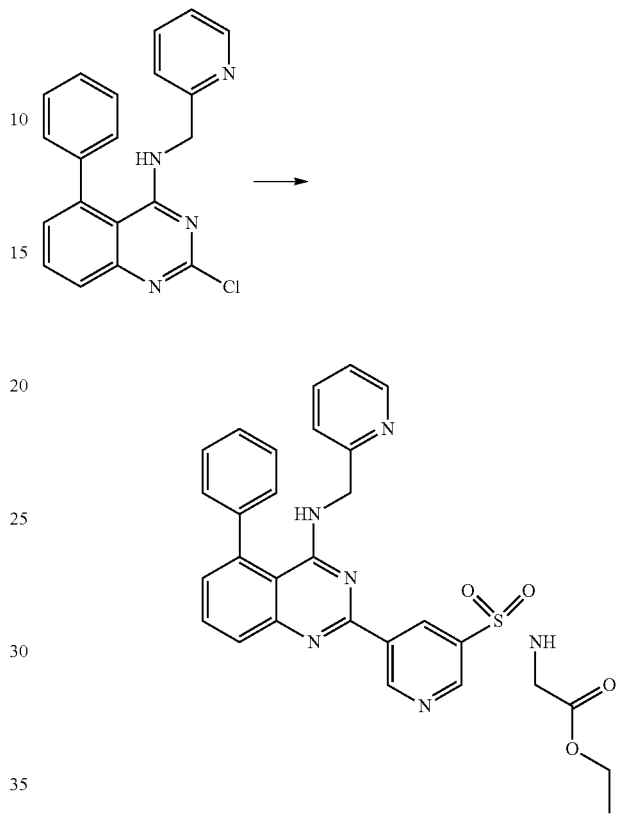

To a solution of methylethyl 2-(5-bromopyridine-3-sulfonamido)acetate (0.20 g, 0.62 mmol) in dioxane (10 mL) was added hexamethylditin (0.30 g, 0.92 mmol) and LiCl (26 mg, 0.62 mmol). The reaction mixture was degassed with nitrogen for 10 min and then charged with Tetrakis triphenyl phosphine palladium (68 mg, 0.061 mmol). The reaction mixture was stirred for 5 h at room temperature under nitrogen atmosphere. After this time, 2-chloro-5-phenyl-N-(pyridin-2-ylmethyl)quinazolin-4-amine (0.17 g, 0.50 mmol) in dioxane (2 mL) was added drop wise and the reaction mixture was heated to reflux for 18 h. The reaction mixture was quenched by the addition of water and extracted with ethyl acetate. The combined organic extracts were washed successively with water and brine, dried, filtered and concentrated under reduced pressure. The resulting residue was purified by flash column chromatography on silica gel using 5% methanol in dichloromethane to afford Example 171 (35 mg, 11%) as an off white solid. $^1$H NMR (400 MHz, DMSO-d$_6$) δ (ppm): 9.82 (s, 1H); 9.10 (s, 1H); 9.06 (s, 1H); 8.68 (t, 1H, J=6.0 Hz); 8.24 (d, 1H, J=4.8 Hz); 7.94 (dd, 1H, J=1.2, 8.0 Hz); 7.86 (t, 1H, 5.6 Hz); 7.73 (dt, 1H, J=1.6, 8.0 Hz); 7.62-7.50 (m, 5H); 7.33-7.36 (m, 2H); 7.26-7.23 (m, 1H); 6.96 (s, 1H); 4.76 (d, 2H, J=4 Hz); 3.93 (q, 2H, J=7.2 Hz); 3.89 (d, 2H, J=6.0 Hz); 1.04 (t, 3H, J=7.2 Hz). LCMS Method U: retention time 1.65 min; [M+1]=555.2; HPLC Method A4: purity 98.9%, retention time=9.15 min.

Example 172

2-Methoxy-5-(5-phenyl-4-(pyridin-2-ylmethyl-amino)quinazolin-2-yl)pyridine-3-sulfonamide

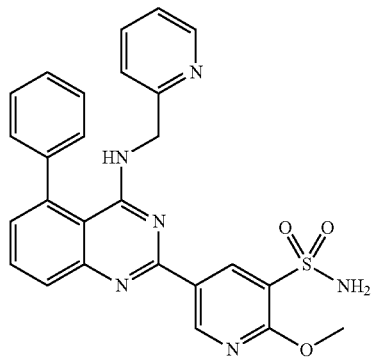

Step 1. Preparation of 2-methoxy-5-(4,4,5,5-tetramethyl-1,3,2-dioxaborolan-2-yl)pyridine-3-sulfonamide

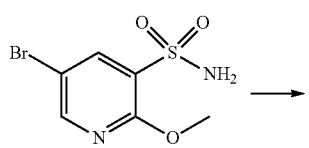

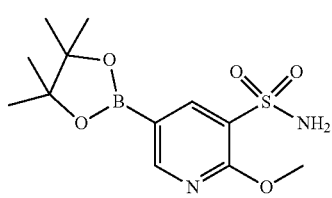

A mixture of 5-bromo-2-methoxypyridine-3-sulfonamide (described in the synthesis of Example 167: 0.15 g, 0.56 mmol), bis(pinacolato)diboron (0.17 g, 0.6 mmol) and potassium acetate (0.22 g, 2.2 mmol) in 1,4-dioxane (10 mL) was degassed with nitrogen for 15 min. After this time, (1,1'-bis(diphenylphosphino)ferrocene)palladium (II) chloride dichloromethane complex (0.036 g, 0.04 mmol) was added and the reaction mixture was again degassed for 10 min. with nitrogen. The reaction mixture was heated in the microwave at 120° C. for 45 min. The reaction mixture was filtered through celite and the filtrate was concentrated under reduced pressure to provide 2-methoxy-5-(4,4,5,5-tetramethyl-1,3,2-dioxaborolan-2-yl)pyridine-3-sulfonamide (0.15 g), which was used without further purification. LCMS Method T: retention time 0.44 min; [M+1]=233.0.

Step 2. Example 172

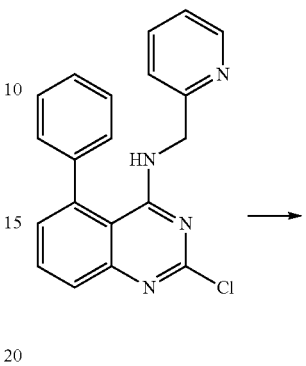

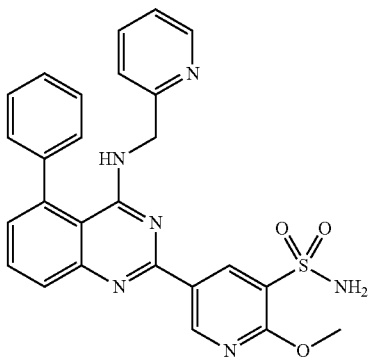 [SMILES: COc1ncc(-c2nc(NCc3ccccn3)c3c(-c4ccccc4)cccc3n2)cc1S(N)(=O)=O]

To a solution of 2-chloro-5-phenyl-N-(pyridin-2-ylmethyl)quinazolin-4-amine (0.19 g, 0.5 mmol) in 1,4-dioxane (5 mL) and H$_2$O (0.55 mL) under nitrogen was added 2-methoxy-5-(4,4,5,5-tetramethyl-1,3,2-dioxaborolan-2-yl)pyridine-3-sulfonamide (0.15 g, 0.60 mmol), and potassium carbonate (0.22 g, 1.6 mmol). The reaction mixture was degassed with nitrogen for 15 min. (1,1'-bis(diphenylphosphino)ferrocene)palladium (II) chloride dichloromethane complex (0.22 mg, 0.02 mmol) was added and the reaction mixture was again degassed for 10 min with nitrogen. The reaction mixture was stirred at 90° C. for 16 h, then allowed to cool to room temperature and quenched by the addition of water. The reaction mixture was transferred to a separation funnel and the aqueous layer extracted with ethyl acetate. The combined organic portions were washed with water and saturated NaCl, dried over Na$_2$SO$_4$, filtered and concentrated under reduced pressure. The concentrate was purified by column chromatography to afford Example 172 (0.060 g, 22% yield). $^1$H NMR (400 MHz, DMSO-d$_6$) δ (ppm): 12.78 (br s, 1H); 9.03 (d, 1H, J=2 Hz); 8.66 (s, 1H); 8.24 (d, 1H, J=4.8 Hz); 7.86-7.75 (m, 2H); 7.71 (t, 1H, J=7.6 Hz); 7.60-7.46 (m, 5H); 7.30-7.20 (m, 3H); 7.07 (br s, 2H); 6.80 (br s, 1H); 4.67 (d, 2H, J=4 Hz). LCMS Method U: retention time 1.32 min; [M+1]=485.0; HPLC Method A4: purity 97.1%, retention time=5.91 min.

Example 173

N-(2-amino-2-oxoethyl)-5-(5-phenyl-4-(pyridin-2-ylmethylamino)quinazolin-2-yl)nicotinamide

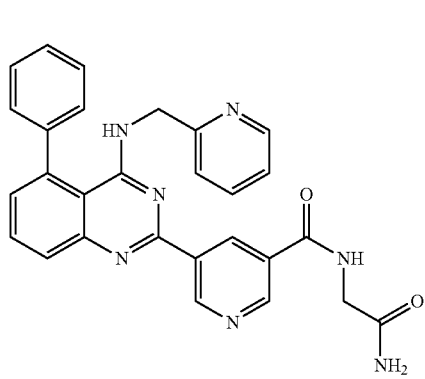 [SMILES: NC(=O)CNC(=O)c1cncc(-c2nc(NCc3ccccn3)c3c(-c4ccccc4)cccc3n2)c1]

Step 1. Preparation of ethyl 2-(5-bromonicotinamido)acetate

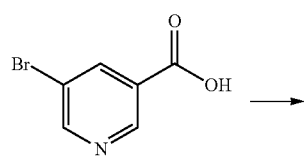

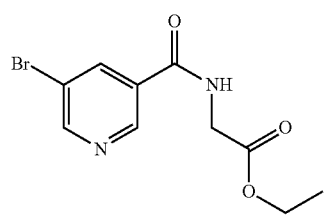

A solution of 5-bromonicotinic acid (4 g, 0.02 mol) in thionyl chloride (25 mL) was heated under reflux for 4 h. The excess thionyl chloride was removed under reduced pressure to provide 5-bromonicotinyl chloride which was used without further purification. To 5-bromonicotinyl chloride (3.5 g, 13.6 mmol) was added glycine ethylester (2.1 g, 20.3 mmol) and diisopropyl ethyl amine (2.6 g, 20.1 mmol) in THF (70 mL) and the reaction mixture stirred at RT for 16 h. The reaction mixture was diluted with EtOAc and washed with brine solution. The combined organic layers were dried over $Na_2SO_4$, filtered and concentrated under reduced pressure and the residue was purified by silica gel column chromatography using 25% EtOAc in hexane to provide ethyl 2-(5-bromonicotinamido)acetate 1.2 g (33%) as a brown solid. LCMS Method T: retention time 1.28 min; [M+1]=288.2

Step 2. Preparation of Example 173

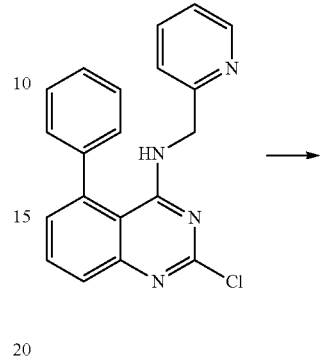

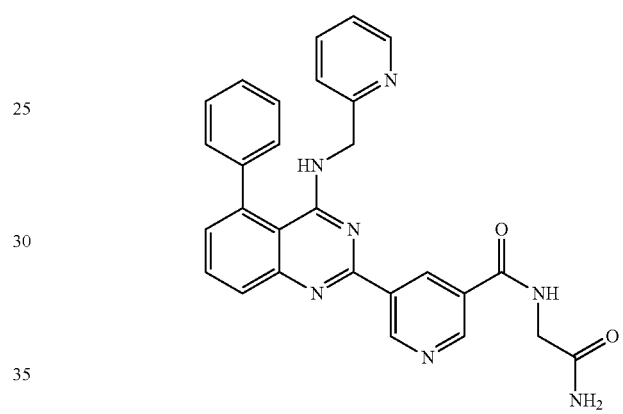

To a solution of N-(2-amino-2-oxoethyl)-5-bromonicotinamide (0.220 g, 0.852 mmol) in dioxane (4 mL), was added hexamethylditin (0.50 g, 1.53 mmol). The reaction mixture was degassed with nitrogen for 15 min. Pd(triphenylphosphine)$_4$ (0.098 g, 0.08 mmol) was added and the reaction mixture was stirred at RT for 6 h. 2-Chloro-5-phenyl-N-(pyridin-2-ylmethyl)quinazolin-4-amine (0.29 g 0.84 mmol) in 1,4-dioxane (3 mL) was added and the resulting mixture was stirred at 95° C. for 16 h, allowed to cool to room temperature and then quenched by the addition of water. The reaction mixture was transferred to a separation funnel and the aqueous layer extracted with ethyl acetate. The combined organic portions were washed with water and saturated NaCl, dried over $Na_2SO_4$, filtered and concentrated under reduced pressure. The concentrate was purified by silica gel column chromatography using dichloromethane/methanol mixture as the eluent to yield Example 173 (12 mg, 4%) as an off-white solid. $^1$H NMR (400 MHz, DMSO-d$_6$) δ (ppm): 9.76 9s, 1H); 9.21 (s, 1H); 9.16 (s, 1H); 9.14-9.11 (m, 1H); 8.24 (d, 1H, J=4.4 Hz); 7.94 (d, 1H, J=4.4 Hz); 7.86 (t, 1H, J=7.6 Hz): 7.73 (dd, 1H, J=7.6, 15.2 Hz); 7.68-7.47 (m, 5H); 7.39-7.30 (m, 2H); 7.24 (dd, 1H, J=5.2, 7.6 Hz); 7.10 (br s, 1H); 6.93 (br s, 1H); 4.77 (d, 2H, J=4 Hz); 3.90 (d, 2H, J=5.6 Hz). LCMS Method Y: retention time 1.70 min; [M+1]=490.2; HPLC Method A1: purity 99.5%, retention time=5.73 min.

Example 174

2-(5-(5-Phenyl-4-(pyridin-2-ylmethylamino)quinazolin-2-yl)pyridine-3-sulfonamido)acetamide

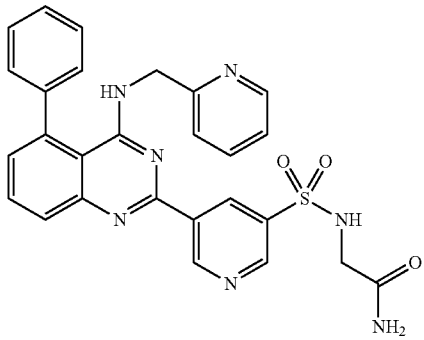 [SMILES: NC(=O)CNS(=O)(=O)c1cncc(-c2nc(NCc3ccccn3)c3c(-c4ccccc4)cccc3n2)c1]

Step 1. Preparation of ethyl 2-(5-bromopyridine-3-sulfonamido)acetate

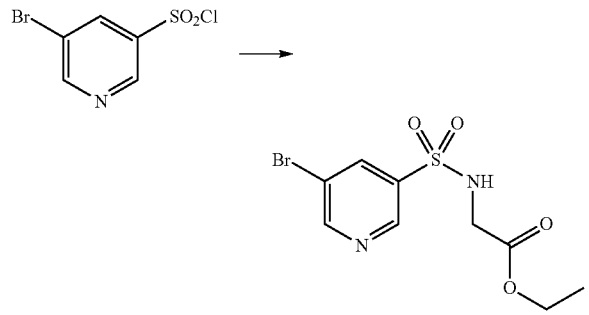

A solution of 5-bromopyridine-3-sulfonyl chloride (3.5 g, 14 mmol) and glycine ethylester (2.1 g, 20 mmol), diisopropyl ethyl amine (2.6 g, 20 mmol) in THF (70 mL) was stirred at room temperature for 16 h. The reaction mixture was partitioned between saturated aqueous sodium chloride and ethyl acetate. The organic solution was separated, dried and evaporated under reduced pressure. The residue was purified using flash silica gel column chromatography using ethyl acetate/hexanes to obtain ethyl 2-(5-bromopyridine-3-sulfonamido)acetate (600 mg, 14%); LCMS Method T: retention time 1.31 min; [M+1]=323,325.

Step 2. Preparation of 2-(5-bromopyridine-3-sulfonamido)acetamide

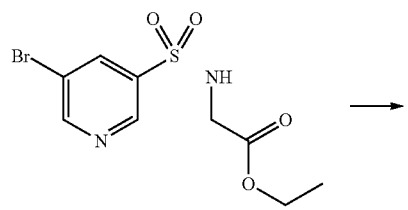

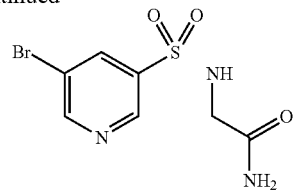

A solution of ethyl 2-(5-bromopyridine-3-sulfonamido)acetate (0.50 g, 1.7 mmol) and ammonia in methanol (2M, 10 mL) was heated to 60° C. in a sealed tube for 4 h. The cooled reaction mixture was concentrated under reduced pressure to yield 2-(5-bromopyridine-3-sulfonamido)acetamide (300 mg, 66%), which was used without further purification. $^1$H NMR (400 MHz, DMSO-$d_6$) δ (ppm): 8.96 (d, 1H, J=2.4 Hz); 8.90 (d, 1H, J=2 Hz); 8.39 (t, 1H, J=2 Hz), 8.21 (br s, 1H), 7.35 (br s, 1H), 7.07 (br s, 1H), 3.5 (s, 2H). LCMS Method D: retention time 0.945 min; [M+1]=294, 296.0.

Step 3. Example 174

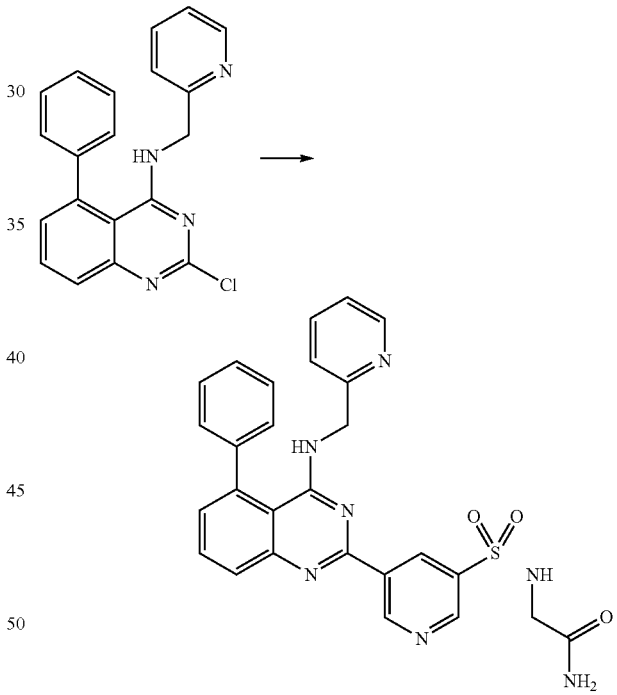

A stirred solution of 2-chloro-5-phenyl-N-(pyridin-2-ylmethyl)quinazolin-4-amine (0.20 g, 0.57 mmol) in dioxane (10 mL) was degassed for 10 min with argon and Pd(TRIPHENYLPHOSPHINE)$_4$ (0.06 g, 0.05 mmol) and hexamethylditin (0.34 g, 1.03 mmol) were added and the resulting reaction mixture was stirred at room temperature for 16 h. 2-(5-bromopyridine-3-sulfonamido)acetamide (0.25 g, 0.86 mmol) was added to the above reaction mixture and the solution heated at 100° C. for an additional 16 h. A precipitate formed and the solids were filtered from the reaction mixture and filtrate concentrated and purified by column chromatography to yield Example 174 (0.060 g, 20%) as a brown solid. $^1$H NMR (400 MHz, DMSO-$d_6$) δ (ppm): 9.80

(s, 1H), 9.11 (s, 1H), 9.05 (s, 1H), 8.25 (d, 1H, J=4.8 Hz), 7.95 (dd, 1H, J=1.2 Hz, J=8.4 Hz), 7.86 (t, 1H, J=8.8 Hz), 7.73 (t, 1H, J=4.4 Hz), 7.61-7.50 (m, 5H), 7.40-7.32 (m, 3H), 7.26-7.24 (m, 1H), 7.07 (br s, 1H), 6.97 (br t, 1H, J=3.6 Hz), 4.76 (d, 2H, J=4 Hz), 3.56 (s, 2H). LCMS Method Y: retention time 1.77 min; [M+1]=526.0; HPLC Method A1: purity 99.2%, retention time=6.709 min.

Example 175

2-Methyl-6-(5-phenyl-4-(yridine-2-ylmethylamino)quinazolin-2-yl)imidazo[1,2-a]pyridine-8-sulfonamide

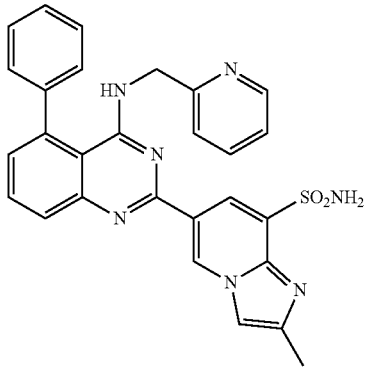 [SMILES: Cc1cn2cc(-c3nc(NCc4ccccn4)c4c(-c5ccccc5)cccc4n3)cc(S(N)(=O)=O)c2n1]

Step 1. Preparation of 2-amino-5-bromopyridine-3-sulfonyl

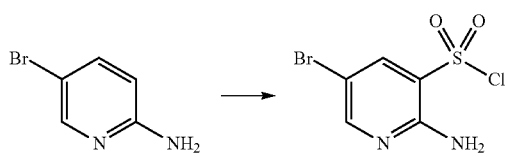 [SMILES: Nc1ccc(Br)cn1 ; Nc1ncc(Br)cc1S(=O)(=O)Cl]

To a cooled (0° C.) solution of chlorosulfonic acid (58 mL) under vigorous stirring was added 5-bromo-2-pyridinamine (86.7 mmol) portion wise. The reaction mixture was then heated at reflux for 3 h. Upon cooling to room temperature, the reaction mixture was poured over ice (100 g) with vigorous stirring. The resulting yellow precipitate was collected by suction filtration, washed with cold water and petroleum ether to provide 2-amino-5-bromopyridine-3-sulfonyl chloride (18 g, 77% yield) as an orange-yellow solid.

Step 2. Preparation of 2-amino-5-bromo-N-tert-butylpyridine-3-sulfonamide

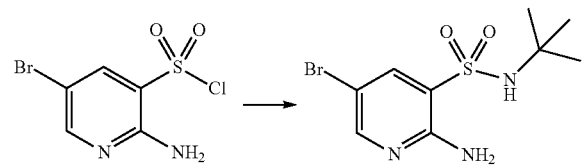 [SMILES: Nc1ncc(Br)cc1S(=O)(=O)Cl ; CC(C)(C)NS(=O)(=O)c1cc(Br)cnc1N]

2-amino-5-bromopyridine-3-sulfonyl chloride (15 g, 55 mmol) was dissolved in THF (125 mL) and at 0° C. t-butylamine (6.5 g, 111 mmol) was added and the reaction mixture was stirred at RT for 2 h. The reaction mixture was concentrated under reduced pressure to yield 2-amino-5-bromo-N-tert-butylpyridine-3-sulfonamide (8.4 g, 49%), which was used without further purification. LCMS Method Y: retention time 1.70 min, [M−1]=306.0.

Step 3. Preparation of 6-bromo-N-tert-butyl-2-methylimidazo[1,2-a]pyridine-8-sulfonamide

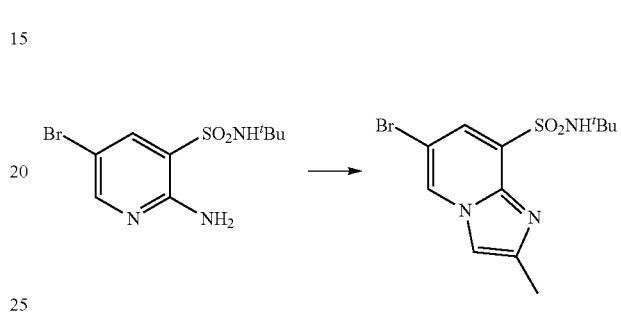

To a solution of 2-amino-5-bromo-N-tert-butylpyridine-3-sulfonamide (3.0 g, 9.7 mmol) in ethanol (6 mL) was added chloroacetone (3.0 mL, 48 mmol) and the reaction mixture was stirred at 80° C. for 48 h. The solvents were evaporated under reduced pressure and the residue was purified by flash silica gel column chromatography (5% methanol in DCM) to yield 6-bromo-N-tert-butyl-2-methylimidazo[1,2-a]pyridine-8-sulfonamide (2.2 g, 66%), which was used without further purification. LCMS Method T: retention time 1.33 min; [M+1]=346.64.

Step 4. Preparation of 6-bromo-2-methylimidazo[1,2-a]pyridine-8-sulfonamide

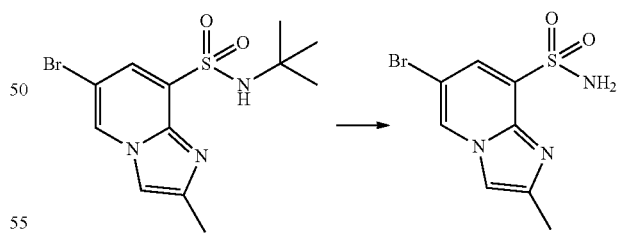

6-bromo-N-tert-butyl-2-methylimidazo[1,2-a]pyridine-8-sulfonamide (1.0 g, 2.8 mmol) was stirred in TFA (6 mL) for 16 h. The TFA was removed in vacuo and a saturated solution of NaHCO₃ was added. The aqueous layer was extracted with DCM, the combined organic portions dried, filtered and concentrated to yield 6-bromo-2-methylimidazo[1,2-a]pyridine-8-sulfonamide (0.45 g, 54%), which was used without further purification. LCMS Method Y: retention time 1.44 min; [M+1]=292.16.

Step 5. Example 175

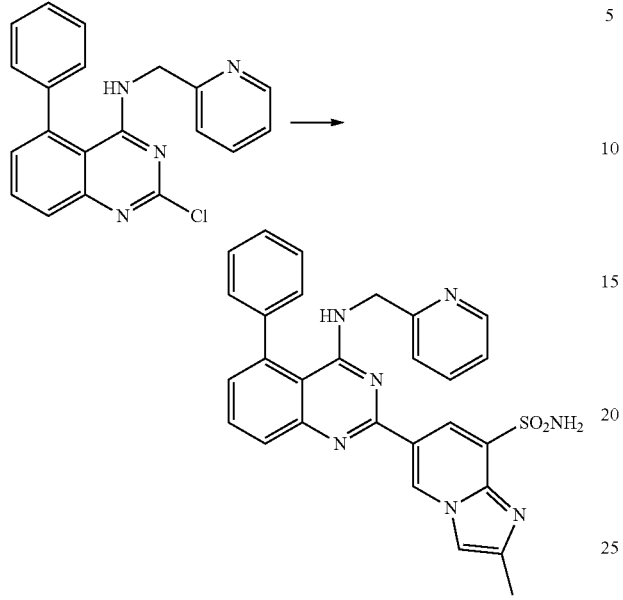

A stirred solution of 6-bromo-2-methylimidazo[1,2-a]pyridine-8-sulfonamide (0.20 g, 0.68 mmol) in dioxane (10 mL) was degassed for 10 min with argon and Pd(PPh$_3$)$_4$ (0.2 g, 0.16 mmol) and hexamethylditin (0.25 mL, 1.2 mmol) were added and the reaction mixture stirred at room temperature for 16 h. 2-Chloro-5-phenyl-N-(pyridin-2-ylmethyl)quinazolin-4-amine (0.58 g, 1.68 mmol) was added and the reaction mixture heated at 100° C. for an additional 16 h. A precipitate formed and the solids were filtered from the reaction mixture and the filtrate was concentrated and purified by silica gel column chromatography using dichloromethane/methanol mixture as the eluent to get pure Example 175 (30 mg, 10%). $^1$H NMR (400 MHz, DMSO-d$_6$) δ (ppm): 9.73 (s, 1H); 8.77 (d, 1H, J=1.2 Hz); 8.28 (d, 1H, J=4.4 Hz); 8.09 (s, 1H); 7.90 (d, 1H, J=8.4 Hz); 7.84 (t, 1H, J=6.8 Hz); 7.75 (dt, 1H, J=6 Hz, 7.6 Hz); 7.61-7.50 (m, 6H); 7.43 (s, 1H); 7.36-7.25 (m, 3H); 6.85 (br s, 1H0; 4.78 (d, 2H, J=4 Hz); 2.46 (s, 3H). LCMS Method X: retention time 1.59 min; [M+1]=522.2; HPLC Method A1: purity 98.3%, retention time=6.63 min.

Example 176

(5-(5-Phenyl-4-(pyridin-2-ylmethylamino)quinazolin-2-yl)pyridin-3-yl)methanol

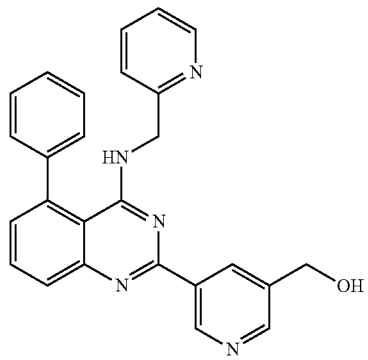 [SMILES: OCc1cncc(-c2nc(NCc3ccccn3)c3c(-c4ccccc4)cccc3n2)c1]

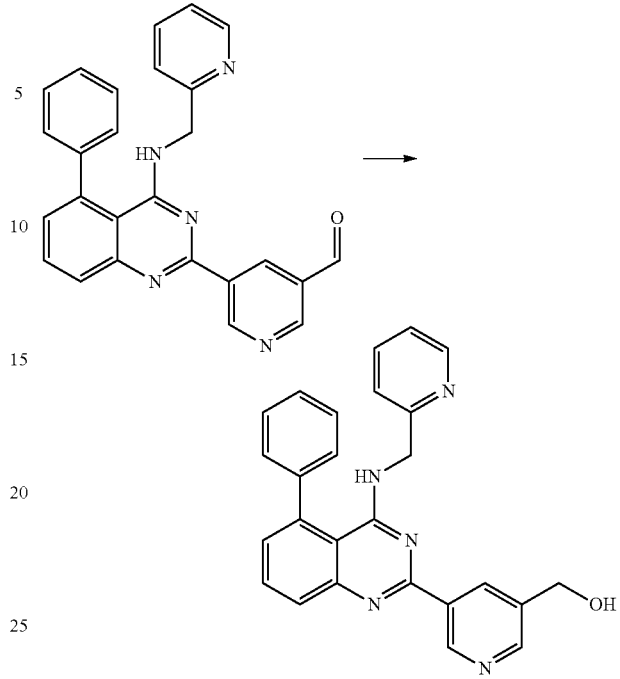

To a solution of 5-(5-phenyl-4-(pyridin-2-ylmethylamino)quinazolin-2-yl) nicotinaldehyde (described in Example 191, 1.0 g, 2.4 mmol) in ethanol (15 mL) was added NaBH$_4$ (0.28 g, 7.2 mmol). The reaction mixture was stirred at RT. A saturated solution of ammonium chloride was added and the aqueous layer was extracted with ethyl acetate. The organic layer was separated, dried, filtered and concentrated under reduced pressure. The resulting residue was purified by silica gel column chromatography using a dichloromethane/methanol mixture as the eluent to provide Example 176 (0.71 g, 71%). $^1$H NMR (400 MHz, DMSO-d$_6$) δ (ppm): 9.51 (s, 1H), 8.72 (s, 1H), 8.63 (s, 1H), 8.23 (d, 1H, J=4.8 Hz), 7.88 (dd, 1H, J=7.6 Hz, 8.4 Hz), 7.85-7.80 (m, 1H), 7.73 (dt, 1H, J=1.2 Hz, 7.6 Hz), 7.61-7.48 (m, 5H), 7.33 (d, 2H, J=19.2 Hz), 7.27 (d, 1H, J=14 Hz), 7.23 (dt, 1H, J=1.6, 7.2 Hz), 6.87 (t, 1H, J=4.0 Hz, 1H), 5.47 (t, 1H, J=5.6), 4.75 (d, 2H, J-4 Hz), 4.67 (d, 2H, J=5.6 Hz). LCMS Method U: retention time 1.46 min; [M+1]=420.2; HPLC Method A4: purity 99.5%, retention time=5.77 min.

Example 177

2-(5-(5-Phenyl-4-(pyridin-2-ylmethylamino)quinazolin-2-yl)pyridin-3-yl)propane-1,3-diol

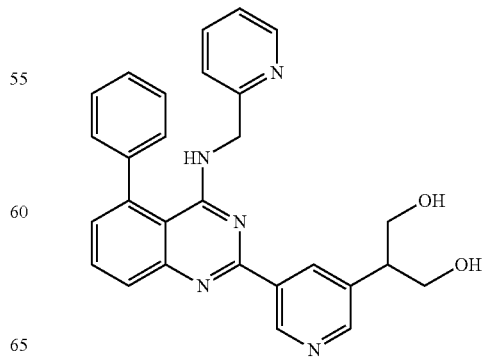

Step 1. Preparation of 2-(5-bromopyridin-3-yl)prop-2-en-1-ol

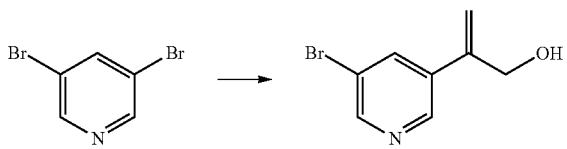

A microwave vial was charged with 3,5-dibromo pyridine (5.00 g, 21.1 mmol), Pd(OAc)$_2$, (0.185 g, 0.820 mmol), 1,3-Bis(diphenylphosphino)propane (0.7 g 1.7 mmol), and 1-butyl-3-methylimidazolium tetrafluoroborate (25 mL) under nitrogen at room temperature. The reaction mixture was degassed three times and allyl alcohol (2.85 g, 49.1 mmol) and triethylamine (4.7 ml, 3.6 mmol) were added. The reaction mixture was heated in microwave reactor at 125° C. for 2 h. After cooling to room temperature, aqueous HCl (20 mL, 10%) was added and the mixture stirred for 1 h. The reaction mixture was treated with saturated Na$_2$CO$_3$ (20 mL) and the aqueous portion extracted with CH$_2$Cl$_2$. The combined organic layers were washed with water and brine, dried with Na$_2$SO$_4$ and evaporated under reduced pressure. The resulting residue was purified by flash silica gel chromatography (SiO$_2$, hexane/EtOAc=8/2) to yield 2-(5-bromopyridin-3-yl)prop-2-en-1-ol (1.6 g, 36%). $^1$H NMR (400 MHz, DMSO-d$_6$) δ (ppm): 8.69 (d, 1H, J=2 Hz), 8.62 (d, 1H, J=2.4 Hz), 8.13 (s, 1H), 5.66 (s, 1H), 5.45 (s, 1H), 5.15 (t, 1H, J=5.2 Hz), 4.35 (d, 2H, J=5.2 Hz). LCMS Method T: retention time 0.96 min; [M+1]=216.

Step 2. Preparation of 2-(5-bromopyridin-3-yl)propane-1,3-diol

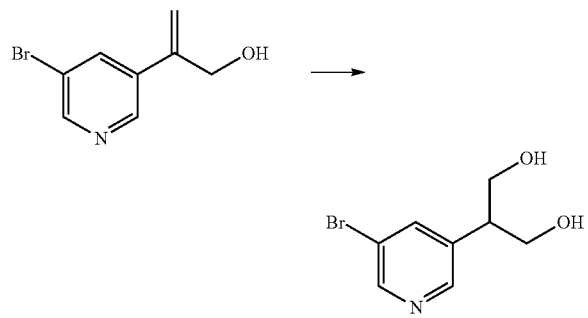

To a stirred solution of 2-(5-bromopyridin-3-yl)prop-2-en-1-ol (0.600 g, 2.79 mmol) in tetrahydrofuran (5 mL) at 0° C. under nitrogen was added borane-methyl sulfide complex (0.85 g, 11 mmol). The reaction mixture was heated to 25° C. and stirred for 5 h. The reaction mixture was cooled to 0° C. and 1.0 N sodium hydroxide (0.8 mL) was added drop wise followed by the addition of hydrogen peroxide (1.0 mL, 35 wt % solution in water). The reaction mixture was stirred at 0° C. for 2 h then partitioned between ethyl acetate and water. The aqueous layer was extracted with ethyl acetate. The organic portions were combined, washed with water, aqueous sodium sulfite and brine, dried with Na$_2$SO$_4$, filtered, and concentrated under reduced pressure. 2-(5-Bromopyridin-3-yl)propane-1,3-diol (0.29 g, 44.7%) was isolated by silica gel column chromatography using 50% EtOAc in hexanes as a yellow oil. $^1$H NMR (400 MHz, DMSO-d$_6$) δ (ppm): 8.53 (d, 1H, J=2 Hz), 8.43 (d, 1H, J=4.8 Hz), 4.92 (s, 1H), 4.69 (t, 1H, J=4.4 Hz), 3.71-3.64 (m, 2H), 3.62-3.58 (m, 2H), 2.87 (t, J=6.4 Hz). LCMS Method W: retention time 0.80 min; [M+1]=232.

Step 3. Preparation of 3-bromo-5-(2,2-dimethyl-1,3-dioxan-5-yl)pyridine

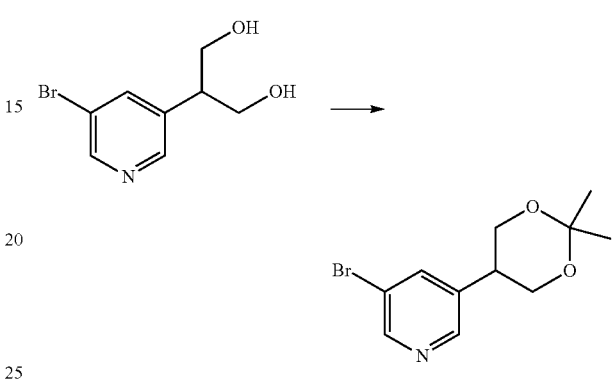

To a solution of 2-(5-bromopyridin-3-yl)propane-1,3-diol (0.12 g, 0.51 mmol) in DCM was added 2,2-dimethoxypropane (0.107 g, 1.03 mmol) and a catalytic amount of p-TSA. The mixture was stirred at room temperature for 3 h. The reaction mixture was quenched by the addition of sat. NaHCO$_3$ solution and the organic layer washed successively with water and brine. The organic layer was concentrated to provide the 3-bromo-5-(2,2-dimethyl-1,3-dioxan-5-yl)pyridine (0.1 g, 71.4%), which was used without further purification. $^1$H NMR (400 MHz, DMSO-d$_6$) δ (ppm): 8.53 (m, 2H), 8.17 (t, 2H, J=2 Hz), 4.00-3.92 (m, 4H), 3.07-3.02 (m, 1H), 1.47 (s, 3H), 1.38 (s, 3H).

Step 4. Preparation of 3-(2,2-dimethyl-1,3-dioxan-5-yl)-5-(4,4,5,5-tetramethyl-1,3,2-dioxaborolan-2-yl)pyridine

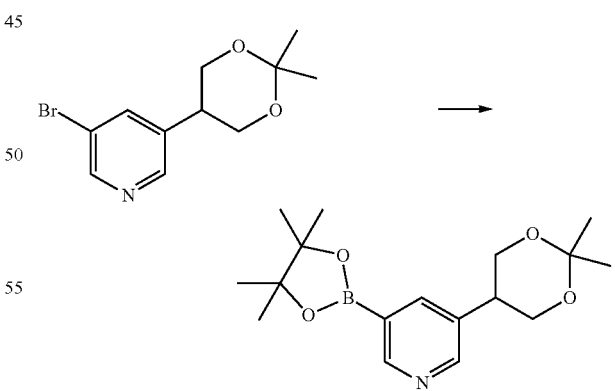

A mixture of 3-bromo-5-(2,2-dimethyl-1,3-dioxan-5-yl) pyridine (0.10 g, 0.37 mmol), bis(pinacolato)diboron (0.112 g, 0.44 mmol) and potassium acetate (0.145 g, 1.40 mmol) in 1,4-dioxane (8 mL) was degassed with nitrogen for 15 min. (1,1'-Bis(diphenylphosphino)ferrocene)palladium (II) chloride dichloromethane complex (24 mg, 0.03 mmol) was added and the mixture was again degassed for 10 min. with nitrogen. The reaction mixture was heated in the microwave reactor at 120° C. for 45 min. After this time, the reaction mixture was filtered through celite and the filtrate was concentrated under reduced pressure to provide crude 3-(2,2-dimethyl-1,3-dioxan-5-yl)-5-(4,4,5,5-tetramethyl-1,3,2-dioxaborolan-2-yl)pyridine (110 mg) as a brown solid, which was used without further purification. LCMS Method W: retention time 1.46 min; [M+1]=320.2.

Step 5. Preparation of 2-(5-(2,2-dimethyl-1,3-dioxan-5-yl)pyridin-3-yl)-5-phenyl-N-(pyridin-2-ylmethyl)quinazolin-4-amine

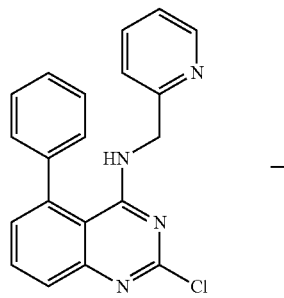

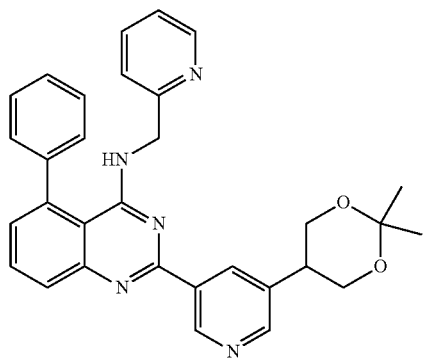

To a solution of 2-chloro-5-phenyl-N-(pyridin-2-ylmethyl) quinazolin-4-amine (80 mg, 0.23 mmol) in 1,4-dioxane (6 mL) and H₂O (0.5 mL) under nitrogen was added 3-(2,2-dimethyl-1,3-dioxan-5-yl)-5-(4,4,5,5-tetramethyl-1,3,2-dioxaborolan-2-yl)pyridine (110 mg, 0.35 mmol), and potassium carbonate (96 mg, 7.0 mmol). The mixture was degassed with nitrogen for 15 min. (1,1'-Bis(diphenylphosphino)ferrocene)palladium (II) chloride dichloromethane complex (12 mg, 0.015 mmol) was added and the reaction mixture was again degassed for 10 min with nitrogen. The reaction mixture was stirred at 90° C. for 16 h, then allowed to cool to room temperature and quenched by the addition of water. The reaction mixture was extracted with ethyl acetate. The combined organic portions were washed with water and saturated NaCl, dried over Na₂SO₄, filtered and concentrated under reduced pressure. The resulting residue was purified by column chromatography using 20% EtOAc in hexanes to provide 2-(5-(2,2-dimethyl-1,3-dioxan-5-yl)pyridin-3-yl)-5-phenyl-N-(pyridin-2-ylmethyl)quinazolin-4-amine (45 mg, 39%). LCMS Method T: retention time 1.75 min; [M+1]=504.2.

Step 6. Example 177

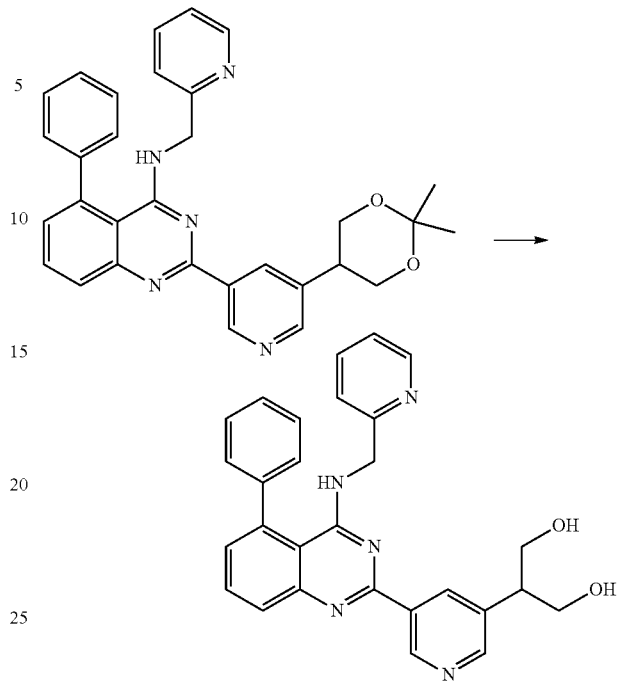

To a solution 2-(5-(2,2-dimethyl-1,3-dioxan-5-yl)pyridin-3-yl)-5-phenyl-N-(pyridin-2-ylmethyl)quinazolin-4-amine (45 mg, 0.83 mmol) in methanol (5 mL) was added pTSA (30 mg, 0.17 mmol) and the mixture was stirred for 2 h. The reaction was quenched by the addition of sat. Na₂CO₃ solution and the volatile solvents removed under reduced pressure. The residue was dissolved in ethyl acetate then washed with water and brine. The organic layer was dried, concentrated and purified by filter column 80% EtOAc in Hexanes to provide 2-(5-(5-phenyl-4-(pyridin-2-ylmethylamino)quinazolin-2-yl)pyridin-3-yl) propane-1,3-diol (18 mg, 44%). ¹H NMR (400 MHz, DMSO-d₆) δ (ppm): 9.74 (s, 1H), 9.60 (d, 1H, J=2 Hz), 9.56 (d, 1H, J=2 Hz), 8.26 (d, 1H, J=4.8 Hz), 7.90 (dd, 1H, J=1.2, 9.2 Hz), 7.83 (t, 1H, J=7.2 Hz), 7.72 (dd, 1H, J=1.8, 7.6 Hz), 7.61-7.50 (m, 5H), 7.38-7.30 (m, 2H), 7.26 (dt, 1H, J=1.2, 8 Hz), 6.80 (br s, 1H), 4.74 (d, 1H, J=4.4 Hz), 4.70 (t, 1H, J=5.2 Hz), 3.85-3.77 (m, 2H), 3.76-3.68 (m, 2H), 3.30-2.95 (m, 1H). LCMS Method T: retention time 1.40 min; [M+1]=464.2; HPLC Method A4: purity 99.4%, retention time=5.48 min.

Example 178

6-(5-phenyl-4-(pyridin-2-ylmethylamino)quinazolin-2-yl)pyrazine-2-sulfonamide

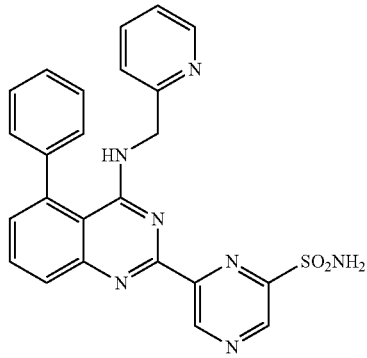 [SMILES: NS(=O)(=O)c1cncc(-c2nc(NCc3ccccn3)c3c(-c4ccccc4)cccc3n2)n1]

Step 1. Preparation of 2-(benzylthio)-6-chloropyrazine

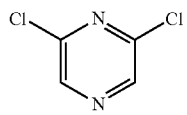  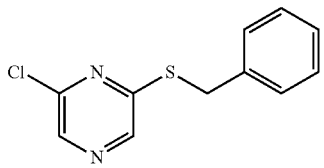

To a stirred solution of 2,6-dichloropyrazine (4.50 g, 30.2 mmol) and potassium carbonate (3.75 g, 27.1 mmol) in DMF (50 mL) was added benzyl mercaptane (3.37 g, 27.1 mmol) in DMF (20 mL). The resulting mixture was stirred for 16 h at room temperature. Water (200 mL) was added to the reaction mixture. The aqueous layer was extracted with ethyl acetate. The organic portions were combined, washed successively with water, aqueous sodium sulfite and brine, dried over anhydrous $Na_2SO_4$, filtered, and concentrated under reduced pressure to afford 2-(benzylthio)-6-chloropyrazine (6.5 g, 97%) as a yellow oil, which was used without further purification. LCMS Method E: retention time 2.058 min; [M+1]=236.6.

Step 2. Preparation of 6-chloropyrazine-2-sulfonyl chloride

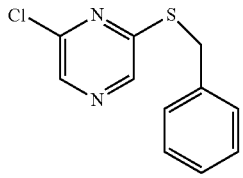  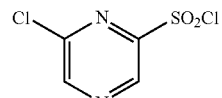

2-(Benzylthio)-6-chloropyrazine (5.00 g, 21.2 mmol) was dissolved in carbon tetra chloride and water mixture (200 ml/50 ml). The reaction solution was purged with chlorine gas at 0° C. for 30 min and diluted with DCM. The organic layer was dried, filtered and concentrated under reduced pressure to yield 6-chloropyrazine-2-sulfonyl chloride as a brown oil.

Step 3. Preparation of 6-chloropyrazine-2-sulfonamide

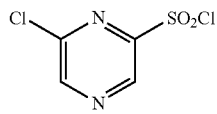  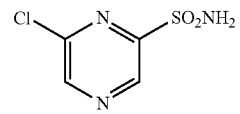

The residue of 6-chloropyrazine-2-sulfonyl chloride from step 1 above was dissolved in THF and purged with ammonia gas at −20° C. for 15 min. The resulting mixture was stirred for 16 h at 50° C. in a sealed tube. The organic solvent was removed under reduced pressure and the residue was purified by column chromatography on silica gel using 2.5% methanol in dichloromethane to afford 6-chloropyrazine-2-sulfonamide (1.6 g, 34%) as white solid. LCMS Method W: retention time 0.638 min; [M+1]=194.0.

Step 4. Example 178

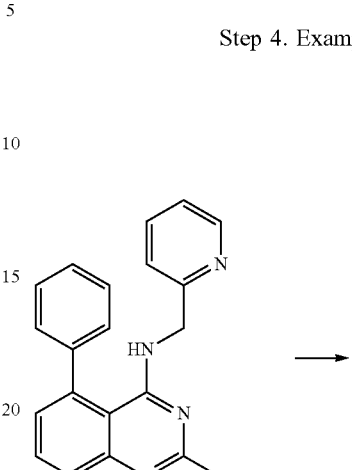

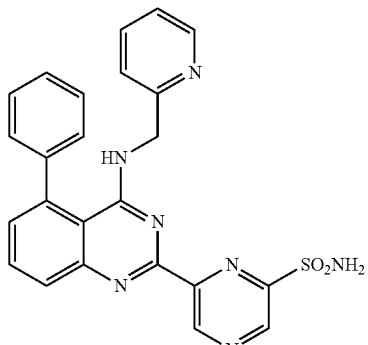

To a stirred solution of 6-chloropyrazine-2-sulfonamide (0.3 g, 1.56 mmol) in dioxane (10 mL) was degassed for 10 min with argon. $Pd(PPh_3)_4$ (0.17 g, 0.156 mmol) and hexamethylditin (0.48 mL, 2.3 mmol) were added and the mixture was stirred at room temperature for 16 h. 2-Chloro-5-phenyl-N-(pyridin-2-ylmethyl)quinazolin-4-amine (0.43 g, 1.24 mmol) and LiCl (0.16 g, 4.68 mmol) in dioxane (2 mL) were added to the reaction mixture through cannula and heated at 100° C. for an additional 16 h. The reaction mixture was concentrated under reduced pressure and water was added. The aqueous layer was extracted with ethyl acetate, and the organic extracts washed with brine, dried, filtered and concentrated under reduced pressure. The residue was purified by column chromatography using 20% acetone in hexanes then further purified by prep HPLC (method H, Column: Waters SunFire 19×100 mm 5 um C18 and TFA/water, acetonitrile as the eluent) to provide 6-(5-phenyl-4-(pyridin-2-ylmethylamino)quinazolin-2-yl)pyrazine-2-sulfonamide (35 mg, 9%). $^1$H NMR (400 MHz, DMSO-$d_6$) δ (ppm): 9.84 (s, 1H),) 9.24 (s, 1H), 8.24 (d, 1H, J=4.8 Hz), 7.98-7.88 (m, 4H), 7.73 (t, 1H, J=7.6 Hz), 7.24 (t, 1H, J=5.6 Hz), 7.00 (br s, 1H), 4.77 (d, 2H, J=3.6 Hz). LCMS Method W: retention time 1.8 min; [M+1]=469.0; HPLC Method A1: purity 98.1%, retention time=6.74 min.

Example 179

2-(5-(3,5-Dimethylisoxazol-4-yl)pyridin-3-yl)-5-phenyl-N-(pyridin-2-ylmethyl)quinazolin-4-amine

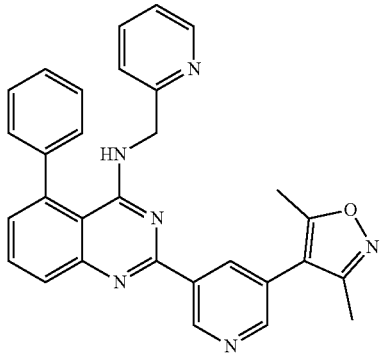 [SMILES: Cc1noc(C)c1-c1cncc(-c2nc(NCc3ccccn3)c3c(-c4ccccc4)cccc3n2)c1]

Step 1. Preparation of 4-(5-bromopyridin-3-yl)-3,5-dimethylisoxazole

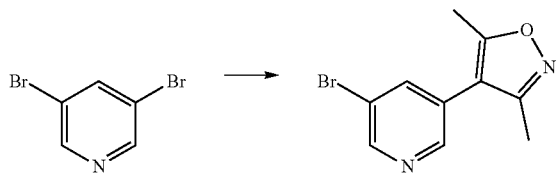

To a solution of 3,5-dibromopyridine (0.20 g, 0.85 mmol) in 1,4-dioxane (8 mL) and H₂O (0.55 mL) under nitrogen was added 3,5-dimethyl-4-(4,4,5,5-tetramethyl-1,3,2-dioxaborolan-2-yl)isoxazole (0.13 g, 0.93 mmol), and potassium carbonate (0.35 g, 2.5 mmol). The reaction mixture was degassed with nitrogen for 15 min. (1,1'-Bis(diphenylphosphino)ferrocene)palladium (II) chloride dichloromethane complex (62 mg, 0.08 mmol) was added and the reaction mixture was again degassed for 10 min with nitrogen. The reaction mixture was stirred at 95° C. for 16 h, then allowed to cool to room temperature and quenched by the addition of water. The reaction mixture was transferred to a separation funnel and the aqueous layer extracted with ethyl acetate. The combined organic portions were washed with water and saturated NaCl, dried over Na₂SO₄, filtered and concentrated under reduced pressure. The residue was purified by column chromatography to provide 4-(5-bromopyridin-3-yl)-3,5-dimethylisoxazole (0.15 g, 71%) as a white solid. LCMS Method T: retention time 1.52 min, [M+1]=253.

Step 2. Preparation of 3,5-dimethyl-4-(5-(4,4,5,5-tetramethyl-1,3,2-dioxaborolan-2-yl)pyridin-3-yl)isoxazole

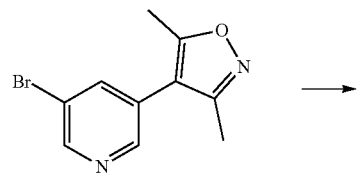

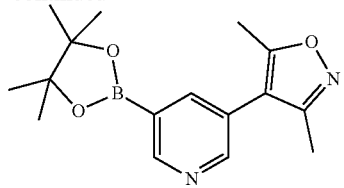

A mixture of 4-(5-bromopyridin-3-yl)-3,5-dimethylisoxazole (0.16 g, 0.63 mmol), bis(pinacolato)diboron (0.24 g, 0.95 mmol) and potassium acetate (0.25 g, 2.4 mmol) in 1,4-dioxane (10 mL) was degassed with nitrogen for 15 min. (1,1'-Bis(diphenylphosphino)ferrocene)palladium (II) chloride dichloromethane complex (0.036 g, 0.05 mmol) was added and the mixture was again degassed for 10 min. with nitrogen. The reaction mixture was heated in the microwave reactor at 120° C. for 45 min. The reaction mixture was filtered through celite and the filtrate was concentrated under reduced pressure to provide 3,5-dimethyl-4-(5-(4,4,5,5-tetramethyl-1,3,2-dioxaborolan-2-yl)pyridin-3-yl)isoxazole (0.17 g), which was used without further purification. LCMS Method T: retention time 0.54 min, [M+1]=219.2.

Step 3. Example 179

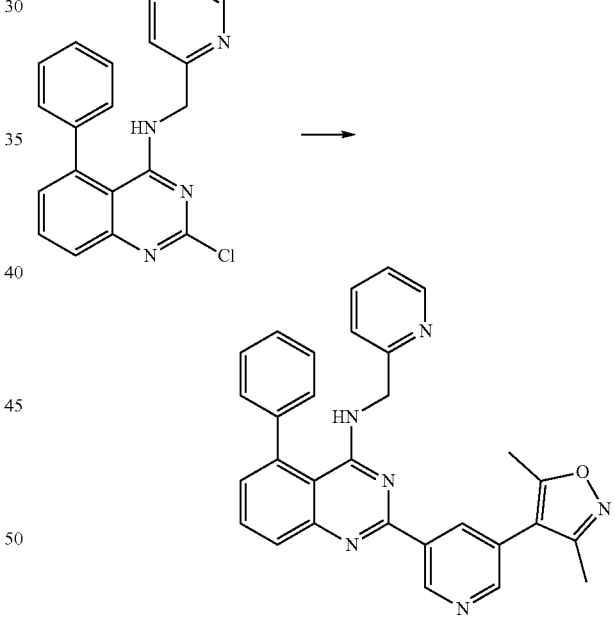

To a solution of 2-chloro-5-phenyl-N-(pyridin-2-ylmethyl)quinazolin-4-amine (0.15 g, 0.43 mmol) in 1,4-dioxane (5 mL) and H₂O (0.55 mL) under nitrogen was added 3,5-Dimethyl-4-(5-(4,4,5,5-tetramethyl-1,3,2-dioxaborolan-2-yl)pyridin-3-yl)isoxazole (0.16 g, 0.73 mmol), and potassium carbonate (0.24 g, 1.7 mmol). The reaction mixture was degassed with nitrogen for 15 min. (1,1'-Bis (diphenylphosphino) ferrocene) palladium (II) chloride dichloromethane complex (0.043 mg, 0.05 mmol) was added and the reaction mixture was again degassed for 10 min with nitrogen. The reaction mixture was stirred at 95° C. for 16 h, then allowed to cool to room temperature and quenched with water. The reaction mixture was transferred to a separation funnel and the aqueous layer extracted with ethyl acetate. The combined organic portions were washed with water and saturated NaCl, dried over $Na_2SO_4$, filtered and concentrated under reduced pressure. The residue was purified by silica gel column chromatography using dichloromethane/methanol mixture as the eluent to provide Example 179 (0.08 g, 38.2%) as an off white solid. $^1$H NMR (400 MHz, DMSO-$d_6$) δ (ppm): 9.72 (d, 1H, J=4 Hz), 8.70 (s, 1H), 8.60 (d, 1H, J=2 Hz), 8.26 (d, 1H, J=2 Hz), 7.94 (br s, 1H), 7.74 (t, 1H, J=7.2 Hz), 7.57 (dt, 1H, J=2 Hz, 7.6 Hz), 7.52-7.48 (br s, 5H), 7.30-7.27 (m, 1H), 7.18-7.10 (m, 2H), 6.70 (br s, 1H), 4.76 (d, 2H, J=4.0 Hz), 2.48 (s, 3H), 2.33 (s, 3H). LCMS Method T: retention time 1.82 min; [M+1]=485.2. HPLC Method A1: purity 98.9%, retention time=7.67 min.

Example 180

6-(5-Phenyl-4-(pyridin-2-ylmethylamino)quinazolin-2-yl)-1H-imidazo[4,5-b]pyridin-2(3H)-one

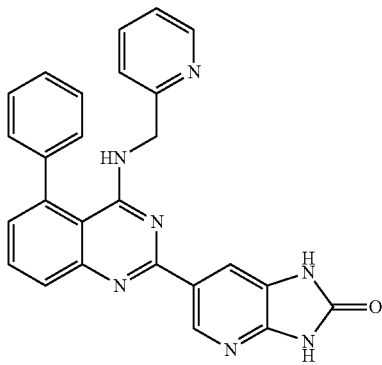 [SMILES: O=c1[nH]c2cc(-c3nc(NCc4ccccn4)c4c(-c5ccccc5)cccc4n3)cnc2[nH]1]

Step 1. Preparation of 6-bromo-1H-imidazo[4,5-b]pyridin-2(3H)-one

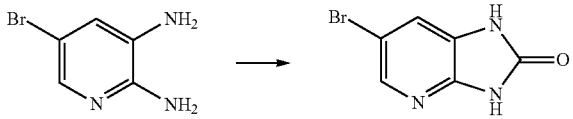 [SMILES: Nc1cc(Br)cnc1N ; O=c1[nH]c2cc(Br)cnc2[nH]1]

A mixture of 5-bromopyridine-2,3-diamine (2 g, 10.6 mmol) and urea (2.5 g, 41.6 mmol) was dissolved in DMF and heated to 100° C. for 16 h. The reaction mixture was diluted with water and extracted with ethyl acetate. The organic layer was dried over $Na_2SO_4$ then concentrated to provide 6-bromo-1H-imidazo[4,5-b]pyridin-2(3H)-one (0.80 g, 36%) as an off white solid which was used without further purification. LCMS Method W: retention time 0.98 min; [M+2]=212, 214.0.

Step 2. Preparation of 6-(4,4,5,5-tetramethyl-1,3,2-dioxaborolan-2-yl)-1H-imidazo[4,5-b]pyridin-2(3H)-one

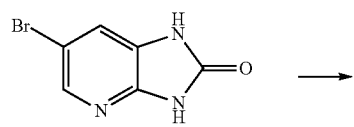

A mixture of 6-bromo-1H-imidazo[4,5-b]pyridin-2(3H)-one (0.500 g, 2.35 mmol), bis(pinacolato)diboron (0.895 g, 3.53 mmol) and potassium acetate (0.924 g, 9.42 mmol) in 1,4-dioxane (10 mL) was degassed with nitrogen for 15 min. (1,1'-Bis(diphenylphosphino)ferrocene)palladium (II) chloride dichloromethane complex (0.192 g, 0.23 mmol) was added and the reaction mixture was again degassed for 10 min. with nitrogen. The reaction mixture was heated in the microwave reactor at 120° C. for 45 min. The reaction mixture was filtered through celite and the filtrate was concentrated under reduced pressure to provide 6-(4,4,5,5-tetramethyl-1,3,2-dioxaborolan-2-yl)-1H-imidazo[4,5-b]pyridin-2(3H)-one (0.3 g, 49%) which was used without further purification. LCMS Method Y: retention time 1.5 min; [M+1]=261.7.

Step 3. Example 180

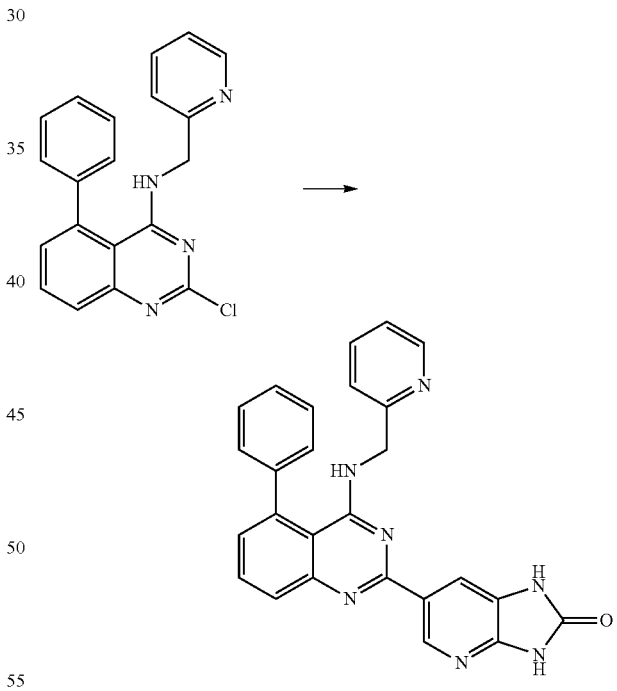

To a solution of 2-chloro-5-phenyl-N-(pyridin-2-ylmethyl)quinazolin-4-amine (0.25 g, 0.72 mmol) in 1,4-dioxane (10 mL) and $H_2O$ (2 mL) under nitrogen was added. 6-(4,4,5,5-tetramethyl-1,3,2-dioxaborolan-2-yl)-1H-imidazo[4,5-b]pyridin-2(3H)-one (0.28 g, 1.1 mmol) and potassium carbonate (0.2 g, 1 mmol). The mixture was degassed with nitrogen for 15 min. (1,1'-bis(diphenylphosphino)ferrocene)palladium (II) chloride dichloromethane complex (0.06 mg, 0.07 mmol) was added and the reaction mixture was again degassed for 10 min with nitrogen. The reaction mixture was stirred at 90° C. for 16 h, then allowed to cool to room temperature and quenched with water. The reaction mixture was transferred to a separation funnel and the aqueous layer extracted with ethyl acetate. The combined organic portions were washed with water and saturated NaCl, dried over $Na_2SO_4$, filtered and concentrated under reduced pressure. The residue was purified by silica gel column chromatography using dichloromethane/methanol mixture as the eluent to provide Example 180 (0.038 g, 12% yield) as brown solid. $^1H$ NMR (400 MHz, DMSO-$d_6$) δ (ppm): 11.14 (br, 1H), 9.06 (s, 1H), 8.25 (d, 1H, J=4.4 Hz), 8.20 (s, 1H), 7.86-7.77 (m, 2H), 7.72 (t, 1H, J=8 Hz), 7.60-7.49 (m, 5H), 7.31 (d, 1H, J=1.2 Hz), 7.26-7.20 (m, 2H), 6.75 (br s, 1H), 4.72 (d, 1H, J=4.0 Hz). LCMS Method T: retention time 1.56 min; [M+1]=446.2.0. HPLC Method A1: purity 99.09%, retention time=5.83 min.

Example 181

2-(5-(5-Phenyl-4-(pyridin-2-ylmethylamino)quinazolin-2-yl)pyridin-3-yl)acetonitrile

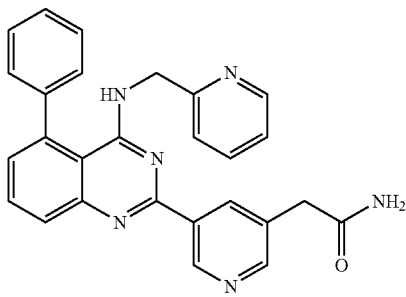 [SMILES: NC(=O)Cc1cncc(-c2nc(NCc3ccccn3)c3c(-c4ccccc4)cccc3n2)c1]

Step 1. Preparation of 3-bromo-5-chloromethyl-pyridine

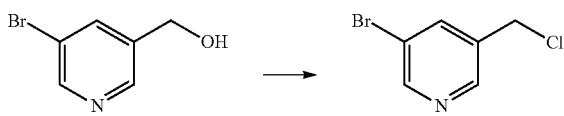 [SMILES: OCc1cncc(Br)c1 ; ClCc1cncc(Br)c1]

To a solution of (5-bromo-pyridin-3-yl)-methanol, (0.500 g, 2.68 mmol) in DCM (10 mL) was added thionyl chloride (0.5 mL) and the resulting solution was stirred at room temperature for 2 h. The reaction mixture was quenched by the addition of water and extracted into DCM. The organic extracts were washed with brine filtered and concentrated under reduced pressure to provide 3-bromo-5-chloromethyl-pyridine (0.45 g, 82%), which was used without further purification.

Step 2. Preparation of 2-(5-bromopyridin-3-yl) acetonitrile

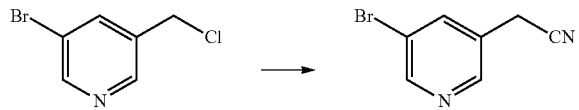 [SMILES: ClCc1cncc(Br)c1 ; N#CCc1cncc(Br)c1]

3-Bromo-5-chloromethyl-pyridine (0.45 g; 2.2 mmol) was dissolved in DMF (10 mL). Potassium cyanide (0.21 g, 3.27 mmol) was added and the reaction mixture was stirred at room temperature for 16 h. The reaction mixture was quenched by the addition of water and extracted with ethyl acetate. The organic phases were washed with water, brine and dried over $Na_2SO_3$ filtered and concentrated under reduced pressure. The residue was purified by silica gel column chromatography using 7% EtOAc in Hexanes to provide 2-(5-bromopyridin-3-yl) acetonitrile (200 mg, 46.5%). $^1H$ NMR (400 MHz, DMSO-$d_6$) δ (ppm): 8.68 (d, 1H, J=2 Hz), 8.51 (d, 1H, J=2 Hz), 7.88 (t, 1H, J=2 Hz), 3.77 (s, 2H).

Step 3. Preparation of 2-(5-(4,4,5,5-tetramethyl-1,3,2-dioxaborolan-2-yl)pyridin-3-yl)acetonitrile

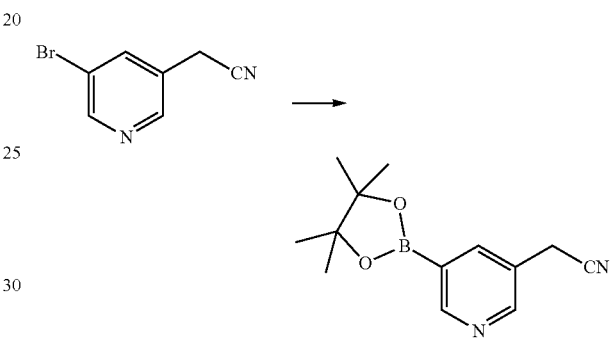

A mixture of 2-(5-bromopyridin-3-yl)acetonitrile (1.5 g, 7.6 mmol), bis (pinacolato)diboron (2.9 g, 12 mmol) and potassium acetate (2.98 g, 30.0 mmol) in 1,4-dioxane (15 mL) was degassed with nitrogen for 15 min. (1,1'-Bis (diphenylphosphino)ferrocene)palladium (II) chloride dichloromethane complex (450 mg, 0.61 mmol) was added and the reaction mixture was again degassed for 10 min. with nitrogen. The reaction mixture was heated in the microwave reactor at 95° C. for 16 h. The reaction mixture was filtered through celite and the filtrate was concentrated under reduced pressure to provide 2-(5-(4,4,5,5-tetramethyl-1,3,2-dioxaborolan-2-yl)pyridin-3-yl)acetonitrile (1.6 g) as brown solid, which was used without further purification. LCMS Method W: retention time 1.34 min; [M+1]=245.2.

Step 4. Example 181

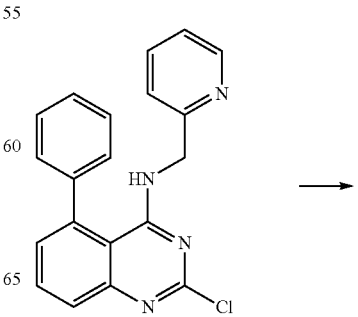

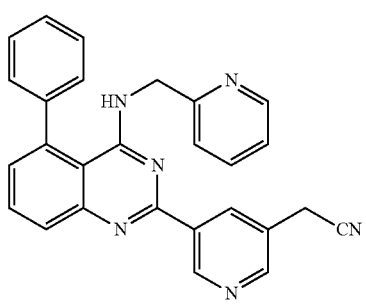

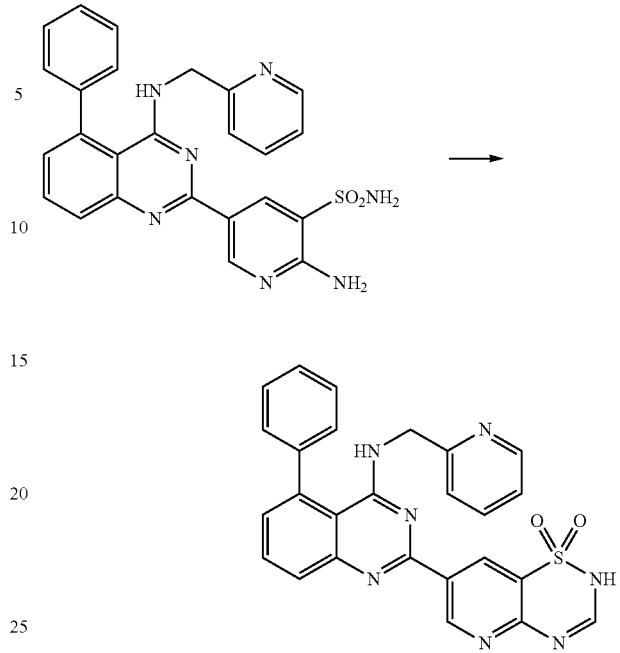

To a solution of 2-chloro-5-phenyl-N-(pyridin-2-ylmethyl) quinazolin-4-amine (180 mg, 0.52 mmol) in 1,4-dioxane (6 mL) and H₂O (0.5 mL) under nitrogen was added. 2-(5-(4,4,5,5-tetramethyl-1,3,2-dioxaborolan-2-yl) pyridin-3-yl)acetonitrile (190 mg, 0.77 mmol), and potassium carbonate (215 mg, 1.55 mmol). The mixture was degassed with nitrogen for 15 min. (1,1'-bis(diphenylphosphino)-ferrocene)palladium (II) chloride dichloromethane complex (38 mg, 0.52 mmol) was added and the reaction mixture was again degassed for 10 min with nitrogen. The reaction mixture was stirred at 95° C. for 16 h, then allowed to cool to room temperature and quenched with water. The reaction mixture was transferred to a separation funnel and the aqueous layer extracted with ethyl acetate. The combined organic portions were washed with water and saturated NaCl, dried over Na₂SO₄, filtered and concentrated under reduced pressure. The residue was purified by silica gel column chromatography using 5% methanol in dichloromethane as the eluent to provide Example 181 (110 mg, 49.6%) as off white solid. $^1$H NMR (400 MHz, DMSO-d₆) δ (ppm): 9.60 (s, 1H); 8.80 (s, 1H0; 8.70 (s, 1H); 8.24 (d, 1H, J=4.8 Hz); 7.90 (dd, 1H, J=1.6, 8.4 Hz); 7.84 (t, 1H, J=7.2 Hz); 7.73 (dt, 1H, J=1.6, 7.6 Hz); 7.62-7.50 (m, 5H); 7.36-7.30 (m, 2H); 7.23 (dd, 1H, J=1.6, 7.2 Hz); 6.89 (t, 1H, J 4 Hz); 4.75 (d, 2H, J=4 Hz); 4.27 (s, 2H). LCMS Method Y: retention time 1.94 min; [M−1]=427.0; HPLC Method A1: purity 99.4%, retention time=6.95 min.

Example 182

2-Amino-5-(5-phenyl-4-(pyridin-2-ylmethylamino)quinazolin-2-yl)pyridine-3-sulfonamide (Example 168, 0.095 g, 0.19 mmol) was dissolved in trimethylorthoformate (10 mL) and refluxed at 110° C. for 16 h. The volatile solvents were evaporated under reduced pressure and the residue was purified by silica gel column chromatography using 30% acetone in hexanes mixture as the eluent to provide Example 182 (4 mg, 4%) as a white solid. $^1$H NMR (400 MHz, DMSO-d₆) δ (ppm): 13.10 (br s, 1H); 9.71 (d, 1H, J=2 Hz); 9.11 (d, 1H, J=2 Hz); 8.24 (d, 1H, J 4.4 Hz); 8.12 (s, 1H); 7.93 (d, 1H, J'² 8.4 Hz); 7.85 (t, 1H, J=8 Hz); 7.73 (dt, 1H, J 1.2, 8 Hz); 7.61-7.49 (m, 5H); 7.33 (dd, 2H, J=8, 10.8 Hz); 7.23 (t, 1H, J=8 Hz); 6.96 (br t, 1H, J=4 Hz); 4.75 (d, 2H, J=8 Hz). LCMS Method W: retention time 1.91 min; [M+1]=494.2; HPLC Method A4: purity 98.0%, retention time=7.65 min.

Example 183

2-(5-(1,2,4-Oxadiazol-3-yl)pyridin-3-yl)-5-phenyl-N-(pyridin-2-ylmethyl)quinazolin-4-amine

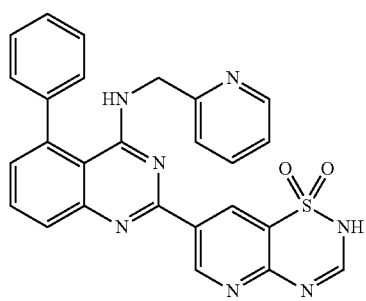 [SMILES: O=S1(=O)NC=Nc2ncc(-c3nc(NCc4ccccn4)c4c(-c5ccccc5)cccc4n3)cc21]

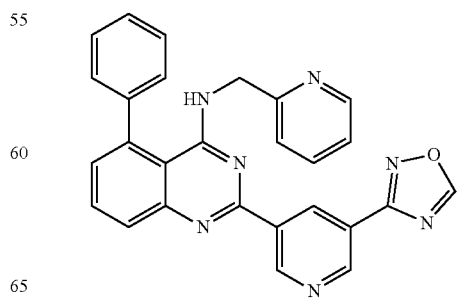

Step 1. Preparation of N-hydroxy-5-(5-phenyl-4-(pyridin-2-ylmethylamino)quinazolin-2-yl)nicotinimidamide

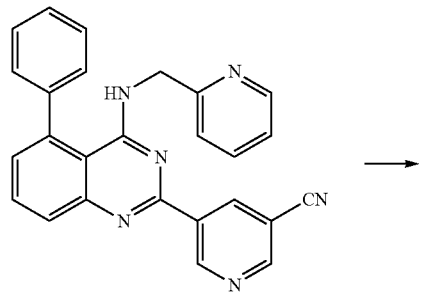

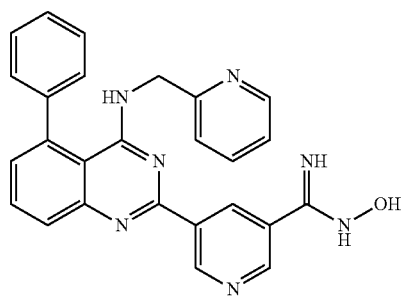

To a solution of ethyl 5-(5-phenyl-4-(pyridin-2-ylmethylamino)quinazolin-2-yl)nicotinonitrile (described in Example 6, 0.10 g, 0.24 mmol) in ethanol (5 mL) was added hydroxylamine hydrochloride (0.033 g, 0.48 mmol) and potassium carbonate (0.076 g, 0.72 mmol). The reaction mixture was heated to reflux at 80° C. for 16 h. The ethanol solvent was evaporated under reduced pressure and the residue was dissolved in DCM, and washed with water. The organic layer was dried, filtered and concentrated to provide N-hydroxy-5-(5-phenyl-4-(pyridin-2-ylmethylamino)quinazolin-2-yl)nicotinimidamide (0.2 g) which was used without further purification. LCMS Method X: retention time 1.788 min; [M+1]=448.0.

Step 2. Example 183

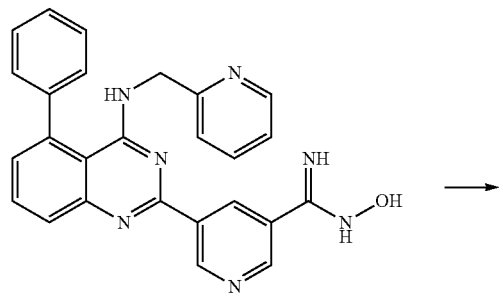

-continued

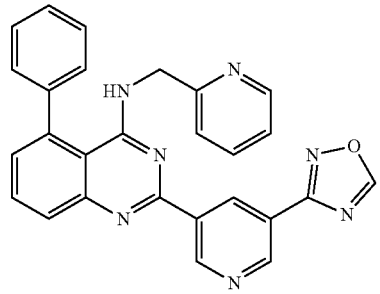 [SMILES: c1ccc(-c2cccc3nc(-c4cncc(-c5ncon5)c4)nc(NCc4ccccn4)c23)cc1]

N-hydroxy-5-(5-phenyl-4-(pyridin-2-ylmethylamino)quinazolin-2-yl)nicotinimidamide (0.10 g, 0.22 mmol) was dissolved in trimethylorthoformate (5 mL) and pTSA (cat.) was added. The reaction mixture was refluxed at 100° C. for 16 h. The volatile solvents were evaporated under reduced pressure and the residue was purified by silica gel column chromatography 1.6% methanol in DCM to provide Example 183 (4 mg, 4% yield) as a white solid. $^1$H NMR (400 MHz, DMSO-$d_6$) δ (ppm): 9.83 (s, 1H), 9.37-9.31 (m, 2H); 8.25 (d, 1H, J=4 Hz); 7.96 (dd, 1H, J=1.2, 8.4 Hz); 7.87 (dd, 1H, J=6.8, 8.4 Hz); 7.73 (dd, 1H, J=1.6, 7.6 Hz): 7.62-7.50 (m, 5H); 7.40-7.33 (m, 2H); 7.24 (dd, 1H, J, =4.8, 6.8 Hz); 6.94 (br s, 1H); 4.77 (d, 2H, J=4.4 Hz). LCMS Method Y: retention time 2.03 min; [M+1]=458.2; HPLC Method A4: purity 94.7%, retention time=7.4 min.

Example 184

2-(5-(5-Phenyl-4-(pyridin-2-ylmethylamino)quinazolin-2-yl)pyridin-3-yl)acetamide

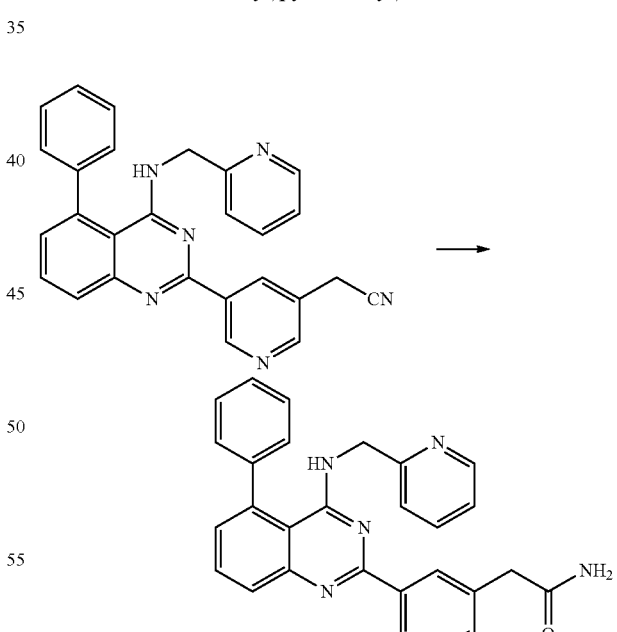

To a solution of 2-(5-(5-phenyl-4-(pyridin-2-ylmethylamino) quinazolin-2-yl)pyridin-3-yl) acetonitrile (Example 181) (70 mg, 20.1 mmol) in ethanol/H$_2$O (3/3 mL) was added sodium hydroxide (40 mg, 1.0 mmol) The mixture was heated under reflux for 2 h. The reaction mixture was quenched by the addition of water (5 mL) and extracted with ethyl acetate. The organic extracts were washed with saturated brine and dried over anhydrous magnesium sulfate and filtered. The solvent was evaporated under reduced pressure and the residue was purified by column chromatography (silica gel. MeOH/DCM, 2.5:97.5) to provide Example 184 (32 mg, 44%) as an off white solid. $^1$H NMR (400 MHz, DMSO-d$_6$) δ (ppm): 9.50 (s, 1H); 8.68 (s, 1H); 8.59 (s, 1H); 8.25 (d, 1H, J=4.4 Hz); 7.89 (dd, 1H, J=1.2, 7.6 Hz); 7.83 (t, 1H, J=7.2 Hz); 7.73 (dt, 1H, J=1.6, 7.6 Hz); 7.65 (br s, 1H); 7.60-7.50 (m, 5H); 7.38-7.30 (m, 2H); 7.23 (t, 1H, J=6.4 Hz); 7.22 (br s, 1H); 6.84 (br s, 1H); 4.75 (d, 2H, J=4 Hz); 3.57 (s, 2H). LCMS Method Y: retention time 1.72 min; [M+1]=447.2; HPLC Method A4: purity 97.8%, retention time=5.48 min.

Example 185

2-(5-(1,3,4-Oxadiazol-2-yl)pyridin-3-yl)-5-phenyl-N-(pyridin-2-ylmethyl)quinazolin-4-amine

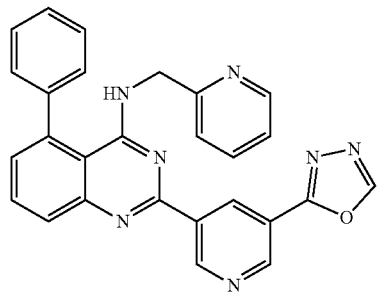 [SMILES: c1ccc(-c2cccc3nc(-c4cncc(-c5nnco5)c4)nc(NCc4ccccn4)c23)cc1]

Step 1. Preparation of 5-(5-phenyl-4-(pyridin-2-ylmethylamino)quinazolin-2-yl)nicotinohydrazide

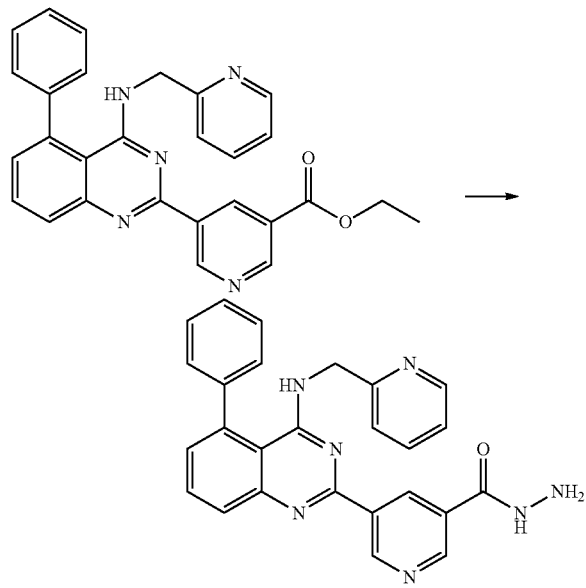

To a solution of ethyl 5-(5-phenyl-4-(pyridin-2-ylmethylamino)quinazolin-2-yl)nicotinate (Example 43) (0.2 g, 0.43 mmol) in ethanol (10 mL) was added hydrazine hydrate (0.1 mL, 2.1 mmol). The reaction mixture was heated to reflux at 80° C. for 16 h. The ethanol was evaporated under reduced pressure and the residue was dissolved in DCM and washed with water. The organic layer was dried and concentrated to provide 5-(5-phenyl-4-(pyridin-2-ylmethylamino)quinazolin-2-yl)nicotinohydrazide (0.2 g, crude), which was used without further purification. LCMS Method E: retention time 1.8 min; [M+1]=447.50.

Step 2. Example 185

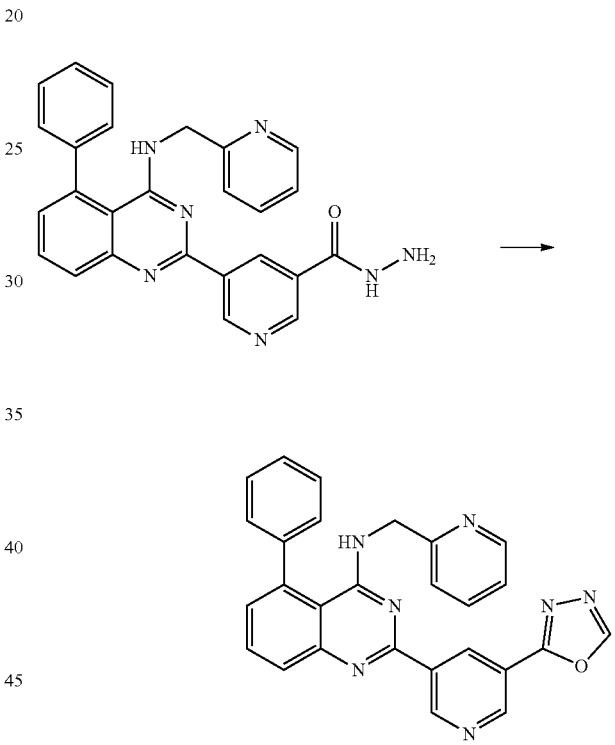

5-(5-Phenyl-4-(pyridin-2-ylmethylamino)quinazolin-2-yl)nicotinohydrazide (0.2 g, 0.44 mmol) was dissolved in trimethylorthoformate (5 mL). pTSA (catalytic) was added and the reaction mixture was heated to reflux at 110° C. for 16 h. The volatile solvents were evaporated under reduced pressure and the residue was purified by silica gel column chromatography 1.7% methanol in DCM to provide Example 185 (4 mg, 2%) as a white solid. $^1$H NMR (400 MHz, DMSO-d$_6$) δ (ppm): 9.86 (s, 1H), 9.53 (s, 1H); 9.33 (s, 1H); 9.31 (s, 1H); 8.25 (br s, 1H); 7.96 (dd, 1H, J=1.2, 1.8 Hz); 7.87 (dd, 1H, J=7.2, 8 Hz); 7.74 (dt, 1H, J=1.8 Hz); 7.62-7.50 (m, 5H); 7.34 (dd, 2H, J=7.2, 12.8 Hz); 7.25 (dd, 1H, J=4.8, 6.4 Hz); 6.95 (t, 1H, J=4 Hz); 4.77 (d, 2H, J=4.4 Hz). LCMS Method Y: retention time 1.91 min; [M+1]=458.2; HPLC Method A1: purity 96.7%, retention time=6.85 min.

Example 186

2-(5-(Oxazol-5-yl)pyridin-3-yl)-5-phenyl-N-(pyridin-2-ylmethyl)quinazolin-4-amine

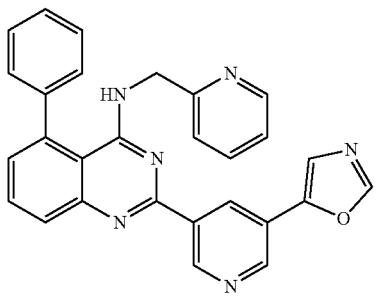 [SMILES: c1ccc(-c2cccc3nc(-c4cncc(-c5cnco5)c4)nc(NCc4ccccn4)c23)cc1]

Step 1. Preparation of 5-(5-bromopyridin-3-yl)oxazole

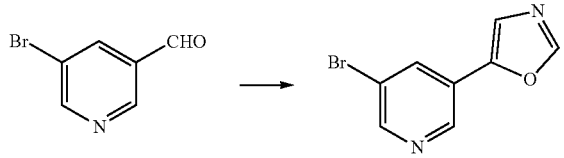 [SMILES: O=Cc1cncc(Br)c1 ; Brc1cncc(-c2cnco2)c1]

To a solution of 5-bromonicotinaldehyde (0.2 g, 1 mmol) in MeOH (5 mL) was added K$_2$CO$_3$ (0.3 g, 2 mmol) followed by TOSMIC (0.27 g, 1.39 mmol). The mixture was heated to 85° C. for 2 h. Methanol was evaporated under reduced pressure and the residue was dissolved in DCM then washed with water. The organic extracts were dried over sodium sulfate, filtered and concentrated. The residue was purified by silica gel column chromatography using 2.1% MeOH in DCM as the eluent to provide 5-(5-bromopyridin-3-yl)oxazole (0.12 g, 50%). LCMS Method Y: retention time 1.39 min; [M+1]=225.0.

Step 2. Preparation of 5-(5-(4,4,5,5-tetramethyl-1,3,2-dioxaborolan-2-yl)pyridin-3-yl)oxazole

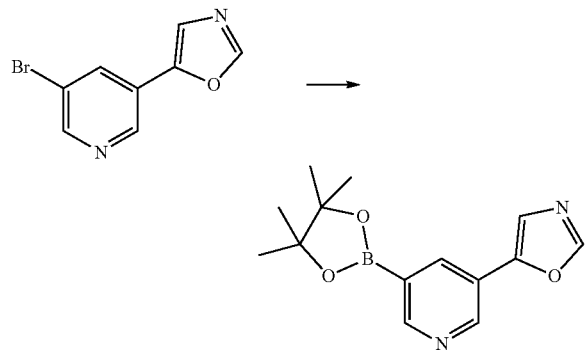

A mixture of 5-(5-bromopyridin-3-yl)oxazole (0.10 g, 0.044 mmol), bis(pinacolato)diboron (0.17 g, 0.60 mmol) and potassium acetate (0.129 g, 1.3 mmol) in 1,4-dioxane (5 mL) was degassed with nitrogen for 15 min. (1,1'-Bis(diphenylphosphino)ferrocene)palladium (II) chloride dichloromethane complex (0.017 g, 0.022 mmol) was added and the mixture was again degassed for 10 min. with nitrogen. The reaction mixture was heated in the microwave at 100° C. for 16 h. The reaction mixture was filtered through celite and the filtrate was concentrated under reduced pressure to provide 5-(5-(4,4,5,5-tetramethyl-1,3,2-dioxaborolan-2-yl)pyridin-3-yl)oxazole (0.1 g), which was used without further purification. LCMS Method W: retention time 1.45 min; [M+1]=273.2.

Step 3. Example 186

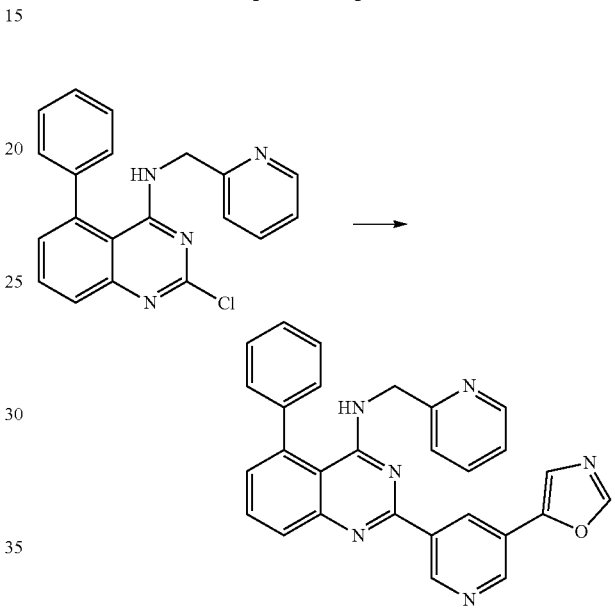

To a solution of 2-chloro-5-phenyl-N-(pyridin-2-ylmethyl)quinazolin-4-amine (0.115 g, 0.330 mmol) in 1,4-dioxane (6 mL) and H$_2$O (1.5 mL) under nitrogen was added, 5-(5-(4,4,5,5-tetramethyl-1,3,2-dioxaborolan-2-yl)pyridin-3-yl)oxazole (0.10 g, 0.36 mmol) and potassium carbonate (0.136 g, 0.990 mmol). The reaction mixture was degassed with nitrogen for 15 min. (1,1'-Bis(diphenylphosphino)-ferrocene)palladium (II) chloride dichloromethane complex (0.026 g, 0.033 mmol) was added and the reaction mixture was again degassed for 10 min with nitrogen. The reaction mixture was stirred at 100° C. for 16 h, then allowed to cool to room temperature and quenched with water. The reaction mixture was transferred to a separation funnel and the aqueous layer extracted with ethyl acetate. The combined organic portions were washed with water and saturated NaCl, dried over Na$_2$SO$_4$, filtered and concentrated under reduced pressure. The residue was purified by silica gel column chromatography using 5% methanol in dichloromethane to provide 2-(5-(oxazol-5-yl)pyridin-3-yl)-5-phenyl-N-(pyridin-2-ylmethyl)quinazolin-4-amine (0.015 g) as a brown solid. $^1$H NMR (400 MHz, DMSO-d$_6$) δ (ppm): 9.70 (s, 1H); 9.03 (s, 1H); 8.27 (d, 2H, J=3.6 Hz); 8.03 (s, 1H0; 7.77 (t, 1H, J=7.6 Hz); 7.70-7.58 (m, 2H); 7.54-7.47 (m, 5H0; 7.33-7.28 (m, 1H); 7.20-7.10 (m, 5H0; 6.82 (br, 1 h); 4.80 (d, 2H, J=4.4 Hz). LCMS Method Y: retention time 1.98 min; [M+1]=457.2; HPLC Method A1: purity 98.7%, retention time=7.09 min.

Example 187

Methyl 3-(5-(5-phenyl-4-(pyridin-2-ylmethylamino)quinazolin-2-yl)pyridin-3-yl)-1,2,4-oxadiazole-5-carboxylate

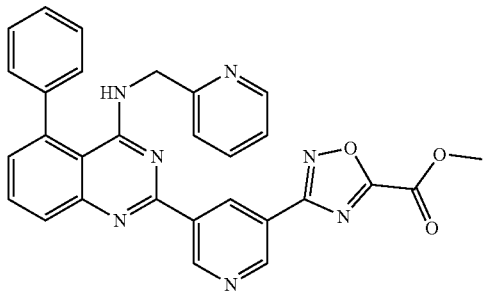 [SMILES: COC(=O)c1nc(-c2cncc(-c3nc(NCc4ccccn4)c4c(-c5ccccc5)cccc4n3)c2)no1]

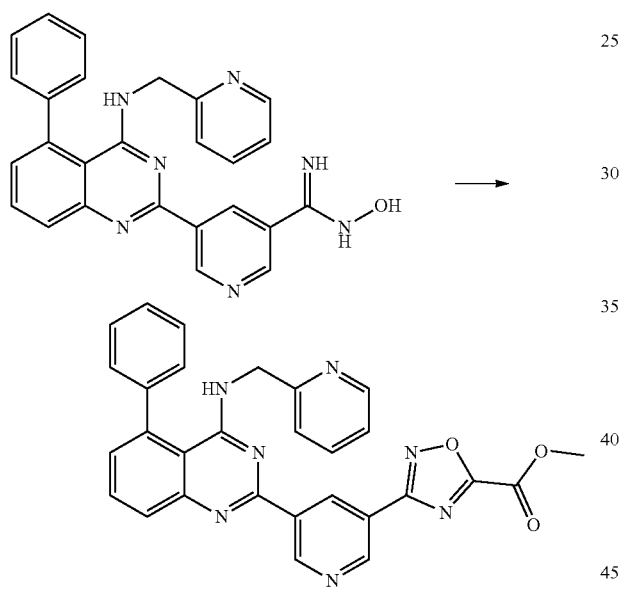

To a solution of N-hydroxy-5-(5-phenyl-4-(pyridin-2-ylmethylamino)quinazolin-2-yl)nicotinimidamide (described in Example 183, 1.0 g, 2.2 mmol) in DCE at 0° C. was added methyl 2-chloro-2-oxoacetate (0.31 mL, 3.3 mmol). The reaction mixture was stirred at room temperature for 2 h. Phosphorus oxychloride (1 mL) was added and the reaction mixture was heated to reflux for 1.5 h. The reaction mixture was quenched by the addition of saturated solution of NaHCO$_3$ and extracted with DCM, dried over sodium sulfate and concentrated. The residue was purified by silica gel column chromatography using 5% methanol in dichloromethane to provide Example 187 (270 mg, 23%) as a white solid. $^1$H NMR (400 MHz, DMSO-d$_6$) δ (ppm): 9.85 (s, 1H); 9.34 (s, 1H0; 8.27 (d, 1H, J=5.2 Hz); 7.98 (dd, 1H, J=1.2, 8 Hz); 7.87 (t, 1H, J=4.8 Hz); 7.76 (t, 1H, J=3 Hz); 7.63-7.53 (m, 5H0; 7.41-7.30 (m, 2H0; 7.24 (t, 1H, J=6 Hz); 6.95 (br s, 1H); 4.77 (d, 2H, J=4 Hz); 4.05 (s, 3H). LCMS Method Y: retention time 2.09 min; [M+1]=516.2; HPLC Method A4: purity 97.4%, retention time=8.77 min.

Example 188

3-(5-(5-Phenyl-4-(pyridin-2-ylmethylamino)quinazolin-2-yl)pyridin-3-yl)-1,2,4-oxadiazole-5-carboxamide

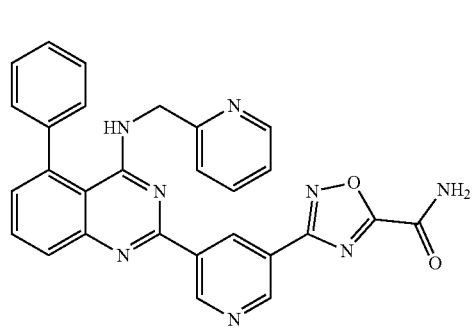

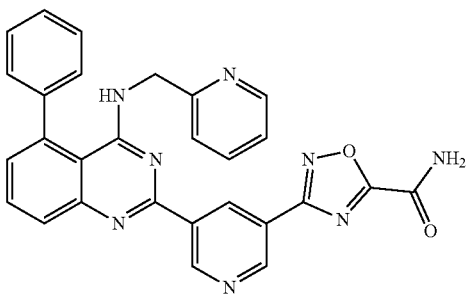 [SMILES: NC(=O)c1nc(-c2cncc(-c3nc(NCc4ccccn4)c4c(-c5ccccc5)cccc4n3)c2)no1]

To a solution of methyl 3-(5-(5-phenyl-4-(pyridin-2-ylmethylamino)quinazolin-2-yl)pyridin-3-yl)-1,2,4-oxadiazole-5-carboxylate (Example 187, 0.080 g, 0.15 mmol) was added ammonia in methanol (10 mL) and the reaction mixture was heated at 60° C. for 4 h. The solvent was evaporated under reduced pressure to provide Example 188 (0.032 g, 45%) as white solid. $^1$H NMR (400 MHz, DMSO-d$_6$, δ): 9.84 (s, 1H); 9.36 (s, 1H0; 9.34 (s, 1H); 8.80 (br s, 1H); 8.35 (br s, 1H); 8.26 (d, 1H, J=4.8 Hz); 7.98 (d, 1H, J=8.4 Hz); 7.87 (t, 1H, J 8 Hz); 7.74 (t, 1H, J=8 Hz); 7.63-7.50 (m, 3H); 7.41-7.33 (m, 2H); 7.25 (t, 1H, J=7.2 Hz); 6.96 (br t, 1H, J=4 Hz); 4.78 (d, 2H, J=4 Hz). LCMS Method Y: retention time 1.89 min, [M+1]=501.2; HPLC Method A1: purity 96.4%, retention time=7.05 min.

Example 189

2-(5-(4H-1,2,4-triazol-4-yl)pyridin-3-yl)-5-phenyl-N-(pyridin-2-ylmethyl)quinazolin-4-amine

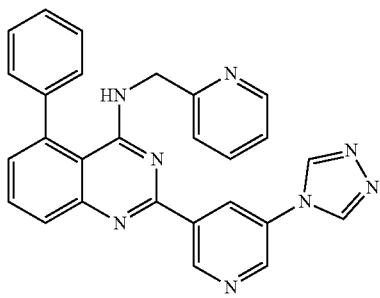 [SMILES: c1ccc(-c2cccc3nc(-c4cncc(-n5cnnc5)c4)nc(NCc4ccccn4)c23)cc1]

Step 1. Preparation of
3-bromo-5-(4H-1,2,4-triazol-4-yl)pyridine

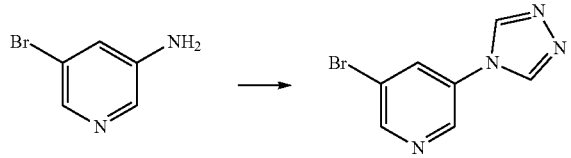 [SMILES: Nc1cncc(Br)c1 ; Brc1cncc(-n2cnnc2)c1]

A mixture of 3-bromo-5-amino pyridine (0.30 g, 1.7 mmol) and N,N-diformaylhydrazine (0.15 g, 1.7 mmol) was heated at 150° C. in sealed tube for 16 h. A precipitate formed which was dissolved in hot ethanol and then filtered. Diethyl ether was added to the filtrate at room temperature and the slurry was stirred overnight. The resulting solid was separated and purified by silica gel column chromatography using ethyl acetate and hexanes mixture as the eluent to provide 3-bromo-5-(4H-1,2,4-triazol-4-yl)pyridine (130 mg, 33% yield) as a white solid. $^1$H NMR (400 MHz, DMSO-$d_6$) δ (ppm): 9.24 (s, 2H); 9.03 (d, 1H, J=2 Hz); 8.79 (d, 1H, J=2 Hz); 8.60 (t, 1H, J=2 Hz).

Step 2. Preparation of 3-(4,4,5,5-tetramethyl-1,3,2-dioxaborolan-2-yl)-5-(4H-1,2,4-triazol-4-yl)pyridine

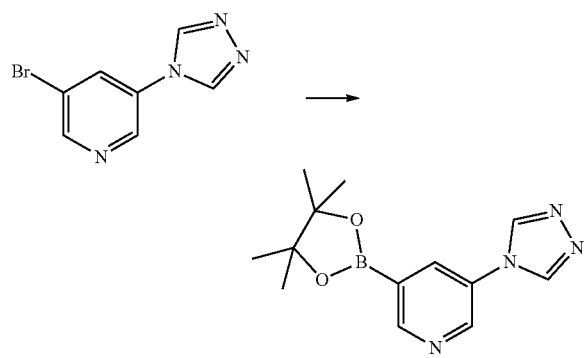

A mixture of 3-bromo-5-(4H-1,2,4-triazol-4-yl)pyridine (0.12 g, 0.50 mmol), bis(pinacolato)diboron (0.16 g, 0.60 mmol) and potassium acetate (0.15 g, 1.5 mmol) in 1,4-dioxane (10 mL) was degassed with nitrogen for 15 min. (1,1'-Bis(diphenylphosphino)ferrocene)palladium (II) chloride dichloromethane complex (0.043 g, 0.05 mmol) was added and the resulting mixture was again degassed for 10 min. with nitrogen. The reaction mixture was heated in the microwave reactor at 120° C. for 45 min. After this time, the reaction mixture was filtered through celite and the filtrate was concentrated under reduced pressure to provide 3-(4,4,5,5-tetramethyl-1,3,2-dioxaborolan-2-yl)-5-(4H-1,2,4-triazol-4-yl)pyridine (150 mg), which was used without further purification.

Step 3. Example 189

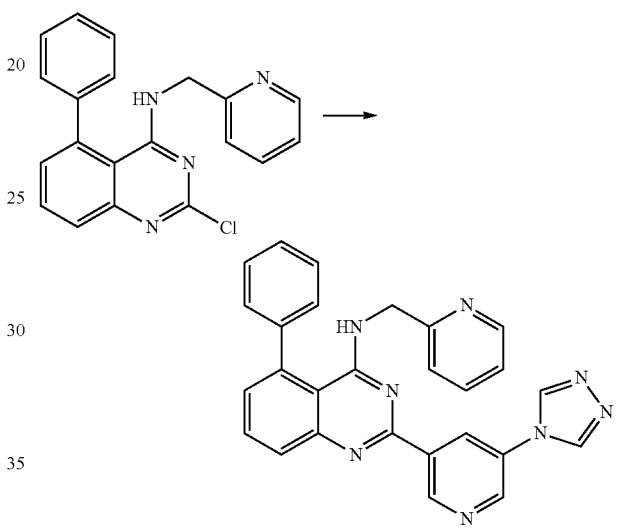

To a solution of 2-chloro-5-phenyl-N-(pyridin-2-ylmethyl)quinazolin-4-amine (180 mg, 0.5 mmol) in 1,4-dioxane (6 mL) and H$_2$O (1 mL) under nitrogen was added 3-(4,4,5,5-tetramethyl-1,3,2-dioxaborolan-2-yl)-5-(4H-1,2,4-triazol-4-yl)pyridine (150 mg, 0.700 mmol) and potassium carbonate (215 mg, 1.50 mmol). Upon completion of addition, the mixture was degassed with nitrogen for 15 min and then. (1,1'-bis(diphenylphosphino)ferrocene)palladium (II) chloride dichloromethane complex (0.041 g, 0.050 mmol) was added. The reaction mixture was again degassed for 10 min with nitrogen. At the conclusion of this period, the reaction mixture was stirred at 90° C. for 16 h, allowed to cool to room temperature and then quenched with water. The reaction mixture was transferred to a separation funnel and the aqueous layer was extracted with ethyl acetate. The combined organic portions were washed with water and saturated NaCl, dried over Na$_2$SO$_4$, filtered and concentrated under reduced pressure. The resulting residue was purified by preparative TLC using 5% methanol in dichloromethane to afford Example 189 (6 mg, 3% yield) as a brown solid. $^1$H NMR (400 MHz, DMSO-$d_6$) δ (ppm): 9.70 (s, 1H), 9.34 (s, 2H), 9.07 (s, 1H), 8.97 (s, 1H), 8.22 (d, 1H, J=4.4 Hz), 7.93 (dd, 1H, J=1.2, 8.4 Hz), 7.86 (t, 1H, J=6 Hz), 7.73 (dt, 1H, J=1.6, 7.6 Hz), 7.50-7.62 (m, 5H); 7.36-7.32 (m, 2H); 7.23 (t, 1H, J=5.6 Hz), 6.97 (t, 1H, J=4 Hz), 4.79 (d, 2H, J=4.0 Hz). LCMS Method Y: retention time 1.79 min; [M−1]=455.2; HPLC Method A3: purity 98.9%, retention time=13.5 min.

Example 190

Methyl 3-(5-(5-phenyl-4-(pyridin-2-ylmethylamino)quinazolin-2-yl)pyridin-3-yl)propanoate

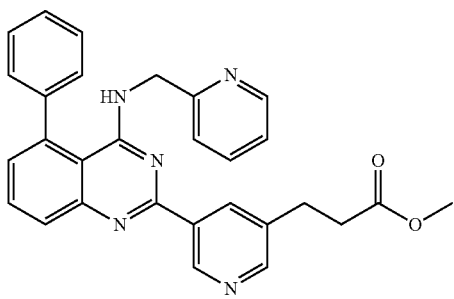 [SMILES: COC(=O)CCc1cncc(-c2nc(NCc3ccccn3)c3c(-c4ccccc4)cccc3n2)c1]

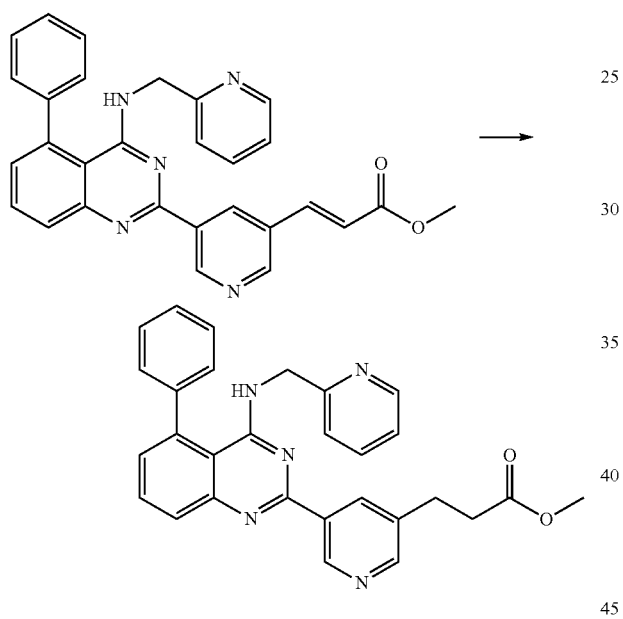

To a solution of (E)-methyl 3-(5-(5-phenyl-4-(pyridin-2-ylmethylamino)quinazolin-2-yl)pyridin-3-yl)acrylate (Example 191, prepared in a similar manner to the procedure described below, 0.3 g, 6.3 mmol) in ethanol (7 mL) was added 10% palladium-on-carbon (100 mg). Upon completion of addition, the reaction mixture was stirred at RT under hydrogen for 16 h. After this time, the reaction mixture was filtered through celite, and the solvent was evaporated under reduced pressure. The resulting residue was purified by silica gel column chromatography using methanol in DCM (2:98) as the eluent to provide Example 190 (180 mg, 60% yield). $^1$H NMR (400 MHz, DMSO-$d_6$) δ (ppm): 9.47 (s, 1H), 8.63-8.57 (m, 2H), 8.23 (br s, 1H), 7.87 (d, 1H, J=6.8 Hz), 7.82 (t, 1H, J=6.8 Hz), 7.72 (dt, 1H, J=2, 7.6 Hz), 7.63-7.49 (m, 5H), 7.36-7.28 (m, 2H), 7.23 (dd, 1H, J=5.2, 6.8 Hz), 6.83 (t, 1H, J=4.4 Hz), 4.73 (d, 2H, J=2 Hz), 3.00 (t, 2H, J=7.6 Hz), 2.76 (t, 2H, J=7.6 Hz). LCMS Method W: retention time 2.17 min; [M+1]=476.2; HPLC Method A1: purity 98.7%, retention time=7.10 min.

Example 191

(E)-methyl 3-(5-(5-phenyl-4-(pyridin-2-ylmethylamino)quinazolin-2-yl)pyridin-3-yl)acrylate

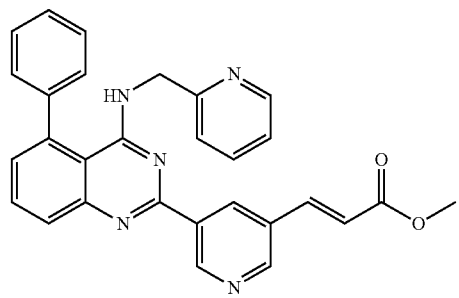 [SMILES: COC(=O)/C=C/c1cncc(-c2nc(NCc3ccccn3)c3c(-c4ccccc4)cccc3n2)c1]

Step 1. Preparation of 5-(5-phenyl-4-(pyridin-2-ylmethylamino)quinazolin-2-yl)nicotinaldehyde To a solution of 2-chloro-5-phenyl-N-(pyridin-2-ylmethyl)quinazolin-4-amine (2 g, 5.7 mmol) in 1,4-dioxane (40 mL) and H$_2$O (8 mL) under nitrogen was added 5-(4,4,5,5-tetramethyl-1,3,2-dioxaborolan-2-yl)nicotinaldehyde (1.48 g, 6.30 mmol), and potassium carbonate (2.39 g, 17.0 mmol). Upon completion of addition, the reaction mixture was degassed with nitrogen for 15 min and then (1,1'-bis(diphenylphosphino)ferrocene)palladium (II) chloride dichloromethane complex (0.46 mg, 0.050 mmol) was added. The reaction mixture was again degassed for 10 min with nitrogen. At the conclusion of this period, the reaction mixture was stirred at 90° C. for 16 h, then allowed to cool to room temperature and quenched by the addition of water. The reaction mixture was transferred to a separation funnel and the aqueous layer was extracted with ethyl acetate. The combined organic portions were washed with water and saturated NaCl, dried over Na$_2$SO$_4$, filtered and concentrated under reduced pressure. The resulting concentrate was purified by silica gel column chromatography using 2.7% MeOH in DCM as eluent to afford 5-(5-phenyl-4-(pyridin- 2-ylmethylamino)quinazolin-2-yl)nicotinaldehyde (1.8 g, 100% yield) as an off-white solid. LCMS Method Y: retention time 1.99 min; [M+1]=418.4.

Step 2. Example 191

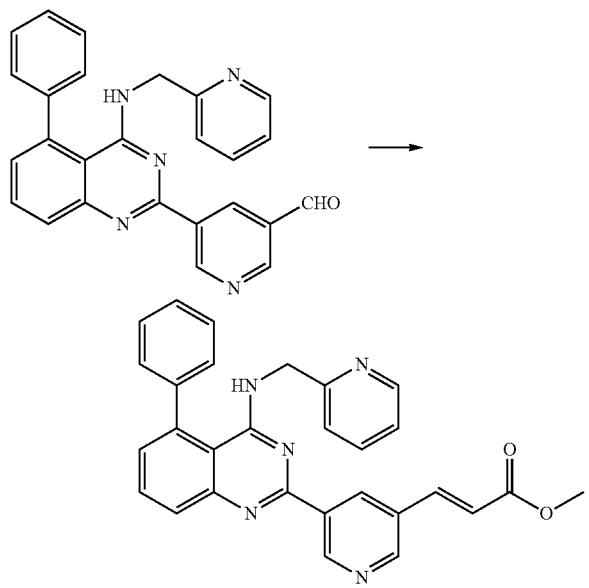

To a solution of 5-(5-phenyl-4-(pyridin-2-ylmethylamino) quinazolin-2-yl)nicotinaldehyde (250 mg, 0.60 mmol) in THF (15 mL) was added methyl (triphenylphosphoranylidine)acetate (300 mg, 0.9 mmol). The resulting solution was stirred at room temperature for 16 h. After this time, the solvent was removed under reduced pressure to yield a residue. The residue was purified by silica gel column chromatography using 20% EtOAc, hexane as the eluent to provide Example 191 (0.18 g, 63%). $^1$H NMR (400 MHz, DMSO-$d_6$) δ (ppm): 9.57 (s, 1H), 8.31 (d, J=4.8, 1H), 8.15 (d, J=8.4 Hz, 1H), 8.04-7.89 (m, 1H), 7.92-7.84 (m, 2H), 7.63-7.55 (m, 5H), 7.51-7.43 (m, 2H), 7.37 (t, J=5.6 Hz, 1H), 7.00 (d, J=16 Hz, 1H), 4.93 (d, J=4 Hz, 2H), 3.79 (s, 3H). LCMS Method Y: retention time 2.15 min; [M+1] =474.1; HPLC Method A1: purity 99.0%, retention time=7.85 min.

Example 192

3-(5-(5-Phenyl-4-(pyridin-2-ylmethylamino)quinazolin-2-yl)pyridin-3-yl)propanamide

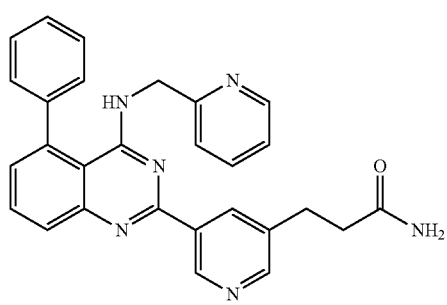 [SMILES: NC(=O)CCc1cncc(-c2nc(NCc3ccccn3)c3c(-c4ccccc4)cccc3n2)c1]

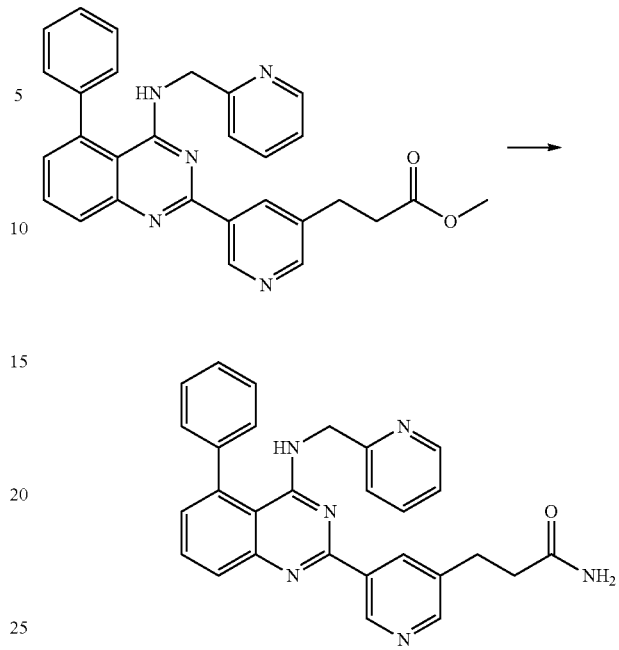

A solution of Example 190 (0.1 g, 0.2 mmol) in NH$_3$ (2.0 M in MeOH, 5 mL) was stirred at room temperature in a sealed vessel for 30 min. After this time, the solid formed was collected by filtration and washed with ice cooled methanol. The solid was further purified by silica gel column chromatography using 5% methanol in DCM as the eluent to provide Example 192 (35 mg, 35%). $^1$H NMR (400 MHz, DMSO-$d_6$) δ (ppm): 9.45 (s, 1H); 8.55 (s, 1H); 8.24 (d, 1H, J=4 Hz); 7.88 (dd, 1H, J=1.2, 8.0 Hz): 7.80 (t, 1H<J=8 Hz); 7.72 (dt, 1H, J=1.2, 8 Hz); 7.60-749 (m, 5H); 7.40-7.30 (m, 2H); 7.29 (dd, 1H, J=1.2, 7.2 Hz); 7.23 (dd, 1H, J=5.2, 6.8 Hz); 6.84 (t, 1H, 3.2 Hz); 4.73 (d, 2H, 4 Hz); 2.95 (t, 2H, J=7.6 Hz); 2.48 (t, 2H, 7.6 Hz). LCMS Method W: retention time 1.64 min; [M+1]=461.2; HPLC Method A1: purity 99.1%, retention time=5.76 min.

Example 193

Methyl 3-(5-phenyl-4-(pyridin-2-ylmethylamino) quinazolin-2-yl)propanoate

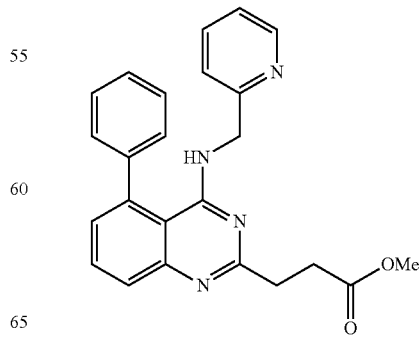

Step 1. Preparation of (E)-methyl 3-(5-phenyl-4-(pyridin-2-ylmethylamino)quinazolin-2-yl) acrylate

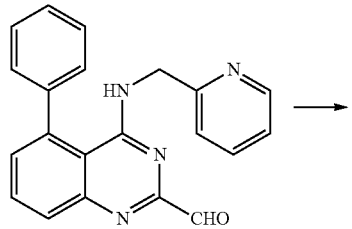

→

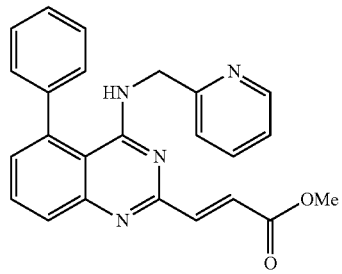

A solution of trimethyl phosphonoacetate (0.225 g 1.00 mmol) in THF (20 mL) was added 95% sodium hydride (0.050 g, 2.0 mmol). Upon the completion of addition, the mixture was stirred at 0° C. for 30 min and then 5-phenyl-4-(pyridin-2-ylmethylamino)quinazoline-2-carbaldehyde (Example 212, prepared in a similar manner to the procedure described below, 0.340 g, 1.00 mmol) was added to the reaction mixture. The resulting mixture was stirred at room temperature for 14 h. After this time, the reaction mixture was quenched with saturated aqueous ammonium chloride solution (50 mL) and extracted with ethyl acetate. The organic layer was washed with saturated brine, dried over anhydrous magnesium sulfate, and filtrated. The filtrate was concentrated and the resulting residue was subjected to silica gel column chromatography using 5% MeOH in chloroform as the eluent to provide (E)-methyl 3-(5-phenyl-4-(pyridin-2-ylmethylamino)quinazolin-2-yl) acrylate (0.30 g, 72%) as a brown solid. LCMS Method V: retention time 1.94 min; [M+1]=411.2.

Step 2. Example 193

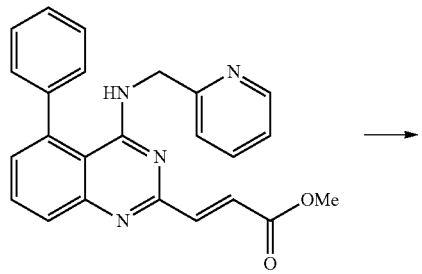

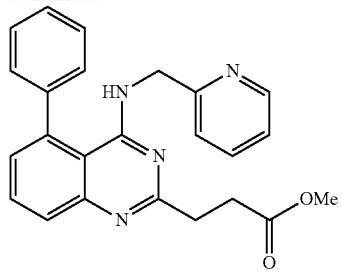

To a solution of (E)-ethyl 3-(5-phenyl-4-(pyridin-2-ylmethylamino)quinazolin-2-yl) acrylate (0.150 g, 0.370 mmol) in MeOH (25 mL) was added 10% palladium-on-carbon (50 mg). The mixture is stirred at room temperature under hydrogen for 14 h. After this time, the mixture was filtered to provide Example 193 (110 mg, 73%). $^1$H NMR (400 MHz, DMSO-$d_6$) δ (ppm): 8.21 (d, 1H, J=4.4 Hz); 7.76-7.66 (m, 3H); 7.55-7.45 (m, 5H); 7.24-7.19 (m, 3H); 6.65 (br s, 1H); 4.54 (d, 2H, J=4.4 Hz); 3.60 (s, 3H0; 3.06 (t, 2H, J=6 Hz); 2.82 (t, 2H, J=6 Hz). LCMS Method Y: retention time 1.87 min; [M+1]=399.4; HPLC Method A1: purity 94.0%, retention time=6.32 min.

Example 194

5-(5-(5-Phenyl-4-(pyridin-2-ylmethylamino)quinazolin-2-yl)pyridin-3-yl)-1,3,4-oxadiazole-2-carboxamide

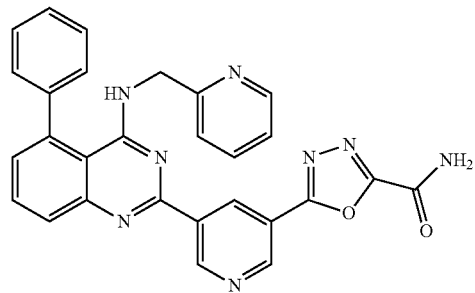 [SMILES: NC(=O)c1nnc(-c2cncc(-c3nc(NCc4ccccn4)c4c(-c5ccccc5)cccc4n3)c2)o1]

Step 1. Preparation of methyl 5-(5-(5-phenyl-4-(pyridin-2-ylmethylamino)quinazolin-2-yl)pyridin-3-yl)-1,3,4-oxadiazole-2-carboxylate

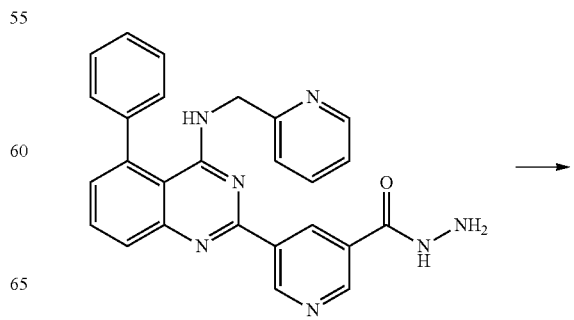

→

-continued

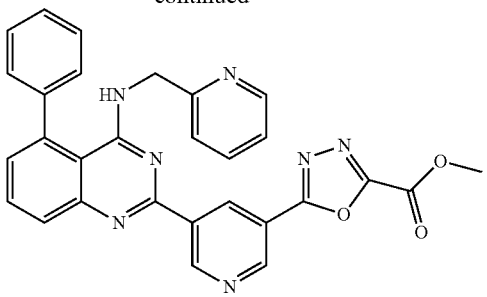

To a solution of 5-(5-phenyl-4-(pyridin-2-ylmethylamino)quinazolin-2-yl)nicotinohydrazide (from Example 185, 0.30 g, 0.66 mmol) in DCM at 0° C. was added methyl 2-chloro-2-oxoacetate (0.062 mL, 0.66 mmol) and potassium carbonate (0.273 g, 1.90 mmol). Upon completion of addition, the mixture was stirred at RT for 16 h. After this time, water was added and the mixture was extracted into DCM, dried and concentrated. The resulting residue was dissolved in DCM. Triflic anhydride (0.187 mL, 1.1 mmol) and pyridine (0.149 mL, 1.8 mmol) were added and the resulting mixture was stirred at RT for 16 h. At the conclusion of this period, the reaction mixture was quenched with water and extracted with DCM (100 mL). The DCM layer was washed with water and brine. Chromatographic purification provided methyl 5-(5-(5-phenyl-4-(pyridin-2-ylmethylamino)quinazolin-2-yl)pyridin-3-yl)-1,3,4-oxadiazole-2-carboxylate (270 mg, 78% yield) as a white solid. $^1$H NMR (400 MHz, DMSO-d$_6$) δ (ppm): 9.81 (s, 1H), 9.17 (s, 1H), 9.09 (s, 1H), 8.24 (d, J=4.4 Hz, 1H), 7.94 (d, J=7.2 Hz, 1H), 7.86 (t, J=7.6 Hz, 1H), 7.75-7.72 (t, J=7.6 Hz, 3H), 7.59-7.51 (m, 5H), 7.34 (d, J=7.2 Hz, 2H), 7.24 (t, J=6.4 Hz, 1H), 6.98 (t, J=3.2 Hz, 1H), 4.77 (d, J=4.0 Hz, 2H). LCMS Method Q: retention time 1.39 min; [M+1]=514.5; HPLC Method B: purity 98.1%, retention time=8.74 min.

Step 2. Example 194

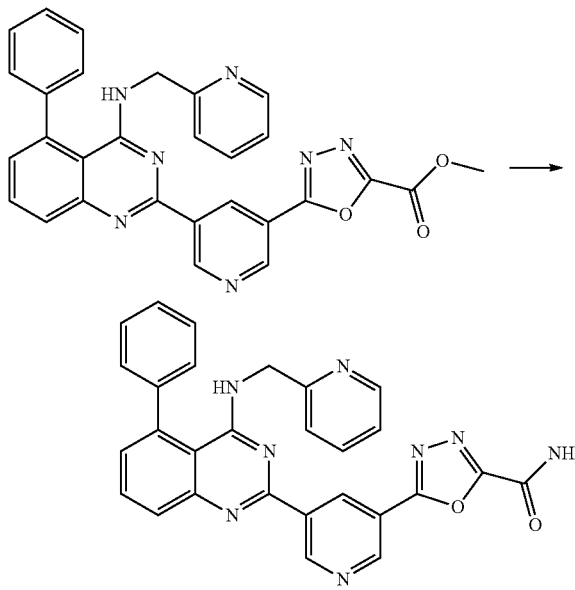

A solution of the methyl 5-(5-(5-phenyl-4-(pyridin-2-ylmethylamino)quinazolin-2-yl)pyridin-3-yl)-1,3,4-oxadiazole-2-carboxylate (0.0700 g, 0.136 mmol) in NH$_3$ (2.0 M in MeOH, 10 mL) was heated at 60° C., in a sealed vessel for 4 h. After this time, the reaction mixture was allowed to cool to room temperature and the solvent was evaporated under reduced pressure to provide the crude product. The crude product was recrystallized from EtOAc/hexanes to provide Example 194 (0.06 g, 99% yield). $^1$H NMR (400 MHz, DMSO-d$_6$) δ (ppm): 9.81 (s, 1H), 9.17 (s, 1H), 9.09 (s, 1H), 8.24 (d, J=4.4 Hz, 1H), 7.94 (d, J=7.2 Hz, 1H), 7.86 (t, J=7.6 Hz, 1H), 7.75-7.72 (t, J=7.6 Hz, 3H), 7.59-7.51 (m, 5H), 7.34 (d, J=7.2 Hz, 2H), 7.24 (t, J=6.4 Hz, 1H), 6.98 (t, J=3.2 Hz, 1H), 4.77 (d, J=4.0 Hz, 2H). LCMS Method Q: retention time 1.39 min; [M+1]=499.50. HPLC Method B: purity 98.1%, retention time=8.74 min.

Example 195

2-(5-(5-Phenyl-4-(pyridin-2-ylmethylamino)quinazolin-2-yl)pyridin-3-yl)propan-2-ol

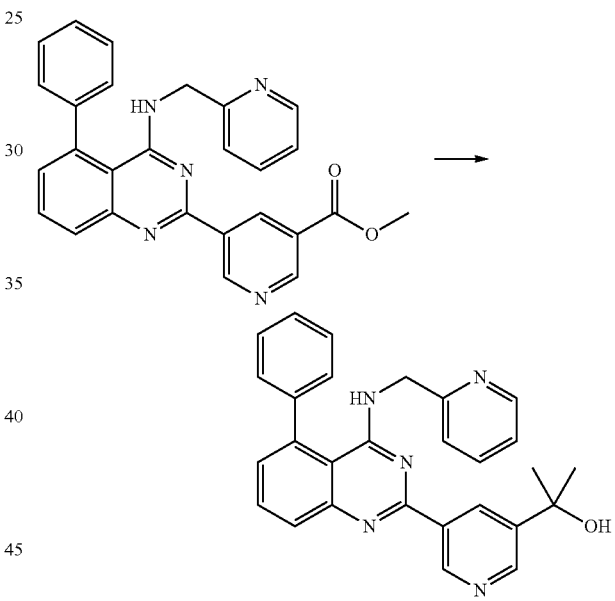

To a solution of methyl 5-(5-phenyl-4-(pyridin-2-ylmethylamino)quinazolin-2-yl)nicotinate (from Example 43, 0.30 g, 0.67 mmol) in THF (10 mL) was added methyl magnesium iodide (3.3 mL, 10 mmol) at 0° C. under nitrogen atmosphere. Upon the completion of addition, the reaction mixture was stirred at room temperature for 16 h. After this time, the reaction mixture was quenched with the addition of water and then extracted with ethyl acetate (50 mL). The combined organic extracts were washed successively with water and brine. The organic layer was dried, filtered and concentrated. The resulting residue was purified by column chromatography on silica gel (5% methanol in dichloromethane) to afford Example 195 (0.090 g, 30% yield) as an off white solid. $^1$H NMR (400 MHz, DMSO-d$_6$) δ (ppm): 9.51 (s, 1H), 8.81 (s, 1H), 8.79 (s, 1H), 8.25 (d, 1H, J=4.4 Hz), 7.92 (d, 1H, J=8.4 Hz), 7.85 (dt, 1H, J=7.2, 8 Hz), 7.74 (m, 1H), 7.60-7.51 (m, 5H), 7.34-7.31 (m, 2H), 7.29-7.22 (m, 1H), 7.24 (t, 1H, J=4.8, 7.6 Hz), 6.80 (s, 1H), 5.36 (s, 1H), 4.75 (d, 2H, J-4 Hz), 1.51 (s, 6H). HPLC Method B:

purity 99.0%, retention time=7.26 min; LCMS Method E: retention time 1.8 min; [M+1]=447.50.

Example 196

(5-(5-Phenyl-4-(pyridin-2-ylmethylamino)quinazolin-2-yl)pyridin-3-yl)methyl isopropylcarbamate

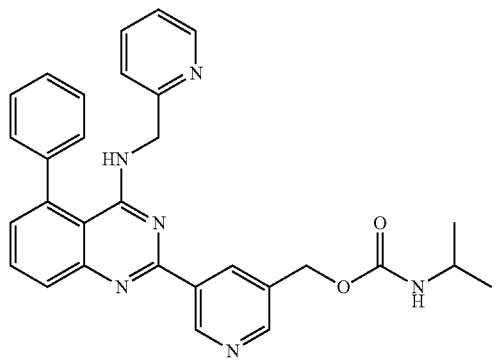 [SMILES: CC(C)NC(=O)OCc1cncc(-c2nc(NCc3ccccn3)c3c(-c4ccccc4)cccc3n2)c1]

Step 1. Preparation of (5-(5-phenyl-4-(pyridin-2-ylmethylamino)quinazolin-2-yl)pyridin-3-yl)methanol

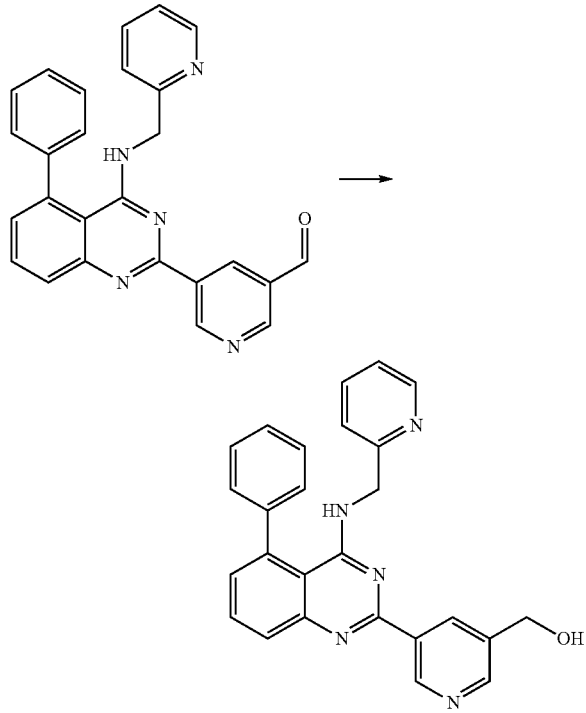 [SMILES: O=Cc1cncc(-c2nc(NCc3ccccn3)c3c(-c4ccccc4)cccc3n2)c1 ; OCc1cncc(-c2nc(NCc3ccccn3)c3c(-c4ccccc4)cccc3n2)c1]

To a solution of 5-(5-phenyl-4-(pyridin-2-ylmethylamino)quinazolin-2-yl) nicotinaldehyde (from example 191, 1.0 g, 2.4 mmol) in ethanol (15 mL) was added NaBH$_4$ (0.28 g, 7.19 mmol). Upon completion of addition, the reaction mixture was stirred at RT for 4 h. After this time, a saturated solution of ammonium chloride was added and the resulting mixture was extracted into ethyl acetate. The organic layer was separated, dried, filtered and concentrated under reduced pressure to yield a residue. The residue was purified by silica gel column chromatography using 2% methanol in DCM as the eluent to provide pure (5-(5-phenyl-4-(pyridin-2-ylmethylamino)quinazolin-2-yl)pyridin-3-yl)methanol (0.71 g, 71% yield). $^1$H NMR (400 MHz, DMSO-d$_6$) δ (ppm): 9.51 (s, 1H), 8.72 (s, 1H), 8.63 (s, 1H), 8.23 (d, 1H, J=4.8 Hz), 7.88 (dd, 1H, J=7.6 Hz, 8.4 Hz), 7.85-7.80 (m, 1H), 7.73 (dt, 1H, J=1.2 Hz, 7.6 Hz), 7.61-7.48 (m, 5H), 7.33 (d, 2H, J=19.2 Hz), 7.27 (d, 1H, J=14 Hz), 7.23 (dt, 1H, J=1.6, 7.2 Hz), 6.87 (t, 1H, J=4.0 Hz, 1H), 5.47 (t, 1H, J=5.6), 4.75 (d, 2H, J-4 Hz), 4.67 (d, 2H, J=5.6 Hz). LCMS Method U: retention time 1.46 min; [M+1]=420.2; HPLC Method A2: purity 99.5%, retention time=5.77 min.

Step 2. Example 196

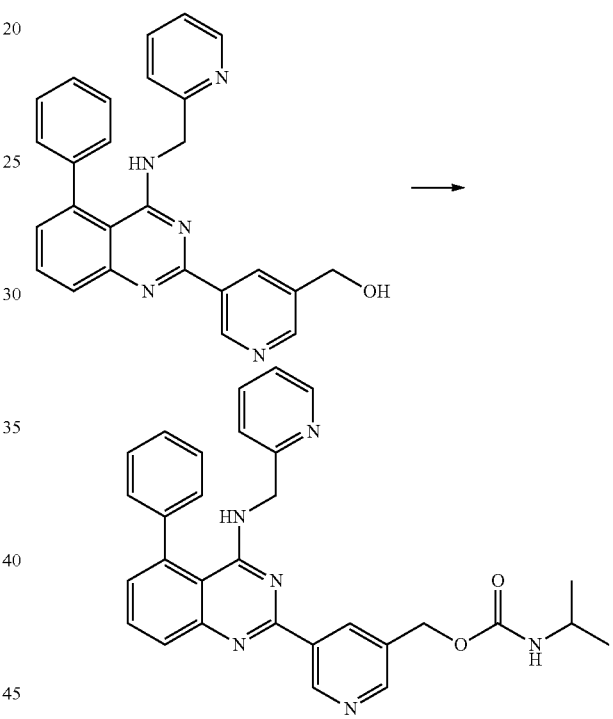

To a solution of (5-(5-phenyl-4-(pyridin-2-ylmethylamino)quinazolin-2-yl)pyridin-3-yl)methanol (0.050 g, 0.12 mmol) in DCM (2 mL) was added DMAP (0.014 g, 0.12 mmol) followed by isopropylisocyanate (0.010 g, 012 mmol) at 0° C. Upon the completion of addition, the reaction mixture was slowly heated to 45° C. where it stirred for 8 h. At the conclusion of this period, the reaction mixture was washed with water and extracted with ethyl acetate. The combined organic extracts were dried, filtered, concentrated under reduced pressure to yield a residue. The residue purified by silica gel column chromatography (2% MeOH in DCM) to provide Example 196 (30 mg, 50% yield). $^1$H NMR (400 MHz, DMSO-d$_6$, δ): 9.59 (s, 1H); 8.75 (s, 1H); 8.70 (s, 1H); 8.24 (d, 1H, J=4.8 Hz); 7.88 9 dd, 1H, J=1.2, 8 Hz); 7.84 (t, 1H, J=7.2 Hz); 7.73 (dt, 1H, J=1.6, 7.6 Hz); 7.60-7.49 (m, 5H); 7.38-7.29 (m, 3H); 7.23 (dd, 1H, J=1.6, 7.2 Hz); 6.87 (br s, 1H); 5.18 (br s, 1H); 4.75 (d, 2H, J=4 HZ); 3.72-3.60 (m, 1H); 1.08 (d, 6H, J=6.4 Hz). LCMS Method Y: retention time 2.00 min, [M+1]=505.4; HPLC Method A1: purity 98.9%, retention time=8.12 min.

Example 197

2-Methyl-1-(5-(5-phenyl-4-(pyridin-2-ylmethyl-amino)quinazolin-2-yl)pyridin-3-yl)propan-1-ol

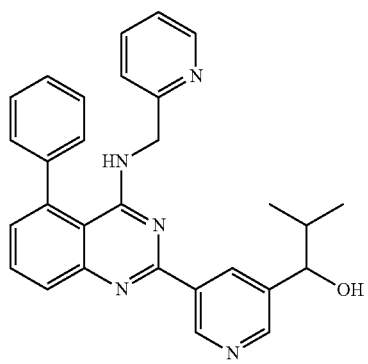 [SMILES: CC(C)C(O)c1cncc(-c2nc(NCc3ccccn3)c3c(-c4ccccc4)cccc3n2)c1]

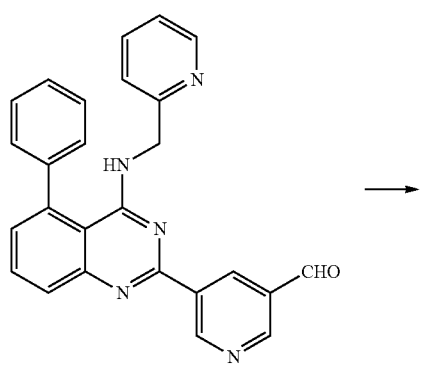

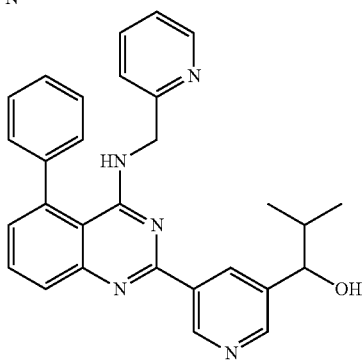

To a solution of 5-(5-phenyl-4-(pyridin-2-ylmethylamino)quinazolin-2-yl)nicotinaldehyde (from example 191, 0.15 g, 0.35 mmol) in THF at −78° C. was added isopropyl magnesium chloride solution (2 M in THF, 10 eq). Upon completion of addition, the reaction mixture was allowed to reach room temperature. Once at the prescribed temperature, the reaction mixture was stirred for 16 h. After this time, the reaction mixture was quenched with a saturated solution of ammonium chloride (2 mL) and then extracted with ethyl acetate. The combined organic layers were dried, concentrated under reduced pressure, and purified by silica gel column chromatography (2% MeOH in DCM) to yield racemic Example 197 (20 mg, 12% yield). The racemate was separated into the corresponding enantiomers using chiral HPLC to provide the pure Enantiomer 1 (4 mg) and Enantiomer 2 (3.5 mg), respectively. CHIRAL HPLC: (CHIRAL PAK IC (250×4.6) mm, 5 micron; mobile phase (85% hexane, 15% ethanol; flow rate: 1 ml/min}. Enantiomer-1: $^1$H NMR (400 MHz, DMSO-$d_6$, δ): 9.51 (s, 1H); 8.69 (s, 1H); 8.60 (s, 1H); 8.26 (d, 1H, J=4.4 Hz); 7.90 (d, 1H, J=7.6 Hz); 8.55 (t, 1H, J=7.2 Hz); 7.73 (dt, 1H, J=1.6, 7.6 Hz); 7.61-7.50 (m, 4H); 7.38-7.30 (m, 2H); 7.24 (t, 1H, J=9.2 Hz); 6.81 (br s, 1H); 5.42 (d, 1H, J=4.4 Hz); 4.74 (d, 2H, J=4 Hz); 4.45 (t, 1H, J=4.8 Hz); 2.00-2.90 (m, 1H); 0.92 (d, 3H, J=6.4 Hz); 0.82 (t, 3H, J=6.4 Hz). LCMS Method T: retention time 1.78 min, [M+1]=462.2; HPLC Method A1: purity 99.0%, retention time=6.93 min. CHIRAL HPLC: retention time 19.78 {CHIRAL PAK IC (250×4.6) mm, 5 micron; mobile phase (hexane (85), Ethanol (15); Flow rate: 1 ml/min}. Enantiomer-2: $^1$H NMR (400 MHz, DMSO-$d_6$, δ): 9.51 (s, 1H); 8.69 (s, 1H); 8.60 (s, 1H); 8.26 (d, 1H, J=4.4 Hz); 7.90 (d, 1H, J=7.6 Hz); 8.55 (t, 1H, J=7.2 Hz); 7.73 (dt, 1H, J 1.6, 7.6 Hz); 7.61-7.50 (m, 4H); 7.38-7.30 (m, 2H); 7.24 (t, 1H, J=9.2 Hz); 6.81 (br s, 1H); 5.42 (d, 1H, J=4.4 Hz); 4.74 (d, 2H, J=4 Hz); 4.45 (t, 1H, J=4.8 Hz); 2.00-2.90 (m, 1H); 0.92 (d, 3H, J=6.4 Hz); 0.82 (t, 3H, J=6.4 Hz). LCMS Method T: retention time 1.78 min, [M+1]=462.2; HPLC Method A1: purity 96.9%, retention time=6.93 min. CHIRAL HPLC: retention time 22.02 {CHIRAL PAK IC (250×4.6) mm, 5 micron; mobile phase (hexane (85), Ethanol (15); Flow rate: 1 ml/min}.

Example 198

2-(5-(5-Phenyl-4-(pyridin-2-ylmethylamino)quinazolin-2-yl)pyridin-3-ylsulfonyl)acetamide

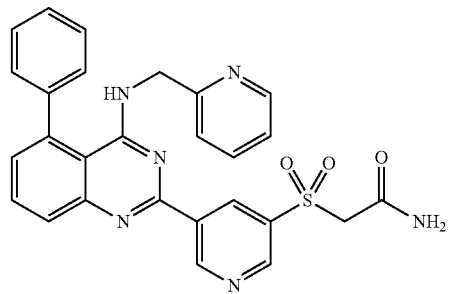 [SMILES: NC(=O)CS(=O)(=O)c1cncc(-c2nc(NCc3ccccn3)c3c(-c4ccccc4)cccc3n2)c1]

Step 1. Preparation of methyl 2-(5-bromopyridin-3-ylthio)acetate

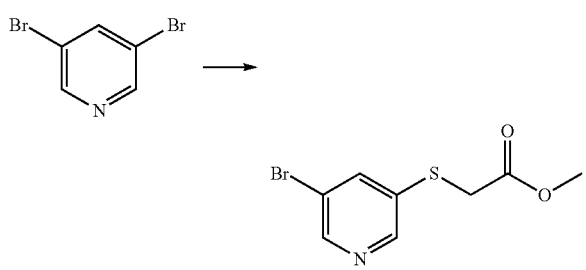

To a solution of sodium hydride (0.518 g, 21.0 mmol) in DMF (5 mL) at 0° C. was added dropwise a solution of methylthioglycolate (2 g, 18 mmol) in DMF (6 mL). Upon completion of addition, the reaction mixture was stirred at RT for 30 min. After this time, a solution of 3,5-dibromopyridine (4.46 g, 18 mmol) in DMF (10 mL) was added dropwise. The resulting reaction mixture was allowed stir at RT for 16 h. At the conclusion of this period, the reaction mixture was quenched by the addition of ice and the resulting slurry was extracted with ethyl acetate. The combined organic layers were dried and concentrated under reduced pressure. The resulting residue was purified by silica gel column chromatography (1.5% methanol in DCM) to yield methyl 2-(5-bromopyridin-3-ylthio)acetate (1.2 g, 24% yield). LCMS Method A: retention time 1.49 min; [M+1]=262.

Step 2. Preparation of methyl 2-(5-bromopyridin-3-ylsulfonyl)acetate

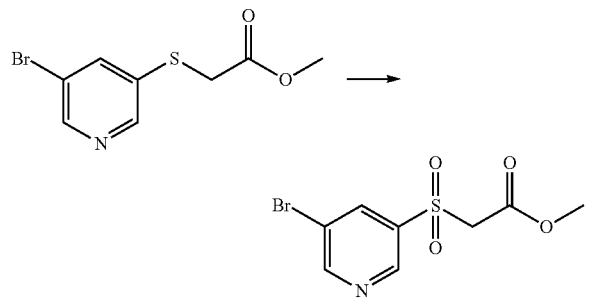

To a solution of methyl 2-(5-bromopyridin-3-ylthio)acetate (1.2 g, 4.6 mmol) in 3:1 MeOH:H$_2$O (12 mL) was added oxone (2.8 g, 4.6 mmol). Upon completion of addition, the reaction mixture was stirred at RT for 5 h. At the conclusion of this period, the reaction mixture was concentrated under reduced pressure and then extracted with DCM. The combined organic layers were dried and concentrated under reduced pressure to yield a residue. The residue was purified by silica gel column chromatography (1.5% methanol in DCM) to yield methyl 2-(5-bromopyridin-3-ylsulfonyl)acetate (0.6 g, 46% yield). $^1$H NMR (400 MHz, DMSO-d$_6$, δ): 9.11 (d, 1H, J=2 Hz); 9.02 (d, 1H, J=2 Hz); 8.57 (t, 1H, J=2 Hz); 4.95 (s, 2H); 3.63 (s, 3H). LCMS Method T: retention time 1.12 min; [M+1]=294.0.

Step 3. Preparation of 2-(5-bromopyridin-3-ylsulfonyl)acetamide

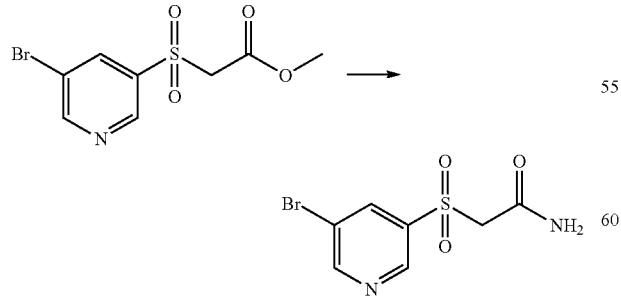

To a solution of methyl 2-(5-bromopyridin-3-ylsulfonyl) acetate (0.2 g, 0.67 mmol) was added 5% ammonia in methanol (10 mL). Upon completion of addition, the reaction mixture was stirred at 60° C. for 4 h. After this time, the reaction mixture was allowed to cool to room temperature. Once at the prescribed temperature, the reaction mixture was concentrated under reduced pressure to afford 2-(5-bromopyridin-3-ylsulfonyl)acetamide (0.2 g) as a white solid. LCMS Method W: retention time 0.92 min; [M−1]=277.0.

Step 4. Preparation of 2-(5-(4,4,5,5-tetramethyl-1,3,2-dioxaborolan-2-yl)pyridin-3-ylsulfonyl)acetamide

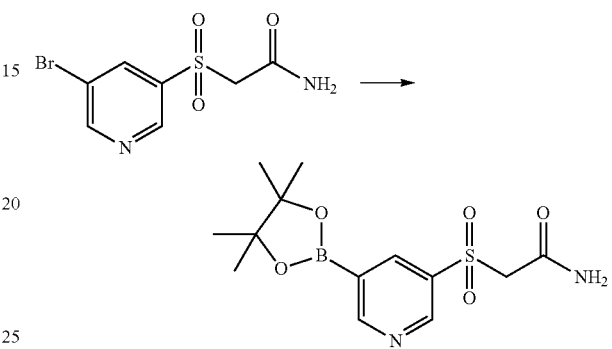

A mixture 2-(5-bromopyridin-3-ylsulfonyl)acetamide (0.2 g, 0.7 mmol), bis(pinacolato)diboron (0.27 g, 1 mmol) and potassium acetate (0.2 g, 2.1 mmol) in 1,4-dioxane (10 mL) was degassed with nitrogen for 15 min. After this time, (1,1'-bis(diphenylphosphino)ferrocene)palladium (II) chloride dichloromethane complex (0.028 g, 0.035 mmol) was added and the resulting mixture was again degassed for 10 min. with nitrogen. The reaction mixture was then heated in the microwave at 100° C. for 16 h. At the conclusion of this period, the reaction mixture was filtered through celite and the filtrate was concentrated under reduced pressure to provide 2-(5-(4,4,5,5-tetramethyl-1,3,2-dioxaborolan-2-yl) pyridin-3-ylsulfonyl)acetamide (0.170 g), which was used without further purification.

Step 5. Example 198

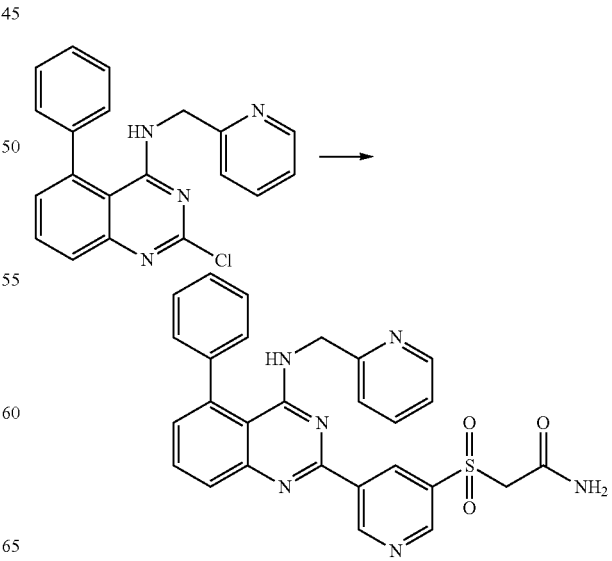

To a solution of 2-chloro-5-phenyl-N-(pyridin-2-ylmethyl)quinazolin-4-amine (from example 1, step 4, 0.182 g, 0.52 mmol) in 1,4-dioxane (6 mL) and H$_2$O (1.2 mL) under nitrogen was added 2-(5-(4,4,5,5-tetramethyl-1,3,2-dioxaborolan-2-yl)pyridin-3-ylsulfonyl)acetamide (0.170 g, 0.57 mmol), and potassium carbonate (0.215 g, 1.56 mmol). Upon completion of addition, the reaction mixture was degassed with nitrogen for 15 min. After this time, (1,1'-bis(diphenylphosphino)-ferrocene)palladium (II) chloride dichloromethane complex (0.042 g, 0.052 mmol) was added. The resulting mixture was again degassed with nitrogen for 10 min. At the conclusion of this period, the reaction mixture was stirred at 100° C. for 16 h, then allowed to cool to room temperature and quenched by the addition of water. Upon the completion of addition, the reaction mixture was transferred to a separation funnel and the aqueous layer was extracted with ethyl acetate. The combined organic portions were washed with water and saturated NaCl, dried over Na$_2$SO$_4$, filtered and concentrated under reduced pressure. The resulting concentrate was purified by column chromatography to afford Example 198 (0.020 g, 8% yield). $^1$H NMR (400 MHz, DMSO-d$_6$, δ): 9.89 (s, 1H); 9.17 (s, 1H); 9.14 (s, 1H); 8.25 (s, 1H); 7.96 (dd, 1H, J=1.6, 4.4 Hz); 7.88 (dd, 1H, J=7.2, 8.4 Hz); 7.73 (dd, 1H, J=2, 7.6 Hz); 7.61-7.50 (m, 5H); 7.45 (br s, 1H); 7.39-7.33 (m, 2H); 7.24 (t, 1H, J=2.4 Hz); 6.96 (br s, 1H); 4.77 (d, 2H, J=4 Hz); 4.49 (s, 2H). LCMS Method Y: retention time 1.83 min, [M−1]=509.0; HPLC Method A1: purity 96.2%, retention time=6.79 min.

Example 199

2-Methyl-2-(5-(5-phenyl-4-(pyridin-2-ylmethylamino)quinazolin-2-yl)pyridin-3-yl)propanenitrile

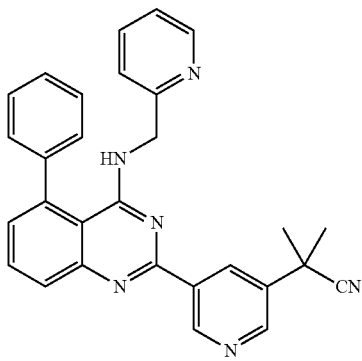 [SMILES: CC(C)(C#N)c1cncc(-c2nc(NCc3ccccn3)c3c(-c4ccccc4)cccc3n2)c1]

Step 1. Preparation of
3-bromo-5-chloromethyl-pyridine

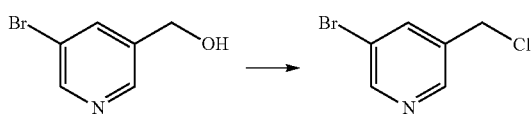 [SMILES: OCc1cncc(Br)c1 ; ClCc1cncc(Br)c1]

To a solution of (5-bromo-pyridin-3-yl)-methanol (0.5 g, 2.68 mmol) in DCM (10 mL) was added thionyl chloride (0.5 mL). The resulting solution was stirred at room temperature for 2 h. After this time, the reaction mixture was quenched with water and extracted into DCM. The organic extracts were washed with brine filtered and concentrated under reduced pressure to give 3-bromo-5-chloromethyl-pyridine (0.45 g, 82%), which was used in the next step without further purification.

Step 2. Preparation of 2-(5-bromopyridin-3-yl)
acetonitrile

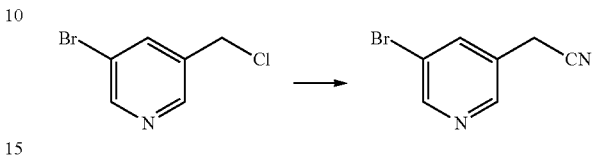

Potassium cyanide (0.21 g, 3.27 mmol) was added to a solution of 3-bromo-5-chloromethyl-pyridine (0.45 g; 2.18 mmol) in DMF (10 mL). Upon completion of addition, the reaction mixture was stirred at room temperature for 16 h. After this time, the reaction mixture was quenched with water and extracted with ethyl acetate. The organic phase was washed with water and brine, dried over Na$_2$SO$_4$, filtered and evaporated. The resulting residue was purified by silica gel column chromatography (10% ethyl acetate in hexane) to provide 2-(5-bromopyridin-3-yl) acetonitrile (200 mg, 46.5%). $^1$H NMR (400 MHz, DMSO-d$_6$) δ (ppm): 8.68 (d, 1H, J=2 Hz), 8.51 (d, 1H, J=2 Hz), 7.88 (t, 1H, J=2 Hz), 3.77 (s, 2H).

Step 3. Preparation of
2-(5-bromopyridin-3-yl)-2-methylpropanenitrile

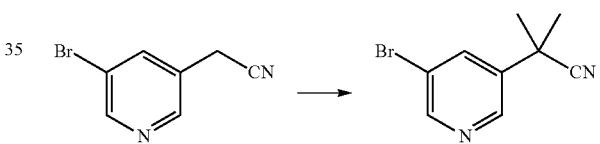

To a suspension of NaH (95%, 0.17 g, 7.1 mmol) in THF was added a solution of 2-(5-bromopyridin-3-yl)acetonitrile (0.7 g, 3.0 mmol) in THF (5 mL) at 0° C. and the resulting reaction mixture stirred at RT for 30 min. At the conclusion of this period, methyl iodide (0.66 mL, 8.9 mmol) was added and then stirring continued for an additional 16 h. After this time, the reaction mixture was quenched by the addition of saturated ammonium chloride solution and then extracted into ethyl acetate. The combined organic portions were concentrated under reduced pressure and the resulting residue was purified by flash column chromatography (15% ethyl acetate in hexanes) to yield 2-(5-bromopyridin-3-yl)-2-methylpropanenitrile (0.35 g, 56%). $^1$H NMR (400 MHz, DMSO-d$_6$) δ (ppm): 8.67 (d, 1H, J=2 Hz), 8.45 (d, 1H, J=2 Hz), 7.73 (t, 1H, J=2 Hz), 2.44 (s, 3H), 2.28 (s, 3H).

Step 4. Preparation of 2-methyl-2-(5-(4,4,5,5-tetramethyl-1,3,2-dioxaborolan-2-yl)pyridin-3-yl)propanenitrile

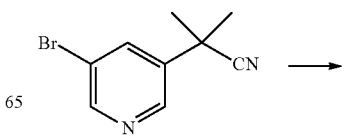

-continued

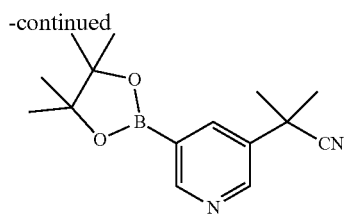

A mixture of 2-(5-bromopyridin-3-yl)-2-methylpropanenitrile (0.4 g, 1.77 mmol), bis(pinacolato)diboron (0.67 g, 2.65 mmol) and potassium acetate (0.69 g, 7.04 mmol) in 1,4-dioxane (15 mL) was degassed with nitrogen for 15 min. After this time, (1,1'-bis(diphenylphosphino)ferrocene)palladium (II) chloride dichloromethane complex (0.11 g, 0.15 mmol) was added. The reaction mixture was again degassed for 10 min with nitrogen and then heated in the microwave at 120° C. for 45 min. At the conclusion of this period, the reaction mixture was filtered through celite and the filtrate was concentrated under reduced pressure to provide 2-methyl-2-(5-(4,4,5,5-tetramethyl-1,3,2-dioxaborolan-2-yl)pyridin-3-yl)propanenitrile (0.53 g), which was used without further purification.

Step 5. Example 199

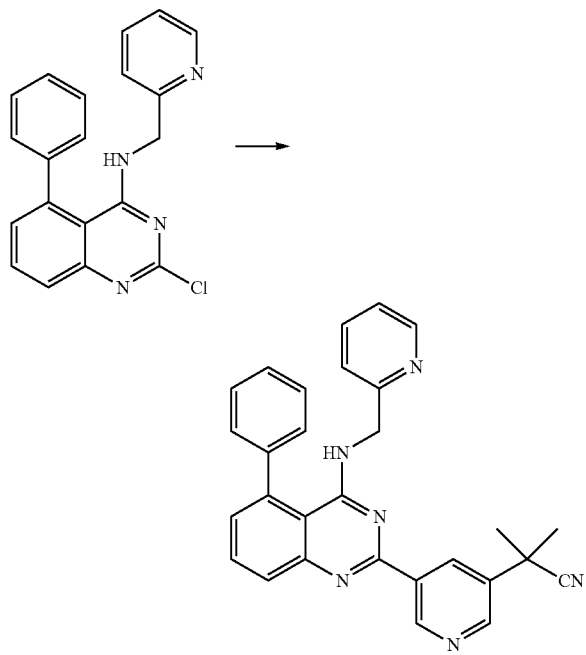

To a solution of 2-chloro-5-phenyl-N-(pyridin-2-ylmethyl)quinazolin-4-amine (from example 1, step 4, 0.4 g, 1 mmol) in 1,4-dioxane (15 mL) and H₂O (1 mL) under nitrogen was added 2-methyl-2-(5-(4,4,5,5-tetramethyl-1,3,2-dioxaborolan-2-yl)pyridin-3-yl)propanenitrile (0.5 g, 2 mmol) and potassium carbonate (0.48 g, 3.5 mmol). Upon completion of addition, the mixture was degassed with nitrogen for 15 min. At the conclusion of this period, (1,1'-bis (diphenylphosphino)ferrocene)palladium (II) chloride dichloromethane complex (85 mg, 0.11 mmol) was added and the reaction mixture was again degassed with nitrogen for 10 min. After this time, the reaction mixture was stirred at 95° C. for 16 h. At the conclusion of this period, the reaction mixture was allowed to cool to room temperature and then quenched by the addition of water. Upon completion of addition, the reaction mixture was transferred to a separation funnel and the aqueous layer was extracted with ethyl acetate. The combined organic portions were washed with water and saturated NaCl, dried over Na₂SO₄, filtered and concentrated under reduced pressure. The resulting residue was purified by column chromatography (2% methanol in dichloromethane) to afford Example 199 (0.38 g, 72% yield) as an off-white solid. $^1$H NMR (400 MHz, DMSO-d₆) δ (ppm): 9.61 (s, 1H), 8.92 (s, 1H), 8.88 (s, 1H), 8.24 (d, 1H, J=4.4 Hz), 7.93 (dd, 1H, J=1.2 Hz, 4.4 Hz), 7.84 (t, 1H, J=8 Hz), 7.73 (dt, 1H, J=1.6, 8 Hz), 7.63-7.50 (m, 5H), 7.36-7.30 (m, 2H), 7.24 (t, 1H, J=5.6 Hz), 6.84 (br s, 1H), 4.75 (d, 2H, J=4.0 Hz), 1.84 (s, 6H). LCMS Method Y: retention time 2.04 min; [M+1]=457.0; HPLC Method A1: purity 99.1%, retention time=8.39 min.

Example 200

2-(5-(5-Phenyl-4-(pyridin-2-ylmethylamino)quinazolin-2-yl)pyridin-3-yl)propanamide

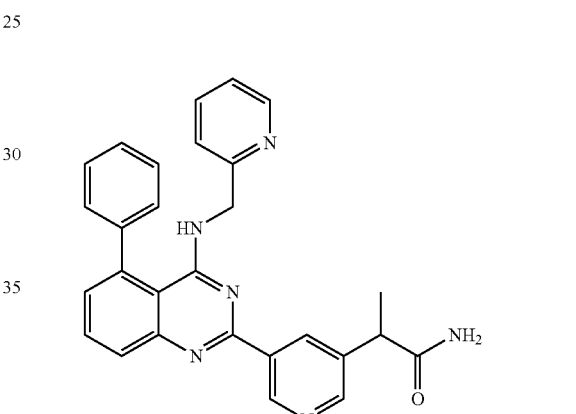

Step 1. Preparation of
2-(5-bromopyridin-3-yl)propanenitrile

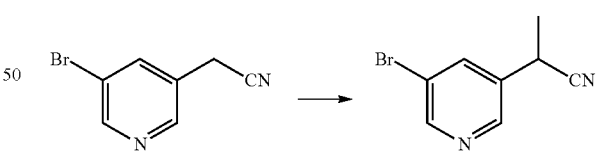

To a suspension of NaH (95%, 113 mg, 4.70 mmol) in DMF was added a solution of 2-(5-bromopyridin-3-yl)acetonitrile (from example 199, 0.8 g, 4 mmol) in DMF. Upon completion of addition, the reaction mixture was stirred at RT for 30 min. After this time, methyl iodide (0.3 mL, 4 mmol) was added and the stirring continued for an additional 4 h. At the conclusion of this period, the reaction mixture was quenched by addition of saturated ammonium chloride solution and then extracted into ethyl acetate. The combined organic portions were concentrated under reduced pressure and the resulting residue was purified by flash column chromatography (30% EtOAc in hexanes) to yield racemic 2-(5-bromopyridin-3-yl)propanenitrile (200 mg, 24%). ¹H NMR (400 MHz, CDCL₃) δ (ppm): 8.67 (d, 1H, J=2 Hz); 8.53 (d, 1H, J=5 Hz); 7.88 (t, 1H, J=5 Hz); 3.94 (q, 1H, J=7.6 Hz); 1.69 (d, 3H, J=7.6 Hz). LCMS Method Y: retention time 1.54 min; [M+1]=212.6.

Step 2. Preparation of 2-(5-(4,4,5,5-tetramethyl-1,3,2-dioxaborolan-2-yl)pyridin-3-yl)propanenitrile

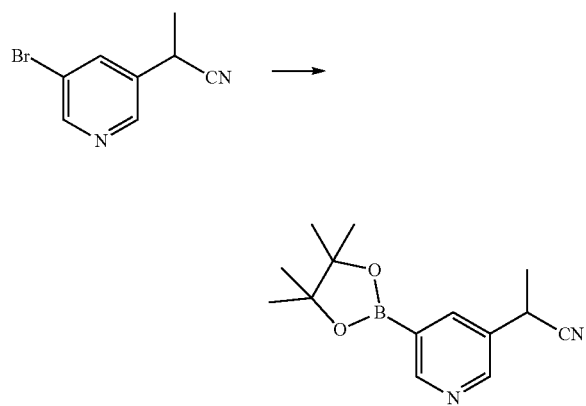 [SMILES: CC(C#N)c1cncc(Br)c1 ; CC(C#N)c1cncc(B2OC(C)(C)C(C)(C)O2)c1]

A mixture of 2-(5-bromopyridin-3-yl)propanenitrile (0.1 g, 0.5 mmol), bis(pinacolato)diboron (0.18 g, 0.70 mmol) and potassium acetate (0.19 g, 1.9 mmol) in 1,4-dioxane (8 mL) was degassed with nitrogen for 15 min. After this time, (1,1'-bis(diphenylphosphino)ferrocene)palladium (II) chloride dichloromethane complex (28 mg, 0.038 mmol) was added and the resulting mixture was again degassed for 10 min. with nitrogen. At the conclusion of this period, the reaction mixture was heated in the microwave at 120° C. for 45 min. After this time, the reaction mixture was filtered through celite and the filtrate was concentrated under reduced pressure to provide racemic 2-(5-(4,4,5,5-tetramethyl-1,3,2-dioxaborolan-2-yl)pyridin-3-yl)propanenitrile (0.12 g), which was used without further purification. LCMS Method Y: retention time 1.83 min; [M+1]=258.8.

Step 3. Preparation of 2-(5-(5-phenyl-4-(pyridin-2-ylmethylamino) quinazolin-2-yl)pyridin-3-yl)propanenitrile

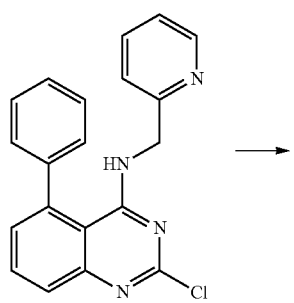

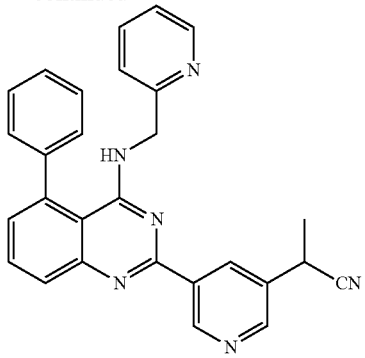

To a solution of 2-chloro-5-phenyl-N-(pyridin-2-ylmethyl)quinazolin-4-amine (from example 1, step 4, 0.12 g, 0.5 mmol) in 1,4-dioxane (8 mL) and H₂O (0.55 mL) under nitrogen was added 2-(5-(4,4,5,5-tetramethyl-1,3,2-dioxaborolan-2-yl)pyridin-3-yl)propanenitrile (0.120 g, 0.4 mmol) and potassium carbonate (0.14 g, 1 mmol). The resulting mixture was degassed with nitrogen for 15 min. After this time, (1,1'-bis(diphenylphosphino)ferrocene)palladium (II) chloride dichloromethane complex (0.26 mg, 0.036 mmol) was added and the reaction mixture was again degassed with nitrogen for 10 min. At the conclusion of this period, the reaction mixture was stirred at 95° C. for 16 h. The reaction mixture was then allowed to cool to room temperature. Once at the prescribed temperature, the reaction mixture was quenched by the addition of water and then transferred to a separation funnel. The aqueous layer was extracted with ethyl acetate. The combined organic portions were washed with water and saturated NaCl, dried over Na₂SO₄, filtered and concentrated under reduced pressure. The resulting concentrate was purified by silica gel column chromatography using 1% methanol in DCM to afford racemic 2-(5-(5-phenyl-4-(pyridin-2-ylmethylamino) quinazolin-2-yl)pyridin-3-yl)propanenitrile (95 mg, 63% yield) as an off white solid. ¹H NMR (400 MHz, DMSO-d₆) δ (ppm): 9.60 (s, 1H), 8.80 (d, 1H, J=2 Hz); 8.77 (s, 1H); 8.26 (d, 1H, J=6 Hz); 7.92 (dd, 1H, J=1.2, 6.8 Hz); 7.85 (t, 1H, J=6.8 Hz); 7.73 (dt, 1H, J=1.6, 7.6 Hz); 7.58-7.52 (m, 5H); 7.34-7.32 (m, 2H); 7.24 (t, 1H, 7.2 Hz); 6.86 (t, 1H, J=4 Hz); 4.76 (d, 2H, J=4.4 Hz); 4.59 (q, 1H, J=7.2 Hz); 1.68 (d, 3H, 7.2 Hz). LCMS Method Y: retention time 1.68 min, [M+1]=443.2.

Step 4. Preparation of 2-(5-(5-phenyl-4-(pyridin-2-ylmethylamino)quinazolin-2-yl)pyridin-3-yl)propanoic acid

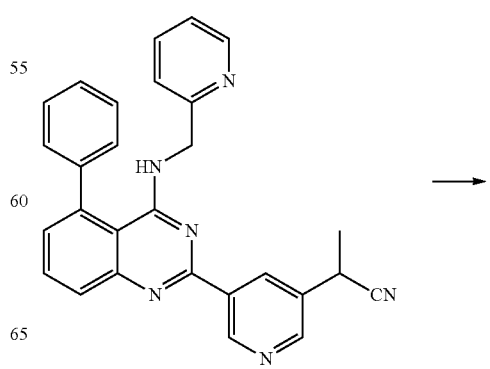

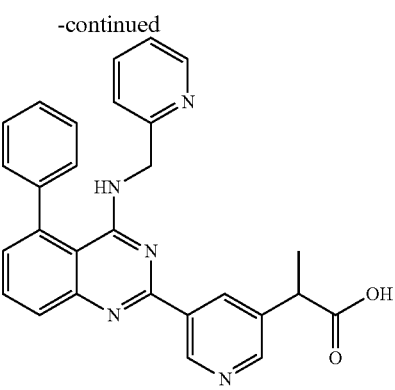

To a solution of racemic of 2-(5-(5-phenyl-4-(pyridin-2-ylmethylamino) quinazolin-2-yl)pyridin-3-yl) propanenitrile (0.08 g, 0.18 mmol) in ethanol/water (3:3 mL) was added solid NaOH (52 mg, 1.1 mmol). Upon completion of addition, the reaction mixture was heated at 95° C. for 16 h. After this time, the reaction mixture allowed to cool to RT and then water was added (5 mL). Upon completion of addition, 1.0 N HCl was added to the reaction mixture to adjust the pH to 6-7. Once at the prescribed pH, the aqueous portion was extracted with ethyl acetate. The combined organic extracts were dried, filtered and concentrated under reduced pressure to yield racemic 2-(5-(5-phenyl-4-(pyridin-2-ylmethylamino)quinazolin-2-yl)pyridin-3-yl)propanoic acid (32 mg, 39% yield).

Step 5. Example 200

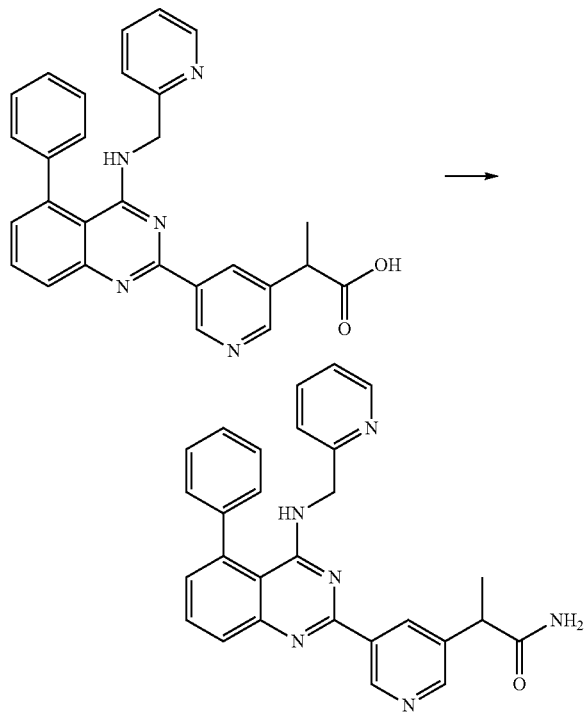

To a solution of racemic 2-(5-(5-phenyl-4-(pyridin-2-ylmethylamino)quinazolin-2-yl)pyridin-3-yl)propanoic acid (0.08 g, 0.2 mmol) in DMF (1.5 mL) was added EDCI (0.04 g, 0.2 mL), HOBt (0.028 g, 0.20 mmol) and DIPEA (0.2 mL, 0.7 mmol) followed by ammonium chloride (0.03 g, 0.7 mmol). The reaction mixture was stirred at room temperature for 2 h. After this time, the reaction mixture was washed and then extracted with ethyl acetate. The combined organic extracts were dried, filtered and concentrated under reduced pressure. The resulting residue was purified by flash silica gel column chromatography (5% methanol in dichloromethane) to obtain racemic Example 200 (35 mg, 43% yield) as an off-white solid. The enantiomers were separated by Chiral HPLC (CHIRAL HPLC: CHIRAL PAK IC (250×4.6) mm, 5 micron; mobile phase 85% hexane, 15% ethanol; Flow rate: 1 ml/min}). Enantiomer-1: $^1$H NMR (400 MHz, DMSO-d$_6$, δ): 9.50 (s, 1H); 8.70 (s, 1H); 8.65 (s, 1H); 8.25 (d, J=4.8 Hz, 1H), 7.91 (dd, J=1.2 Hz, 8.4 Hz, 1H), 7.84 (t, 7.2 Hz, 1H), 7.72 (dt, J=1.6 Hz, 7.6 Hz, 1H), 7.62-7.50 (m, 6 Hz), 7.36-7.30 (m, 2H), 7.23 (dd, J=5.2 Hz, 6.2 Hz, 1H), 6.98 (s, 1H), 6.83 (brs, 1H), 4.74 (d, J=4 Hz, 2H), 3.78 (t, J=7.7 Hz, 1H), 1.44 (d, J=7.2 Hz, 3H). LCMS Method Y: retention time 1.78 min; [M+1]=461.0; HPLC Method A1: purity 99.8%, retention time=6.04 min. CHIRAL HPLC: retention time 15.43 {CHIRAL PAK IC (250×4.6) mm, 5 micron; mobile phase 85% hexane, 15% ethanol; Flow rate: 1 ml/min}. Enantiomer-2: $^1$H NMR (400 MHz, DMSO-d$_6$, δ): 9.50 (s, 1H); 8.70 (s, 1H); 8.65 (s, 1H); 8.25 (d, J=4.8 Hz, 1H), 7.91 (dd, J=1.2 Hz, 8.4 Hz, 1H), 7.84 (t, 7.2 Hz, 1H), 7.72 (dt, J=1.6 Hz, 7.6 Hz, 1H), 7.62-7.50 (m, 6 Hz), 7.36-7.30 (m, 2H), 7.23 (dd, J=5.2 Hz, 6.2 Hz, 1H), 6.98 (s, 1H), 6.83 (brs, 1H), 4.74 (d, J=4 Hz, 2H), 3.78 (t, J=7.7 Hz, 1H), 1.44 (d, J=7.2 Hz, 3H). LCMS Method Y: retention time 1.78 min; [M+1]=461.0; HPLC Method A1: purity 99.6%, retention time=6.06 min. CHIRAL HPLC: retention time 19.08 {CHIRAL PAK IC (250×4.6) mm, 5 micron; mobile phase 85% hexane, 15% ethanol; Flow rate: 1 ml/min}.

Example 201

Methyl 5-(5-(5-phenyl-4-(pyridin-2-ylmethylamino) quinazolin-2-yl)pyridin-3-yl)-1,3,4-oxadiazole-2-carboxylate

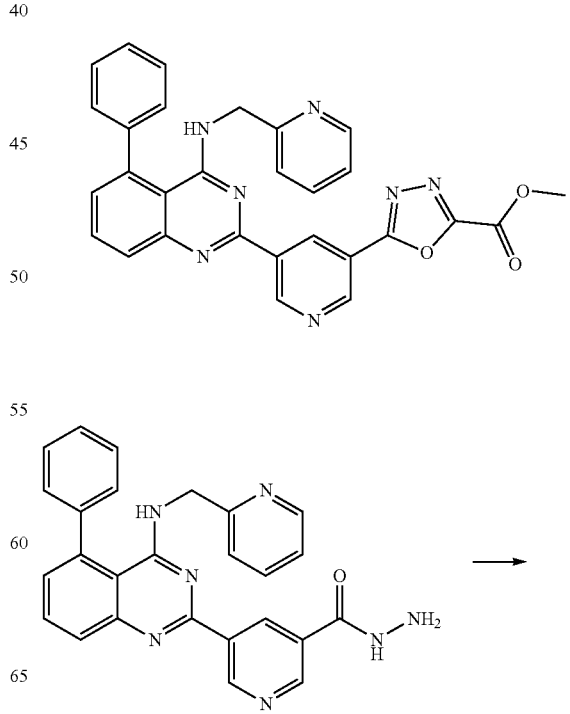

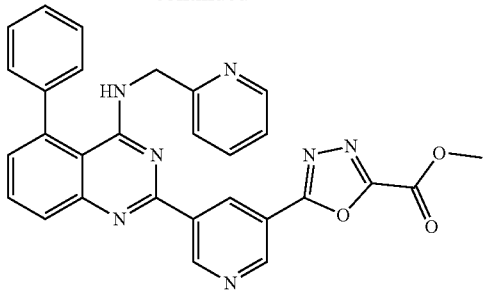 [SMILES: COC(=O)c1nnc(-c2cncc(-c3nc(NCc4ccccn4)c4c(-c5ccccc5)cccc4n3)c2)o1]

To a solution of 5-(5-phenyl-4-(pyridin-2-ylmethylamino) quinazolin-2-yl)nicotinohydrazide (from example 185, 0.3 g, 0.66 mmol) in DCM (3 mL) at 0° C. was added methyl 2-chloro-2-oxoacetate (0.062 mL, 0.66 mmol) and potassium carbonate (0273 g, 1.90 mmol). Upon completion of addition, the reaction mixture was stirred at RT for 16 h. After this time, water was added (2 mL) and the reaction mixture was extracted into DCM. The combined organic portions were dried and concentrated under reduced pressure. The resulting residue was dissolved in DCM (3 mL) and trifluoromethanesulfonic anhydride (0.19 mL, 1.1 mmol) and pyridine (0.149 mL, 1.80 mmol) were added. Upon completion of addition, the reaction mixture was stirred at RT for 16 h. At the conclusion of this period, the reaction mixture was quenched by the addition of water and then extracted with DCM. The combined organic portions were washed successively with water and brine, dried, filtered and concentrated under reduced pressure to yield a residue. The residue was purified using flash column chromatography (2% methanol in dichloromethane) to yield Example 201 (270 mg, 35% yield) as a white solid. $^1$H NMR (400 MHz, DMSO-$d_6$) δ (ppm): 9.87 (s, 1H0; 9.36 (s, 1H0; 9.32 9s, 1H); 8.26 (d, 1H, J=4.4 Hz); 7.98 (dd, 1H, J=1.2, 8.4 Hz); 7.87 (dd, 1H, J=1.4, 4 Hz); 7.74 (dt, 1H, J=1.6, 7.6 Hz); 7.62-7.50 (m, 5H); 7.39-7.31 (m, 2H); 7.24 (dd, 1H, J=5.2, 6.8 Hz); 6.95 (br t, 1H, J=4.4 Hz); 4.77 (d, 2H, J=4 Hz); 4.05 (s, 3H). LCMS Method Y: retention time 2.07 min; [M+1]=516.0; HPLC Method A1: purity 96.4%, retention time=8.75 min.

Example 202

1-(5-(5-Phenyl-4-(pyridin-2-ylmethylamino)quinazolin-2-yl)pyridin-3-yl)ethanol

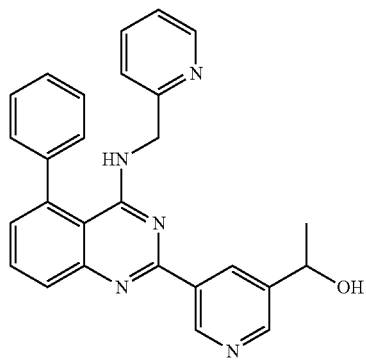 [SMILES: CC(O)c1cncc(-c2nc(NCc3ccccn3)c3c(-c4ccccc4)cccc3n2)c1]

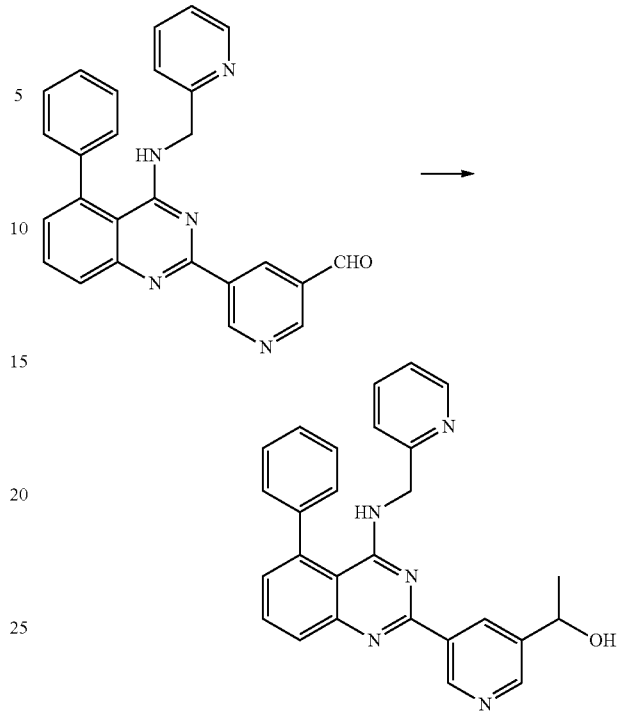

To a solution of 5-(5-phenyl-4-(pyridin-2-ylmethylamino) quinazolin-2-yl)nicotinaldehyde (from example 191, 0.3 g, 0.7 mmol) in THF (5 mL) at 0° C. was added methylmagnesium bromide solution (3 M in THF, 0.7 mL, 2 mmol). Upon completion of addition, the reaction mixture was stirred at room temperature for 5 h. After this time, the reaction mixture was quenched by the addition of saturated solution of ammonium chloride (2 mL) and then extracted into ethyl acetate. The combined organic layers were dried, filtered concentrated to yield a residue. The residue purified by column chromatography to yield racemic Example 202 (20 mg, 7% yield), which was separated into the corresponding enantiomers by chiral HPLC {CHIRAL PAK IC 250×4.6 mm, 5 micron; mobile phase 85% hexane, 15% ethanol; Flow rate: 1 ml/min} to provide pure Enantiomer 1 (11 mg) and Enantiomer 2 (12 mg), respectively. Enantiomer 1: $^1$H NMR (400 MHz, DMSO-$d_6$, δ): 9.50 (d, 1H, J=2 Hz); 8.73 (s, 1H); 8.65 (d, 1H, J=2 Hz); 8.24 (d, 1H, J=4.8 Hz); 7.90 (dd, 1H, J 1.2, 8.4 Hz); 7.83 (dd, 1H, J=7.2, 8.4 Hz); 7.71 (dt, 1H, J=1.6, 7.6 Hz); 7.60-7.49 (m, 5H); 7.38-7.27 (m, 2H); 7.23 (dd, 1H, J=3.2, 6.8 Hz); 6.82 (br t, 1H, J=4 Hz); 5.45 (d, 2H, J=4 Hz); 4.92 (t, 1H, J=3.6 Hz); 4.74 (d, 2H, J=4 Hz); 1.45 (d, 3H, J=6.8 Hz). LCMS Method V: retention time 1.60 min, [M+1]=434.2; HPLC Method A1: purity 99.8%, retention time=6.30 min. CHIRAL HPLC: retention time 16.27 {CHIRAL PAK IC (250×4.6) mm, 5 micron; mobile phase 85% hexane, 15% ethanol; Flow rate: 1 ml/min}. Enantiomer 2: $^1$H NMR (400 MHz, DMSO-$d_6$, δ): 9.50 (d, 1H, J=2 Hz); 8.73 (s, 1H); 8.65 (d, 1H, J=2 Hz); 8.24 (d, 1H, J=4.8 Hz); 7.90 (dd, 1H, J=1.2, 8.4 Hz); 7.83 (dd, 1H, J=7.2, 8.4 Hz); 7.71 (dt, 1H, J=1.6, 7.6 Hz); 7.60-7.49 (m, 5H); 7.38-7.27 (m, 2H); 7.23 (dd, 1H, J=3.2, 6.8 Hz); 6.82 (br t, 1H, J=4 Hz); 5.45 (d, 2H, J=4 Hz); 4.92 (t, 1H, J=3.6 Hz); 4.74 (d, 2H, J=4 Hz); 1.45 (d, 3H, J=6.8 Hz). LCMS Method T: retention time 1.61 min, [M+1]=434.2; HPLC Method A1: purity 96.8%, retention time=6.23 min. CHIRAL HPLC: retention time 21.02 {CHIRAL PAK IC (250×4.6) mm, 5 micron; mobile phase 85% hexane, 15% ethanol; Flow rate: 1 ml/min}.

Example 203

4-(5-Phenyl-4-(pyridin-2-ylmethylamino)quinazolin-2-yl)thiazol-2-amine

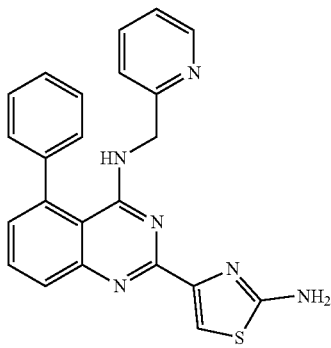 [SMILES: Nc1nc(-c2nc(NCc3ccccn3)c3c(-c4ccccc4)cccc3n2)cs1]

Step 1. Preparation of 2-(1-ethoxyvinyl)-5-phenyl-N-(pyridin-2-ylmethyl)quinazolin-4-amine

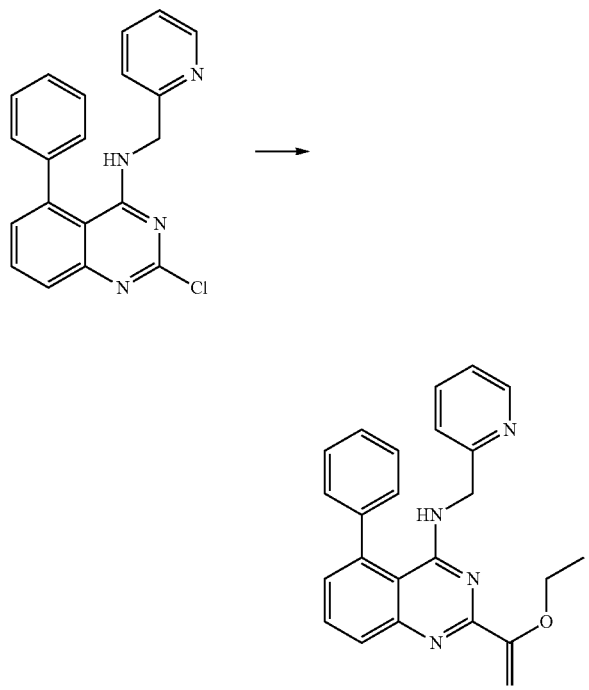

To 2-chloro-5-phenyl-N-(pyridin-2-ylmethyl)quinazolin-4-amine (1.0 g, 2.88 mmol) was added 1,4-dioxane (15 mL) and the resulting solution degassed with nitrogen. Pd(TPP)$_2$Cl$_2$ (0.202 g, 0.288 mmol) and tributyl(1-ethoxyvinyl)stannane (5.2 g, 14 mmol) were added under a nitrogen stream and the reaction mixture was heated to 90° C. where it stirred for 16 h. After this time, the reaction mixture was allowed to cool to room temperature. Once at the prescribed temperature, the reaction mixture was concentrated under reduced pressure and the resulting residue was purified by neutral alumina column chromatography (20% ethyl acetate, hexane) to yield 2-(1-ethoxyvinyl)-5-phenyl-N-(pyridin-2-ylmethyl)quinazolin-4-amine (940 mg, 85% yield) as a white solid. $^1$H NMR (400 MHz, DMSO-d$_6$) δ (ppm): 8.23 (d, 1H, J=4.4 Hz), 7.75-7.85 (m, 2H), 7.70 (dt, 1H, J=2, 7.6 Hz), 7.45-7.58 (m, 5H), 7.20-7.30 (m, 3H), 6.61 (br s, 1H), 4.61 (s, 1H), 4.60 (d, 2H, J=4 Hz), 3.94 (q, 2H, J=6.8 Hz), 1.40 (t, 3H, J=6.8 Hz). LCMS Method Y: retention time 1.952 min, [M+1]=383.2.

Step 2. Preparation of 2-bromo-1-(5-phenyl-4-(pyridin-2-ylmethylamino)quinazolin-2-yl)ethanone

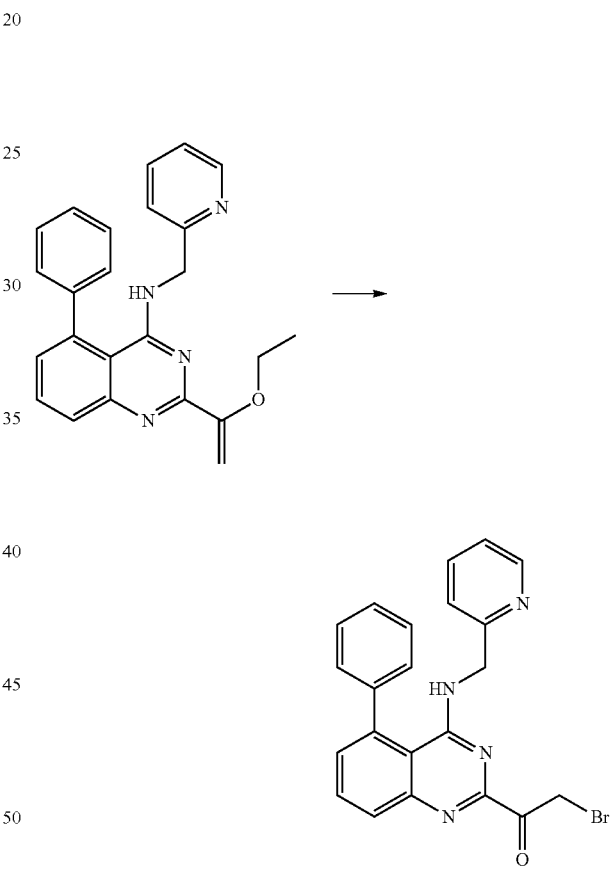

N-bromosuccinimide (0.55 g, 3.1 mmol) was added to 1,4-dioxane/water (3:1) (20 mL). 2-(1-Ethoxyvinyl)-5-phenyl-N-(pyridin-2-ylmethyl)quinazolin-4-amine (0.59 g, 1.5 mmol) was then added in small portions at 0° C. Upon completion of addition, the reaction mixture was stirred at room temperature for 20 min. After this time, water was added and the aqueous portion was extracted twice with DCM. The combined organic layers were dried, filtered and evaporated under reduced pressure to yield 2-bromo-1-(5-phenyl-4-(pyridin-2-ylmethylamino)quinazolin-2-yl)ethanone (600 mg, 69% purity by LCMS), which was used without further purification. LCMS Method Y: retention time 1.996 min, [M+1]=433.

307

Step 3. Example 203

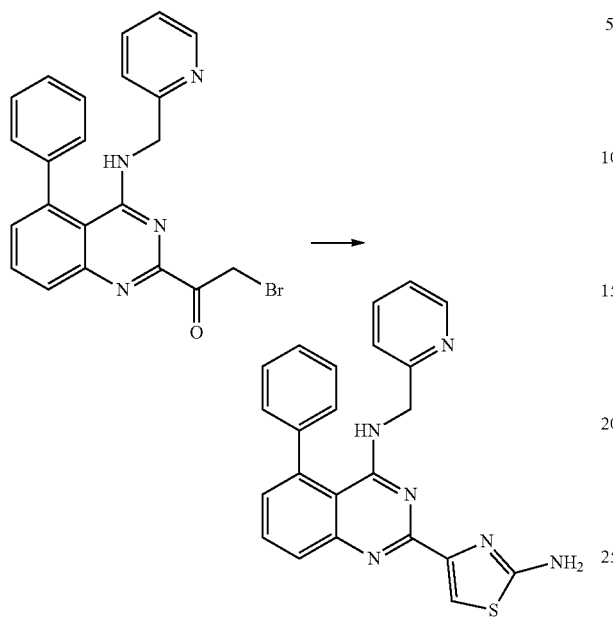

To a solution of 2-bromo-1-(5-phenyl-4-(pyridin-2-ylmethylamino)quinazolin-2-yl)ethanone (75 mg, 0.17 mmol) in ethanol (7 mL) was added thiourea (14 mg, 0.17 mmol) and the reaction mixture heated to 70° C. for 1 h. After this time, the ethanol was evaporated under reduced pressure and DCM (25 mL) was added. Upon the completion of addition, the organic portion was washed with 10% sodium bicarbonate solution and the aqueous layer was extracted with DCM (2×20 mL). The combined organic phases were dried and evaporated under reduced pressure to yield a residue. The residue was purified by silica gel chromatography (8% methanol in dichloromethane) to provide Example 203 (25 mg, 35%) as a black semi-solid. $^1$H NMR (400 MHz, DMSO-$d_6$, δ): 8.24 (d, 1H, J=4.8 Hz); 7.80-7.67 (m, 3H); 7.45-7.59 (m, 6H); 7.20-7.30 (m, 3H); 7.07 (s, 2H); 6.56 (br s, 1H); 4.65 (d, 2H, J=4.4 Hz). LCMS Method V: retention time 1.59 min, [M+1]=411.2; HPLC Method A1: purity 97.6%, retention time=6.52 min.

Example 204

(4-Aminopiperidin-1-yl)(3-(5-(5-phenyl-4-(pyridin-2-ylmethylamino)quinazolin-2-yl)pyridin-3-yl)-1,2,4-oxadiazol-5-yl)methanone

308

Step 1. Preparation of tert-butyl 1-(3-(5-(5-phenyl-4-(pyridin-2-ylmethylamino)-quinazolin-2-yl)pyridin-3-yl)-1,2,4-oxadiazole-5-carbonyl)piperidin-4-ylcarbamate

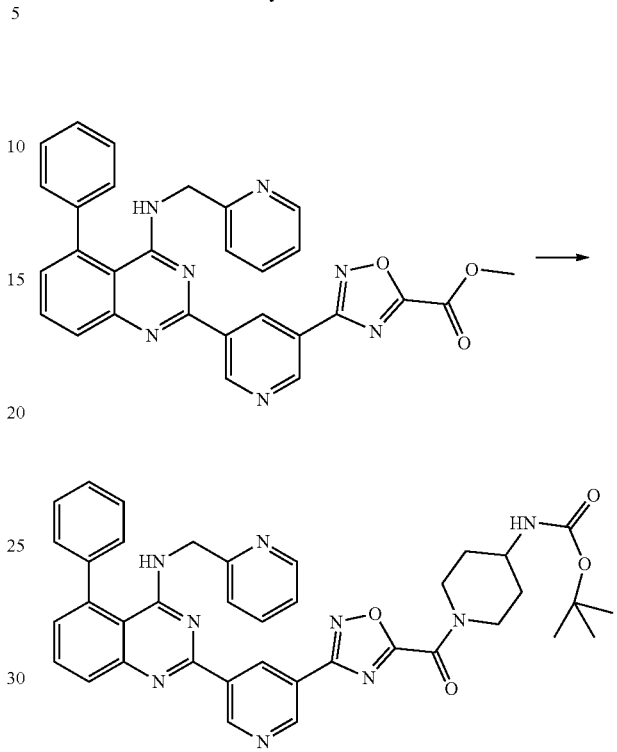

To a solution of methyl 3-(5-(5-phenyl-4-(pyridin-2-ylmethylamino)quinazolin-2-yl)pyridin-3-yl)-1,2,4-oxadiazole-5-carboxylate (from example 187, 0.2 g, 0.38 mmol) in ethanol (10 mL) was added 4-(Boc-amino)piperidine (0.389 g, 1.90 mmol). Upon completion of addition, the reaction mixture was heated to 80° C. where it stirred for 16 h. At the conclusion of this period, the ethanol was evaporated and the resulting residue was purified by flash silica gel column chromatography (1.6% methanol in DCM) to yield tert-butyl 1-(3-(5-(5-phenyl-4-(pyridin-2-ylmethylamino)quinazolin-2-yl)pyridin-3-yl)-1,2,4-oxadiazole-5-carbonyl)piperidin-4-ylcarbamate (0.1 g, 38% yield) as yellow solid. LCMS Method T: retention time 2.08 min; [M+1]=684.2.

Step 2. Example 204

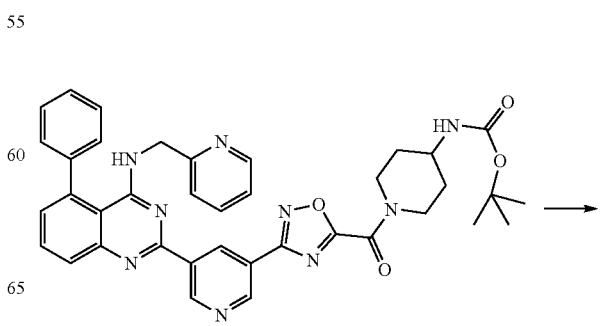

-continued

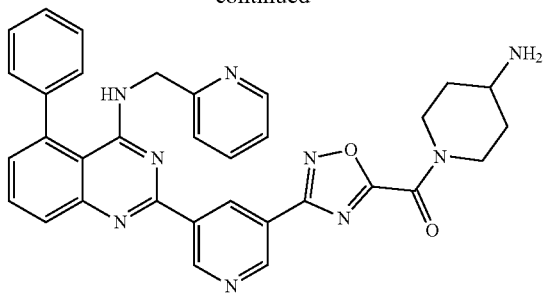

To a solution of tert-butyl 1-(3-(5-(5-phenyl-4-(pyridin-2-ylmethylamino)quinazolin-2-yl)pyridin-3-yl)-1,2,4-oxadiazole-5-carbonyl)piperidin-4-ylcarbamate (0.1 g, 0.1 mmol) in ether (3 mL) was added ether HCl (2 mL). The reaction mixture was stirred at RT for 16 h. After this time, a precipitate formed and the solution was decanted from the reaction mixture. The resulting solid was recrystallized from ether to yield Example 204 (0.022 g, 26% yield). $^1$H NMR (400 MHz, DMSO-$d_6$) δ (ppm): 9.54 (s, 1H), 8.26 (d, 1H, J=4 Hz); 7.96 (dd, 1H, J=1.2, 8 Hz); 7.87 (dd, 1H, J=7.2, 8 Hz); 7.72 (dd, 1H, J=1.6, 7.6 Hz); 7.63-7.50 (m, 2H); 7.39-7.33 (m, 2H); 7.25 (t, 1H, J=5.6 Hz); 6.95 (br s, 1H); 4.77 (d, 2H, J=2 Hz); 4.30 (br d, 1H, J=12 Hz); 4.02 (br d, 1H, J=12 Hz); 3.40-3.36 (m, 1H); 3.21-3.13 (m, 1H); 3.04-2.95 (m, 1H); 1.95-1.80 (m, 2H); 1.43-1.28 (m, 2H). LCMS Method T: retention time 1.65 min; [M+1]=584.2; HPLC Method A1: purity 96.1%, retention time=6.08 min.

Example 205

1-(5-(5-Phenyl-4-(pyridin-2-ylmethylamino)quinazolin-2-yl)pyridin-3-yl)cyclopropanecarbonitrile

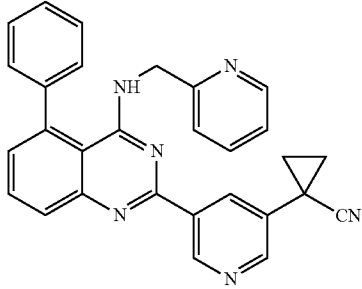 [SMILES: N#CC1(c2cncc(-c3nc(NCc4ccccn4)c4c(-c5ccccc5)cccc4n3)c2)CC1]

Step 1. Preparation of 1-(5-bromopyridin-3-yl)cyclopropanecarbonitrile

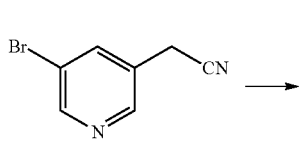

A suspension of 7 mL NaOH (50/50 w/w in H$_2$O) was charged with 2-(5-bromopyridin-3-yl)acetonitrile (from example 199: 0.36 g, 1.9 mmol). 1-Bromo-2-chloroethane (0.29 g, 2.01 mmol) was added followed by a catalytic amount of benzyl triethylammonium chloride (5 mg). The reaction mixture was stirred for 20 h at 60° C. and then poured into water. The resulting solution was extracted into ethyl acetate. The combined organic extracts were washed successively with water and brine, dried over Na$_2$SO$_4$ filtered and then concentrated to yield 1-(5-bromopyridin-3-yl)cyclopropanecarbonitrile (0.25 g, 41%), which was used without further purification. $^1$H NMR (400 MHz, CDCL$_3$) δ (ppm): 8.49 (d, 1H, J=2 Hz); 7.78 (d, 1H, J=4 Hz); 3.94 (q, 2H, J=7.6 Hz); 1.69 (d, 3H, J=7.6 Hz). LCMS Method Y: retention time 1.54 min; [M+1]=212.6.

Step 2. Preparation of 1-(5-(4,4,5,5-tetramethyl-1,3,2-dioxaborolan-2-yl)pyridin-3-yl)cyclopropanecarbonitrile

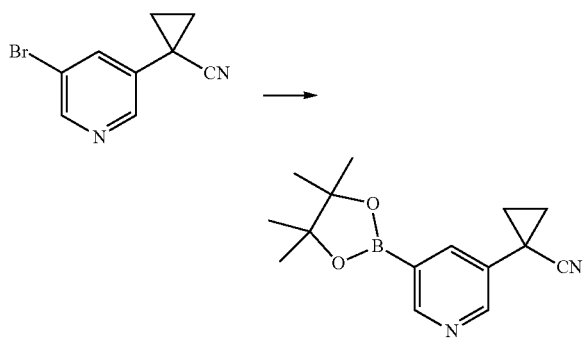

A mixture of 1-(5-bromopyridin-3-yl)cyclopropanecarbonitrile (0.25 g, 1.1 mmol), bis(pinacolato)diboron (0.31 g, 1.2 mmol) and potassium acetate (0.44 g, 4.5 mmol) in 1,4-dioxane (8 mL) was degassed with nitrogen for 15 min. After this time, (1,1'-bis(diphenylphosphino)ferrocene)palladium (II) chloride dichloromethane complex (94 mg, 0.12 mmol) was added and the reaction mixture was again degassed for 10 min with nitrogen. The reaction mixture was then heated in the microwave reactor at 120° C. for 45 min. At the conclusion of this period, the reaction mixture was filtered through celite and the filtrate was concentrated under reduced pressure to provide 1-(5-(4,4,5,5-tetramethyl-1,3,2-dioxaborolan-2-yl)pyridin-3-yl)cyclopropanecarbonitrile (0.28 g), which was used without further purification. LCMS Method Y: retention time 1.83 min; [M+1]=258.8.

Step 3. Example 205

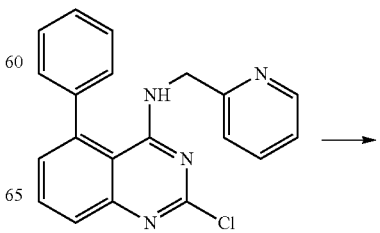

-continued

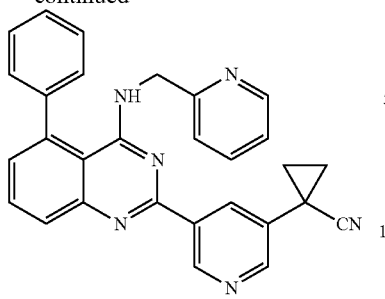

To a solution of 2-chloro-5-phenyl-N-(pyridin-2-ylmethyl)quinazolin-4-amine (from example 1, step 4, 0.12 g, 0.34 mmol) in 1,4-dioxane (8 mL) and H₂O (0.55 mL) under nitrogen was added 1-(5-(4,4,5,5-tetramethyl-1,3,2-dioxaborolan-2-yl)pyridin-3-yl)cyclopropanecarbonitrile (0.12 g, 0.37 mmol), and potassium carbonate (0.15 g, 1.11 mmol). The reaction mixture was degassed with nitrogen for 15 min. (1,1'-Bis (diphenyphosphino) ferrocene)palladium (II) chloride dichloromethane complex (27 mg, 0.037 mmol) was added and the reaction mixture was again degassed for 10 min with nitrogen. The reaction mixture was stirred at 95° C. for 16 h, then allowed to cool to room temperature and quenched by the addition of water. The reaction mixture was transferred to a separation funnel and the aqueous layer extracted with ethyl acetate. The combined organic portions were washed with water and saturated NaCl, dried over Na₂SO₄, filtered and concentrated under reduced pressure. The resulting residue was purified by column chromatography (2% methanol in DCM) to afford Example 205 (85 mg, 55% yield) as an off-white solid. ¹H NMR (400 MHz, DMSO-d₆) δ (ppm): 9.57 (s, 1H), 8.80 (d, 1H, J=2 Hz); 8.77 (s, 1H); 8.26 (d, 1H, J=6 Hz); 7.92 (dd, 1H, J=1.2, 6.8 Hz); 7.85 (t, 1H, J=6.8 Hz); 7.73 (dt, 1H, J=1.6, 7.6 Hz); 7.58-7.52 (m, 5H); 7.34-7.32 (m, 2H); 7.24 (t, 1H, 7.2 Hz); 6.86 (t, 1H, J=4 Hz); 4.75 (d, 2H, J=4.4 Hz); 1.90 (dd, 2H, J=4.8, 8 Hz); 1.90 (dd, 2H, J=4.8, 8 Hz). LCMS Method V: retention time 1.78 min, [M+1]=455.2; HPLC Method A1: purity 97.7%, retention time=7.75 min.

Example 206

2-(5-(5-Phenyl-4-(pyridin-2-ylmethylamino)quinazolin-2-yl)pyridin-3-yl)ethanesulfonamide

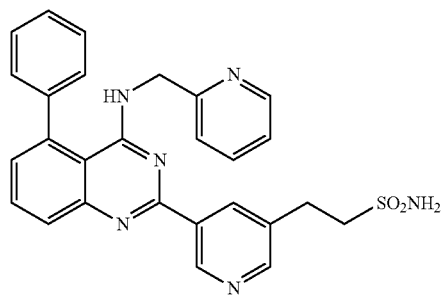 [SMILES: NS(=O)(=O)CCc1cncc(-c2nc(NCc3ccccn3)c3c(-c4ccccc4)cccc3n2)c1]

Step 1. Preparation of tert-butyl(diphenylphosphoryl)methylsulfonylcarbamate

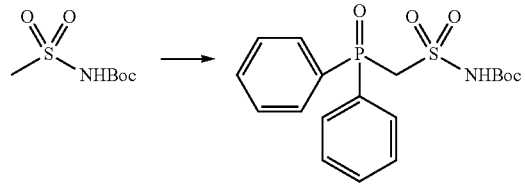 [SMILES: CC(C)(C)OC(=O)NS(C)(=O)=O ; CC(C)(C)OC(=O)NS(=O)(=O)CP(=O)(c1ccccc1)c1ccccc1]

To a solution of tert-butyl methylsulfonylcarbamate (2 g, 10 mmol) in THF (25 mL) at −78° C. was added LDA (2 M in THF, 15.4 mL, 30.7 mmol). Upon completion of addition, the reaction mixture stirred for 10 min and then diphenylphosphinic chloride (2.42 g, 10.2 mmol) was added dropwise to the reaction at −78° C. After 90 min, water (100 mL) was added and the reaction mixture was diluted with ethyl acetate (250 mL). The aqueous layer was adjusted to pH 5 with 5% aqueous HCl. The white precipitate that formed was filtered and the solid dried in vacuo to give tert-butyl (diphenylphosphoryl)methylsulfonylcarbamate (2.9 g, 72% yield) as a white solid.

Step 2. Preparation of (E)-tert-butyl 2-(5-(5-phenyl-4-(pyridin-2-ylmethylamino) quinazolin-2-yl) pyridin-3-yl) vinylsulfonylcarbamate

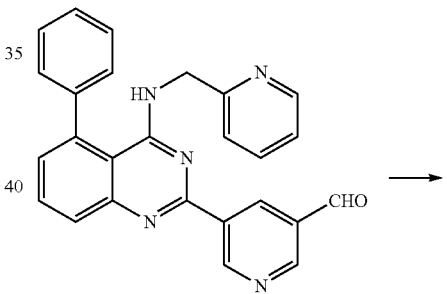

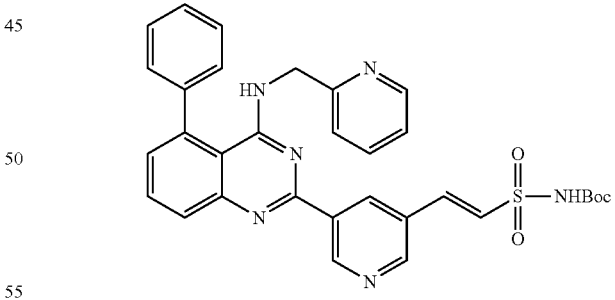

A solution of tert-butyl {[(diphenylphosphoryl)methyl]sulfonyl}carbamate (0.400 g, 1.01 mmol) in N,N-dimethylformamide (20 mL) was added 95% sodium hydride (0.06 g, 2 mmol) and the reaction mixture was stirred at 0° C. for 1 h. 5-(5-phenyl-4-(pyridin-2-ylmethylamino)quinazolin-2-yl)nicotinaldehyde (from example 191: 0.505 g, 1.21 mmol) was added to the reaction mixture, and the resulting mixture was stirred at room temperature for 18 h. Saturated aqueous ammonium chloride solution (100 mL) was added to the reaction mixture, and the resulting mixture was extracted with ethyl acetate. The combined organic layers were

313 washed with saturated brine, dried over anhydrous magnesium sulfate, and filtered. The filtrate was concentrated, and the resulting residue was subjected to silica gel column chromatography (CHCl$_3$-MeOH 95:5). The resulting material was crystallized from CH$_2$Cl$_2$-hexane to give the (E)-tert-butyl 2-(5-(5-phenyl-4-(pyridin-2-ylmethylamino) quinazolin-2-yl) pyridin-3-yl) vinylsulfonylcarbamate (0.450 g, 62% yield) as a brown solid. LCMS Method Y: retention time 1.90 min; [M+1]=595.4.

Step 3. Example 206

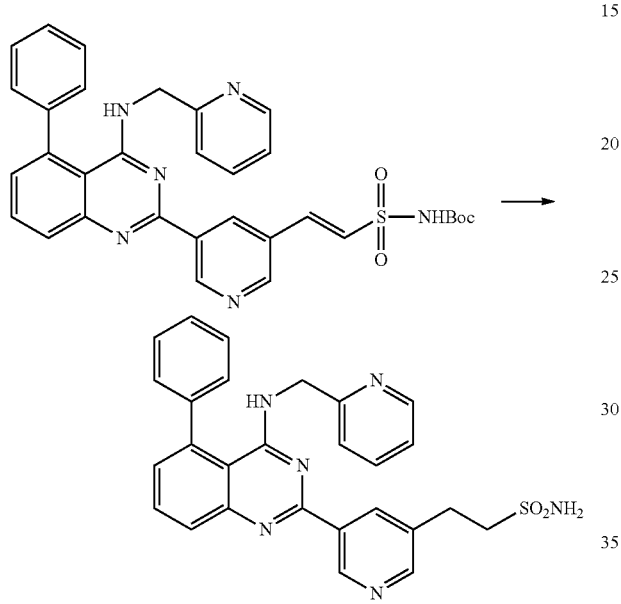

To a solution of (E)-tert-butyl 2-(5-phenyl-4-(pyridin-2-ylmethylamino) quinazolin-2-yl)vinylsulfonylcarbamate (0.210 g, 0.410 mmol) in MeOH (10 mL) was added 10% palladium-on-carbon (20 mg) and the reaction mixture stirred at RT under a hydrogen atmosphere for 14 h. The reaction mixture was filtered and. the filtrate was concentrated under reduced pressure to yield a residue. Trifluoroacetic acid (15 mL) was added to the residue and the reaction mixture was stirred at room temperature for 2 h. After this time, the reaction mixture was concentrated under reduced pressure, sodium bicarbonate solution was added, and the resulting mixture was extracted with ethyl acetate. The combined organic layers were washed with saturated brine, dried over anhydrous magnesium sulfate, and filtered. The filtrate was concentrated, and the resulting residue was subjected to silica gel column chromatography (CHCl$_3$—MeOH 95:5) followed by recrystallization (CHCl$_3$-hexane) to give Example 206 (0.115 g, 65%) as a white solid. $^1$H NMR (400 MHz, DMSO-d$_6$) δ (ppm): 9.49 (br s, 1H), 8.63 (brm, 2H), 8.27 (m, 1H), 7.91-7.82 (m, 2H), 7.74 (m, 1H), 7.59-7.55 (m, 5H), 7.28-7.21 (m, 1H), 6.95 (m, 2H), 6.82 (brs, 1H), 4.75 (d, J=4.0 Hz, 2H), 3.42 (t, J=5.6 Hz, 2H), 3.21 (t, J=8 Hz, 2H). LCMS Method Y: retention time 1.59 min; [M+1]=497.2; HPLC Method A1: purity 99.6%, retention time=7.96 min.

314

Example 207

1-(5-Phenyl-4-(pyridin-2-ylmethylamino)quinazolin-2-yl)cyclopropanecarbonitrile

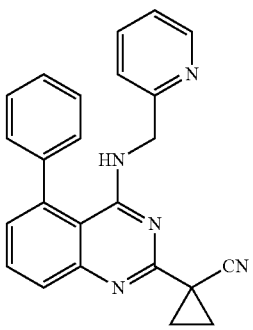 [SMILES: N#CC1(c2nc(NCc3ccccn3)c3c(-c4ccccc4)cccc3n2)CC1]

Step 1. Preparation of 3-(1-cyanocyclopropanecarboxamido)biphenyl-2-carboxamide

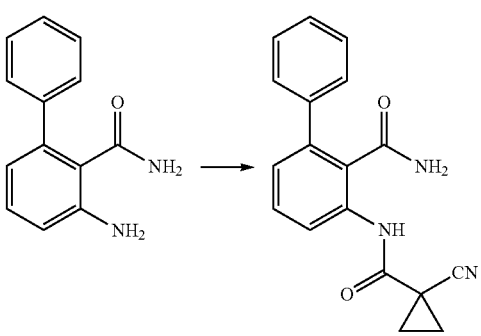 [SMILES: NC(=O)c1c(N)cccc1-c1ccccc1 ; N#CC1(C(=O)Nc2cccc(-c3ccccc3)c2C(N)=O)CC1]

To a solution of 1-cyanocyclopropanecarboxylic acid (0.75 g, 7 mmol) in DCM (40 mL) was added HATU (3.5 g, 10 mmol) and DIPEA (3.4 mL, 20 mmol). After stirring at room temperature for 1 h, 3-aminobiphenyl-2-carboxamide (from example 218: 1 g, 5 mmol) was added and the reaction mixture stirred for an additional 16 h. The reaction mixture was washed with water and the organic phase dried, filtered, concentrated under reduced pressure and purified by silica gel chromatography (60% ethyl acetate in hexanes) to provide 3-(1-cyanocyclopropanecarboxamido)biphenyl-2-carboxamide (0.75 g, 74% yield) as a white solid. LCMS Method T: retention time 1.53 min; [M+1]=306.2.

Step 2. Preparation of 1-(4-oxo-5-phenyl-3,4-dihydroquinazolin-2-yl)cyclopropanecarbonitrile

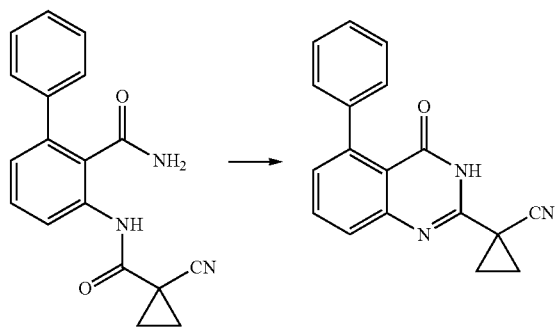 [SMILES: N#CC1(C(=O)Nc2cccc(-c3ccccc3)c2C(N)=O)CC1 ; N#CC1(c2nc3cccc(-c4ccccc4)c3c(=O)[nH]2)CC1]

To a solution 3-(1-cyanocyclopropanecarboxamido)biphenyl-2-carboxamide (0.7 g, 2 mmol) in methanol was added saturated aqueous Na$_2$CO$_3$ (23 mmol) and the reaction mixture stirred at 80° C. for 30 min. The reaction mixture was concentrated under reduced pressure and the resulting residue was diluted with ethyl acetate then washed with water. The organic extracts were dried, concentrated and purified by silica gel chromatography (4% MeOH in DCM) to yield 1-(4-oxo-5-phenyl-3,4-dihydroquinazolin-2-yl)cyclopropanecarbonitrile (0.65 g, 99% yield) as a white solid. LCMS Method T: retention time 1.810 min; [M+1] =288.2.

Step 3. Example 207

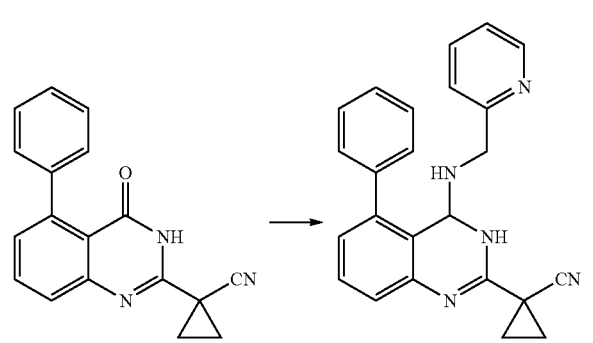 [SMILES: N#CC1(c2nc3cccc(-c4ccccc4)c3c(=O)[nH]2)CC1 ; N#CC1(C2=Nc3cccc(-c4ccccc4)c3C(NCc3ccccn3)N2)CC1]

To a solution of 1-(4-oxo-5-phenyl-3,4-dihydroquinazolin-2-yl)cyclopropanecarbonitrile) (0.15 g, 0.52 mmol) in acetonitrile (3 mL) at room temperature was added DBU (0.25 g, 1.6 mmol) and BOP (0.3 g, 0.7 mmol) and the reaction mixture stirred for 30 min. Aminomethylpyridine (0.1 ml, 0.93 mmol) was added and the resulting reaction mixture stirred for an additional 16 h. The reaction mixture was concentrated under reduced pressure and the resulting residue was purified by silica gel column chromatography (2% MeOH in DCM) to give Example 207 (0.05 g, 25% yield) as a white solid. $^1$H NMR (400 MHz, DMSO-d$_6$, δ): 8.23 (s, 1H); 7.82-7.62 (m, 3H); 7.60-7.46 (m, 5H); 7.21-7.28 (m, 3H); 6.76 (t, 1H, J=4 Hz); 4.52 (d, 2H, J=4 Hz); 1.78-1.74 (m, 4H). LCMS LC-MS Method V: retention time 1.80 min, [M+1]=378.2; HPLC Method A1: purity 95.2%, retention time=8.75 min.

Example 208

N-((5-(5-phenyl-4-(pyridin-2-ylmethylamino)quinazolin-2-yl)pyridin-3-yl)methyl)methanesulfonamide

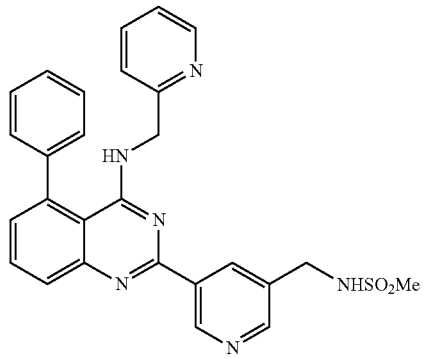

Step 1. Preparation of 2-(5-(aminomethyl)pyridin-3-yl)-5-phenyl-N-(pyridin-2-ylmethyl)quinazolin-4-amine

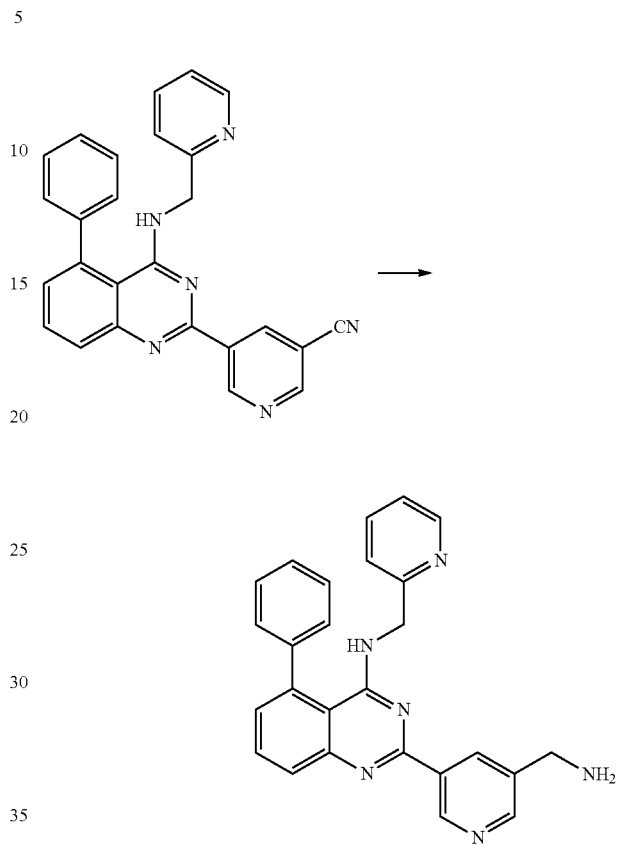

To a solution of 5-(5-phenyl-4-(pyridin-2-ylmethylamino) quinazolin-2-yl)nicotinonitrile (from example 183: 200 mg, 0.48 mmol) in 5% ammonia in methanol (5 mL) was added Ra—Ni (catalytic) and the resulting slurry was stirred under hydrogen atmosphere for 16 h. After this time, the reaction mixture was filtered and the filtrate was concentrated under reduced pressure to yield 2-(5-(aminomethyl)pyridin-3-yl)-5-phenyl-N-(pyridin-2-ylmethyl)quinazolin-4-amine (0.1 g, 50% yield), which was used without further purification.

Step 2. Example 208

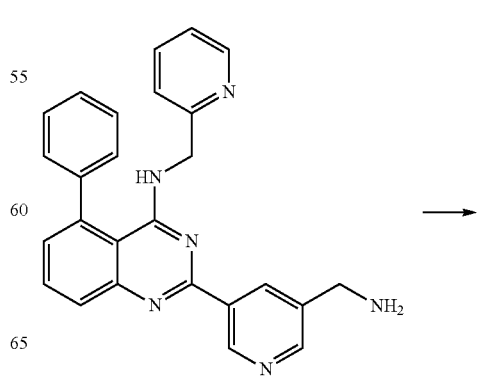

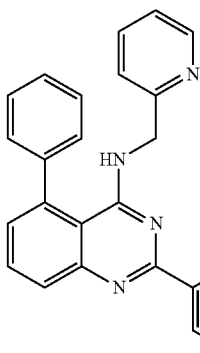

To a stirred solution of 2-(5-(aminomethyl)pyridin-3-yl)-5-phenyl-N-(pyridin-2-ylmethyl)quinazolin-4-amine (0.1 g, 0.2 mmol) and TEA (0.063 mL, 0.46 mmol) in DCM (3 mL) was added methanesulfonyl chloride (0.24 mL, 0.3 mmol) drop wise at 0° C. The reaction mixture was stirred for 1 h and then quenched by the addition of water (1 mL). The resulting solution was extracted with DCM. The combined organic extracts were washed successively with water and brine and dried, over $Na_2SO_4$, filtered and the filtrate concentrated under reduced pressure. The resulting residue was chromatographed on silica gel (MeOH/DCM, 2:98) to provide Example 208 (40 mg, 34%). $^1$H NMR (400 MHz, DMSO-$d_6$, δ): 9.56 (s, 1H); 8.79 (s, 1H); 8.69 (s, 1H); 8.25 (d, 1H, J=4 Hz); 7.91 (dd, 1H, J=1.6, 4 Hz); 7.84 (t, 1H, J=8 Hz); 7.80-7.70 (m, 2H); 7.61-7.50 (m, 5H); 7.38-7.30 (m, 2H); 7.25 (br s, 1H); 6.85 (s, 1H); 4.76 (d, 2H, J=4 Hz); 4.35 (s, 2H); 2.98 (s, 3H). LCMS Method T: retention time 1.52 min; [M+1]=497.2; HPLC Method A1: purity 98.5%, retention time=6.42 min.

Example 209

Ethyl 5-(5-phenyl-4-(pyridin-2-ylmethylamino)quinazolin-2-yl)isoxazole-3-carboxylate

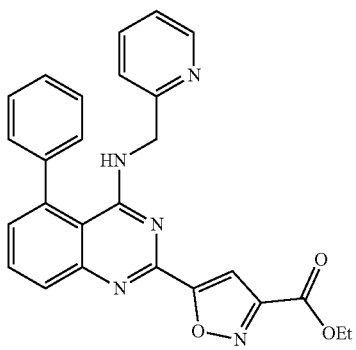 [SMILES: CCOC(=O)c1cc(-c2nc(NCc3ccccn3)c3c(-c4ccccc4)cccc3n2)on1]

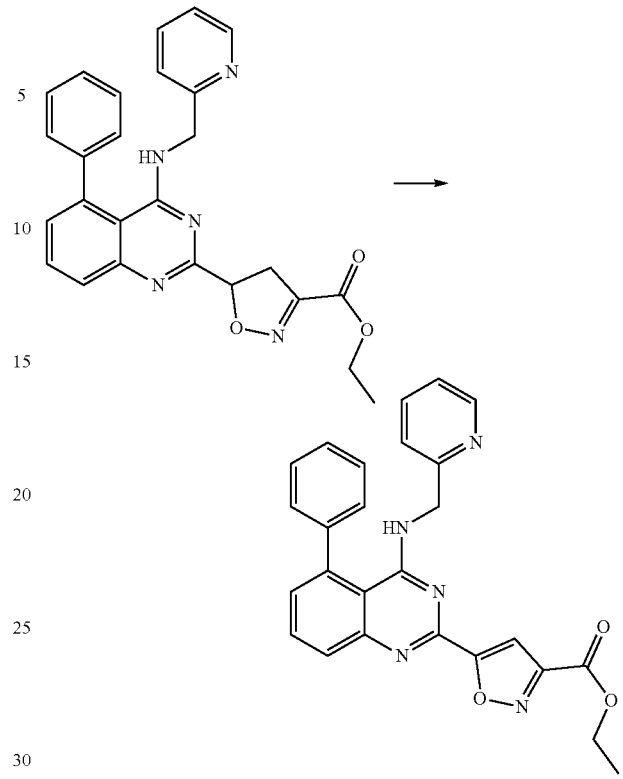

A solution of ethyl 5-(5-phenyl-4-(pyridin-2-ylmethylamino)quinazolin-2-yl)-4,5-dihydroisoxazole-3-carboxylate (from example 215, see the procedure describe below, 0.30 g, 0.66 mmol), DDQ (0.06 g, 0.3 mmol) in toluene (15 mL) was heated at 75° C. for 16 h. After this time, the reaction mixture was concentrated under reduced pressure and the resulting residue was purified by ISCO chromatography (40% ethyl acetate in hexanes) to obtain Example 209 (0.075 g, 25% yield) as an off white solid. $^1$H NMR (400 MHz, DMSO-$d_6$, δ): 8.30 (s, 1H); 8.21 (s, 1H); 7.99-7.87 (m, 3H); 7.73 (dt, 1H, J=1.6, 7.6 Hz); 7.63-7.48 (m, 6H); 7.40-7.32 (m, 2H); 7.24 (dd, 1H, J=5.6, 7.2 Hz); 7.03 (br s, 1H); 4.71 (d, 2H, J=4 Hz). LCMS Method T: retention time 1.81 min; [M+1]=423.2; HPLC Method A1: purity 99.3%, retention time=7.31 min.

Example 210

Ethyl 4-(5-phenyl-4-(pyridin-2-ylmethylamino)quinazolin-2-yl)thiazole-2-carboxylate

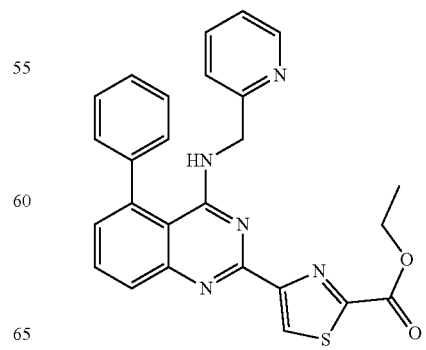

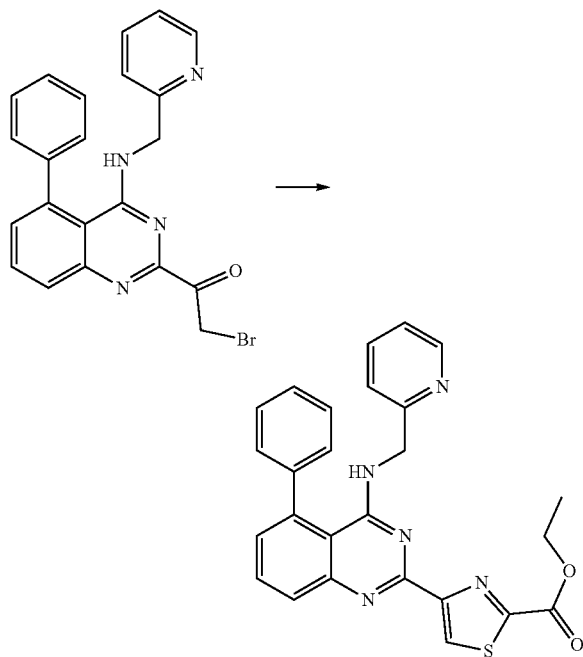

2-Bromo-1-(5-phenyl-4-(pyridin-2-ylmethylamino)qui-nazolin-2-yl)ethanone (from example 203: 0.5 g, 1 mmol) was dissolved in ethanol (20 mL) and ethyl thiooxamate (0.15 g, 1.2 mmol) was added. The reaction mixture was stirred at 70° C. for 1 hour. The ethanol was evaporated under reduced pressure and the resulting residue was dissolved in DCM (25 mL). The organic portion was washed with 10% sodium bicarbonate solution and the aqueous layer was extracted with DCM (2×20 mL). The combined organic phases were dried and evaporated under reduced pressure. The resulting residue was purified by ISCO chromatography (30% ethyl acetate in hexanes) to yield Example 210 (0.13 g, 24% yield). $^1$H NMR (400 MHz, DMSO-$d_6$, δ): 8.94 (s, 1H); 8.24 (d, 1H, J=4 Hz); 7.96 (d, 1H, J=8.8 Hz); 7.87 (t, 1H, J=8 Hz); 7.74 (t, 1H, mmol 8 Hz) 7.50-7.60 (m, 5H) 7.30-7.36 (m, 2H) 7.25 (t, 1H, J=6 Hz); 6.95 (br s, 1H); 4.75 (d, 2H, J=4 Hz); 4.47 (q, 2H, J=7.2 Hz); 1.41 (t, 3H, J=7.2 Hz). LC2MS Method W: Retention time 2.243 min, [M+]=468.2; HPLC Method A1: purity 94.4%, retention time=7.522 min.

Example 211

Tert-butyl 4-(5-phenyl-4-(pyridin-2-ylmethylamino) quinazolin-2-yl)piperidine-1-carboxylate

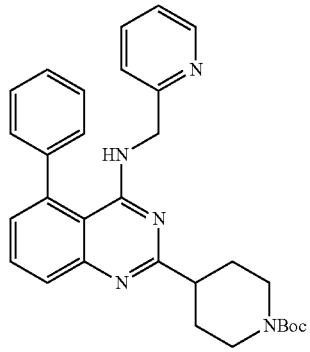 [SMILES: CC(C)(C)OC(=O)N1CCC(c2nc(NCc3ccccn3)c3c(-c4ccccc4)cccc3n2)CC1]

Step 1. Preparation of tert-butyl 4-(2-carbamoylbiphenyl-3-ylcarbamoyl) piperidine-1-carboxylate

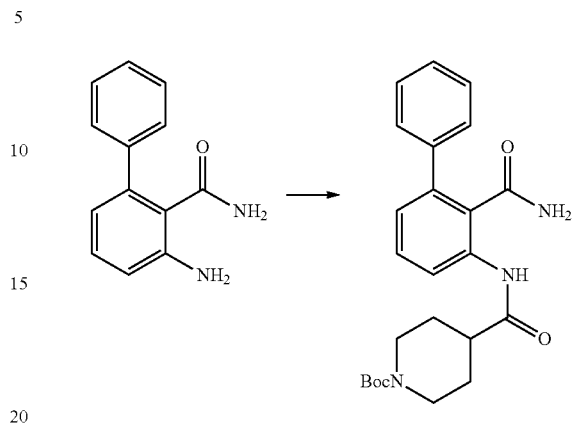

To a solution of 1-(tert-butoxycarbonyl)piperidine-4-carboxylic acid (2.4 g, 10 mmol) in DCM (40 mL) was added HATU (5.3 g, 14 mmol) and DIPEA (3.6 mL, 28 mmol) and the reaction mixture was stirred at room temperature for 1 h. 3-Aminobiphenyl-2-carboxamide (from Example 218) (1.5 g, 7.07 mmol) was added and the resulting mixture stirred for an additional 16 h. The reaction mixture was washed with water, the organic portion dried, filtered and concentrated under reduced pressure. The resulting residue was purified by ISCO chromatography (50% ethyl acetate in hexanes) to yield tert-butyl 4-(2-carbamoylbiphenyl-3-ylcarbamoyl) piperidine-1-carboxylate (1.0 g, 22% yield) as a white solid. LCMS Method T: retention time 1.71 min; [M+1]=423.0.

Step 2. Preparation of tert-butyl 4-(4-oxo-5-phenyl-3,4-dihydroquinazolin-2-yl)piperidine-1-carboxylate

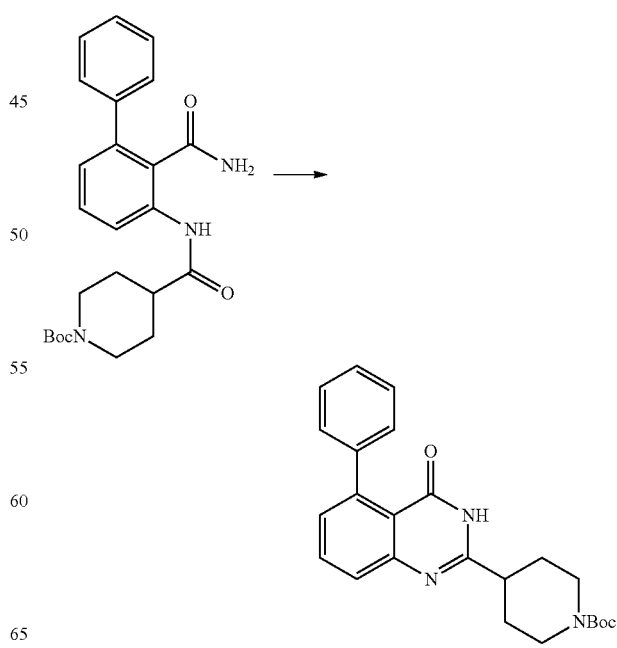

To a solution tert-butyl 4-(2-carbamoylbiphenyl-3-ylcarbamoyl)piperidine-1-carboxylate (1.0 g, 2.4 mmol) in methanol was added NaOMe (2.6 mL, 25% in MeOH, 12.3 mmol). The resulting reaction mixture was stirred at RT for 14 h. After this time, the reaction mixture was concentrated under reduced pressure and the resulting residue was diluted with ethyl acetate and then washed with water. The organic portion was dried, concentrated under reduced pressure to yield a residue. The residue was purified by ISCO chromatography (30% EtOAc in hexanes) to yield tert-butyl 4-(4-oxo-5-phenyl-3,4-dihydroquinazolin-2-yl)piperidine-1-carboxylate (0.60 g, 67% yield) as a white solid. LCMS Method W: retention time 2.07 min; [M+1]=422.2.

Step 3. Example 211

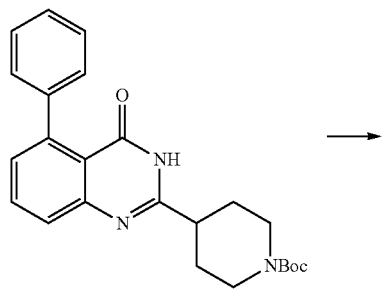

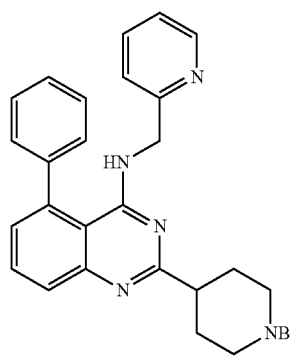

To a solution of tert-butyl 4-(4-oxo-5-phenyl-3,4-dihydroquinazolin-2-yl)piperidine-1-carboxylate (0.6 g, 1 mmol) in acetonitrile (20 mL) at room temperature was added DBU (0.45 g, 2.96 mmol) and BOP (0.98 g, 2.22 mmol). The reaction mixture was stirred for 30 min and then aminomethylpyridine (0.24 g 2.22 mmol) was added. The resulting solution was stirred for an additional 16 h. The reaction mixture was then concentrated under reduced pressure and the resulting residue was purified by silica gel chromatography (20% EtOAc in hexanes) to provide Example 211 (0.32 g, 45% yield) as a white solid. $^1$H NMR (400 MHz, DMSO-$d_6$) δ (ppm): 8.20 (br s, 1H); 7.86-7.68 (m, 3H); 7.60-7.52 (m, 5H), 7.32-7.17 (m, 3H), 6.64 (br, 1H), 4.60 (br s, 2H), 4.04 (br d, 2H, J=8.8 Hz), 3.03-2.79 (br m, 3H), 1.94 (br t, 2H, J=13.6 Hz), 1.72 (dd, 2H, J=11.2 Hz, J=20 Hz), 1.43 (s, 9H). LCMS Method W: retention time 1.80 min, [M+1]=475.2; HPLC Method A1: purity 97.4%, retention time=8.08 min.

Example 212

(Z)-methyl 2-amino-3-(5-phenyl-4-(pyridin-2-ylmethylamino)quinazolin-2-yl)acrylate

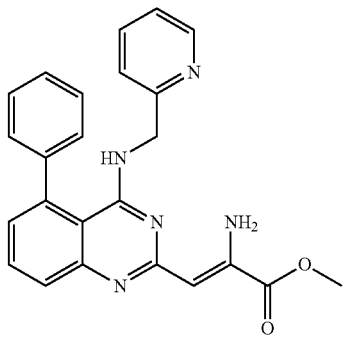 [SMILES: COC(=O)/C(N)=C/c1nc(NCc2ccccn2)c2c(-c3ccccc3)cccc2n1]

Step 1. Preparation of methyl 2,2-diethoxyacetimidate

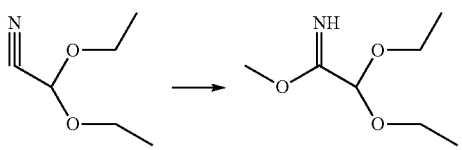

To a stirred solution of diethoxyacetonitrile (5 g, 38.75 mmol) in dry methanol (80 mL) was added 1 mL of a 20% solution of sodium methoxide. After the addition, the reaction mixture was stirred at RT for 24 h, quenched with solid $CO_2$, and then concentrated. The resulting residue was diluted with water and extracted with chloroform. The organic layer was washed with brine and dried over $Na_2SO_4$ to yield methyl 2,2-diethoxyacetimidate (6 g, 96%). $^1$H NMR (400 MHz, DMSO-$d_6$) δ (ppm): 7.95 (s, 1H),), 4.82 (s, 1H), 3.66 (s, 3H), 3.49 (q, 4H, J=7.2 Hz); 1.16-1.13 (t, 3H, J=7.2 Hz).

Step 2. Preparation of 5-chloro-2-(diethoxymethyl)quinazolin-4(3H)-one

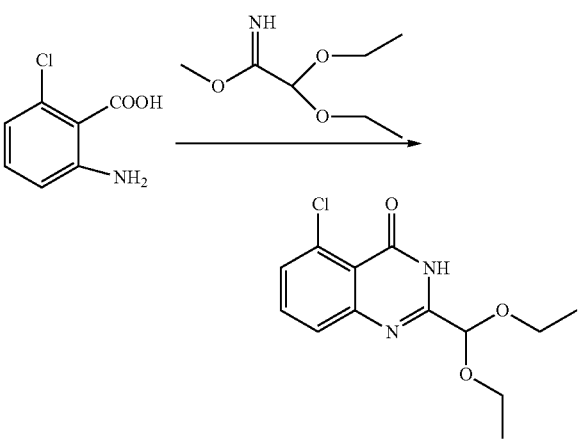

To a stirred solution of 6-chloro anthranilic acid (6 g, 34.97 mmol) in EtOH (60 mL) under nitrogen atmosphere was added 1.5 equivalent of TEA (14 mL, 104.9 mmol). Upon completion of addition, the mixture was heated to 50° C. where it stirred for 30 min. After this time, a methyl 2,2-diethoxyacetimidate (6 g, 41.96 mmol) in ethanol solution was added through syringe and the resulting mixture was heated to reflux where it stirred for 24 h. At the conclusion of this period, the reaction mixture was cooled to RT and the volatiles were evaporated. The resulting residue was diluted with water, extracted with DCM and washed with brine solution. The crude product was purified by column chromatography (25% ethyl acetate in hexane) to provide 5-chloro-2-(diethoxymethyl)quinazolin-4(3H)-one (7 g, 60% yield). LCMS Method W: retention time 1.5 min; [M+1]=283.

Step 3. Preparation of 2-(diethoxymethyl)-5-phenylquinozoline-4(3H)one

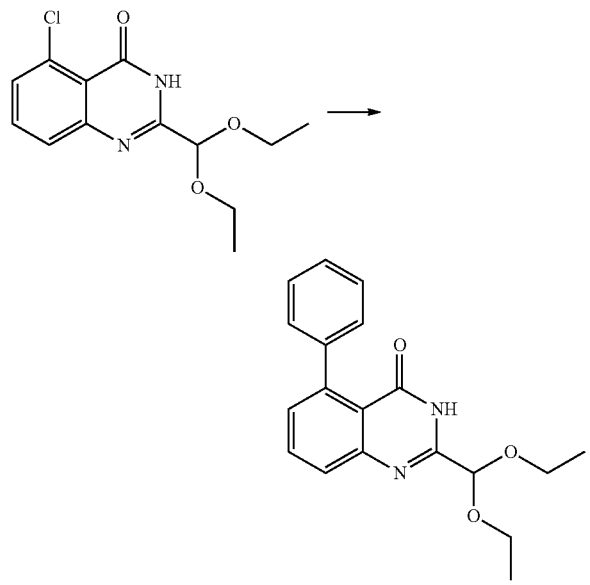

To a solution of 5-chloro 2-(diethoxymethyl)quinozoline-4(3H)-one (5 g, 0.17.68 mmol) in a dioxane-water mixture (45:15 mL) was added phenyl boronic acid (2.8 g, 22.9 mmol) and potassium carbonate (7.32 g, 53.05 mmol). The reaction mixture was degassed with nitrogen for 30 min and then tetrakis triphenyl phosphine palladium (2.04 g, 1.76 mmol) was added. The resulting mixture was heated to reflux where it stirred for 24 h. At the conclusion of this period, the reaction mixture was cooled to RT, concentrated and then diluted with water. The resulting mixture was filtered through celite, washed with DCM and then extracted with DCM. The organic layer was dried over $Na_2SO_4$, diluted with ethyl acetate, washed with water and brine, and then dried over $Na_2SO_4$. The crude product was purified by silica gel chromatography (25% ethyl acetate in hexane) to provide 2-(diethoxymethyl)-5-phenylquinozoline-4(3H)one (4.5 g, 78% yield). LCMS Method V: retention time 1.62 min; [M+1]=325.0.

Step 4. Preparation of 2-(diethoxymethyl)-5-Phenyl-N-(pyridinyl-2-methyl)quinozoline-4-amine

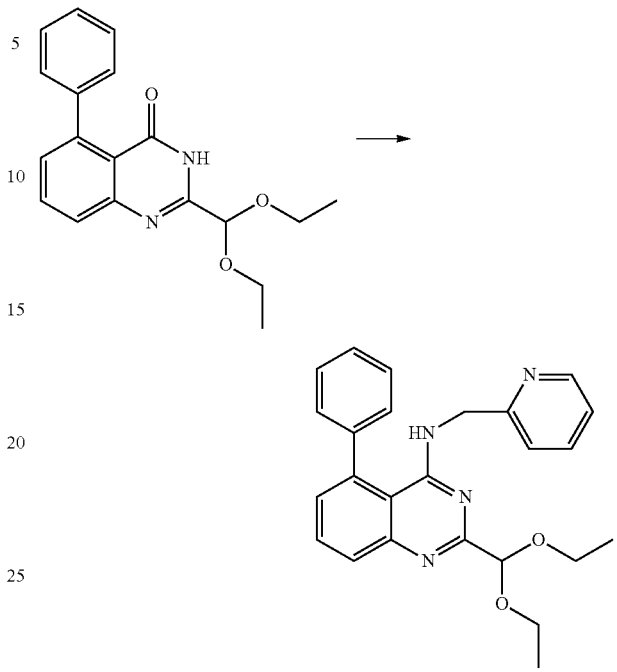

To a solution of 2-(diethoxymethyl)-5-Phenylquinozoline-4(3H)one (5 g, 15.4 mmol) in acetonitrile (50 mL) under nitrogen atmosphere was added BOP reagent (10.25 g, 23.12 mmol) followed by DBU (6.3 mL, 46.2 mmol). The reaction mixture was stirred at RT for an hour and then a solution of 2-aminomethyl pyridine (2.5 mL, 23.12 mmol) in acetonitrile was added. The resulting mixture was stirred at RT under nitrogen for 20 h. After this time, the solution was concentrated under reduced pressure and diluted with water. The aqueous solution was extracted with ethyl acetate and then washed with brine solution. The crude product was purified using silica gel chromatography (23% ethyl acetate in hexane) to provide 2-(diethoxymethyl)-5-Phenyl-N-(pyridinyl-2-methyl)quinozoline-4-amine (3.3 g, 52%). $^1$H NMR (400 MHz, DMSO-$d_6$) δ (ppm): 8.21-(s, 1H), 7.80-7.75 (m, 2H), 7.72-7.19 (m, 1H), 7.55-747 (m, 5H), 7.29-7.21 (m, 3H), 6.72 (s, 1H), 5.33 (s, 1H), 4.58 (d, 2H, J=4 Hz); 3.77-3.60 (m, 4H), 1.17-1.13 (t, 6H, J=6.8 Hz). LCMS Method V: retention time 1.69 min; [M+1]=415.0.

Step 5. Preparation of 5-phenyl-4-(pyridin-2-ylmethylamino)quinazoline-2-carbaldehyde

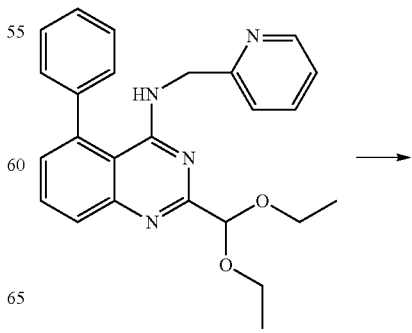

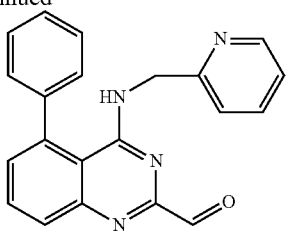

To a solution of 2-(diethoxymethyl)-5-phenyl-N-(pyridinyl-2-methyl)quinozoline-4-amine (3 g, 7.24 mmol) in 1,4 dioxane (30 mL) under nitrogen atmosphere was added HCl (30 mL, 6M). The resulting mixture was heated at 90'C for 4 h. After this time, the mixture was cooled to ambient temperature and then concentrated under reduced pressure. This mixture was diluted with water, neutralized with solid Na$_2$CO$_3$ and then extracted with DCM. The organic layer was dried with sodium sulphate and evaporated under reduced pressure to yield 5-phenyl-4-(pyridin-2-ylmethylamino)quinazoline-2-carbaldehyde (1.5 g, 42%). LCMS Method V: retention time 1.70 min; [M+1]=340.0.

Step 6. Preparation of (Z)-methyl 2-(benzyloxycarbonylamino)-3-(5-phenyl-4-(pyridin-2-ylmethylamino)quinazolin-2-yl)acrylate

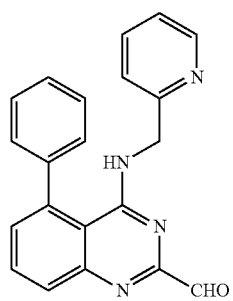

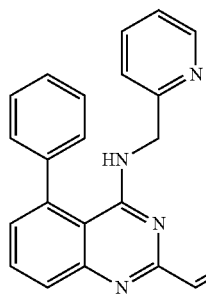

To a solution of 5-phenyl-4-(pyridin-2-ylmethylamino)quinazoline-2-carbaldehyde (0.9 g, 3 mmol) in THF (10 mL) was added methyl 2-benzyloxycarbonylamino-2-(dimethoxyphosphinyl)acetate (0.96 g, 2.9 mmol) followed by tetramethyguanidine (0.66 mL. 5.3 mmol). The resulting solution was stirred at RT for 3 h. After this time, the reaction mixture was diluted with ethyl acetate, washed successively with water and brine, dried over Na$_2$SO$_4$, filtered then and concentrated under reduced pressure. The resulting residue was purified by silica gel chromatography (30% ethyl acetate in hexane) to yield (Z)-methyl 2-(benzyloxycarbonylamino)-3-(5-phenyl-4-(pyridin-2-ylmethyl- amino)quinazolin-2-yl)acrylate (0.7 g (48% yield). LCMS Method V: retention time 1.94 min; [M+1]=546.0.

Step 7. Example 212

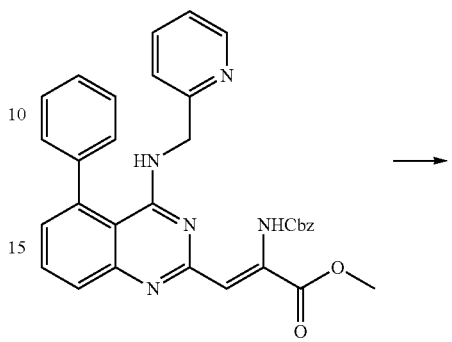

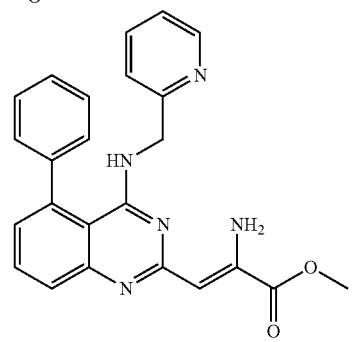

To a solution of (Z)-methyl 2-(benzyloxycarbonylamino)-3-(5-phenyl-4-(pyridin-2-ylmethylamino)quinazolin-2-yl) acrylate (0.4 g, 0.7 mmol) in MeOH (7 mL) was added 10% palladium-on-carbon (40 mg). Upon completion of addition, the reaction mixture was stirred at RT under an atmosphere of hydrogen for 20 h. After this time, the reaction mixture was filtered through celite and the filtrate was evaporated under reduced pressure. The resulting residue was purified by chromatography on silica gel (23% ethyl acetate in hexane) to yield Example 212 (0.3 g, 88% yield). $^1$H NMR (400 MHz, DMSO-d$_6$) δ (ppm): 8.21 (d, 1H, J 4.4 Hz); 7.72-7.68 (m, 3H), 7.54-7.45 (m, 5H), 7.25-7.21 (m, 2H), 7.14 (d, 1H, J 6 Hz); 5.97 (s, 1H), 4.55 (d, 2H, J=2.8 Hz), 3.84 (s, 1H). LCMS Method V: retention time 1.74 min; [M+1]=412.0; HPLC Method A2: purity 97.7%, retention time=8.90 min.

Example 213

5-(5-(5-Phenyl-4-(pyridin-2-ylmethylamino)quinazolin-2-yl)pyridin-3-yl)-1,3,4-oxadiazol-2-amine

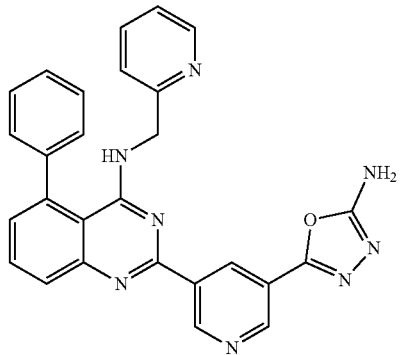 [SMILES: Nc1nnc(-c2cncc(-c3nc(NCc4ccccn4)c4c(-c5ccccc5)cccc4n3)c2)o1]

327

Step 1. Preparation of 5-bromonicotinohydrazide

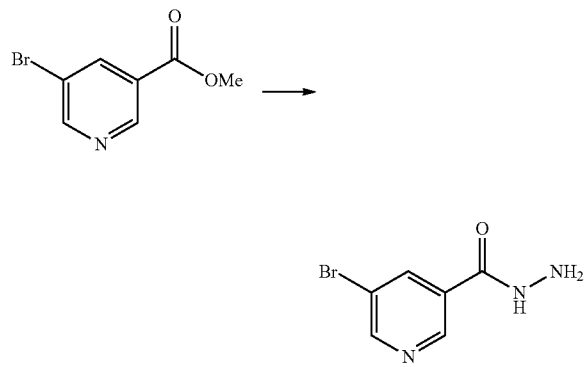 [SMILES: COC(=O)c1cncc(Br)c1 ; NNC(=O)c1cncc(Br)c1]

To a solution methyl 5-bromonicotinate (5 g, 23 mmol) in ethanol (40 mL) was added hydrazine hydrate (6 mL, 115 mmol). The reaction mixture was refluxed at 90° C. for 4 h. After this time, the reaction mixture was evaporated to dryness and then redissolved in ethyl acetate. The organic layer was washed with water, dried and evaporated to yield 5-bromonicotinohydrazide (3.4 g, 72%). LCMS Method T: retention time 0.573 min; [M+1]=216.0, 218.0.

Step 2. Preparation of 5-(5-bromopyridin-3-yl)-1,3,4-oxadiazol-2-amine

328

Step 3. Preparation of 5-(5-(4,4,5,5-tetramethyl-1,3,2-dioxaborolan-2-yl)pyridin-3-yl)-1,3,4-oxadiazol-2-amine

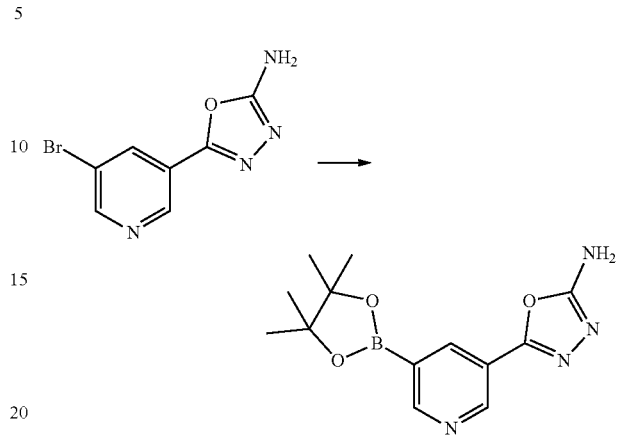

A mixture of 5-(5-bromopyridin-3-yl)-1,3,4-oxadiazol-2-amine (0.2 g, 0.8 mmol), bis(pinacolato)diborone (0.28 g, 1.0 mmol) and potassium acetate (0.25 g, 2.5 mmol) in 1,4-dioxane (8 mL) was degassed with nitrogen for 15 min. After this time, (1,1'-bis(diphenylphosphino)ferrocene)palladium (II) chloride dichloromethane complex (0.055 g 0.06 mmol) was added and the reaction mixture was again degassed for 10 min. with nitrogen. The reaction mixture was then heated in a microwave at 120° C. for 45 min. At the conclusion of this period, the reaction mixture was filtered through celite and the filtrate was concentrated under reduced pressure to provide crude 5-(5-(4,4,5,5-tetramethyl-1,3,2-dioxaborolan-2-yl)pyridin-3-yl)-1,3,4-oxadiazol-2-amine (0.3 g), which was used without further purification.

Step 4. Example 213

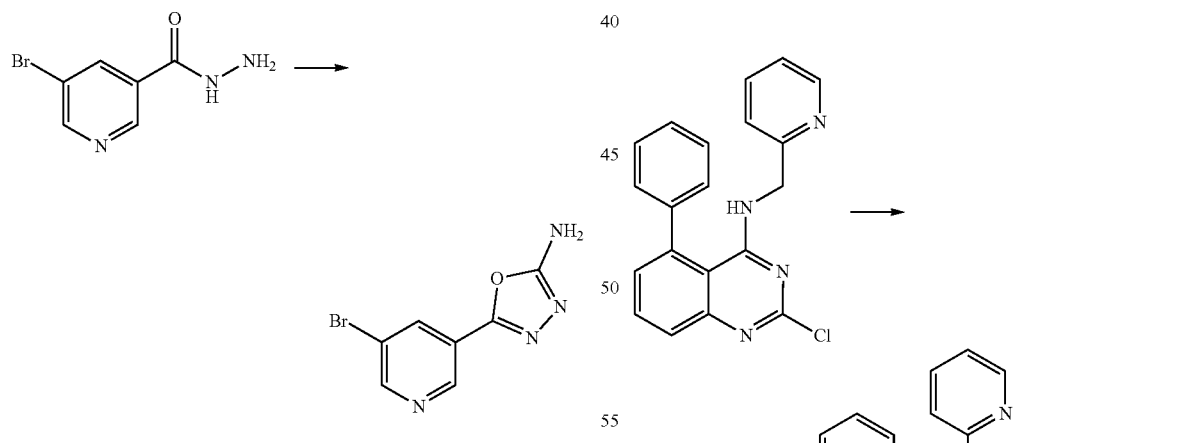

To a solution 5-bromonicotinohydrazide (2 g, 9 mmol) in dioxane (48 mL) was added sodium bicarbonate (0.78 g, 9.2 mmol) and 20 mL of water. The reaction mixture was allowed to stir for 10 min. and then cynogen bromide (1.17 g, 10 mmol) was added. The resulting clear solution was allowed to stir overnight at ambient temperature. At the conclusion of this period, a pinkish precipitate was collected by filtration to yield 5-(5-bromopyridin-3-yl)-1,3,4-oxadiazol-2-amine (3.4 g, 72% yield). LCMS Method Y: retention time 1.43 min; [M+1]=239.0, 241.0.

To a solution of 2-chloro-5-phenyl-N-(pyridin-2-ylmethyl)quinazolin-4-amine (from example 1, step 4, 0.2 g, 0.5 mmol) in 1,4-dioxane (5 mL) and H₂O (0.55 mL) under nitrogen was added 5-(5-(4,4,5,5-tetramethyl-1,3,2-dioxaborolan-2-yl)pyridin-3-yl)-1,3,4-oxadiazol-2-amine (0.2 g, 0.7 mmol) and potassium carbonate (0.24 g, 1.7 mmol). The reaction mixture was degassed with nitrogen for 15 min. After this time, (1,1'-bis(diphenylphosphino)ferrocene)palladium (II) chloride dichloromethane complex (0.047 g, 0.050 mmol) was added and the reaction mixture was again degassed for 10 min with nitrogen. At the conclusion of this period, the reaction mixture was stirred at 90° C. for 16 h, and then allowed to cool to room temperature. Once at the prescribe temperature, the reaction mixture was quenched by the addition of water. The reaction mixture was then transferred to a separation funnel and the aqueous layer was extracted with ethyl acetate. The combined organic portions were washed with water and saturated NaCl, dried over Na₂SO₄, filtered and concentrated under reduced pressure. The resulting residue was purified by silica gel column chromatography (5% methanol in dichloromethane) afford Example 213 (0.067 g, 10% yield) as an off-white solid. ¹H NMR (400 MHz, DMSO-d₆) δ (ppm): 9.71 (s, 1H); 9.11 (s, 2H); 8.25-8.23 (m, 1H0; 7.92 (d, 1H<J=8 Hz); 7.86 (t, 1H, J=8 Hz); 7.73 (t, 1H, J=8 Hz); 7.60-7.50 (m, 5H), 7.46 (br s, 2H); 7.37-7.31 (m, 2H); 7.22 (t, 1H, J=4 Hz); 6.93 (br s, 1H); 4.76 (d, 2H, J=4 Hz). LCMS Method W: retention time 1.80 min; [M+1]=473.2; HPLC Method A4: purity 95.9%, retention time=6.11 min.

Example 214

4-(5-Phenyl-4-(pyridin-2-ylmethylamino)quinazolin-2-yl)thiazole-2-carboxamide

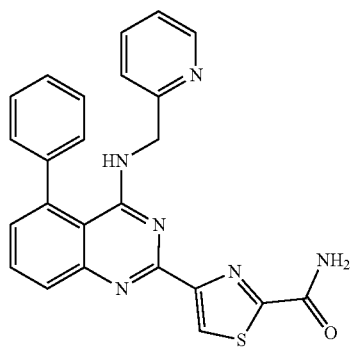

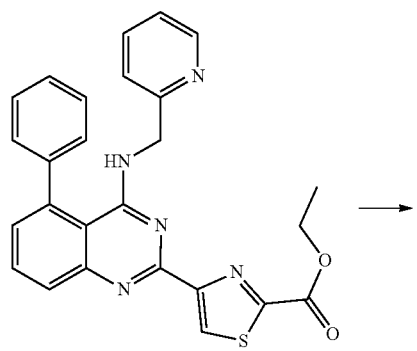

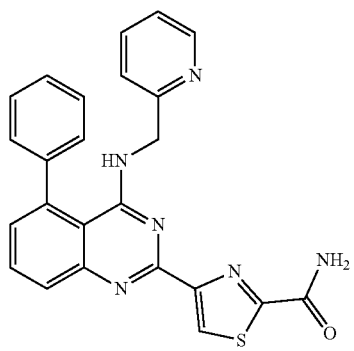 [SMILES: NC(=O)c1nc(-c2nc(NCc3ccccn3)c3c(-c4ccccc4)cccc3n2)cs1]

A solution of ethyl 4-(5-phenyl-4-(pyridin-2-ylmethylamino)quinazolin-2-yl)thiazole-2-carboxylate (from example 210, 90 mg, 0.19 mmol) in NH₃ (2.0 M in MeOH, 5 mL) was stirred at RT in a sealed vessel for 30 min. The solid formed was filtered and washed with ice cooled methanol. The solid was further purified by preparative HPLC (Method S) to provide Example 214 (35 mg, 42% yield). ¹H NMR (400 MHz, DMSO-d₆) δ (ppm): 8.79 (s, 1H); 8.26 (s, 1H); 8.22 (s, 1H); 7.97 (br s, 1H); 7.90-7.81 (m, 2H); 7.73 (dt, 1H, J=2, 7.6 Hz); 7.61-7.49 (m, 5H); 7.32-7.30 (m, 2H); 7.26-7.20 (m, 1H); 6.77 (t, 1H, J=4.8 Hz); 4.73 (d, 2H, J=4.8 Hz). LCMS Method W: retention time 1.85 min; [M+1]=439.2; HPLC Method A1: purity 95.2%, retention time=6.26 min. Preparative HPLC Method: S.

Example 215

1-(5-(5-Phenyl-4-(pyridin-2-ylmethylamino)quinazolin-2-yl)-4,5-dihydroisoxazol-3-yl)butan-1-one

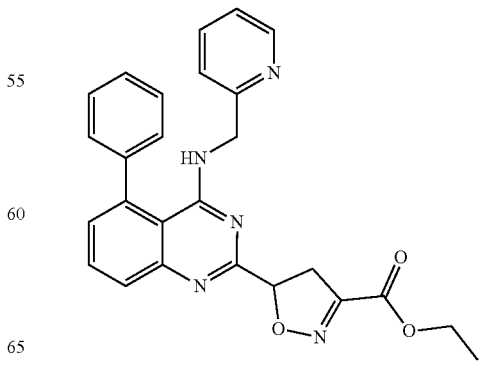

Step 1. Preparation of 5-phenyl-N-(pyridin-2-ylmethyl)-2-vinylquinazolin-4-amine

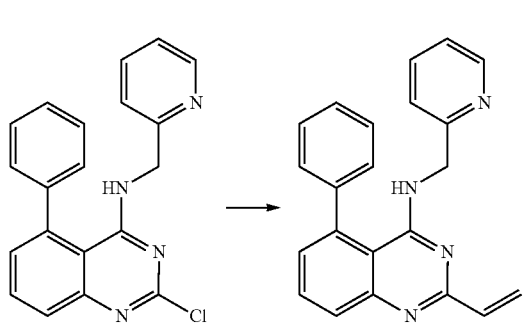 [SMILES: Clc1nc(NCc2ccccn2)c2c(-c3ccccc3)cccc2n1 ; C=Cc1nc(NCc2ccccn2)c2c(-c3ccccc3)cccc2n1]

To a solution of 2-chloro-5-phenyl-N-(pyridin-2-ylmethyl)quinazolin-4-amine (0.5 g, 1.44 mmol) in 1,4-dioxane (10 mL) was added Pd(TPP)$_2$Cl$_2$ (0.101 g, 0.144 mmol) and tributylvinyltin (2.285 g, 7.20 mmol) under a nitrogen stream. Upon completion of addition, the reaction mixture was heated to reflux at 90° C. for 16 h. After this time, the reaction mixture was allowed to cool to room temperature and then concentrated under reduced pressure. The resulting residue was purified by silica gel column chromatography (20% ethyl acetate, hexane) to yield 5-phenyl-N-(pyridin-2-ylmethyl)-2-vinylquinazolin-4-amine (0.38 g, 78% yield) as a white solid. $^1$H NMR (400 MHz, DMSO-d$_6$) δ (ppm): 8.22 (dd, 1H, J=4.8 Hz), 7.76 (d, 1H, J=1.6 Hz), 7.75 (s, 1H), 7.70 (dt, 1H, J=2 Hz, 8 Hz), 7.45-7.56 (m, 5H), 7.20-7.28 (m, 3H), 6.72 (dd, 1H, J=10.4 Hz, 17.2 Hz), 6.64 (t, 1H, J=3.6 Hz), 6.56 (dd, 1H, J=1.6 Hz, 17.2 Hz), 5.67 (d, 1H, J=10.4 Hz), 4.62 (d, 2H, J=4.0 Hz). LCMS Method T: retention time 1.500 min; [M+1]=339.2; HPLC Method A2: purity 98.1%, retention time=8.74 min.

Step 2. Preparation of (Z)-ethyl 2-chloro-2-(hydroxyimino)acetate

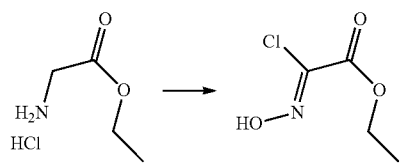

To a solution of glycine ester hydrochloride (2 g, 14 mmol) in 3 mL water was added conc. HCl (1.2 mL). Upon completion of addition, the resulting solution was cooled to −5° C. and then a solution of sodium nitrite (1 g, 14 mmol) in water (1.4 mL) was added. The resulting mixture was stirred at 0° C. for 10 min and then another solution of sodium nitrite (1 g, 14 mmol) in water (1.4 mL) was added. The resulting mixture was stirred at 0° C. for 45 min. At the conclusion of this period, a brine solution was added. The reaction mixture was extracted with ether, dried and evaporated under reduced pressure to yield (Z)-ethyl 2-chloro-2-(hydroxyimino)acetate (1.6 g, 76%), was taken to the next step immediately without further purification.

Step 3. Example 215

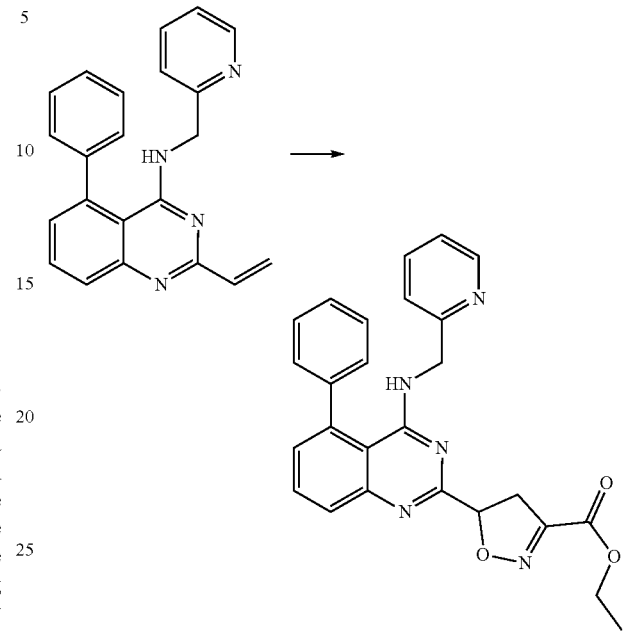

A solution of 5-phenyl-N-(pyridin-2-ylmethyl)-2-vinylquinazolin-4-amine (0.4 g, 1 mmol), (Z)-ethyl 2-chloro-2-(hydroxyimino)acetate (0.534 g, 3.54 mmol) and triethylamine (0.358 g, 3.54 mmol) in DCM (10 mL) was stirred at room temperature for 16 h. After this time, the reaction mixture was concentrated under reduced pressure to yield a residue. The residue was purified by ISCO chromatography (30% ethyl acetate in hexane) to yield Example 215 (0.2 g, 38% yield) as an off-white solid. $^1$H NMR (400 MHz, DMSO-d$_6$) δ (ppm): 8.21 (d, 1H, J=4 Hz), 7.88-7.80 (m, 2H), 7.68 (dd, 1H, J=1.6 Hz, 8.0 Hz), 7.60-7.47 (m, 5H), 7.32 (dd, 1H, J=2.4, 6.0 Hz), 7.25-7.20 (m, 2H), 6.78 (br s, 1H), 5.74 (dd, 1H, J=8, 12 Hz), 4.54 (dd, 2H, J=4, 6.8 Hz), 4.31 (q, 2H, J=8.0 Hz), 3.73 (dd, 1H, J=8, 17.6 Hz), 3.60 (dd, 1H, J=5.6, 17.2 Hz), 1.30 (t, 3H, J=7.2 Hz). LCMS Method W: retention time 2.033 min; [M+1]=454.4; HPLC Method A2: purity 95.1%, retention time=8.65 min.

Example 216

4-(5-Phenyl-4-(pyridin-2-ylmethylamino)quinazolin-2-yl)but-3-yn-1-ol

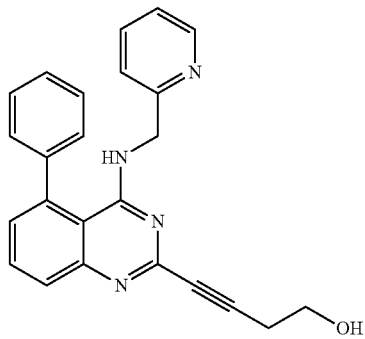 [SMILES: OCCC#Cc1nc(NCc2ccccn2)c2c(-c3ccccc3)cccc2n1]

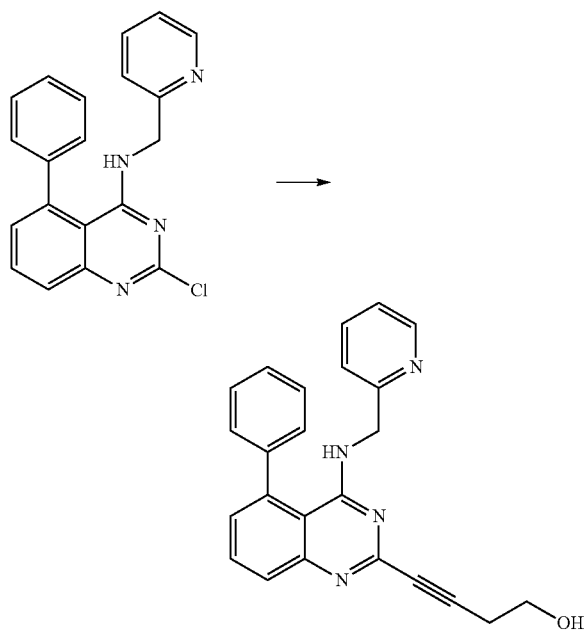

A solution of 2-chloro-5-phenyl-N-(pyridin-2-ylmethyl)quinazolin-4-amine (from example 1, step 4, 0.3 g, 0.9 mmol) and homopropargyl alcohol (0.07 mL, 1 mmol) in acetonitrile (10 mL) was degassed with nitrogen and then Pd(TPP)$_2$Cl$_2$ (0.060 g, 0.085 mmol), triethylamine (0.4 mL, 4 mmol) and CuI (0.016 g, 0.080 mmol) were added. The resulting reaction mixture was heated at 60° C. for 16 h. After this time, the reaction mixture was filtered through celite. The resulting filtrate was diluted with ethyl acetate and then washed successively with water and brine. The organic layer was dried, filtered and concentrated under reduced pressure to yield a residue. The residue was purified by silica gel chromatography (2% methanol in hexanes) to yield Example 216 (0.15 g, 46% yield) as an off-white solid. $^1$H NMR (400 MHz, DMSO-d$_6$) δ (ppm): 8.18 (br s, 1H); 7.88 (t, 1H, J=8 Hz); 7.77-7.72 (m, 2H); 7.60-7.48 (m, 5H); 7.38-7.30 (m, 3H); 7.26-7.22 (m 1H); 4.62 (d, 2H, J 4 Hz); 3.66 (t, 2H, 6.8 Hz); 2.67 (t, 2H, J=6.8 Hz). LCMS Method W: retention time 1.72 min; [M+1]=381.2; HPLC Method A1: purity 98.5%, retention time=6.03 min.

Example 217

2-((5-(5-Phenyl-4-(pyridin-2-ylmethylamino)quinazolin-2-yl)pyridin-3-yl)methylsulfonyl)acetamide

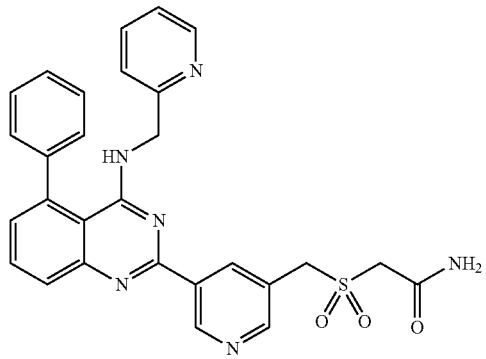 [SMILES: NC(=O)CS(=O)(=O)Cc1cncc(-c2nc(NCc3ccccn3)c3c(-c4ccccc4)cccc3n2)c1]

Step 1. Preparation of methyl 2-((5-bromopyridin-3-yl)methylthio)acetate

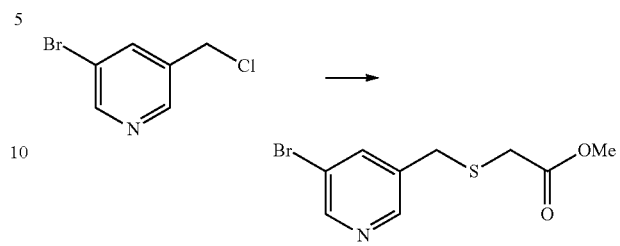

To a solution of 3-bromo-5-(chloromethyl)pyridine (from example 199, (1.2 g, 5.8 mmol) in acetonitrile (15 mL) was added K$_2$C$_{O3}$ (0.97 g, 7.0 mmol) followed by methyl 2-mercaptoacetate (0.57 mL, 6.4 mmol). The resulting solution was stirred at room temperature for 16 h. After this time, the reaction mixture was filtered and the filtrate was diluted with ethyl acetate and washed with water. The organic portion was dried, filtered and concentrated under reduced pressure. The resulting residue was purified by silica gel chromatography (30% ethyl acetate in hexane) to yield methyl 2-((5-bromopyridin-3-yl)methylthio)acetate (1.2 g, 80% yield). LCMS Method Y: retention time 1.66 min; [M+1]=276.0.

Step 2. Preparation of 2-((5-bromopyridin-3-yl)methylthio)acetamide

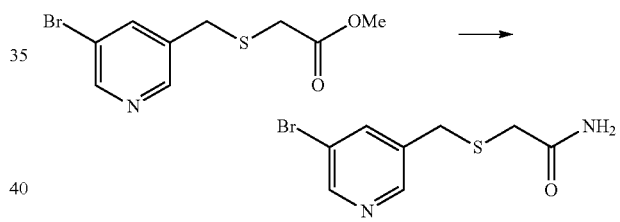

A solution of methyl 2-((5-bromopyridin-3-yl)methylthio)acetate (1.2 g, 4.5 mmol) in NH$_3$ (2.0 M in MeOH, 40 mL) was heated at 80° C. in a sealed vessel for 2 h. After this time, the reaction mixture was allowed to cool to room temperature and then the solvent was evaporated under reduced pressure. The resulting residue was recrystallized from EtOAc/hexanes to provide 2-((5-bromopyridin-3-yl)methylthio)acetamide (0.8 g, 72% yield). LCMS Method W: retention time 1.08 min; [M+1]=263.0.

Step 3. Preparation of 2-(5-bromopyridin-3-yl)methylsulfonyl)acetamide

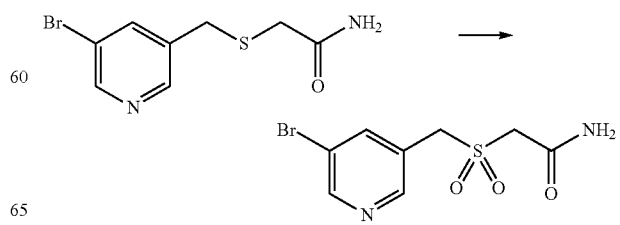

To a solution of 2-((5-bromopyridin-3-yl)methylthio)acetamide (0.8 g, 3.0 mmol) in MeOH:H₂O (30:10 mL) was added Oxone® (2.5 g, 3.9 mmol). The resulting reaction mixture was stirred at room temperature for 2 h. After this time, the solvent was evaporated and the resulting residue was dissolved in EtOAc and washed with water. The organic portion was concentrated to provide 2-(5-bromopyridin-3-yl)methylsulfonyl)acetamide (0.6 g, 67%). LCMS Method T: retention time 0.68 min; [M+1]=293.

Step 4. Preparation of 2-((5-(4,4,5,5-tetramethyl-1, 3,2-dioxaborolan-2-yl)pyridin-3-yl)methylsulfonyl) acetamide

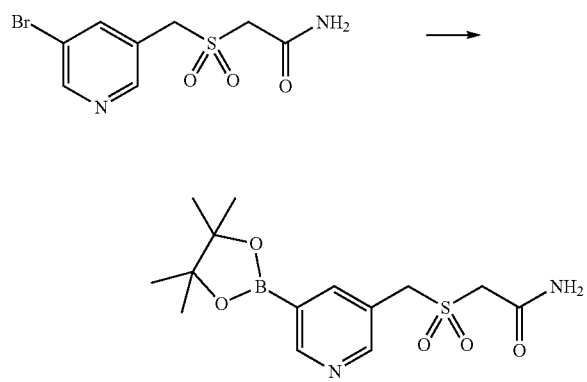 [SMILES: NC(=O)CS(=O)(=O)Cc1cncc(Br)c1 ; CC1(C)OB(c2cncc(CS(=O)(=O)CC(N)=O)c2)OC1(C)C]

A mixture of 2-(5-bromopyridin-3-yl)methylsulfonyl)acetamide (10.3 g, 1.00 mmol), bis(pinacolato)diboron (0.337 g, 1.30 mmol) and potassium acetate (0.3 g, 3.0 mmol) in 1,4-dioxane (10 mL) was degassed with nitrogen for 15 min. After this time, (1,1'-bis(diphenylphosphino)ferrocene)palladium (II) chloride dichloromethane complex (0.066 mg, 0.08 mmol) was added and the reaction mixture was again degassed for 10 min. with nitrogen. The reaction mixture was heated in the microwave reactor at 120° C. for 45 min. At the conclusion of this period, the reaction mixture was filtered through celite and the filtrate was concentrated under reduced pressure to provide 2-((5-(4,4,5,5-tetramethyl-1,3, 2-dioxaborolan-2-yl)pyridin-3-yl)methylsulfonyl)acetamide (440 mg) as a brown solid, which was used without further purification.

Step 5. Example 217

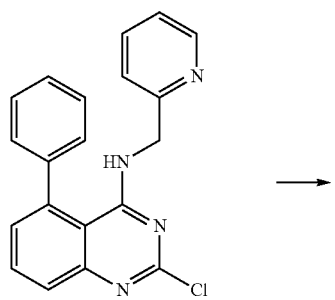

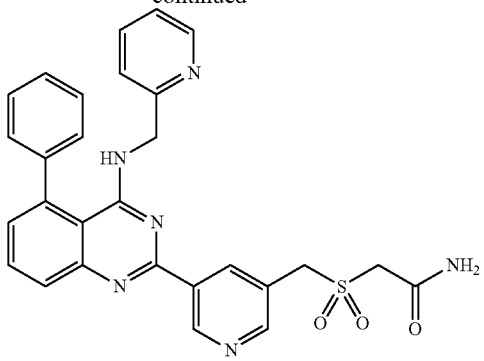

To a solution of 2-chloro-5-phenyl-N-(pyridin-2-ylmethyl)quinazolin-4-amine (from example 1, step 4, 0.3 g, 0.9 mmol) in 1,4-dioxane (10 mL) and H₂O (2 mL) under nitrogen was added 2-((5-(4,4,5,5-tetramethyl-1,3,2-dioxaborolan-2-yl)pyridin-3-yl)methylsulfonyl)acetamide (0.3 g, 0.9 mmol), and potassium carbonate (0.36 g, 2.6 mmol). The reaction mixture was degassed with nitrogen for 15 min and then (1,1'-bis(diphenylphosphino)ferrocene)palladium (II) chloride dichloromethane complex (0.07 g, 0.08 mmol) was added. The reaction mixture was again degassed for 10 min with nitrogen and then stirred at 90° C. for 16 h. At the conclusion of this period, the reaction mixture was allowed to cool to room temperature and then quenched by the addition of water. The reaction mixture was transferred to a separation funnel and the aqueous layer was extracted with ethyl acetate. The combined organic portions were washed with water and saturated NaCl, dried over Na₂SO₄, filtered and concentrated under reduced pressure. The resulting concentrate was purified by preparative TLC (5% methanol in dichloromethane) to provide Example 217 (100 mg, 22% yield) as an off white solid. ¹H NMR (400 MHz, DMSO-d₆) δ (ppm): 9.62 (s, 1H); 9.84 (s, 1H); 8.84 (s, 1H); 8.23 (br s, 1H); 7.92-7.88 (m, 1H); 7.85 (t, 2H, J=4 Hz); 7.72 (t, 1H, J=8 Hz); 7.60-7.50 (m, 6H); 7.40-7.28 (m, 2H); 7.22 (t, 1H, J=8 Hz); 6.85 (br s, 1H); 4.85 (s, 2H); 4.73 (d, 2H, J=4 HZ); 4.06 (s, 2H). LCMS Method W: retention time 1.70 min; [M+1]=525.2; HPLC Method A2: purity 99.5%, retention time=5.91 min.

Example 218

5-Phenyl-N-(pyridin-2-ylmethyl)-2-(2,2,5-trimethyl-1,3-dioxan-5-yl)quinazolin-4-amine

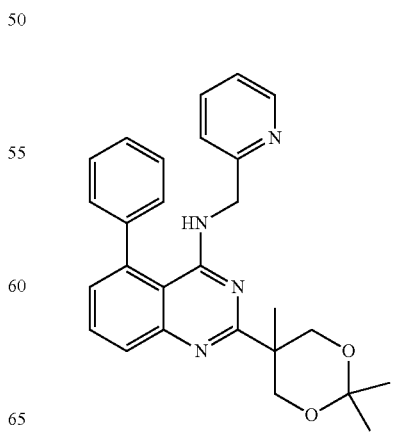

Step 1. Preparation of 3-aminobiphenyl-2-carbonitrile

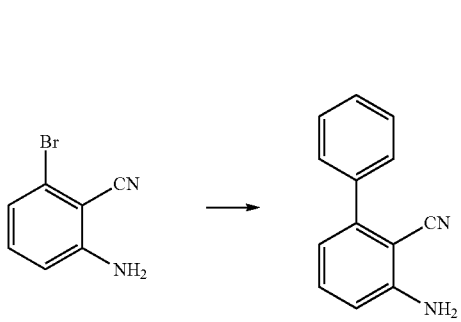 [SMILES: N#Cc1c(N)cccc1Br ; N#Cc1c(N)cccc1-c1ccccc1]

To a solution of 2-amino-6-bromobenzonitrile (5 g, 0.025 mmol) in toluene (70 mL) was added KOAc (5 g, 0.05 mmol), phenylboronic acid (4.27 g, 0.035 mmol) and cat. Pd(TPP)$_2$Cl$_2$. The reaction mixture was heated to 115° C. for 16 h. After this time, the reaction mixture was filtered and the volatiles were evaporated to yield as residue. The residue was purified by column chromatography (1% EtOAc in hexanes) to provide 3-aminobiphenyl-2-carbonitrile (3.2 g, 65% yield) as light yellow solid. LCMS Method Z: retention time 3.65 min; [M+]=195.2.

Step 2. Preparation of 3-aminobiphenyl-2-carboxamide

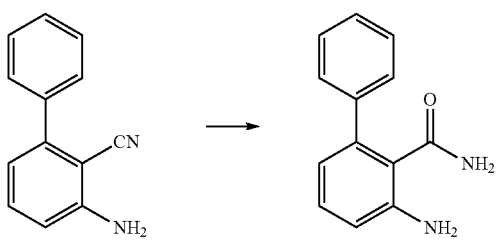 [SMILES: N#Cc1c(N)cccc1-c1ccccc1 ; NC(=O)c1c(N)cccc1-c1ccccc1]

A solution of 3-aminobiphenyl-2-carbonitrile (4 g, 20 mmol) in ethanol (20 mL) and aqueous NaOH (8 g, 200 mmol) was heated at 100° C. in the microwave reactor for 1 h 30 min. After this time, the ethanol was evaporated under reduced pressure and the resulting residue was extracted with ethyl acetate. The organic extracts were concentrated under reduced pressure to yield a residue. The residue was purified by silica gel chromatography (50% EtOAc in hexane) to give 3-aminobiphenyl-2-carboxamide (3.1 g, 72% yield) as a brown solid. $^1$H NMR (400 MHz, DMSO-d$_6$) δ (ppm): 7.40-7.30 (m, 5H), 7.15 (br s, 1H), 7.11 (t, 1H, J=8 Hz), 6.72 (dd, 1H, J=0.8, 8 Hz), 6.52 (dd, 1H, J=0.8, 8 Hz), 5.13 (s, 1H). LCMS Method W: retention time 1.28 min; [M+1]=213.0.

Step 3. Preparation of N-(2-carbamoylbiphenyl-3-yl)-2,2,5-trimethyl-1,3-dioxane-5-carboxamide

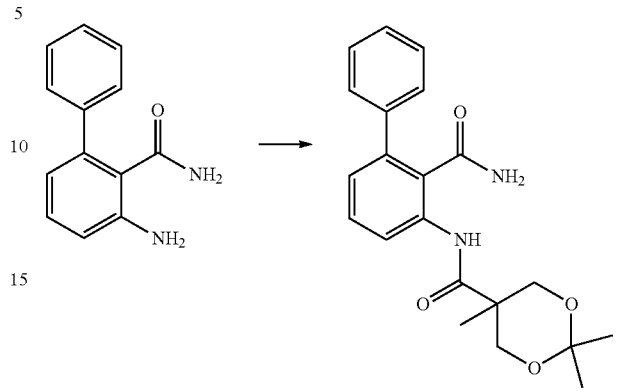

To a solution of the commercially available 2,2,5-trimethyl-1,3-dioxane-5-carboxylic acid (0.6 g, 4 mmol) in DCM (30 mL) was added HATU (1.8 g, 4.7 mmol) and DIPEA (1.6 mL, 23.5 mmol). The reaction mixture was stirred at room temperature for 1 h. After this time, 3-aminobiphenyl-2-carboxamide (0.6 g, 2.35 mmol) was added and the resulting solution was stirred for 16 h. At the conclusion of this period, the reaction mixture was washed with water, dried, filtered and concentrated under reduced pressure. The resulting residue was purified by silica gel chromatography (25% ethyl acetate in hexanes) to yield N-(2-carbamoylbiphenyl-3-yl)-2,2,5-trimethyl-1,3-dioxane-5-carboxamide (0.25 g, 24% yield) as a white solid. LCMS Method Y: retention time 1.69 min; [M+1]=367.2.

Step 4. Preparation of 5-phenyl-2-(2,2,5-trimethyl-1,3-dioxan-5-yl)quinazolin-4(3H)-one

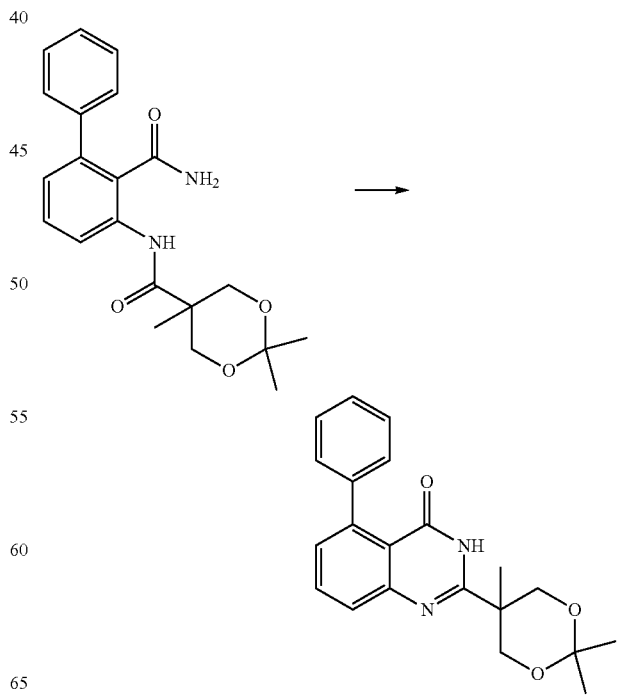

To a solution N-(2-carbamoylbiphenyl-3-yl)-2,2,5-trimethyl-1,3-dioxane-5-carboxamide (0.23 g, 0.62 mmol) in methanol was added NaOMe (0.25 mL, 25% in MeOH, 1.2 mmol) and the reaction mixture stirred at 50° C. for 1 h. After this time, the reaction mixture was concentrated and the resulting residue was diluted with ethyl acetate then washed with water. The organic portion was dried and concentrated under reduced pressure to yield a residue. The residue was purified by silica gel chromatography (30% ethyl acetate in hexanes) to yield pure 5-phenyl-2-(2,2,5-trimethyl-1,3-dioxan-5-yl)quinazolin-4(3H)-one (0.2 g, 91% yield) as a white solid. $^1$H NMR (400 MHz, DMSO-d$_6$) δ (ppm): 11.49 (br s, 1H), 7.77 (t, 1H, J=8 Hz), 7.64 (d, 1H, J=8 Hz), 7.36-7.28 (m, 5H), 7.21 (d, 1H, J=8 Hz), 4.27 (d, 2H, J=12 Hz), 3.91 (d, 2H, J=12 Hz), 1.40 (s, 3H), 1.35 (d, 6H, 10.2 Hz). LCMS Method W: retention time 2.01 min; [M+1]=351.

Step 5. Example 218

To a solution of 5-phenyl-2-(2,2,5-trimethyl-1,3-dioxan-5-yl)quinazolin-4(3H)-one (0.22 g, 0.62 mmol) in acetonitrile (10 mL) at room temperature was added DBU (0.24 g, 1.57 mmol) and BOP reagent (0.36 g, 0.81 mmol). The reaction mixture was stirred for 30 min and then aminomethylpyridine (0.11 mL, 1.1 mmol) was added. The resulting solution was stirred for 16 h. After this time, the reaction mixture was concentrated under reduced pressure and the resulting residue was purified by silica gel chromatography (30% EtOAc in hexanes) to give Example 219 (0.18 g, 67% yield) as a white solid. $^1$H NMR (400 MHz, DMSO-d$_6$, δ): 8.26 (br s, 1H); 7.80-7.69 (m, 3H); 7.59-7.45 (m, 5H); 7.27-7.20 (m, 3H); 6.53 (br s, 1H); 4.55 (d, 2H, J=4 Hz); 4.31 (d, 2H, J=7.6 Hz); 3.79 (d, 2H, J=7.6 Hz); 1.38 (d, 6H, J=4.8 Hz); 1.33 (s, 3H). LCMS Method W: retention time 2.37 min, [M+1]=441; HPLC Method A1: purity 96.7%, retention time=6.87 min.

Example 219

2-Methyl-2-(5-phenyl-4-(pyridin-2-ylmethylamino)quinazolin-2-yl)propane-1,3-diol

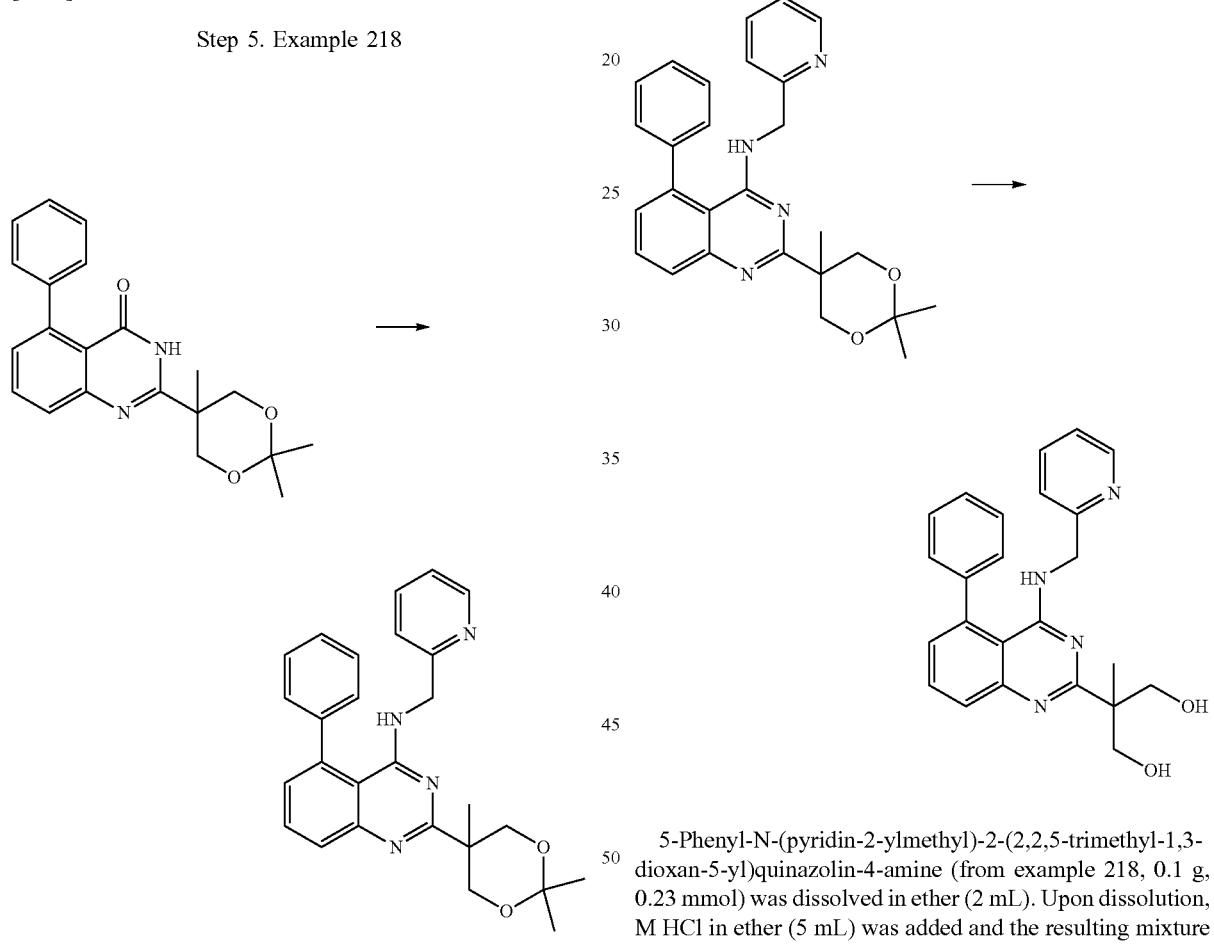

5-Phenyl-N-(pyridin-2-ylmethyl)-2-(2,2,5-trimethyl-1,3-dioxan-5-yl)quinazolin-4-amine (from example 218, 0.1 g, 0.23 mmol) was dissolved in ether (2 mL). Upon dissolution, M HCl in ether (5 mL) was added and the resulting mixture was stirred at RT for 4 h. After this time, the resulting solution was neutralized with sat. NaHCO$_3$ solution. The ether was evaporated and the aqueous layer residue was extracted in ethyl acetate. The organic extracts were dried and evaporated. The resulting residue was purified by silica gel column chromatography (2% methanol in dichloromethane) to yield Example 219 (56 mg, 62% yield). $^1$H NMR (400 MHz, DMSO-d$_6$, δ): 8.24 (br s, 1H); 7.80-7.63 (m, 3H); 7.54-7.44 (m, 5H); 7.24-7.20 (m, 3H); 6.56 (br s, 1H); 4.57 (s, 2H), 4.56 (d, 2H, J=6 Hz); 3.77 (d, 4H, J=6 Hz); 1.23 (s, 3H). LCMS Method W: retention time 1.77 min, [M+1]=401; HPLC Method A1: purity 95.14%, retention time=9.78 min.

Example 220

3-(5-Phenyl-4-(pyridin-2-ylmethylamino)quinazolin-2-yl)isoxazole-5-carboxamide

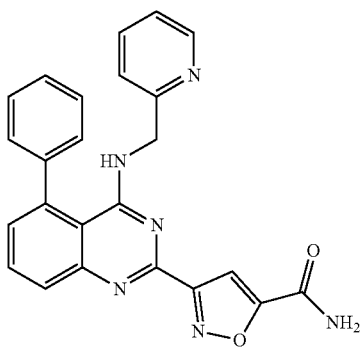 [SMILES: NC(=O)c1cc(-c2nc(NCc3ccccn3)c3c(-c4ccccc4)cccc3n2)no1]

Step 1. Preparation of (E)-5-phenyl-4-(pyridin-2-ylmethylamino)quinazoline-2-carbaldehyde

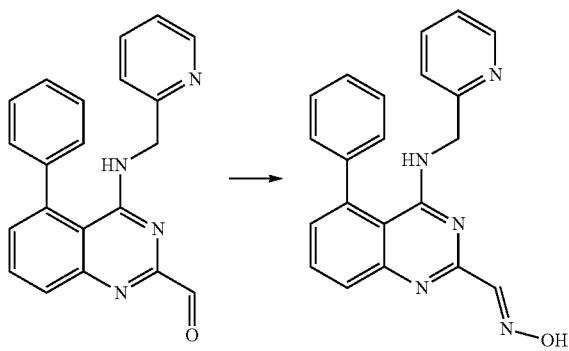 [SMILES: O=Cc1nc(NCc2ccccn2)c2c(-c3ccccc3)cccc2n1 ; O/N=C/c1nc(NCc2ccccn2)c2c(-c3ccccc3)cccc2n1]

A solution of 5-phenyl-4-(pyridin-2-ylmethylamino)quinazoline-2-carbaldehyde (from example 212, 0.62 g, 1.8 mmol), hydroxylamine hydrochloride (0.19 g, 2.8 mmol) and sodium acetate (0.30 g, 3.7 mmol) in water (10 mL) was heated at 100° C. for 30 min. After this time, the reaction mixture was allowed to cool to RT and then extracted with DCM (2×50 mL). The combined organic portions were concentrated under reduced pressure and the resulting residue was purified by silica gel chromatography (0.8% MeOH in DCM) to provide (E)-5-phenyl-4-(pyridin-2-ylmethylamino)quinazoline-2-carbaldehyde (0.4 g, 60% yield) as a yellow solid. LCMS Method W: retention time 1.703 min, [M+1]=356.2.

Step 2. Preparation of methyl 3-(5-phenyl-4-(pyridin-2-ylmethylamino)quinazolin-2-yl)isoxazole-5-carboxylate

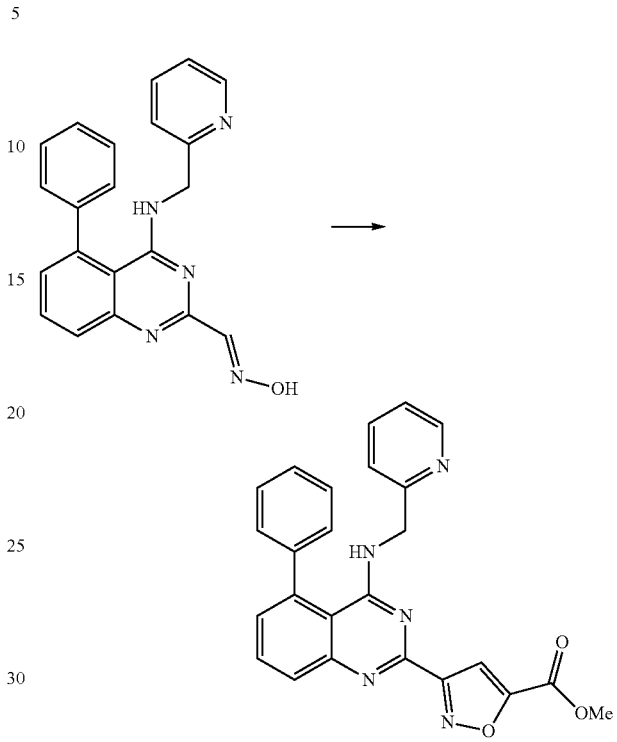

To a solution of (E)-5-phenyl-4-(pyridin-2-ylmethylamino)quinazoline-2-carbaldehyde oxime (0.32 g, 0.90 mmol) and methylpropriolate (0.227 g, 2.70 mmol) in acetonitrile was added CrO₂ (magtrieve) (0.75 g, 9.0 mmol). The reaction mixture was heated at 80° C. for 2 h. After this time, the reaction mixture was allowed to cool to RT. Once at the prescribed temperature, the reaction mixture was diluted with ethyl acetate and filtered through celite. The filtrate was evaporated under reduced pressure and the resulting residue was purified by silica gel chromatography (1.5% MeOH in DCM) to provide methyl 3-(5-phenyl-4-(pyridin-2-ylmethylamino)quinazolin-2-yl)isoxazole-5-carboxylate (120 mg, 30% yield) as an off white solid. LCMS Method W: retention time 2.185 min, [M+1]=438.2.

Step 3. Example 220

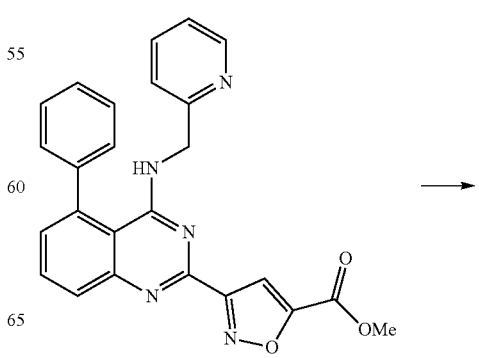

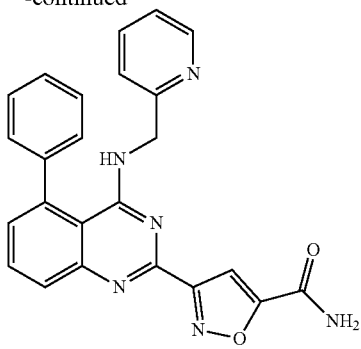

A solution of 3-(5-phenyl-4-(pyridin-2-ylmethylamino)quinazolin-2-yl)isoxazole-5-carboxylate (90 mg, 0.199 mmol) in NH$_3$ (2.0 M in MeOH, 5 mL) was heated at 60° C. in a sealed vessel for 8 h. After this time, the reaction mixture was allowed to cool to room temperature and the solvent was evaporated under reduced pressure. The resulting residue was purified by preparative HPLC (Method S) to provide Example 220 (35 mg, 42% yield). $^1$H NMR (400 MHz, DMSO-d$_6$, δ): 8.45 (s, 1H); 8.21 (s, 1H); 8.05 (s, 1H); 7.92-7.85 (m, 2H); 7.73 (dt, 1H, J=1.2, 7.6 Hz); 7.67 (s, 1H); 7.60-7.49 (m, 5H); 7.40-7.30 (m, 3H); 7.24 (t, 1H, J=5.6 Hz); 7.00 (t, 1H, J=4 Hz); 4.69 (d, 2H, J=4 Hz). LCMS Method W: Retention time 1.74 min, [M+1]=423.2; HPLC Method A1: purity 99.3%, retention time=6.78 min.

Example 221

N-((1-(5-phenyl-4-(pyridin-2-ylmethylamino)quinazolin-2-yl)cyclopropyl)methyl)methanesulfonamide

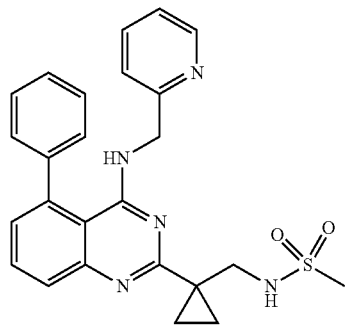 [SMILES: CS(=O)(=O)NCC1(c2nc(NCc3ccccn3)c3c(-c4ccccc4)cccc3n2)CC1]

Step 1. Preparation of 2-(1-(aminomethyl)cyclopropyl)-5-phenyl-N-(pyridin-2-ylmethyl)quinazolin-4-amine

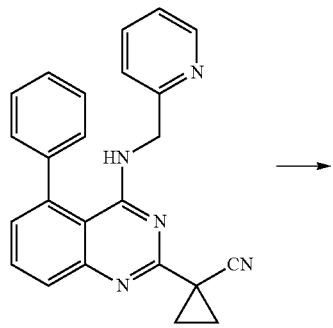

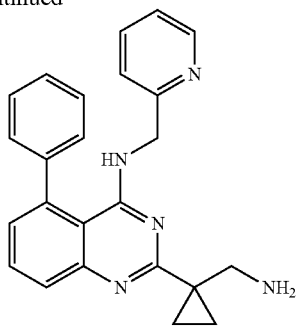

To a solution of 1-(5-phenyl-4-(pyridin-2-ylmethylamino)quinazolin-2-yl)cyclopropanecarbonitrile (Example 207, 0.6 g, 2 mmol) in 7 M ammonia methanol (10 mL) was added Ra—Ni (200 mg). The resulting slurry was stirred under hydrogen atmosphere for 16 h. After this time, the reaction mixture was filtered and filtrate was concentrated under reduced pressure to yield 2-(1-(aminomethyl)cyclopropyl)-5-phenyl-N-(pyridin-2-ylmethyl)quinazolin-4-amine (380 mg, 63% yield), which was used without further purification.

Step 2. Example 221

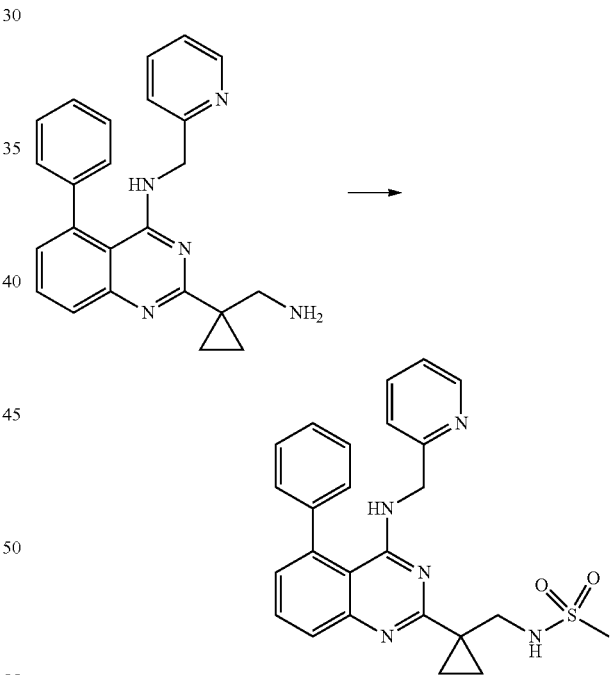

To a stirred solution of 2-(1-(aminomethyl)cyclopropyl)-5-phenyl-N-(pyridin-2-ylmethyl)quinazolin-4-amine (60 mg, 0.16 mmol) and TEA (0.05 ml, 0.43 mmol) in DCM (5 mL) was added methanesulfonyl chloride (0.015 mL, 0.18 mmol) dropwise at 0° C. The reaction mixture was allowed to reach RT where it stirred for 2 h. After this time, the reaction mixture was quenched with water and then extracted with EtOAc. The combined organic extracts were washed successively with water and brine, dried, and filtered. The filtrate was concentrated under reduced pressure to yield a residue. The residue was purified by silica gel chromatography (15% EtOAc, hexane) to provide Example 221 (25 mg, 36% yield) as a solid. $^1$H NMR (400 MHz, DMSO-d$_6$, δ): 8.25 (d, 1H, J=4.4 Hz); 7.80-7.68 (m, 3H); 7.60-7.43 (m, 5H); 7.27-7.15 (m, 3H); 6.95 (t, 1H, J=6 Hz), 6.53 (s, 1H), 4.54 (d, 2H, J=4 Hz), 3.54 (d, 2H, J=6.4 Hz), 2.99 (s, 3H), 1.30 (d, 2H, J=2.4 Hz, 1.01 (d, 2H, J=2.4 Hz). LCMS Method V: retention time 1.77 min, [M+1]=460.0; HPLC Method A1: purity 99.1%, retention time=6.29 min.

Example 222

N-((1-(5-phenyl-4-(pyridin-2-ylmethylamino)quinazolin-2-yl)cyclopropyl)methyl)sulfamide

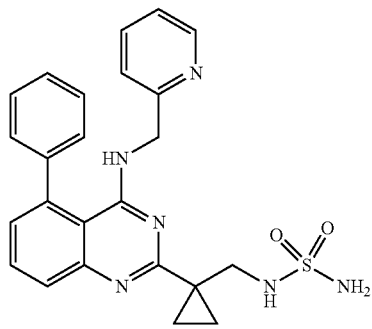 [SMILES: NS(=O)(=O)NCC1(c2nc(NCc3ccccn3)c3c(-c4ccccc4)cccc3n2)CC1]

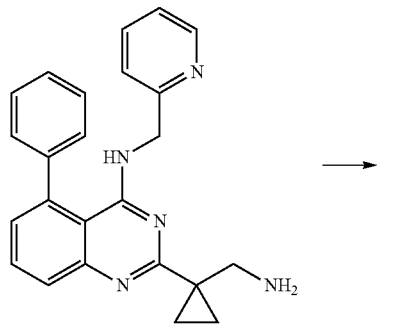

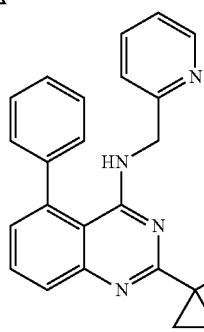

To a solution chlorosulfonylisocyanate (0.03 mL, 0.2 mmol) in DCM (1 mL) was added t-BuOH (0.16 mL, 0.21 mmol) at 0° C. The reaction mixture was stirred for 10 min. After this time, the reaction mixture was added to a mixture of 2-(1-(aminomethyl)cyclopropyl)-5-phenyl-N-(pyridin-2-ylmethyl) quinazolin-4-amine (from example 221, 80 mg, 0.21 mmol) and TEA (0.043 ml, 0.42 mmol) in DCM at 0° C. The resulting reaction mixture was stirred for an additional 3 h at room temperature. At the conclusion of this period, the reaction mixture was quenched with water (15 mL) and then extracted with DCM. The combined organic extracts were washed successively with water and brine, dried with Na$_2$SO$_4$, filtered and concentrated under reduced pressure to yield a residue. TFA (2 mL) was added to the residue and the resulting reaction mixture was stirred for 2 h and then concentrated in vacuo. The resulting residue was diluted with EtOAc (20 mL) and washed successively with saturated NaHCO$_3$ and brine, dried over Na$_2$SO$_4$ filtered and the solvent was removed under reduced pressure. The resulting residue was purified by silica gel chromatography (5% MeOH in DCM) to yield Example 222 (25 mg, 27% yield). $^1$H NMR (400 MHz, DMSO-d$_6$, δ): 8.24 (dd, 1H, J=1.2 Hz, 7.2 Hz); 7.67-7.80 (m, 3H); 7.58-7.43 (m, 5H); 7.28-7.16 (m, 3H); 6.63 (s, 2H), 6.53 (br s, 1H), 6.48-6.43 (m, 1H), 4.52 (d, 2H, J=4 Hz), 3.45 (d, 2H, J=7.6 Hz), 1.28 (d, 2H, J=4 Hz), 1.02 (d, 2H, J=4 Hz). LCMS Method W: retention time 1.93 min, [M+1]=461.2; HPLC Method A1: purity 96.5%, retention time=5.91 min.

Example 223

4-(5-Phenyl-4-(pyridin-2-ylmethylamino)quinazolin-2-yl)piperidine-1-sulfonamide

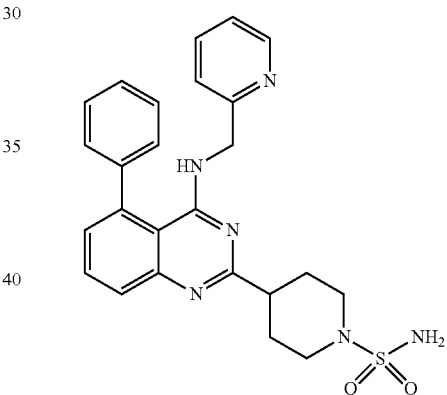

Step 1. Preparation of 5-phenyl-2-(piperidin-4-yl)-N-(pyridin-2-ylmethyl)quinazolin-4-amine

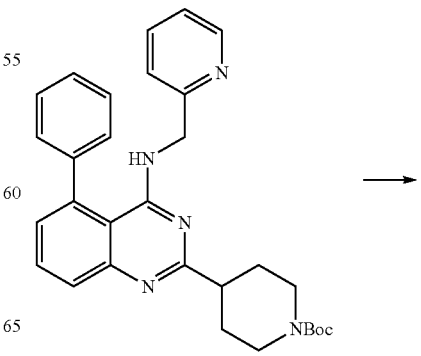

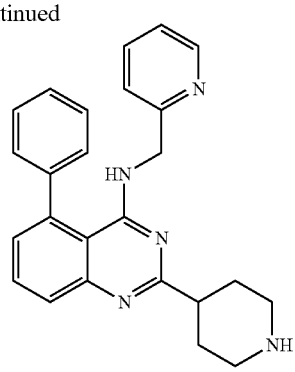

Tert-butyl 4-(5-phenyl-4-(pyridin-2-ylmethylamino)quinazolin-2-yl)piperidine-1-carboxylate (Example 211, 0.2 g 0.4 mmol) was dissolved in 10 mL HCl (2 M in ether). The reaction mixture stirred at RT for 16 h. After this time, the solvent was removed under reduced pressure. The resulting residue was neutralized with sat. $NaHCO_3$ and the aqueous phase was extracted into DCM. The combined organic extracts were concentrated under reduced pressure and the resulting residue was purified by recrystallization with EtOAc to yield 5-phenyl-2-(piperidin-4-yl)-N-(pyridin-2-ylmethyl)quinazolin-4-amine (0.13 g, 76% yield). $^1$H NMR (400 MHz, DMSO-$d_6$) δ (ppm): 8.21 (d, 1H, J=4.0 Hz), 7.77-7.66 (m, 3H), 7.58-7.40 (m, 5H), 7.30-7.15 (m, 3H), 6.57 (br s, 1H), 4.56 (d, 2H, J=4.0 Hz), 3.05 (d, 2H, J=12.0 Hz), 2.80-2.70 (m, 1H), 2.60 (t, 2H, J=8.0 Hz), 1.95-1.80 (m, 2H), 1.80-1.65 (m, 2H). LCMS Method W: retention time 1.43 min, [M+1]=396.2; HPLC Method A1: purity 96.4%, retention time=9.00 min.

Step 2. Example 223

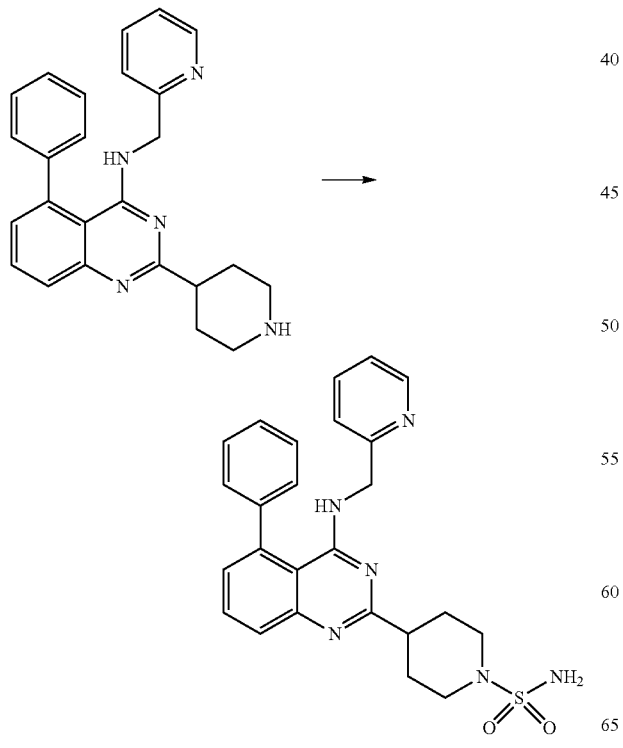

To a solution chlorosulfonylisocyanate (0.035 g, 0.25 mmol) in DCM (5 mL) was added t-BuOH (0.019 g, 0.25 mmol) at RT. The reaction mixture was stirred for 10 min and then TEA (0.038 g, 0.37 mmol) was added followed by 5-phenyl-2-(piperidin-4-yl)-N-(pyridin-2-ylmethyl)quinazolin-4-amine (0.1 g, 0.3 mmol) in DCM. The resulting reaction mixture was stirred for an additional 3 h. After this time, the reaction mixture was diluted with water and then extracted in EtOAc. The combined organic extracts were dried and concentrated under reduced pressure to yield a residue. The residue was treated with etherial HCl (4 ml, 2 M solution). The resulting solution was concentrated under reduced pressure and the resulting residue was purified by recrystallization using EtOAc to yield Example 223 (0.038 g, 32% yield). $^1$H NMR (400 MHz, DMSO-$d_6$) δ (ppm): 8.20 (s, 1H), 7.80-7.66 (m, 3H), 7.58-7.43 (m, 5H), 7.27 (d, 1H, J=8.0 Hz), 7.24-7.18 (m, 2H), 6.73 (br s, 2H), 6.65 (t, 1H, J=4.0 Hz), 4.58 (d, 1H, J=8.0 Hz), 3.55 (d, 2H, J=12.0 Hz), 2.81-2.64 (m, 3H), 2.10-2.04 (m, 2H), 2.00-1.86 (m, 2H). LCMS Method V: retention time 1.62 min, [M+1]=475; HPLC Method A1: purity 98.7%, retention time=6.26 min.

Example 224

5-(5-Phenyl-4-(pyridin-2-ylmethylamino)quinazolin-2-yl)isoxazole-3-carboxamide

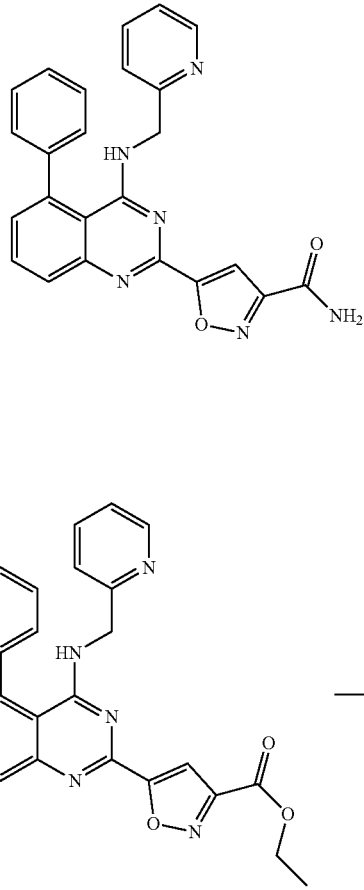

-continued

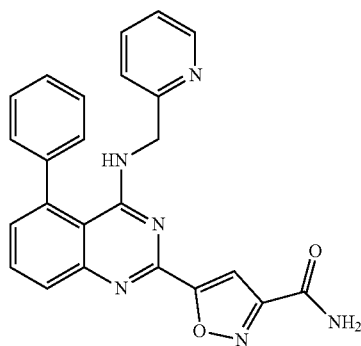 [SMILES: NC(=O)c1cc(-c2nc(NCc3ccccn3)c3c(-c4ccccc4)cccc3n2)on1]

A solution of the ethyl 5-(5-phenyl-4-(pyridin-2-ylmethylamino)quinazolin-2-yl)isoxazole-3-carboxylate (from example 209, 0.075 g, 0.17 mmol) in $NH_3$ (2.0 M in MeOH, 5 mL) was heated at 60° C. in a sealed vessel for 16 h. After this time, the reaction mixture was allowed to cool to room temperature. Once at the prescribed temperature, the solid formed was filtered and washed with ice cooled methanol to provide Example 224 (31 mg, 44% yield). $^1$H NMR (400 MHz, DMSO-$d_6$) δ (ppm): 8.29 (s, 1H), 8.21 (d, 1H, J=2 Hz), 7.87-7.95 (m, 3H), 7.73 (dt, 1H, J=1.6, 8 Hz), 7.45-7.64 (m, 5H), 7.37 (dt, 2H, J=1.6, 6.8 Hz, 2H), 7.25 (dd, 1H, J=6.0, 7.2 Hz), 4.70 (d, 2H, J=4 Hz). LCMS Method W: retention time 1.817 min; [M+1]=423.2; HPLC Method A1: purity 99.3%, retention time=7.31 min.

Examples 225 to 322

Examples 225 to 322 were synthesized via similar procedures described above. HPLC/MS data for each compound was collected using methods E-Z1 and the molecular mass determined by MS (ES) by the formula m/z. Both the retention time and MS data for Examples 225 to 322 are listed in Table 1c, wherein MW=molecular weight.

TABLE 1c

| Example | Structure | MW | LCMS Data | LCMS Method |
|---|---|---|---|---|
| 225 | 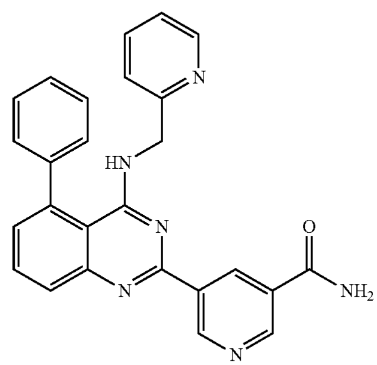 [SMILES: NC(=O)c1cncc(-c2nc(NCc3ccccn3)c3c(-c4ccccc4)cccc3n2)c1] | 432.477 | [M + 1] 433.0 Rt 1.86 min | E |
| 226 | 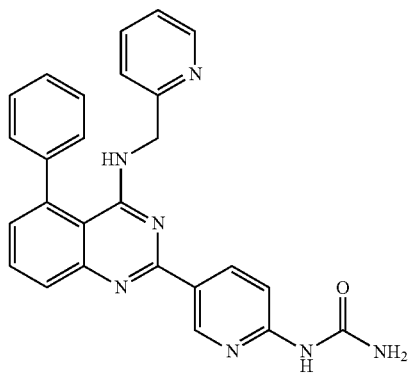 [SMILES: NC(=O)Nc1ccc(-c2nc(NCc3ccccn3)c3c(-c4ccccc4)cccc3n2)cn1] | 447.491 | [M + 1] 448.0 Rt 1.50 min | O |

TABLE 1c-continued

| Example | Structure | MW | LCMS Data | LCMS Method |
|---|---|---|---|---|
| 227 | 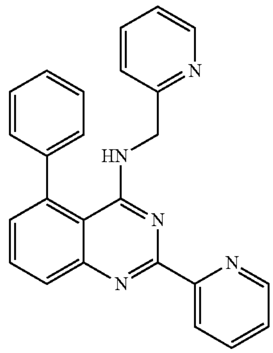 [SMILES: c1ccc(-c2cccc3nc(-c4ccccn4)nc(NCc4ccccn4)c23)cc1] | 389.452 | [M + 1] 390.0 Rt1.58 min | O |
| 228 | 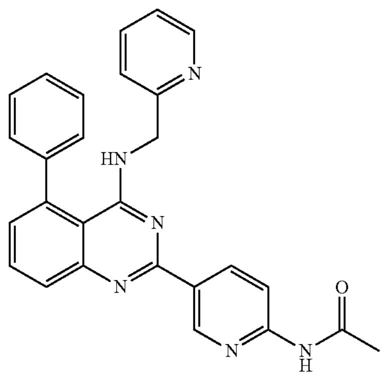 [SMILES: CC(=O)Nc1ccc(-c2nc(NCc3ccccn3)c3c(-c4ccccc4)cccc3n2)cn1] | 446.503 | [M + 1] 447.0 Rt1.49 min | O |
| 229 | 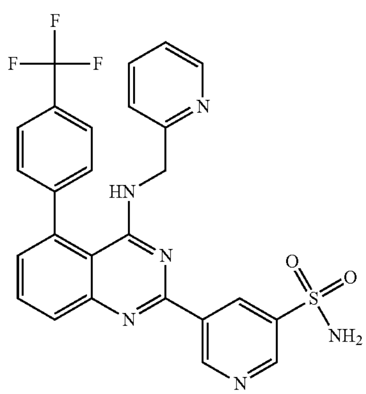 [SMILES: NS(=O)(=O)c1cncc(-c2nc(NCc3ccccn3)c3c(-c4ccc(C(F)(F)F)cc4)cccc3n2)c1] | 536.528 | [M + 1] 537.0 Rt1.73 min | O |
| 230 | 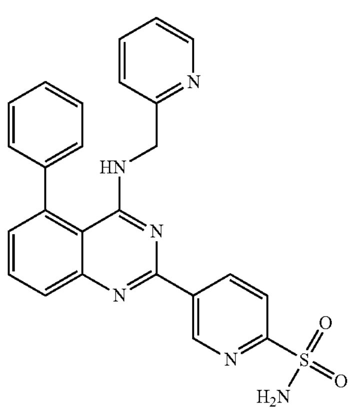 | 468.53 | [M + 1] 469.0 Rt1.41 min | O |

TABLE 1c-continued

| Example | Structure | MW | LCMS Data | LCMS Method |
|---|---|---|---|---|
| 231 | 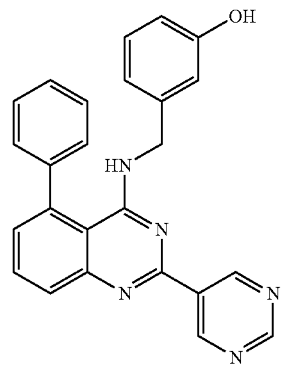 [SMILES: Oc1cccc(CNc2nc(-c3cncnc3)nc3cccc(-c4ccccc4)c23)c1] | 405.451 | [M + 1] 406.2 Rt2.50 min | Z1 |
| 232 | 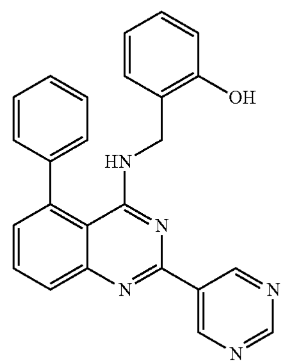 [SMILES: Oc1ccccc1CNc1nc(-c2cncnc2)nc2cccc(-c3ccccc3)c12] | 405.451 | [M + 1] 406.2 Rt2.58 min | Z1 |
| 233 | 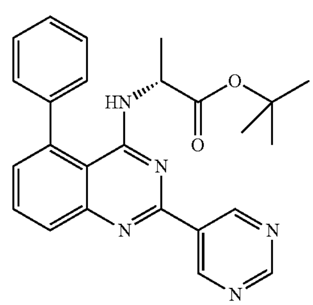 [SMILES: C[C@@H](Nc1nc(-c2cncnc2)nc2cccc(-c3ccccc3)c12)C(=O)OC(C)(C)C] | 427.498 | [M + 1] 428.2 Rt3.12 min | Z1 |
| 234 | 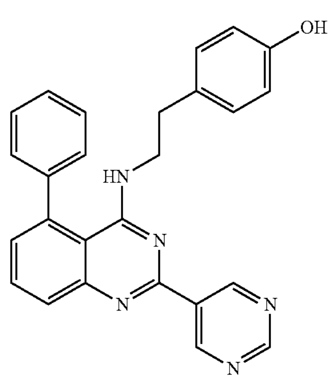 [SMILES: Oc1ccc(CCNc2nc(-c3cncnc3)nc3cccc(-c4ccccc4)c23)cc1] | 419.478 | [M + 1] 420.2 Rt2.56 min | Z1 |

TABLE 1c-continued

| Example | Structure | MW | LCMS Data | LCMS Method |
|---------|-----------|-----|-----------|-------------|
| 235 | 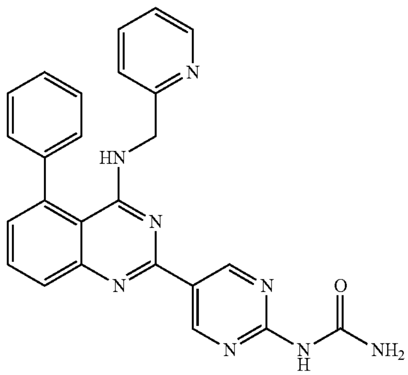 [SMILES: NC(=O)Nc1ncc(-c2nc(NCc3ccccn3)c3c(-c4ccccc4)cccc3n2)cn1] | 448.479 | [M + 1] 449.2 Rt1.89 min | Y |
| 236 | 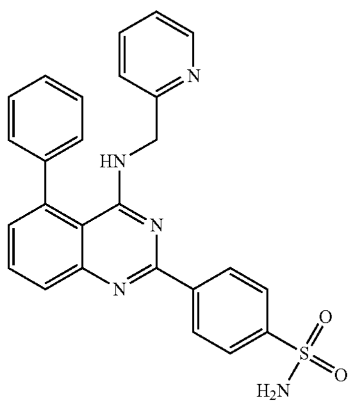 [SMILES: NS(=O)(=O)c1ccc(-c2nc(NCc3ccccn3)c3c(-c4ccccc4)cccc3n2)cc1] | 467.542 | [M + 1] 468.2 Rt1.98 min | Y |
| 237 | 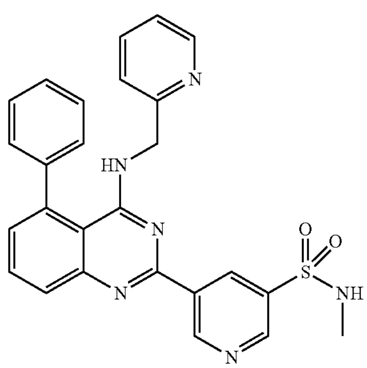 [SMILES: CNS(=O)(=O)c1cncc(-c2nc(NCc3ccccn3)c3c(-c4ccccc4)cccc3n2)c1] | 482.557 | [M + 1] 483.2 Rt1.99 min | Y |
| 238 | 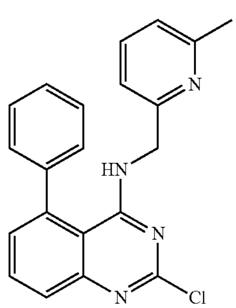 [SMILES: Cc1cccc(CNc2nc(Cl)nc3cccc(-c4ccccc4)c23)n1] | 360.839 | [M + 1] 361.20 Rt1.55 min | T |

TABLE 1c-continued

| Example | Structure | MW | LCMS Data | LCMS Method |
|---------|-----------|-----|-----------|-------------|
| 239 | 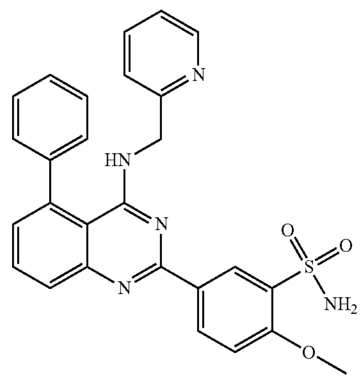 [SMILES: COc1ccc(-c2nc(NCc3ccccn3)c3c(-c4ccccc4)cccc3n2)cc1S(N)(=O)=O] | 497.568 | [M + 1] 498.2 Rt1.48 min | T |
| 240 | 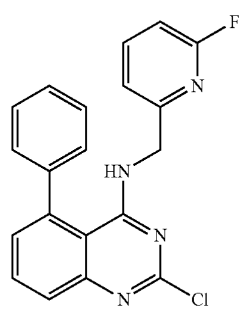 [SMILES: Fc1cccc(CNc2nc(Cl)nc3cccc(-c4ccccc4)c23)n1] | 364.803 | [M + 1] 365.2 Rt2.05 min | T |
| 241 | 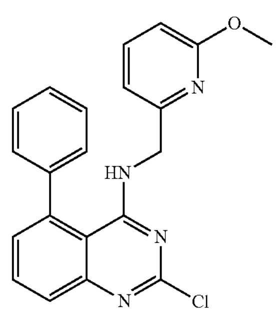 [SMILES: COc1cccc(CNc2nc(Cl)nc3cccc(-c4ccccc4)c23)n1] | 376.839 | [M + 1] 377.2 Rt2.14 min | T |
| 242 | 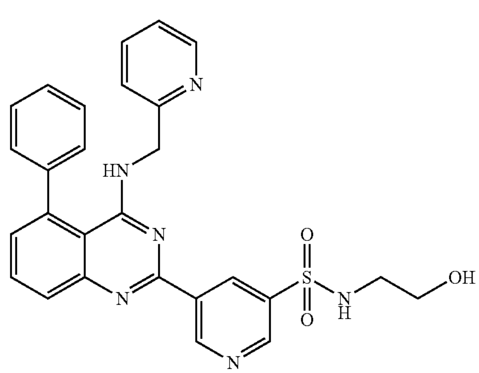 [SMILES: O=S(=O)(NCCO)c1cncc(-c2nc(NCc3ccccn3)c3c(-c4ccccc4)cccc3n2)c1] | 512.583 | [M + 1] 513.2 Rt1.80 min | Y |

TABLE 1c-continued

| Example | Structure | MW | LCMS Data | LCMS Method |
|---|---|---|---|---|
| 243 | 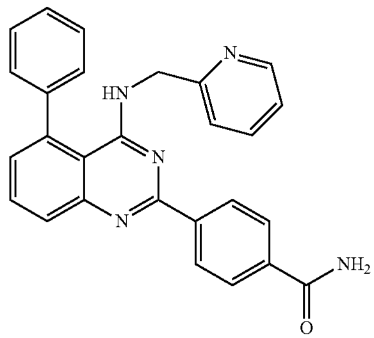 [SMILES: NC(=O)c1ccc(-c2nc(NCc3ccccn3)c3c(-c4ccccc4)cccc3n2)cc1] | 431.489 | [M + 1] 432.2 Rt2.40 min | Z1 |
| 244 | 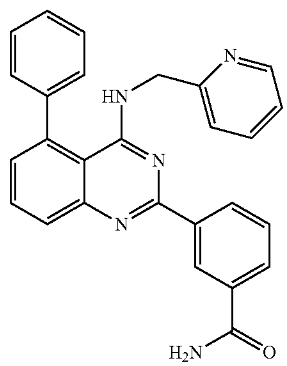 [SMILES: NC(=O)c1cccc(-c2nc(NCc3ccccn3)c3c(-c4ccccc4)cccc3n2)c1] | 431.489 | [M + 1] 432.2 Rt2.40 min | Z1 |
| 245 | 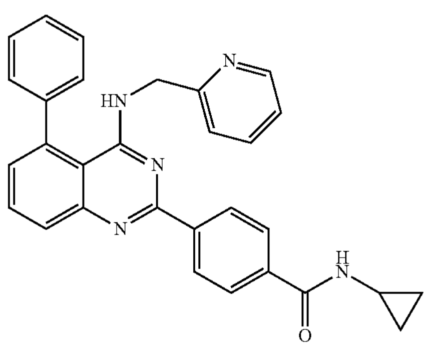 [SMILES: O=C(NC1CC1)c1ccc(-c2nc(NCc3ccccn3)c3c(-c4ccccc4)cccc3n2)cc1] | 471.552 | [M + 1] 472.2 Rt2.68 min | Z1 |
| 246 | 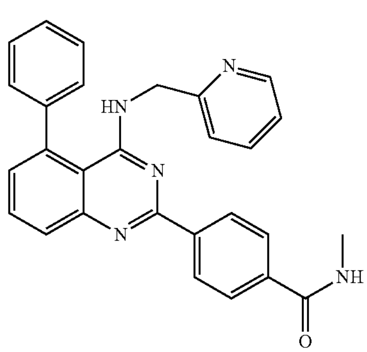 [SMILES: CNC(=O)c1ccc(-c2nc(NCc3ccccn3)c3c(-c4ccccc4)cccc3n2)cc1] | 445.515 | [M + 1] 446.2 Rt2.50 min | Z1 |

TABLE 1c-continued

| Example | Structure | MW | LCMS Data | LCMS Method |
|---|---|---|---|---|
| 247 | 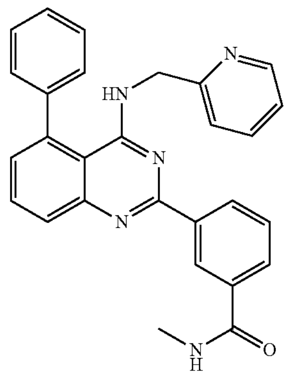 [SMILES: CNC(=O)c1cccc(-c2nc(NCc3ccccn3)c3c(-c4ccccc4)cccc3n2)c1] | 445.515 | [M + 1] 446.2 Rt2.53 min | Z1 |
| 248 | 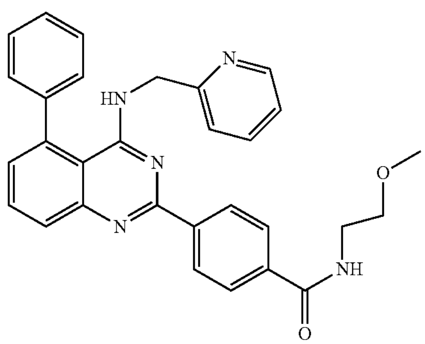 [SMILES: COCCNC(=O)c1ccc(-c2nc(NCc3ccccn3)c3c(-c4ccccc4)cccc3n2)cc1] | 489.568 | [M + 1] 490.2 Rt2.59 min | Z1 |
| 249 | 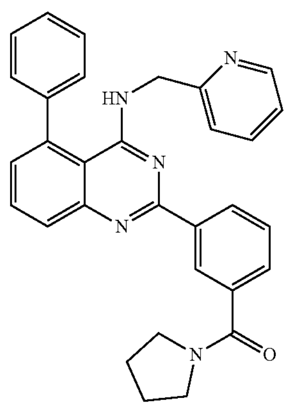 [SMILES: O=C(c1cccc(-c2nc(NCc3ccccn3)c3c(-c4ccccc4)cccc3n2)c1)N1CCCC1] | 485.579 | [M + 1] 486.2 Rt2.84 min | Z1 |
| 250 | 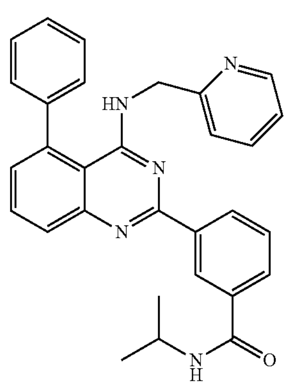 [SMILES: CC(C)NC(=O)c1cccc(-c2nc(NCc3ccccn3)c3c(-c4ccccc4)cccc3n2)c1] | 473.568 | [M + 1] 474.2 Rt2.87 min | Z1 |

TABLE 1c-continued

| Example | Structure | MW | LCMS Data | LCMS Method |
|---|---|---|---|---|
| 251 | 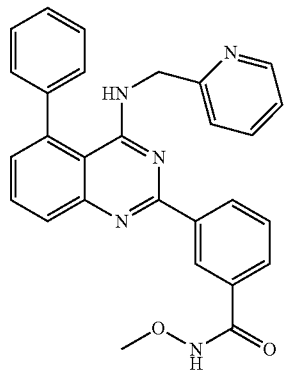 [SMILES: CONC(=O)c1cccc(-c2nc(NCc3ccccn3)c3c(-c4ccccc4)cccc3n2)c1] | 461.515 | [M + 1] 462.2 Rt2.52 min | Z1 |
| 252 | 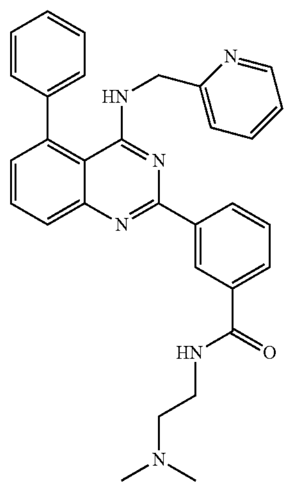 [SMILES: CN(C)CCNC(=O)c1cccc(-c2nc(NCc3ccccn3)c3c(-c4ccccc4)cccc3n2)c1] | 502.609 | [M + 1] 503.2 Rt2.57 min | Z1 |
| 253 | 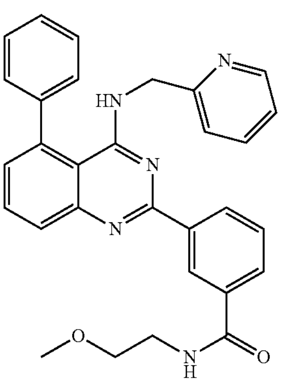 [SMILES: COCCNC(=O)c1cccc(-c2nc(NCc3ccccn3)c3c(-c4ccccc4)cccc3n2)c1] | 489.568 | [M + 1] 490.2 Rt2.63 min | Z1 |
| 254 | 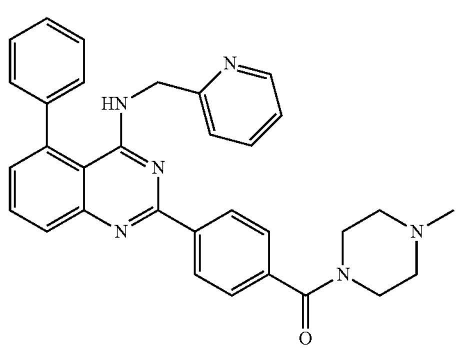 [SMILES: CN1CCN(C(=O)c2ccc(-c3nc(NCc4ccccn4)c4c(-c5ccccc5)cccc4n3)cc2)CC1] | 514.62 | [M + 1] 515.2 Rt2.58 min | Z1 |

TABLE 1c-continued

| Example | Structure | MW | LCMS Data | LCMS Method |
|---|---|---|---|---|
| 255 | 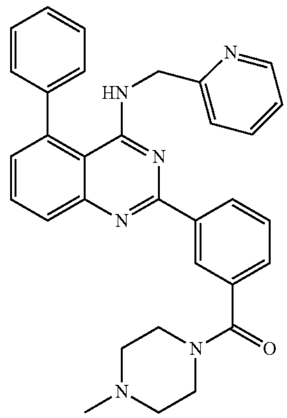 [SMILES: CN1CCN(C(=O)c2cccc(-c3nc(NCc4ccccn4)c4c(-c5ccccc5)cccc4n3)c2)CC1] | 514.62 | [M + 1] 515.2 Rt 2.58 min | Z1 |
| 256 | 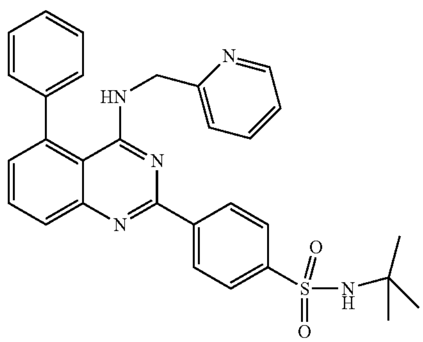 [SMILES: CC(C)(C)NS(=O)(=O)c1ccc(-c2nc(NCc3ccccn3)c3c(-c4ccccc4)cccc3n2)cc1] | 523.649 | [M + 1] 524.2 Rt 3.24 min | Z1 |
| 257 | 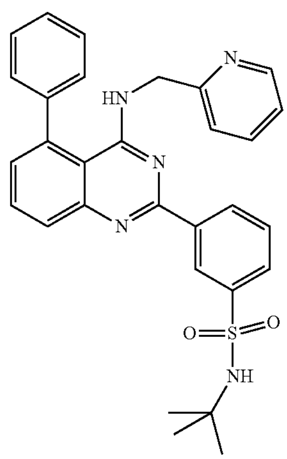 [SMILES: CC(C)(C)NS(=O)(=O)c1cccc(-c2nc(NCc3ccccn3)c3c(-c4ccccc4)cccc3n2)c1] | 523.649 | [M + 1] 524.2 Rt 3.23 min | Z1 |
| 258 | 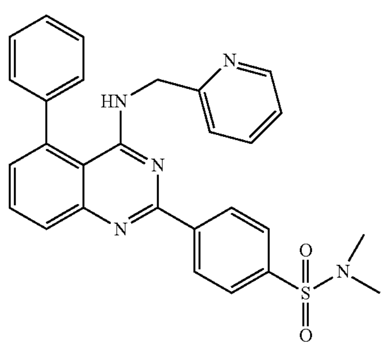 [SMILES: CN(C)S(=O)(=O)c1ccc(-c2nc(NCc3ccccn3)c3c(-c4ccccc4)cccc3n2)cc1] | 495.595 | [M + 1] 496.2 Rt 3.13 min | Z1 |

TABLE 1c-continued

| Example | Structure | MW | LCMS Data | LCMS Method |
|---|---|---|---|---|
| 259 | 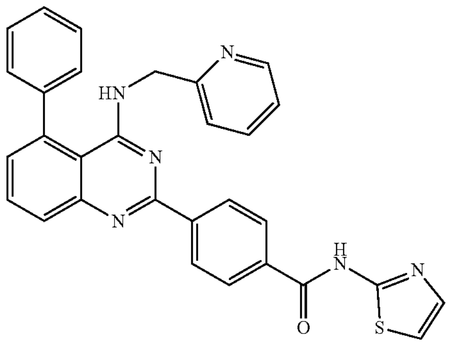 [SMILES: O=C(Nc1nccs1)c1ccc(-c2nc(NCc3ccccn3)c3c(-c4ccccc4)cccc3n2)cc1] | 514.6 | [M + 1] 515.2 Rt2.99 min | Z1 |
| 260 | 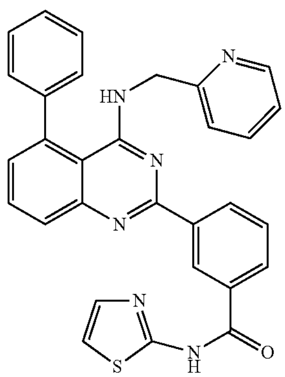 [SMILES: O=C(Nc1nccs1)c1cccc(-c2nc(NCc3ccccn3)c3c(-c4ccccc4)cccc3n2)c1] | 514.6 | [M + 1] 515.2 Rt3.04 min | Z1 |
| 261 | 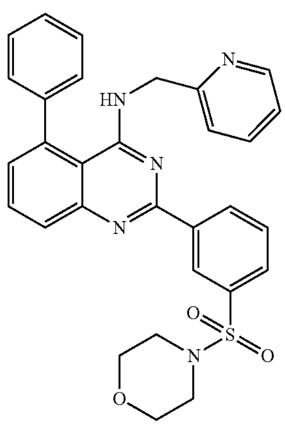 [SMILES: O=S(=O)(c1cccc(-c2nc(NCc3ccccn3)c3c(-c4ccccc4)cccc3n2)c1)N1CCOCC1] | 537.632 | [M + 1] 538.2 Rt3.05 min | Z1 |
| 262 | 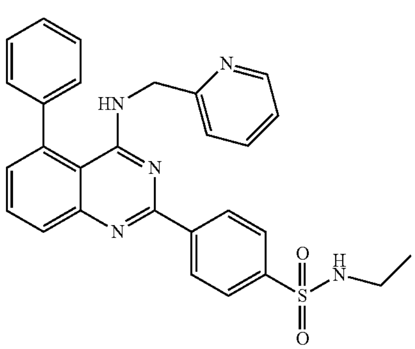 [SMILES: CCNS(=O)(=O)c1ccc(-c2nc(NCc3ccccn3)c3c(-c4ccccc4)cccc3n2)cc1] | 495.595 | [M + 1] 496.2 Rt2.96 min | Z1 |

TABLE 1c-continued

| Example | Structure | MW | LCMS Data | LCMS Method |
|---|---|---|---|---|
| 263 | 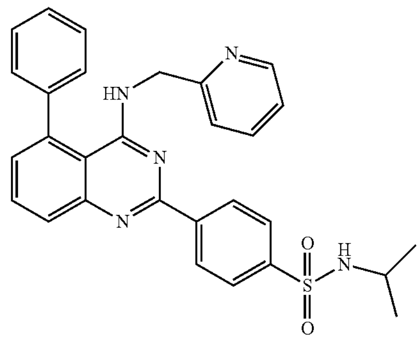 [SMILES: CC(C)NS(=O)(=O)c1ccc(-c2nc(NCc3ccccn3)c3c(-c4ccccc4)cccc3n2)cc1] | 509.622 | [M + 1] 510.2 Rt3.10 min | Z1 |
| 264 | 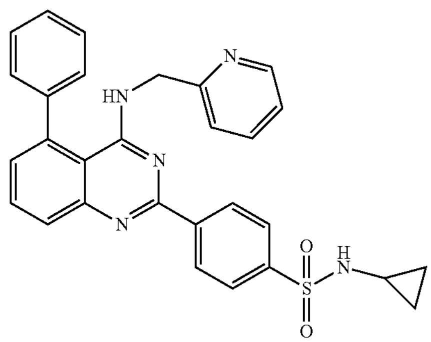 [SMILES: O=S(=O)(NC1CC1)c1ccc(-c2nc(NCc3ccccn3)c3c(-c4ccccc4)cccc3n2)cc1] | 507.606 | [M + 1] 508.2 Rt3.01 min | Z1 |
| 265 | 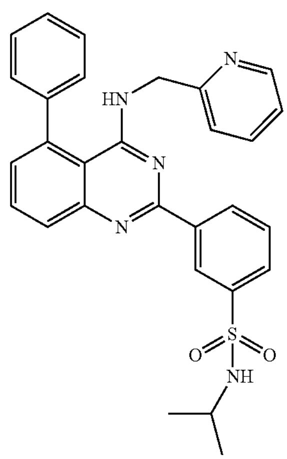 [SMILES: CC(C)NS(=O)(=O)c1cccc(-c2nc(NCc3ccccn3)c3c(-c4ccccc4)cccc3n2)c1] | 509.622 | [M + 1] 510.2 Rt3.09 min | Z1 |
| 266 | 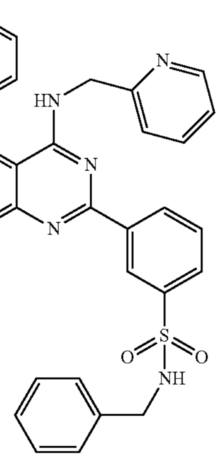 | 557.665 | [M + 1] 558.2 Rt3.23 min | Z1 |

TABLE 1c-continued

| Example | Structure | MW | LCMS Data | LCMS Method |
|---|---|---|---|---|
| 267 | 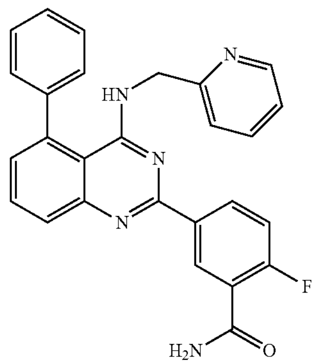 [SMILES: NC(=O)c1cc(-c2nc(NCc3ccccn3)c3c(-c4ccccc4)cccc3n2)ccc1F] | 449.479 | [M + 1] 450.2 Rt2.54 min | Z1 |
| 268 | 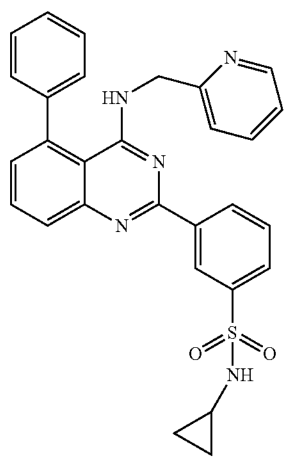 [SMILES: O=S(=O)(NC1CC1)c1cccc(-c2nc(NCc3ccccn3)c3c(-c4ccccc4)cccc3n2)c1] | 507.606 | [M + 1] 508.2 Rt2.99 min | Z1 |
| 269 | 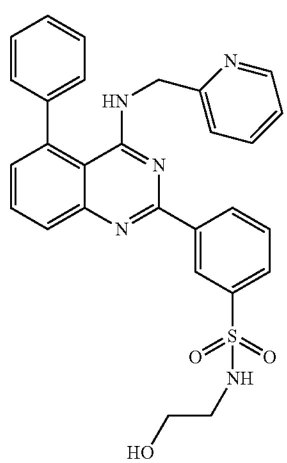 [SMILES: O=S(=O)(NCCO)c1cccc(-c2nc(NCc3ccccn3)c3c(-c4ccccc4)cccc3n2)c1] | 511.595 | [M + 1] 512.2 Rt2.50 min | Z1 |

TABLE 1c-continued

| Example | Structure | MW | LCMS Data | LCMS Method |
|---|---|---|---|---|
| 270 | 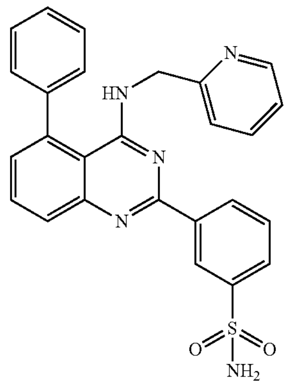 [SMILES: NS(=O)(=O)c1cccc(-c2nc(NCc3ccccn3)c3c(-c4ccccc4)cccc3n2)c1] | 467.542 | [M + 1] 468.2 Rt 2.53 min | Z1 |
| 271 | 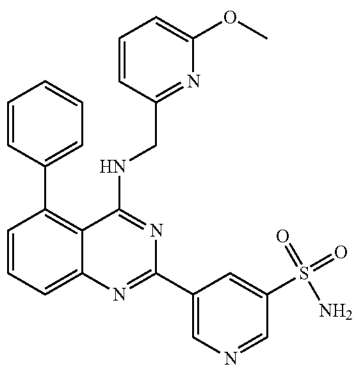 [SMILES: COc1cccc(CNc2nc(-c3cncc(S(N)(=O)=O)c3)nc3cccc(-c4ccccc4)c23)n1] | 498.556 | [M + 1] 499.2 Rt 2.03 min | W |
| 272 | 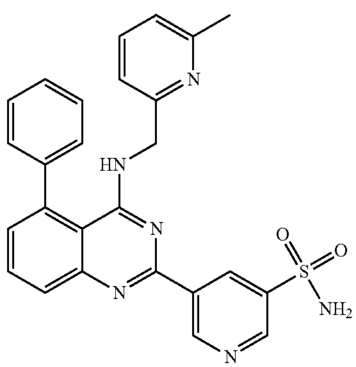 [SMILES: Cc1cccc(CNc2nc(-c3cncc(S(N)(=O)=O)c3)nc3cccc(-c4ccccc4)c23)n1] | 482.557 | [M + 1] 483.2 Rt 1.91 min | W |
| 273 | 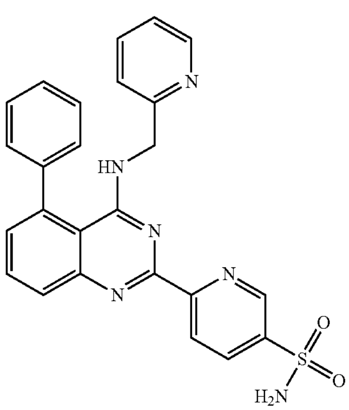 | 468.53 | [M + 1] 469.2 Rt 1.52 min | T |

TABLE 1c-continued

| Example | Structure | MW | LCMS Data | LCMS Method |
|---|---|---|---|---|
| 274 | 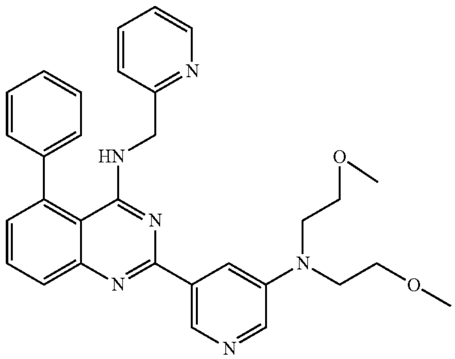 [SMILES: COCCN(CCOC)c1cncc(-c2nc(NCc3ccccn3)c3c(-c4ccccc4)cccc3n2)c1] | 520.625 | [M + 1] 521.2 Rt1.76 min | T |
| 275 | 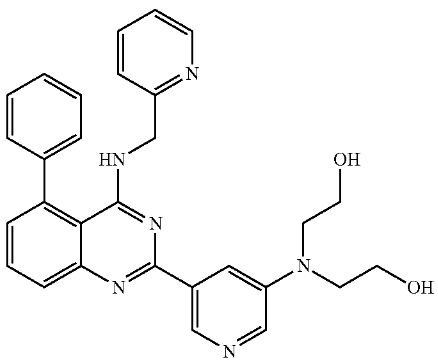 [SMILES: OCCN(CCO)c1cncc(-c2nc(NCc3ccccn3)c3c(-c4ccccc4)cccc3n2)c1] | 492.572 | [M + 1] 493.4 Rt1.73 min | Y |
| 276 | 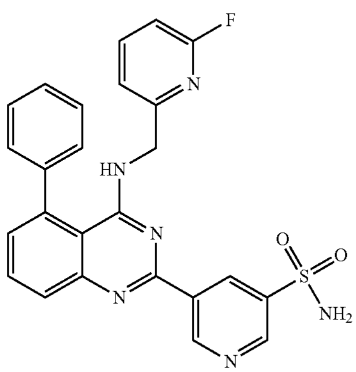 [SMILES: NS(=O)(=O)c1cncc(-c2nc(NCc3cccc(F)n3)c3c(-c4ccccc4)cccc3n2)c1] | 486.521 | [M + 1] 487.2 Rt1.95 min | W |
| 277 | 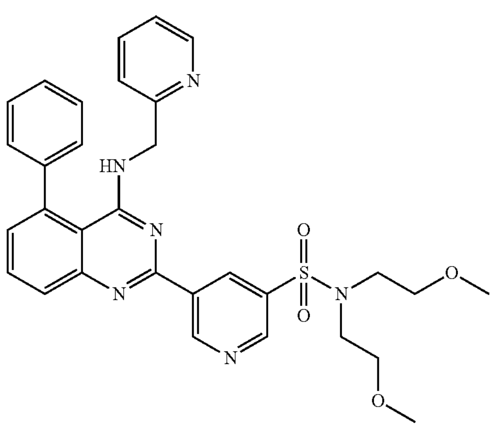 [SMILES: COCCN(CCOC)S(=O)(=O)c1cncc(-c2nc(NCc3ccccn3)c3c(-c4ccccc4)cccc3n2)c1] | 584.689 | [M + 1] 585.2 Rt1.83 min | T |

TABLE 1c-continued

| Example | Structure | MW | LCMS Data | LCMS Method |
|---------|-----------|-----|-----------|-------------|
| 278 | 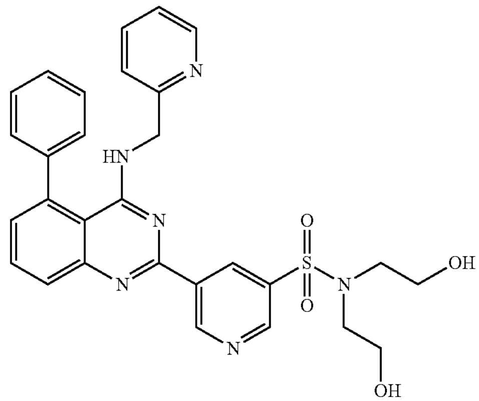 [SMILES: O=S(=O)(c1cncc(-c2nc(NCc3ccccn3)c3c(-c4ccccc4)cccc3n2)c1)N(CCO)CCO] | 556.635 | [M + 1] 557.2 Rt1.56 min | T |
| 279 | 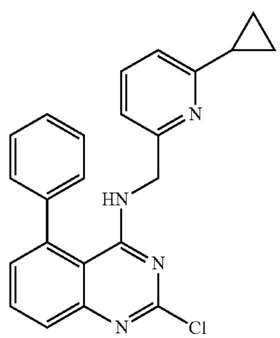 [SMILES: Clc1nc(NCc2cccc(C3CC3)n2)c2c(-c3ccccc3)cccc2n1] | 386.877 | [M + 1] 387.2 Rt2.17 min | Y |
| 280 | 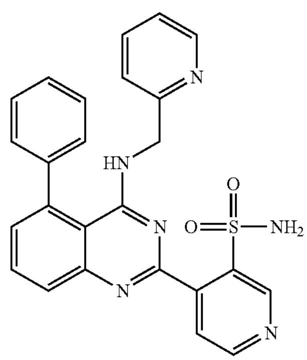 [SMILES: NS(=O)(=O)c1cnccc1-c1nc(NCc2ccccn2)c2c(-c3ccccc3)cccc2n1] | 468.53 | [M + 1] 469.2 Rt1.84 min | Y |
| 281 | 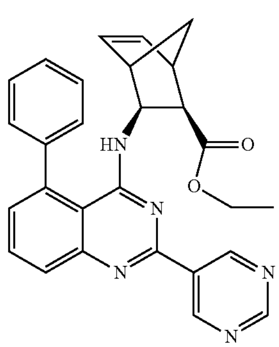 [SMILES: CCOC(=O)[C@@H]1C2C=CC(C2)[C@@H]1Nc1nc(-c2cncnc2)nc2cccc(-c3ccccc3)c12] | 463.53 | [M + 1] 464.2 Rt3.16 min | Z1 |

TABLE 1c-continued

| Example | Structure | MW | LCMS Data | LCMS Method |
|---------|-----------|-----|-----------|-------------|
| 282 | 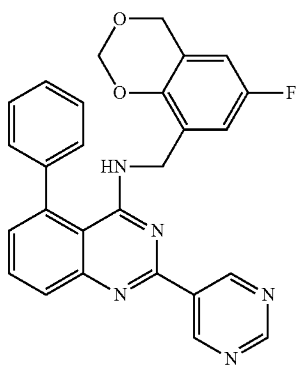 [SMILES: Fc1cc(CNc2nc(-c3cncnc3)nc3cccc(-c4ccccc4)c23)c2c(c1)COCO2] | 465.478 | [M + 1] 466.2 Rt3.00 min | Z1 |
| 283 | 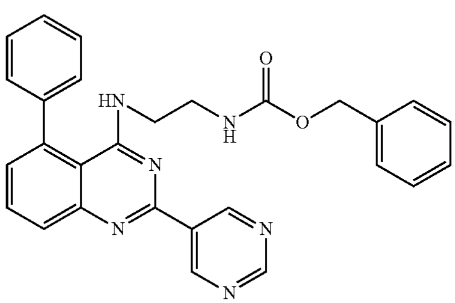 [SMILES: O=C(NCCNc1nc(-c2cncnc2)nc2cccc(-c3ccccc3)c12)OCc1ccccc1] | 476.529 | [M + 1] 477.2 Rt2.74 min | Z1 |
| 284 | 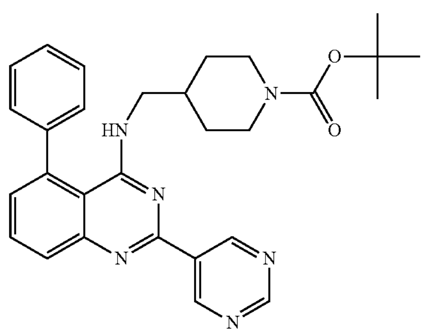 [SMILES: CC(C)(C)OC(=O)N1CCC(CNc2nc(-c3cncnc3)nc3cccc(-c4ccccc4)c23)CC1] | 496.603 | [M + 1] 497.2 Rt3.34 min | Z1 |
| 285 | 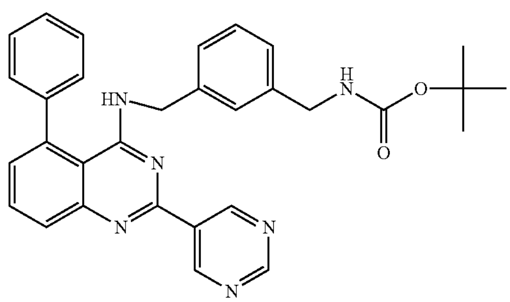 [SMILES: CC(C)(C)OC(=O)NCc1cccc(CNc2nc(-c3cncnc3)nc3cccc(-c4ccccc4)c23)c1] | 518.609 | [M + 1] 519.2 Rt3.17 min | Z1 |

TABLE 1c-continued

| Example | Structure | MW | LCMS Data | LCMS Method |
|---|---|---|---|---|
| 286 | 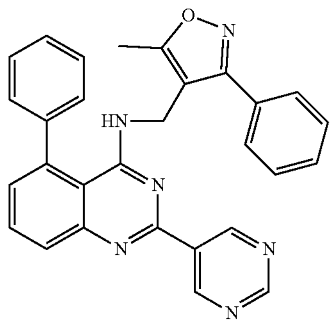 [SMILES: Cc1onc(-c2ccccc2)c1CNc1nc(-c2cncnc2)nc2cccc(-c3ccccc3)c12] | 470.525 | [M + 1] 471.2 Rt2.97 min | Z1 |
| 287 | 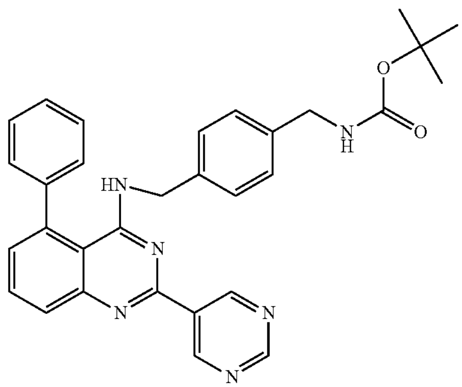 [SMILES: CC(C)(C)OC(=O)NCc1ccc(CNc2nc(-c3cncnc3)nc3cccc(-c4ccccc4)c23)cc1] | 518.609 | [M + 1] 519.2 Rt3.16 min | Z1 |
| 288 | 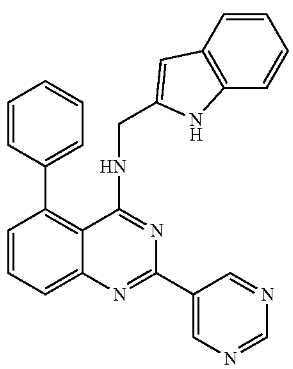 [SMILES: c1ccc(-c2cccc3nc(-c4cncnc4)nc(NCc4cc5ccccc5[nH]4)c23)cc1] | 428.488 | [M + 1] 429.2 Rt3.01 min | Z1 |
| 289 | 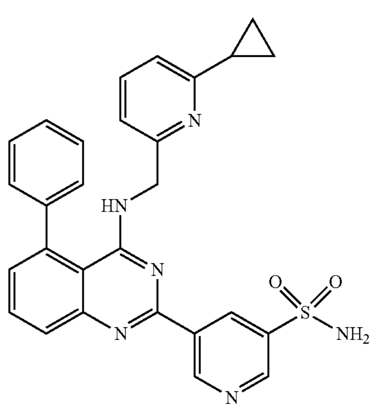 [SMILES: NS(=O)(=O)c1cncc(-c2nc(NCc3cccc(C4CC4)n3)c3c(-c4ccccc4)cccc3n2)c1] | 508.594 | [M + 1] 509.2 Rt1.58 min | T |

TABLE 1c-continued

| Example | Structure | MW | LCMS Data | LCMS Method |
|---|---|---|---|---|
| 290 | 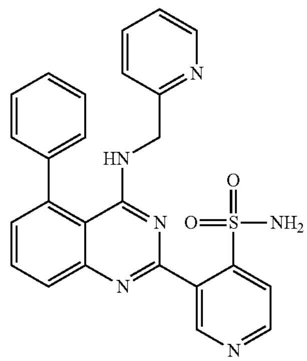 [SMILES: NS(=O)(=O)c1ccncc1-c1nc(NCc2ccccn2)c2c(-c3ccccc3)cccc2n1] | 468.53 | [M + 1] 469.2 Rt1.42 min | T |
| 291 | 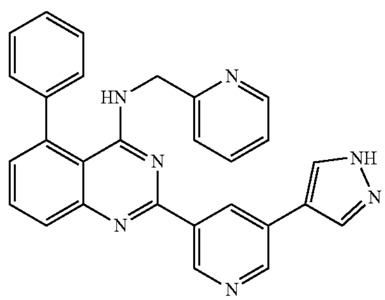 [SMILES: c1ccc(-c2cccc3nc(-c4cncc(-c5cn[nH]c5)c4)nc(NCc4ccccn4)c23)cc1] | 455.513 | [M + 1] 456.2 Rt1.86 min | Y |
| 292 | 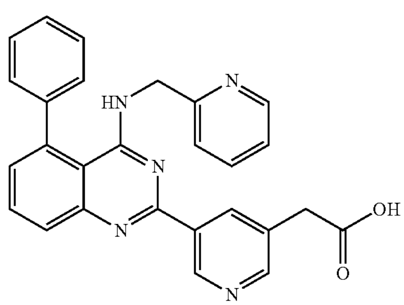 [SMILES: O=C(O)Cc1cncc(-c2nc(NCc3ccccn3)c3c(-c4ccccc4)cccc3n2)c1] | 447.488 | [M + 1] 448.2 Rt1.36 min | W |
| 293 | 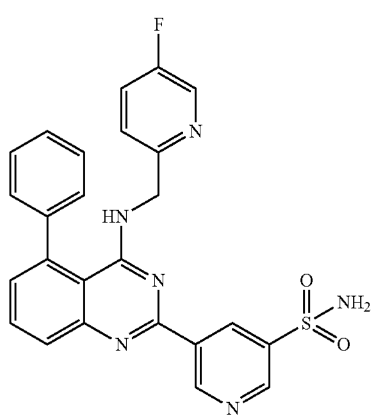 [SMILES: NS(=O)(=O)c1cncc(-c2nc(NCc3ccc(F)cn3)c3c(-c4ccccc4)cccc3n2)c1] | 486.521 | [M − 1] 485.0 Rt1.93 min | Y |

TABLE 1c-continued

| Example | Structure | MW | LCMS Data | LCMS Method |
|---------|-----------|-----|-----------|-------------|
| 294 | 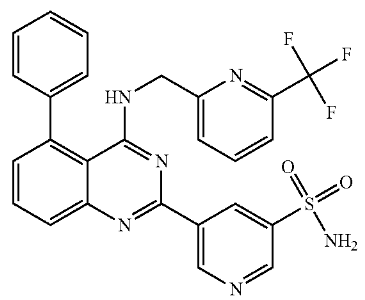 [SMILES: NS(=O)(=O)c1cncc(-c2nc(NCc3cccc(C(F)(F)F)n3)c3c(-c4ccccc4)cccc3n2)c1] | 536.528 | [M + 1] 537.0 Rt1.96 min | T |
| 295 | 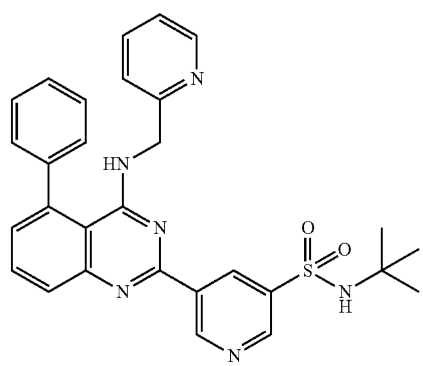 [SMILES: CC(C)(C)NS(=O)(=O)c1cncc(-c2nc(NCc3ccccn3)c3c(-c4ccccc4)cccc3n2)c1] | 524.637 | [M − 1] 523.2 Rt2.10 min | Y |
| 296 | 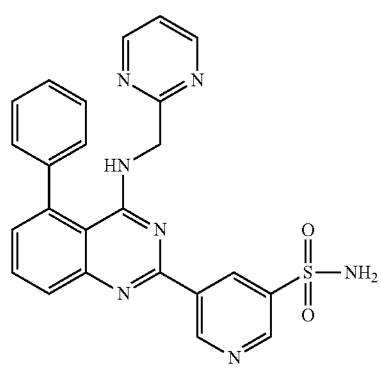 [SMILES: NS(=O)(=O)c1cncc(-c2nc(NCc3ncccn3)c3c(-c4ccccc4)cccc3n2)c1] | 469.518 | [M + 1] 470.2 Rt1.64 min | T |
| 297 | 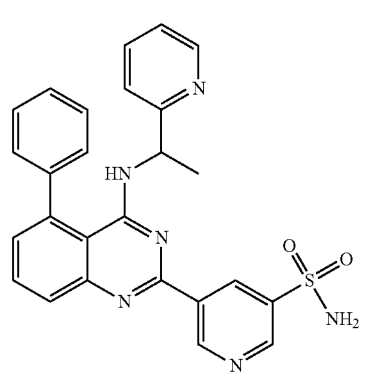 [SMILES: CC(Nc1nc(-c2cncc(S(N)(=O)=O)c2)nc2cccc(-c3ccccc3)c12)c1ccccn1] | 482.557 | [M + 1] 483.2 Rt1.66 min | T |

TABLE 1c-continued

| Example | Structure | MW | LCMS Data | LCMS Method |
|---|---|---|---|---|
| 298 | 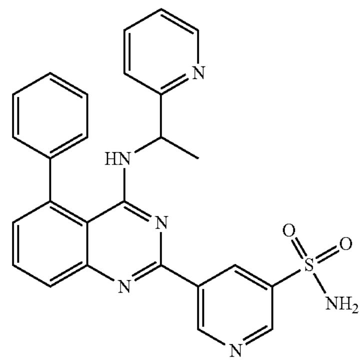 [SMILES: CC(Nc1nc(-c2cncc(S(N)(=O)=O)c2)nc2cccc(-c3ccccc3)c12)c1ccccn1] | 482.557 | [M + 1] 483.2 Rt1.65 min | T |
| 299 | 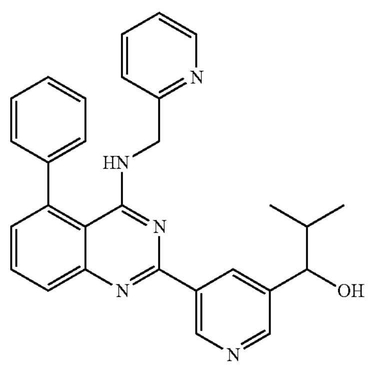 [SMILES: CC(C)C(O)c1cncc(-c2nc(NCc3ccccn3)c3c(-c4ccccc4)cccc3n2)c1] | 461.558 | [M + 1] 462.2 Rt1.78 min | T |
| 300 | 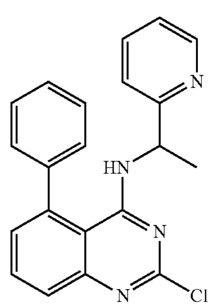 [SMILES: CC(Nc1nc(Cl)nc2cccc(-c3ccccc3)c12)c1ccccn1] | 360.839 | [M + 1] 361.0 Rt1.87 min | T |
| 301 | 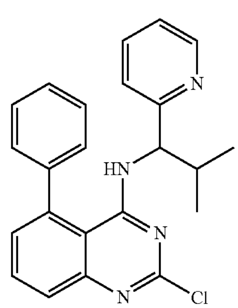 [SMILES: CC(C)C(Nc1nc(Cl)nc2cccc(-c3ccccc3)c12)c1ccccn1] | 388.893 | [M + 1] 389.2 Rt1.98 min | T |

TABLE 1c-continued

| Example | Structure | MW | LCMS Data | LCMS Method |
|---------|-----------|-----|-----------|-------------|
| 302 | 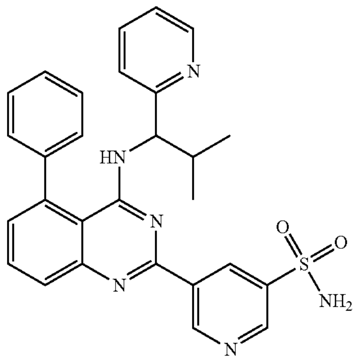 [SMILES: CC(C)C(Nc1nc(-c2cncc(S(N)(=O)=O)c2)nc2cccc(-c3ccccc3)c12)c1ccccn1] | 510.61 | [M + 1] 511.2 Rt1.79 min | T |
| 303 | 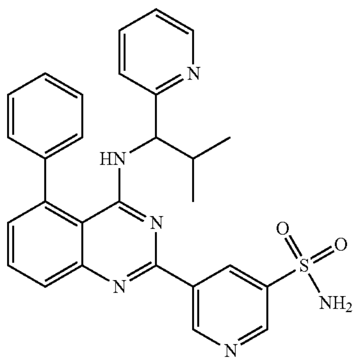 [SMILES: CC(C)C(Nc1nc(-c2cncc(S(N)(=O)=O)c2)nc2cccc(-c3ccccc3)c12)c1ccccn1] | 510.61 | [M + 1] 511.2 Rt1.79 min | T |
| 304 | 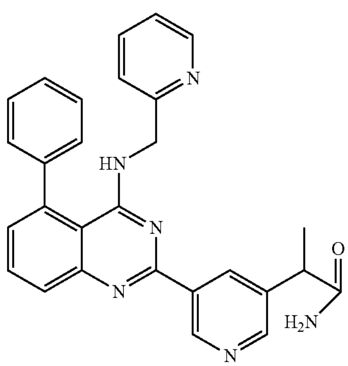 [SMILES: CC(C(N)=O)c1cncc(-c2nc(NCc3ccccn3)c3c(-c4ccccc4)cccc3n2)c1] | 460.53 | [M + 1] 461.0 Rt1.78 min | Y |
| 305 | 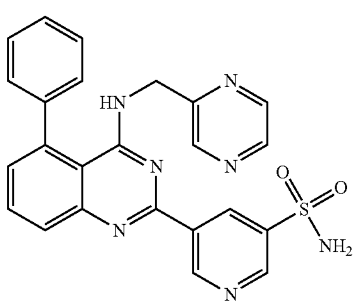 [SMILES: NS(=O)(=O)c1cncc(-c2nc(NCc3cnccn3)c3c(-c4ccccc4)cccc3n2)c1] | 469.518 | [M + 1] 470.0 Rt1.72 min | W |

TABLE 1c-continued

| Example | Structure | MW | LCMS Data | LCMS Method |
|---|---|---|---|---|
| 306 | 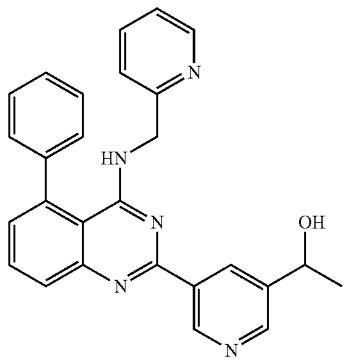 [SMILES: CC(O)c1cncc(-c2nc(NCc3ccccn3)c3c(-c4ccccc4)cccc3n2)c1] | 433.504 | [M + 1] 434.2 Rt1.60 min | V |
| 307 | 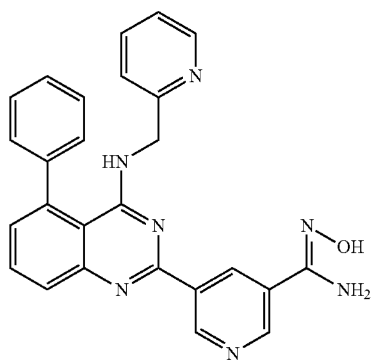 [SMILES: N/C(=N\O)c1cncc(-c2nc(NCc3ccccn3)c3c(-c4ccccc4)cccc3n2)c1] | 447.491 | [M + 1] 447.9 Rt1.79 min | Y |
| 308 | 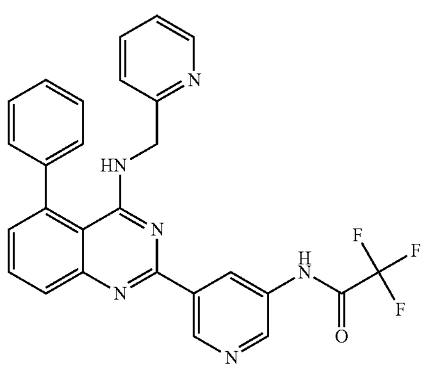 [SMILES: O=C(Nc1cncc(-c2nc(NCc3ccccn3)c3c(-c4ccccc4)cccc3n2)c1)C(F)(F)F] | 500.475 | [M − 1] 499.0 Rt1.75 min | V |
| 309 | 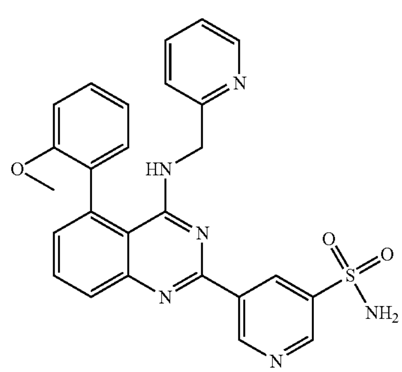 [SMILES: COc1ccccc1-c1cccc2nc(-c3cncc(S(N)(=O)=O)c3)nc(NCc3ccccn3)c12] | 498.556 | [M + 1] 499.2 Rt1.83 min | W |

TABLE 1c-continued

| Example | Structure | MW | LCMS Data | LCMS Method |
|---|---|---|---|---|
| 310 | 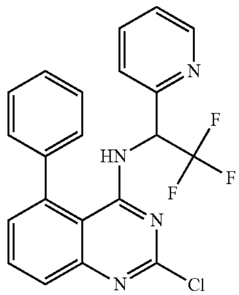 [SMILES: FC(F)(F)C(Nc1nc(Cl)nc2cccc(-c3ccccc3)c12)c1ccccn1] | 414.811 | [M + 1] 415.0 Rt2.16 min | T |
| 311 | 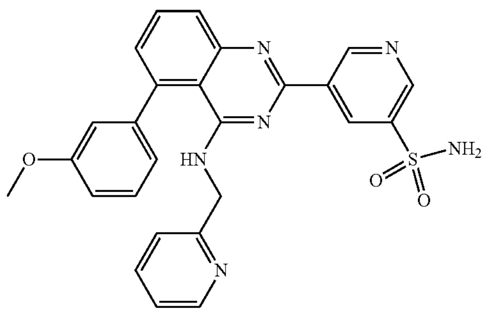 [SMILES: COc1cccc(-c2cccc3nc(-c4cncc(S(N)(=O)=O)c4)nc(NCc4ccccn4)c23)c1] | 498.556 | [M + 1] 499.2 Rt1.87 min | W |
| 312 | 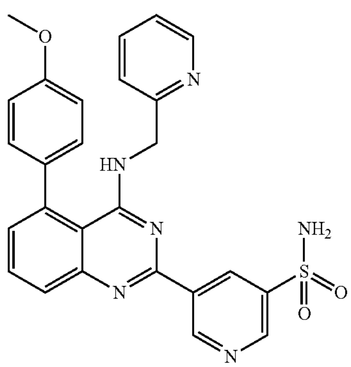 [SMILES: COc1ccc(-c2cccc3nc(-c4cncc(S(N)(=O)=O)c4)nc(NCc4ccccn4)c23)cc1] | 498.556 | [M + 1] 499.2 Rt1.64 min | V |
| 313 | 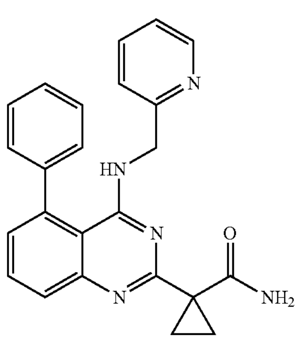 [SMILES: NC(=O)C1(c2nc(NCc3ccccn3)c3c(-c4ccccc4)cccc3n2)CC1] | 395.456 | [M + 1] 396.2 Rt1.43 min | T |

TABLE 1c-continued

| Example | Structure | MW | LCMS Data | LCMS Method |
|---------|-----------|-----|-----------|-------------|
| 314 | 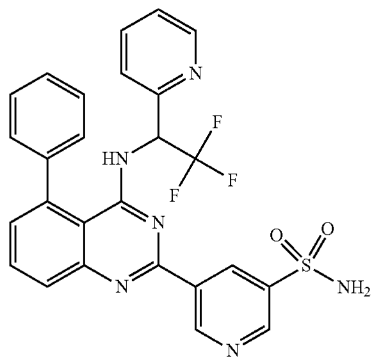 [SMILES: NS(=O)(=O)c1cncc(-c2nc(NC(c3ccccn3)C(F)(F)F)c3c(-c4ccccc4)cccc3n2)c1] | 536.528 | [M + 1] 537.2 Rt2.05 min | T |
| 315 | 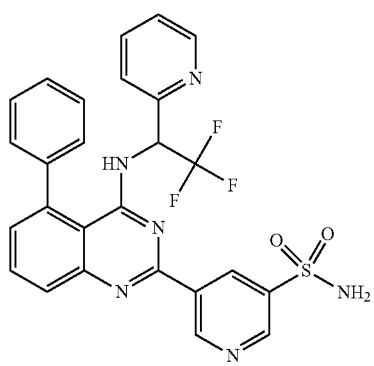 [SMILES: NS(=O)(=O)c1cncc(-c2nc(NC(c3ccccn3)C(F)(F)F)c3c(-c4ccccc4)cccc3n2)c1] | 536.528 | [M + 1] 537.2 Rt2.05 min | T |
| 316 | 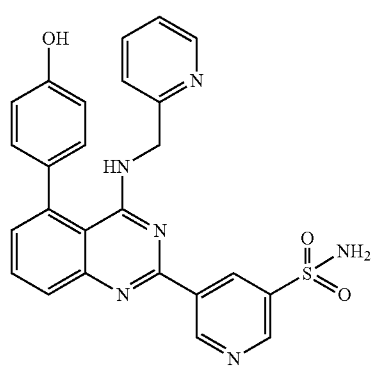 [SMILES: NS(=O)(=O)c1cncc(-c2nc(NCc3ccccn3)c3c(-c4ccc(O)cc4)cccc3n2)c1] | 484.53 | [M + 1] 485.2 Rt1.69 min | Y |
| 317 | 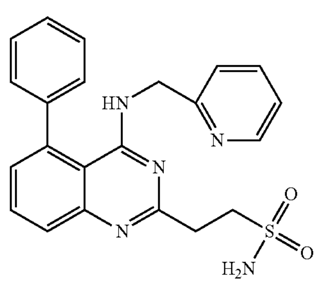 [SMILES: NS(=O)(=O)CCc1nc(NCc2ccccn2)c2c(-c3ccccc3)cccc2n1] | 419.499 | [M − 1] 418.0 Rt1.73 min | Y |

TABLE 1c-continued

| Example | Structure | MW | LCMS Data | LCMS Method |
|---|---|---|---|---|
| 318 | 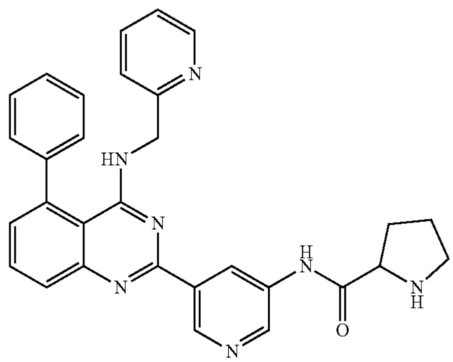 [SMILES: O=C(Nc1cncc(-c2nc(NCc3ccccn3)c3c(-c4ccccc4)cccc3n2)c1)C1CCCN1] | 501.582 | [M + 1] 502.2 Rt1.58 min | V |
| 319 | 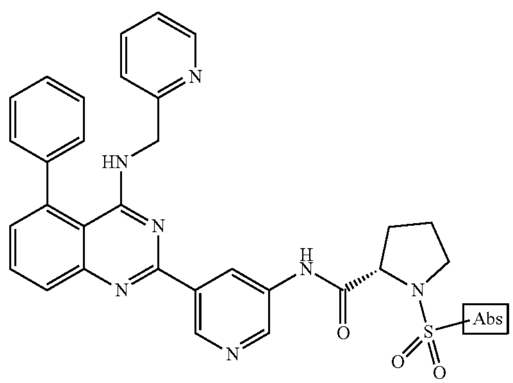 [SMILES: CS(=O)(=O)N1CCC[C@H]1C(=O)Nc1cncc(-c2nc(NCc3ccccn3)c3c(-c4ccccc4)cccc3n2)c1] | 579.672 | [M + 1] 580.2 Rt1.87 min | W |
| 320 | 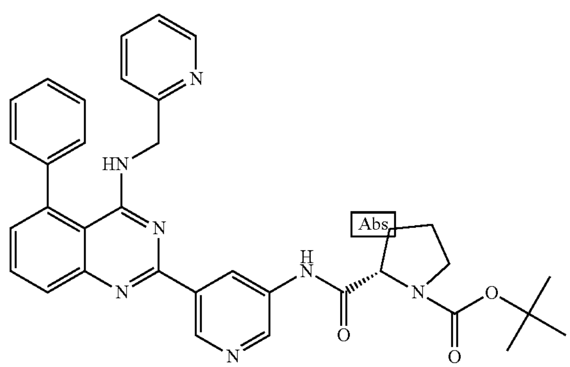 [SMILES: CC(C)(C)OC(=O)N1CCC[C@H]1C(=O)Nc1cncc(-c2nc(NCc3ccccn3)c3c(-c4ccccc4)cccc3n2)c1] | 601.697 | [M − 1] 600.2 Rt2.16 min | W |
| 321 | 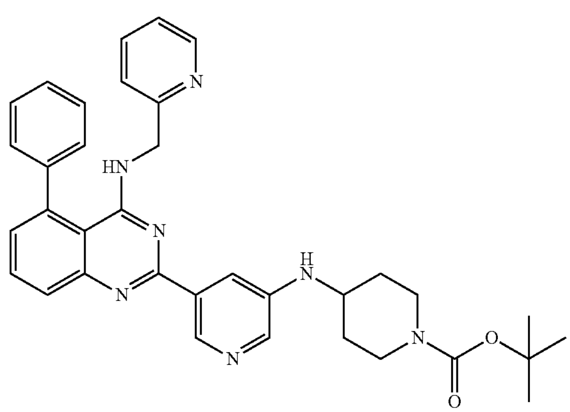 [SMILES: CC(C)(C)OC(=O)N1CCC(Nc2cncc(-c3nc(NCc4ccccn4)c4c(-c5ccccc5)cccc4n3)c2)CC1] | 587.714 | [M + 1] 588.2 Rt1.865 min | V |

| Example | Structure | MW | LCMS Data | LCMS Method |
|---|---|---|---|---|
| 322 | 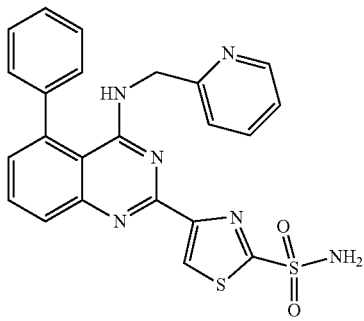 [SMILES: NS(=O)(=O)c1nc(-c2nc(NCc3ccccn3)c3c(-c4ccccc4)cccc3n2)cs1] | 474.578 | [M + 1] 475.2 Rt1.84 min | W |

Example 323

4-(5-Phenyl-4-(pyridin-2-ylmethylamino)quinazolin-2-yl)thiazole-2-sulfonamide

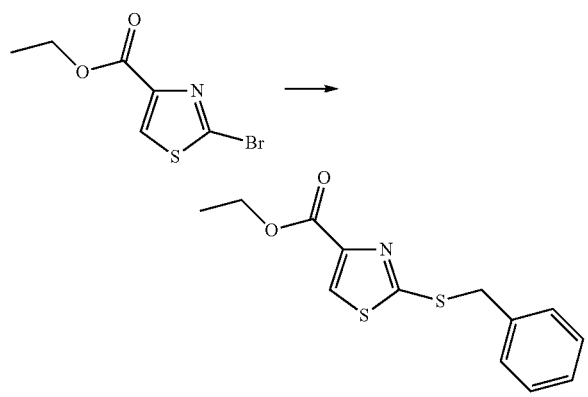

Step 1. Preparation of ethyl 2-(benzylthio)thiazole-4-carboxylate

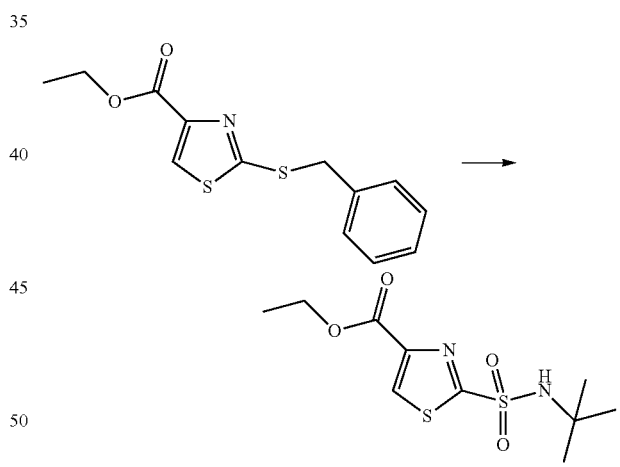

To a solution of ethyl 2-bromothiazole-4-carboxylate (2.0 g, 8.40 mmol) in DMF (15 mL) was added $K_2CO_3$ (1.16 g, 8.40 mmol) followed by benzyl mercaptan (1.07 g, 8.40 mmol) in DMF (5 mL) over 20 min. Upon completion of addition, the reaction mixture was stirred at RT for 16 h. After this time, the reaction mixture was diluted with water and extracted in EtOAc. The combined organic layers were dried over $Na_2SO_4$, filtered and concentrated under reduced pressure. The resulting concentrate was purified by silica gel chromatography (10% EtOAc in hexane) to provide ethyl 2-(benzylthio)thiazole-4-carboxylate (2.0 g, 87% yield). $^1$H NMR (400 MHz, DMSO-$d_6$) δ (ppm): 8.42 (s, 1H); 7.47-45 (m, 2H); 7.36-7.28 (m, 3H); 4.52 (s, 2H); 4.31 (q, 2H, J=7.2 Hz); 1.31 (t, 3H, J=7.2 Hz).

Step 2. Preparation of ethyl 2-(N-tert-butylsulfamoyl)thiazole-4-carboxylate

A solution of ethyl 2-(benzylthio)thiazole-4-carboxylate (2.0 g, 7.10 mmol) in $CCl_4/H_2O$ (100/10 mL) was cooled to 0-5° C. Chlorine gas was bubbled through the solution for 30 min. After this time, the excess chlorine gas was evaporated by flushing with a stream of nitrogen. The reaction mixture was then diluted with dichloromethane and washed with brine. The combined organic layers were dried over $Na_2SO_4$, filtered and concentrated to yield the crude sulfonyl chloride. The crude sulfonyl chloride was dissolved in THF (50 mL) followed by the addition of tert-butyl amine (10 mL) in sealed tube. The contents of the tube were heated to 60° C. for 16 h. At the conclusion of this period, the volatiles were evaporated. The resulting residue was washed with water and extracted into EtOAc. The combined organic layers were dried over Na$_2$SO$_4$, filtered and concentrated to provide ethyl 2-(N-tert-butylsulfamoyl)thiazole-4-carboxylate (1.8 g, 90% yield) as off white solid. $^1$H NMR (400 MHz, DMSO-d$_6$) δ (ppm): 8.78 (s, 1H); 8.0 (br s, 1H); 4.34 (q, 2H, J=7.2 Hz); 1.31 (t, 3H, J=7.2 Hz); 1.18 (s, 9H).

Step 3. Preparation of ethyl 2-(N-tert-butylsulfamoyl)thiazole-4-carboxylate

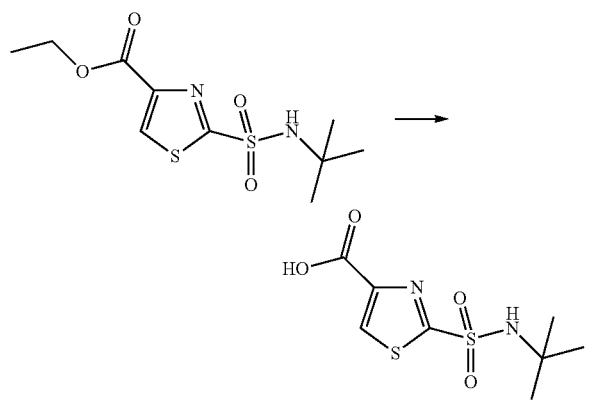

To a solution of ethyl 2-(N-tert-butylsulfamoyl)thiazole-4-carboxylate (1.8 g, 6.1 mmol) in 50 mL THF-EtOH (1:1) was added LiOH (0.07 g, 18.3 mmol). The resulting mixture was stirred for 4 h. After this time, the reaction mixture was neutralized with HCl (1.0 M, aq), diluted with water and then extracted into EtOAc. The combined organic layers were dried over Na$_2$SO$_4$, filtered and concentrated to provide ethyl 2-(N-tert-butylsulfamoyl)thiazole-4-carboxylate (1.6 g, 99% yield) as a white solid. LCMS Method V: retention time 0.93 min; [M+1]=263.0.

Step 4. Preparation of 2-(N-tert-butylsulfamoyl)-N-(2-carbamoylbiphenyl-3-yl)thiazole-4-carboxamide

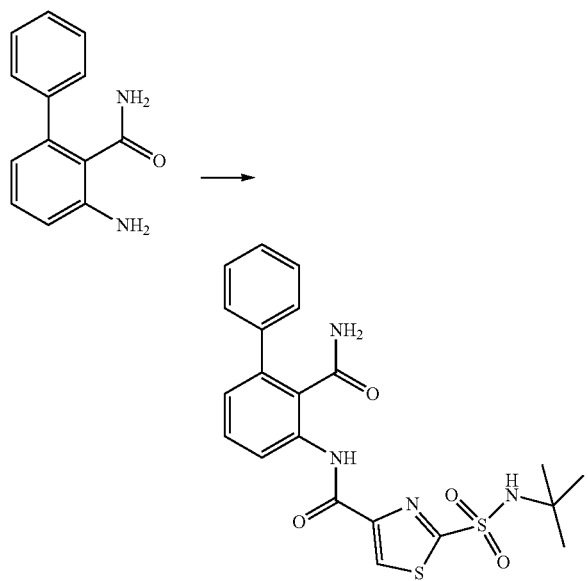

To a solution of 2-(N-tert-butylsulfamoyl)thiazole-4-carboxylic acid (0.56 g, 2.1 mmol) in DCM (50 mL) was added HATU (1.41 g, 2.8 mmol) and DIPEA (1.04 ml, 5.6 mmol). The reaction mixture was stirred at room temperature for 1 h and then 3-aminobiphenyl-2-carboxamide (from example 218, 0.3 g, 1.4 mmol) was added. The resulting solution was stirred for an additional 16 h. After this time, the reaction mixture was washed with water, dried, filtered and concentrated under reduced pressure to yield a residue. The residue was purified by silica gel chromatography (30% EtOAc in hexane) to provide 2-(N-tert-butylsulfamoyl)-N-(2-carbamoylbiphenyl-3-yl)thiazole-4-carboxamide (0.11 g, 17% yield) as white solid. LCMS Method V: retention time 1.85 min; [M+1]=459.2.

Step 5. Preparation of (N-tert-butyl-4-(4-hydroxy-5-phenylquinazolin-2-yl)thiazole-2-sulfonamide

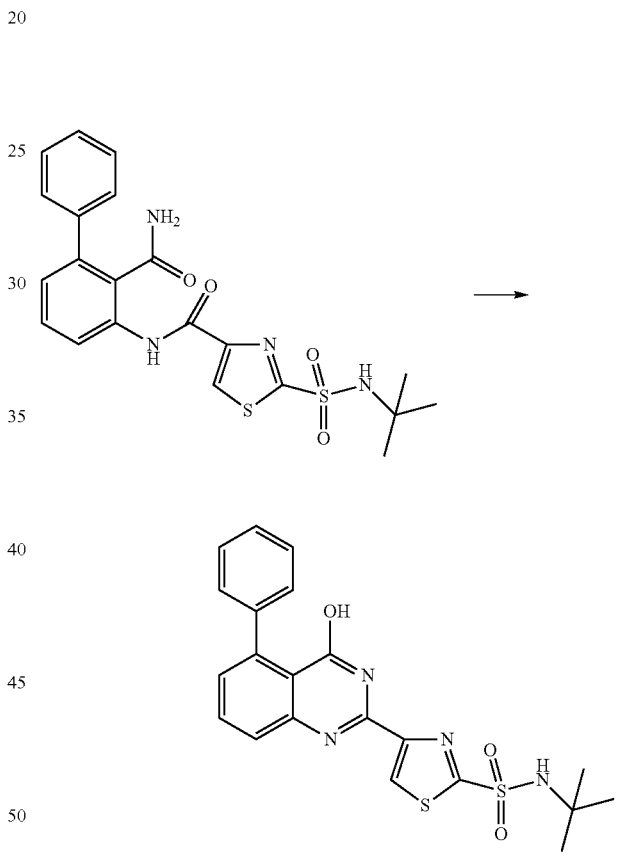

To a solution 2-(N-tert-butylsulfamoyl)-N-(2-carbamoylbiphenyl-3-yl)thiazole-4-carboxamide (0.11 g, 0.24 mmol) in methanol (10 mL) was added NaOMe (0.25 ml, 25% in MeOH, 1.2 mmol). The resulting mixture was stirred at RT for 16 h. After this time, the reaction mixture was concentrated, diluted with ethyl acetate and washed with water. The combined organic layers were dried over Na$_2$SO$_4$, filtered and concentrated under reduced pressure. The resulting residue was purified by silica gel chromatography (40% EtOAc in hexane) to provide (N-tert-butyl-4-(4-hydroxy-5-phenylquinazolin-2-yl)thiazole-2-sulfonamide (0.10 g, 100% yield) as a white solid. LCMS Method V: retention time 2.01 min; [M+1]=441.2.

403

Step 6. Preparation of 5-phenyl-N-(pyridin-2-ylmethyl)-2-(2,2,5-trimethyl-1,3-dioxan-5-yl)quinazolin-4-amine

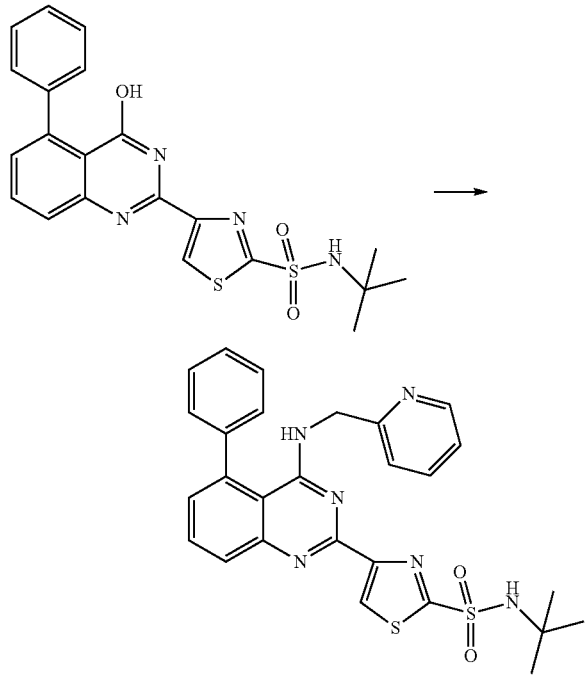

To a solution of 5-phenyl-2-(2,2,5-trimethyl-1,3-dioxan-5-yl)quinazolin-4(3H)-one (0.22 g, 0.62 mmol) in MeCN (10 mL) at room temperature was added DBU (0.24 g, 1.57 mmol) and BOP reagent (0.36 g, 0.81 mmol). Upon completion of addition, the reaction mixture was stirred for 30 min. Aminomethylpyridine (0.11 ml, 1.13 mmol) was added and the resulting mixture was stirred for an additional 16 h. After this time, the reaction mixture was concentrated and purified by silica gel column chromatography (2% MeOH in DCM) to provide 5-phenyl-N-(pyridin-2-ylmethyl)-2-(2,2,5-trimethyl-1,3-dioxan-5-yl)quinazolin-4-amine (0.18 g, 68% yield) as a white solid. LCMS Method V: retention time 2.21 min, [M+1]=531.2.

Step 7. Example 323

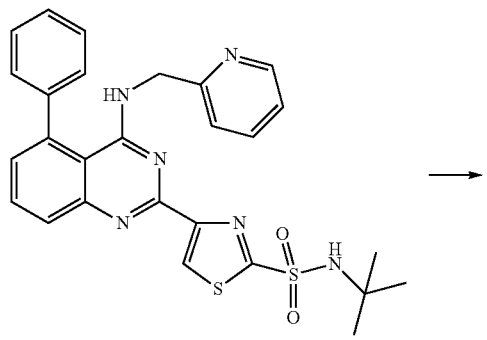

404

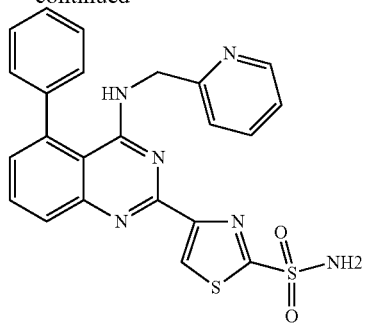

A solution of N-tert-butyl-4-(5-phenyl-4-(pyridin-2-ylmethylamino)quinazolin-2-yl)thiazole-2-sulfonamide (0.05 g 0.10 mmol) in TFA (10 mL) was heated at 50° C. for 8 h. After this time, the TFA was evaporated off under reduced pressure to yield a residue. The residue was made basic by the addition of 10% sodium bicarbonate solution and then extracted into DCM. The combined organic layers were dried over $Na_2SO_4$, filtered and concentrated under reduced pressure. The resulting residue was purified by recrystallization using DCM/hexane to provide Example 323 (30 mg, 78% yield) as a brownish yellow solid. $^1$H NMR (400 MHz, DMSO-$d_6$, δ): 8.80 (s, 1H); 8.25 (s, 1H); 8.19 (br s, 1H); 7.90-7.80 (m, 2 h); 7.65 (dt, 1H, J=1.6, 6.8 Hz); 7.60-7.48 (m, 5H); 7.32-7.20 (m, 3H); 6.78 (t, 1H, J=4 Hz); 4.71 (d, 2H, J=4 Hz). LCMS Method R: retention time 1.65 min, [M+1]=472.8; HPLC Method A1: purity 95.8%, retention time=12.5 min.

Example 324

5-(5-Phenyl-4-(pyridin-2-ylmethylamino)quinazolin-2-yl)thiazole-2-sulfonamide

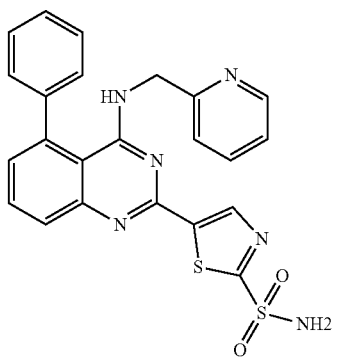 [SMILES: NS(=O)(=O)c1ncc(-c2nc(NCc3ccccn3)c3c(-c4ccccc4)cccc3n2)s1]

Step 1. Preparation of 2-(benzylthio)-5-bromothiazole

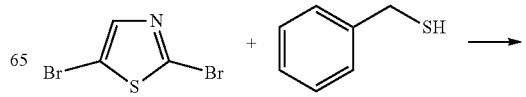

-continued

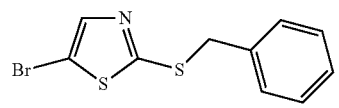

To a solution of 2,5-dibromothiazole (2.0 g, 8.23 mmol) in DMF (15 mL) was added K₂CO₃ (1.16 g, 8.40 mmol) followed by benzyl mercaptan (1.07 g, 8.40 mmol) in DMF (10 mL) over a period of 20 min. The reaction mixture was stirred at RT for over night. After this time, the reaction mixture was diluted with water and extracted in EtOAc. The combined organic layers were dried over Na₂SO₄, filtered and concentrated under reduced pressure. The resulting crude product was purified by silica gel chromatography (0.2% EtOAc in hexane) to yield 2-(benzylthio)-5-bromothiazole (2.3 g, 97.5% yield) as a brown solid. $^1$H NMR (400 MHz, DMSO-d₆, δ): 7.56 (s, 1H); 7.25-7.36 (m, 5H); 4.39 (s, 2H). $^1$H LCMS Method V: Retention time 2.319 min, [M+1]=286.

Step 2. Preparation of 5-bromo-N-tert-butylthiazole-2-sulfonamide

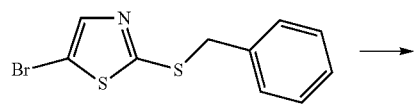

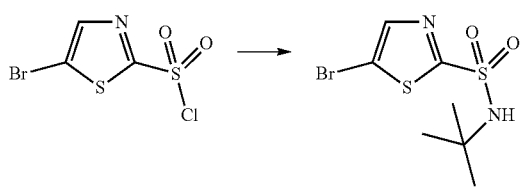

A solution of 2-(benzylthio)-5-bromothiazole (2.3 g 8.00 mmol) was dissolved in CCl₄/H₂O (100/10 mL) and then cooled to 0-5° C. Chlorine gas was bubbled through the reaction mixture for 30 min. After this time, the excess chlorine gas was evaporated by flushing the reaction mixture with a stream of nitrogen. The reaction mixture was diluted with dichloromethane and washed with brine. The combined organic layers were dried over Na₂SO₄, filtered and concentrated to provide the crude sulfonyl chloride. The crude sulfonyl chloride was dissolved in THF (50 mL) and then tert-butyl amine (10 mL) was added in sealed tube. The contents of the tube were heated to 60° C. for 16 h. After this time, the volatiles were evaporated and washed with water and extracted into EtOAc. The combined organic layers were dried over Na₂SO₄, filtered and concentrated. The resulting residue was purified by silica gel chromatography (10% EtOAc/hexane) to provide 5-bromo-N-tert-butylthiazole-2-sulfonamide (1.0 g, 41.5% yield) as a white solid. NMR (400 MHz, DMSO-d₆, δ): 8.41 (s, 1H); 8.17 (s, 1H); 1.25 (s, 9H). LCMS Method V: Retention time 1.861 min, [M−1]=297.

Step 3 . . . Preparation of N-tert-butyl-5-(5-phenyl-4-(pyridin-2-ylmethylamino)quinazolin-2-yl)thiazole-2-sulfonamide

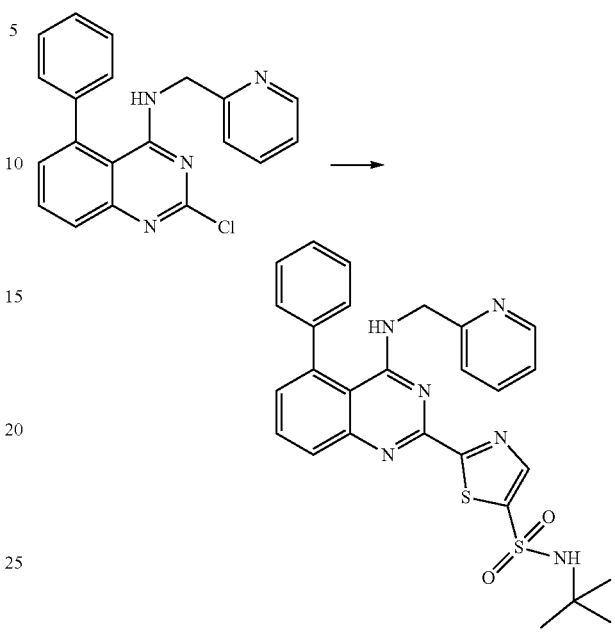

To a stirring suspension of 5-bromo-N-tert-butylthiazole-2-sulfonamide (0.50 g, 1.67 mmol) in 1,4-dioxane (10 mL) was added lithium chloride (0.210 g, 5.03 mmol), followed by hexamethylditin (0.820 g, 2.50 mmol). After degassing with nitrogen, Pd(TPP)₄ (0.19 g, 0.16 mmol) was added. The resultant suspension was stirred for over night at RT. 2-Chloro-5-phenyl-N-(pyridin-2-ylmethyl)quinazolin-4-amine (0.46 g, 1.33 mmol) was dissolved in 1,4-dioxane (3 mL) and then added to the reaction mixture. Upon completion of addition, the reaction mixture was heated at 90° C. for 24 h. After this time, the solvent was evaporated, water was added and the mixture was extracted with DCM. The combined organic layers were dried over Na₂SO₄, filtered and concentrated. The resulting residue was purified by recrystallization with ethyl acetate and further purified by preparative HPLC (method H) to provide N-tert-butyl-5-(5-phenyl-4-(pyridin-2-ylmethylamino)quinazolin-2-yl)thiazole-2-sulfonamide (32 mg, 4.2%) as a yellow solid. LCMS Method V: Rt 2.47 min; [M+1]=531.2; HPLC Method A1: purity 97.3%, retention time=10.89 min.

Step 4. Example 324

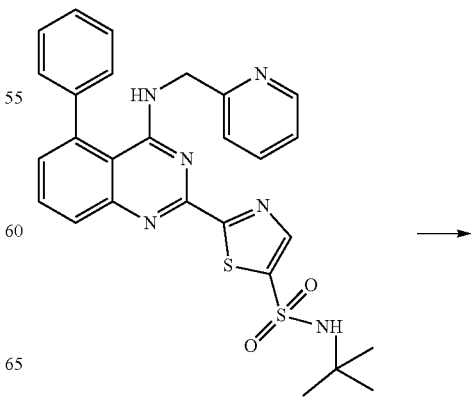

-continued

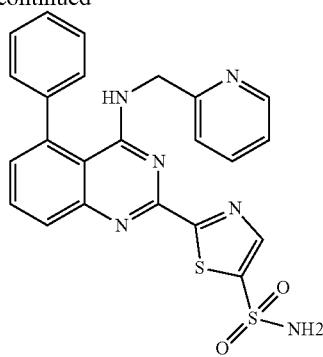

A solution of N-tert-butyl-5-(5-phenyl-4-(pyridin-2-ylmethylamino)quinazolin-2-yl)thiazole-2-sulfonamide (0.03 g 0.05 mmol) in TFA (5 ml) was heated at 80° C. for 8 h. After this time, the TFA was evaporated. The reaction mixture was basified with 10% sodium bicarbonate solution and then extracted in DCM. The combined organic layers were dried over $Na_2SO_4$, filtered and concentrated to yield a residue. The residue was purified by recrystallization with DCM/hexane to provide Example 324 (23 mg, 86% yield) as a brownish yellow solid. $^1$H NMR (400 MHz, DMSO-$d_6$, δ): 8.68 (s, 1H); 8.21 (s, 1H); 8.19 (br s, 1H); 7.83-7.80 (m, 2 h); 7.62 (dt, 1H, J=1.6, 6.8 Hz); 7.61-7.49 (m, 5H); 7.32-7.28 (m, 2H); 7.23-7.20 (m, 1H); 6.94 (t, 1H, J=4 Hz); 4.68 (d, 2H, J=4 Hz). LCMS Method T: Rt 1.63 min; [M+1]=475.0; HPLC Method A1: purity 99.0%, retention time=8.05 min.

It is noted that the proceeding examples, while illustrative of the present invention, are not in sequential order and some example numbers may be missing.

Utility

In general, compounds of the present invention, such as particular compounds disclosed in the preceding examples, have been shown to inhibit the $K_v1$ subfamily of voltage-gated K+ channels (for example, by displaying % inhibition values ≥29%, preferably ≥30%, more preferably ≥40%, even more preferably ≥50%, at 0.3 micromolar concentration in an assay such as those set forth below). By displaying activity as inhibitors of the $K_v1$ subfamily of voltage-gated K+ channels, compounds of the present invention are expected to be useful in the treatment of human diseases associated with the $K_v1$ subfamily of voltage-gated K+ channels.

Assays to determine the degree of activity of a compound as an $I_{Kur}$ inhibitor are well known in the art and are described in references such as J. Gen. Physiol., 101(4): 513-543 (April 1993), and Br. J. Pharmacol., 115(2):267-274 (May 1995).

Assays to determine the degree of activity of a compound as an inhibitor of other members of the $K_v1$ subfamily are also well known in the art. For example, inhibition of $K_v1.1$, $K_v1.2$ and $K_v1.3$ can be measured using procedures described by Grissmer, S. et al., Mol. Pharmacol., 45(6): 1227-1234 (June 1994); inhibition of $K_v1.4$ can be measured using procedures described by Petersen, K. R. et al., Pflugers Arch., 437(3):381-392 (February 1999); inhibition of $K_v1.6$ can be measured using procedures described by Bowlby, M. R. et al., J. Neurophysiol. 73(6):2221-2229 (June 1995); and inhibition of $K_v1.7$ can be measured using procedures described by Kalman, K. et al., J. Biol. Chem., 273(10): 5851-5857 (Mar. 6, 1998).

Compounds of the present invention were tested in one of the assays described immediately above and the results shown in Table 2 below were obtained.

TABLE 2

| Example | Kv 1.5 (% inhibition at 0.3 uM) |
|---|---|
| 7 | 95.7 |
| 22 | 60.4 |
| 29 | 65.3 |
| 31 | 98.2 |
| 32 | 53.1 |
| 38 | 61.3 |
| 40 | 59.8 |
| 42 | 96.4 |
| 46 | 98.7 |
| 50 | 96.1 |
| 97 | 98.7 |
| 105 | 98.7 |
| 107 | 50.3 |
| 108 | 98.1 |
| 110 | 51.8 |
| 111 | 61.5 |
| 130 | 96.2 |
| 134 | 98.4 |
| 137 | 55.6 |

Find below in Table 3 data for disclosed compounds (See U.S. Pat. No. 7,713,983). It is believed that this data demonstrates the unexpected ability of the compounds of the present invention to significantly increase the inhibition of the $K_v1$ subfamily of voltage-gated K+ channels.

TABLE 3

| Compound | Kv 1.5 (% inhibition at 0.3 uM) | Replicates |
|---|---|---|
| Example 578 U.S. Pat. No. 7,713,983 | 20.5 ± 2.3 | 2 |
| Example 580 U.S. Pat. No. 7,713,983 | 5.3 ± 5.1 | 2 |
| Example 68 U.S. Pat. No. 7,713,983 | 8.5 ± 6.9 | 2 |
| Example 82 U.S. Pat. No. 7,713,983 | 5.6 ± 3.8 | 2 |

In addition, compounds of the present invention, such as particular compounds disclosed in the preceding examples, were evaluated for their effectiveness as inhibitors of kinase receptor activity. The compounds were tested in the assay(s) set forth below for inhibition of kinase activity and results are shown in Table 4. Based on the results, it is believed that the compounds of the present invention, such as particular compounds disclosed in the preceding examples, are not effective in inhibiting kinase receptor activity and therefore would not be effective as inhibitors or modulators of kinase receptor activity.

Caliper Kinase Assay

The analyses were performed in U-bottom 384-well plates. The final assay volume was 30 μl prepared from 15 μl additions of enzyme and substrates (fluoresceinated peptide and ATP) and test compounds in assay buffer (20 mM HEPES pH 7.4, 10 mM $MgCl_2$, 0.015% Brij35 and 4 mM DTT). The reaction was initiated by the combination of purified protein kinase with substrates and test compounds. The reaction was incubated at room temperature for 60 min. and terminated by adding 30 µl of 35 mM EDTA to each sample. The reaction mixture was analyzed on the Caliper LABCHIP® 3000 (Caliper, Hopkinton, Mass.) by electrophoretic separation of the fluorescent substrate and phosphorylated product. Inhibition data were calculated by comparison to no enzyme control reactions for 100% inhibition and vehicle-only reactions for 0% inhibition. The ATP was used at a final concentration equivalent to the Km and the peptide substrate concentration was 1.5 µM. Dose response curves were generated to determine the concentration required to inhibit 50% of kinase activity ($IC_{50}$). Compounds were dissolved at 10 mM in dimethylsulfoxide (DMSO) and evaluated at eleven concentrations. $IC_{50}$ values were derived by non-linear regression analysis.

ing supraventricular arrhythmias, atrial arrhythmias, atrial flutter, atrial fibrillation, complications of cardiac ischemia, and use as heart rate control agents; angina pectoris including relief of Prinzmetal's symptoms, vasospastic symptoms and variant symptoms; gastrointestinal disorders including reflux esauphagitis, functional dispepsia, motility disorders (including constipation and diarrhea), and irritable bowel syndrome; disorders of vascular and visceral smooth muscle including asthma, chronic obstructive pulmonary disease, adult respiratory distress syndrome, peripheral vascular disease (including intermittent claudication), venous insufficiency, impotence, cerebral and coronary spasm and Raynaud's disease; inflammatory and immunological disease including inflammatory bowel disease, rheumatoid arthritis, graft rejection, asthma. chronic obstructive pulmonary disease, cystic fibrosis and atherosclerosis; cell proliferative

TABLE 4

| Example | LLE Flt3 (IC50, uM) | LLE GSK3B (IC50, uM) | LLE IGF1R (IC50, uM) | LLE IKKE (IC50, uM) | LLE IRAK-4 (IC50, uM) | LLE IRAK1 (IC50, uM) | LLE mAurA (IC50, uM) | LLE PIM1 (IC50, uM) | LLE_ABL1 (% INH, 50uM) | LLE_AURORA-B (IC50, uM) |
|---|---|---|---|---|---|---|---|---|---|---|
| 1 | — | 50.00 | — | 50.00 | 50.00 | 50.00 | — | — | — | 50.00 |
| 7 | — | 50.00 | — | — | 50.00 | — | — | — | — | — |
| 19 | 10.11 | 5.15 | 17.58 | 50.00 | 18.69 | — | 39.84 | 33.81 | 32.37 | — |

| Example | LLE_BMX (IC50, uM) | LLE_BTK (IC50, uM) | LLE_CDK2E (IC50, uM) | LLE_CDK5 (IC50, uM) | LLE_CDK5/p25 (IC50, uM) |
|---|---|---|---|---|---|
| 1 | 50.00 | 50.00 | 50.00 | — | — |
| 7 | 50.00 | 50.00 | 50.00 | — | — |
| 19 | — | 19.17 | 50.00 | 50.00 | 50.00 |

| Example | LLE_CK1A1 (IC50, uM) | LLE_CK2A1 (IC50, uM) | LLE_CK2A2 (IC50, uM) | LLE_IGF1R (IC50, uM) | LLE_IRAK1 (IC50, uM) |
|---|---|---|---|---|---|
| 1 | — | — | — | — | 50.00 |
| 7 | — | — | 50.00 | — | — |
| 19 | 50.00 | 50.00 | 25.52 | 17.58 | — |

| Example | LLE_ITK (IC50, uM) | LLE_JAK1 (IC50, uM) | LLE_JAK2 (IC50, uM) | LLE_JAK3 (IC50, uM) | LLE_LcK (IC50, uM) | LLE_LYNA (IC50, uM) | LLE_mAurA (IC50, uM) | LLE_PIM1 (IC50, uM) | LLE_PLK1 (IC50, uM) | LLE_SRC (IC50, nM) |
|---|---|---|---|---|---|---|---|---|---|---|
| 1 | 50.00 | — | 23.87 | 50.00 | 50.00 | 50.00 | — | — | — | — |
| 7 | 50.00 | — | 50.00 | 50.00 | 50.00 | 50.00 | — | — | — | — |
| 19 | — | 50.00 | 17.79 | 23.84 | — | — | 39.84 | 33.81 | 50.00 | 50.00 |

| Example | LLE_TAK1 (IC50, uM) | LLE_TBK1 (IC50, uM) | LLE_TEC (IC50, uM) | LLE_TPL2 CAL (IC50, uM) | LLE_TXK (IC50, uM) | LLE_TYK2_887 (IC50, uM) |
|---|---|---|---|---|---|---|
| 1 | 50.00 | 50.00 | 50.00 | — | 50.00 | 50.00 |
| 7 | — | — | 50.00 | — | — | 50.00 |
| 19 | — | — | — | 11.90 | — | 50.00 |

In view of the foregoing, it is believed that compounds of the present invention show unexpected advantages over compounds previously disclosed in the art. It is believed that compounds of the present invention demonstrate a desirable combination of $K_v1$ subfamily inhibitory activity and minimal potency against kinases or Na+ ion channel. In addition, it is believed that Example 7 demonstrates a desirable combination of $K_v1$ subfamily inhibitory activity and pharmacological characteristics including a surprisingly low degree of brain penetration across species in combination with indications of high efficacy and improved safety criteria, for example, improved ion channel selectivity as measured by hERG and Na+ ion channel studies.

Compounds within the scope of the present invention inhibit the $K_v1$ subfamily of voltage-gated K+ channels, and as such are believed to be useful in the treatment and/or prevention of various disorders: cardiac arrhythmias, including disorders including restenosis and cancer (including leukemia); disorders of the auditory system; disorders of the visual system including macular degeneration and cataracts; diabetes including diabetic retinopathy, diabetic nephropathy and diabetic neuropathy; muscle disease including myotonia and wasting; peripheral neuropathy; cognitive disorders; migraine; memory loss including Alzheimer's and dementia; CNS mediated motor dysfunction including Parkinson's disease, and ataxia; epilepsy; and other ion channel mediated disorders.

As inhibitors of the $K_v1$ subfamily of voltage-gated K+ channels compounds of the present invention are believed to be useful to treat a variety of further disorders including resistance by transplantation of organs or tissue, graft-versus-host diseases brought about by medulla ossium transplantation, rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenicmicroorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis comeae, corneal leukoma, ocular pemphigus, Mooren's ulcer Scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyperresponsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene B4-mediated diseases, Coeliaz diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia osses dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastatis of carcinoma and hypobaropathy, disease caused by histamine or leukotriene-C4 release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect, cytomegalovirus infection, HCMV infection, AIDS, cancer, senile dementia, trauma, and chronic bacterial infection.

The compounds of the present invention are suspected antiarrhythmic agents which are useful in the prevention and treatment (including partial alleviation or cure) of arrhythmias. As inhibitors of $K_v1.5$, compounds within the scope of the present invention are particularly useful in the selective prevention and treatment of supraventricular arrhythmias such as atrial fibrillation, and atrial flutter. By "selective prevention and treatment of supraventricular arrhythmias" is meant the prevention or treatment of supraventricular arrhythmias wherein the ratio of the prolongation of the atrial effective refractory period to the prolongation of the ventricular effective refractory period is greater than 1:1. This ratio can also be greater than 4:1, even greater than 10:1. In addition, the ratio may be such that prolongation of the atrial effective refractory response period is achieved without significantly detectable prolongation of the ventricular effective refractory period.

In addition, the compounds within the scope of the present invention block $I_{Kur}$, and thus may be useful in the prevention and treatment of all $I_{Kur}$-associated conditions. An "$I_{Kur}$-associated condition" is a disorder which may be prevented, partially alleviated or cured by the administration of an $I_{Kur}$ blocker. The $K_v1.5$ gene is known to be expressed in stomach tissue, intestinal/colon tissue, the pulmonary artery, and pancreatic beta cells. Thus, administration of an $I_{Kur}$ blocker can provide useful treatment for disorders such as: reflux esauphagitis, functional dispepsia, constipation, asthma, and diabetes. Additionally, $K_v1.5$ is known to be expressed in the anterior pituitary. Thus, administration of an $I_{Kur}$ blocker can stimulate growth hormone secretion. $I_{Kur}$ inhibitors can additionally be useful in cell proliferative disorders such as leukemia, and autoimmune diseases such as rheumatoid arthritis and transplant rejection.

The present invention thus provides methods for the prevention or treatment of one or more of the aforementioned disorders, comprising the step of administering to a subject in need thereof an effective amount of at least one compound of the formula I, Ia, Ib, and/or Ic, preferably compounds exemplified in the examples, more preferably, Examples 7, 22, 29, 31, 32, 38, 40, 42, 46, 50, 97, 105, 107, 108, 110, 111, 130, 134 and 137, even more preferably, Examples 7, 32, and 101, still even more preferably, Examples 7 and 101. Other therapeutic agents such as those described below may be employed with the inventive compounds in the present methods. In the methods of the present invention, such other therapeutic agent(s) may be administered prior to, simultaneously with or following the administration of the compound(s) of the present invention.

Dosage and Formulation

The present invention also provides pharmaceutical compositions comprising at least one of the compounds of the formula I, Ia, Ib, and/or Ic, preferably compounds exemplified in the examples, more preferably, Examples 7, 22, 29, 31, 32, 38, 40, 42, 46, 50, 97, 105, 107, 108, 110, 111, 130, 134 and 137, even more preferably, Examples 7, 32, and 101, still even more preferably, Examples 7 and 101, or salts thereof capable of preventing or treating one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula I, Ia, Ib, and/or Ic, preferably compounds exemplified in the examples, more preferably, Examples 7, 22, 29, 31, 32, 38, 40, 42, 46, 50, 97, 105, 107, 108, 110, 111, 130, 134 and 137, even more preferably, Examples 7, 32, and 101, still even more preferably, Examples 7 and 101, may be administered by any suitable means, for example, orally, such as in the form of tablets, capsules, granules or powders; sublingually; bucally; parenterally, such as by subcutaneous, intravenous, intramuscular, or intrastemal injection or infusion techniques (e.g., as sterile injectable aqueous or non aqueous solutions or suspensions); nasally such as by inhalation spray; topically, such as in the form of a cream or ointment; or rectally such as in the form of suppositories; in dosage unit formulations containing non toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. In the case where the compounds of formula I, Ia, Ib, and/or Ic, preferably compounds exemplified in the examples, more preferably, Examples 7, 22, 29, 31, 32, 38, 40, 42, 46, 50, 97, 105, 107, 108, 110, 111, 130, 134 and 137, even more preferably, Examples 7, 32, and 101, still even more preferably, Examples 7 and 101, are being administered to prevent or treat arrhythmias, the compounds may be administered to achieve chemical conversion to normal sinus rhythm, or may optionally be used in conjunction with electrical cardioconversion.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula I, Ia, Ib, and/or Ic, preferably compounds exemplified in the examples, more preferably, Examples 7, 22, 29, 31, 32, 38, 40, 42, 46, 50, 97, 105, 107, 108, 110, 111, 130, 134 and 137, even more preferably, Examples 7, 32, and 101, still even more preferably, Examples 7 and 101, may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (AVICEL®) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non toxic, parenterally acceptable diluents or solvents, such as mannitol, 1,3 butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders, including: other antiarrhythmic agents such as Class I agents (e.g., propafenone), Class II agents (e.g., carvadiol and propranolol), Class III agents (e.g., sotalol, dofetilide, amiodarone, azimilide and ibutilide), Class IV agents (e.g., diltiazem and verapamil), 5HT antagonists (e.g., sulamserod, serraline and tropsetron), and dronedarone; calcium channel blockers (both L-type and T-type) such as diltiazem, verapamil, nifedipine, amlodipine and mybefradil; Cyclooxygenase inhibitors (i.e., COX-1 and/or COX-2 inhibitors) such as aspirin, indomethacin, ibuprofen, piroxicam, naproxen, CELEBREX®, VIOXX® and NSAIDs; anti-platelet agents such as GPIIb/IIIa blockers (e.g., abciximab, eptifibatide and tirofiban), P2Y12 antagonists (e.g., clopidogrel, cangrelor, ticlopidine and CS-747), P2Y1 antagonists, thromboxane receptor antagonists (e.g., ifetroban), aspirin, and PDE-III inhibitors (e.g., dipyridamole) with or without aspirin; diuretics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone; anti-hypertensive agents such as alpha adrenergic blockers, beta adrenergic blockers, calcium channel blockers, diuretics, renin inhibitors, ACE inhibitors, (e.g., captropril, zofenopril, fosinopril, enalapril, ceranopril, cilazopril, delapril, pentopril, quinapril, ramipril, lisinopril), A II antagonists (e.g., losartan, irbesartan, valsartan), ET antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), nitrates, and combinations of such anti-hypertensive agents; antithrombotic/thrombolytic agents such as tissue plasminogen activator (tPA), recombinant tPA, tenecteplase (TNK), lanoteplase (nPA), factor VIIa inhibitors, factor Xa inhibitors (such as razaxaban), XIa inhibitors, thromin inhibitors (e.g., hirudin and argatroban), PAI-1 inhibitors (i.e., inactivators of tissue plasminogen activator inhibitors), a2-antiplasmin inhibitors, streptokinase, urokinase, prourokinase, anisoylated plasminogen streptokinase activator complex, and animal or salivary gland plasminogen activators; anticoagulants such as warfarin and heparins (including unfractionated and low molecular weight heparins such as enoxaparin and dalteparin); HMG-CoA reductase inhibitors such as pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin); other cholesterol/lipid lowering agents such as squalene synthetase inhibitors, fibrates, and bile acid sequestrants (e.g., QUESTRAN®); antipoliferative agents such as cyclosporin A, TAXOL®, FK 506, and adriamycin; antitumor agents such as TAXOL®, adriamycin, epothilones, cisplatin and carboplatin; antidiabetic agents such as biguanides (e.g., metformin), glucosidase inhibitors (e.g., acarbose), insulins, meglitinides (e.g., repaglinide), sulfonylureas (e.g., glimepiride, glyburide and glipizide), biguanide/glyburide combinations (i.e., GLUCOVANCE®), thiozolidinediones (e.g., troglitazone, rosiglitazone and pioglitazone), PPAR-gamma agonists, aP2 inhibitors, and DP4 inhibitors; thyroid mimetics (including thyroid receptor antagonists) (e.g., thyrotropin, polythyroid, KB-130015, and dronedarone); Mineralocorticoid receptor antagonists such as spironolactone and eplerinone; growth hormone secretagogues; anti-osteoporosis agents (e.g., alendronate and raloxifene); hormone replacement therapy agents such as estrogen (including conjugated estrogens in premarin), and estradiol; antidepressants such as nefazodone and sertraline; antianxiety agents such as diazepam, lorazepam, buspirone, and hydroxyzine pamoate; oral contraceptives; anti-ulcer and gastroesophageal reflux disease agents such as famotidine, ranitidine, and omeprazole; anti-obesity agents such as orlistat; cardiac glycosides including digitalis and ouabain; phosphodiesterase inhibitors including PDE III inhibitors (e.g., cilostazol), and PDE V inhibitors (e.g., sildenafil); protein tyrosine kinase inhibitors; steroidal anti-inflammatory agents such as prednisone, and dexamethasone; and other anti-inflammatory agents such as ENBREL®. The combinations can be co-formulated or in the form of kits packaged to provide appropriate dosages for co-administration.

The above other therapeutic agents, when employed in combination with the compounds of the present invention, may be used, for example, in those amounts indicated in the *Physicians' Desk Reference* (PDR) or as otherwise determined by one of ordinary skill in the art.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon particular embodiments, it will be obvious to those of ordinary skill in the art that variations in the particular compounds and methods may be used and that it is intended that the invention may be practiced otherwise than as specifically described herein. Accordingly, this invention includes all modifications encompassed within the spirit and scope of the invention as defined by the claims that follow.

What is claimed is:
1. A compound, wherein the compound is

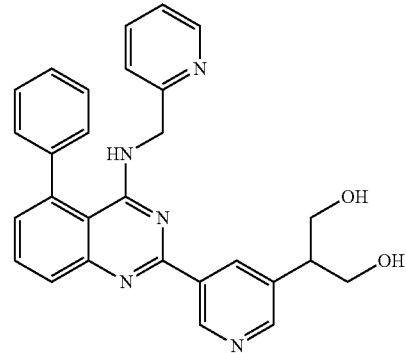 [SMILES: OCC(CO)c1cncc(-c2nc(NCc3ccccn3)c3c(-c4ccccc4)cccc3n2)c1]

or salt thereof.

2. A pharmaceutical composition comprising a therapeutically effective amount of the compound of claim 1 or salt thereof.

3. The pharmaceutical composition of claim 2, further comprising at least one other therapeutic agent, wherein the other therapeutic agent is selected from anti-arrhythmic agents, calcium channel blockers, anti-platelet agents, anti-hypertensive agents, anti thrombotic/anti thrombolytic agents, anti-coagulants, HMG-CoA reductase inhibitors, anti diabetic agents, thyroid mimetics, mineralocorticoid receptor antagonists, and cardiac glycosides.

4. A method of treating arrhythmia comprising administering to a patient in need thereof an effective amount of the compound of claim 1.

5. A method of controlling heart rate comprising administering to a patient in need thereof an effective amount of the compound of claim 1.

6. A compound, wherein the compound is

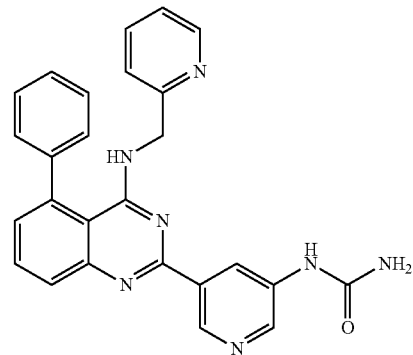 [SMILES: NC(=O)Nc1cncc(-c2nc(NCc3ccccn3)c3c(-c4ccccc4)cccc3n2)c1]

or salt thereof.

7. A pharmaceutical composition comprising a therapeutically effective amount of the compound of claim 6 or salt thereof.

8. The pharmaceutical composition of claim 7, further comprising at least one other therapeutic agent, wherein the other therapeutic agent is selected from anti-arrhythmic agents, calcium channel blockers, anti-platelet agents, anti-hypertensive agents, anti thrombotic/anti thrombolytic agents, anti-coagulants, HMG-CoA reductase inhibitors, anti diabetic agents, thyroid mimetics, mineralocorticoid receptor antagonists, and cardiac glycosides.

9. A method of treating arrhythmia comprising administering to a patient in need thereof an effective amount of the compound of claim 6.

10. A method of controlling heart rate comprising administering to a patient in need thereof an effective amount of the compound of claim 6.

11. A compound, wherein the compound is

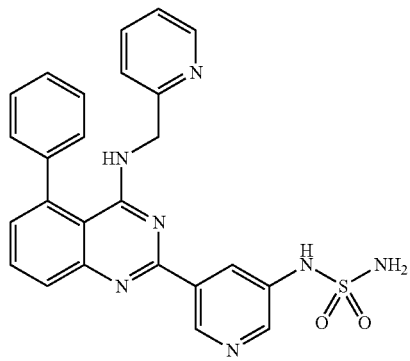 [SMILES: NS(=O)(=O)Nc1cncc(-c2nc(NCc3ccccn3)c3c(-c4ccccc4)cccc3n2)c1]

or salt thereof.

12. A pharmaceutical composition comprising a therapeutically effective amount of the compound of claim 11 or salt thereof.

13. The pharmaceutical composition of claim 12, further comprising at least one other therapeutic agent, wherein the other therapeutic agent is selected from anti-arrhythmic agents, calcium channel blockers, anti-platelet agents, anti-hypertensive agents, anti thrombotic/anti thrombolytic agents, anti-coagulants, HMG-CoA reductase inhibitors, anti diabetic agents, thyroid mimetics, mineralocorticoid receptor antagonists, and cardiac glycosides.

14. A method of treating arrhythmia comprising administering to a patient in need thereof an effective amount of the compound of claim 11.

15. A method of controlling heart rate comprising administering to a patient in need thereof an effective amount of the compound of claim 11.

* * * * *